US012588407B2

(12) United States Patent
Kim et al.

(10) Patent No.: US 12,588,407 B2
(45) Date of Patent: Mar. 24, 2026

(54) ORGANIC LIGHT-EMITTING ELEMENT

(71) Applicant: LG CHEM, LTD., Seoul (KR)

(72) Inventors: Minjun Kim, Daejeon (KR); Dong Hoon Lee, Daejeon (KR); Hyoung Seok Kim, Daejeon (KR); Sangwoo Lee, Daejeon (KR); Sung Jae Lee, Daejeon (KR); Sunmin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 358 days.

(21) Appl. No.: 17/271,292

(22) PCT Filed: Feb. 28, 2020

(86) PCT No.: PCT/KR2020/002861
§ 371 (c)(1),
(2) Date: Feb. 25, 2021

(87) PCT Pub. No.: WO2020/175948
PCT Pub. Date: Sep. 3, 2020

(65) Prior Publication Data

US 2021/0359223 A1 Nov. 18, 2021

(30) Foreign Application Priority Data

Feb. 28, 2019 (KR) ........................ 10-2019-0024130

(51) Int. Cl.
*H01L 51/00* (2006.01)
*C07C 211/61* (2006.01)
(Continued)

(52) U.S. Cl.
CPC .......... *H10K 85/615* (2023.02); *C07C 211/61* (2013.01); *C07D 209/86* (2013.01);
(Continued)

(58) Field of Classification Search
None
See application file for complete search history.

(56) References Cited

U.S. PATENT DOCUMENTS 8,940,412 B2 * 1/2015 Takashima ............. C09K 11/06 548/440
2004/0251816 A1 12/2004 Leo et al.
(Continued)

FOREIGN PATENT DOCUMENTS

CN 105980521 9/2016
CN 107721861 A 2/2018
(Continued)

OTHER PUBLICATIONS

Machine English translation of Kawamura et al. (JP 2004-231547 A). Sep. 26, 2023.*

*Primary Examiner* — Jay Yang
(74) *Attorney, Agent, or Firm* — Bryan Cave Leighton Paisner LLP

(57) ABSTRACT

Provided is an organic light-emitting element comprising: a first electrode; a second electrode provided to face the first electrode; and an organic material layer provided between the first electrode and the second electrode, in which the organic material layer comprises a layer comprising a compound of Formula 1:

(Continued)

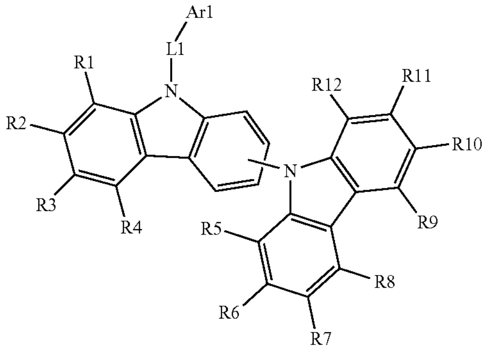

wherein: L1 is a direct bond, or a substituted or unsubstituted arylene or heteroarylene group; Ar1 is a substituted or unsubstituted aryl or heteroaryl group; R1 to R12 are each independently hydrogen, a nitrile group, a halogen, or a substituted or unsubstituted alkyl, silyl, aryl or heteroaryl group, or adjacent groups bond together to form a ring; and any two adjacent R1 to R4 bond together to form a substituted or unsubstituted aromatic ring, and a layer comprising a compound of Formula 2:

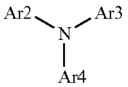

wherein: Ar2 to Ar4 are each independently a substituted or unsubstituted aryl group having 6 to 20 carbon atoms, or -L2-Z.

4 Claims, 1 Drawing Sheet

(51) Int. Cl.

| | |
|---|---|
| ***C07D 209/86*** | (2006.01) |
| ***C07D 307/91*** | (2006.01) |
| ***C07D 333/76*** | (2006.01) |
| ***C07D 403/14*** | (2006.01) |
| ***C07D 405/14*** | (2006.01) |
| ***C07D 409/14*** | (2006.01) |
| ***C09K 11/06*** | (2006.01) |
| ***H10K 85/60*** | (2023.01) |
| *H10K 50/11* | (2023.01) |
| *H10K 50/18* | (2023.01) |
| *H10K 101/10* | (2023.01) |

(52) U.S. Cl.

CPC ......... *C07D 307/91* (2013.01); *C07D 333/76* (2013.01); *C07D 403/14* (2013.01); *C07D 405/14* (2013.01); *C07D 409/14* (2013.01); *C09K 11/06* (2013.01); *H10K 85/633* (2023.02); *H10K 85/636* (2023.02); *H10K 85/6572* (2023.02); *H10K 85/6574* (2023.02); *H10K 85/6576* (2023.02); *C07C 2603/18* (2017.05); *C07C 2603/26* (2017.05); *C07C 2603/42* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/18* (2023.02); *H10K 50/181* (2023.02); *H10K 85/622* (2023.02); *H10K 85/626* (2023.02); *H10K 2101/10* (2023.02)

(56) References Cited

U.S. PATENT DOCUMENTS

| | | | | |
|---|---|---|---|---|
| 2015/0194622 | A1 | 7/2015 | Yamamoto et al. | |
| 2016/0336518 | A1 | 11/2016 | Chun et al. | |
| 2017/0117485 | A1 | 4/2017 | Cho et al. | |
| 2018/0102479 | A1 | 4/2018 | Mujica-Fernaud et al. | |
| 2018/0114907 | A1 | 4/2018 | Takada et al. | |
| 2018/0123042 | A1 | 5/2018 | Cha et al. | |
| 2018/0175301 | A1 | 6/2018 | Ookuma et al. | |
| 2018/0222844 | A1 * | 8/2018 | Kato .................... | H10K 85/633 |
| 2019/0006591 | A1 * | 1/2019 | Yamaki ................ | C07D 307/91 |
| 2019/0131542 | A1 | 5/2019 | Kim et al. | |
| 2019/0273216 | A1 | 9/2019 | Suruga et al. | |
| 2019/0367494 | A1 | 12/2019 | Parham et al. | |
| 2020/0028082 | A1 | 1/2020 | Lee et al. | |
| 2020/0048226 | A1 | 2/2020 | Kim et al. | |

FOREIGN PATENT DOCUMENTS

| | | | | |
|---|---|---|---|---|
| CN | 107848949 | A | | 3/2018 |
| CN | 107848950 | A | | 3/2018 |
| CN | 107849001 | A | | 3/2018 |
| CN | 109890812 | A | | 6/2019 |
| CN | 110024155 | | | 7/2019 |
| JP | 2004231547 | A | * | 8/2004 |
| KR | 10-2014-0103392 | | | 8/2014 |
| KR | 10-2015-0071624 | | | 6/2015 |
| KR | 10-2016-0022764 | | | 3/2016 |
| KR | 10-2016-0022768 | | | 3/2016 |
| KR | 10-2017-0082995 | | | 7/2017 |
| KR | 10-2017-0119291 | | | 10/2017 |
| KR | 10-2018-0017130 | | | 2/2018 |
| KR | 10-2018-0030064 | | | 3/2018 |
| KR | 10-2018-0030560 | | | 3/2018 |
| KR | 10-2018-0031385 | | | 3/2018 |
| KR | 10-2018-0041581 | | | 4/2018 |
| KR | 10-2018-0044799 | | | 5/2018 |
| KR | 10-2018-0051356 | | | 5/2018 |
| KR | 10-2018-0053121 | | | 5/2018 |
| KR | 10-2018-0109749 | | | 10/2018 |
| KR | 10-2018-0125369 | | | 11/2018 |
| KR | 10-2019-0024130 | | | 2/2019 |
| TW | 201600519 | | | 1/2016 |
| TW | 201730149 | | | 9/2017 |
| TW | 201829734 | | | 8/2018 |
| TW | 201833104 | | | 9/2018 |
| WO | WO-2010/074087 | A1 | * | 7/2010 |
| WO | 2013-187894 | | | 12/2013 |
| WO | 2017-022729 | | | 2/2017 |
| WO | 2017-022730 | | | 2/2017 |
| WO | WO-2017/022729 | A1 | * | 2/2017 |
| WO | WO-2017/022730 | A1 | * | 2/2017 |
| WO | 2017-119792 | | | 7/2017 |
| WO | 2018-182300 | | | 10/2018 |
| WO | 2018-212435 | | | 11/2018 |

* cited by examiner

[Figure 1]
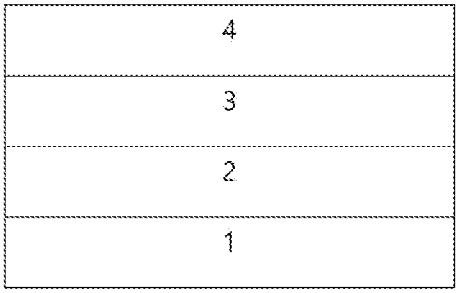
[Figure 2]
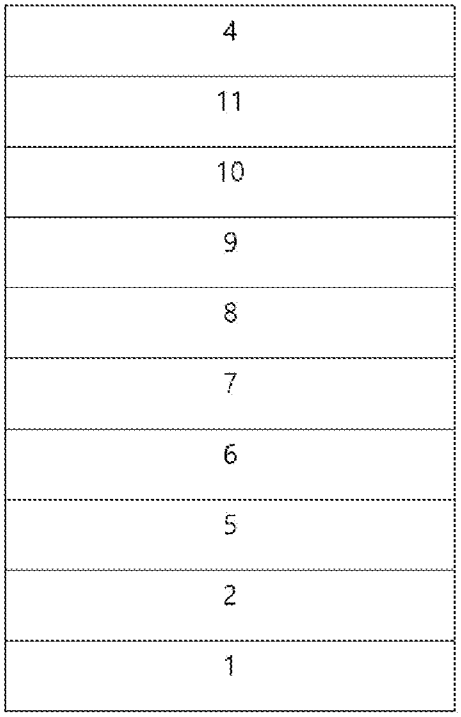

ORGANIC LIGHT-EMITTING ELEMENT

CROSS-REFERENCE TO RELATED APPLICATION(S)

This application is a National Stage Application of International Application No. PCT/KR2020/002861 filed on Feb. 28, 2020, which claims priority to and the benefit of Korean Patent Application No. 10-2019-0024130 filed in the Korean Intellectual Property Office on Feb. 28, 2019, the entire contents of which are incorporated herein by reference.

TECHNICAL FIELD

The present specification relates to an organic light emitting device.

BACKGROUND

In general, an organic light emitting phenomenon refers to a phenomenon in which electric energy is converted into light energy by using an organic material. An organic light emitting device using the organic light emitting phenomenon usually has a structure comprising a positive electrode, a negative electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In such a structure of the organic light emitting device, if a voltage is applied between the two electrodes, holes are injected from the positive electrode into the organic material layer and electrons are injected from the negative electrode into the organic material layer, and when the injected holes and electrons meet each other, an exciton is formed, and light is emitted when the exciton falls down again to a ground state.

There is a continuous need for developing a new material for the aforementioned organic light emitting device.

BRIEF DESCRIPTION

Technical Problem

The present specification provides an organic light emitting device.

Technical Solution

The present invention provides an organic light emitting device comprising: a first electrode; a second electrode provided to face the first electrode; and an organic material layer provided between the first electrode and the second electrode, wherein the organic material layer comprises a layer comprising a compound of the following Formula 1 and a layer comprising a compound of the following Formula 2:

Formula 1

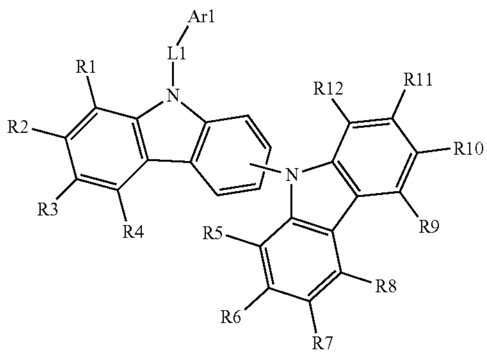

wherein in Formula 1:

L1 is a direct bond, a substituted or unsubstituted arylene group, or a substituted or unsubstituted heteroarylene group;

Ar1 is a substituted or unsubstituted aryl group or a substituted or unsubstituted heteroaryl group;

R1 to R12 are the same as or different from each other, and are each independently hydrogen, a nitrile group, a halogen group, a substituted or unsubstituted alkyl group, a substituted or unsubstituted silyl group, a substituted or unsubstituted aryl group, or a substituted or unsubstituted heteroaryl group, or adjacent groups are bonded to each other to form a ring; and any two adjacent substituents of R1 to R4 are bonded to each other to form a substituted or unsubstituted aromatic ring;

Formula 2

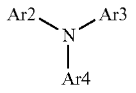

wherein in Formula 2:

Ar2 to Ar4 are the same as or different from each other, and are each independently a substituted or unsubstituted aryl group having 6 to 20 carbon atoms or -L2-Z;

L2 is a direct bond, a phenylene group that is unsubstituted or substituted with deuterium, or a biphenylylene group that is unsubstituted or substituted with deuterium; and Z is a substituted or unsubstituted aryl group having 6 to 20 carbon atoms or a substituted or unsubstituted heteroaryl group.

Advantageous Effects

The organic light emitting device according to an exemplary embodiment of the present specification can improve low driving voltage, high efficiency, and service life.

DESCRIPTION OF THE DRAWINGS

FIGS. 1 and 2 illustrate an organic light emitting device according to an exemplary embodiment of the present specification.

EXPLANATION OF REFERENCE NUMERALS AND SYMBOLS

1: Substrate
2: First electrode
3: Organic material layer
4: Second electrode
5: Hole injection layer
6: Hole transport layer
7: Hole transport auxiliary layer
8: Electron blocking layer
9: Light emitting layer
10: Hole blocking layer
11: Electron injection and transport layer

DETAILED DESCRIPTION

Hereinafter, the present specification will be described in more detail.

The present specification provides an organic light emitting device comprising: a first electrode; a second electrode provided to face the first electrode; and an organic material layer provided between the first electrode and the second electrode, in which the organic material layer comprises a layer comprising the compound of Formula 1 and a layer comprising the compound of Formula 2.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of deuterium, a nitrile group, a substituted or unsubstituted alkyl group, a substituted or unsubstituted cycloalkyl group, a substituted or unsubstituted silyl group, a substituted or unsubstituted alkoxy group, a substituted or unsubstituted arylamine group, a substituted or unsubstituted aryl group, and a substituted or unsubstituted heterocyclic group or being substituted with a substituent to which two or more substituents are linked among the substituents exemplified above, or having no substituent. For example, "the substituent to which two or more substituents are linked" can be an aryl group substituted with an aryl group, an aryl group substituted with a heteroaryl group, a heterocyclic group substituted with an aryl group, an aryl group substituted with an alkyl group, and the like.

In the present specification, an alkyl group can be straight-chained or branched, and the number of carbon atoms thereof is not particularly limited, but is preferably 1 to 30. Specifically, the number of carbon atoms thereof is preferably 1 to 20. More specifically, the number of carbon atoms thereof is preferably 1 to 10. Specific examples thereof comprise: a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethylpropyl group, a 1,1-dimethylpropyl group, an isohexyl group, a 2-methylpentyl group, a 4-methylhexyl group, a 5-methylhexyl group, and the like, but are not limited thereto.

In the present specification, a cycloalkyl group is not particularly limited, but has preferably 3 to 30 carbon atoms, and more preferably 3 to 20 carbon atoms. Specific examples thereof comprise: a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, an alkoxy group can be straight-chained, branched, or cyclic. The number of carbon atoms of the alkoxy group is not particularly limited, but is preferably 1 to 30. Specifically, the number of carbon atoms thereof is preferably 1 to 20. More specifically, the number of carbon atoms thereof is preferably 1 to 10. Specific examples thereof comprise a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group, a benzyloxy group, a p-methylbenzyloxy group, and the like, but are not limited thereto.

In the present specification, an amine group can be selected from the group consisting of $-NH_2$, an alkylamine group, an N-alkylarylamine group, an arylamine group, an N-arylheteroarylamine group, an N-alkylheteroarylamine group, and a heteroarylamine group, and the number of carbon atoms thereof is not particularly limited, but is preferably 1 to 30. Specific examples of the amine group comprise a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, an N-phenylnaphthylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenyl terphenylamine group, an N-phenanthrenylfluorenylamine group, an N-biphenylfluorenylamine group, and the like, but are not limited thereto.

In the present specification, a silyl group can —SiRaRbRc, and Ra, Rb, and Rc are the same as or different from each other, and can be each independently hydrogen, a substituted or unsubstituted alkyl group, or a substituted or unsubstituted aryl group. Specific examples of the silyl group comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, an aryl group is not particularly limited, but has preferably 6 to 20 carbon atoms. The aryl group can be monocyclic or polycyclic. Examples of the monocyclic aryl group comprise a phenyl group, a biphenyl group, a terphenyl group, and the like, but are not limited thereto. Examples of the polycyclic aryl group comprise a naphthyl group, an anthracenyl group, a phenanthryl group, a triphenyl group, a pyrenyl group, a fluorenyl group, and the like, but are not limited thereto.

In the present specification, the "adjacent" group can mean a substituent substituted with an atom directly linked to an atom in which the corresponding substituent is substituted, a substituent disposed to be sterically closest to the corresponding substituent, or another substituent substituted with an atom in which the corresponding substituent is substituted. For example, two substituents substituted at the ortho position in a benzene ring and two substituents substituted with the same carbon in an aliphatic ring can be interpreted as groups which are "adjacent" to each other.

In the present specification, examples of an arylamine group comprise a substituted or unsubstituted monoarylamine group, a substituted or unsubstituted diarylamine group, or a substituted or unsubstituted triarylamine group. The aryl group in the arylamine group can be a monocyclic aryl group or a polycyclic aryl group. The arylamine group comprising two or more aryl groups can comprise a monocyclic aryl group, a polycyclic aryl group, or both a monocyclic aryl group and a polycyclic aryl group. For example, the aryl group in the arylamine group can be selected from the above-described examples of the aryl group.

In the present specification, a heteroaryl group comprises one or more atoms other than carbon, that is, one or more heteroatoms, and specifically, the heteroatom can comprise one or more atoms selected from the group consisting of O, N, Se, S, and the like. The number of carbon atoms thereof is not particularly limited, but is preferably 2 to 30, and more preferably 2 to 20, and the heteroaryl group can be monocyclic or polycyclic. Examples of the heteroaryl group comprise a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group, and the like, but are not limited thereto.

In the present specification, the above-described description on the aryl group can be applied to an arylene group except for a divalent arylene group.

In the present specification, the above-described description on the heteroaryl group can be applied to a heteroarylene group except for a divalent heteroarylene group.

In an exemplary embodiment of the present specification, Formula 1 can be the following Formula 1-1 or 1-2:

Formula 1-1

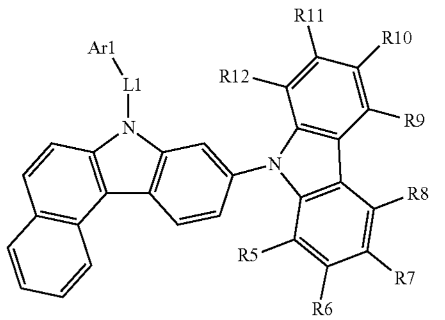

Formula 1-2

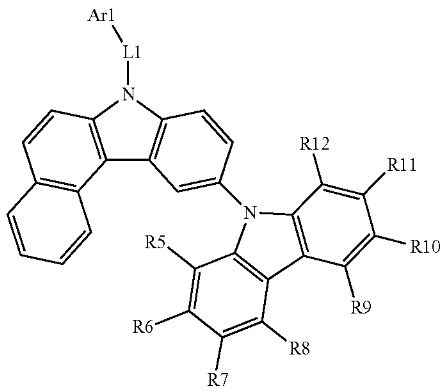

wherein in Formulae 1-1 and 1-2:

L1, Ar1, and R5 to R12 are the same as defined in Formula 1.

In an exemplary embodiment of the present specification, Formula 1 can be any one of the following Formulae 1-3 to 1-6:

Formula 1-3

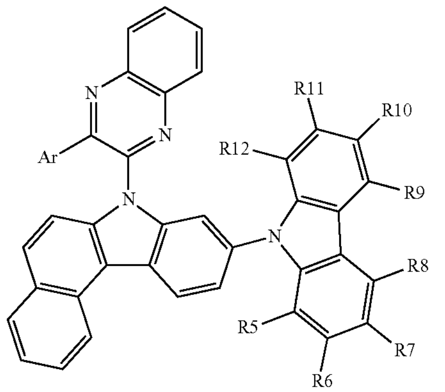

-continued

Formula 1-4

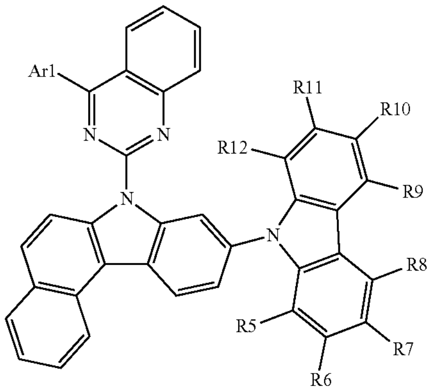

Formula 1-5

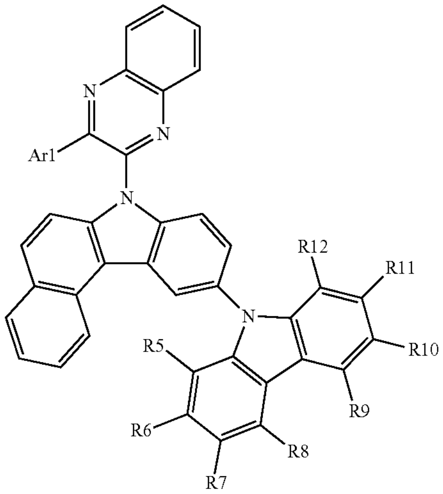

Formula 1-6

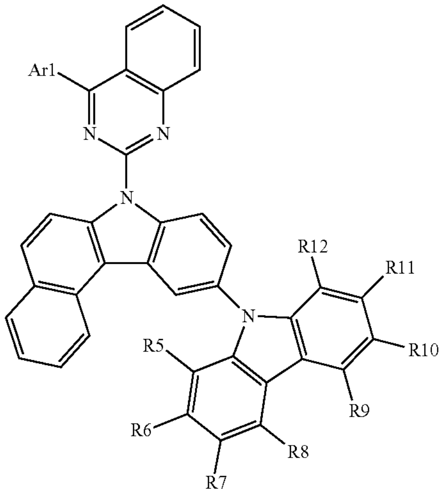

wherein in Formulae 1-3 to 1-6:

Ar1, and R5 to R12 are the same as defined in Formula 1.

In an exemplary embodiment of the present invention, L1 is a direct bond, a substituted or unsubstituted arylene group having 6 to 20 carbon atoms, or a substituted or unsubstituted heteroarylene group having 3 to 30 carbon atoms.

In an exemplary embodiment of the present invention, L1 is a direct bond.

In an exemplary embodiment of the present invention, L1 is an arylene group.

In an exemplary embodiment of the present invention, L1 is a heteroarylene group.

In an exemplary embodiment of the present invention, L1 is a heteroarylene group having 3 to 30 carbon atoms, which comprises one or more of N, O, or S.

In an exemplary embodiment of the present invention, Ar1 is a substituted or unsubstituted aryl group having 6 to 20 carbon atoms, or a substituted or unsubstituted heteroaryl group having 3 to 30 carbon atoms.

In an exemplary embodiment of the present invention, Ar1 is an aryl group having 6 to 20 carbon atoms.

In an exemplary embodiment of the present invention, Ar1 is a heteroaryl group having 6 to 30 carbon atoms.

In an exemplary embodiment of the present invention, Ar1 is a phenyl group, a biphenyl group, a terphenyl group, a dimethylfluorene group, a quaterphenyl group, a naphthyl group, an anthracene group, a phenanthrene group, a pyrene group, or a triphenylene group.

In an exemplary embodiment of the present invention, Ar1 is a carbazole group that is unsubstituted or substituted with dibenzofuran, dibenzothiophene, or a phenyl group.

In an exemplary embodiment of the present invention, Ar2 and Ar3 are the same as each other.

In an exemplary embodiment of the present invention, Ar2 and Ar3 are different from each other.

In an exemplary embodiment of the present invention Ar2 and Ar3 are each independently a phenyl group, a biphenyl group, a terphenyl group, a naphthyl group, a phenanthryl group, a triphenylene group, a fluorene group that is substituted with an alkyl group, a dibenzofuran group, a dibenzothiophene group, or a carbazole group. Further, these can be further substituted with deuterium.

In an exemplary embodiment of the present invention, L2 is a direct bond, a phenylene group that is unsubstituted or substituted with deuterium, or a biphenylylene group that is unsubstituted or substituted with deuterium.

In an exemplary embodiment of the present invention, Z is a substituted or unsubstituted polycyclic aryl group having 6 to 20 carbon atoms.

In an exemplary embodiment of the present invention, Z is a polycyclic aryl group having 6 to 20 carbon atoms, which is unsubstituted or substituted with deuterium, an alkyl group, or an aryl group.

In an exemplary embodiment of the present invention, Z is a substituted or unsubstituted heteroaryl group having 3 to 30 carbon atoms.

In an exemplary embodiment of the present invention, Z is a heteroaryl group having 3 to 30 carbon atoms, which is unsubstituted or substituted with deuterium, an alkyl group, or an aryl group.

In an exemplary embodiment of the present invention, Ar4 is a substituted or unsubstituted aryl group.

In an exemplary embodiment of the present invention, Ar4 is a substituted or unsubstituted aryl group having 6 to 20 carbon atoms.

In an exemplary embodiment of the present invention, Ar4 is an aryl group having 6 to 20 carbon atoms, which is unsubstituted or substituted with an aryl group.

In an exemplary embodiment of the present invention, Formula 2 does not comprise a spirobifluorene group, and the like because the number of carbon atoms of an aryl group that can be included in Formula 2 is 6 to 20.

In an exemplary embodiment of the present specification, the compound of Formula 1 is any one compound selected from the following compounds:

-continued
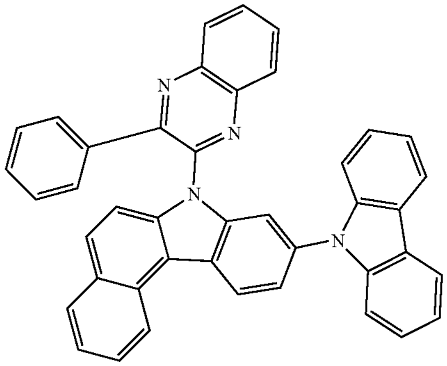
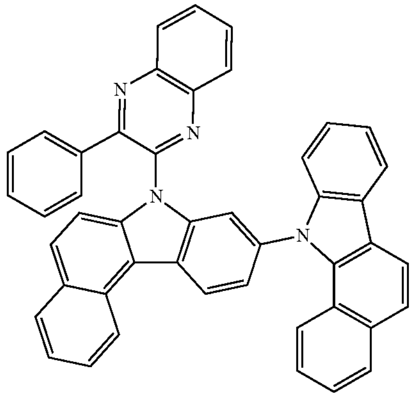
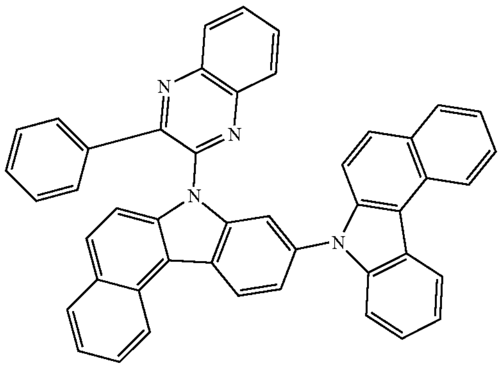
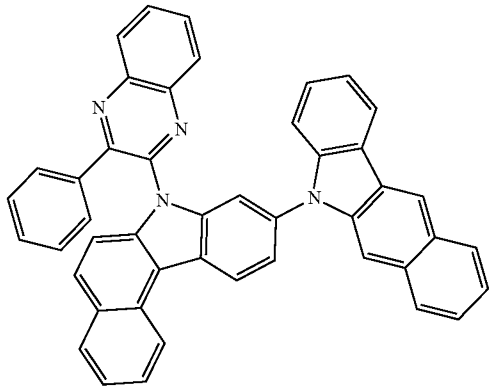
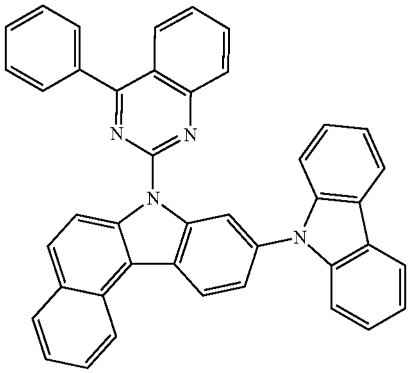
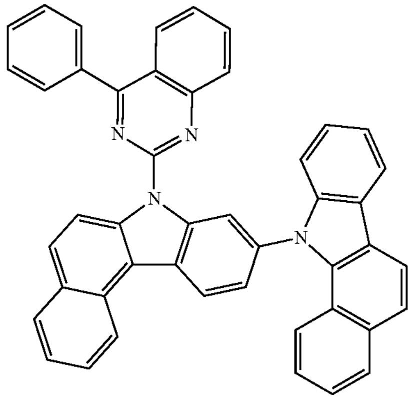
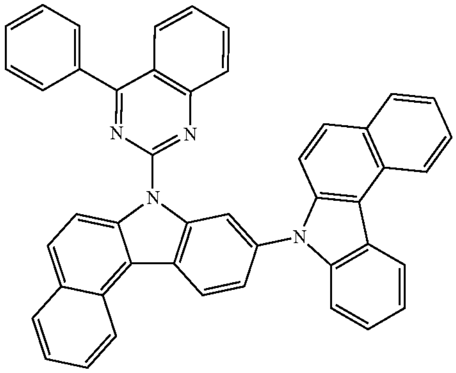
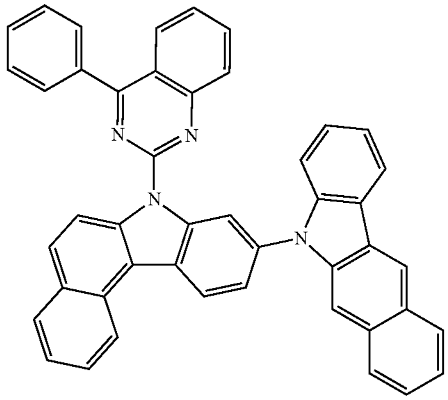

-continued
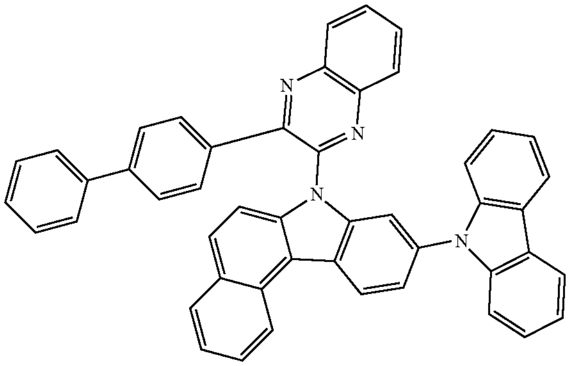
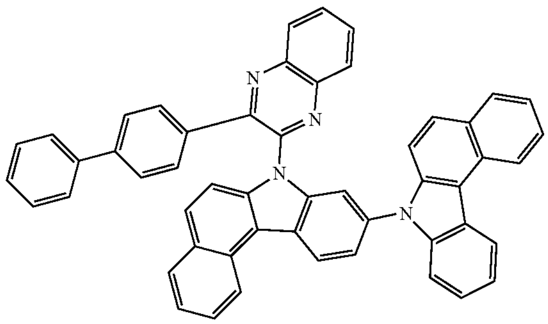
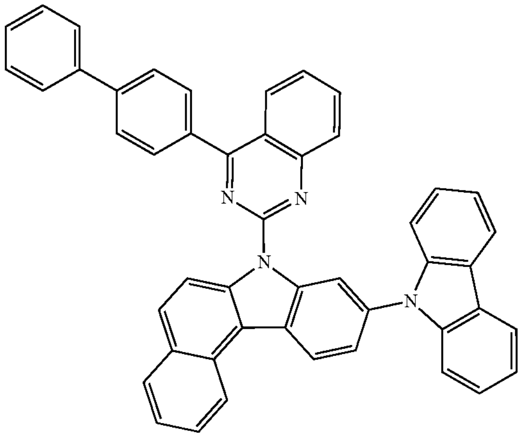
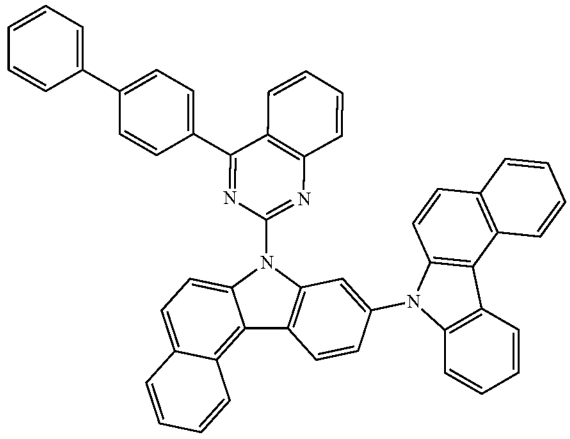
-continued
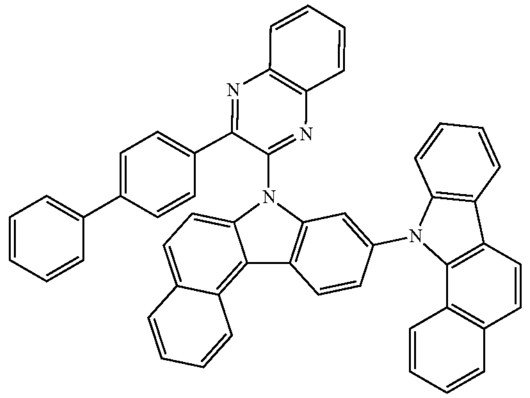
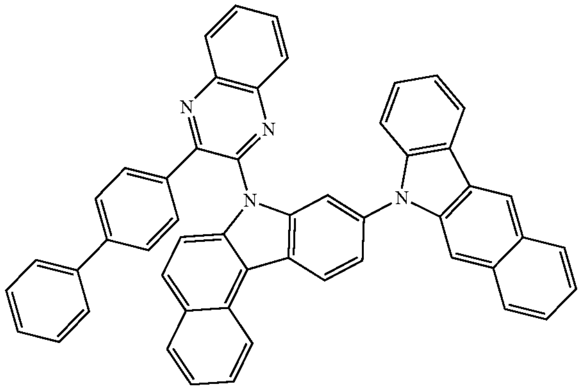
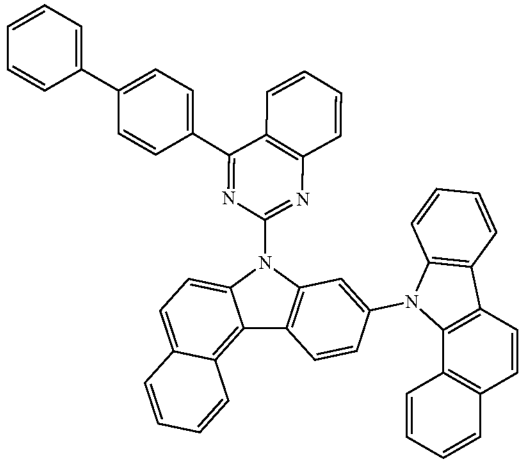
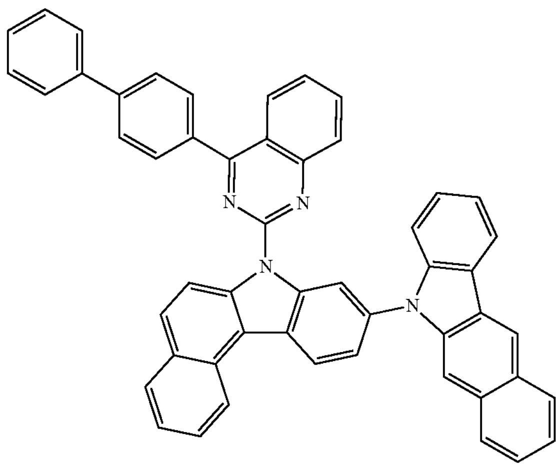

-continued
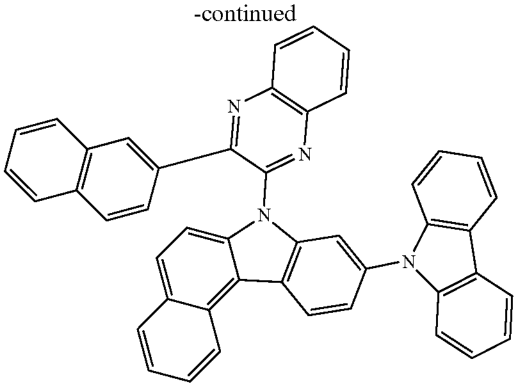
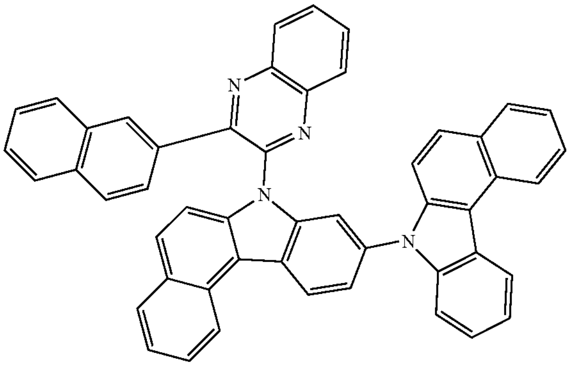
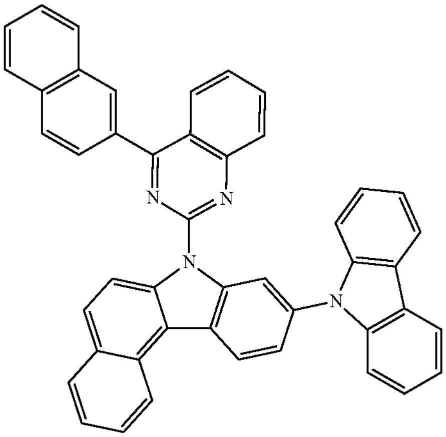
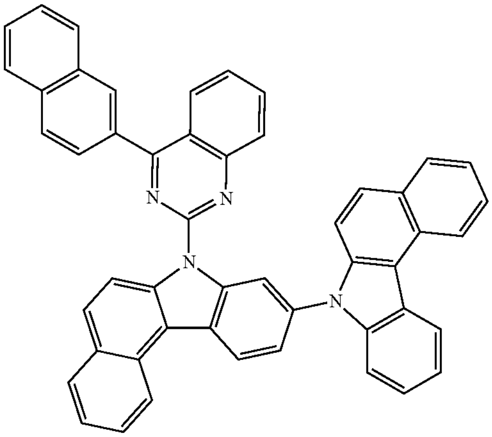
-continued
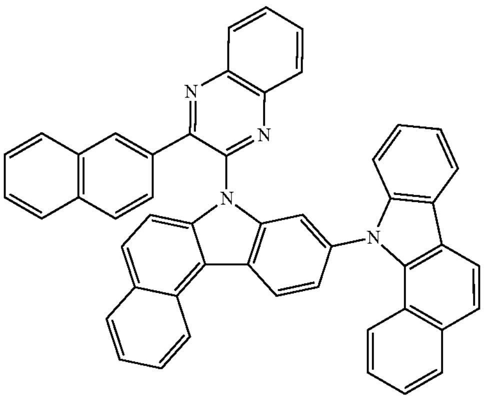
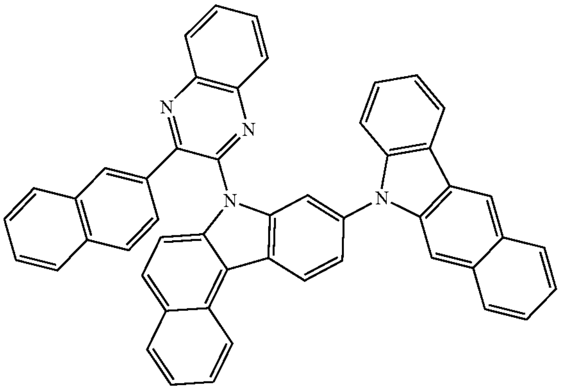
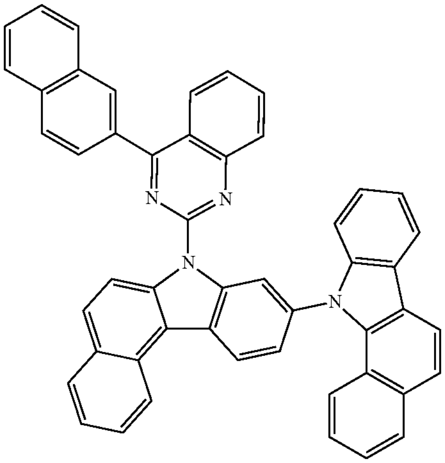
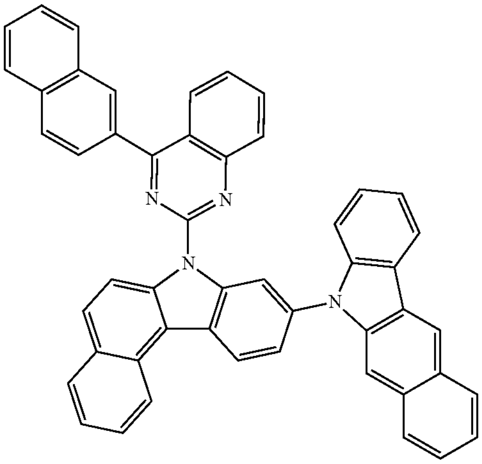

-continued
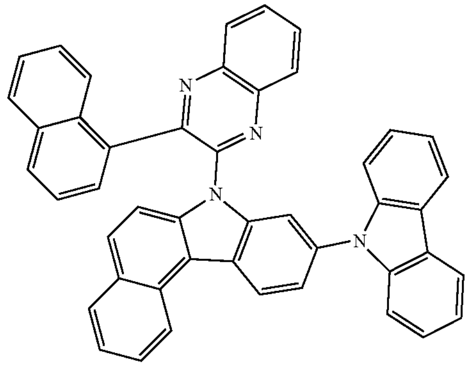
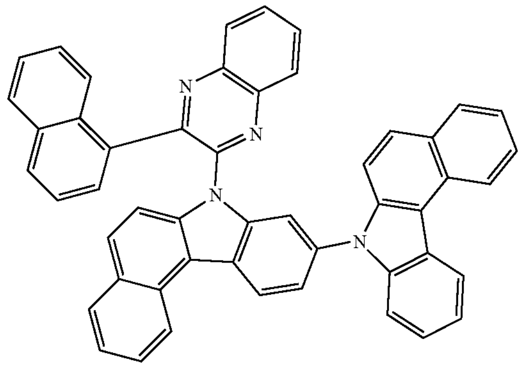
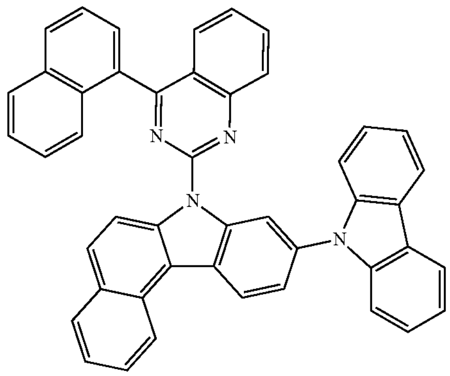
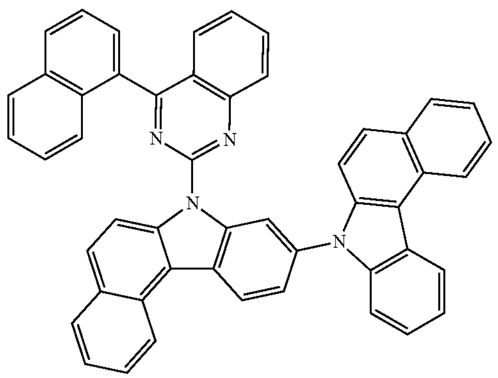
-continued
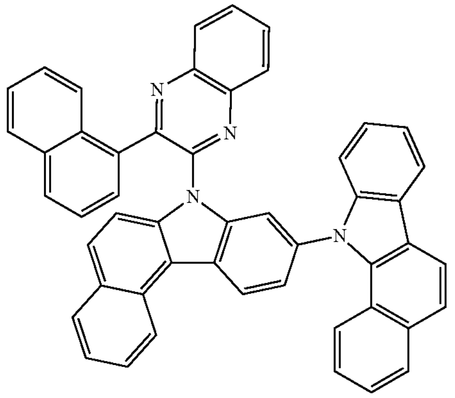
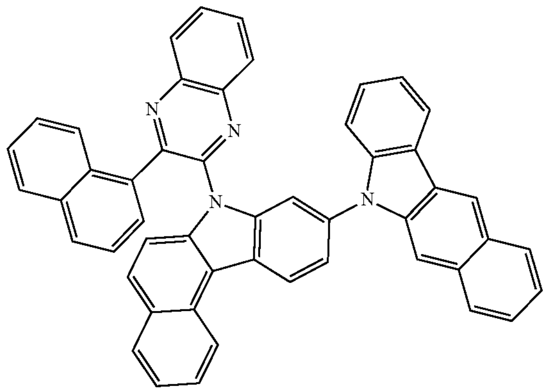
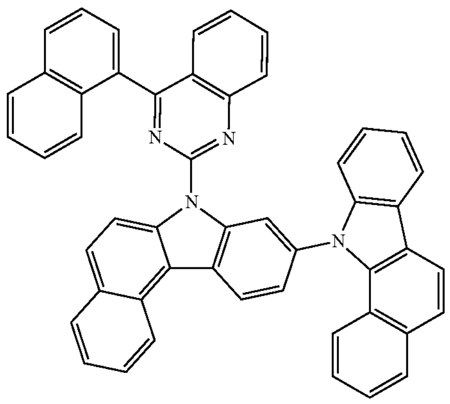
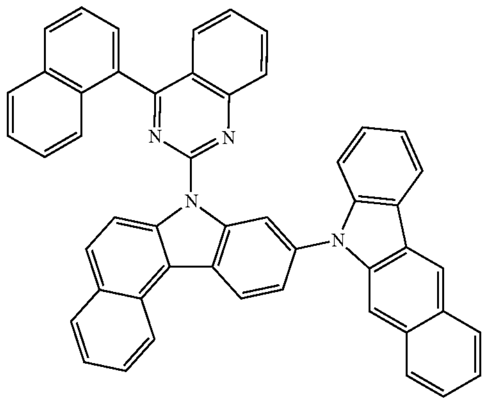

-continued
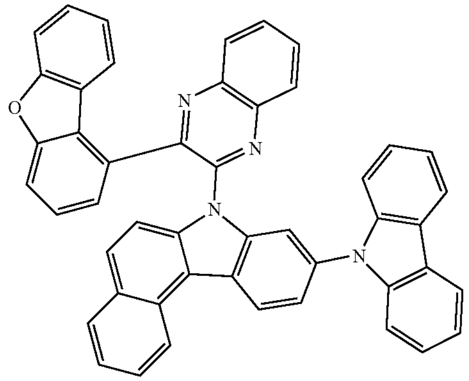
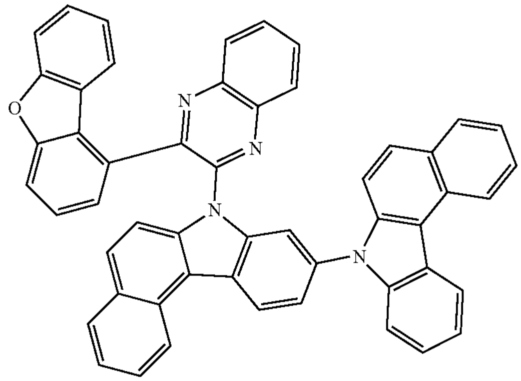
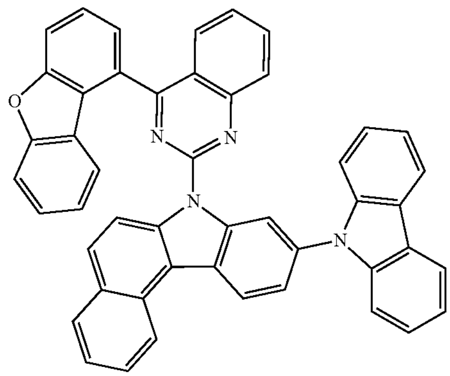
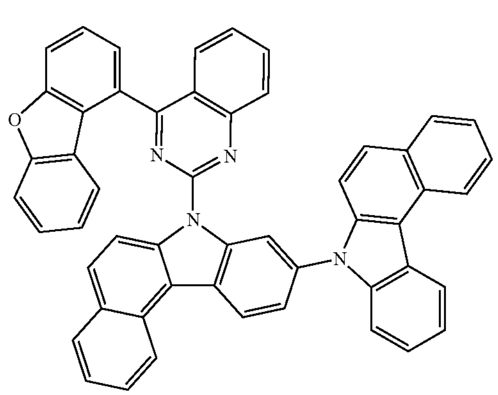
-continued
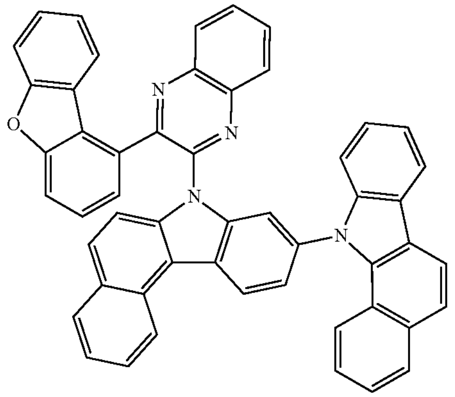
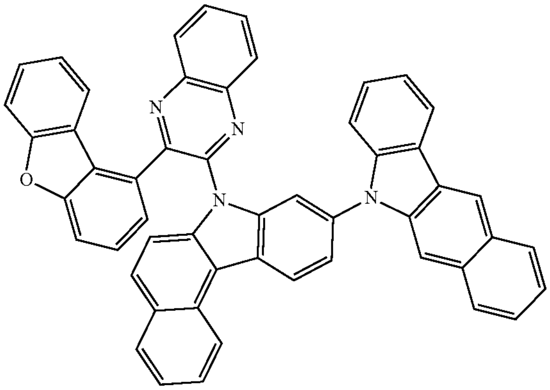
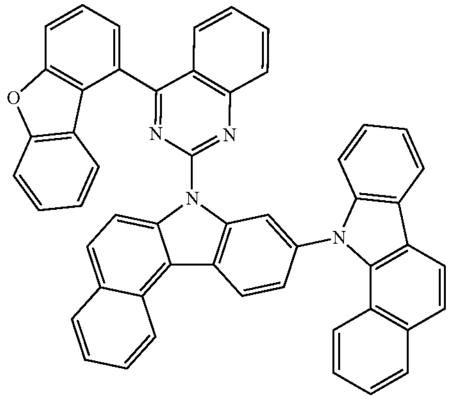
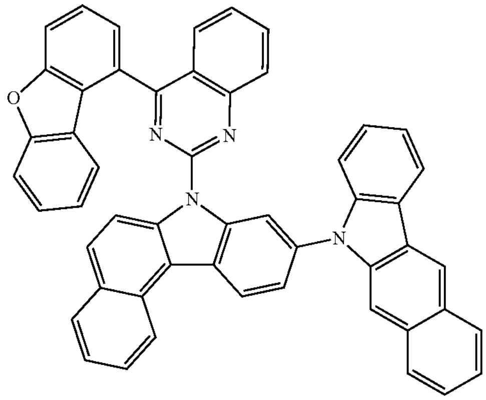

-continued
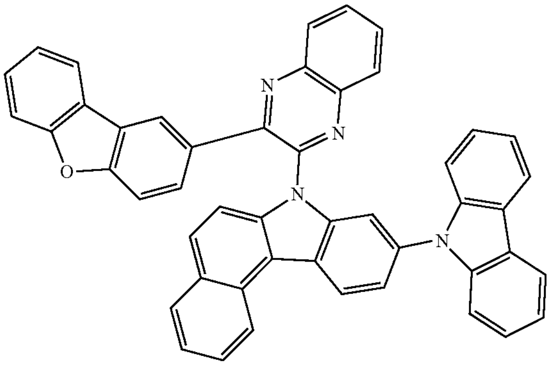
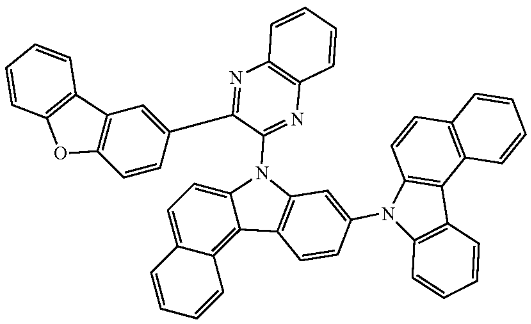
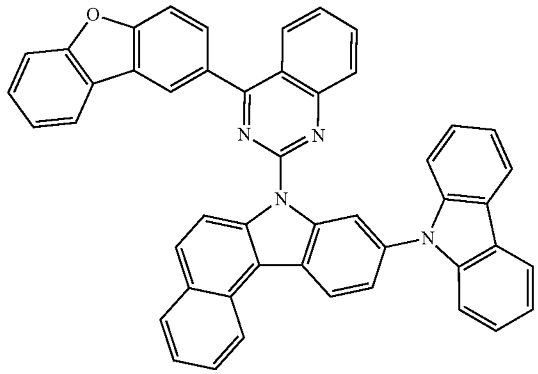
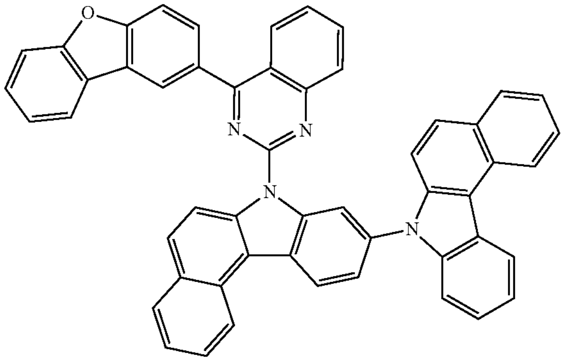
-continued
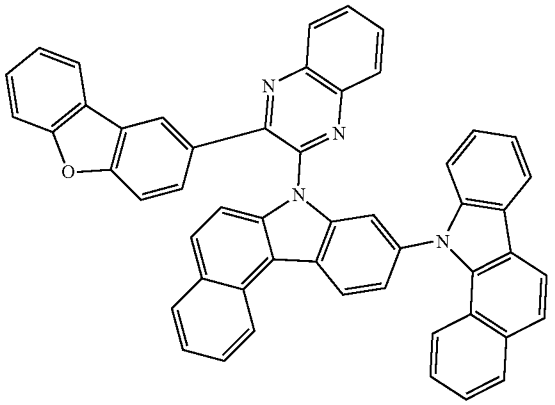
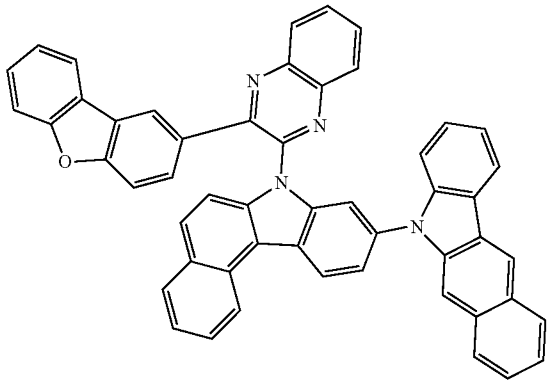
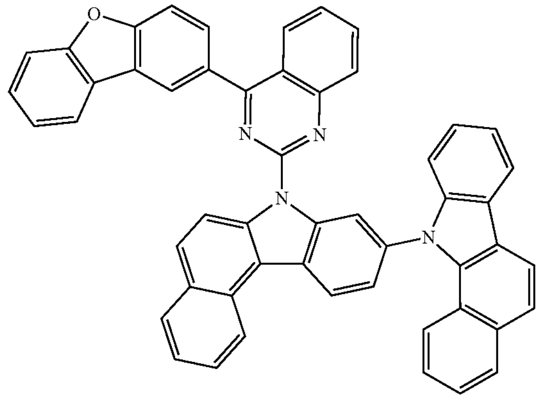
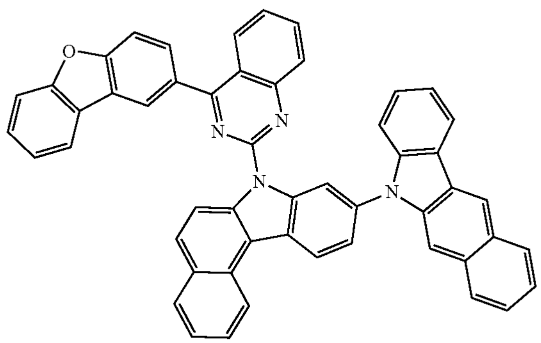

-continued
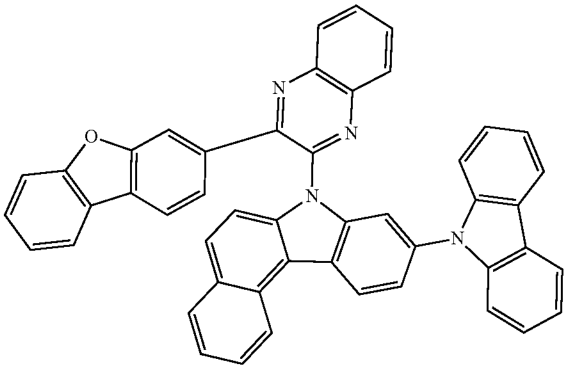
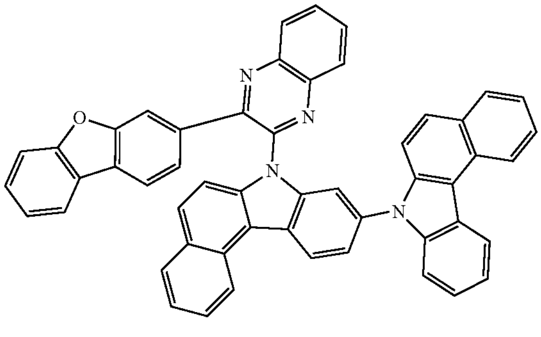
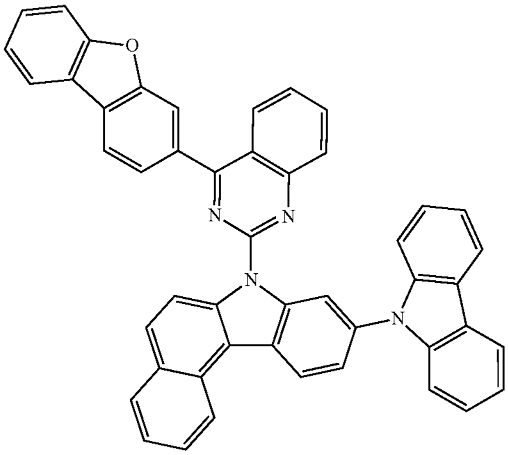
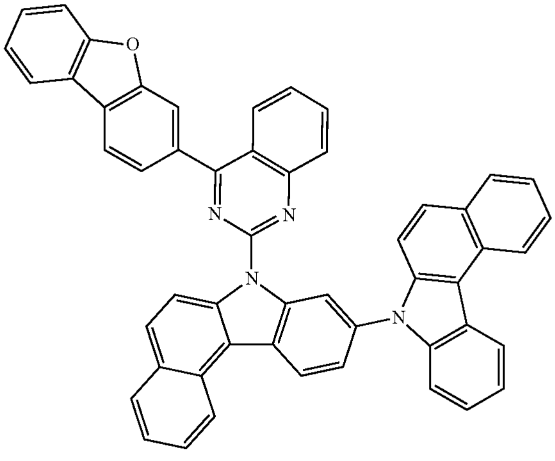
-continued
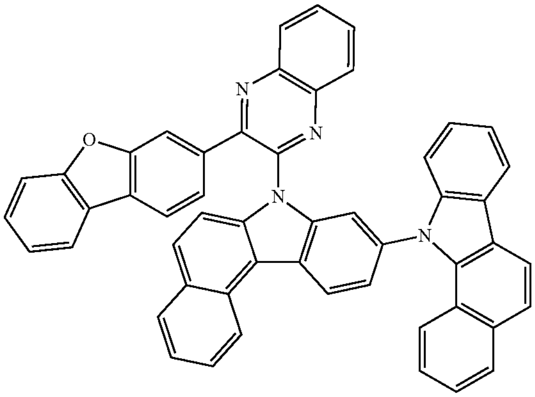
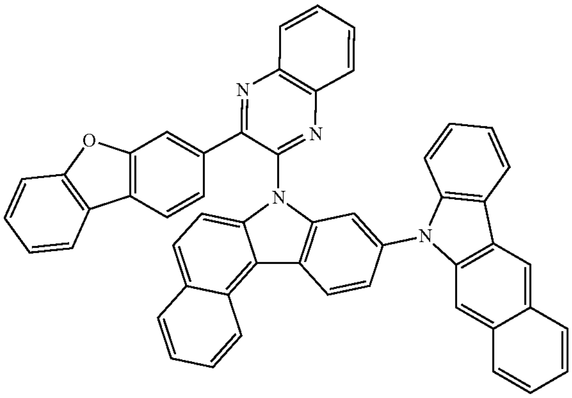
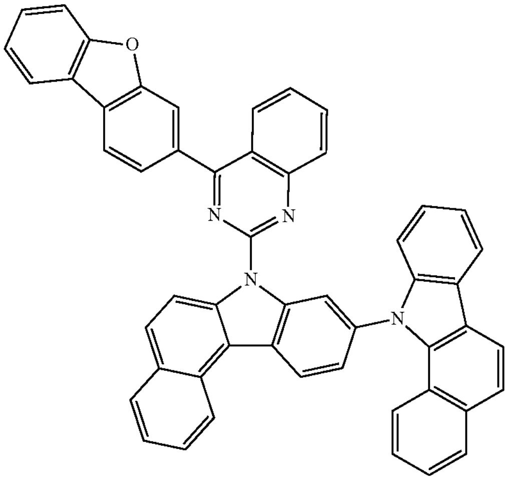

-continued
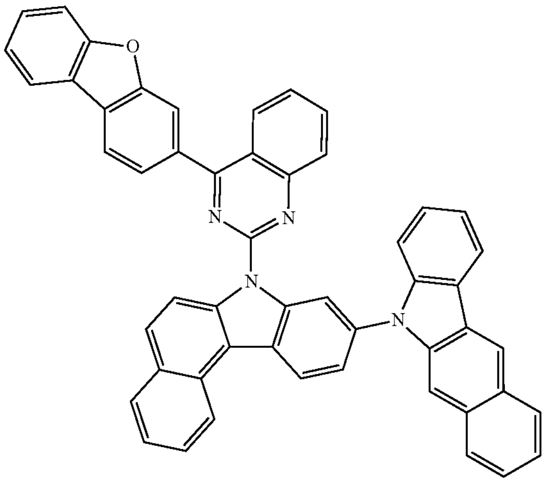
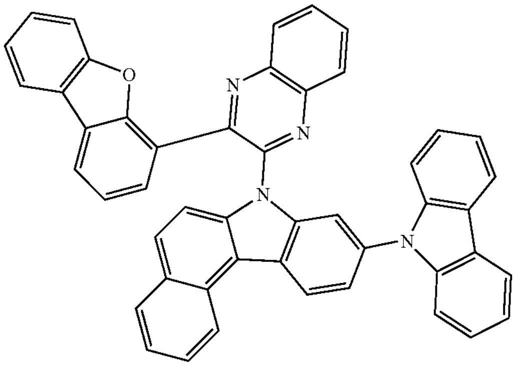
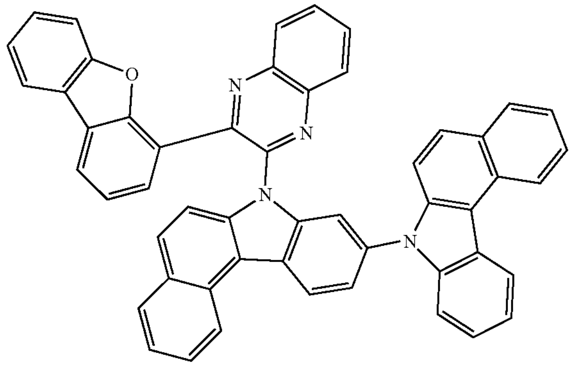
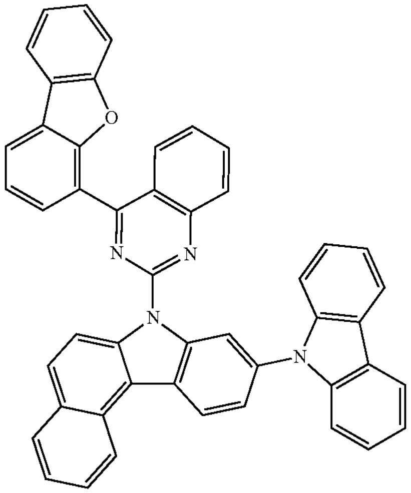
-continued
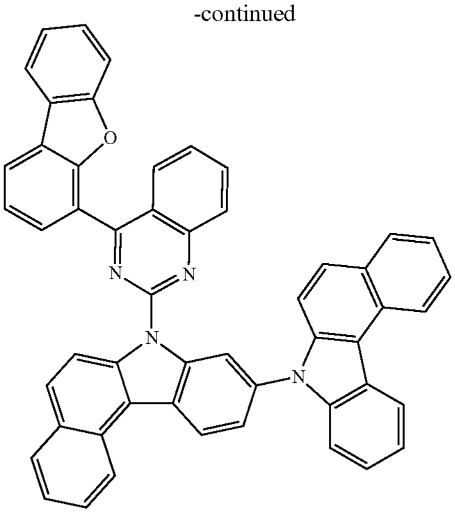
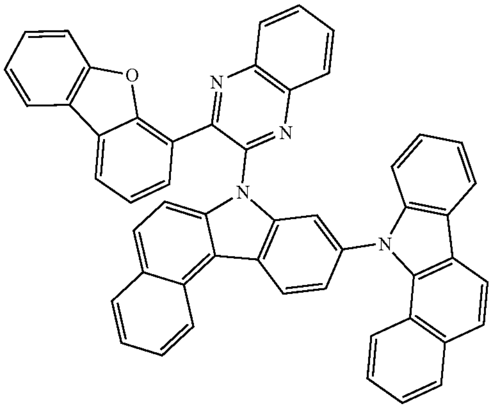
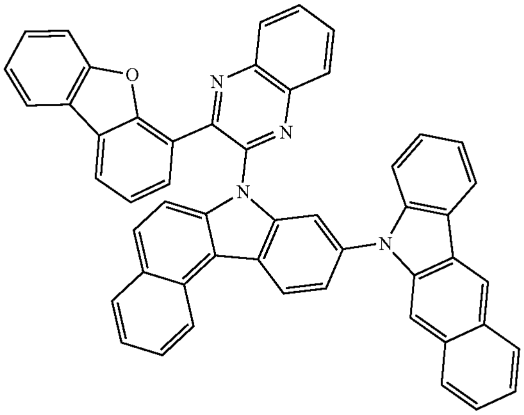

-continued
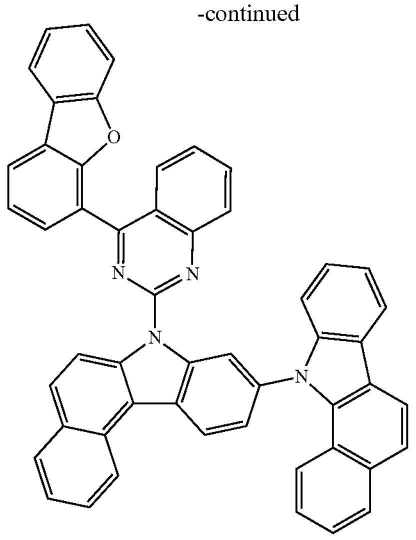
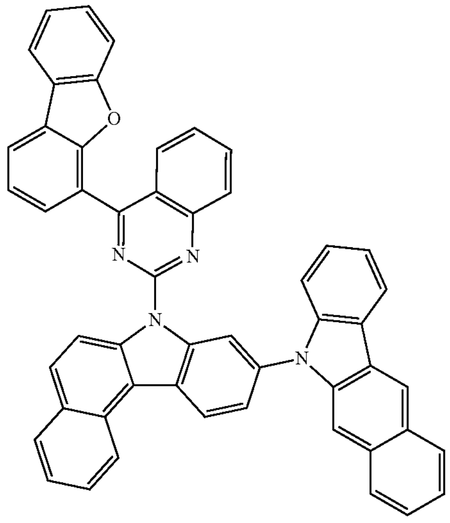
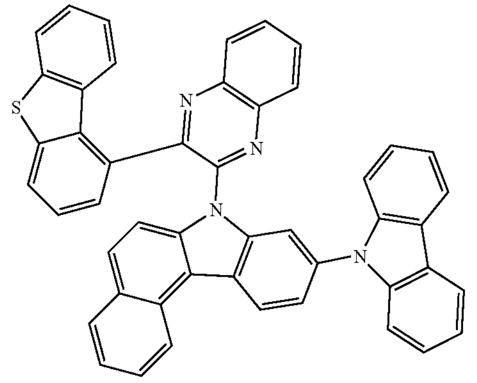
-continued
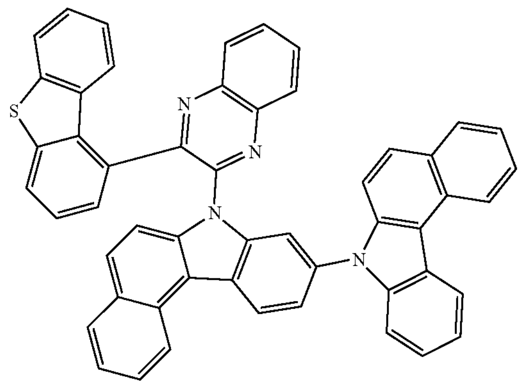
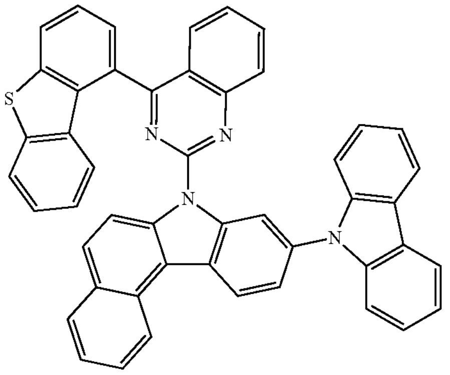
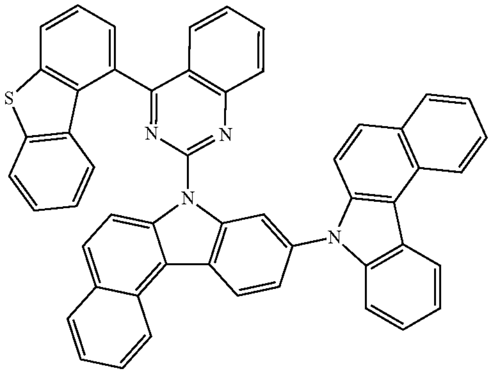
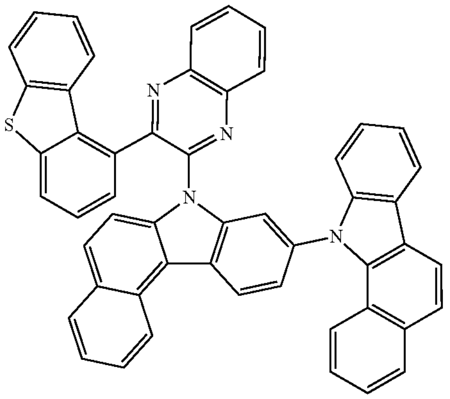

-continued
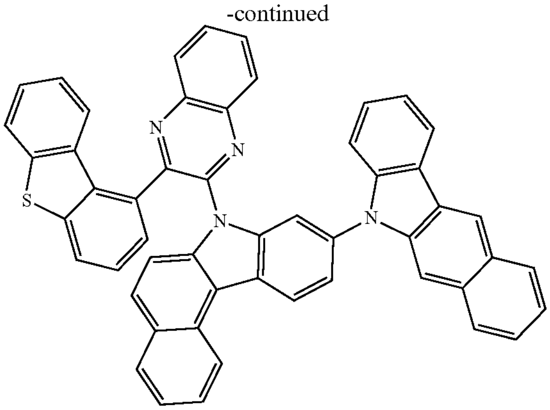
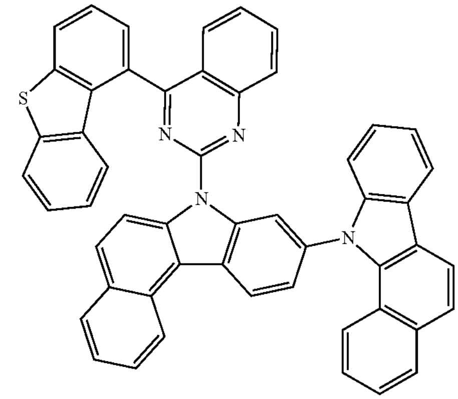
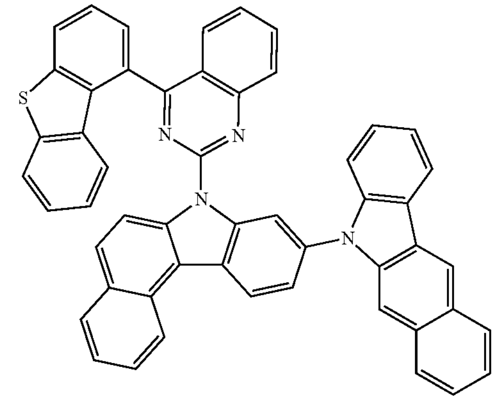
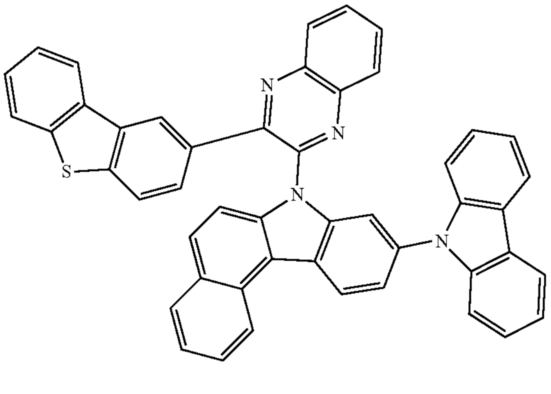
-continued
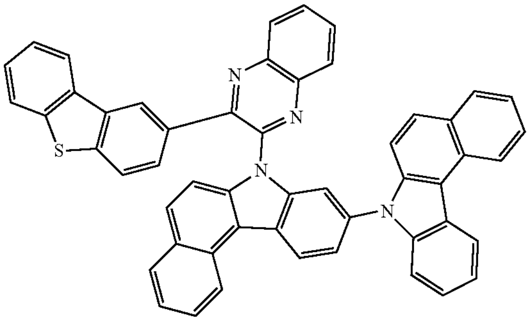
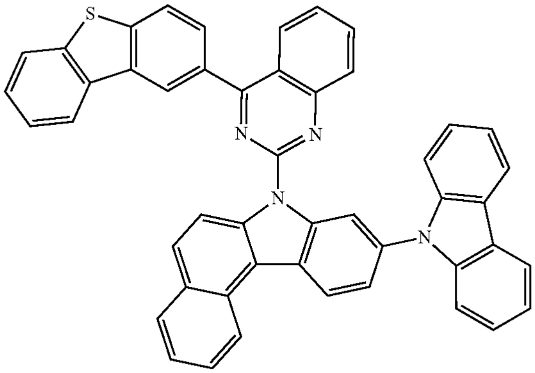
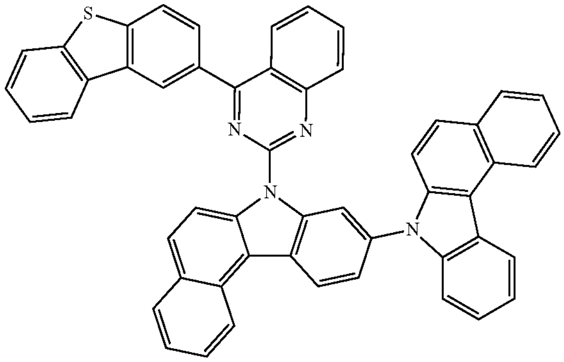
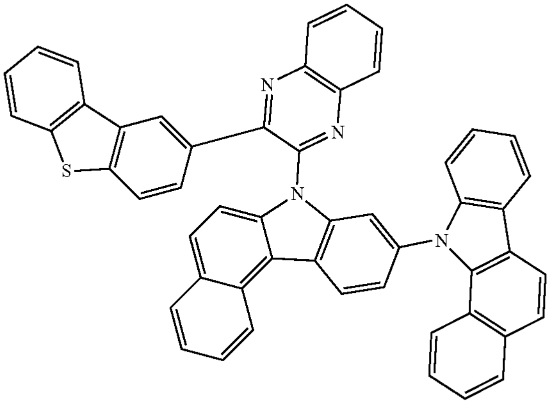

-continued
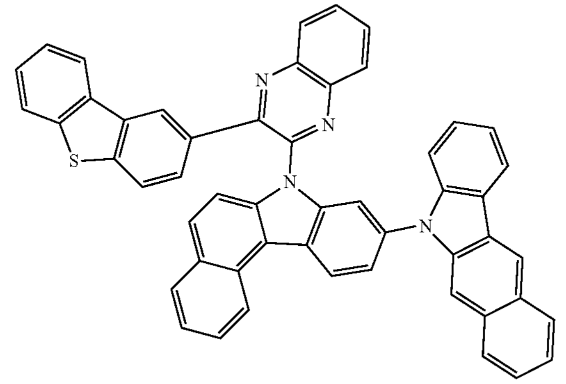
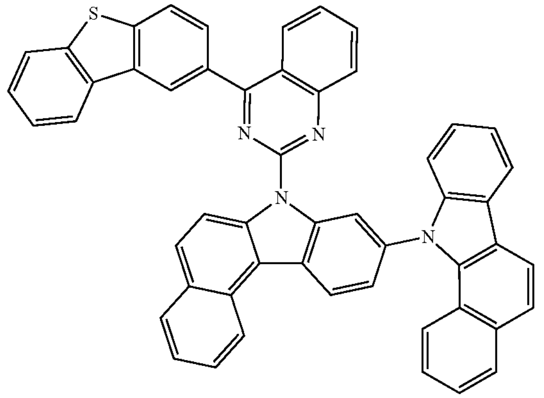
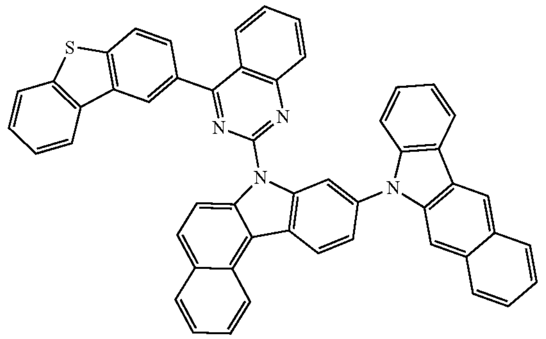
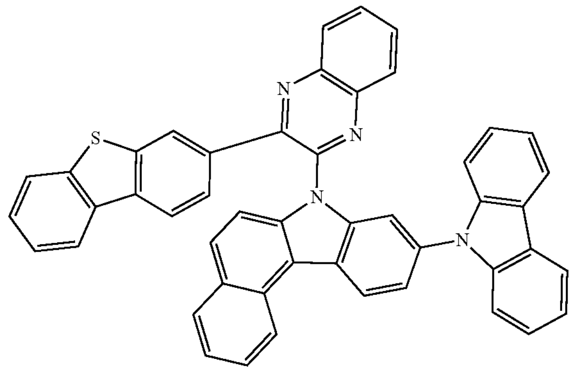
-continued
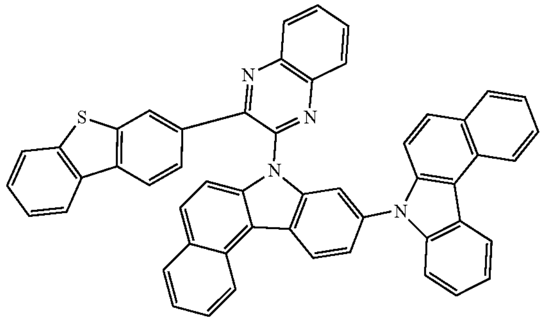
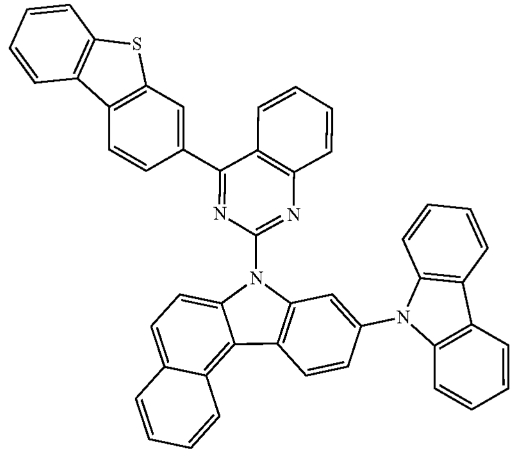
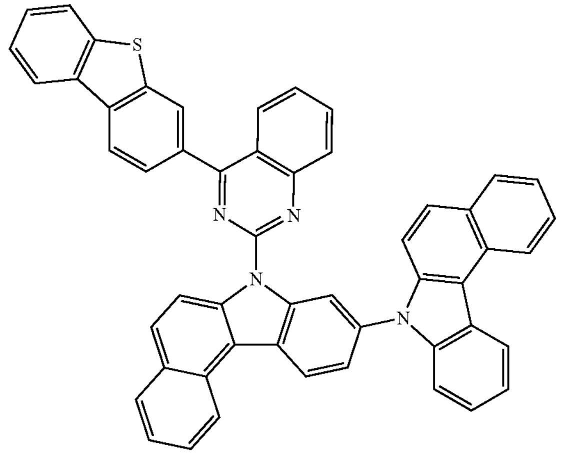
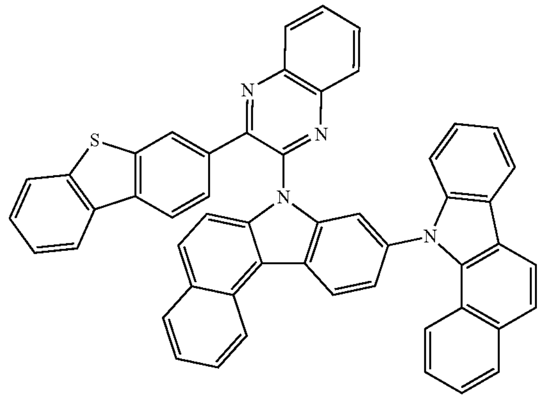

-continued
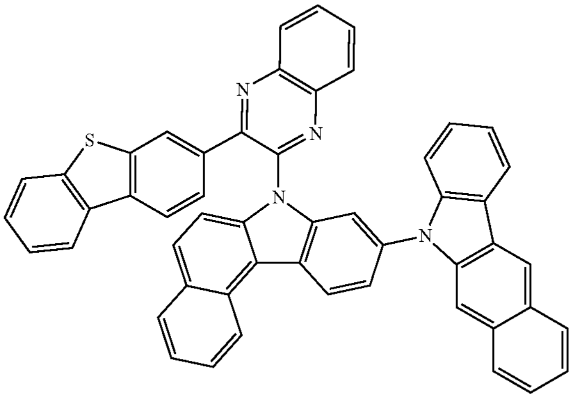
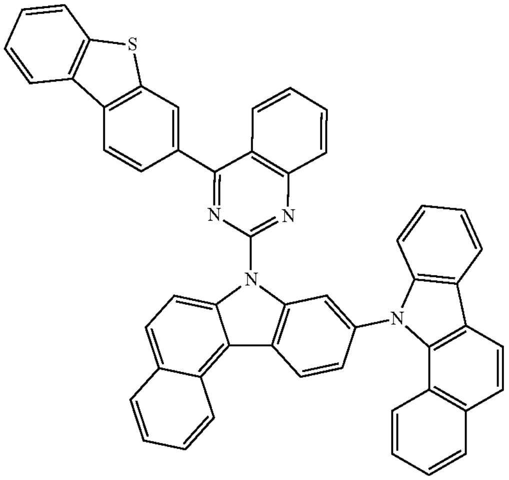
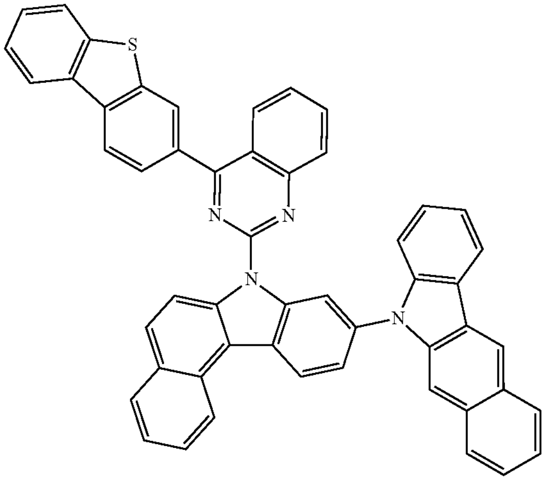
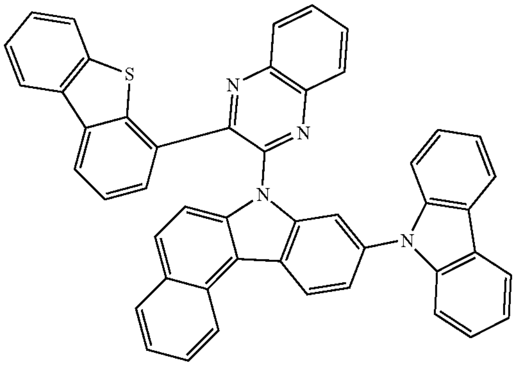
-continued
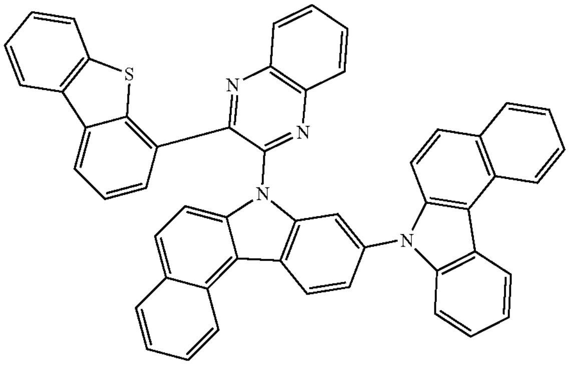
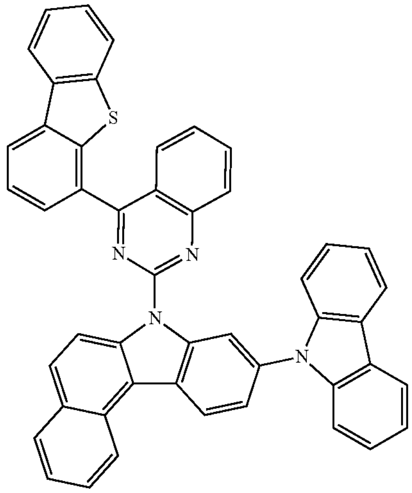
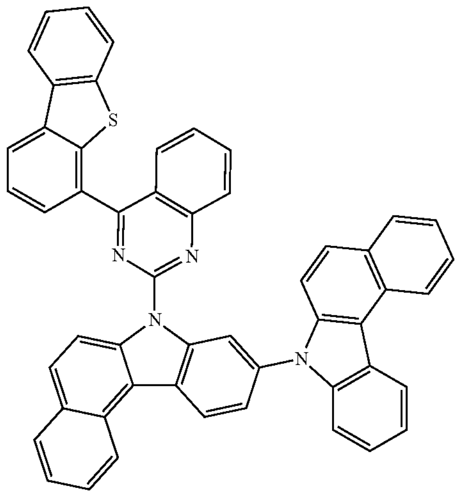

-continued
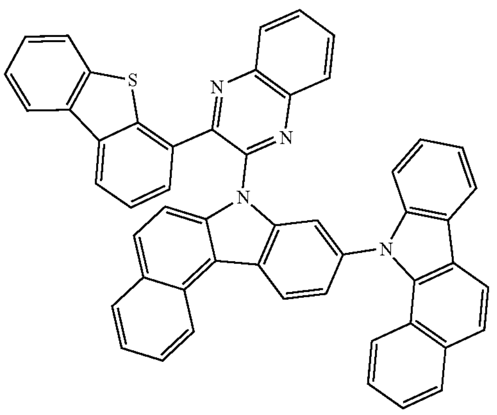
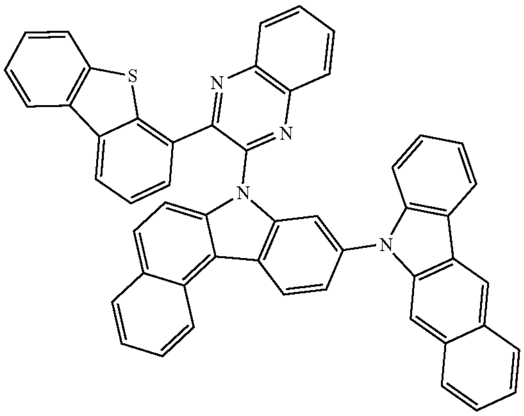
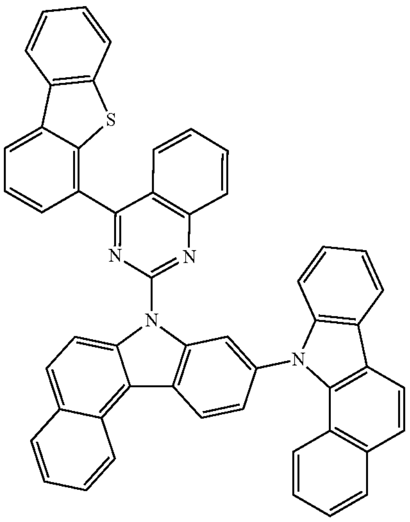
-continued
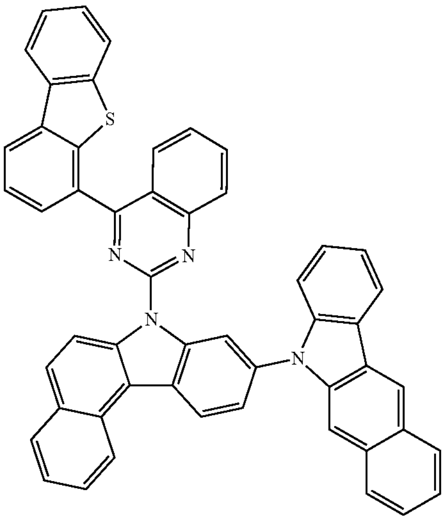
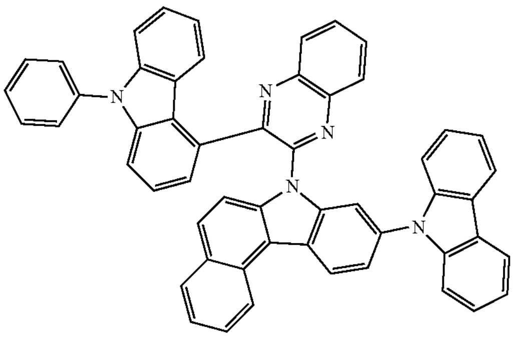
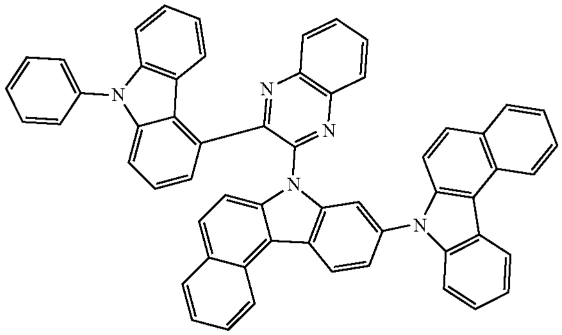
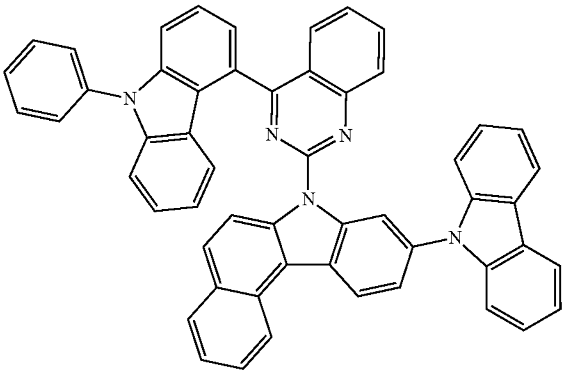

-continued
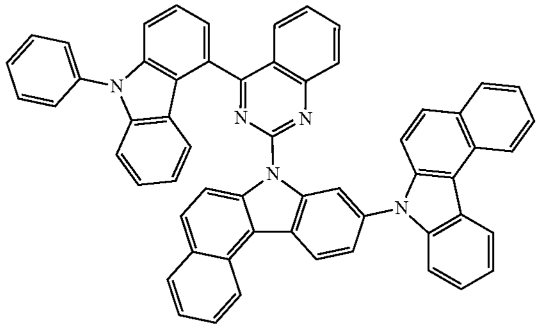
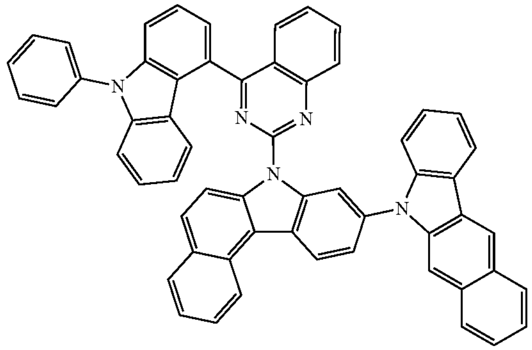
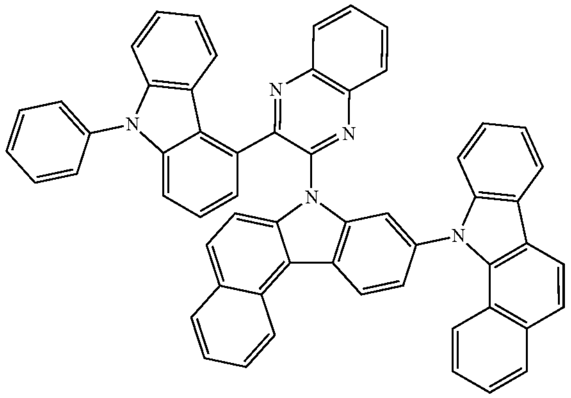
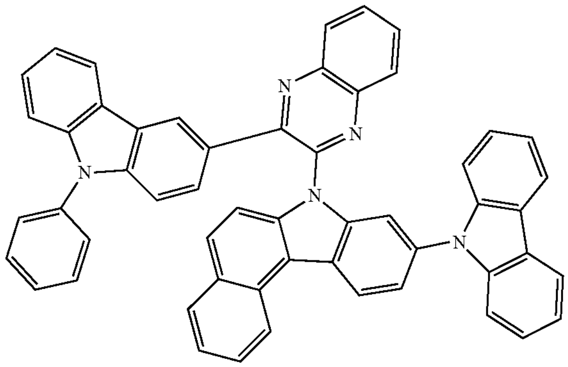
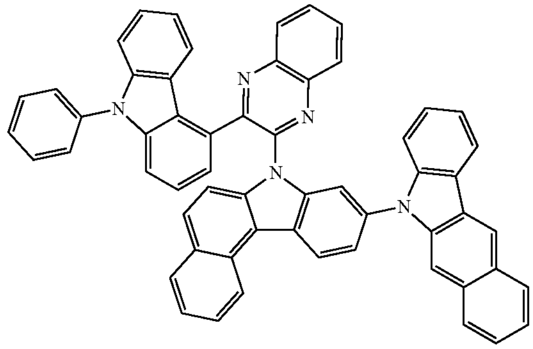
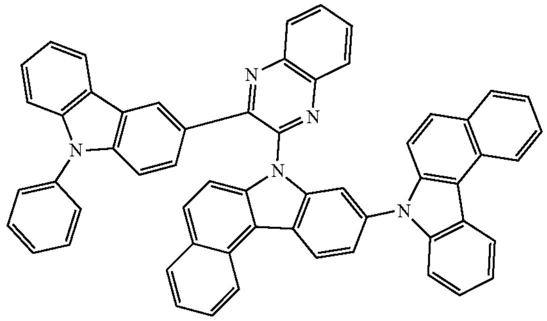
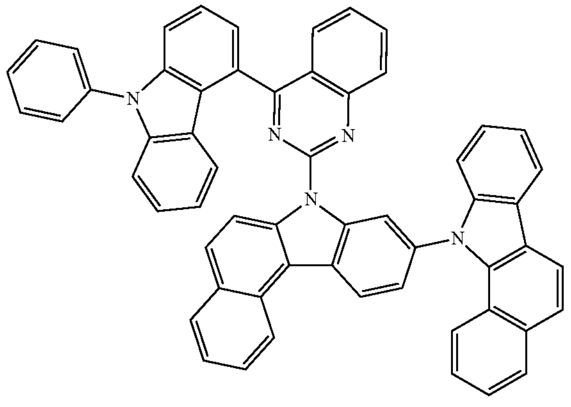
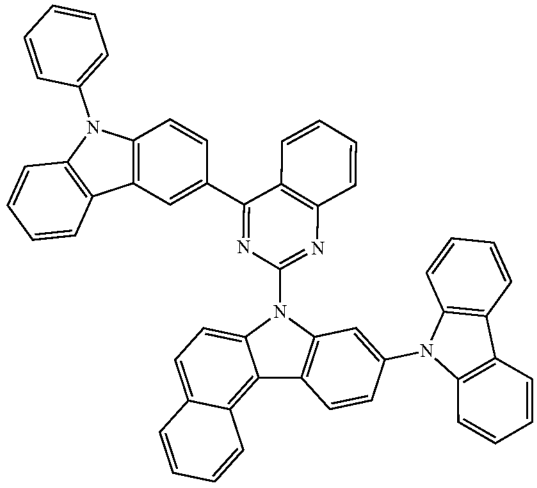
-continued -continued
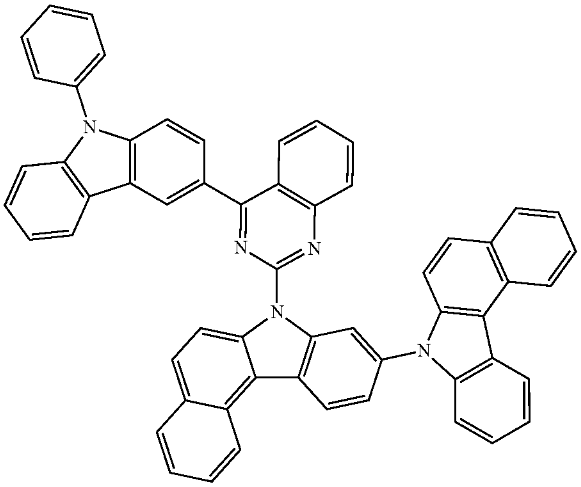
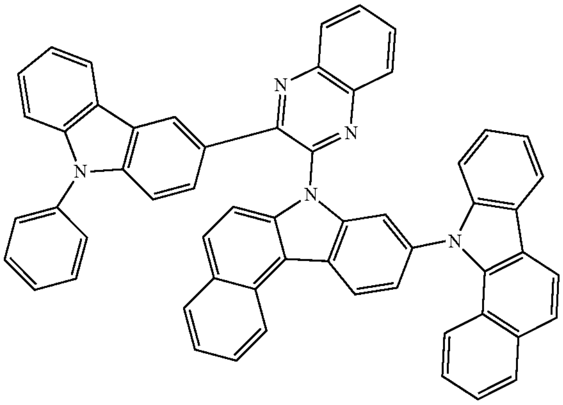
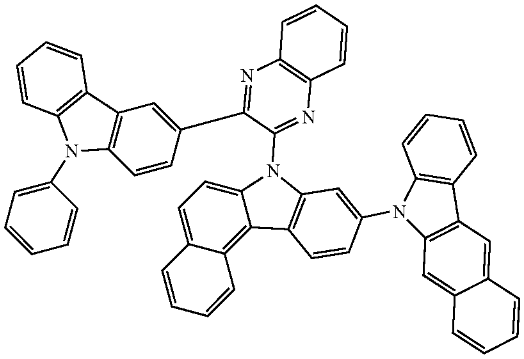
-continued
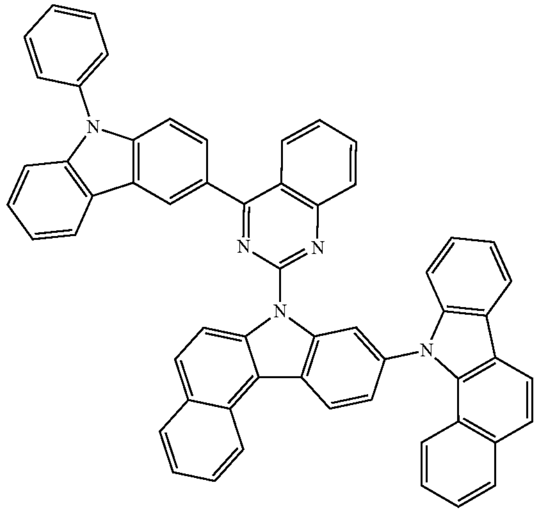
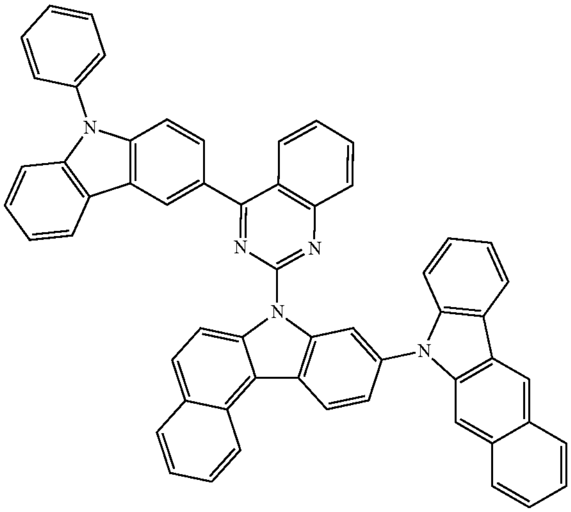
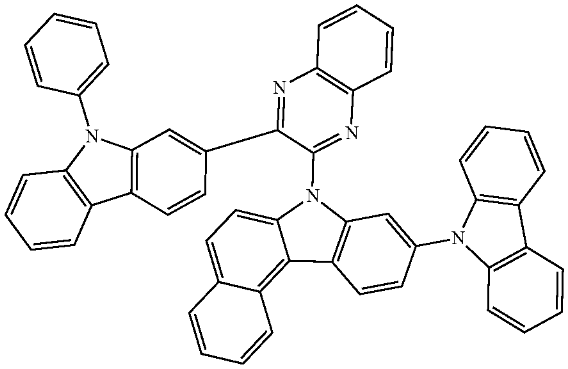
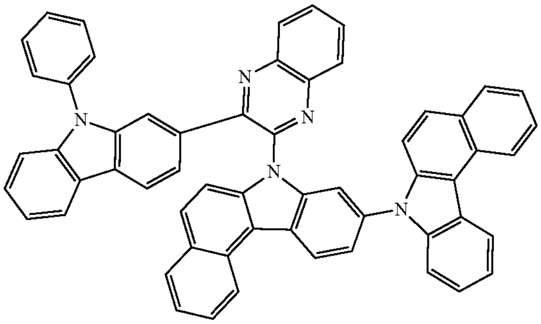

-continued
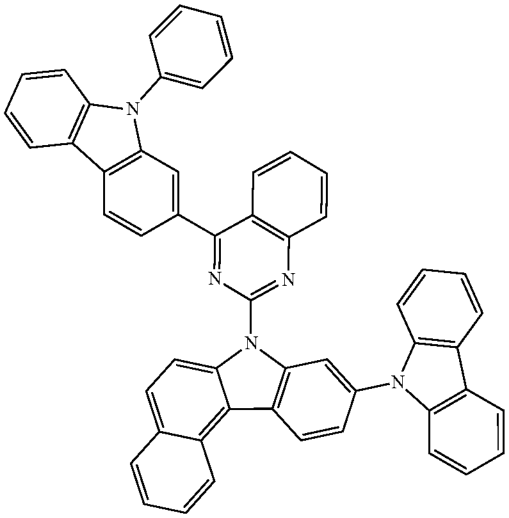
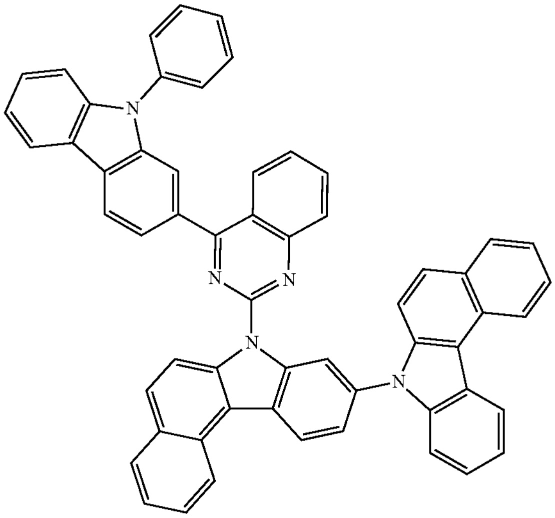
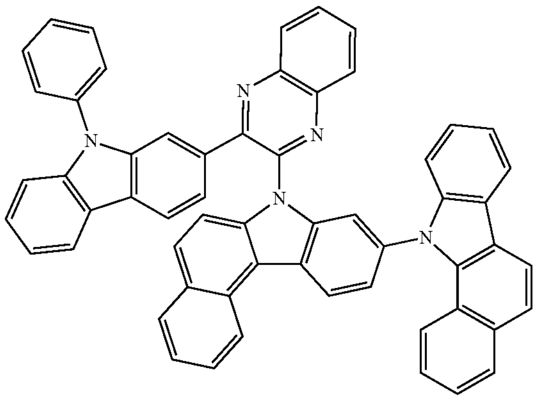
-continued
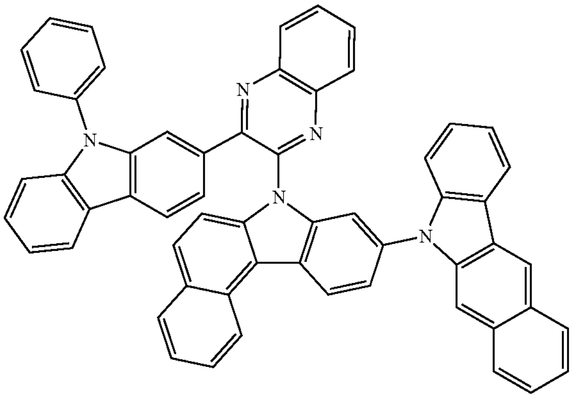
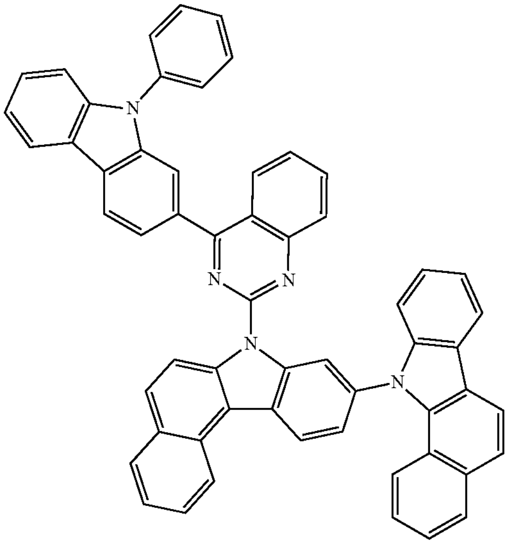
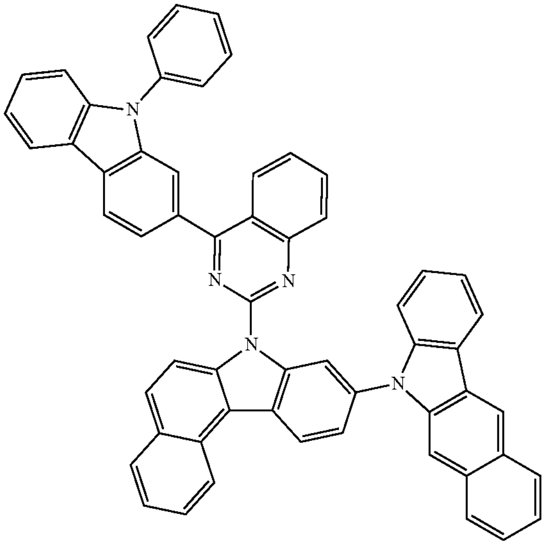

-continued
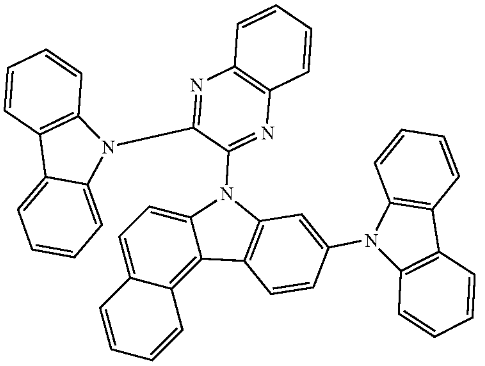
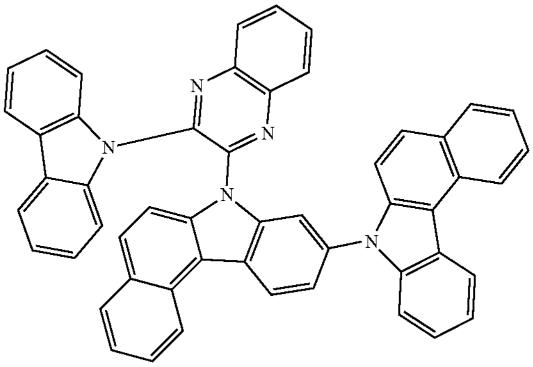
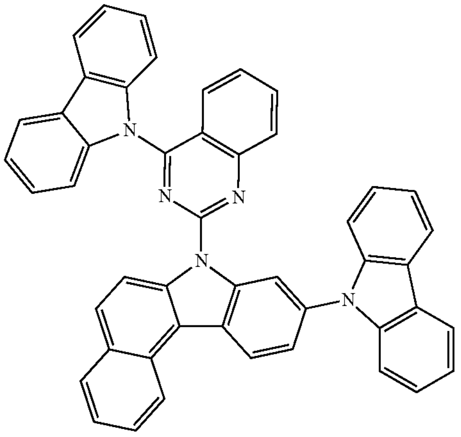
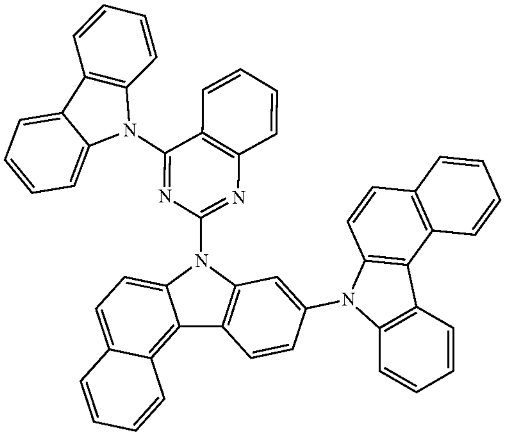
-continued
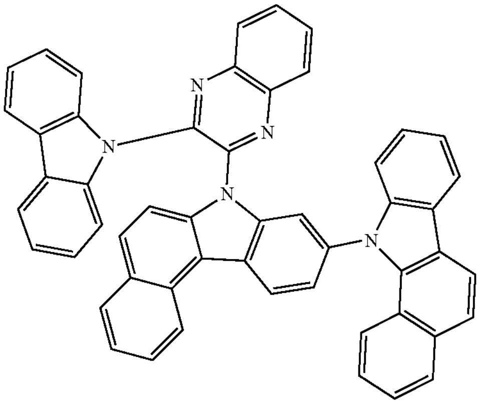
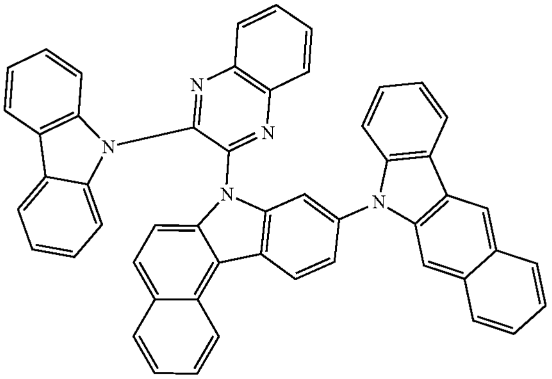
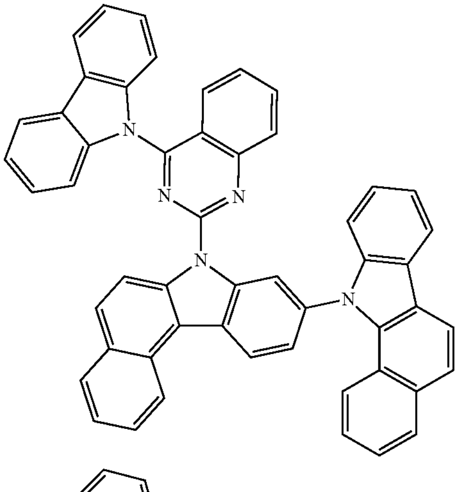
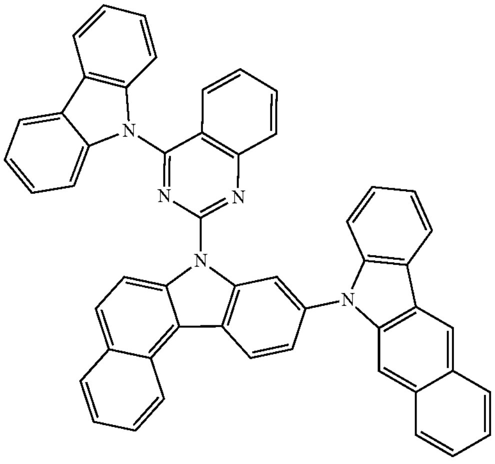

-continued
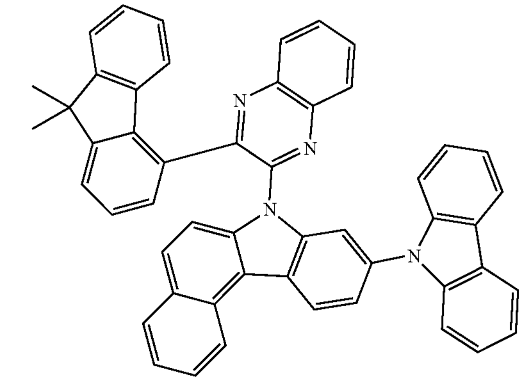
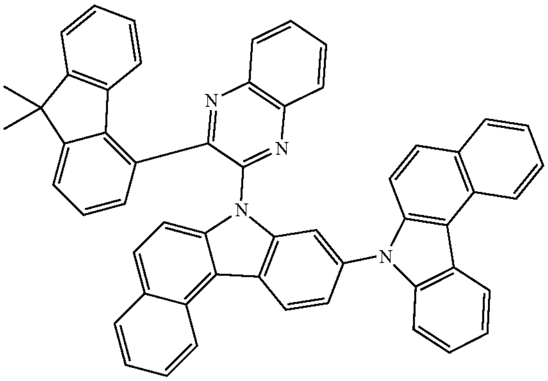
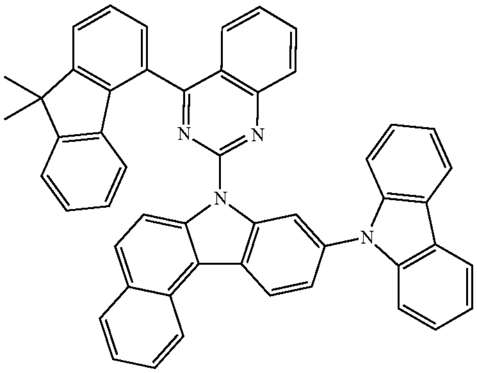
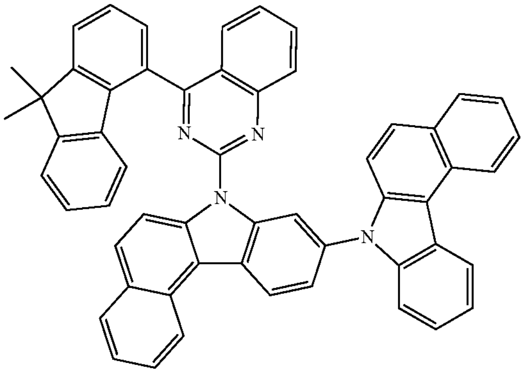
-continued
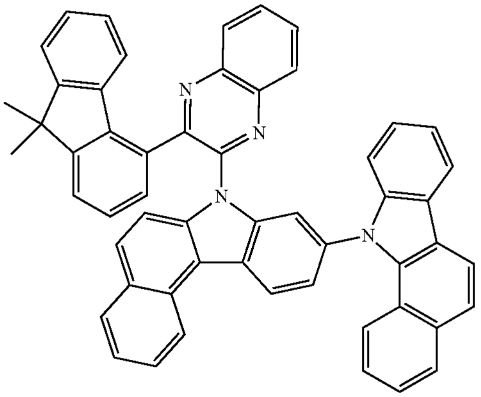
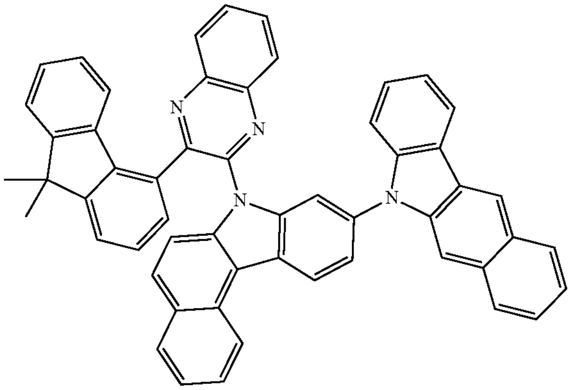
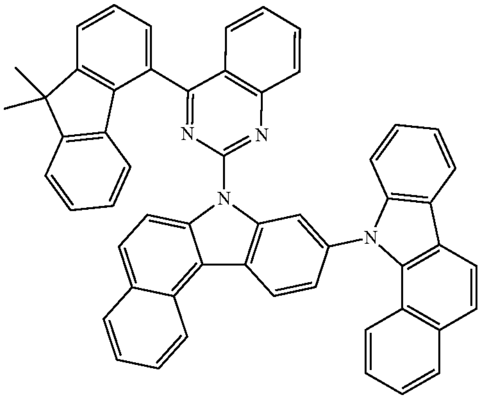
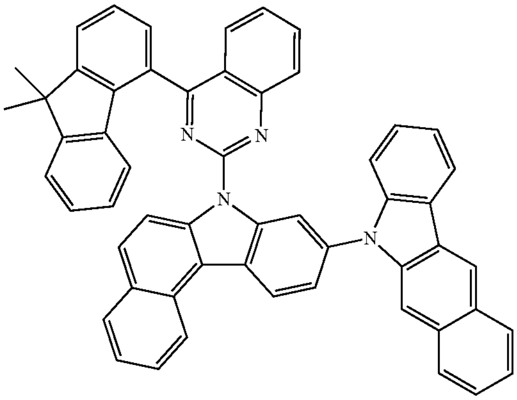

-continued
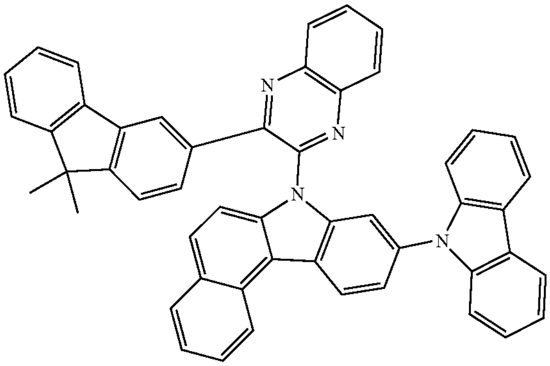
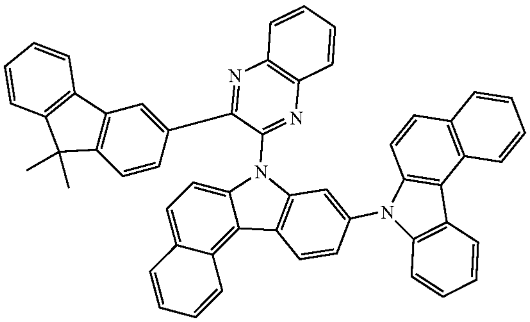
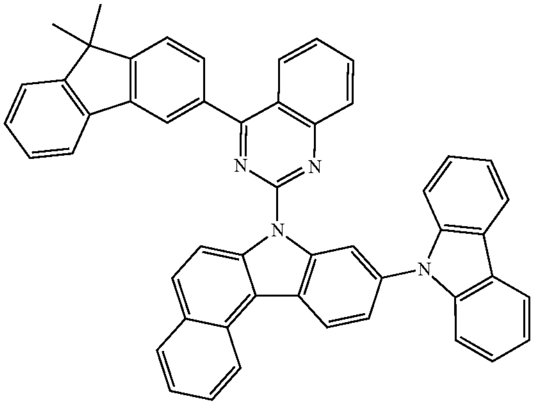
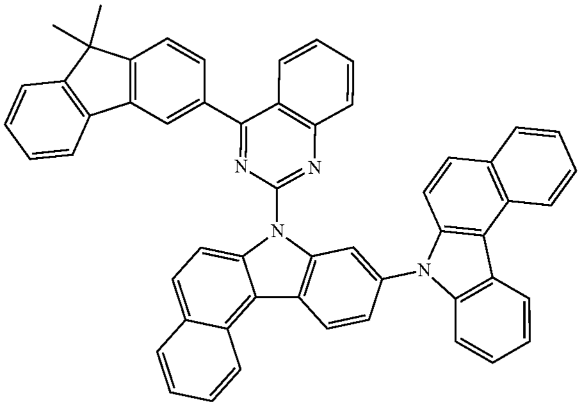
-continued
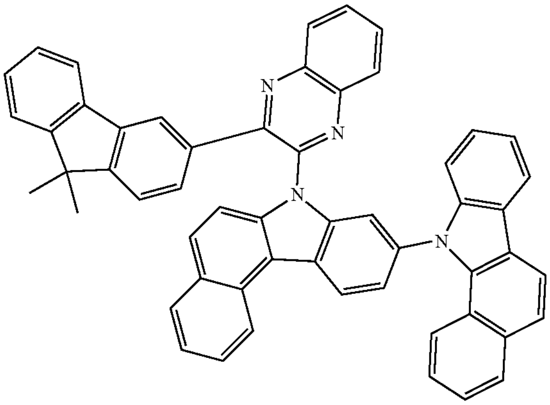
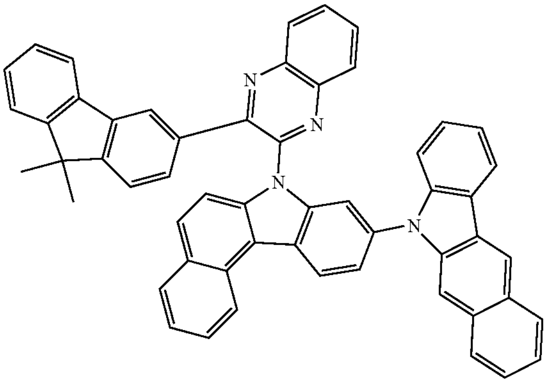
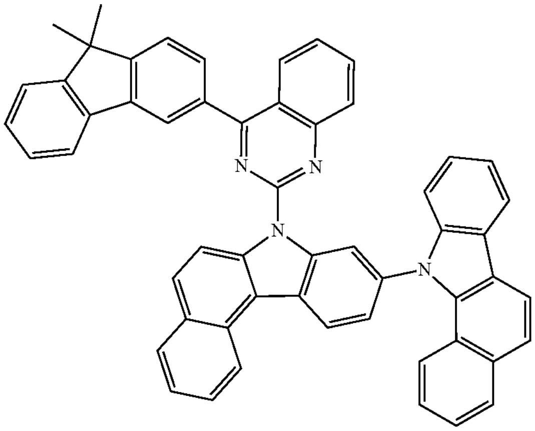
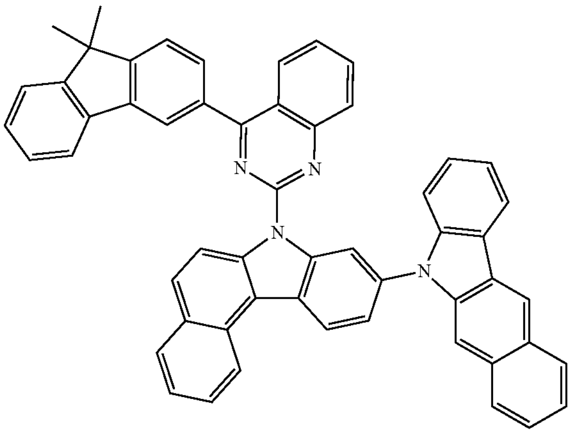

-continued
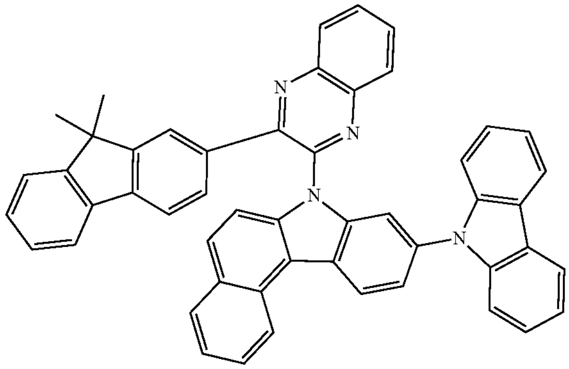
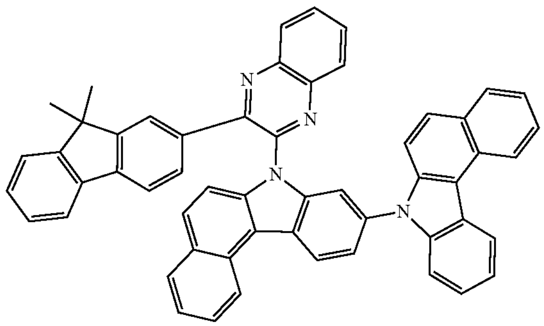
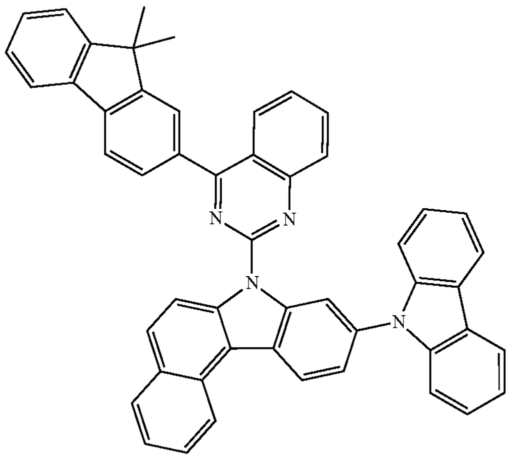
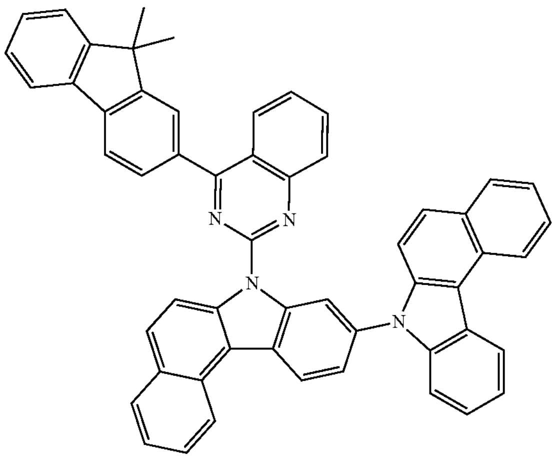
-continued
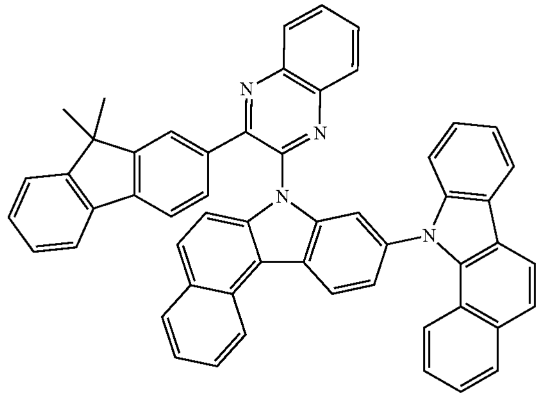
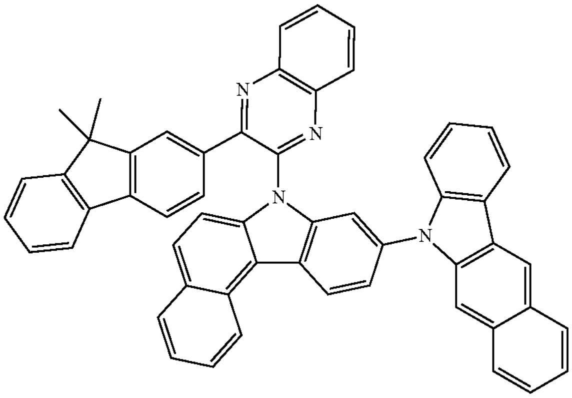
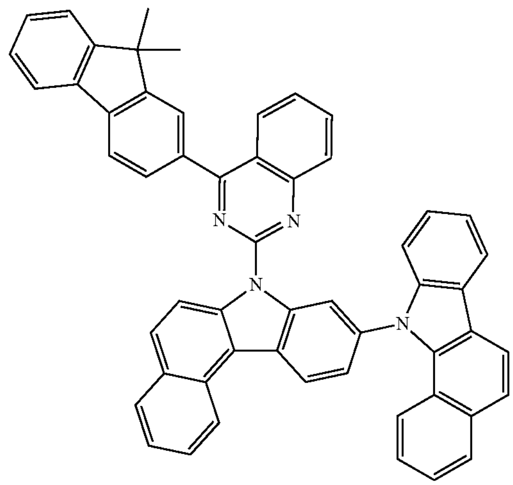

-continued
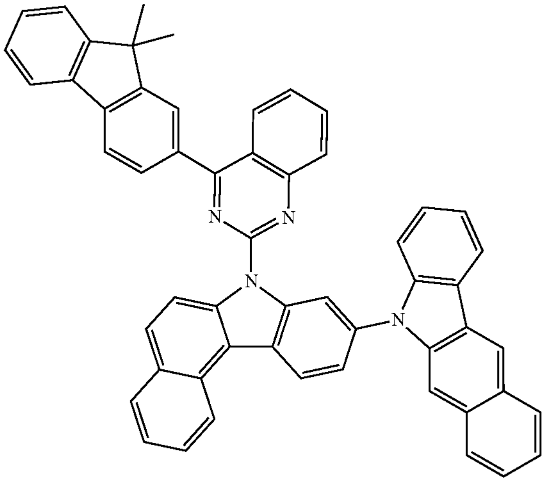
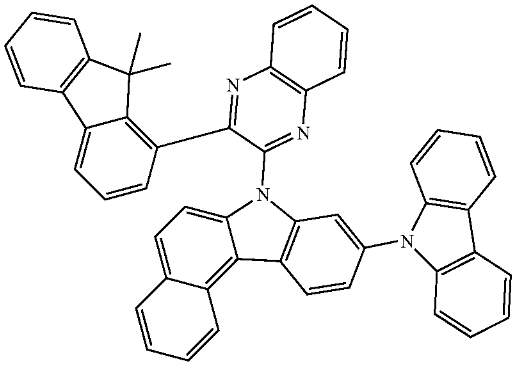
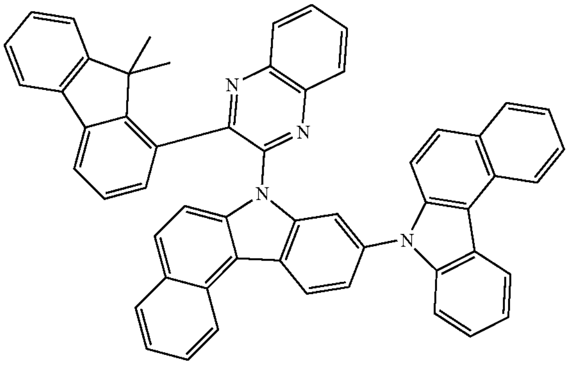
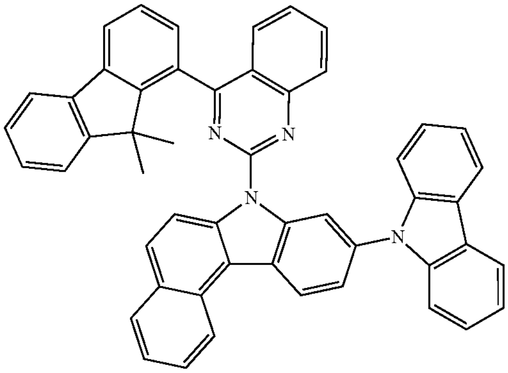
-continued
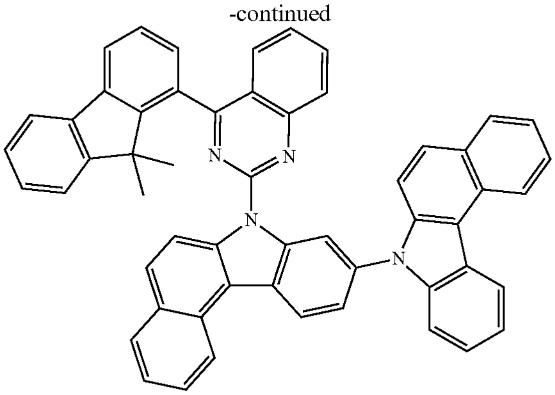
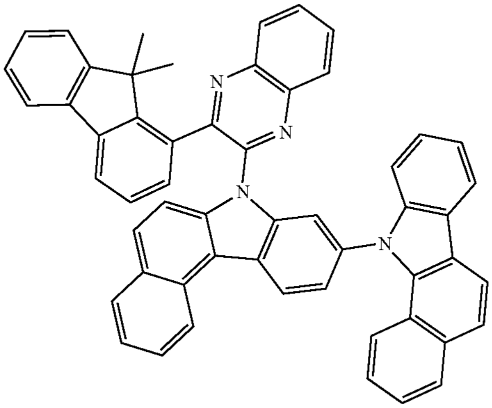
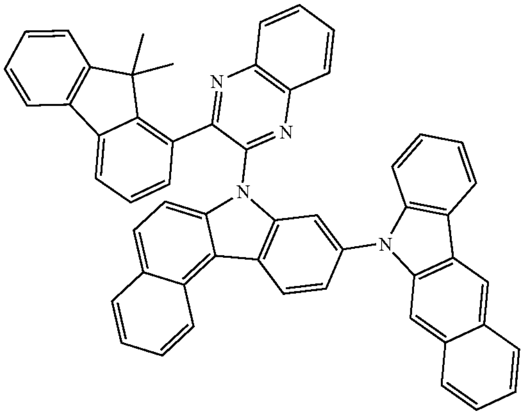
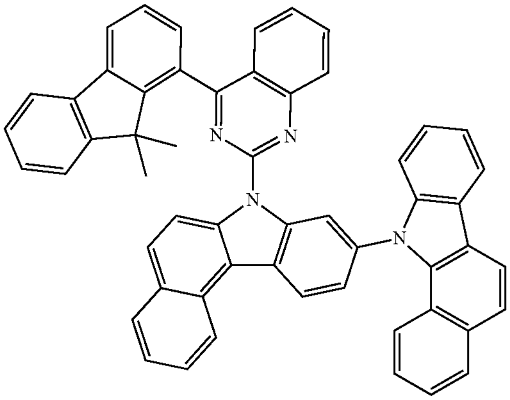

-continued
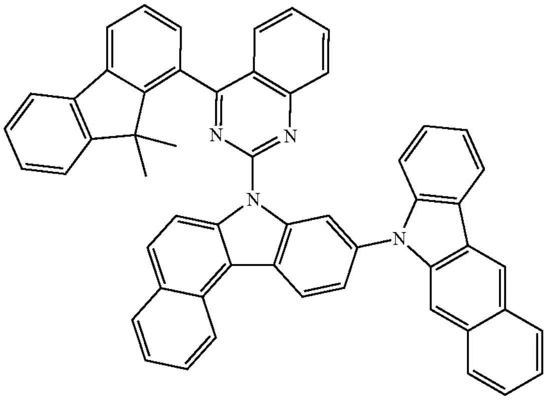
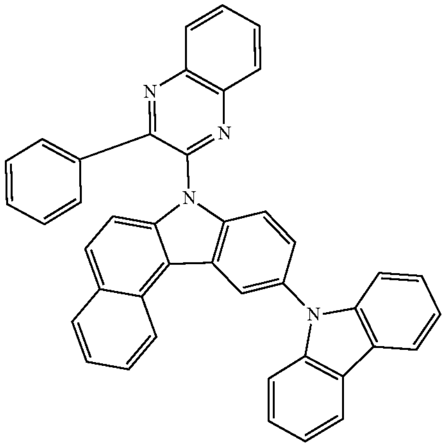
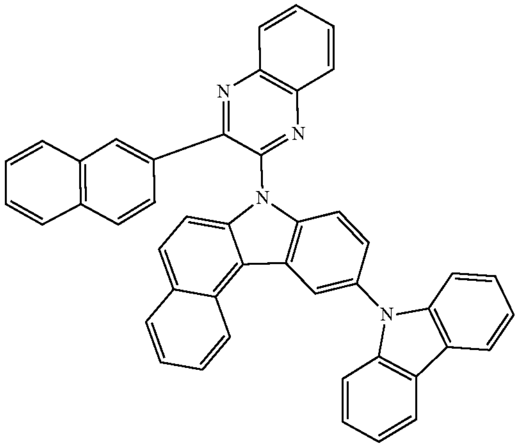
-continued
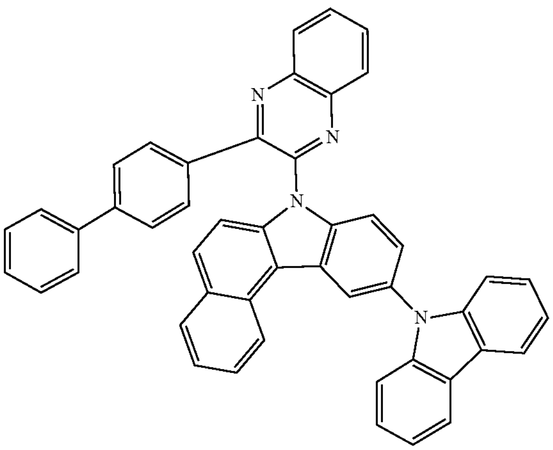
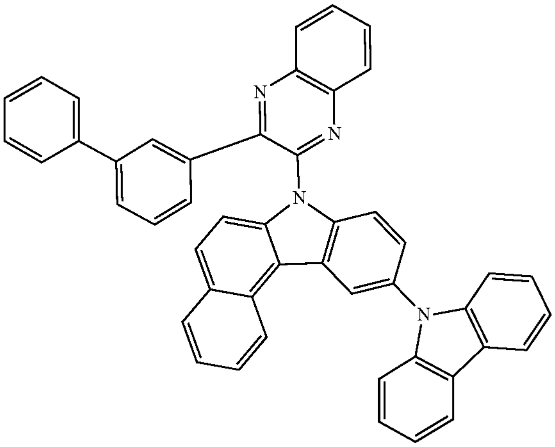
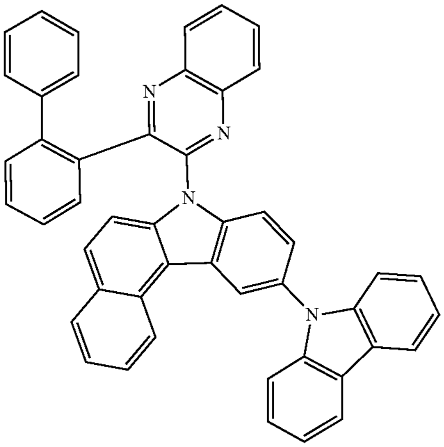

-continued
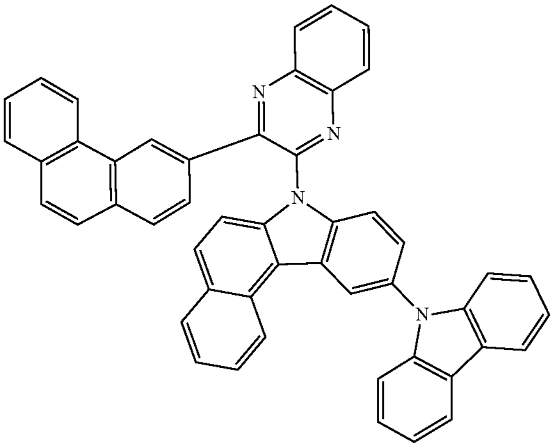
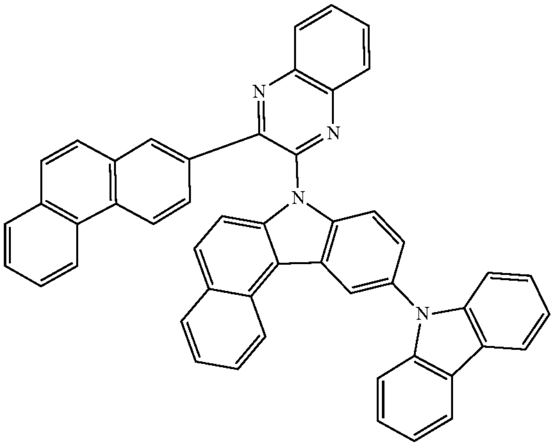
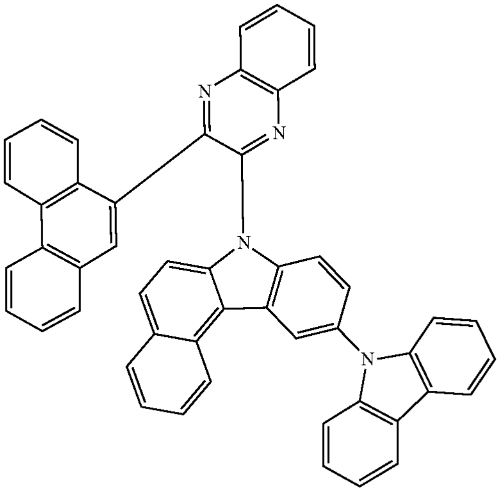
-continued
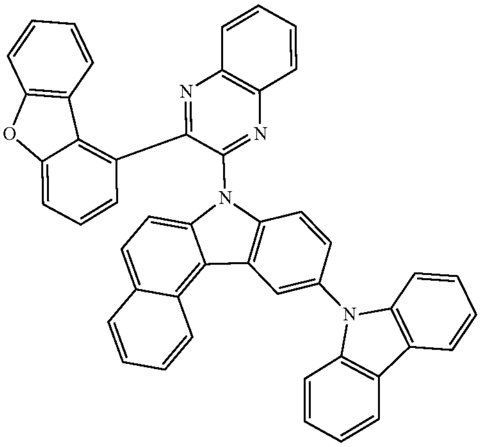
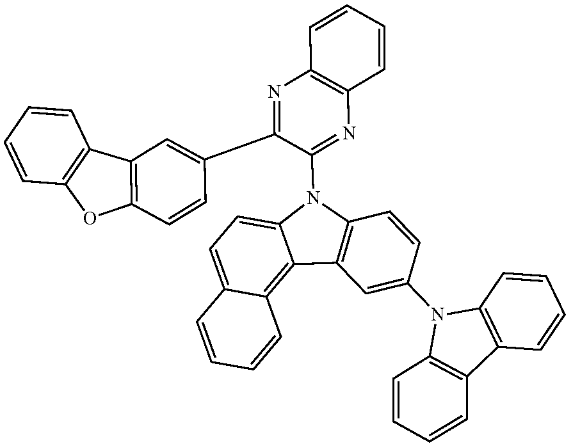
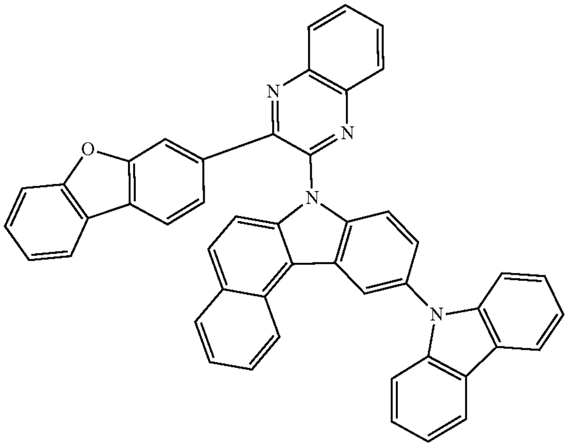

-continued
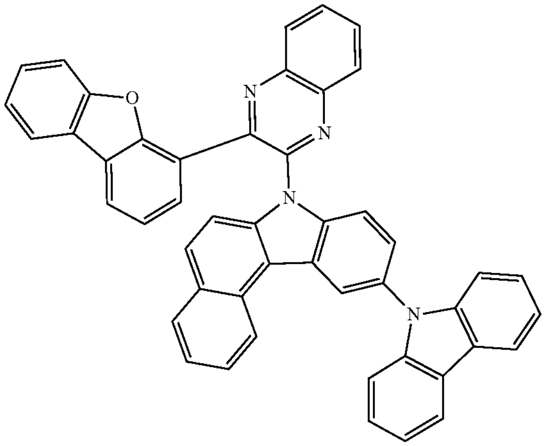
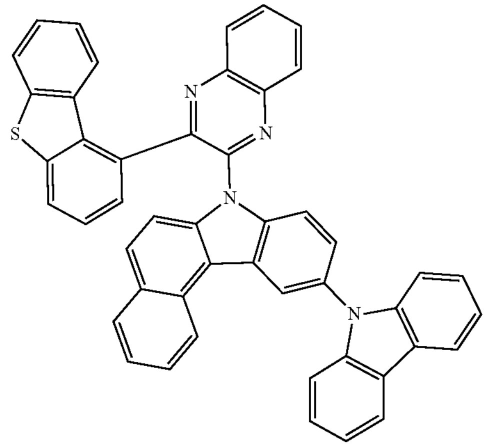
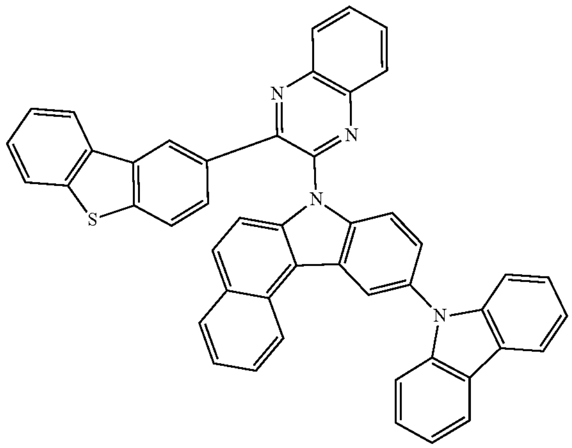
-continued
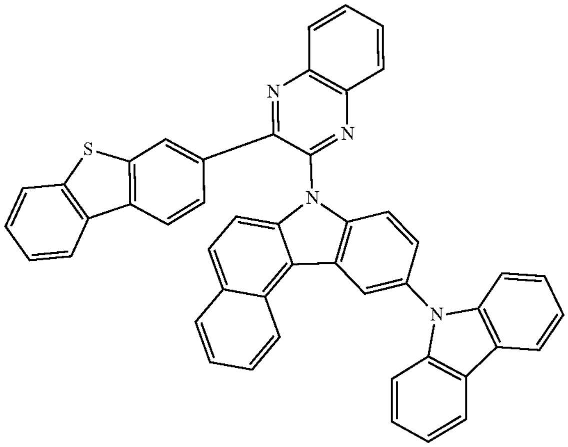
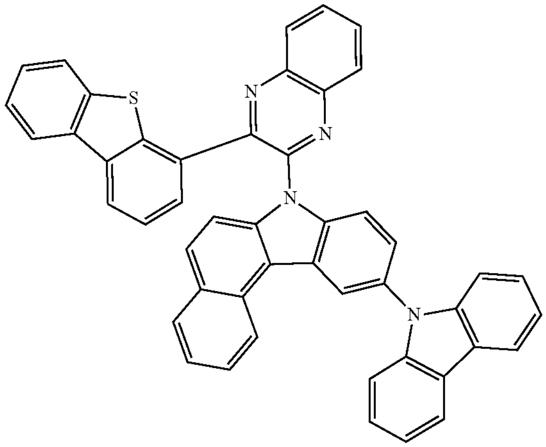
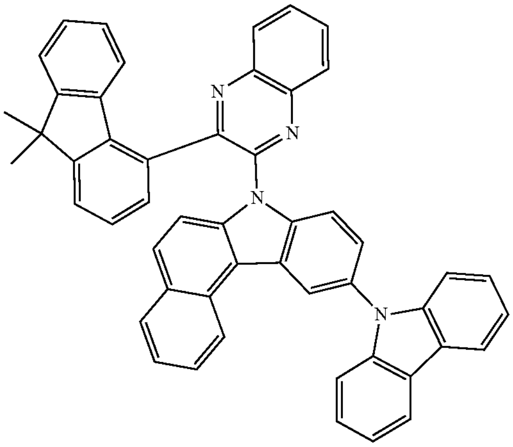

-continued
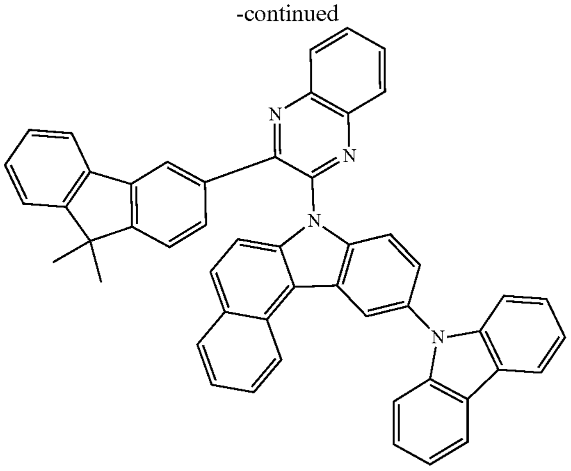
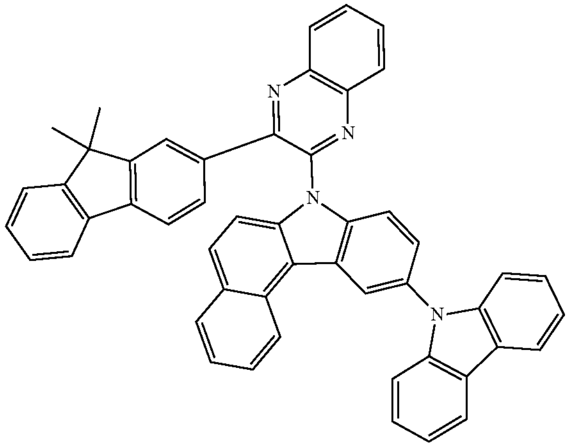
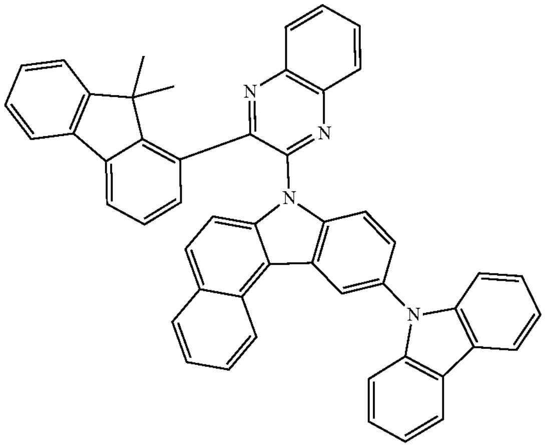
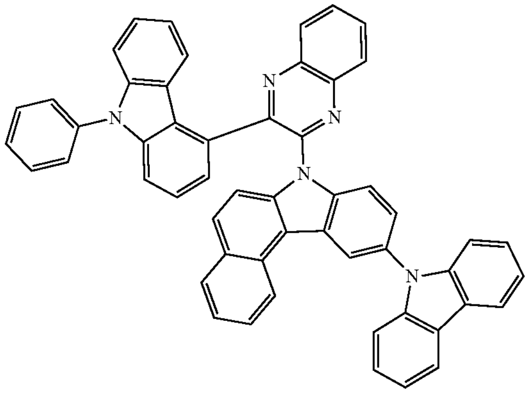
-continued
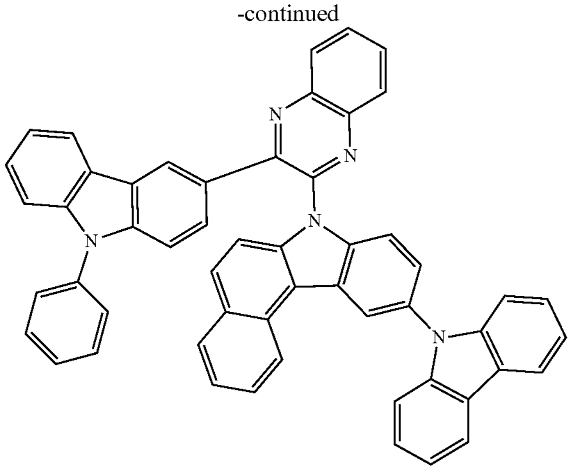
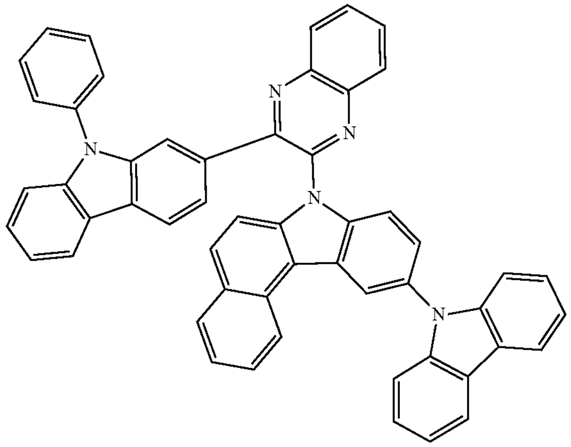
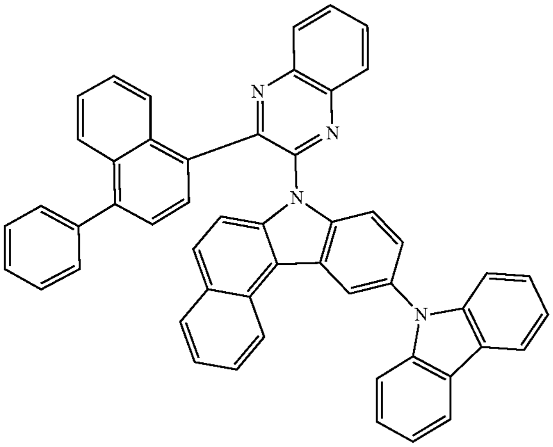
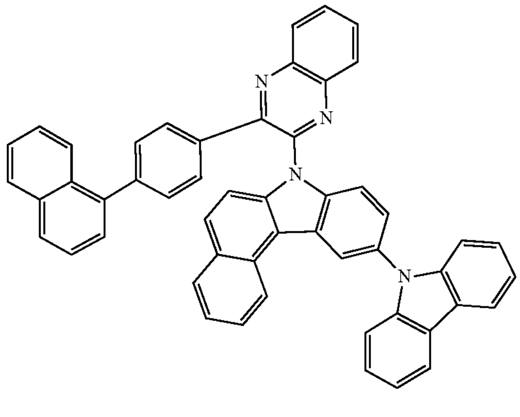

-continued
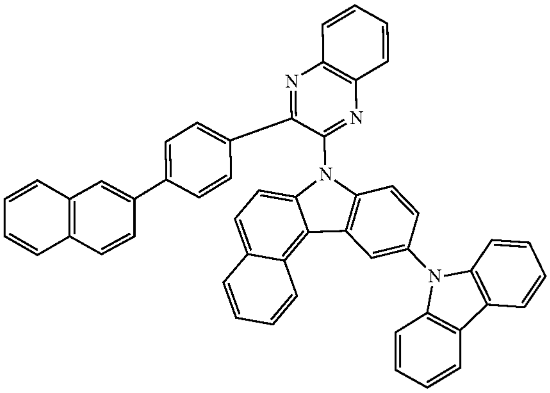
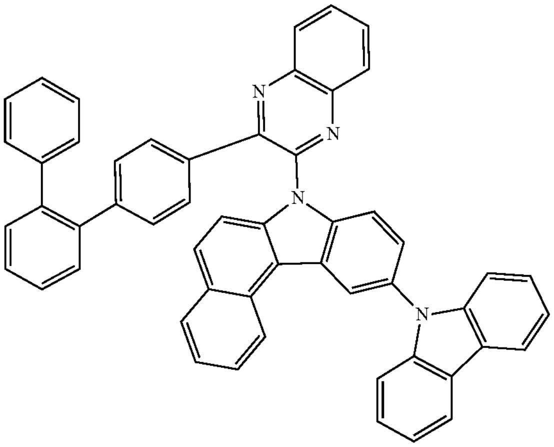
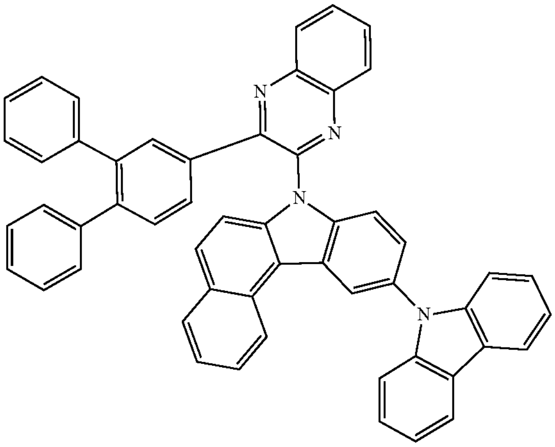
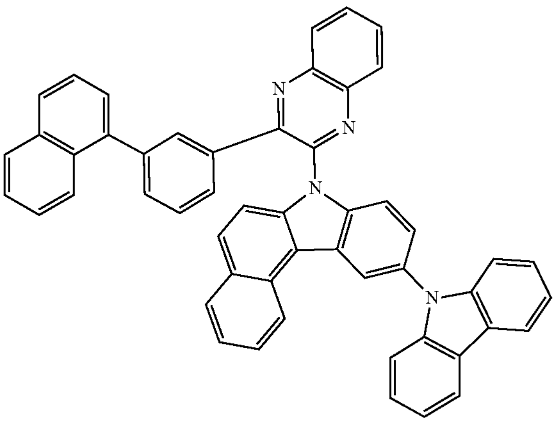
-continued
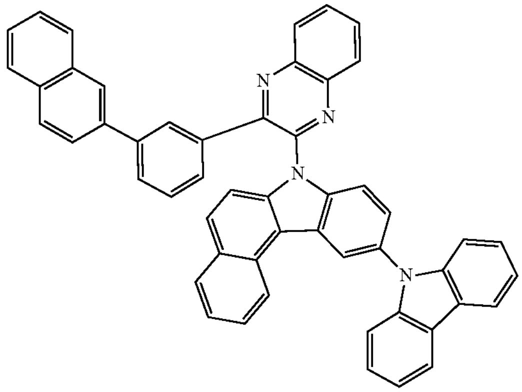
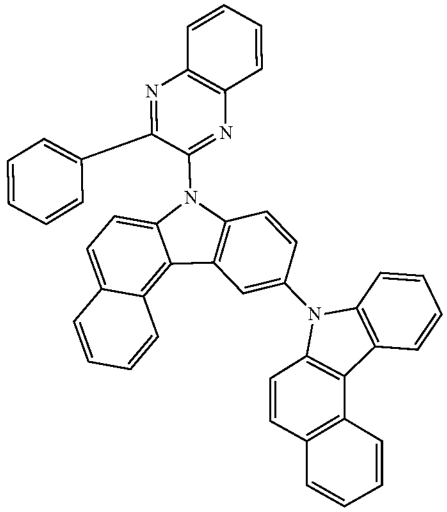
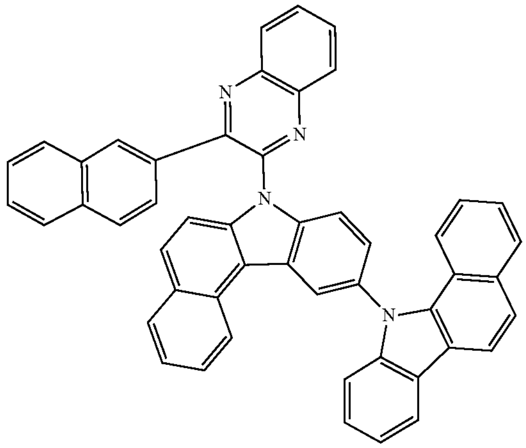

-continued
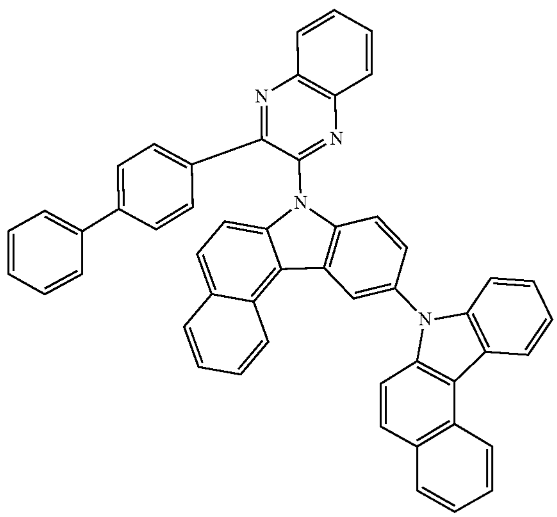
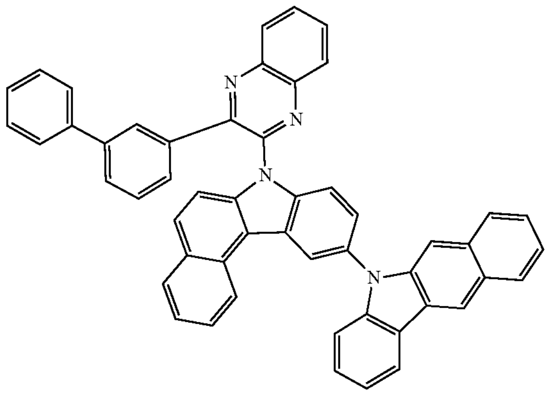
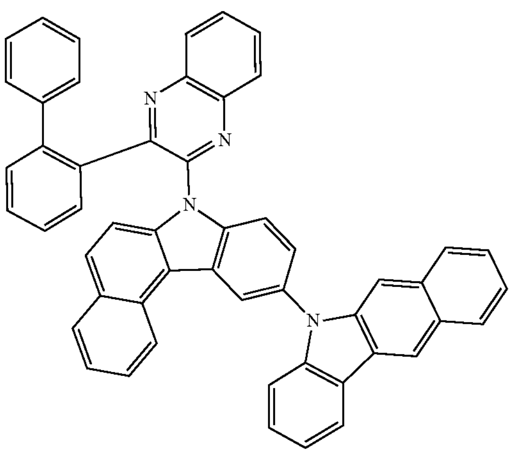
-continued
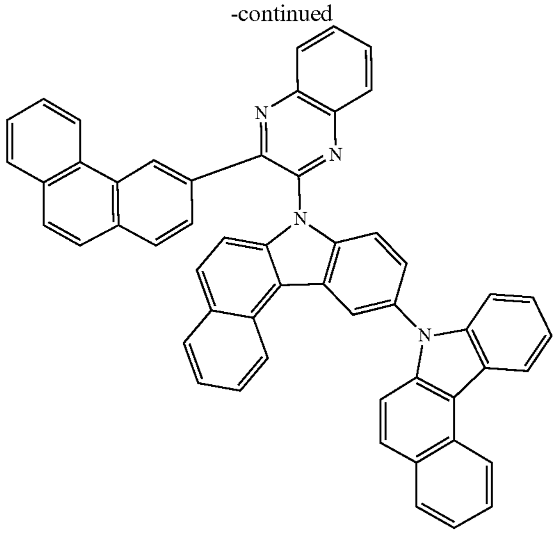
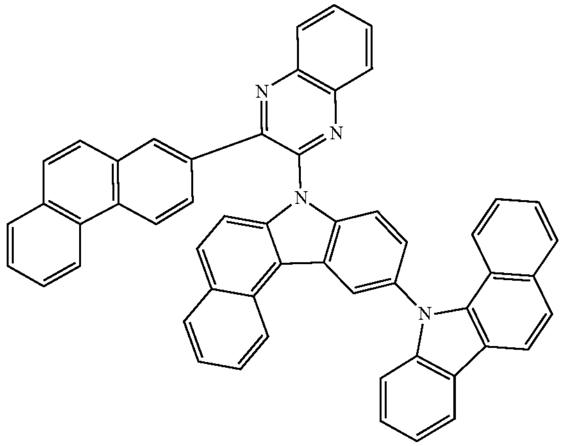
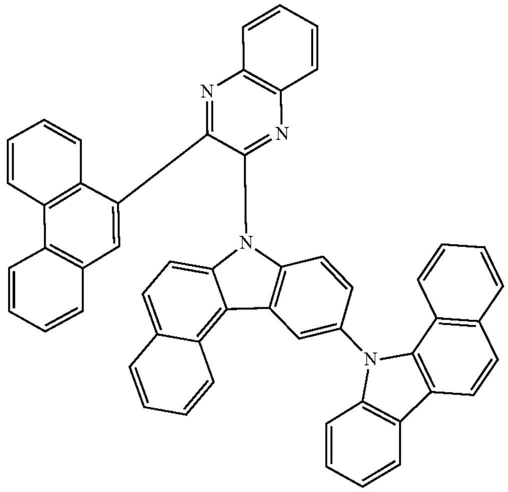

-continued
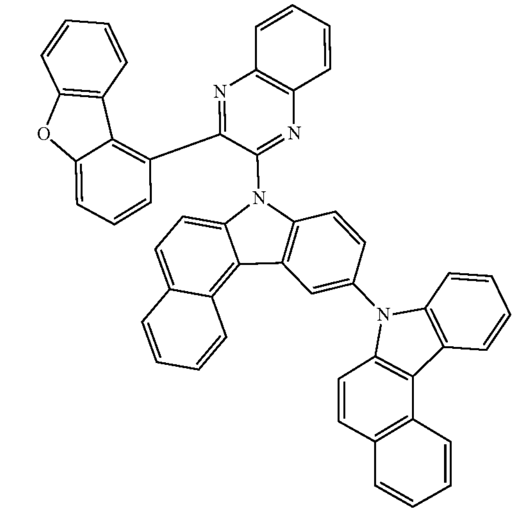
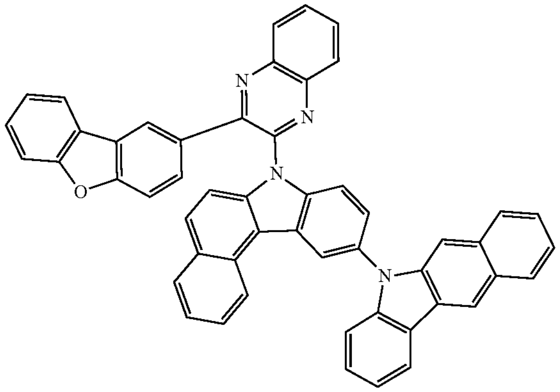
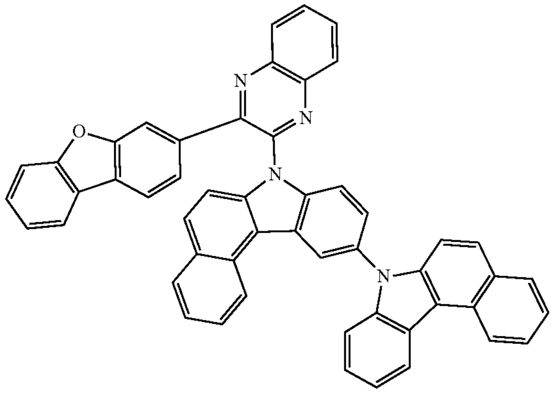
-continued
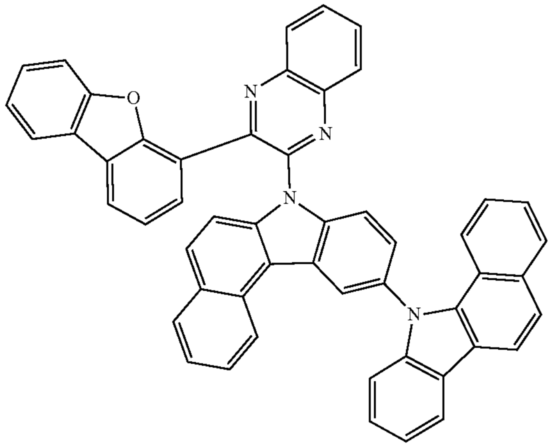
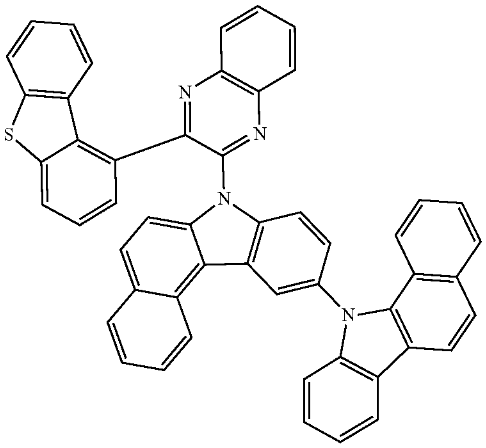
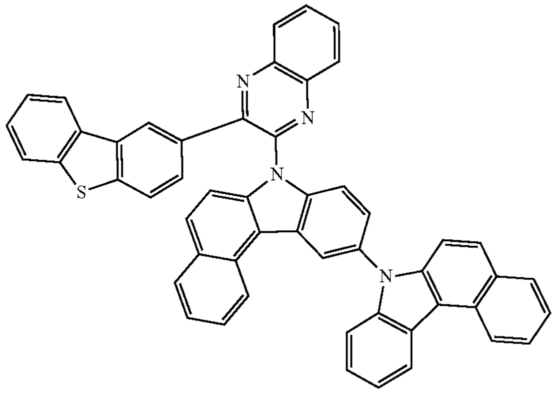
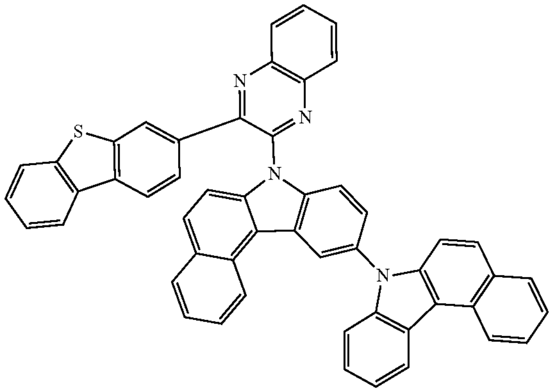

-continued
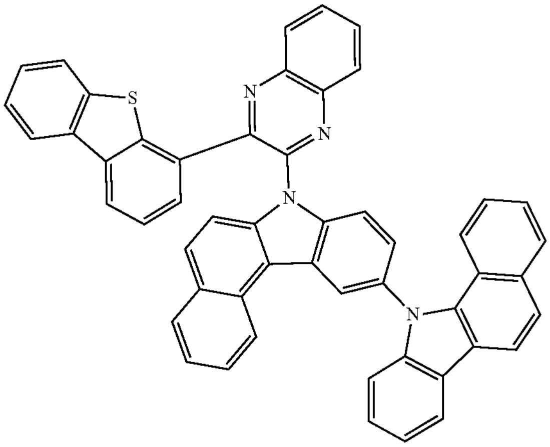
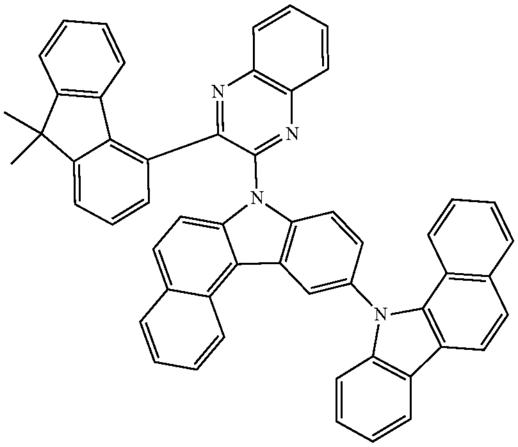
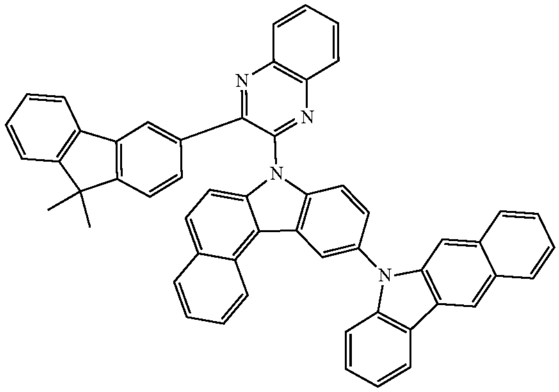
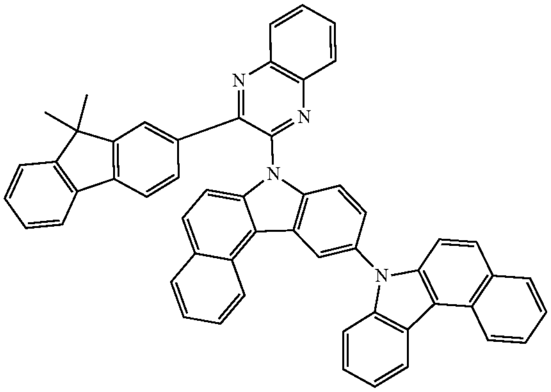
-continued
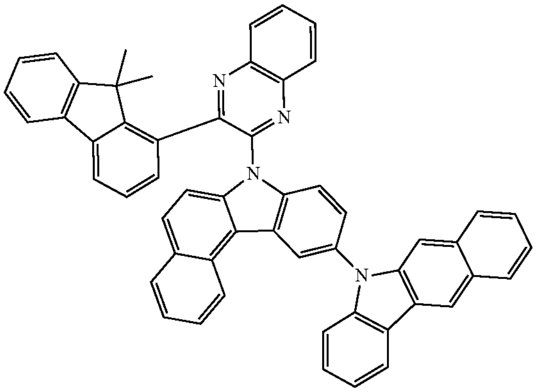
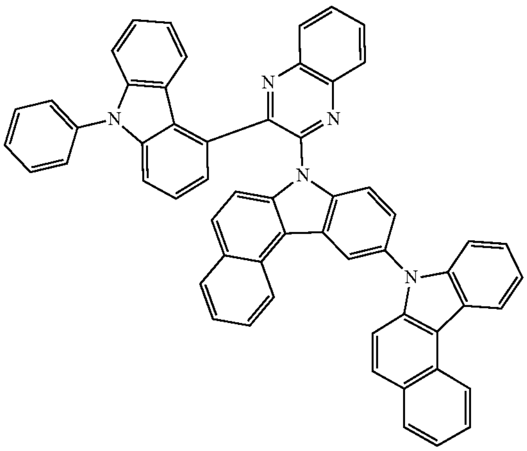
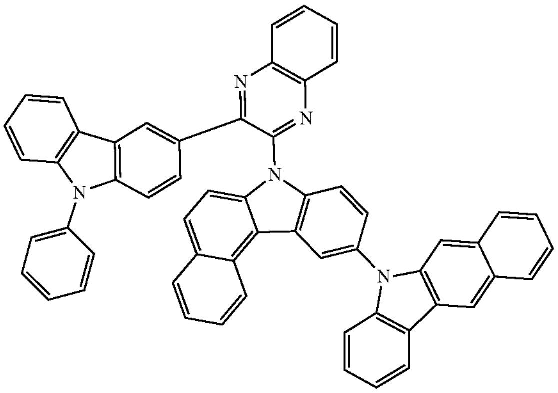

-continued
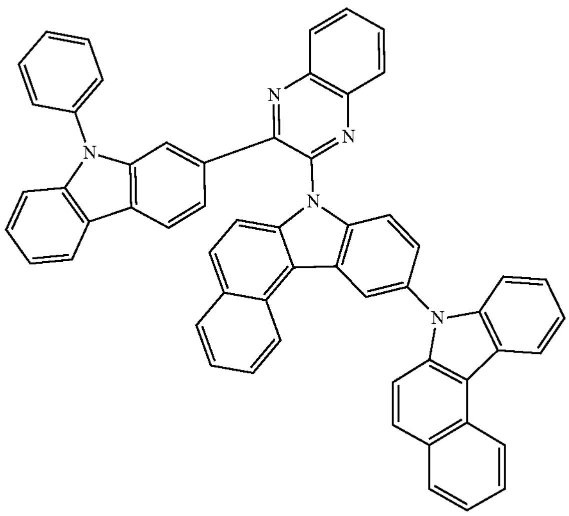
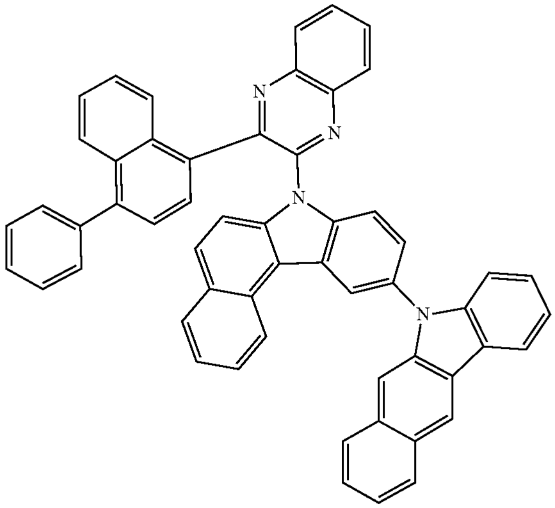
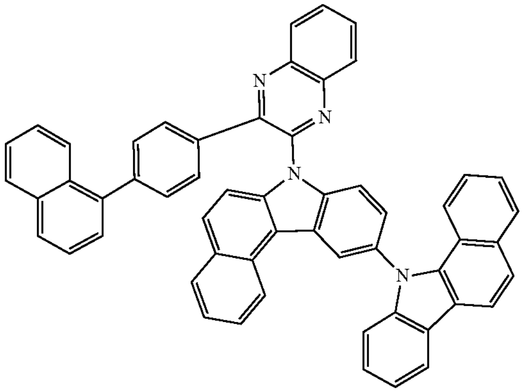
-continued
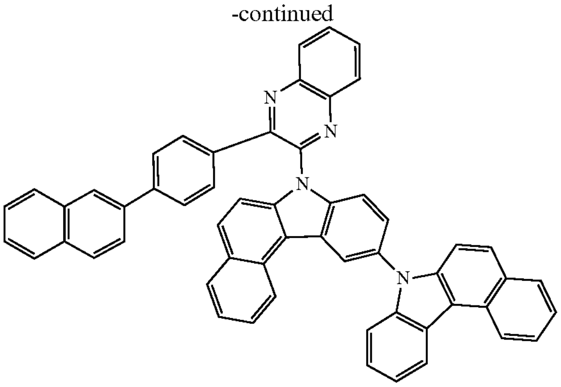
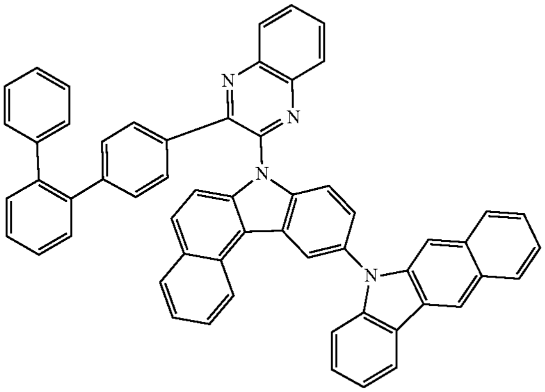
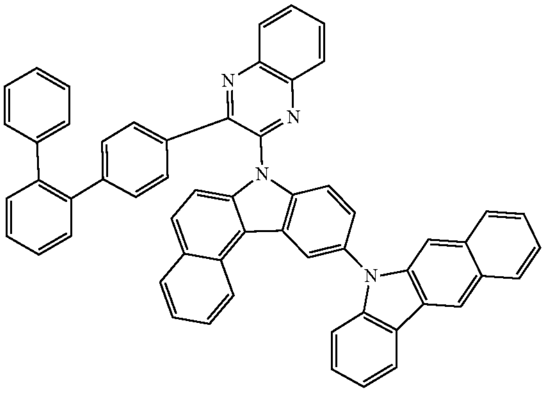
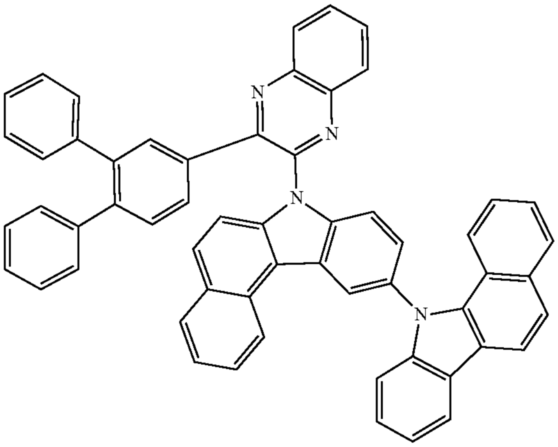

-continued
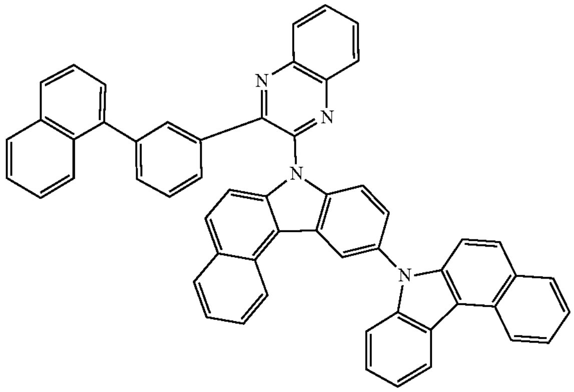
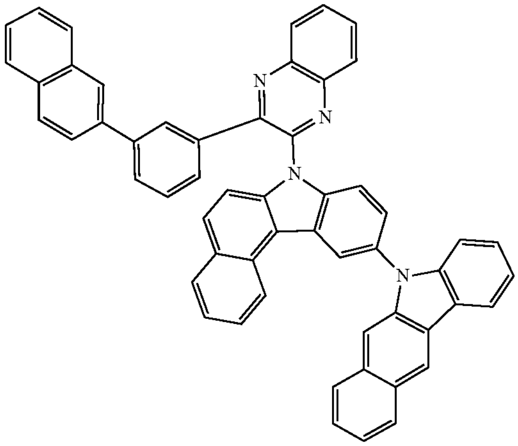
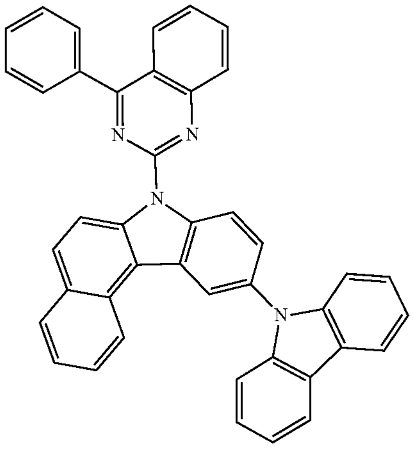
-continued
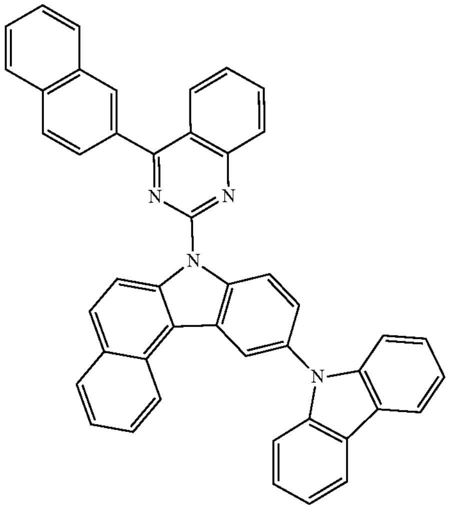
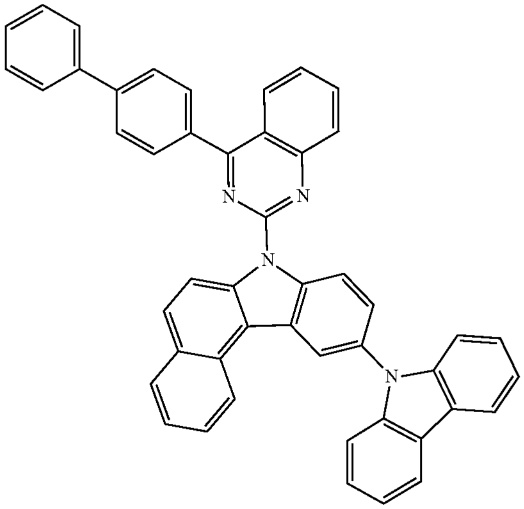
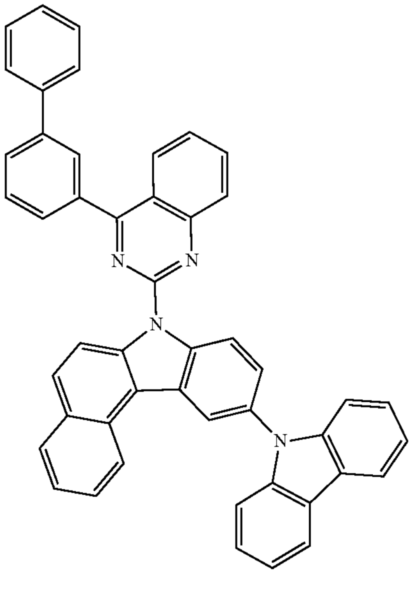

-continued
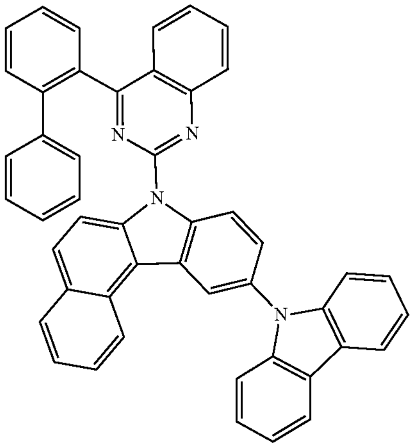
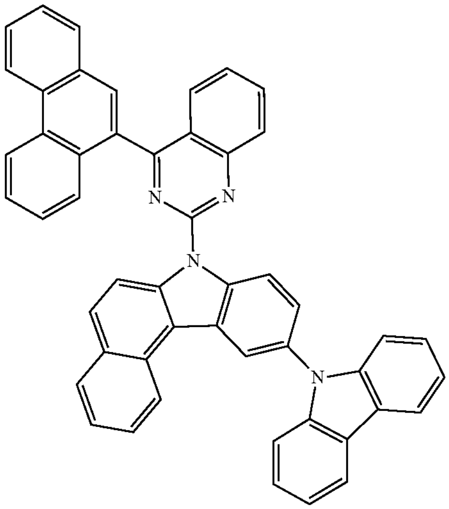
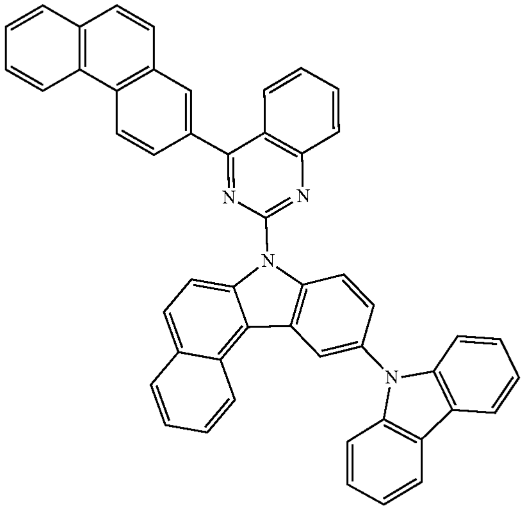
-continued
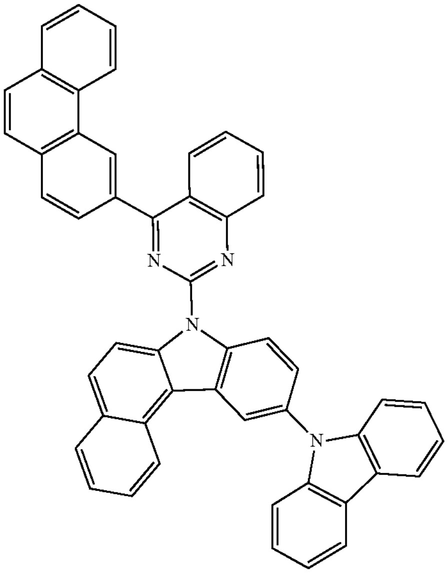
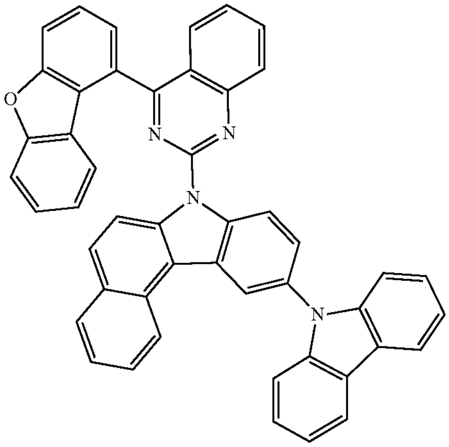
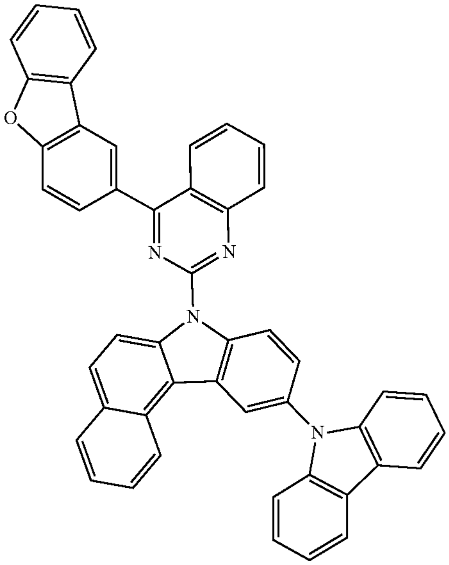

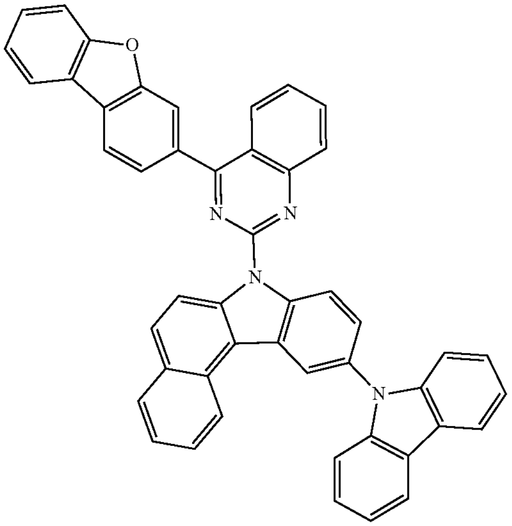
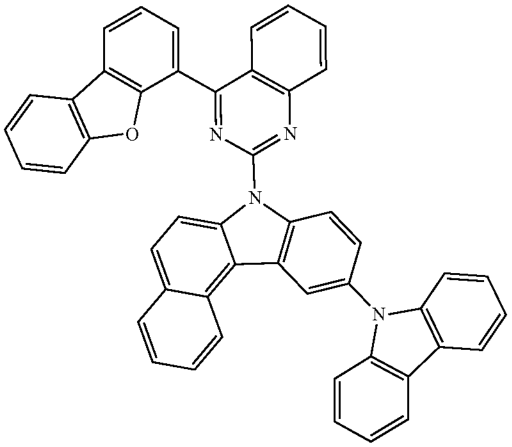
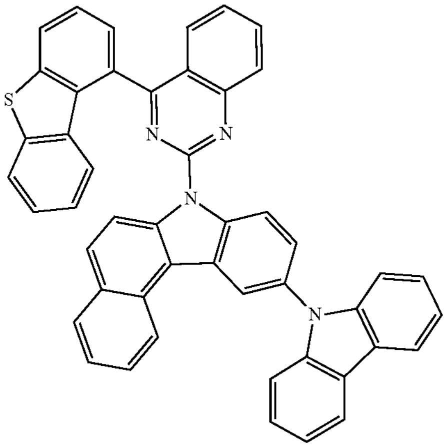
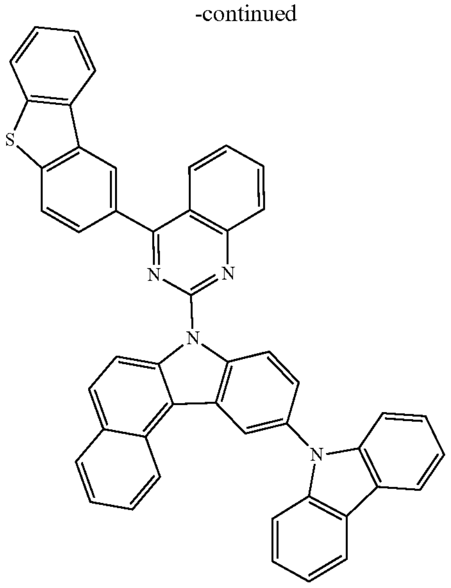
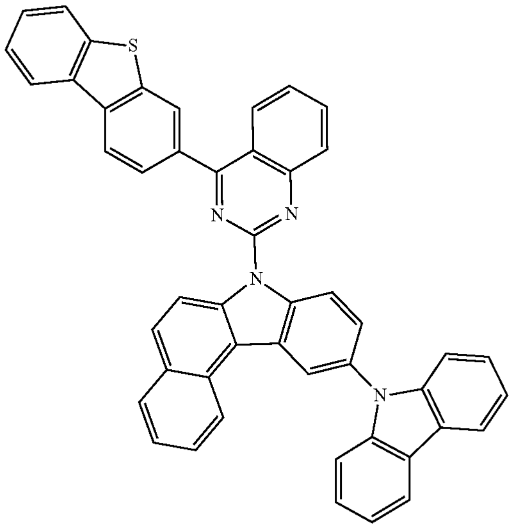
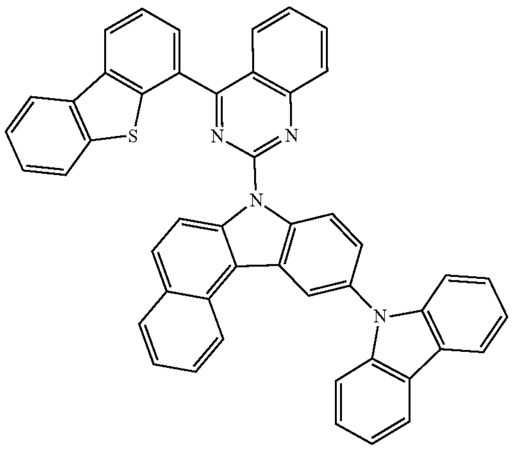 [SMILES: c1ccc2c(c1)ccc1c2c2cc(-n3c4ccccc4c4ccccc43)ccc2n1-c1nc(-c2cccc3c2oc2ccccc23)c2ccccc2n1]

-continued
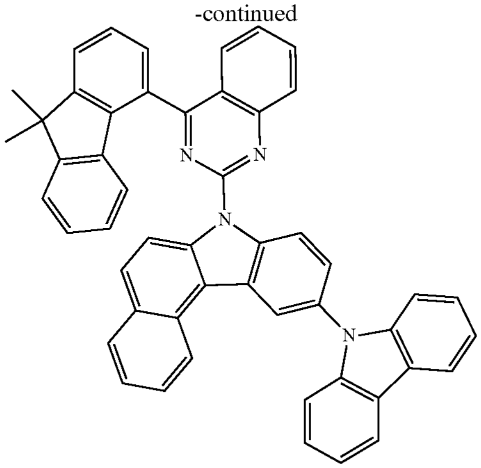
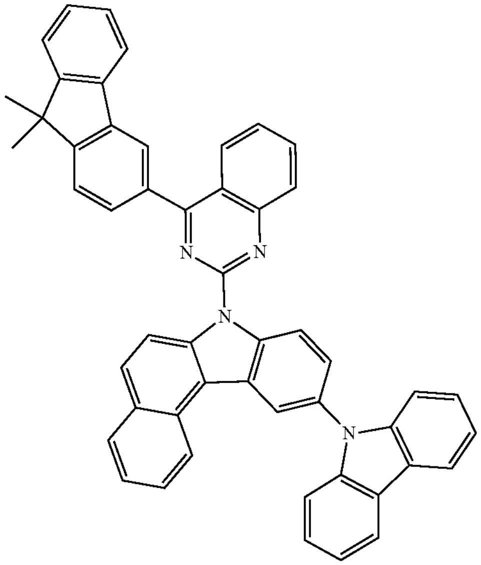
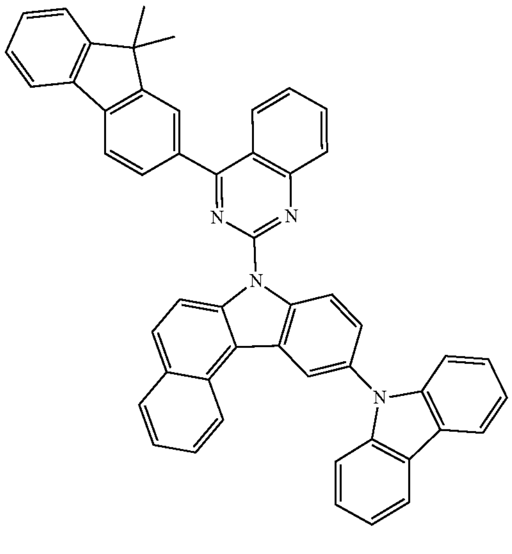
-continued
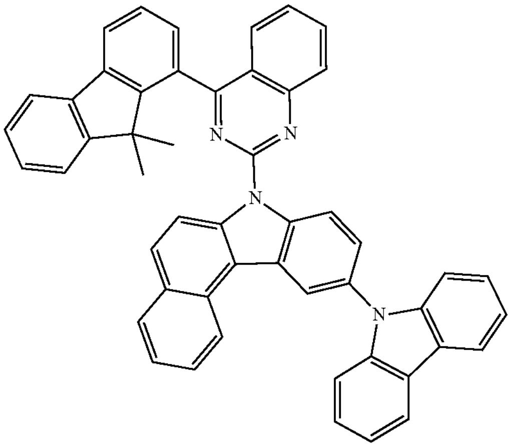 [SMILES: CC1(C)c2ccccc2-c2cccc(-c3nc(-n4c5ccc(-n6c7ccccc7c7ccccc76)cc5c5c6ccccc6ccc54)nc4ccccc34)c21]
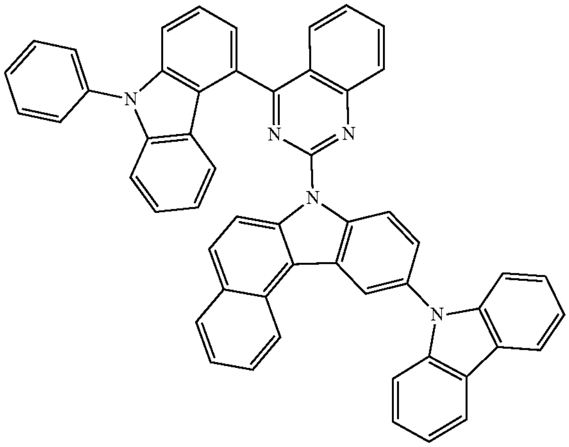
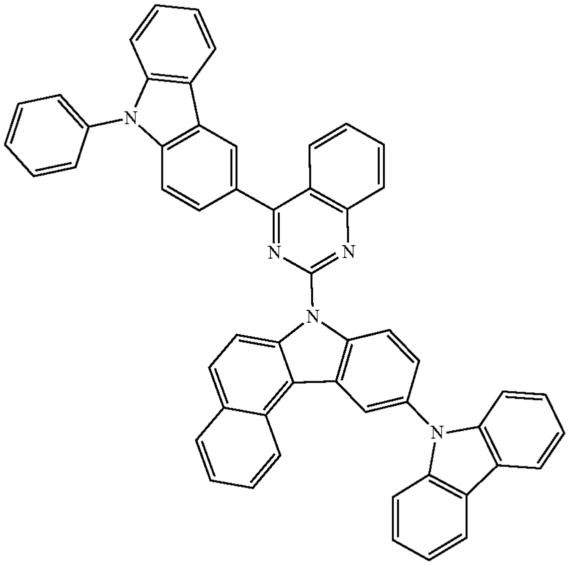

-continued
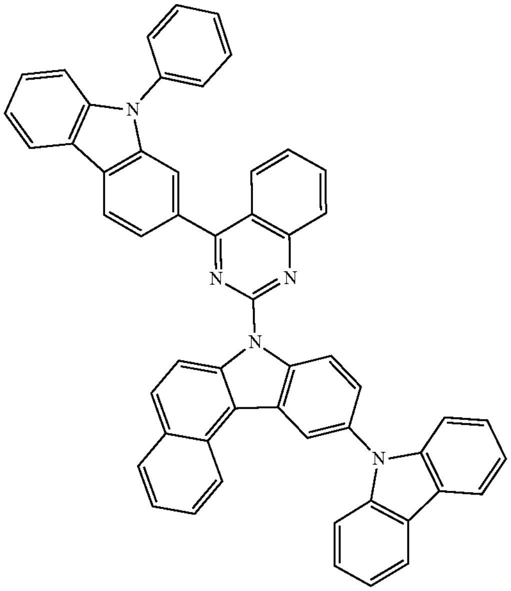
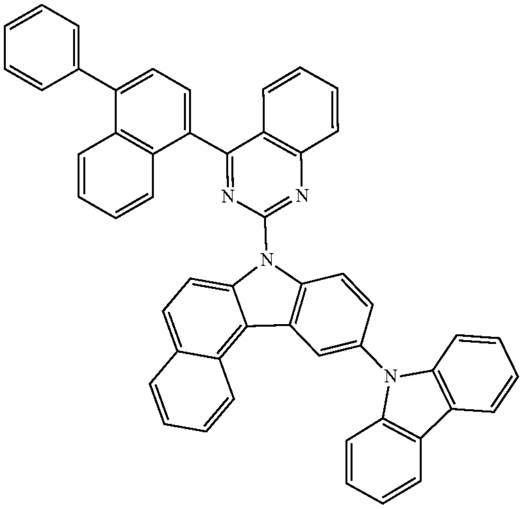
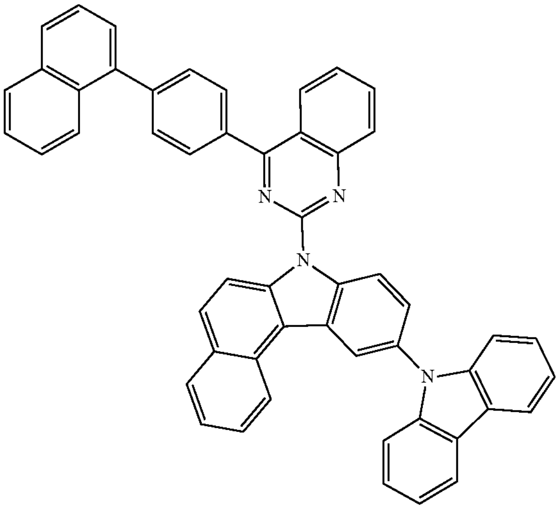
-continued
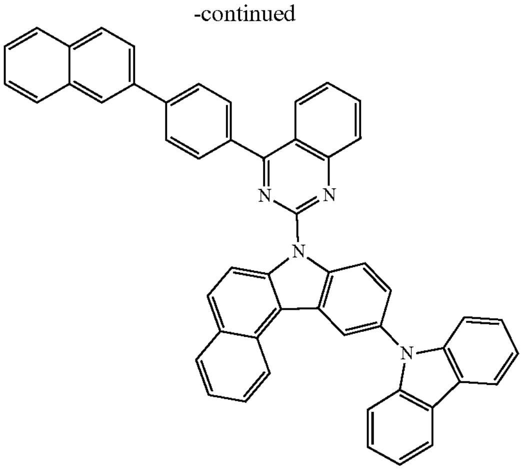
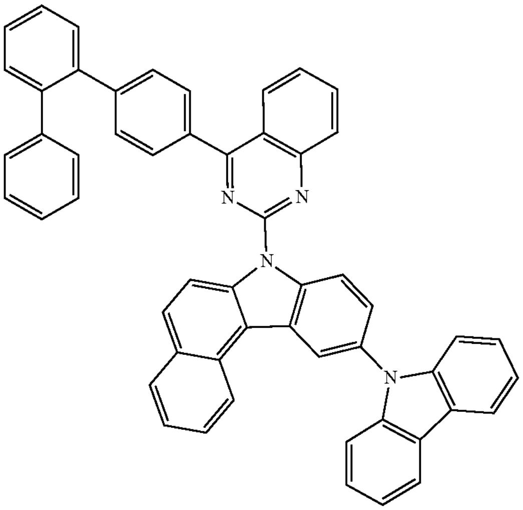
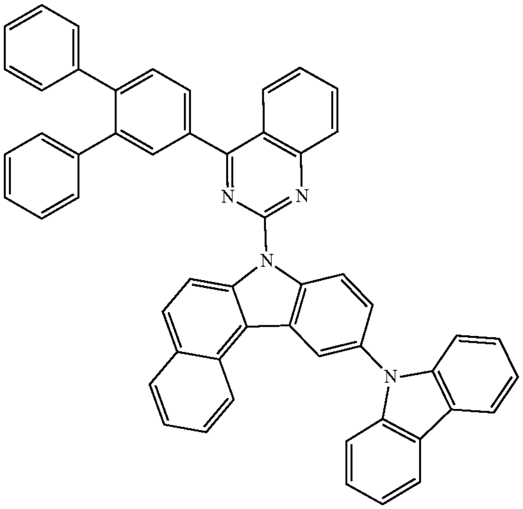

-continued
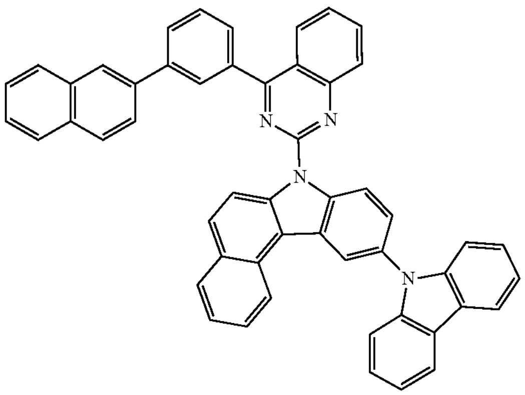
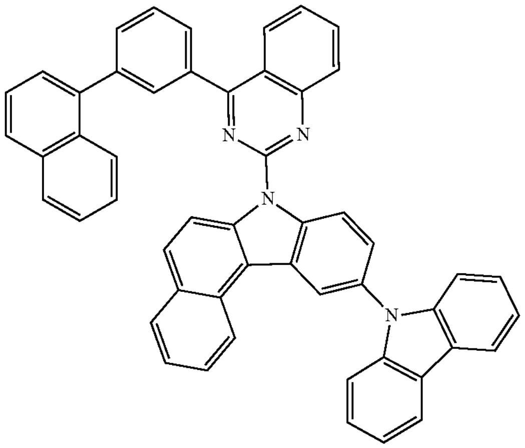 [SMILES: c1cc(-c2cccc3ccccc23)cc(-c2nc(-n3c4ccc(-n5c6ccccc6c6ccccc65)cc4c4c5ccccc5ccc43)nc3ccccc23)c1]
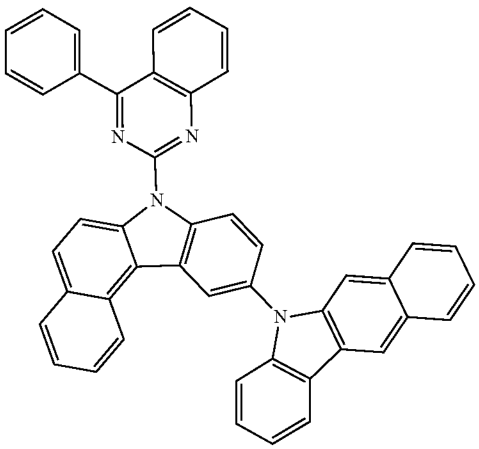
-continued
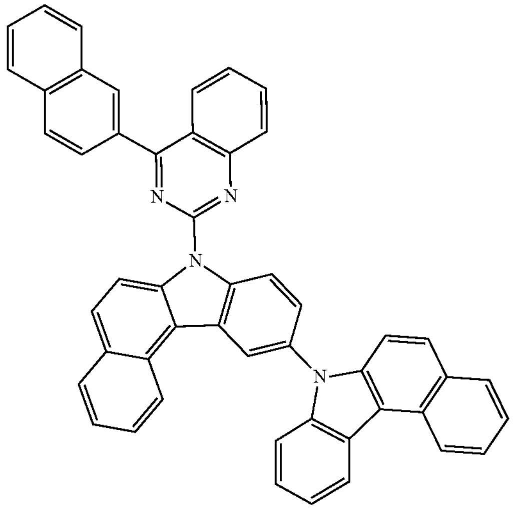
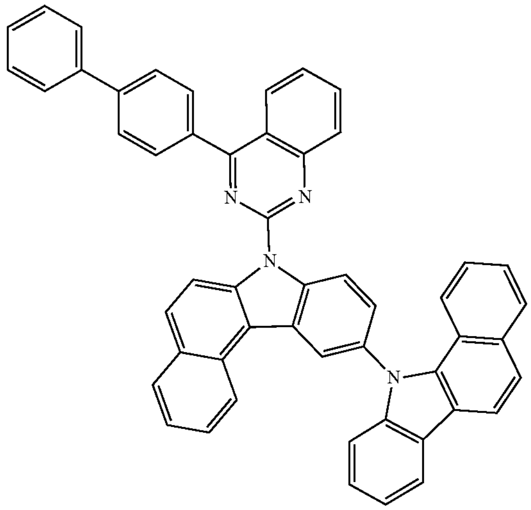
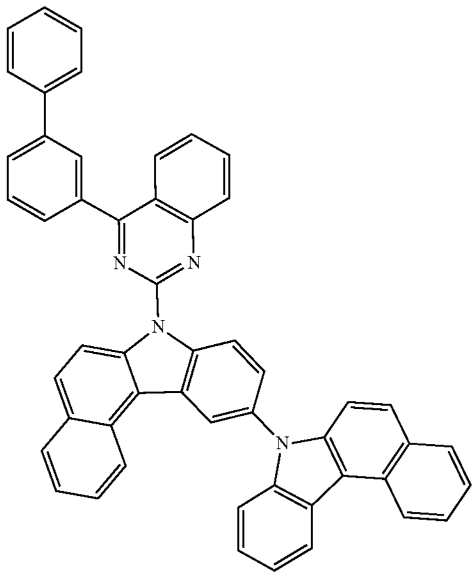

-continued
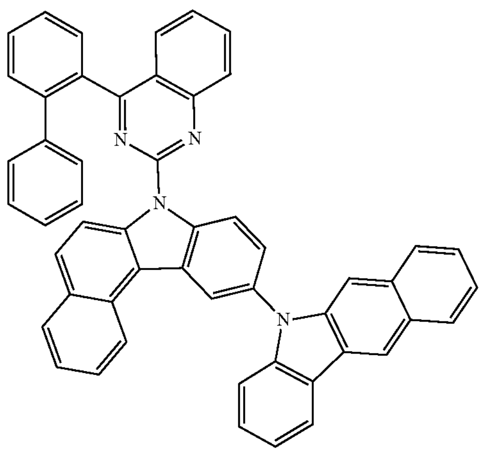
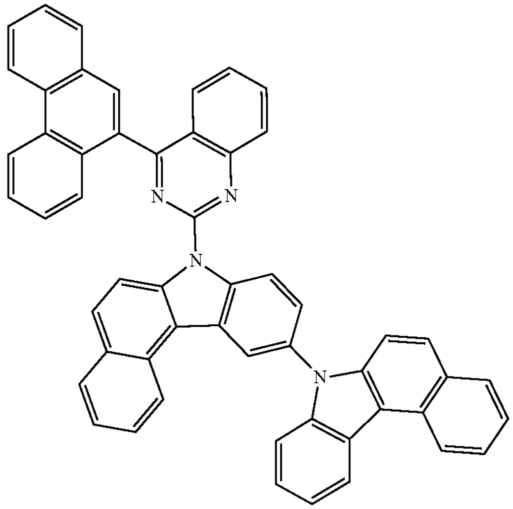
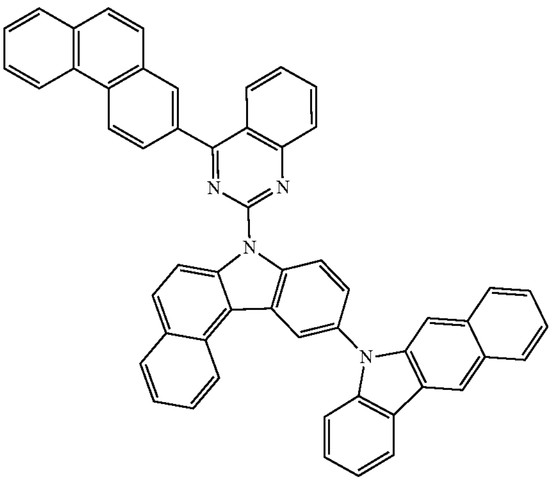
-continued
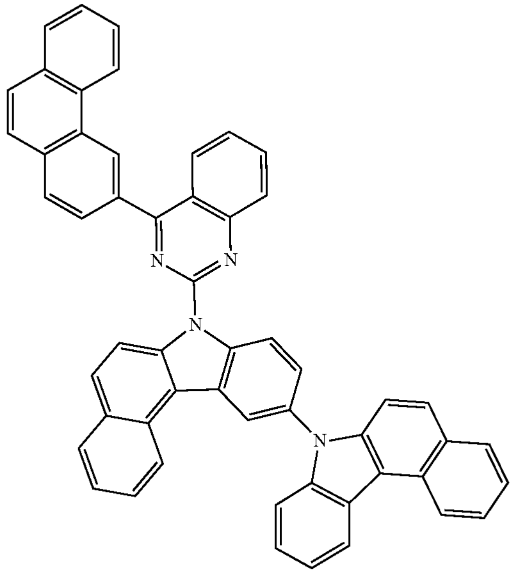
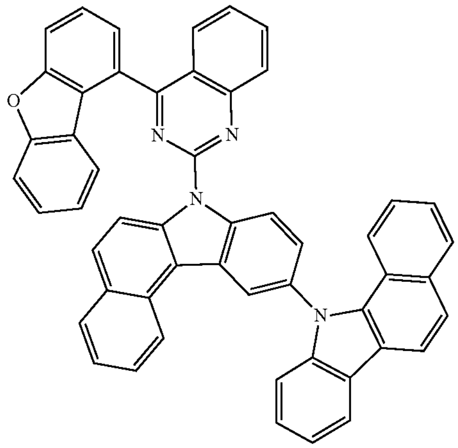
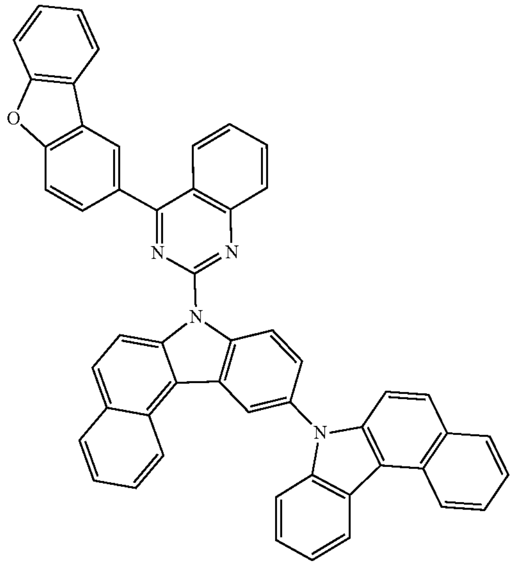

-continued
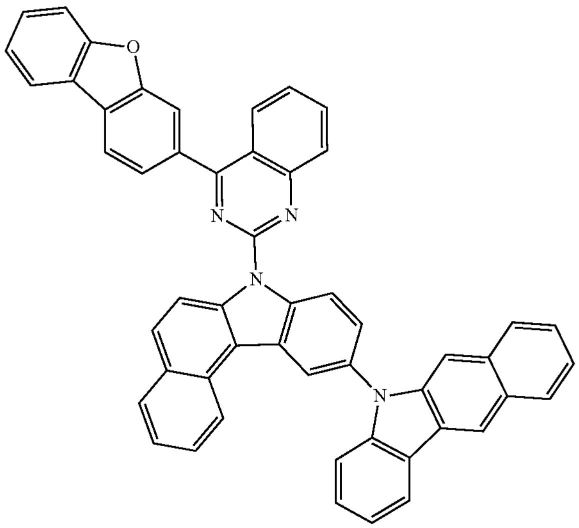
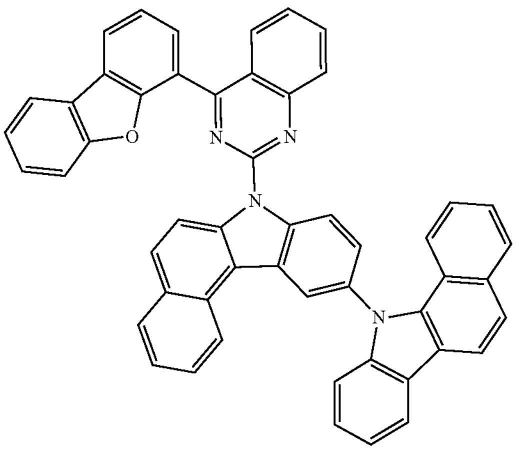 [SMILES: c1ccc2c(c1)ccc1c2c2cc(-n3c4ccccc4c4ccc5ccccc5c43)ccc2n1-c1nc(-c2cccc3c2oc2ccccc23)c2ccccc2n1]
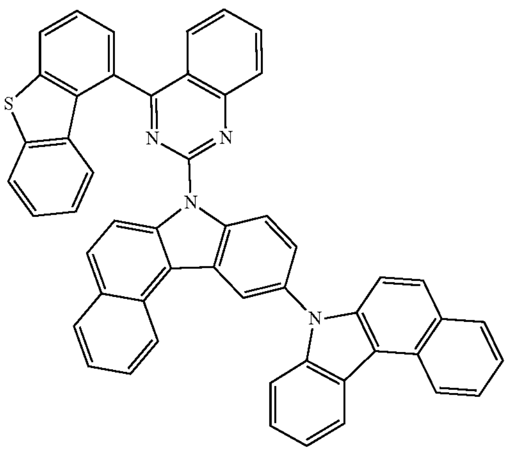
-continued
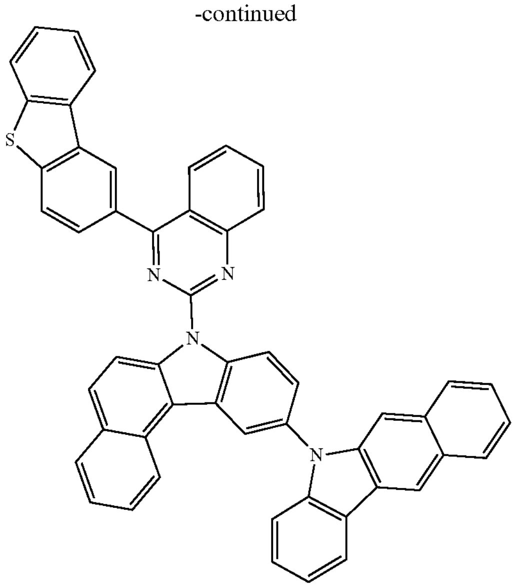
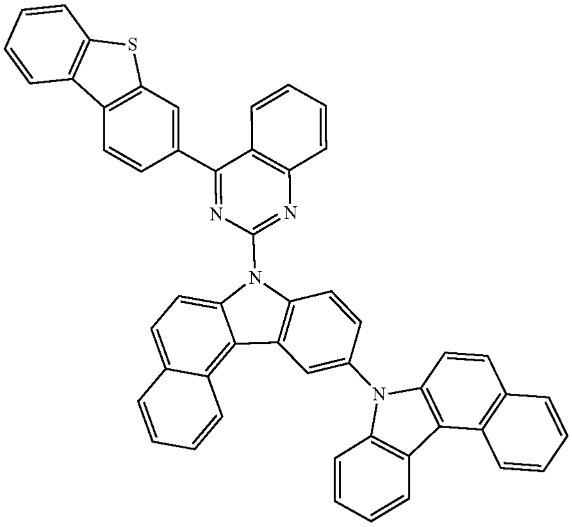
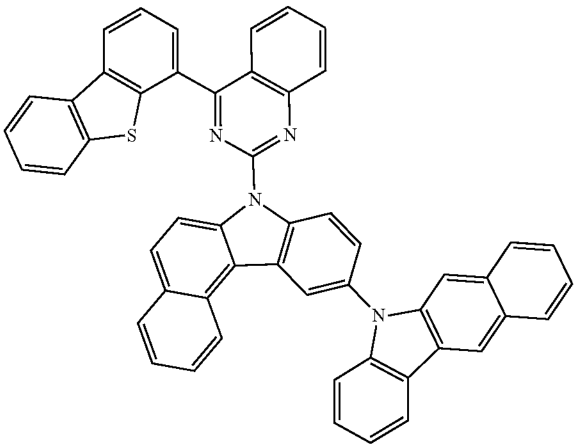 [SMILES: c1ccc2cc3c(cc2c1)c1ccccc1n3-c1ccc2c(c1)c1c3ccccc3ccc1n2-c1nc(-c2cccc3c2sc2ccccc23)c2ccccc2n1]

-continued
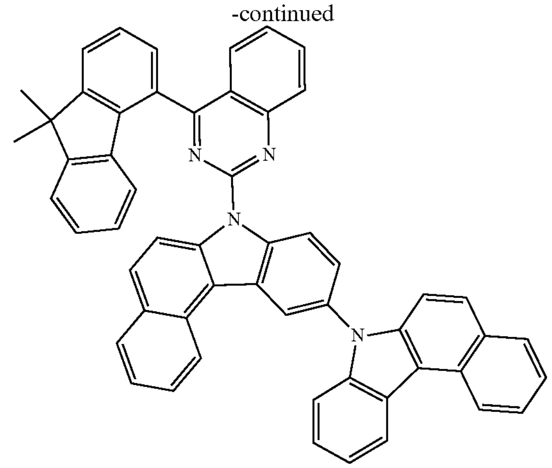
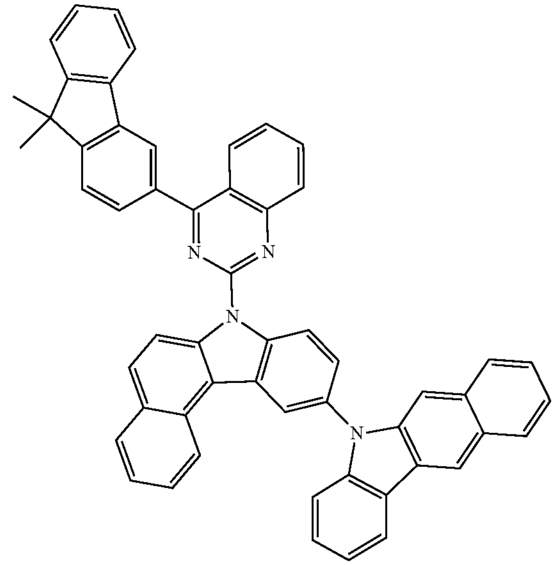
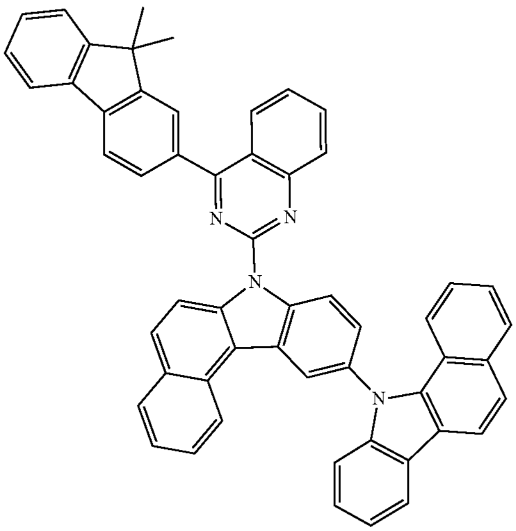
-continued
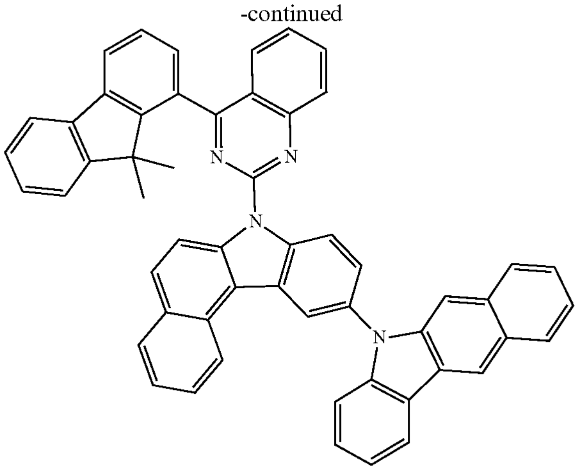
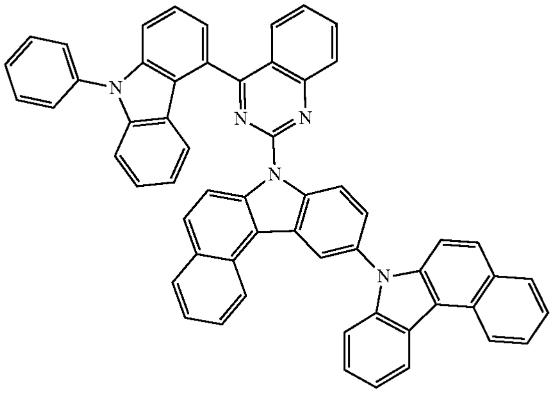
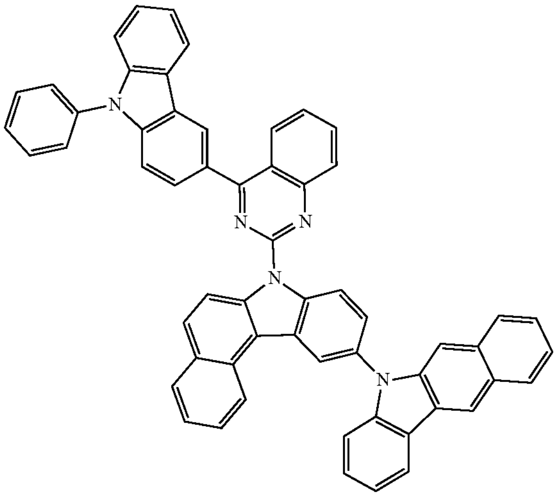

-continued
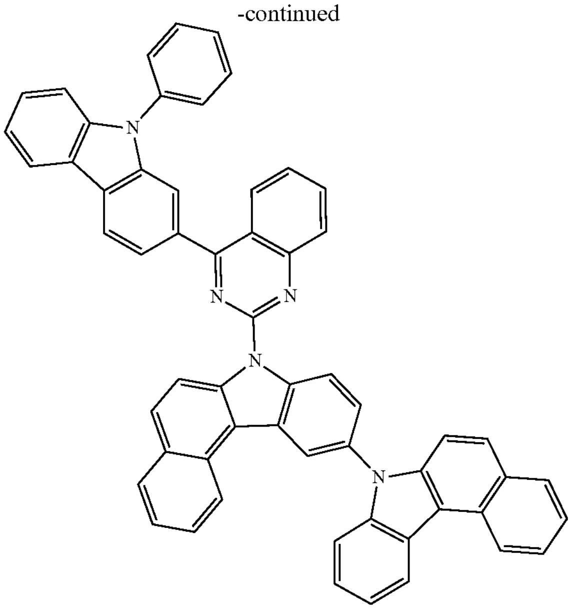
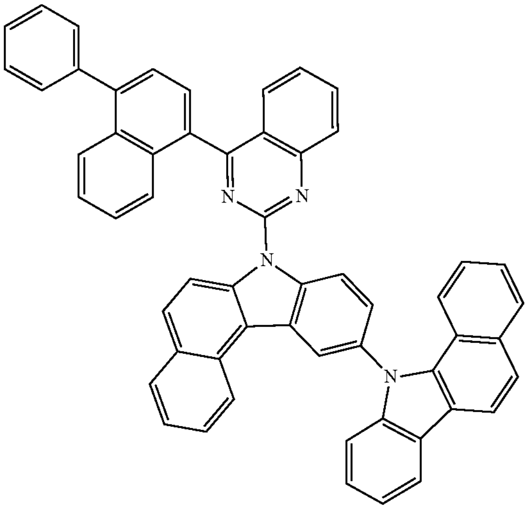
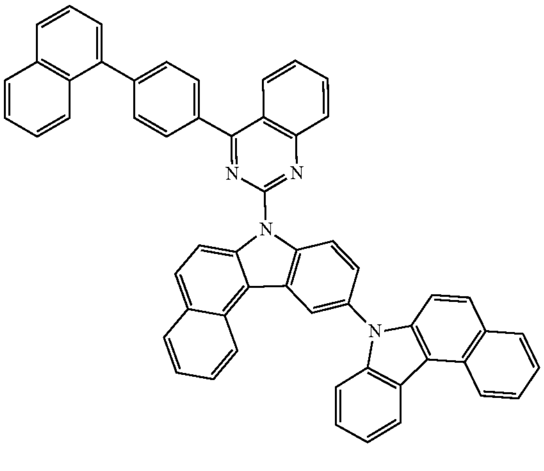
-continued
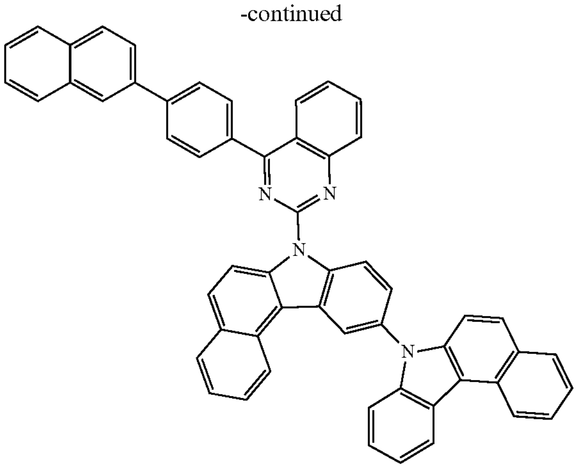
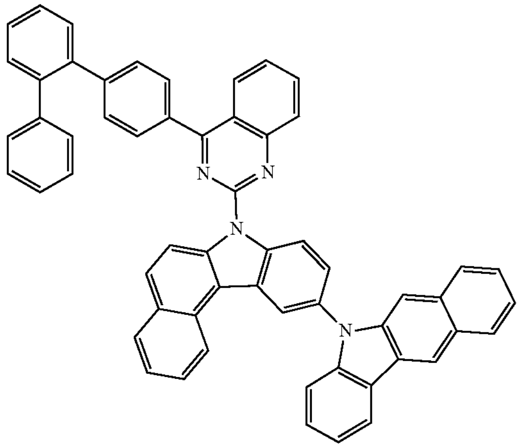
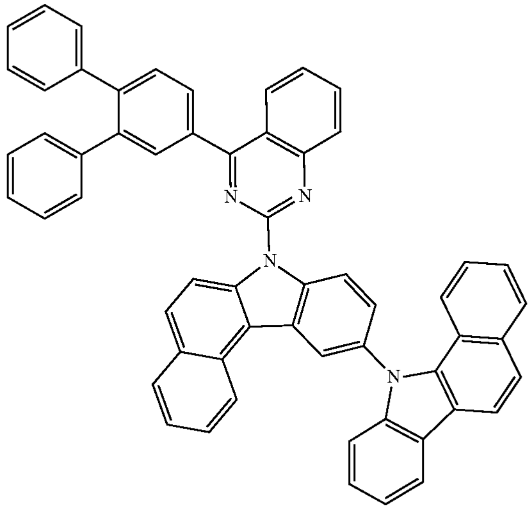

-continued
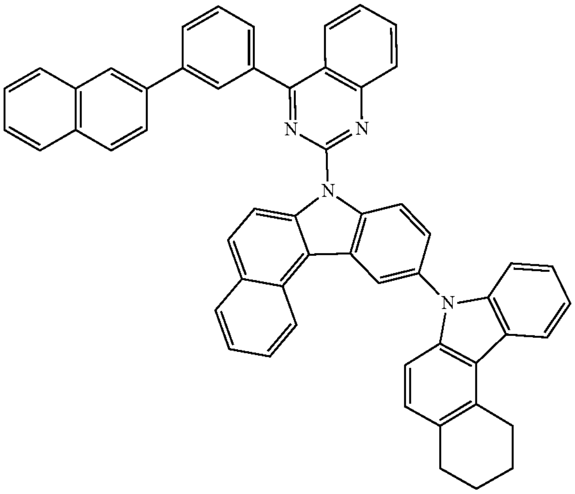
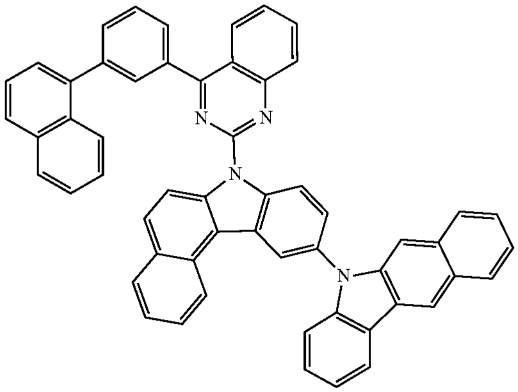 [SMILES: c1cc(-c2cccc3ccccc23)cc(-c2nc(-n3c4ccc(-n5c6ccccc6c6cc7ccccc7cc65)cc4c4c5ccccc5ccc43)nc3ccccc23)c1]
In an exemplary embodiment of the present specification, the compound of Formula 2 is any one compound selected from the following compounds:
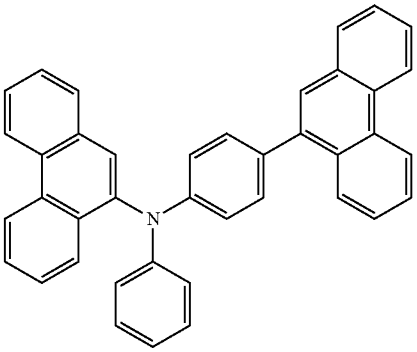
-continued
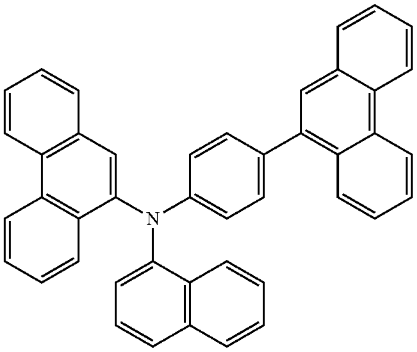
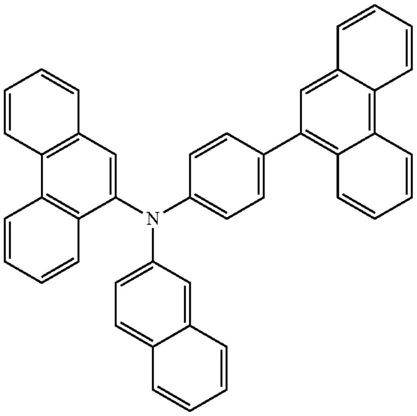
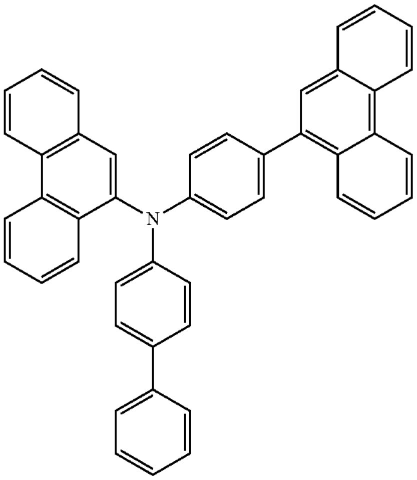
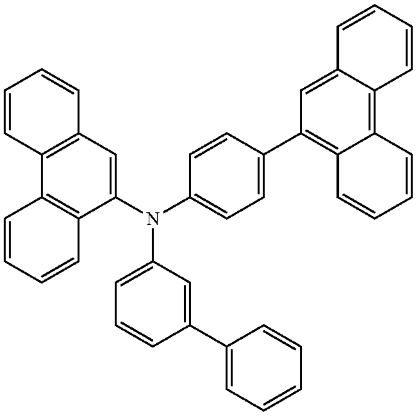

-continued
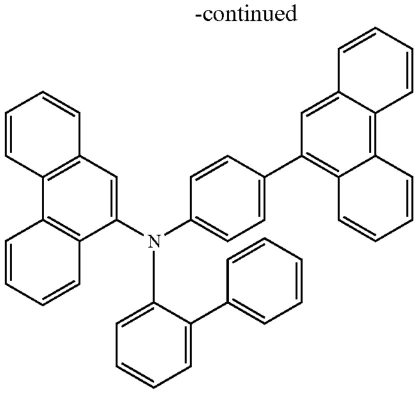
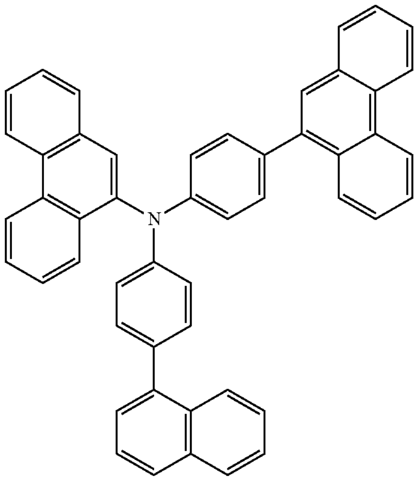
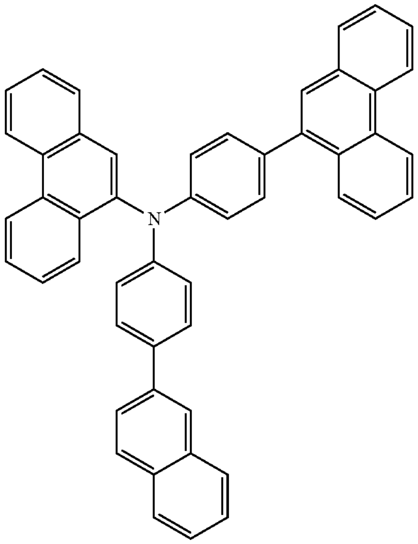
-continued
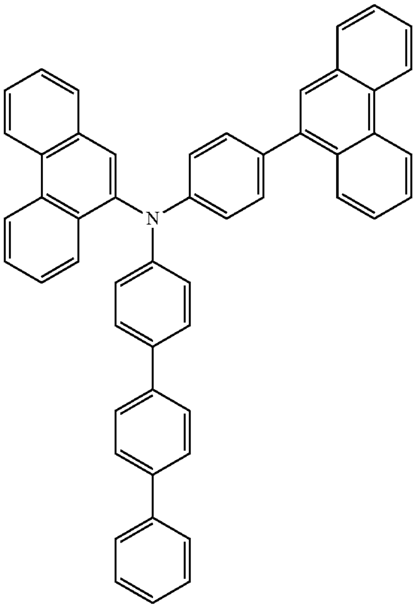
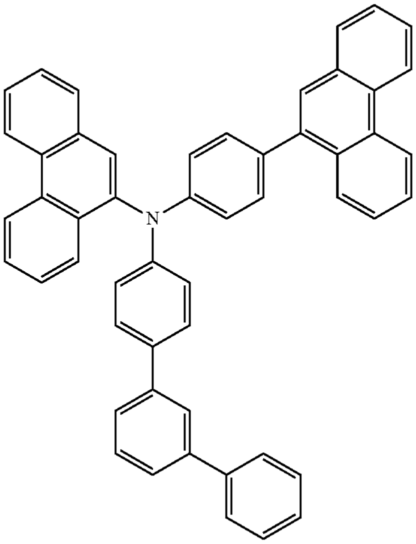
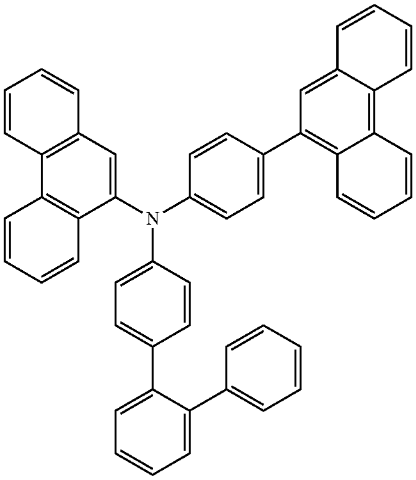

-continued
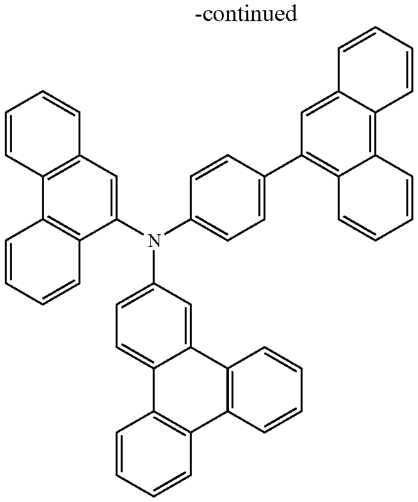
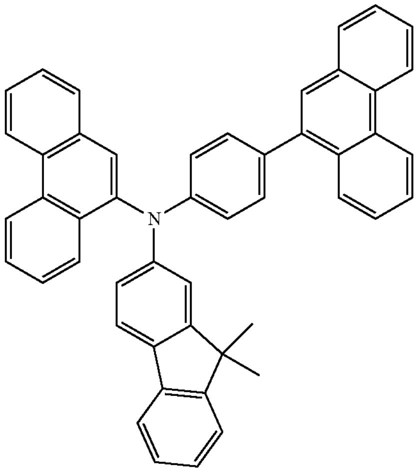
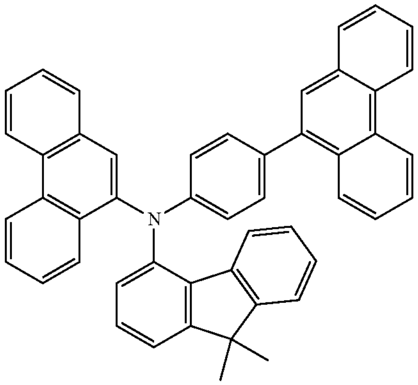
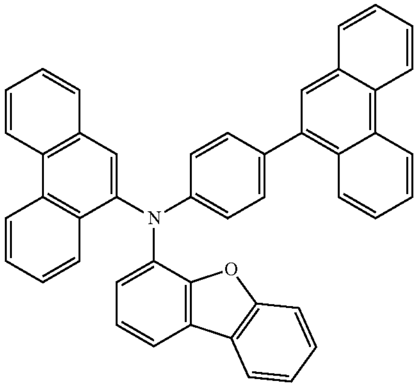
-continued
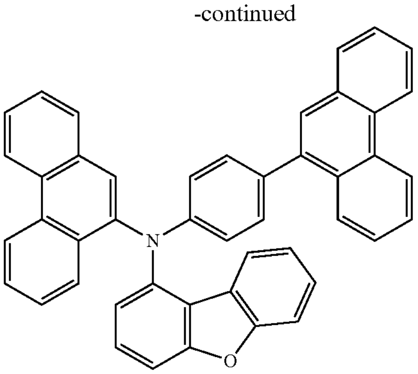
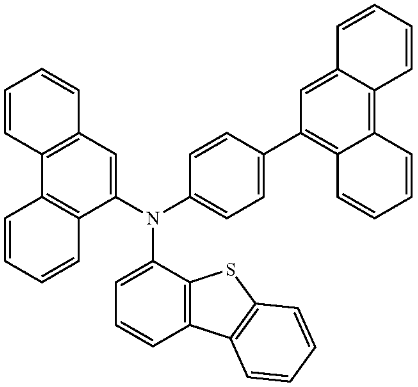
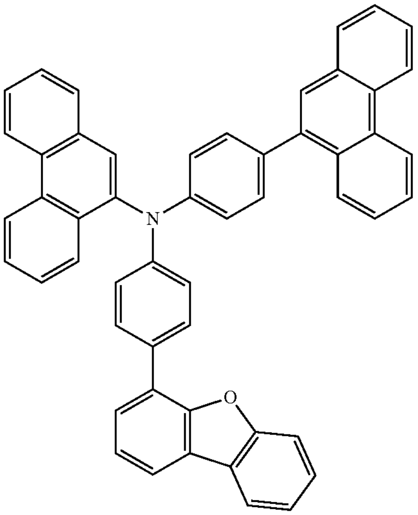
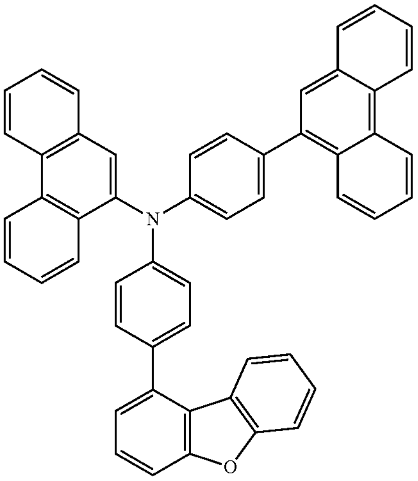

-continued
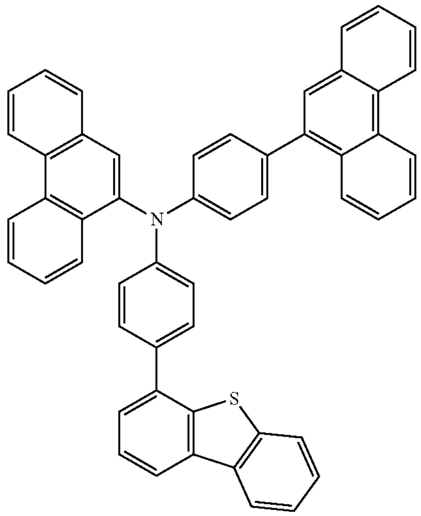
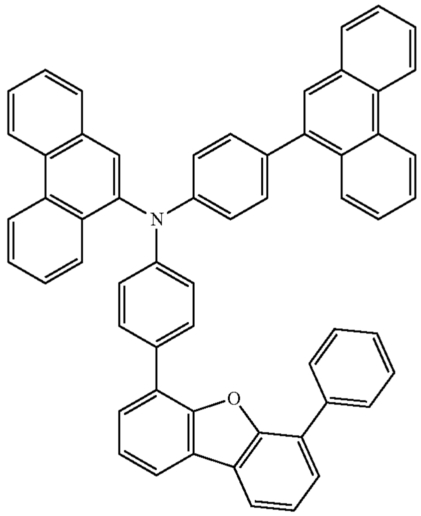
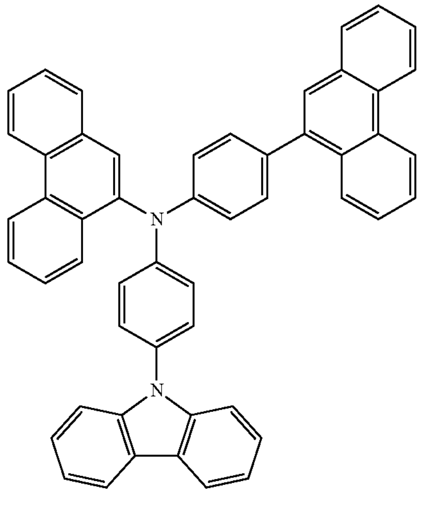
-continued
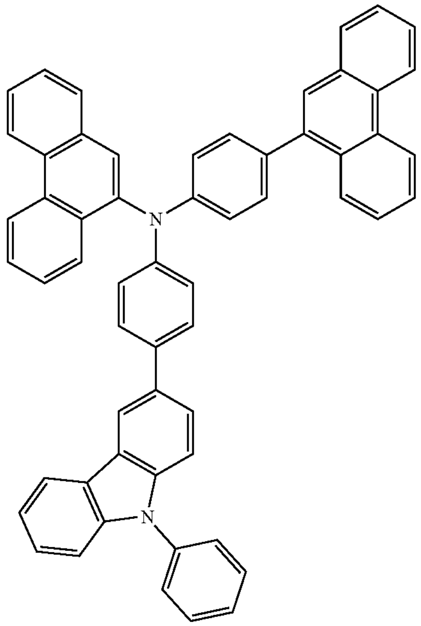
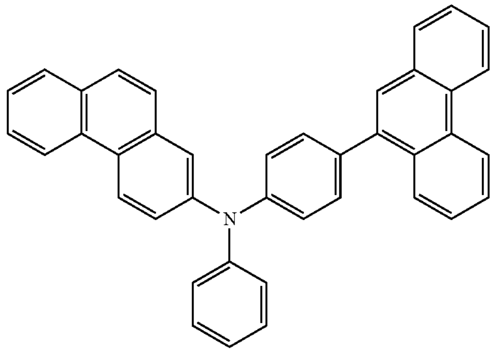
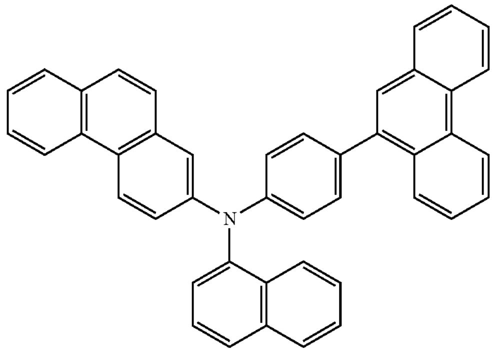

-continued
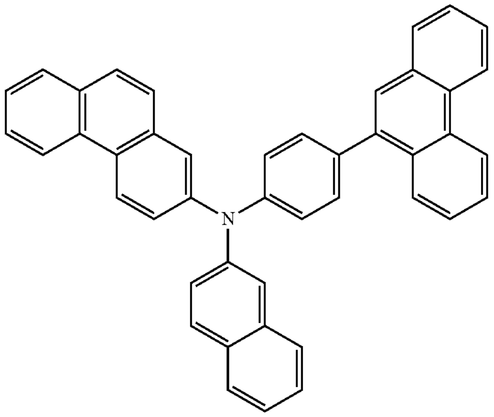
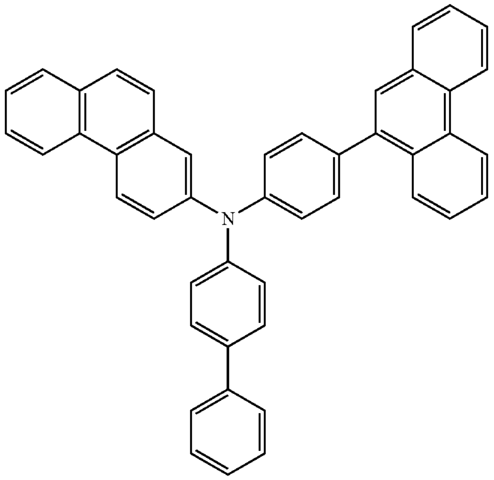
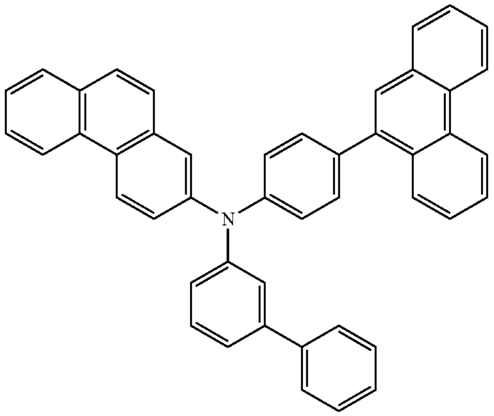
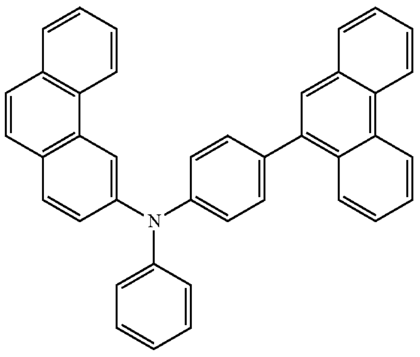
-continued
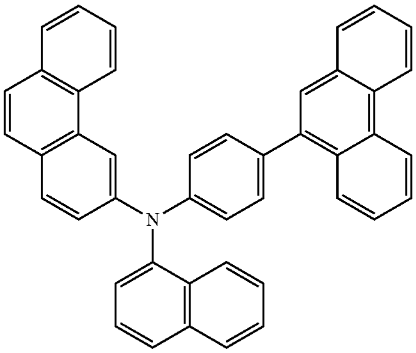
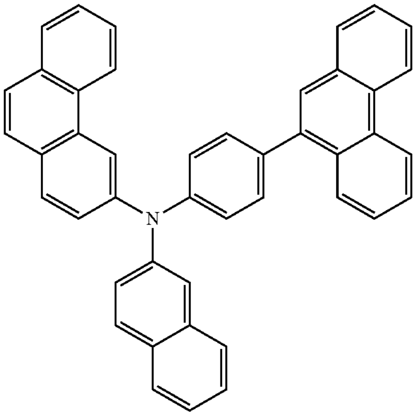
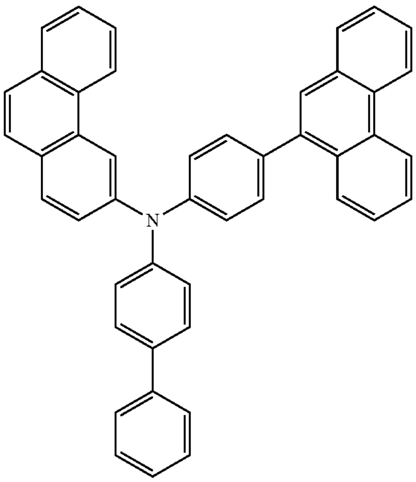
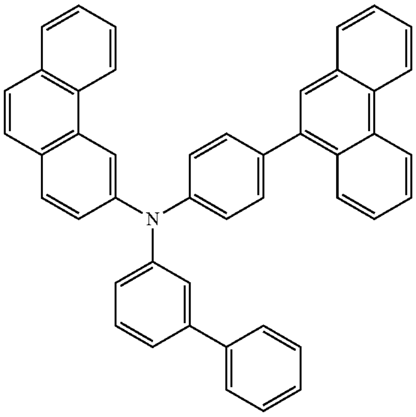

-continued
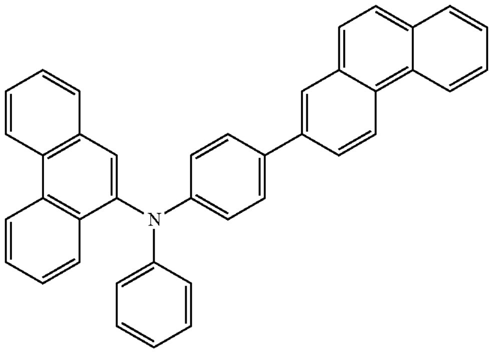
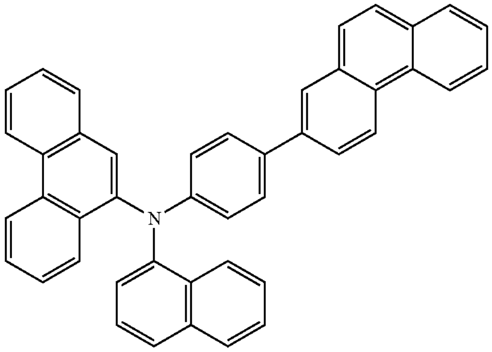
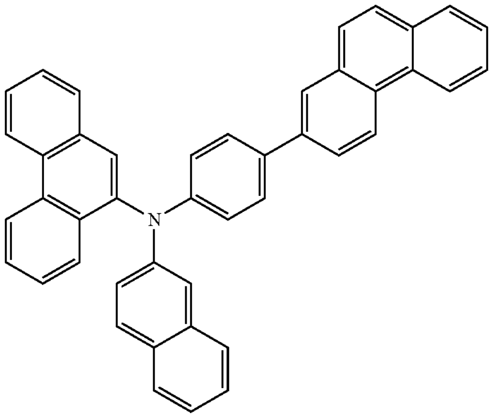
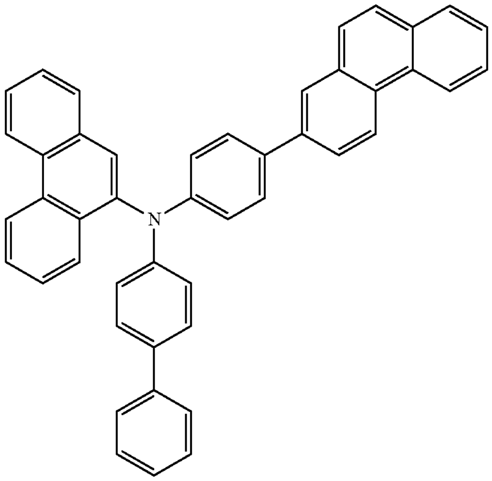
-continued
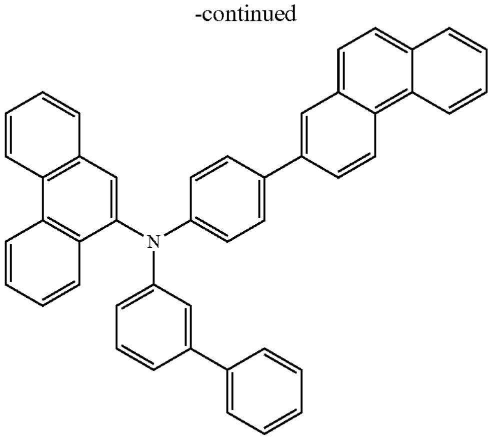
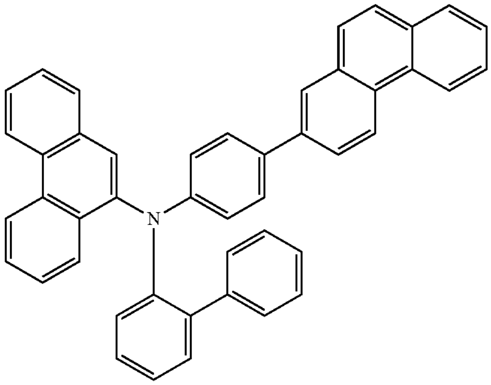
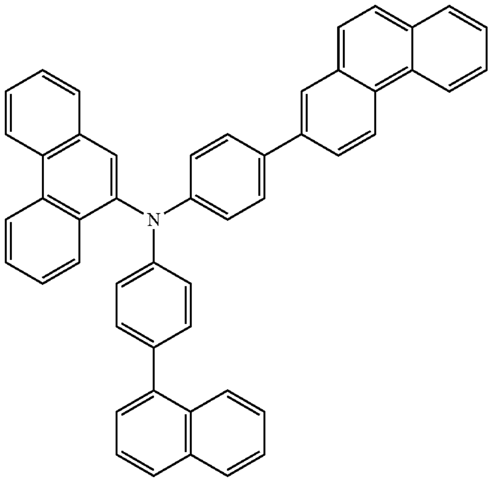

-continued
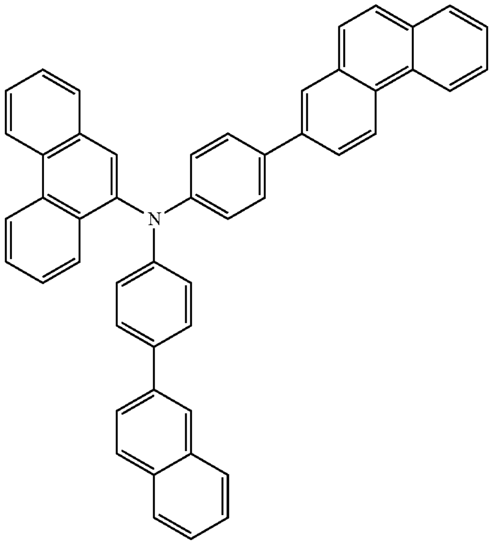
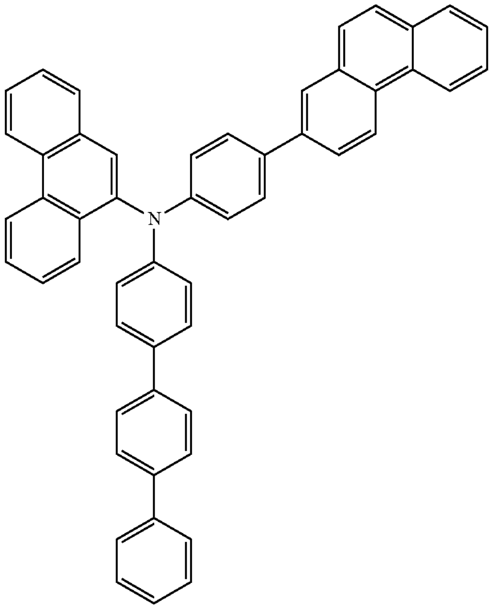
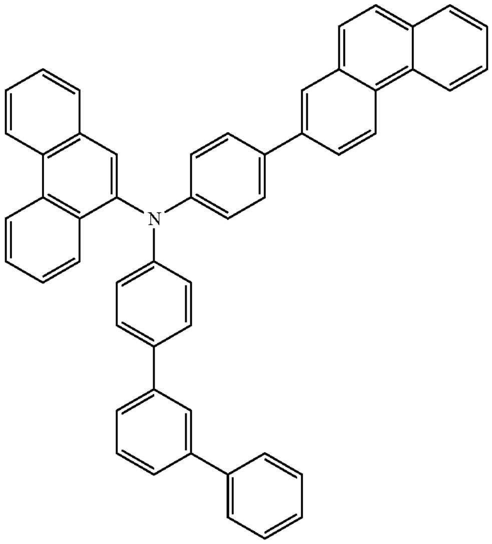
-continued
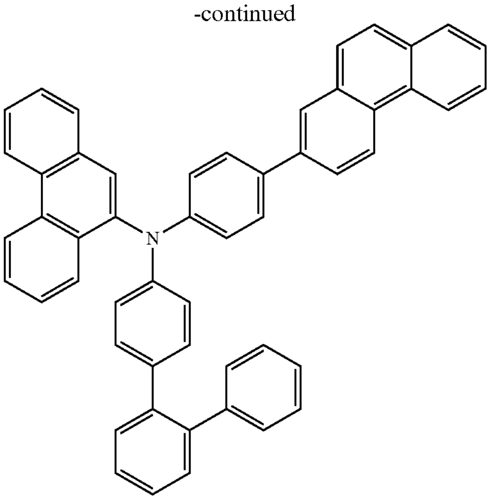
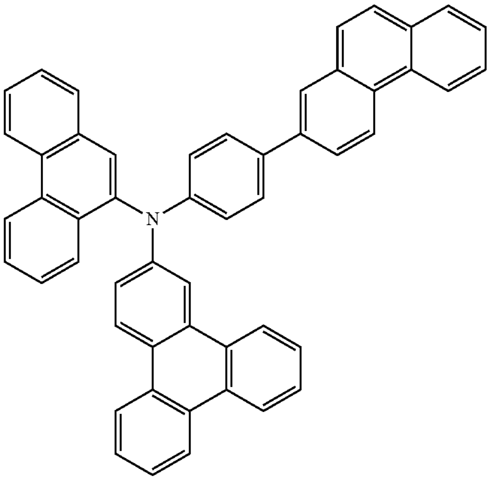
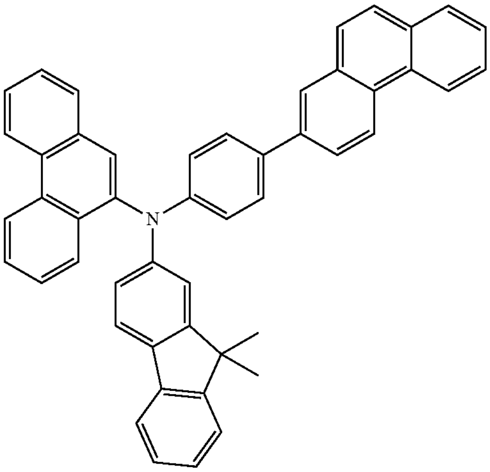

-continued
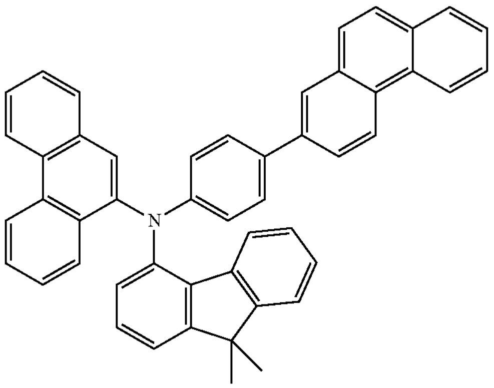
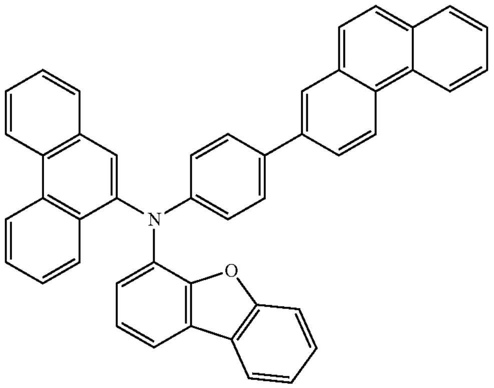
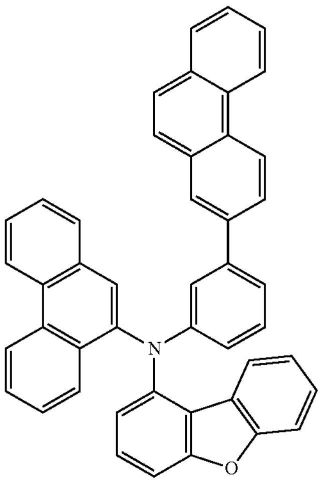
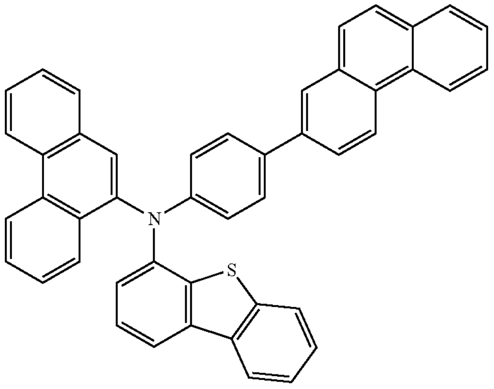
-continued
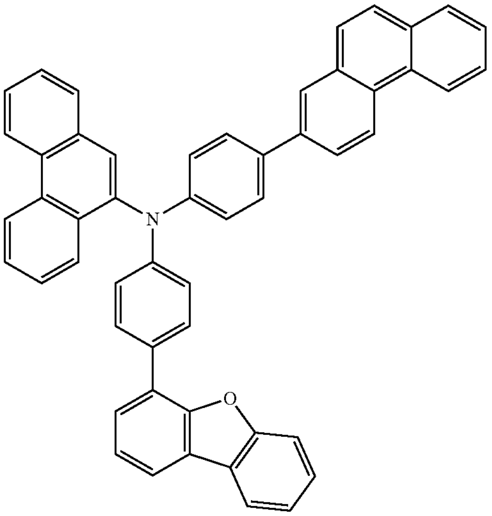
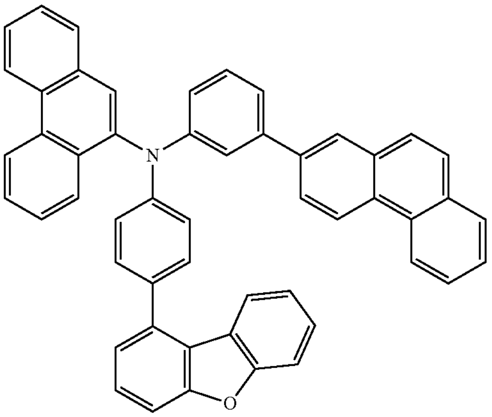
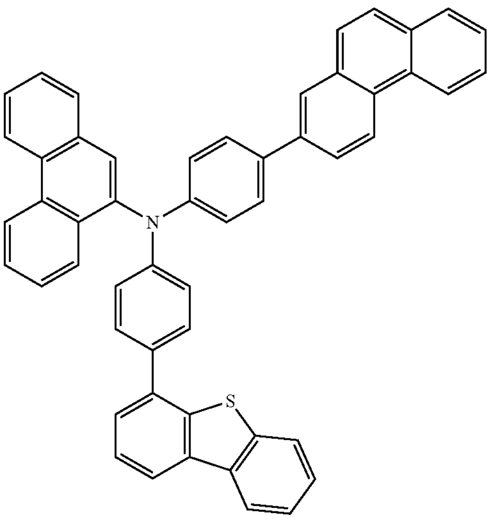

-continued
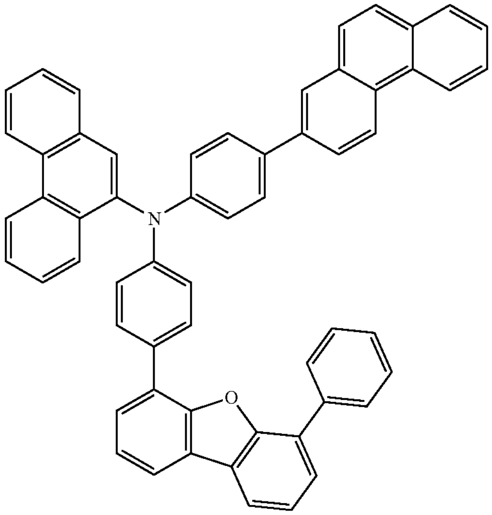
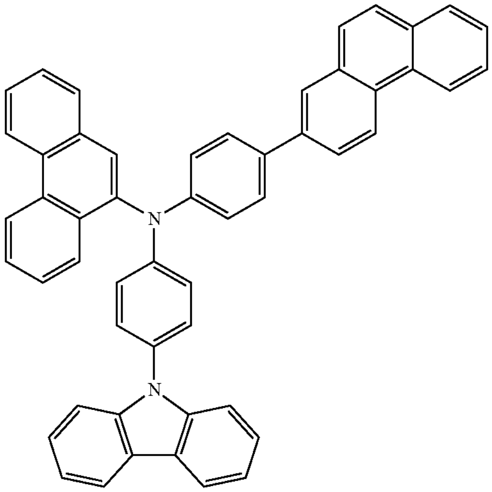
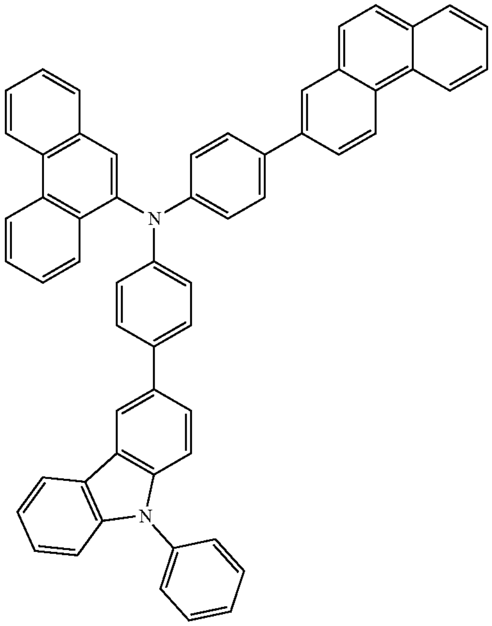
-continued
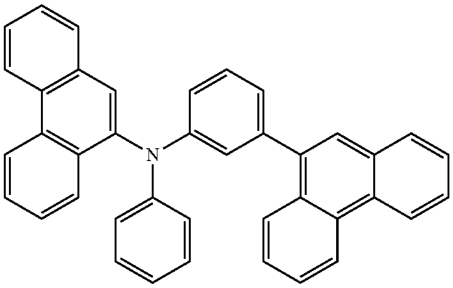
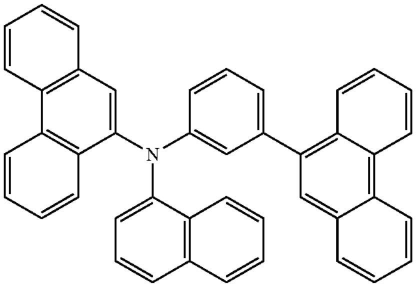
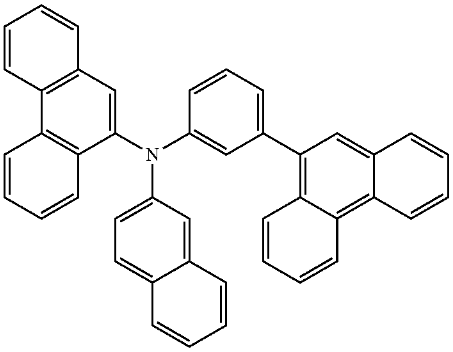
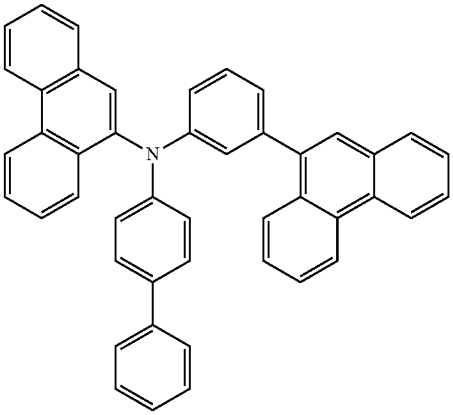
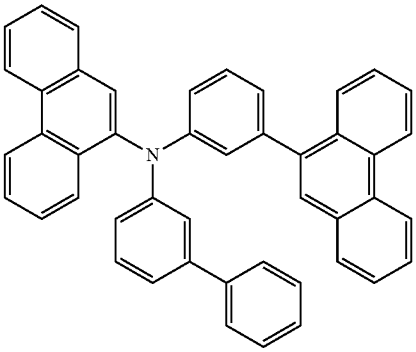

-continued
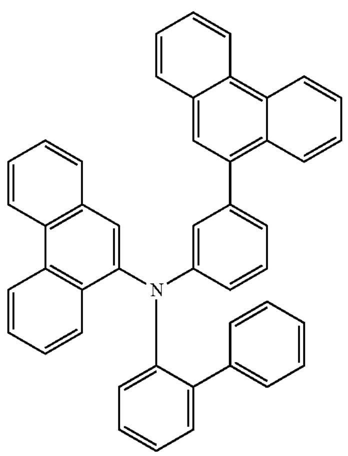
-continued
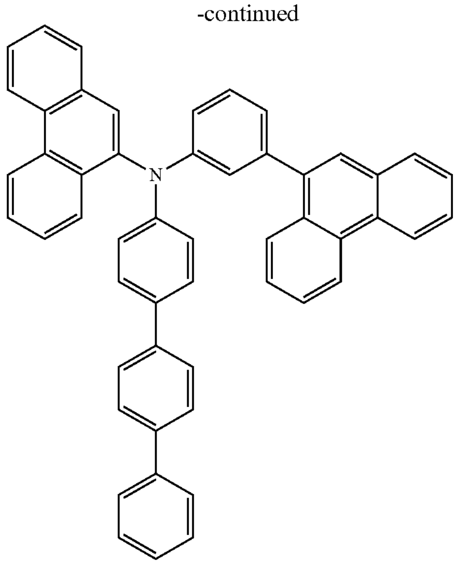
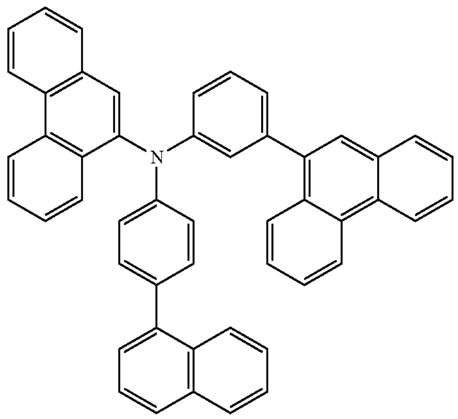
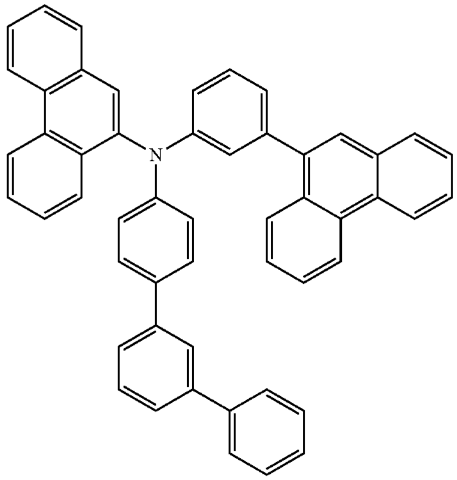
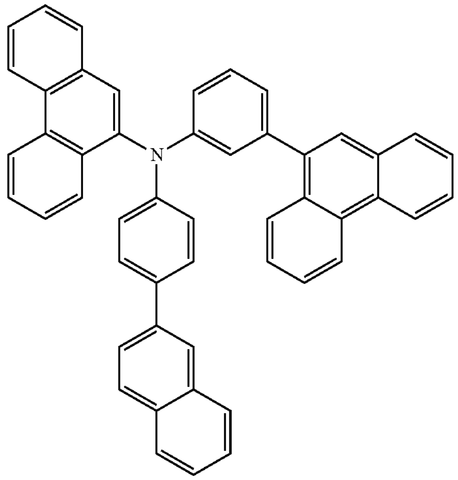
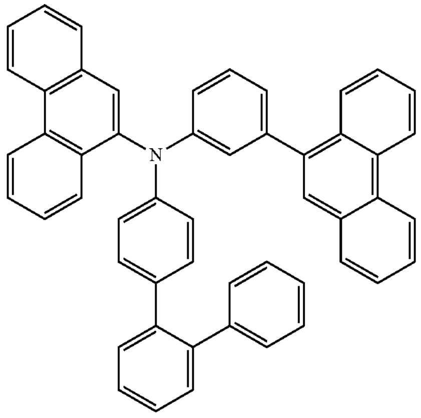

-continued
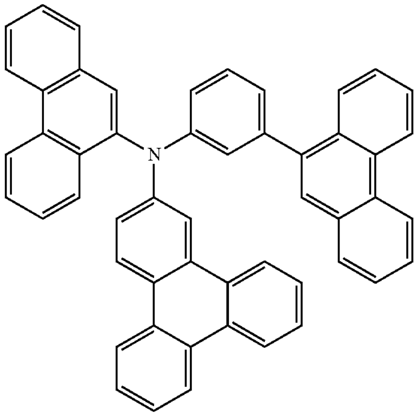
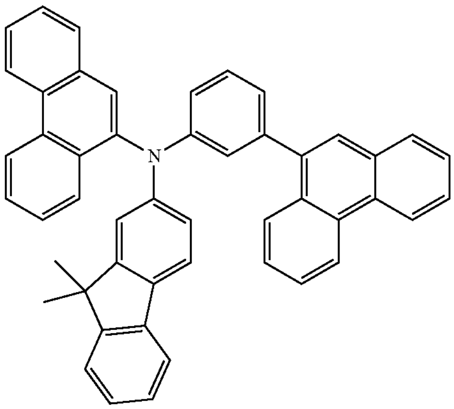
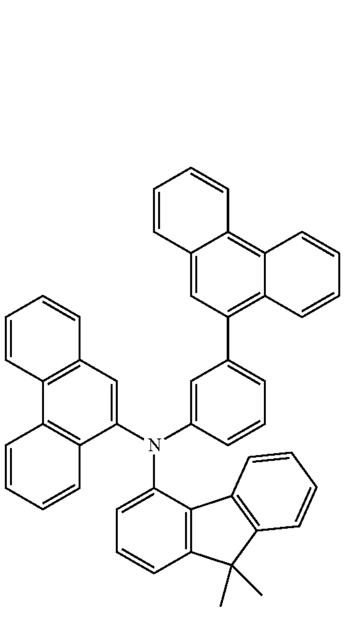
-continued
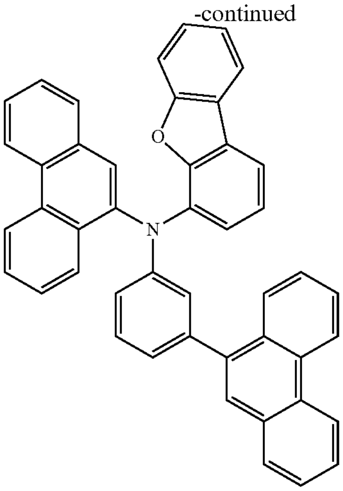
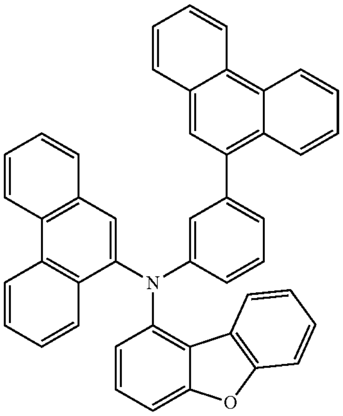
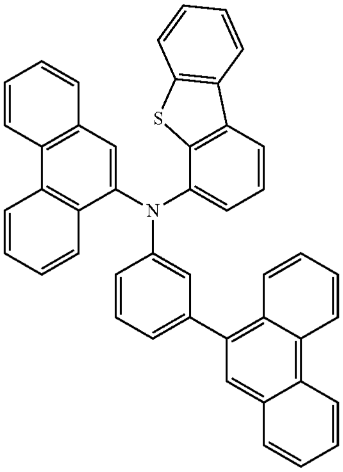

-continued
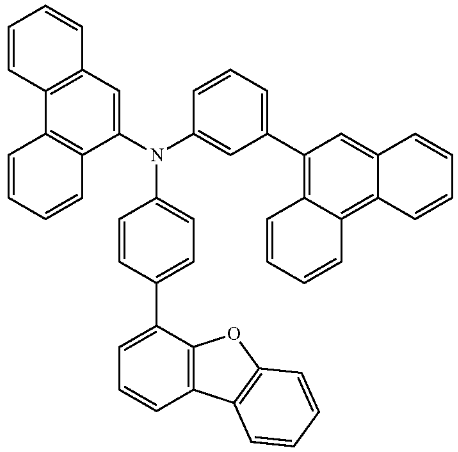
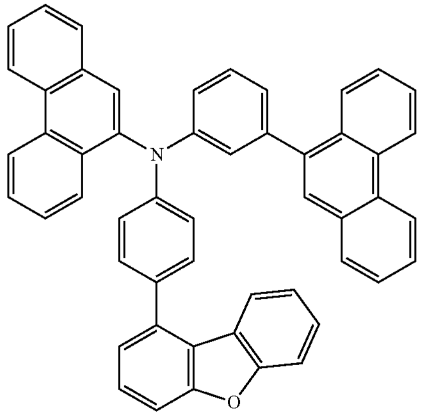
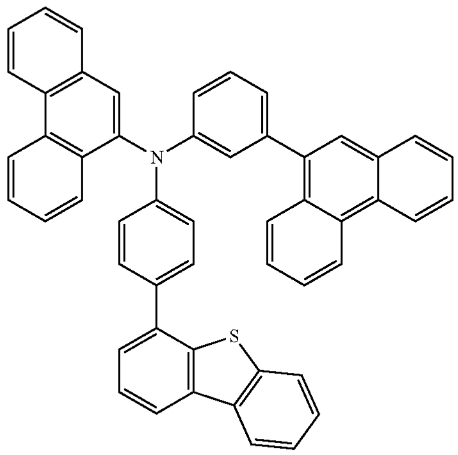
-continued
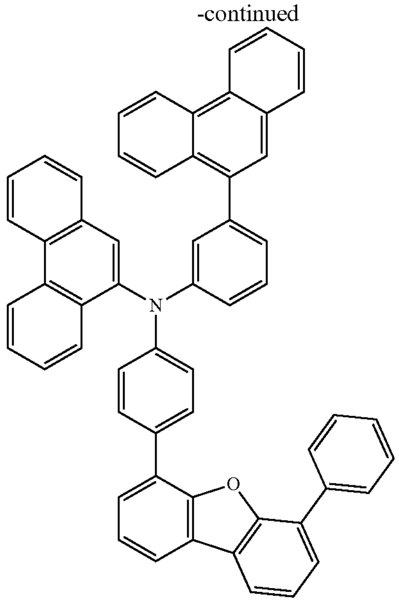
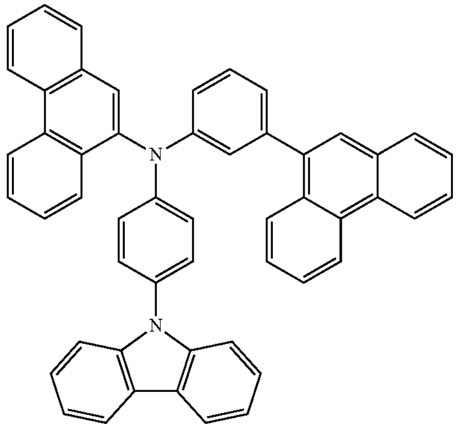
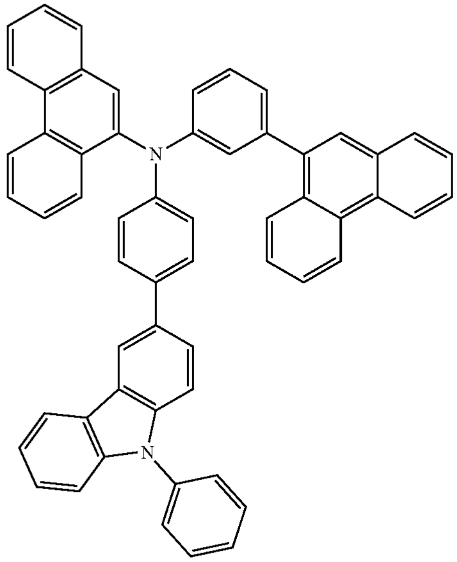

-continued
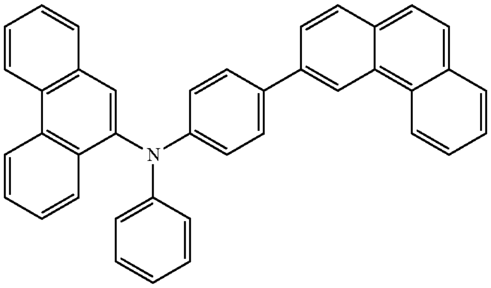
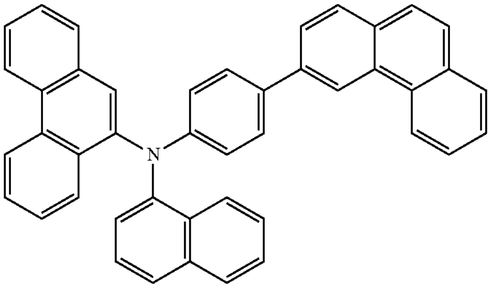
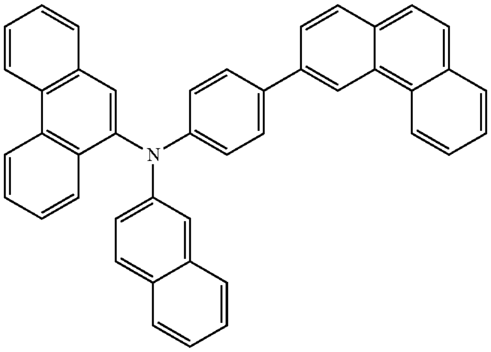
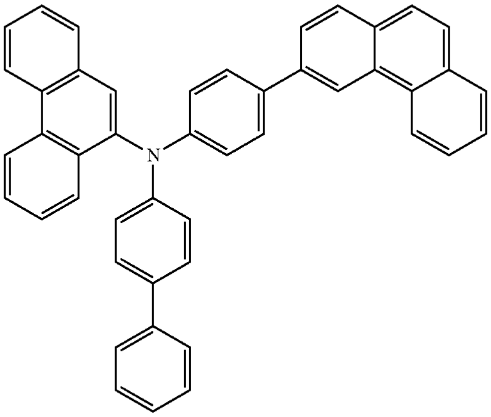
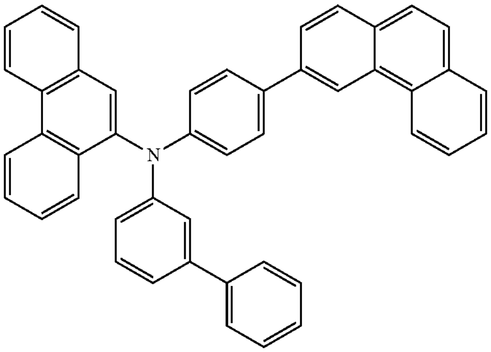
-continued
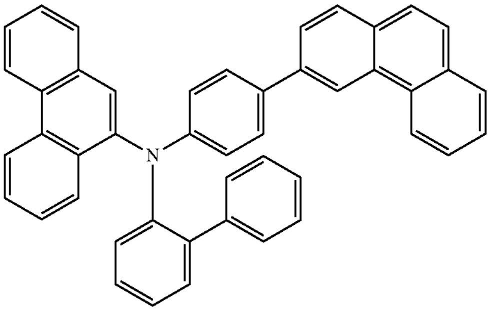
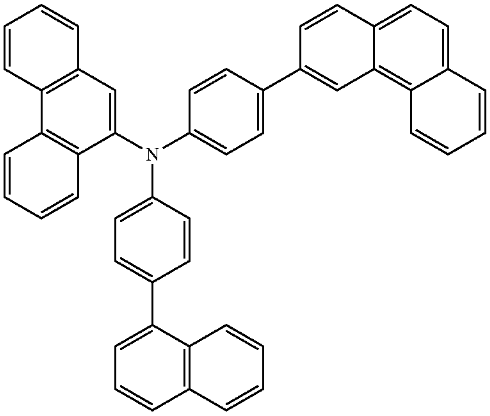
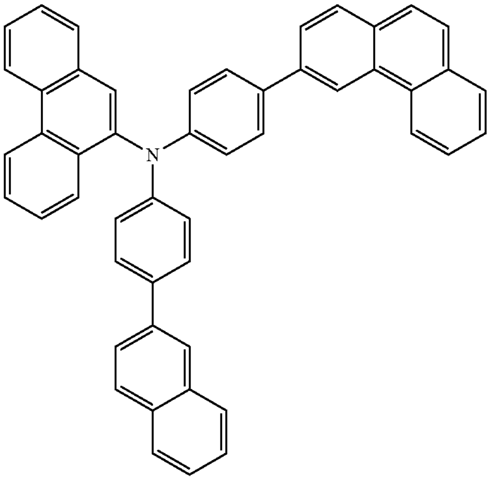

-continued
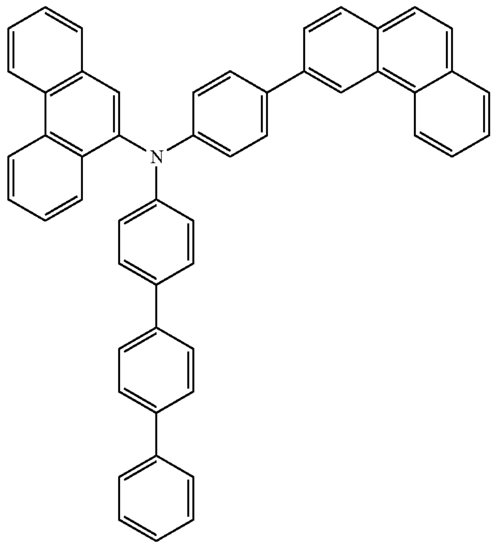
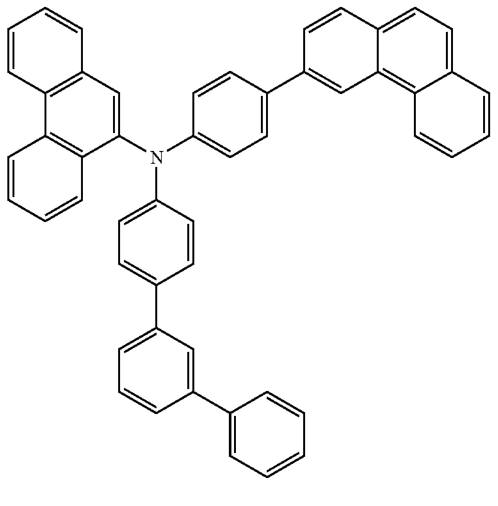
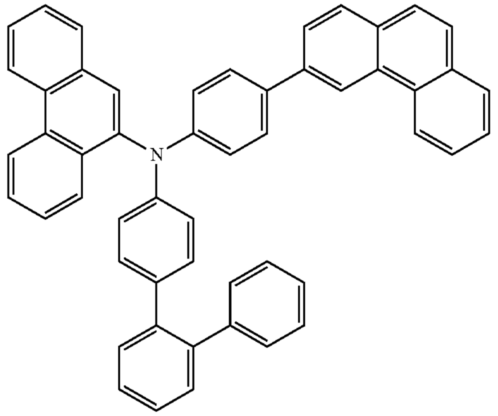
-continued
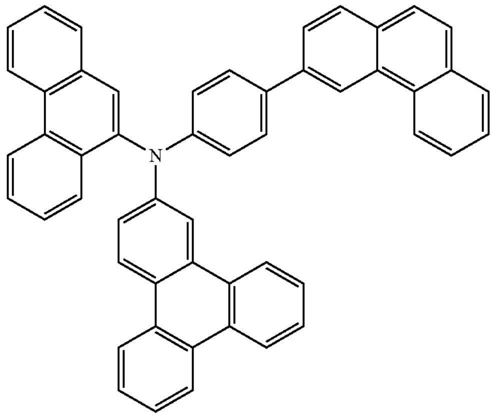
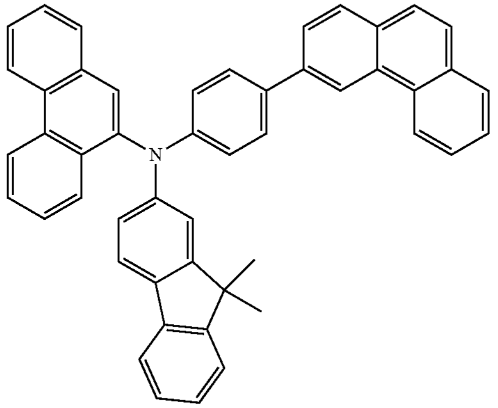
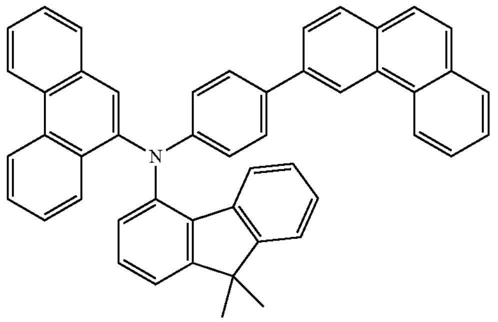
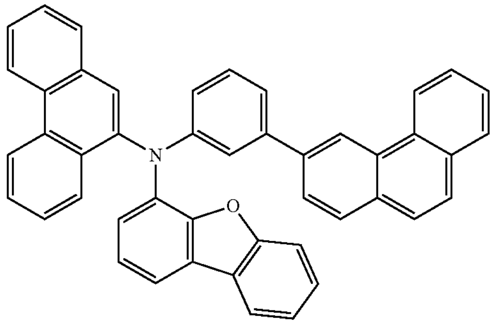

-continued
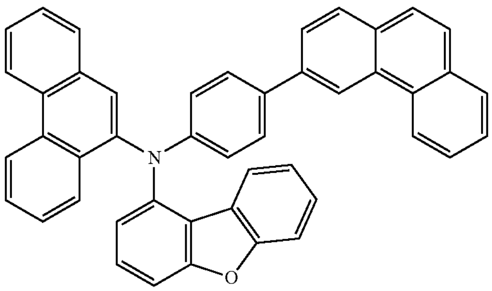
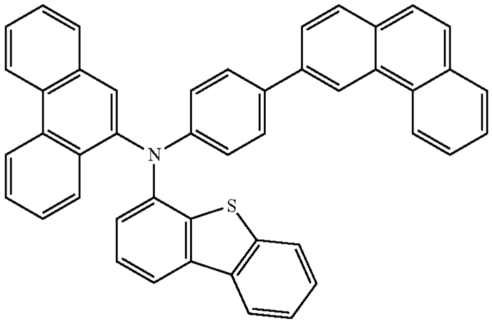
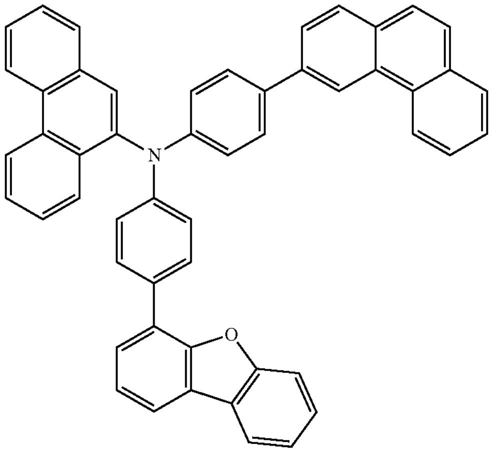
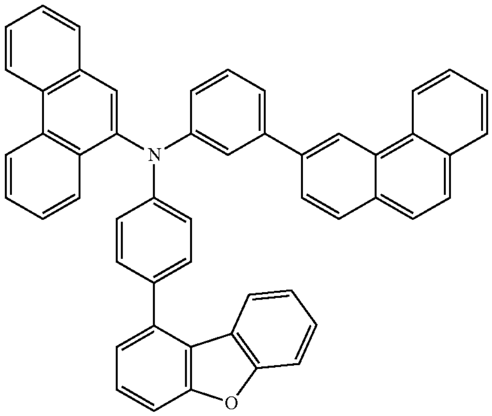
-continued
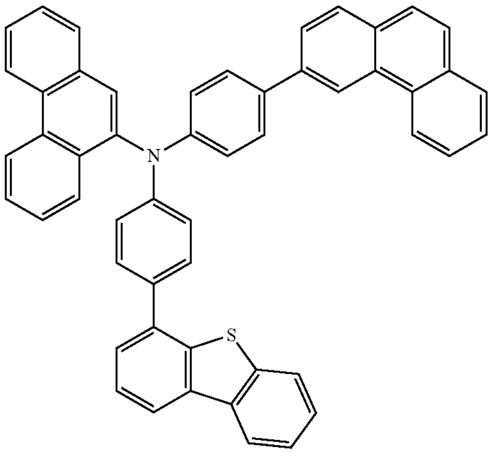
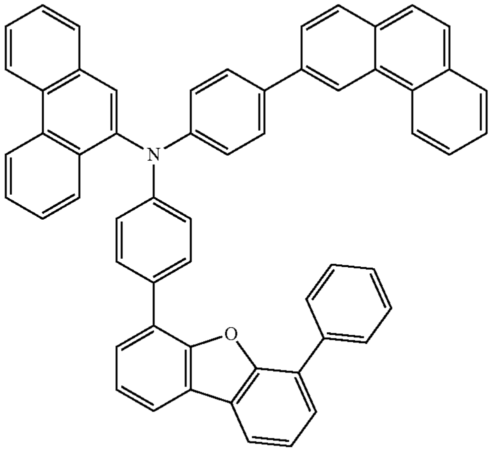
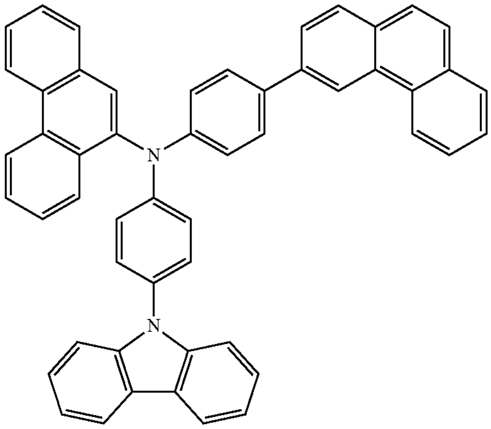

-continued
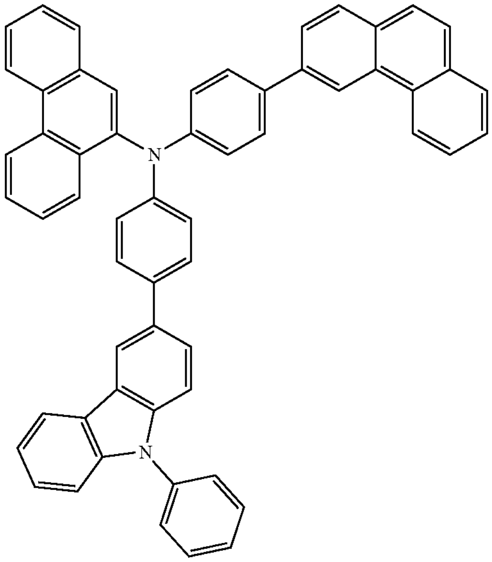
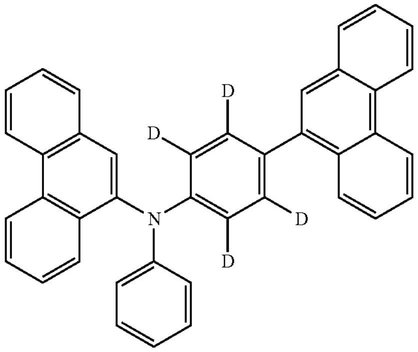
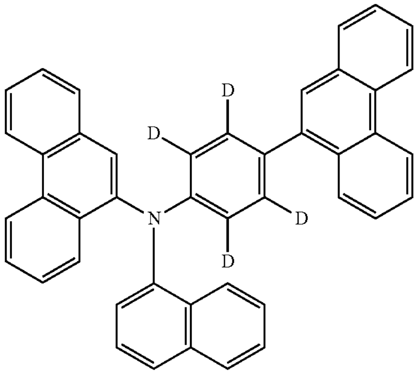
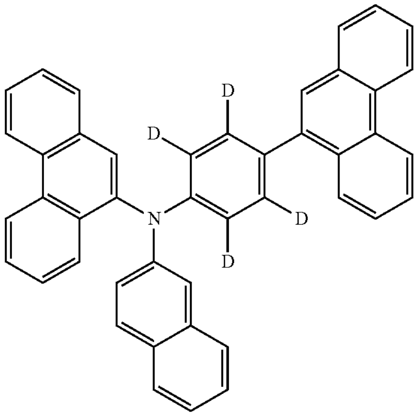
-continued
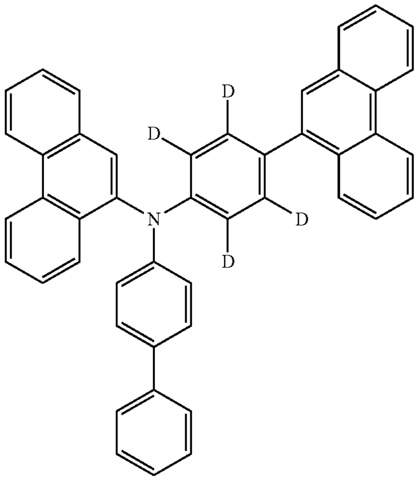
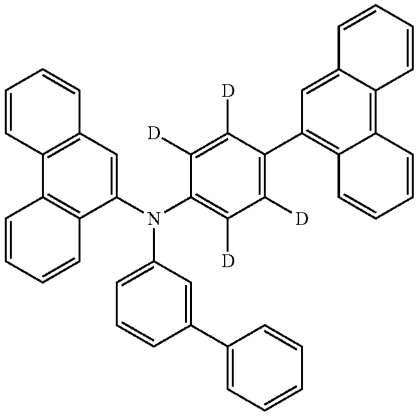
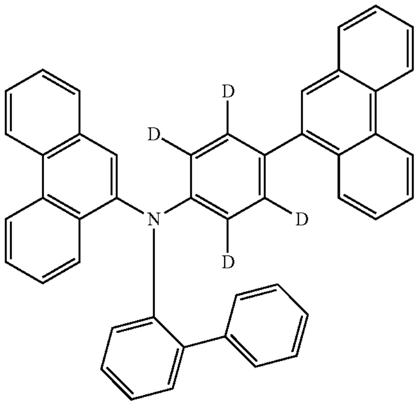

-continued
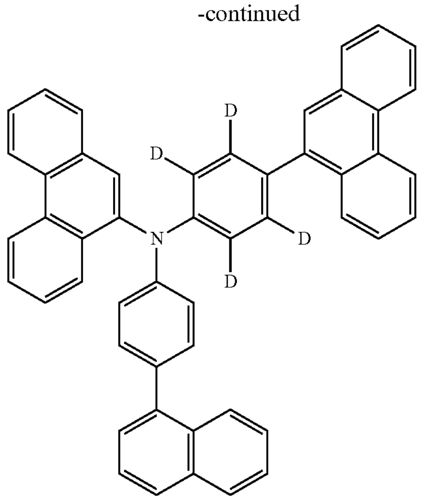
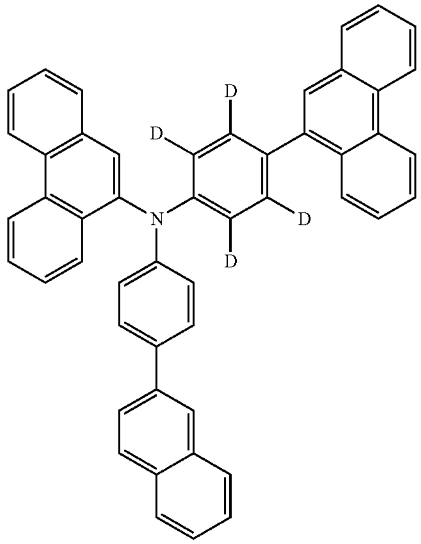
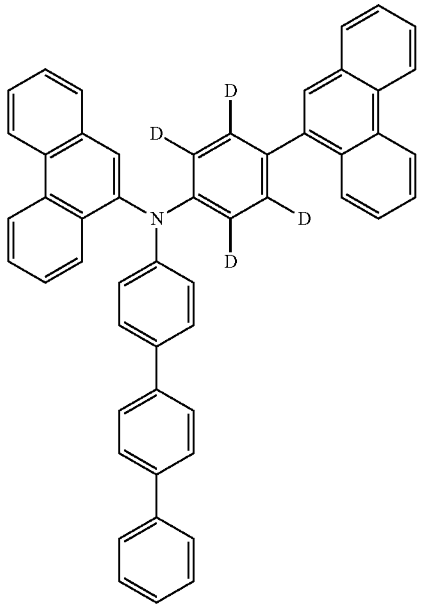
-continued
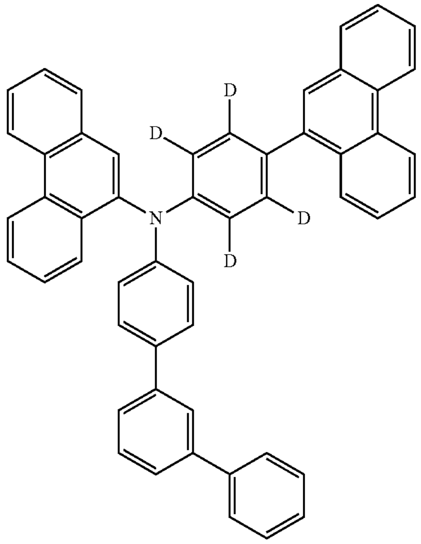
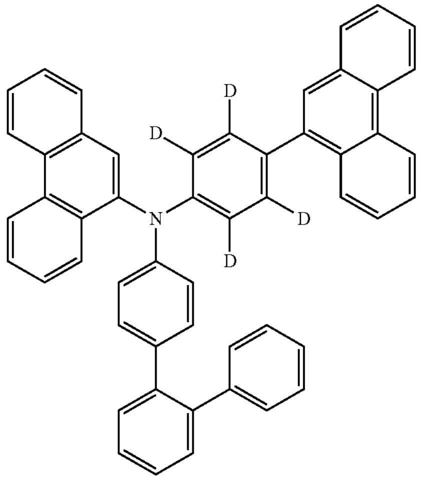
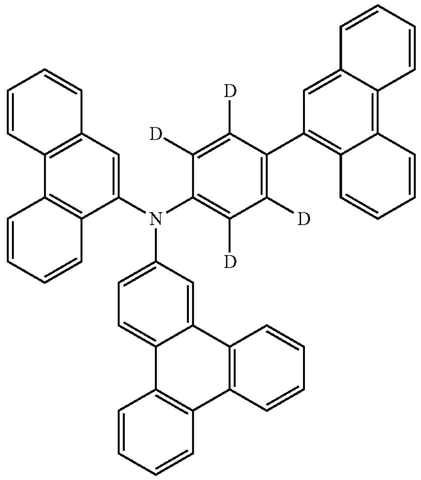

-continued
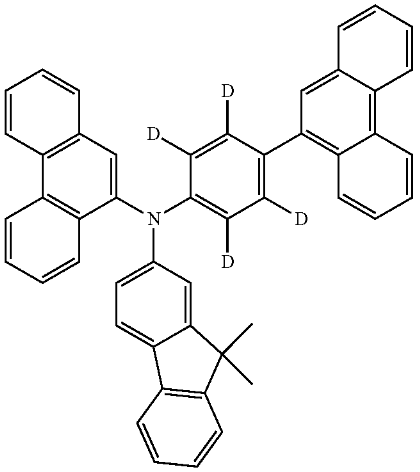
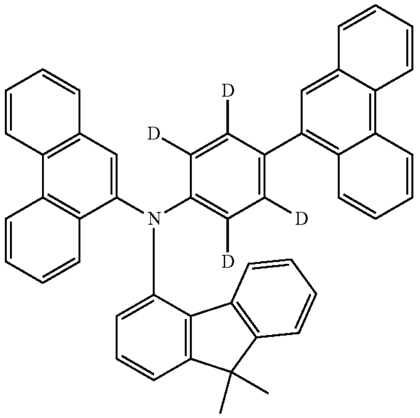
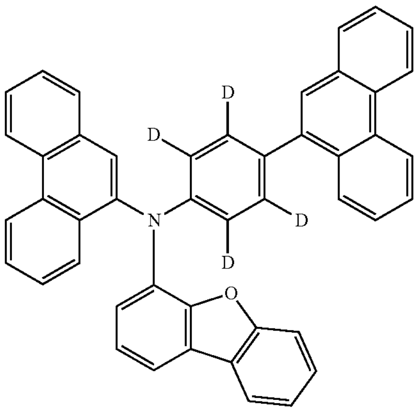
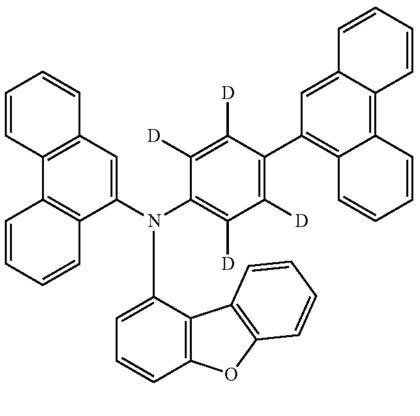
-continued
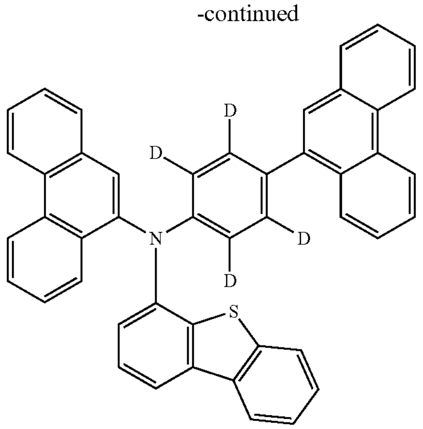
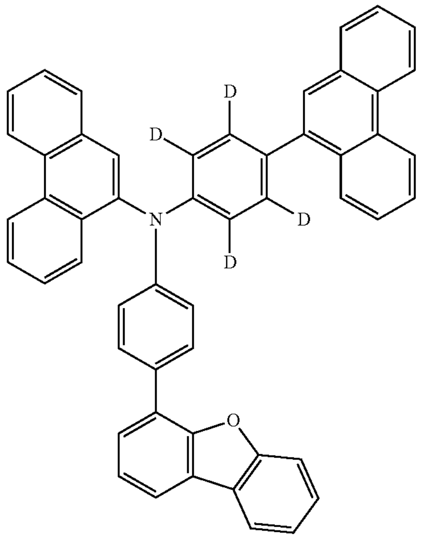
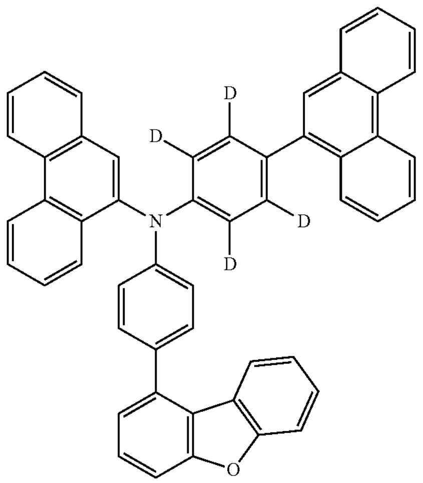

-continued
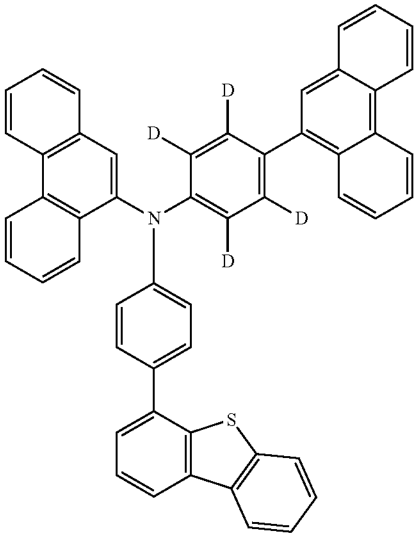
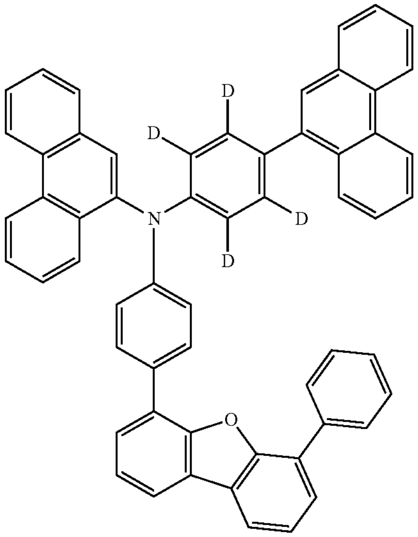
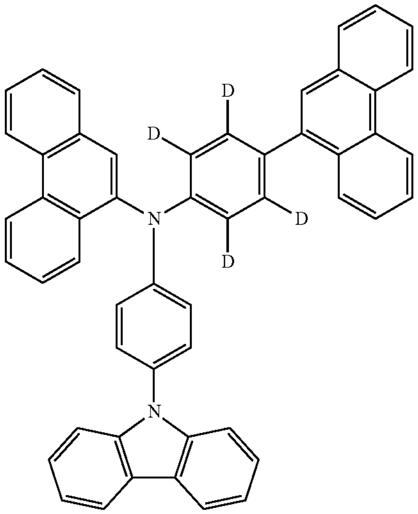
-continued
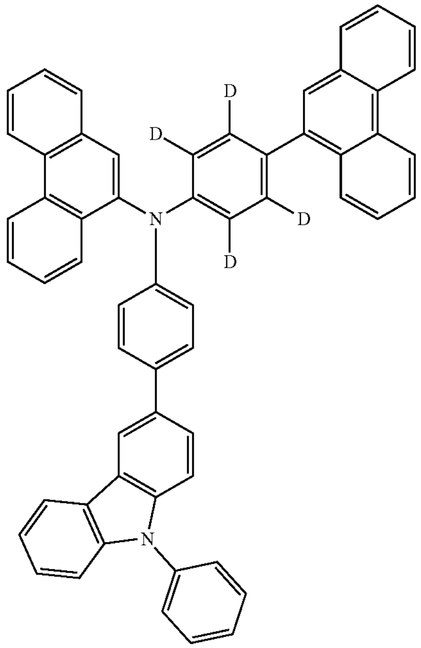
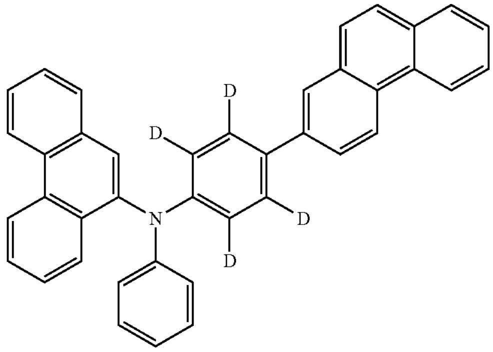
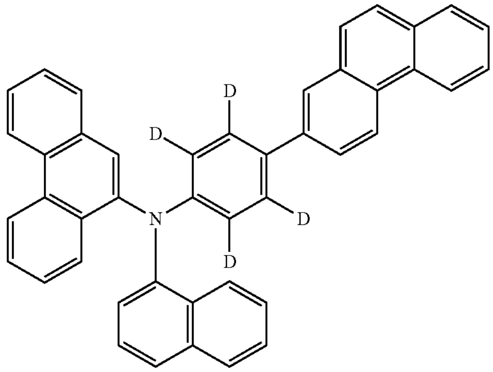

-continued
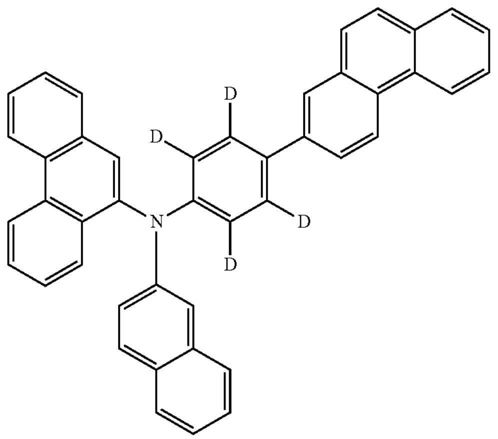
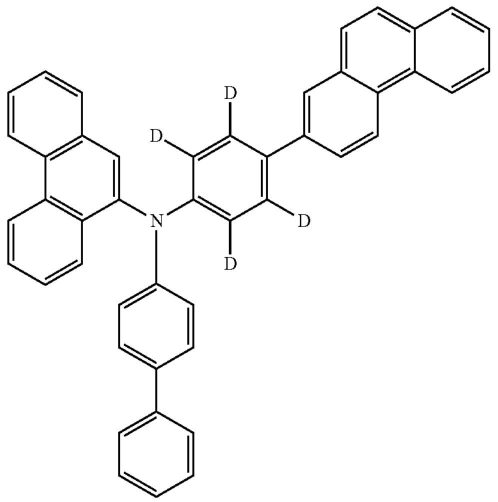
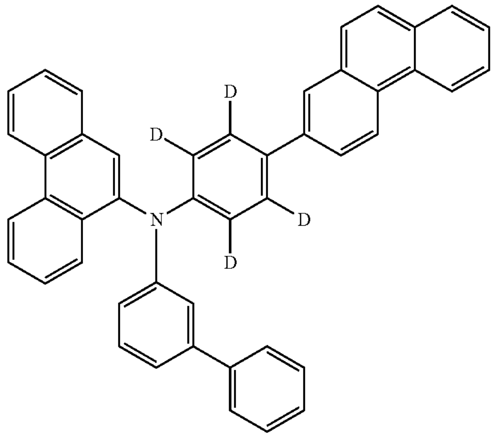
-continued
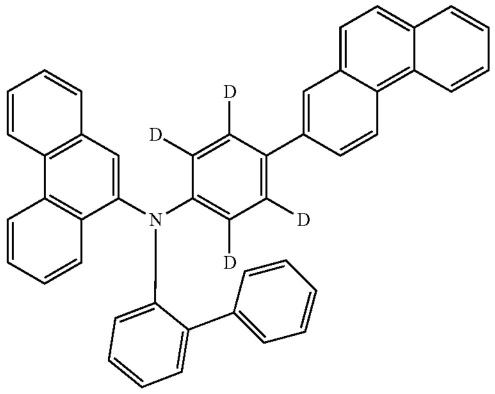
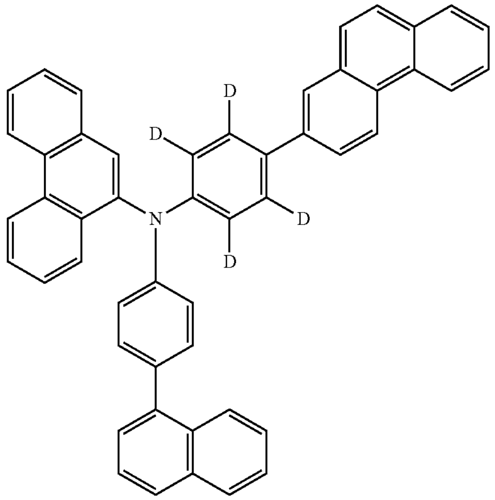
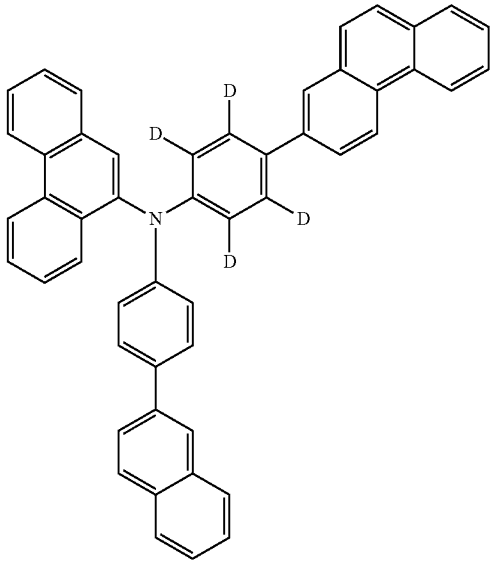

-continued
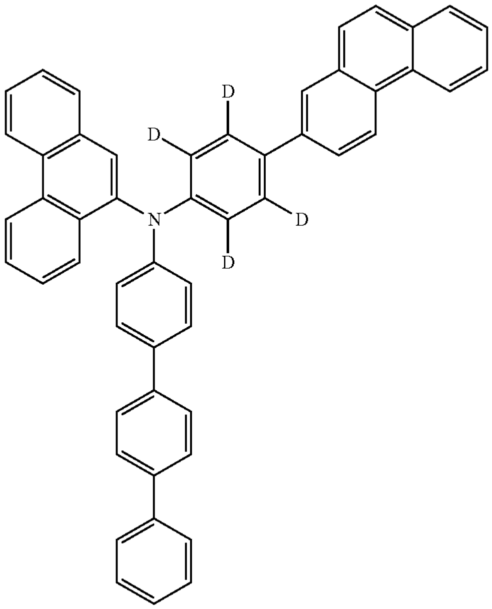
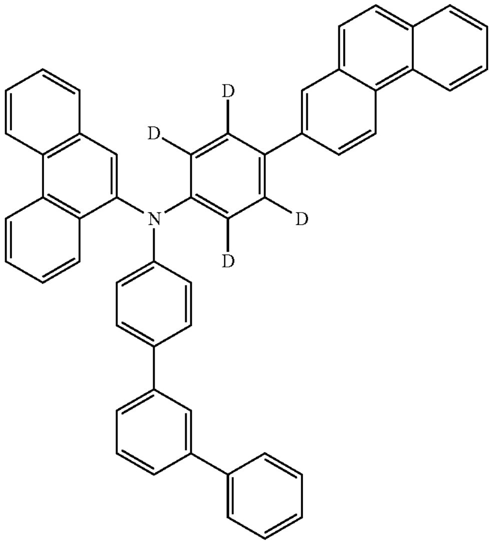
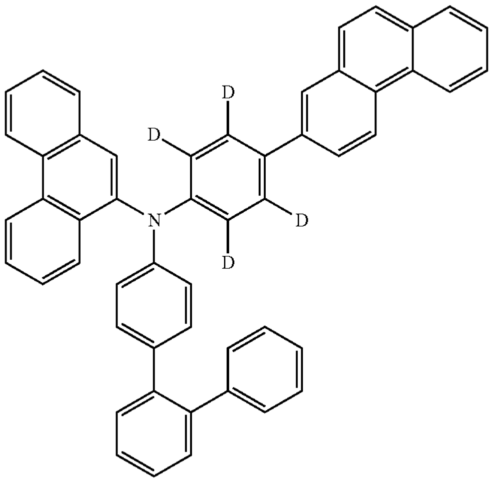
-continued
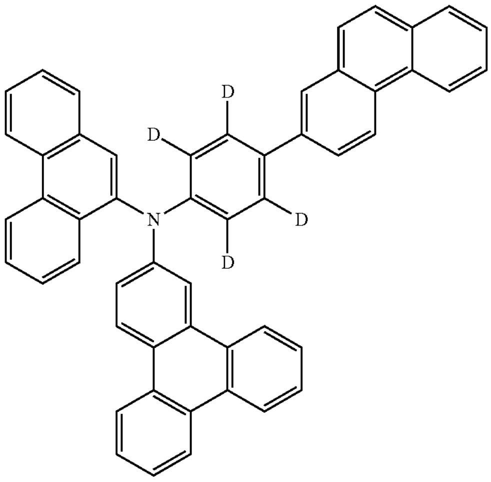
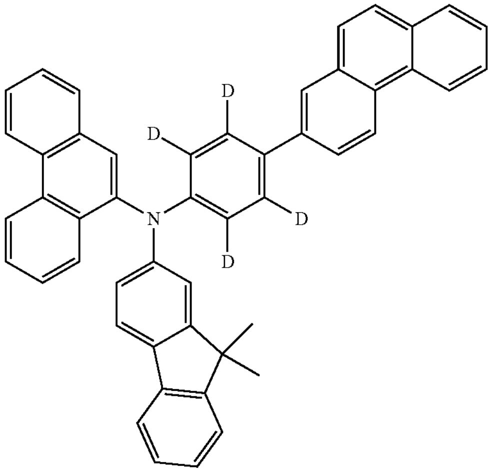
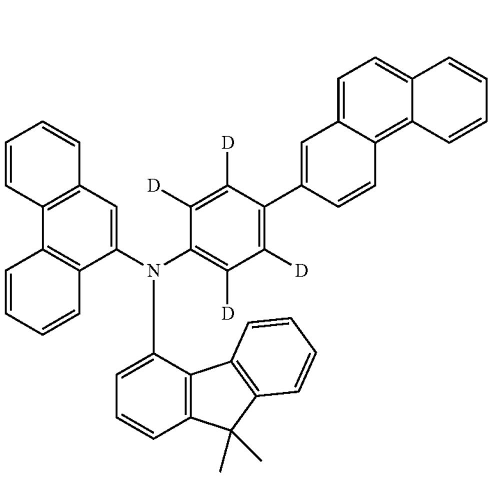

-continued
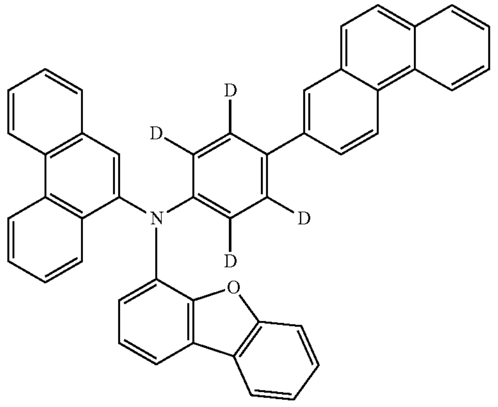
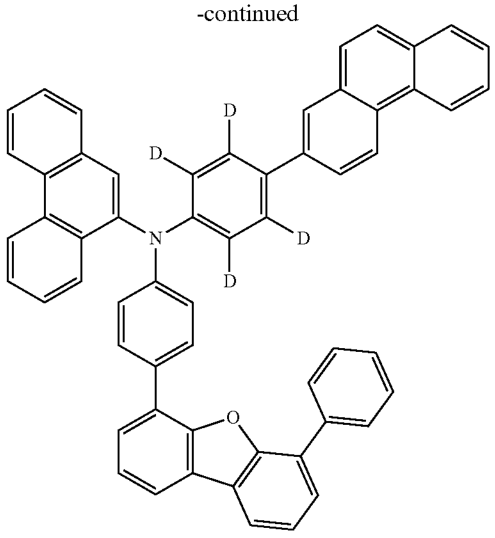
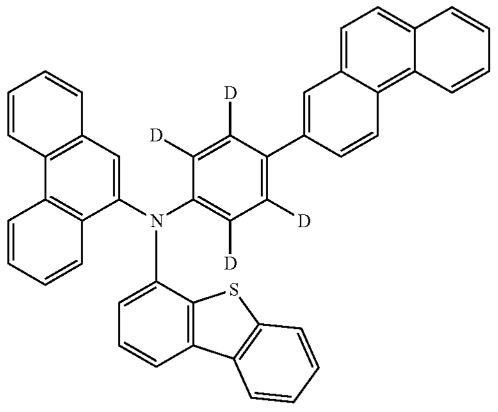
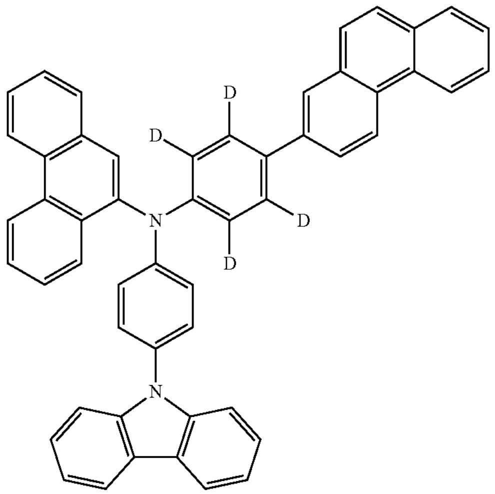
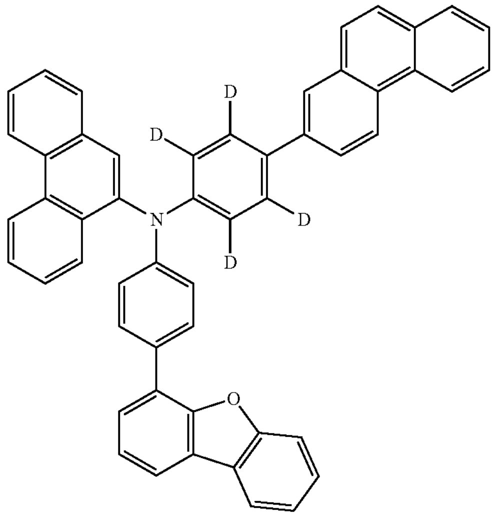
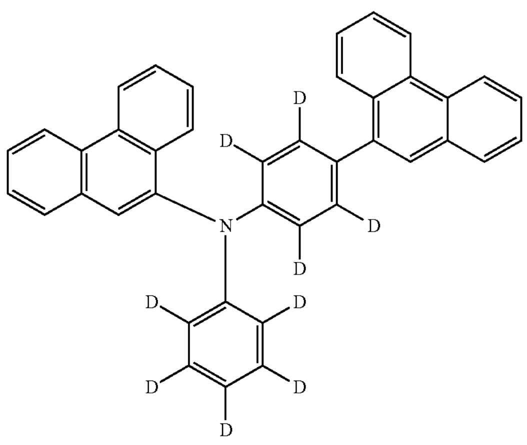
-continued

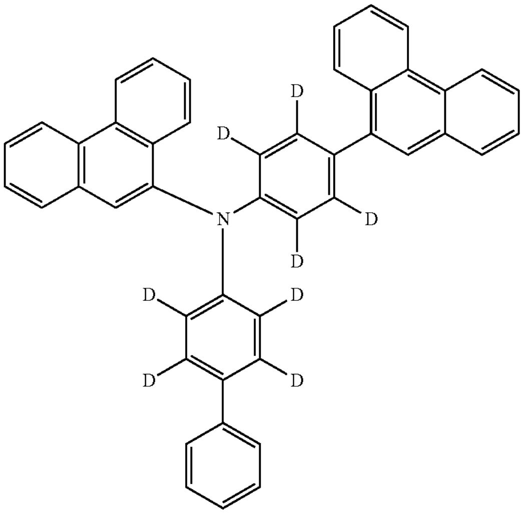
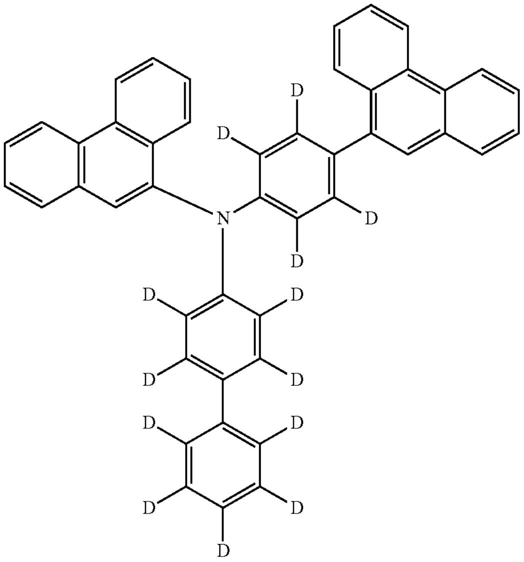
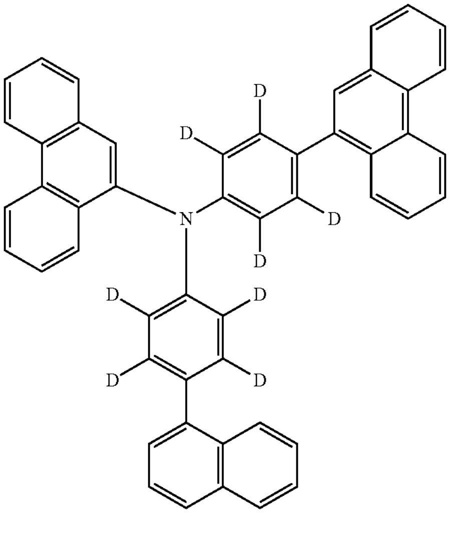
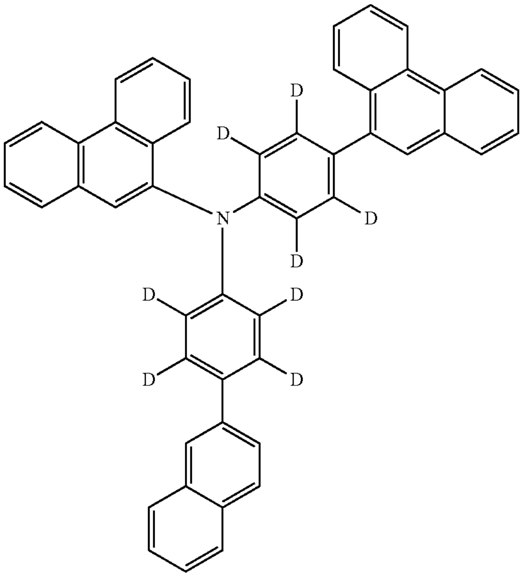
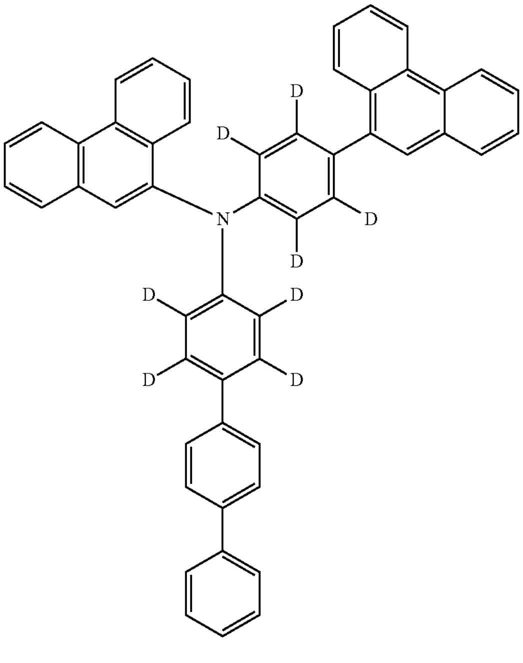

-continued
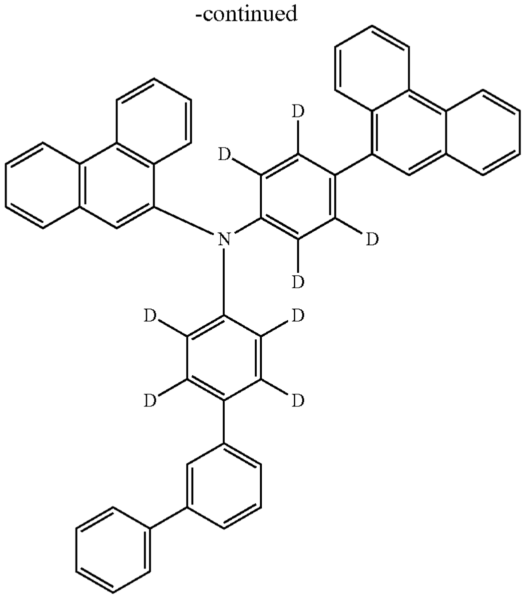
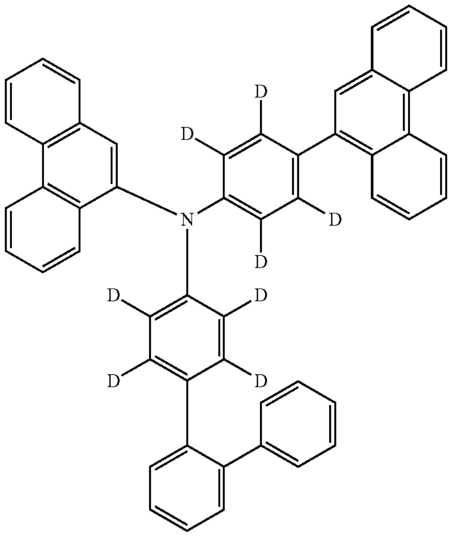
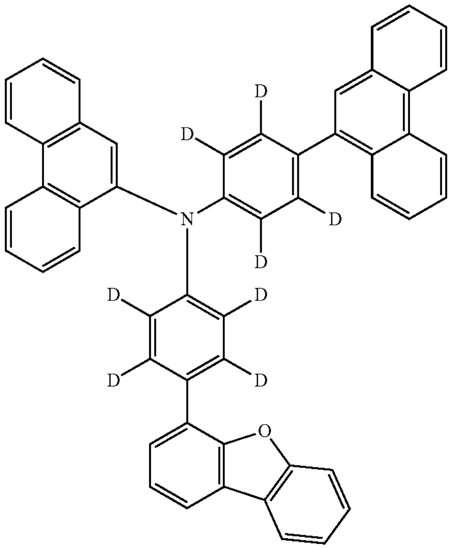
-continued
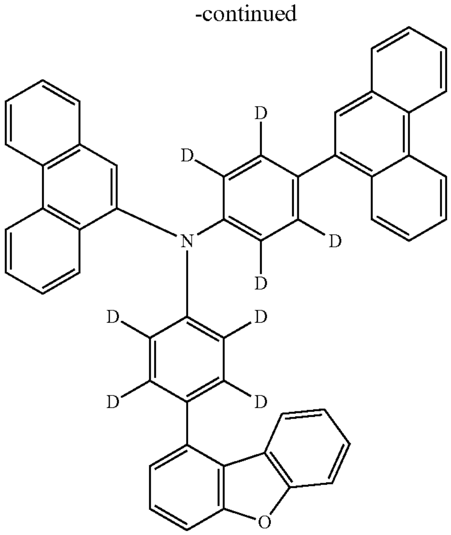
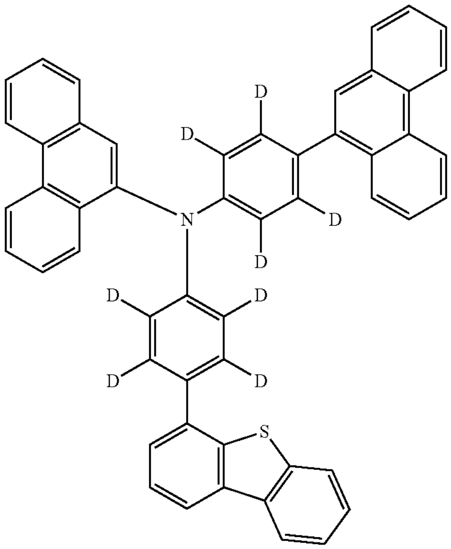
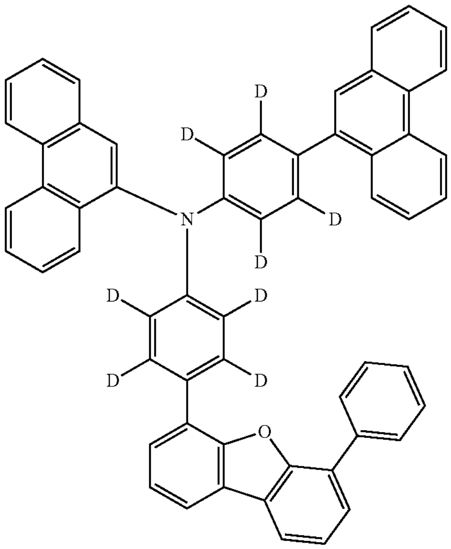

-continued
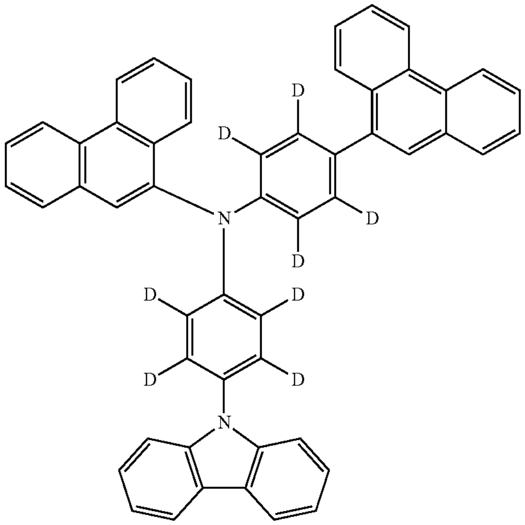
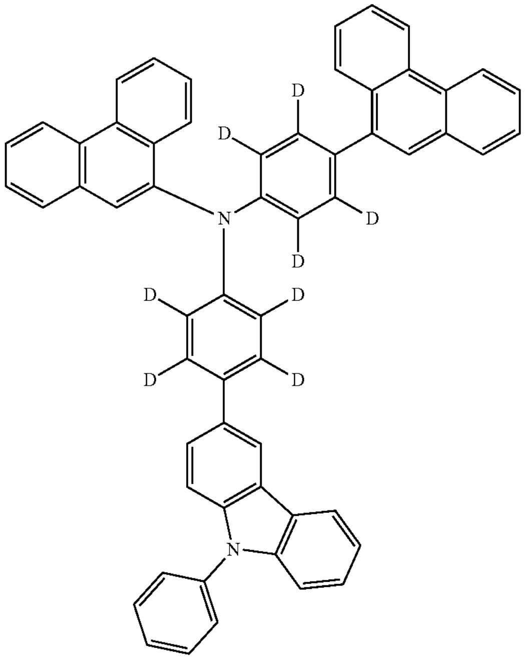
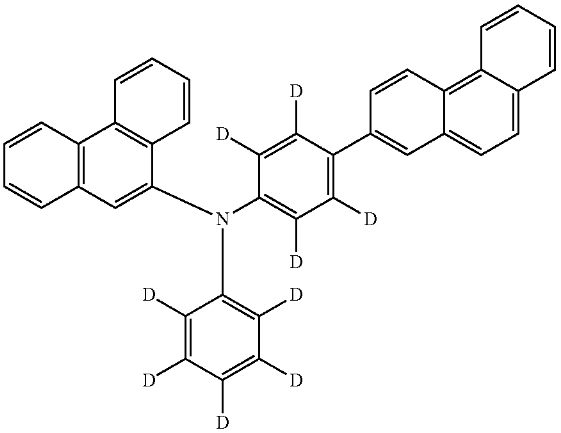
-continued
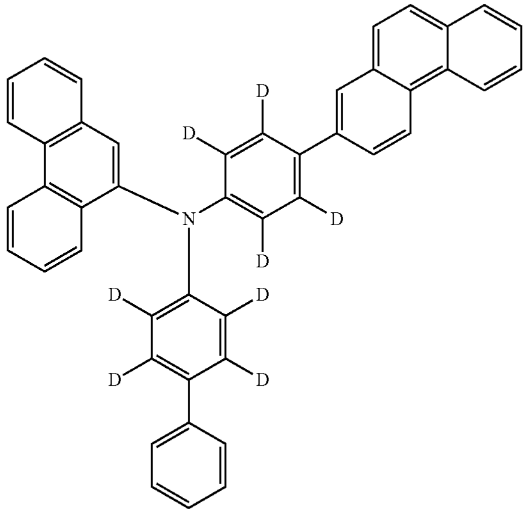
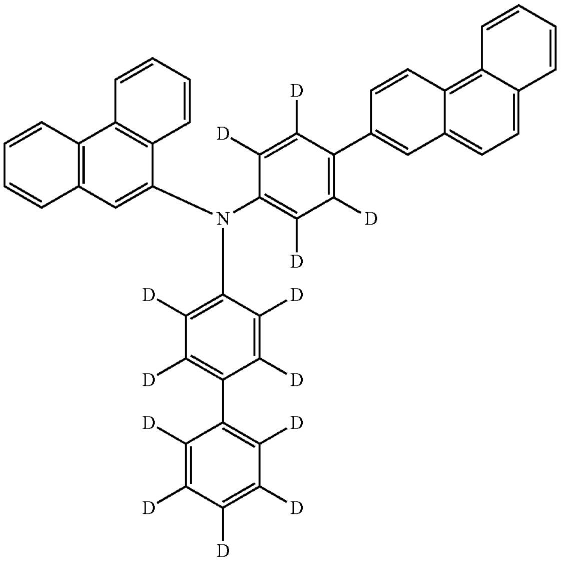
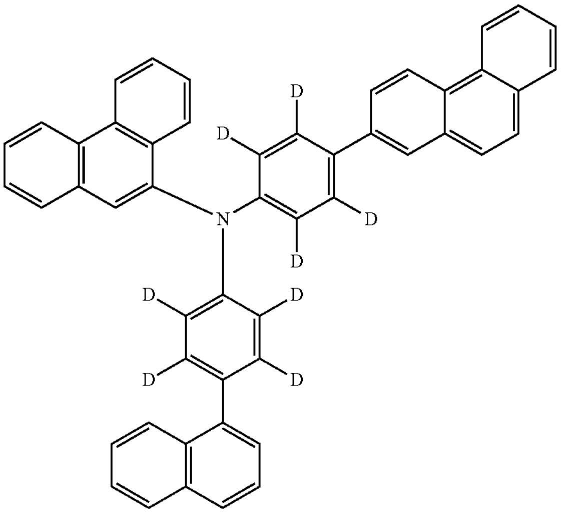

-continued
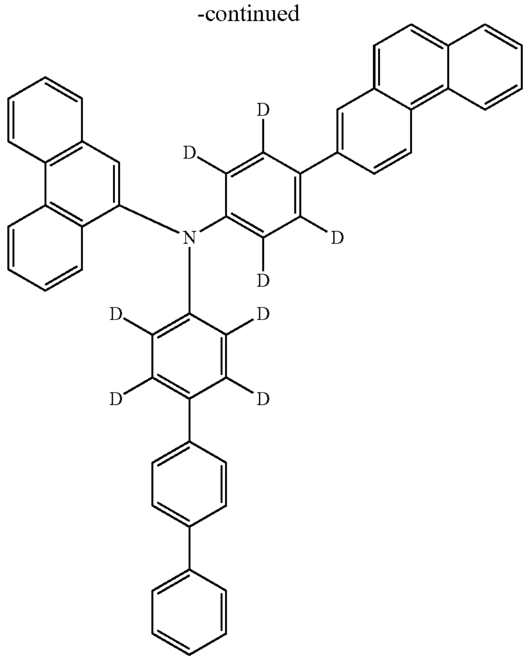
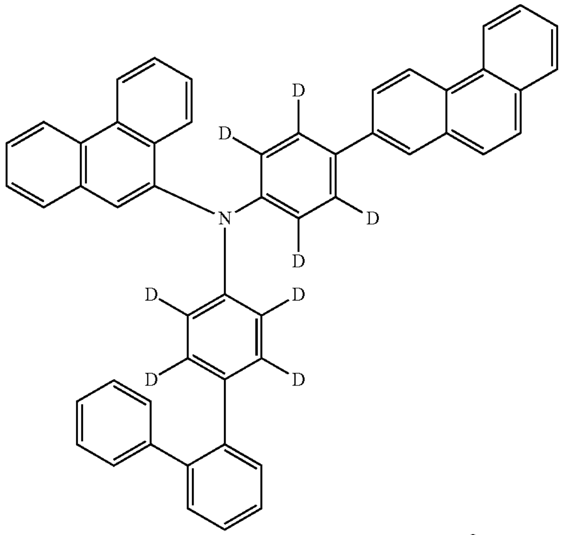
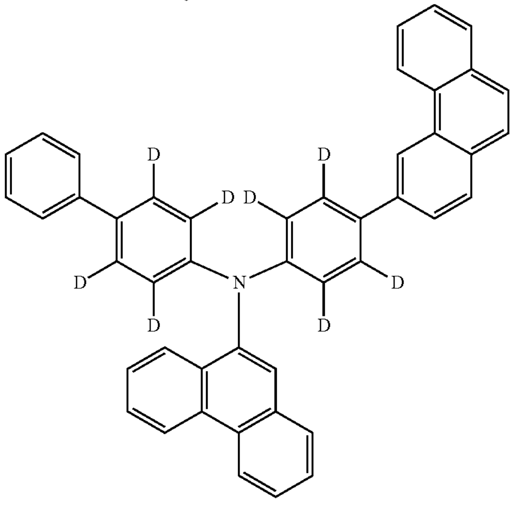
-continued
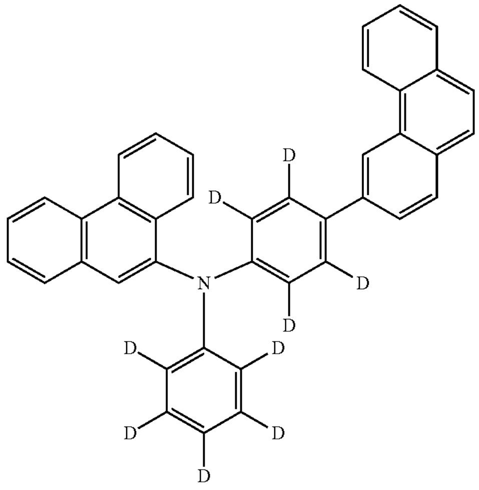
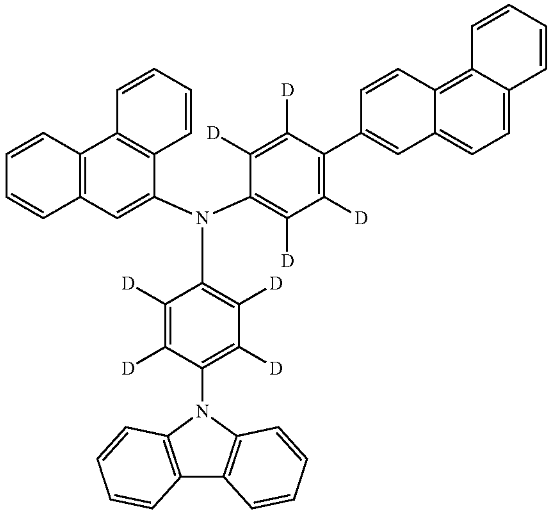
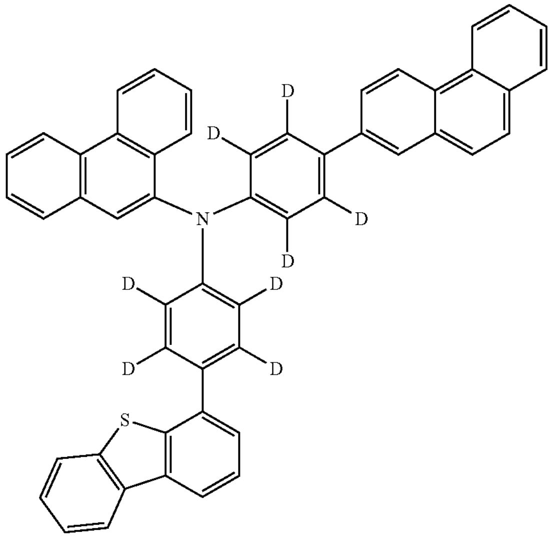

-continued
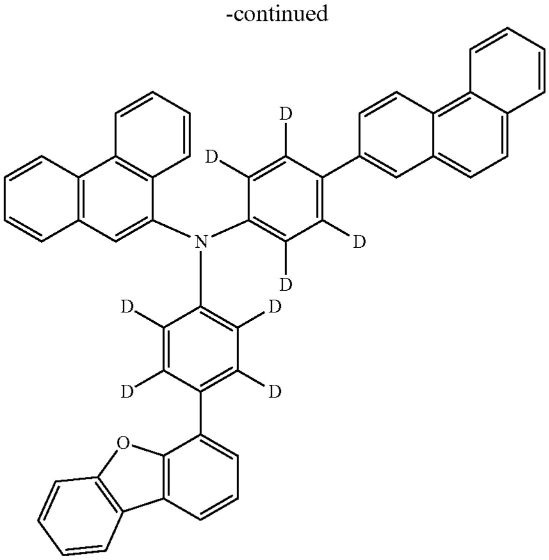
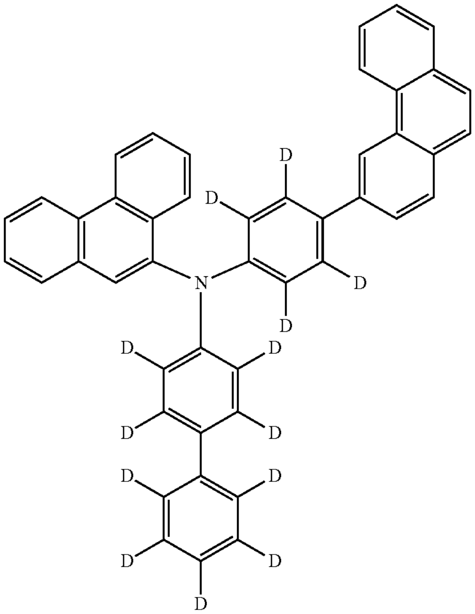
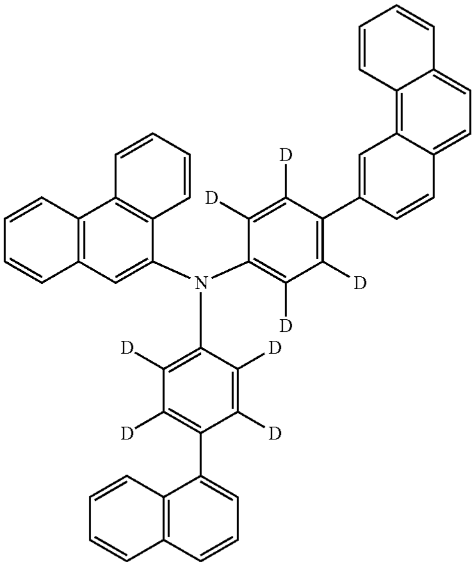
-continued
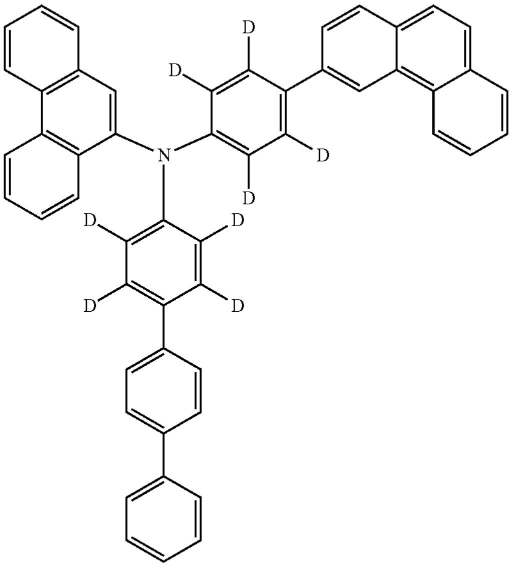
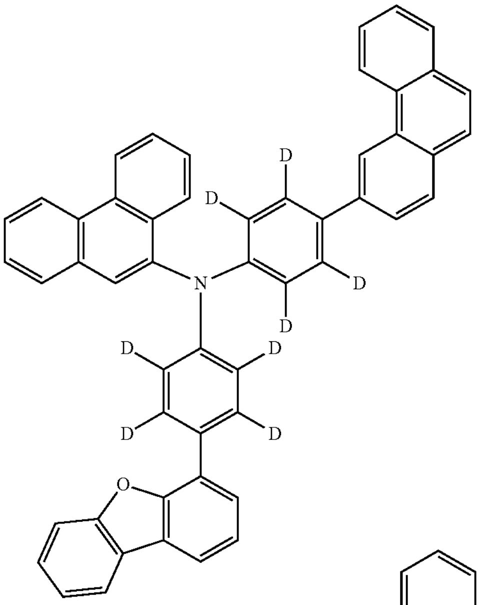
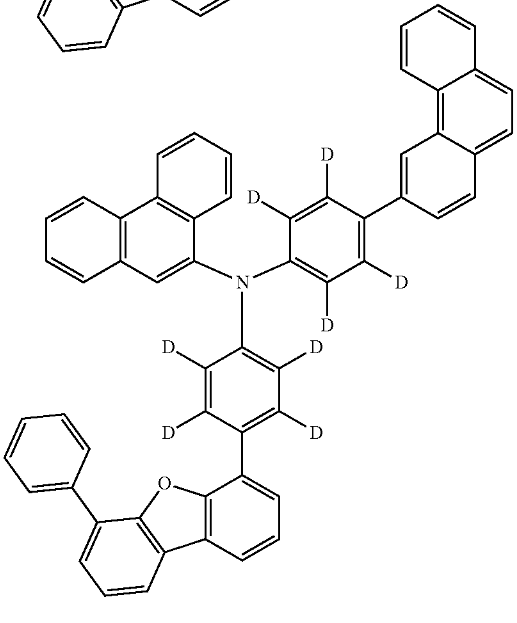

-continued
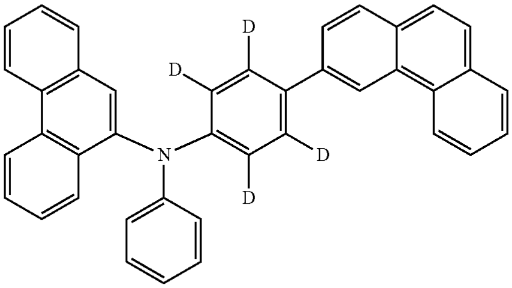
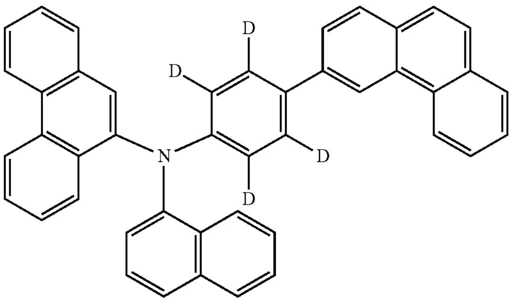
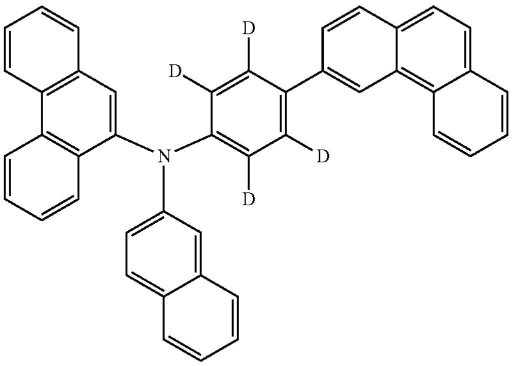
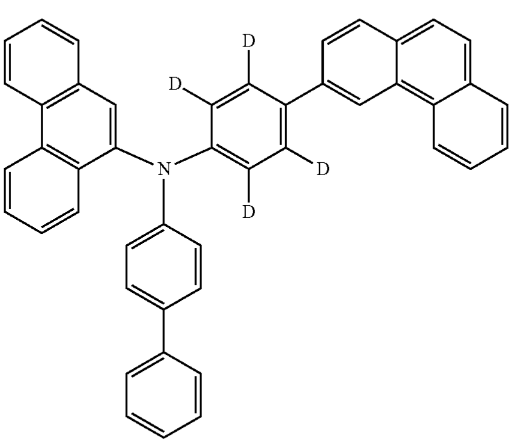
-continued
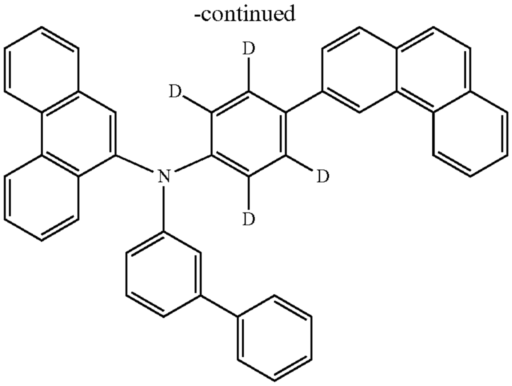
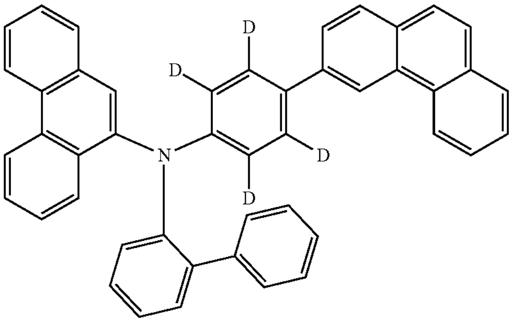
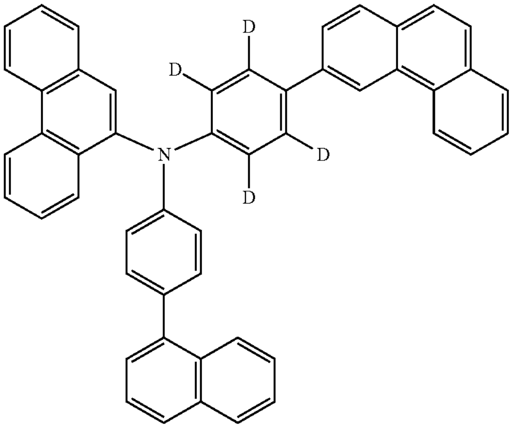
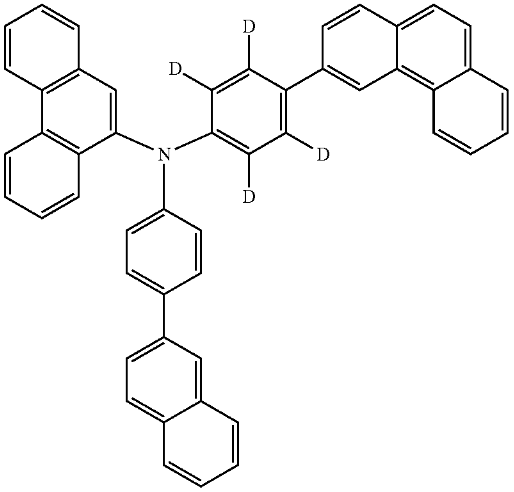

-continued
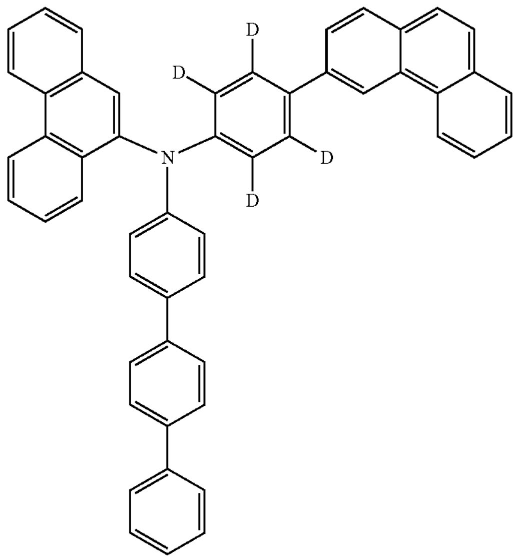
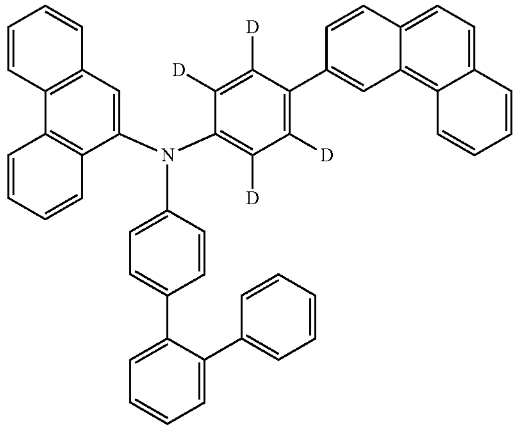
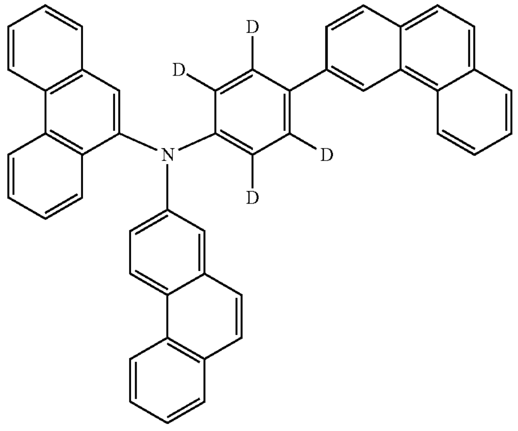
-continued
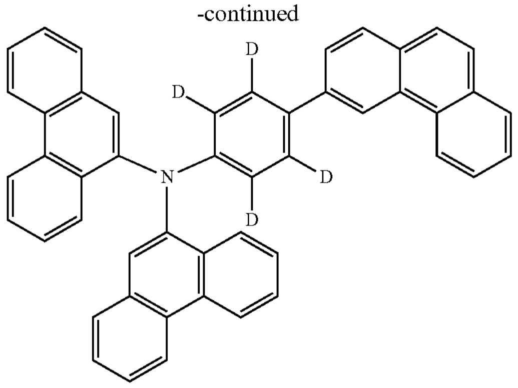
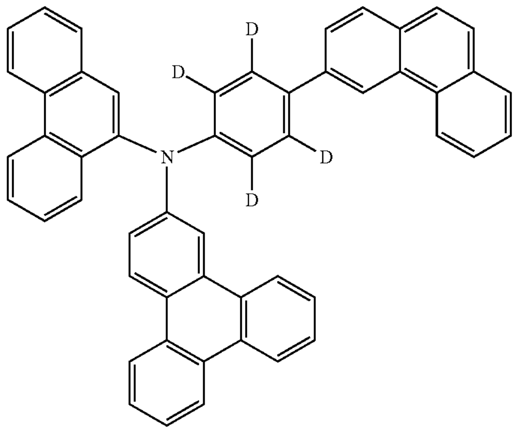
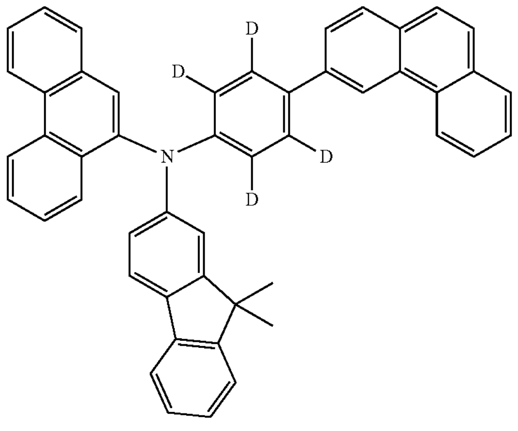
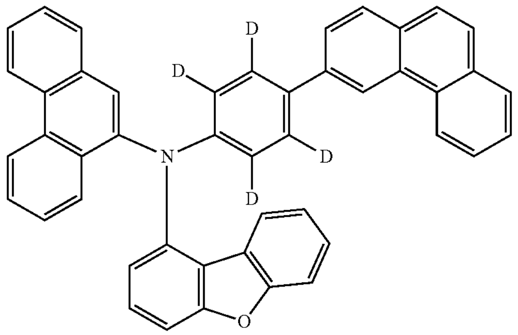

-continued
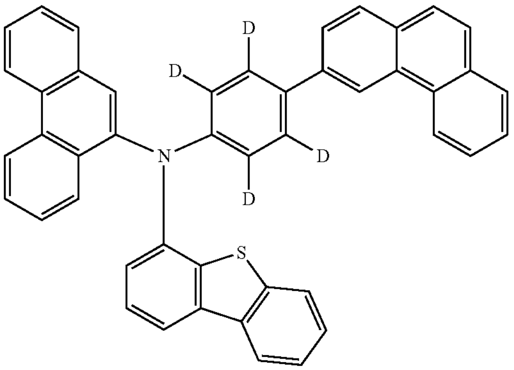
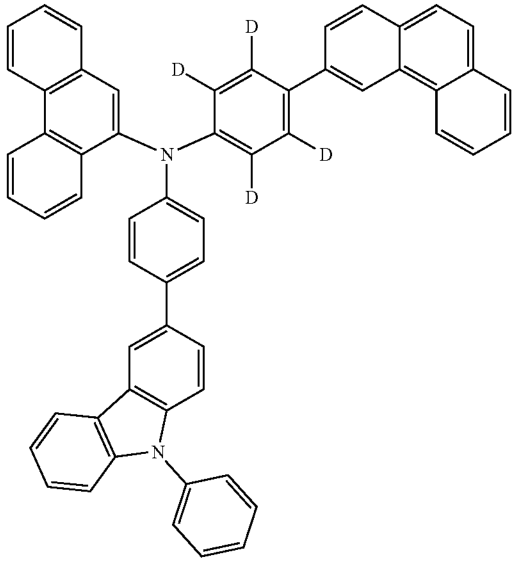
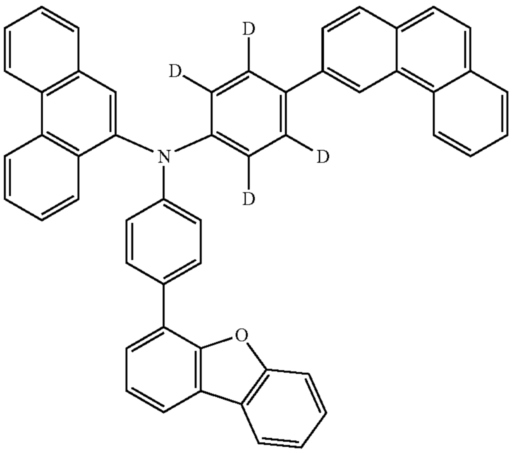
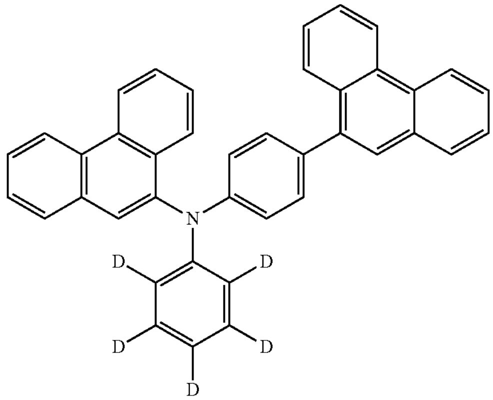
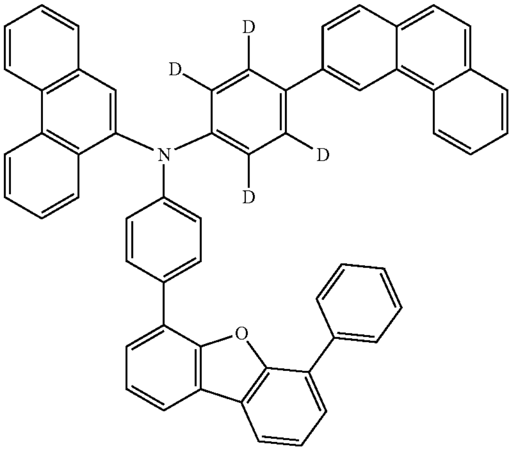
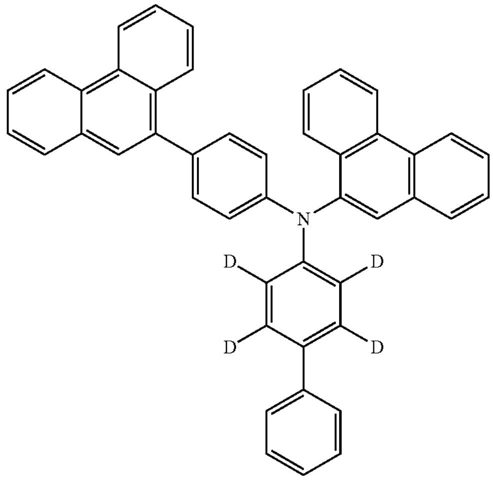
-continued -continued
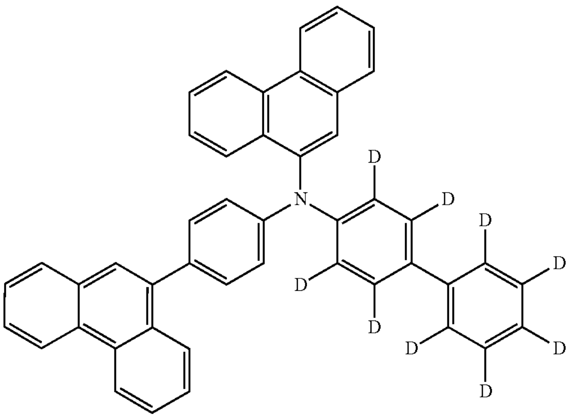
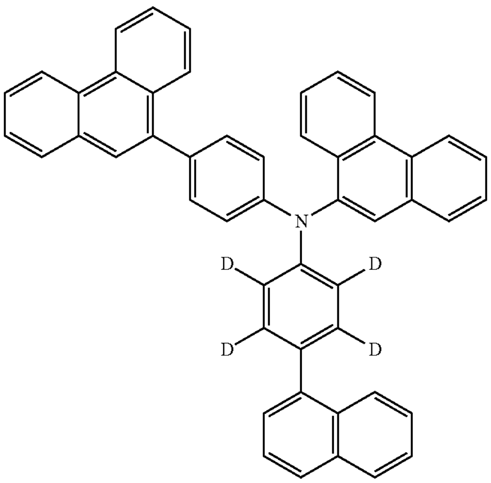
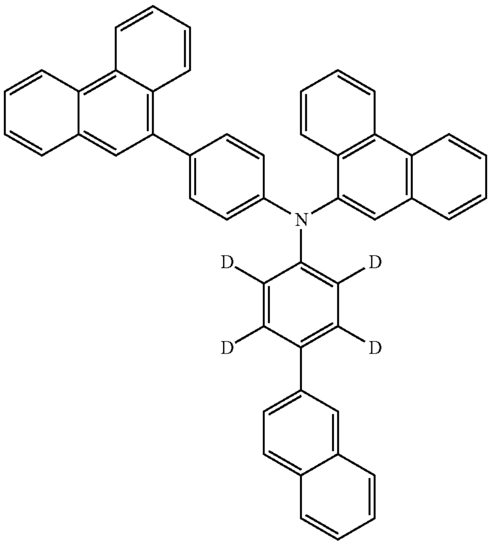
-continued
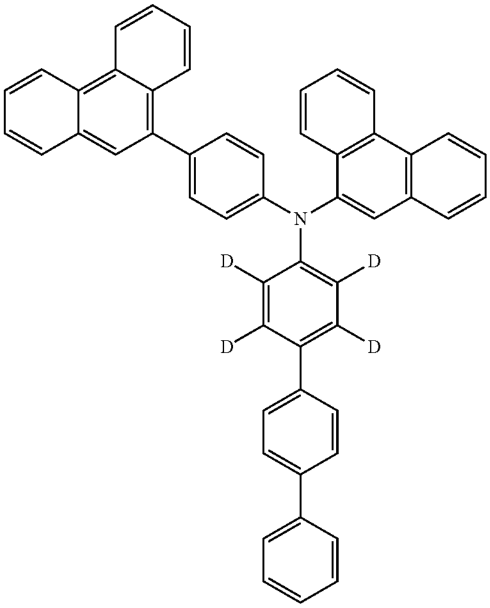
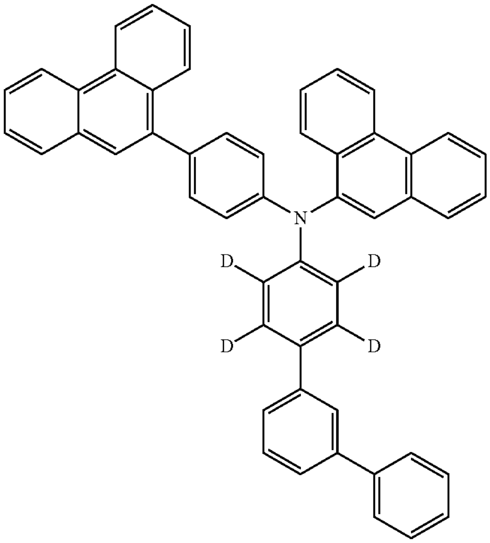
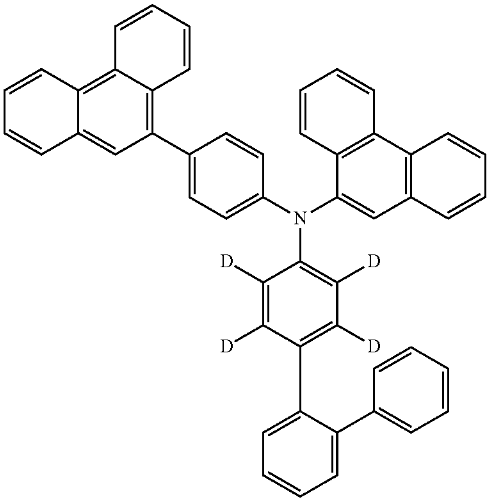

-continued
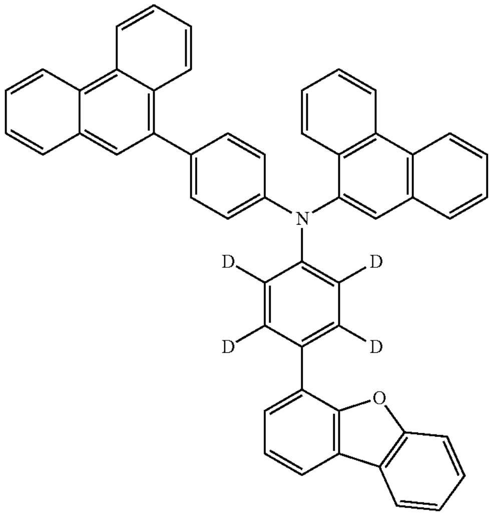
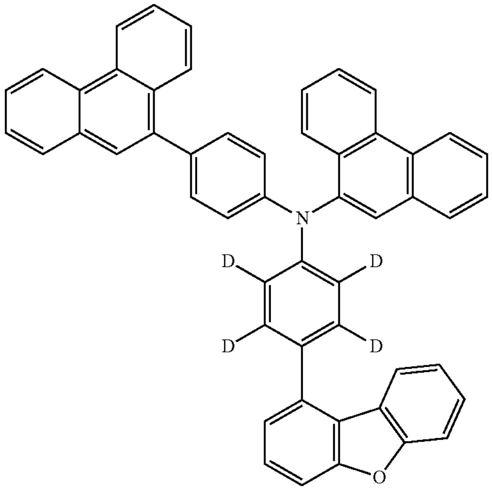
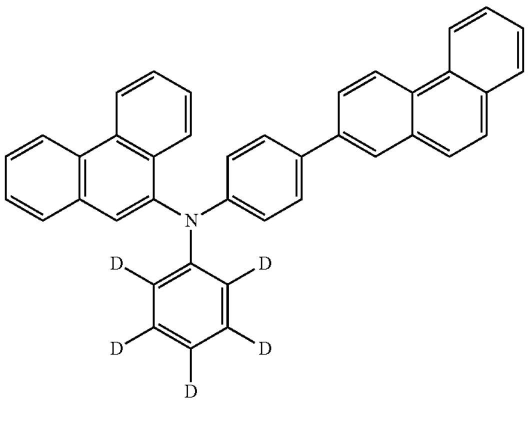
-continued
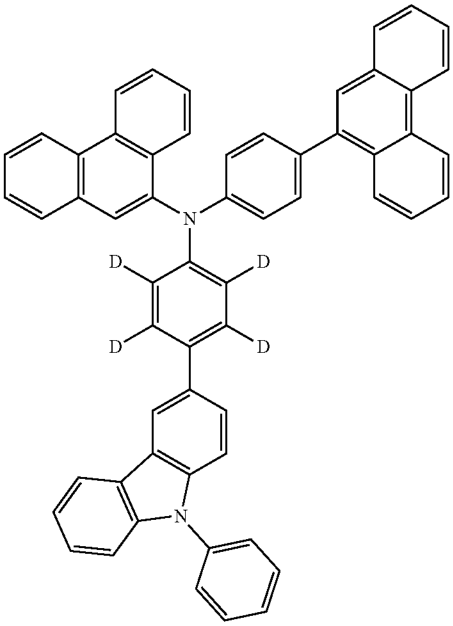
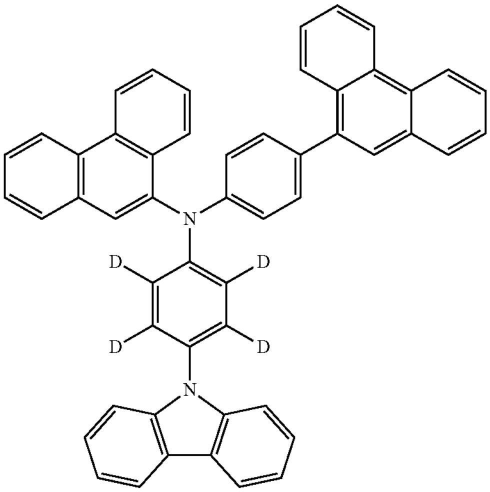
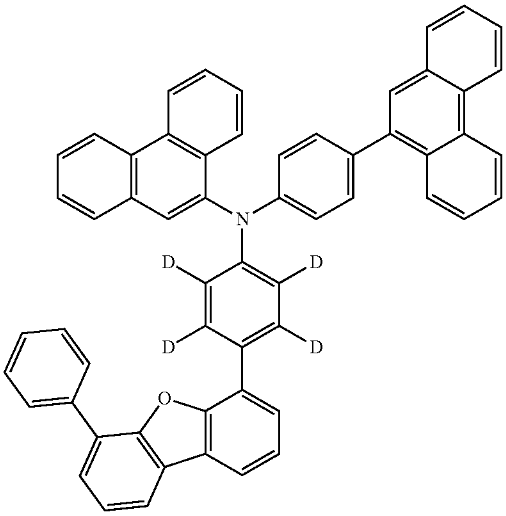

-continued
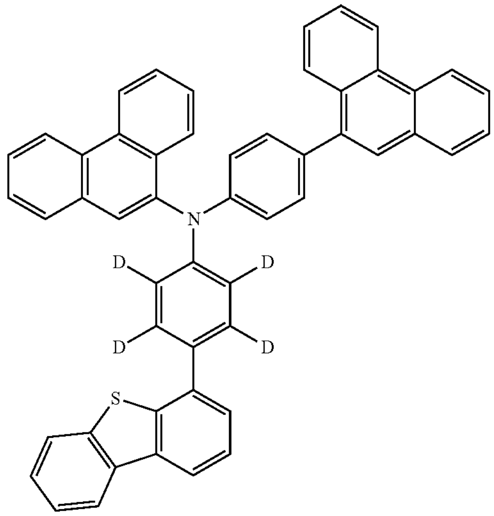
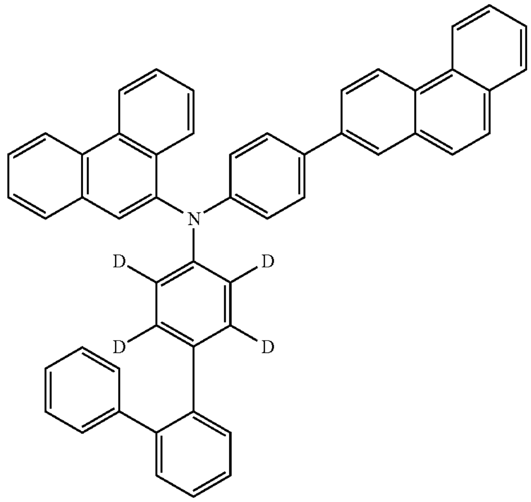
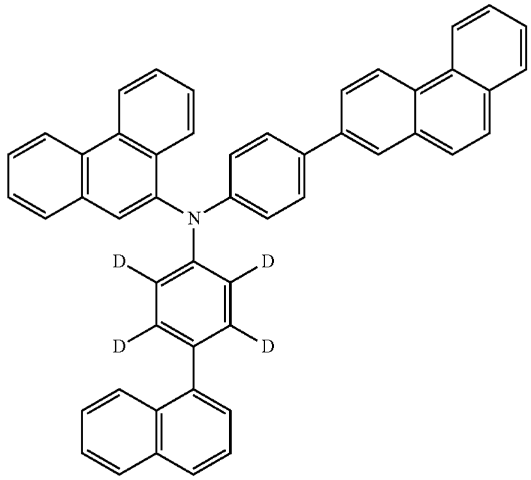
-continued
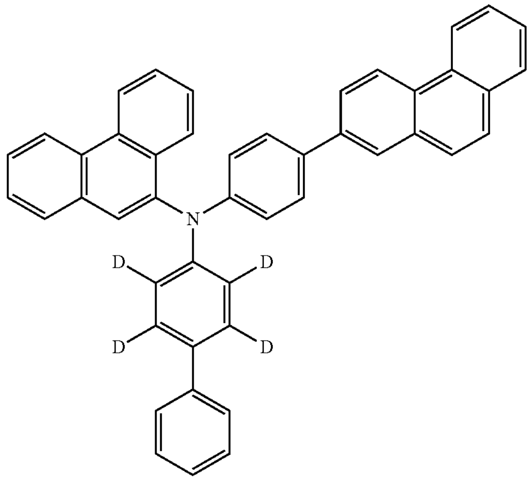
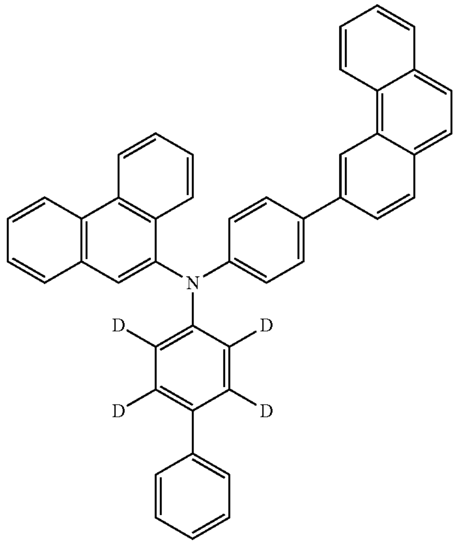
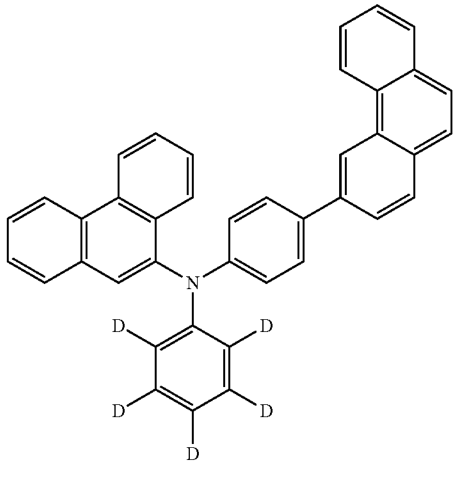

-continued
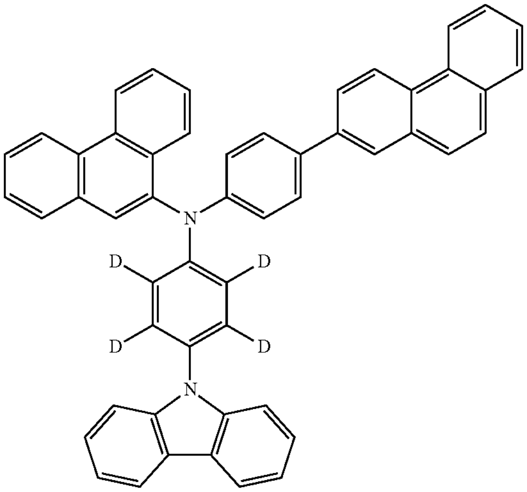
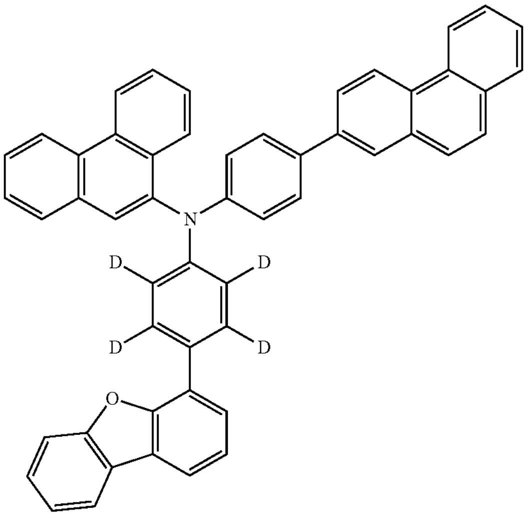
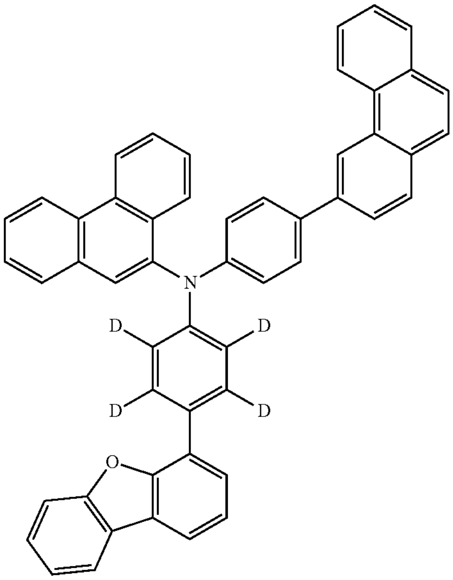
-continued
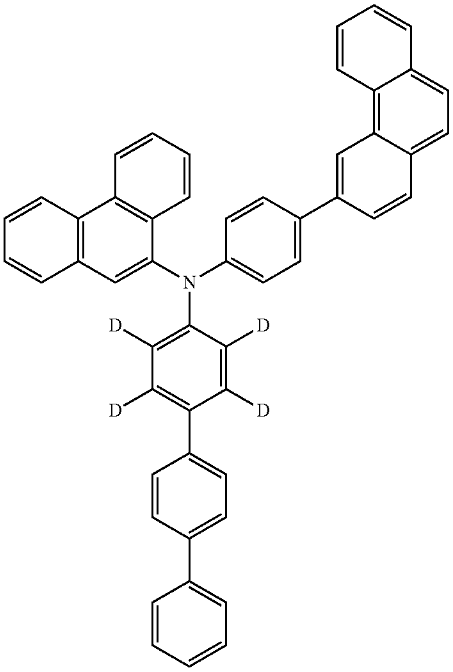
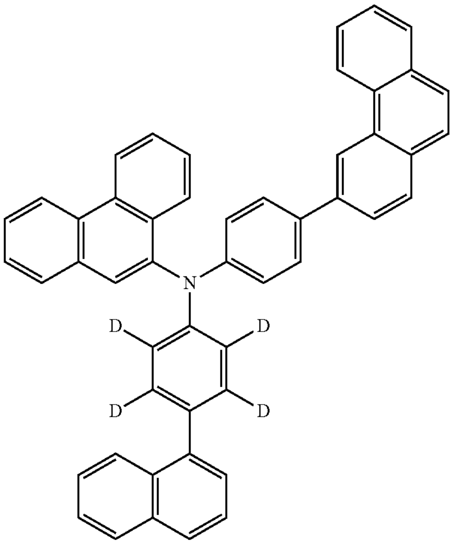
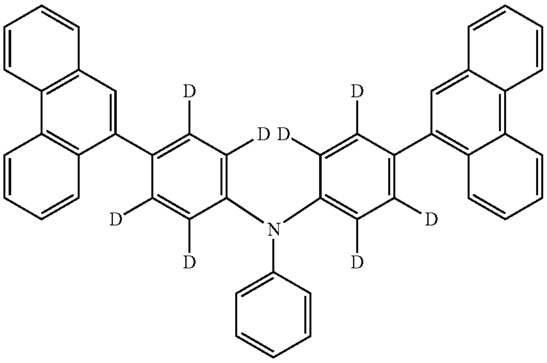

-continued
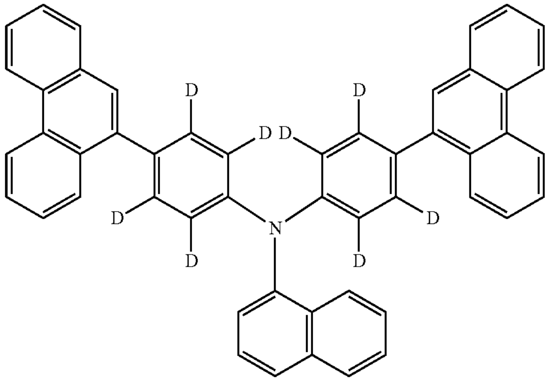
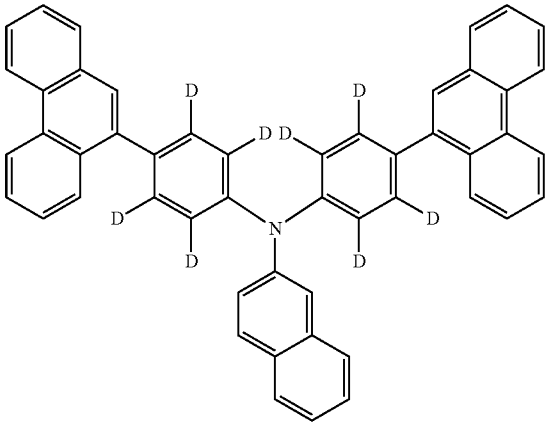
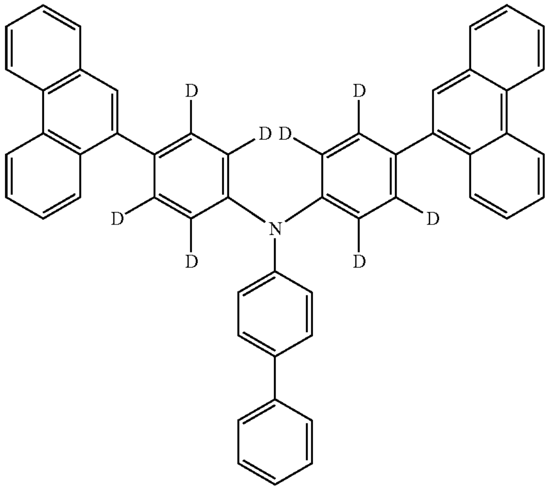
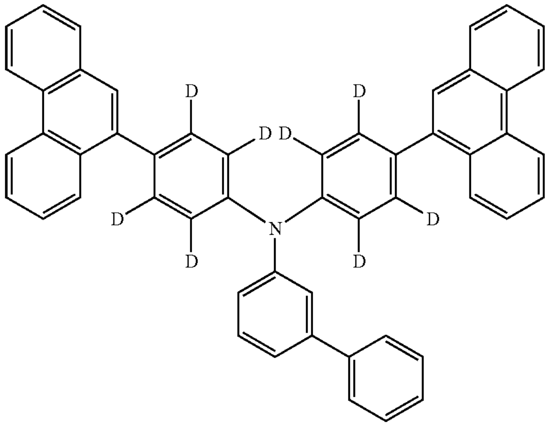
-continued
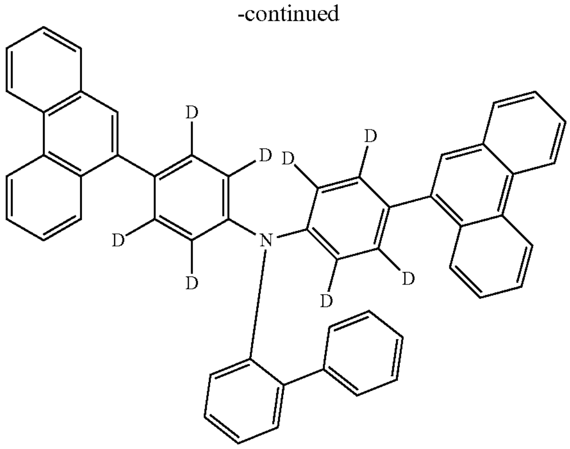
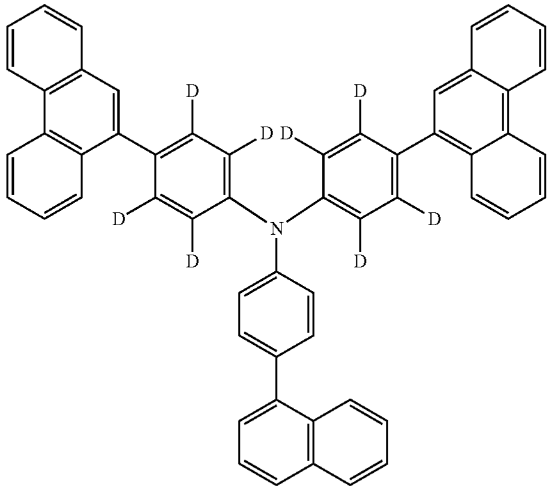
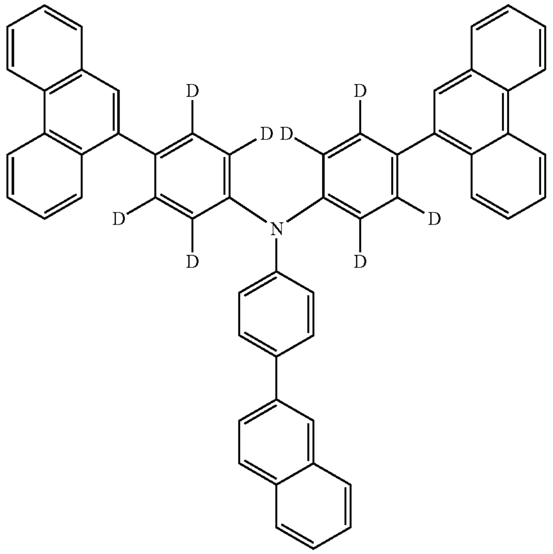

-continued
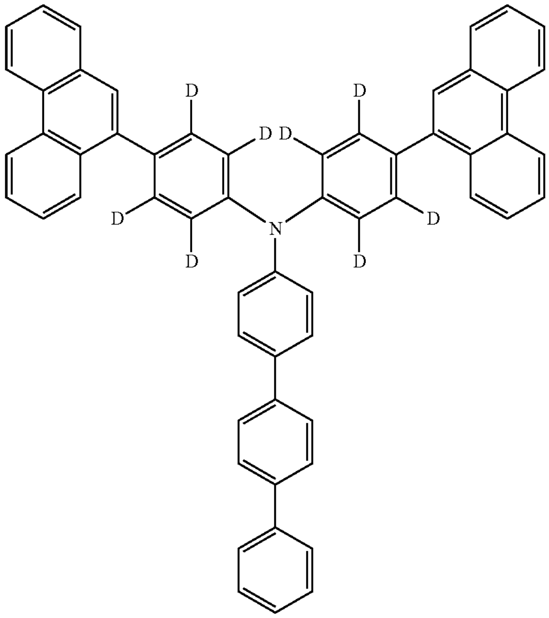
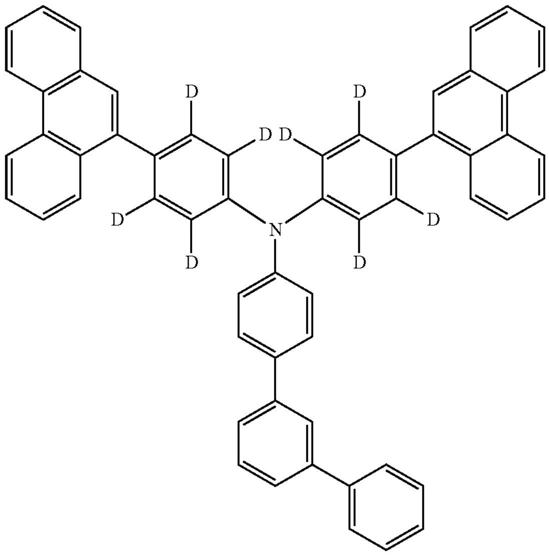
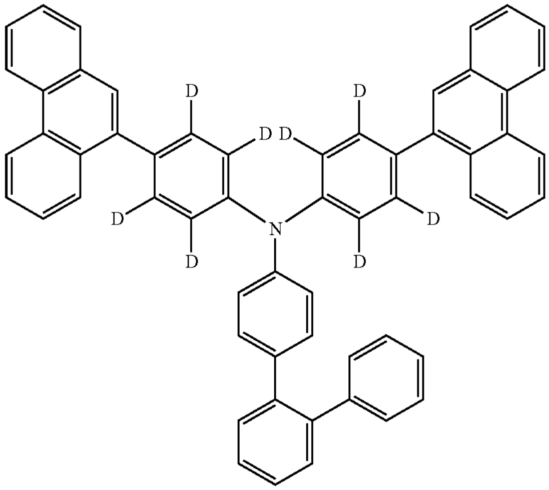
-continued
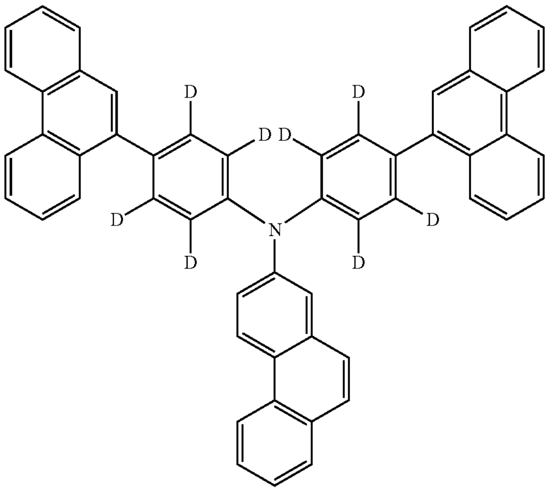
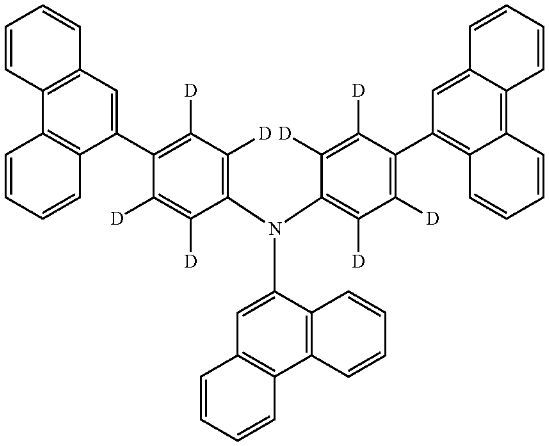
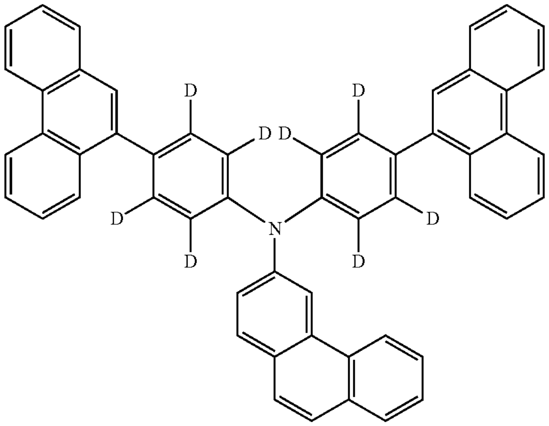

-continued
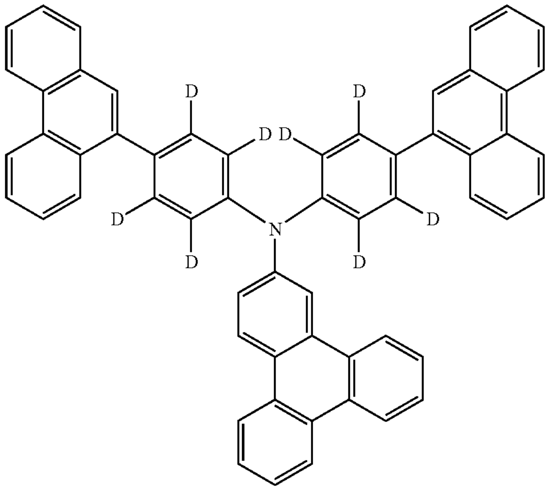
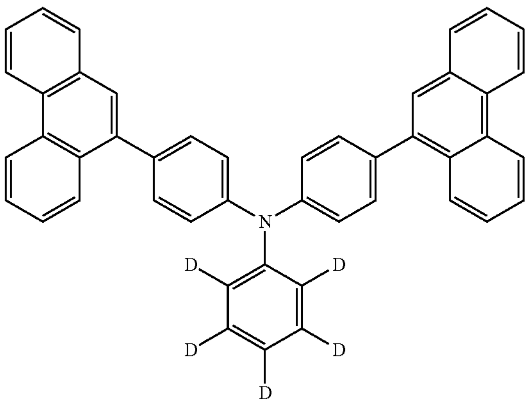
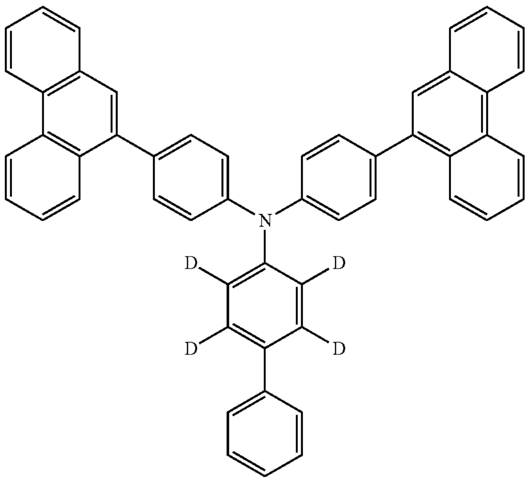
-continued
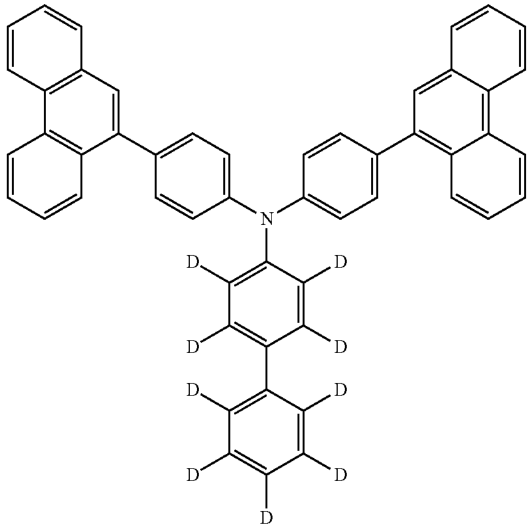
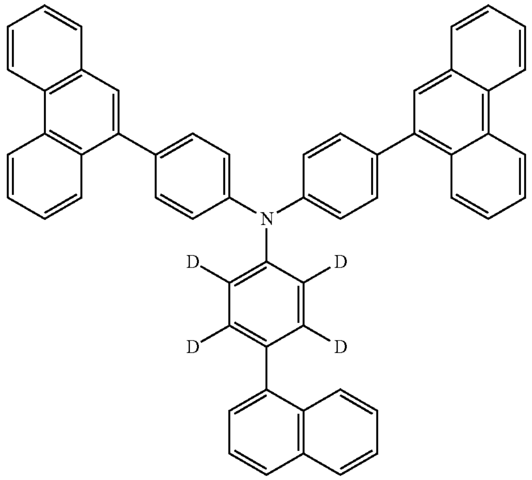
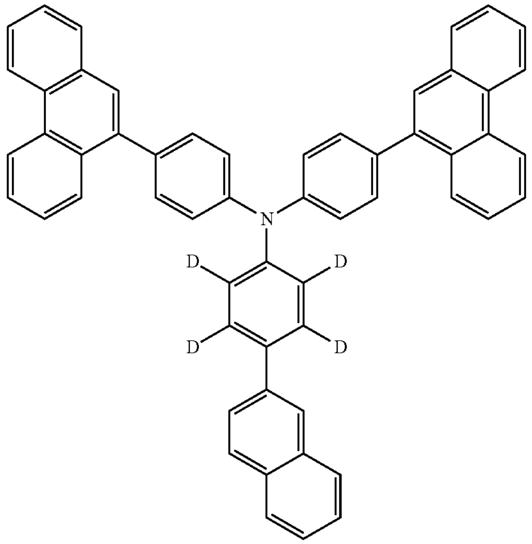

-continued
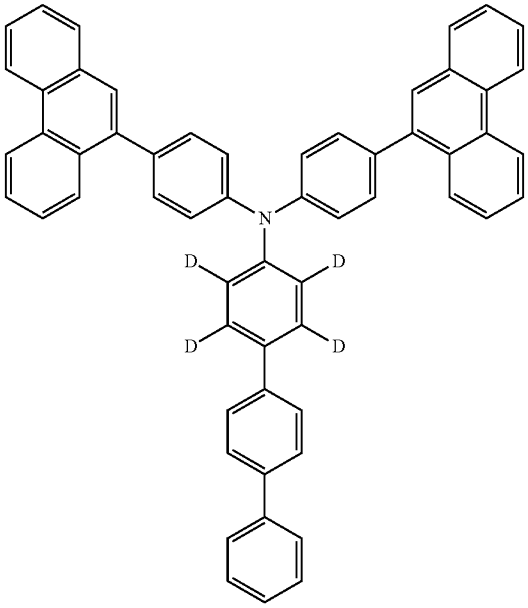
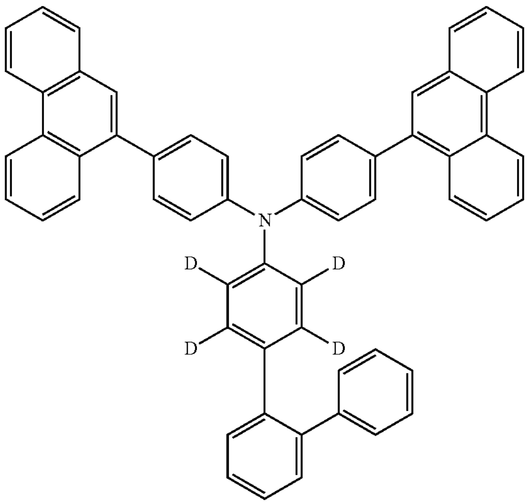
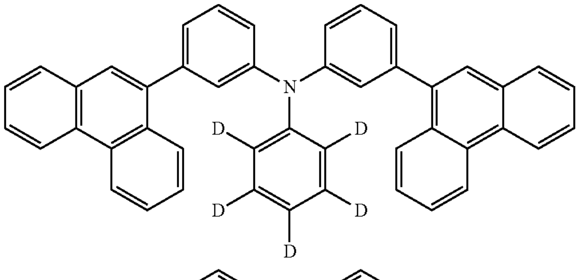
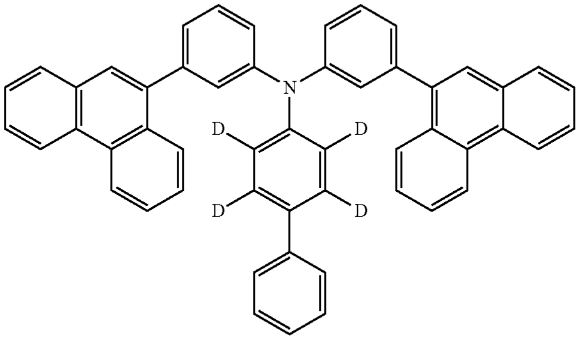
-continued
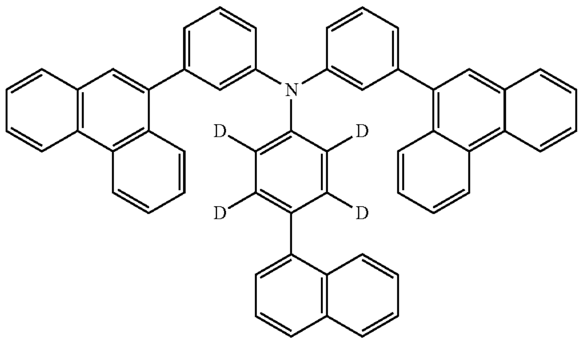
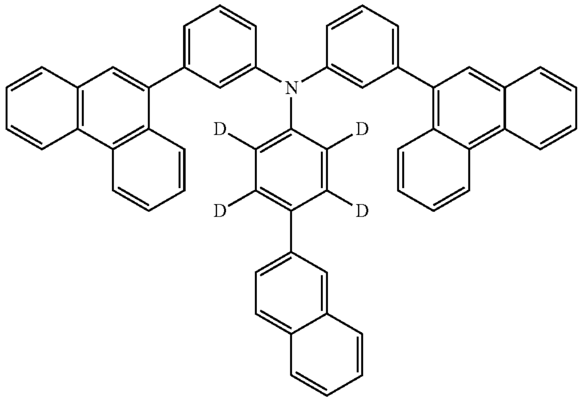
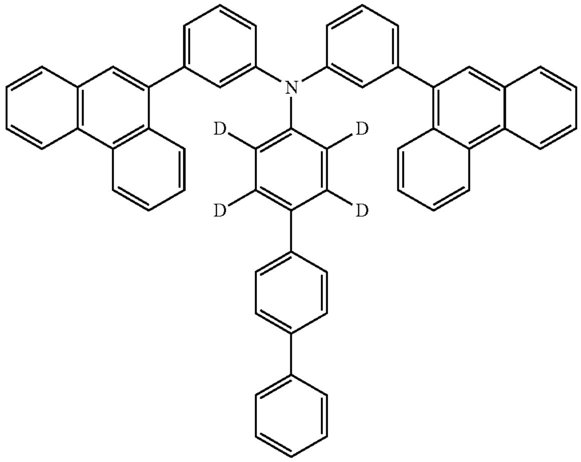
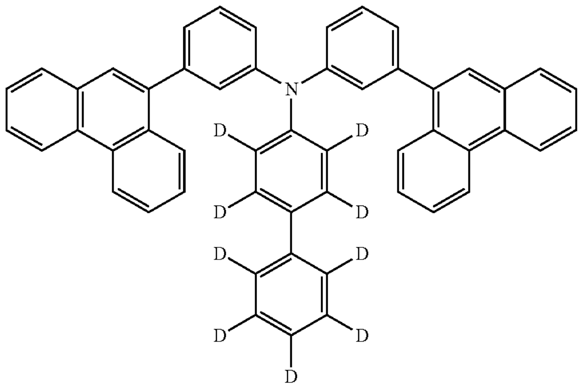

-continued
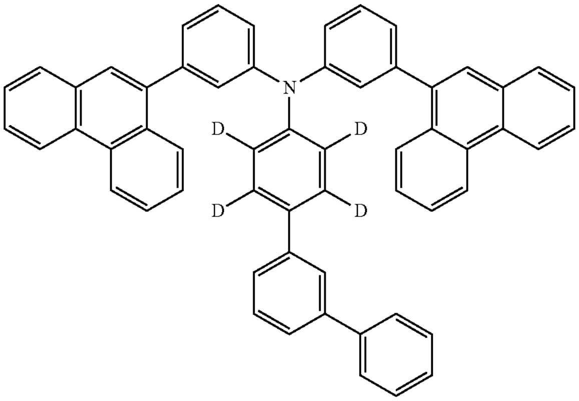
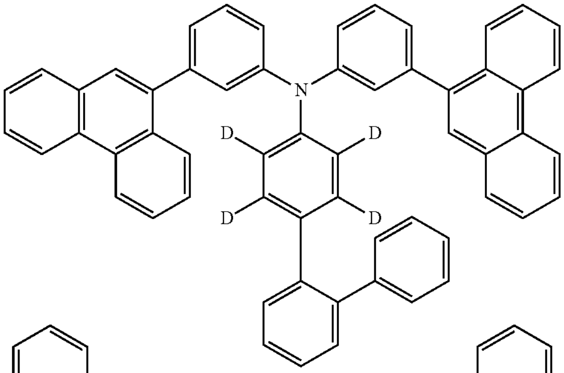
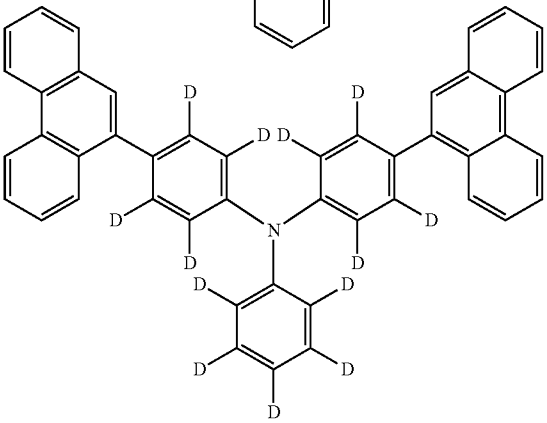
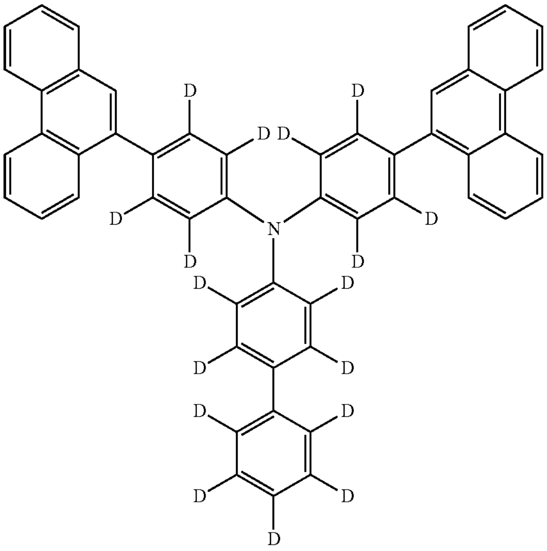
-continued
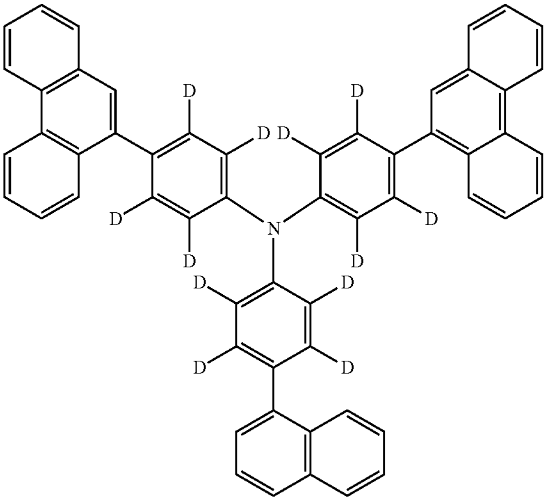
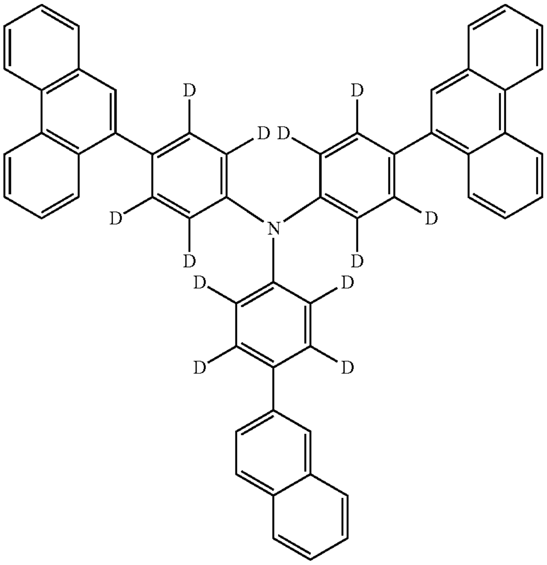
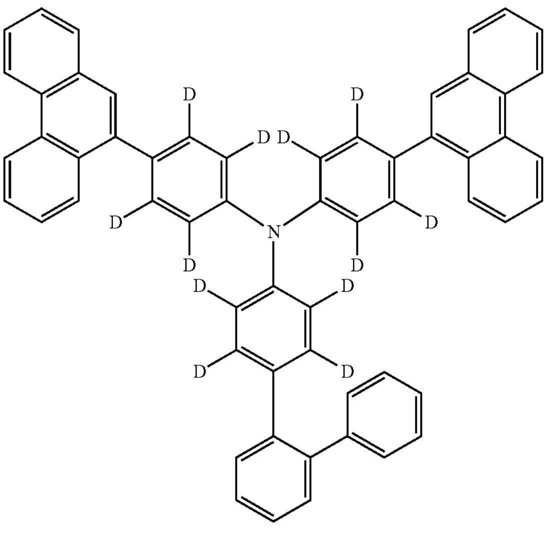

-continued
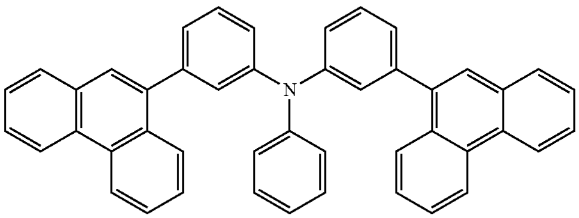
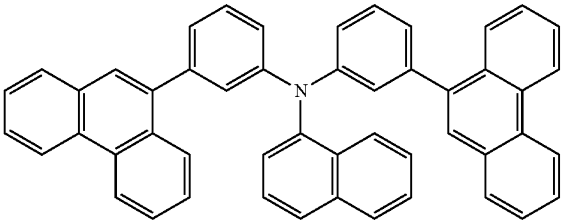
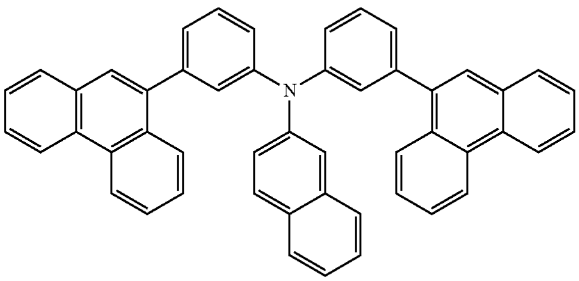
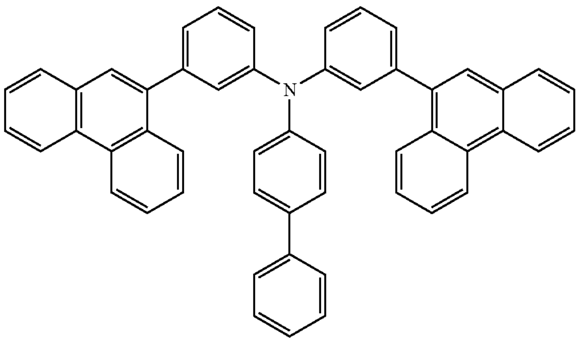
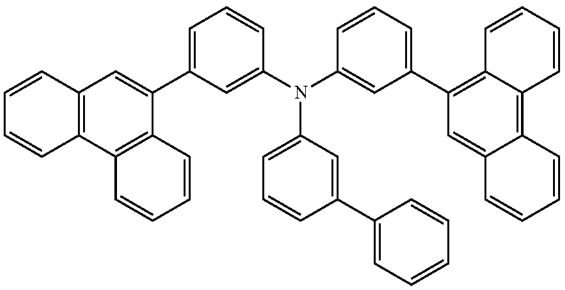
-continued
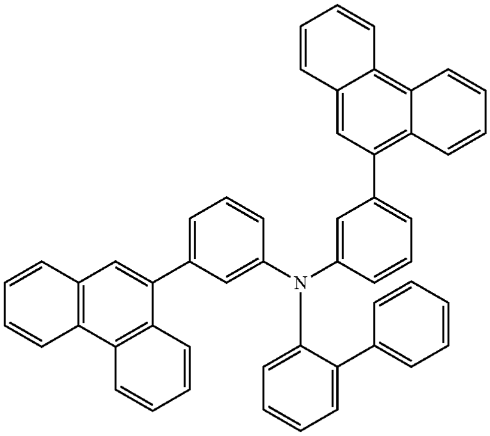
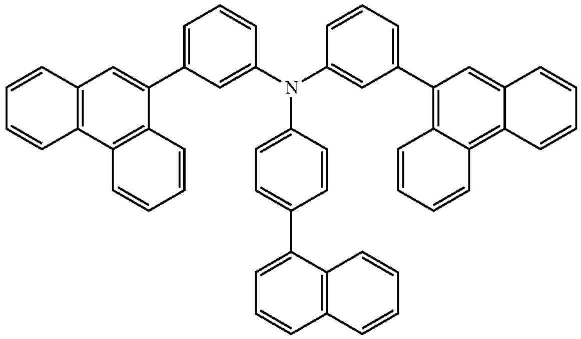
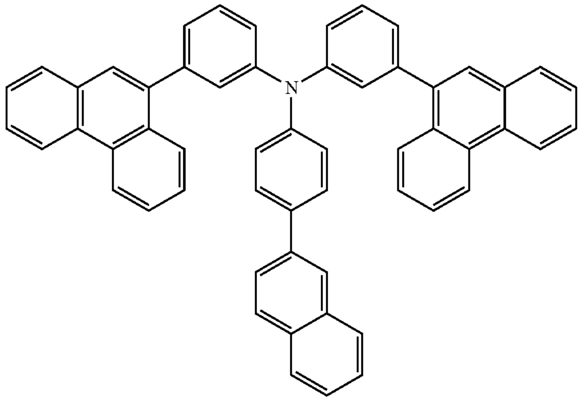
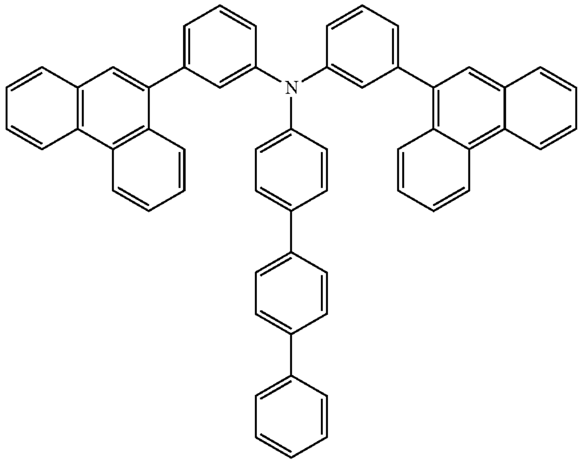

-continued
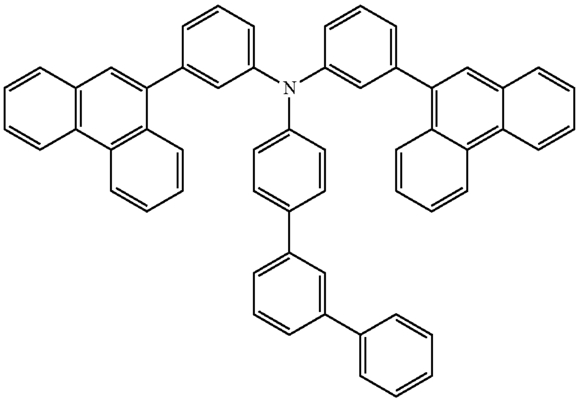
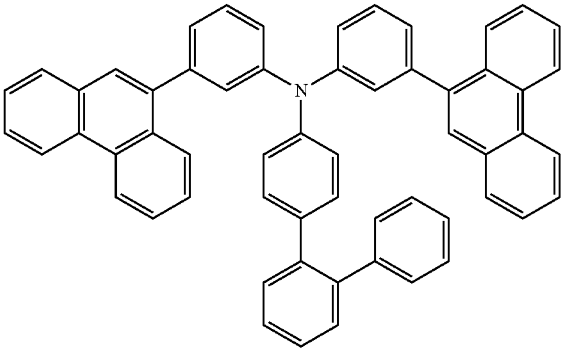
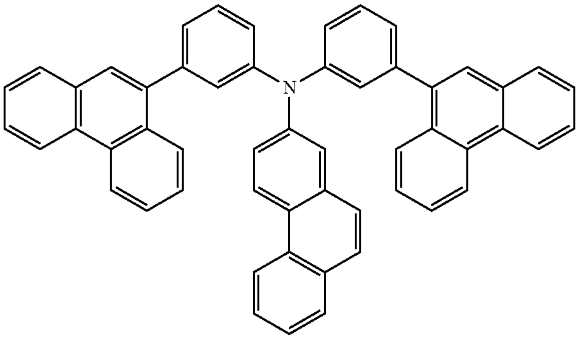
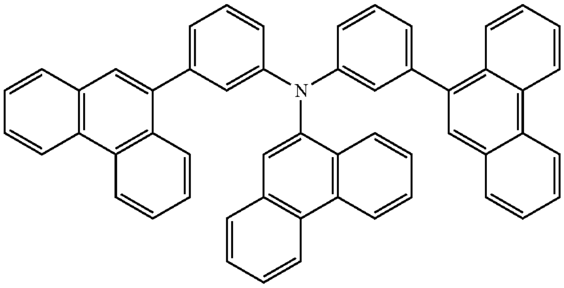
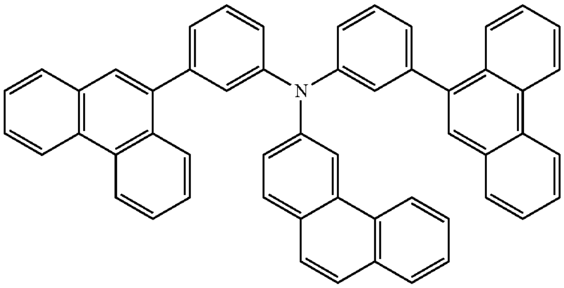
-continued
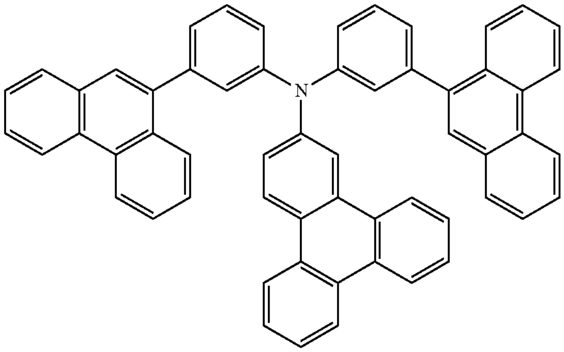
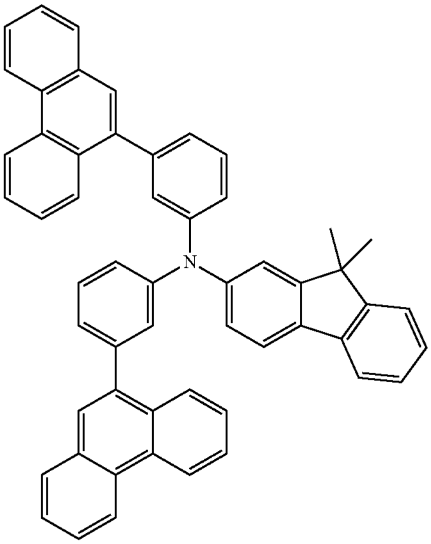
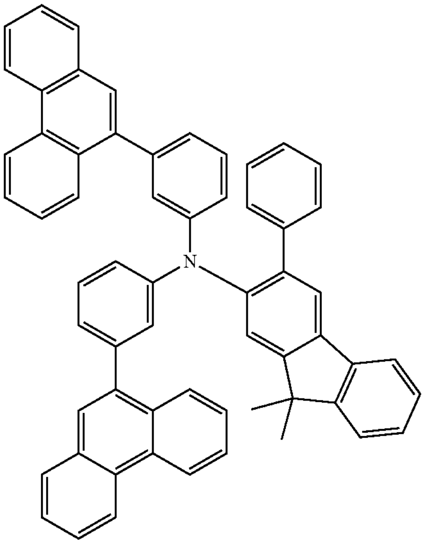

-continued
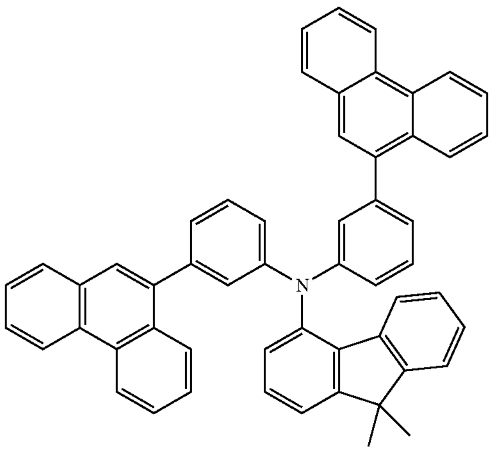
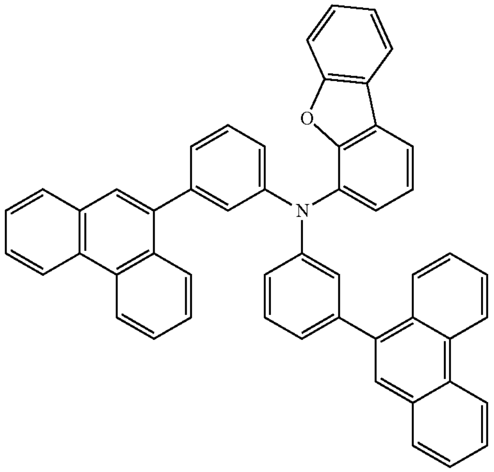
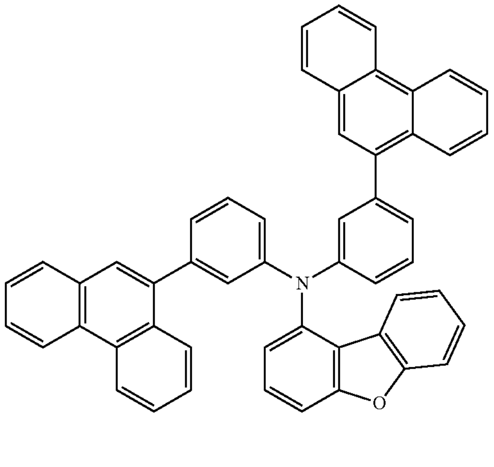
-continued
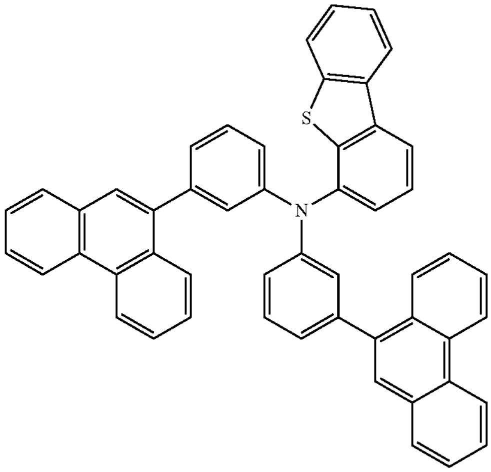
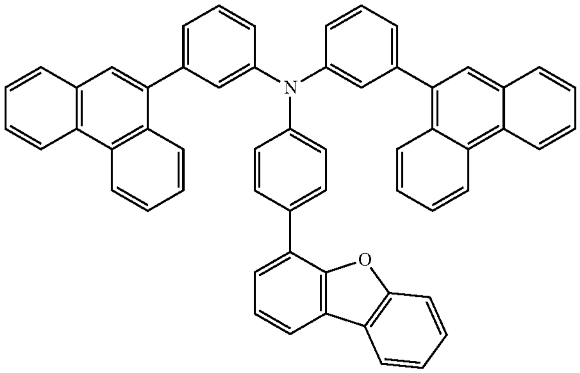
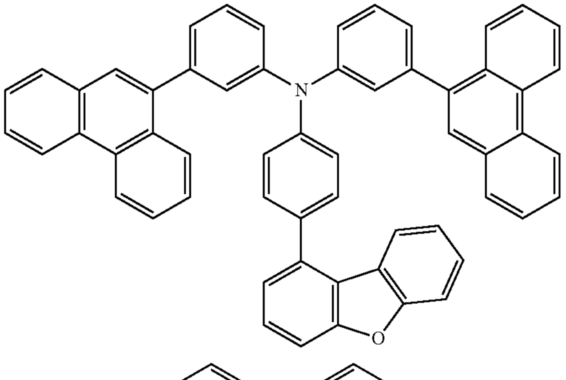
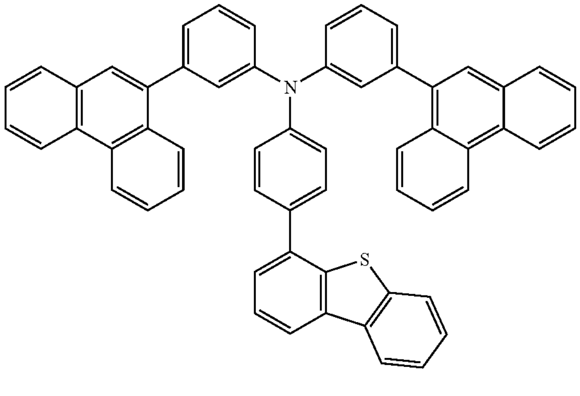

-continued
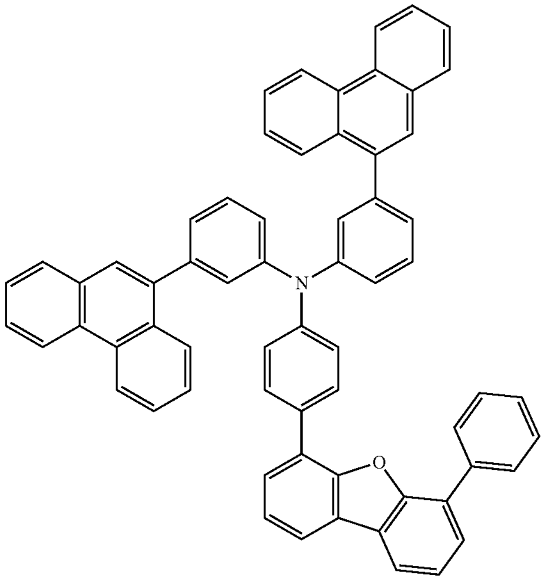
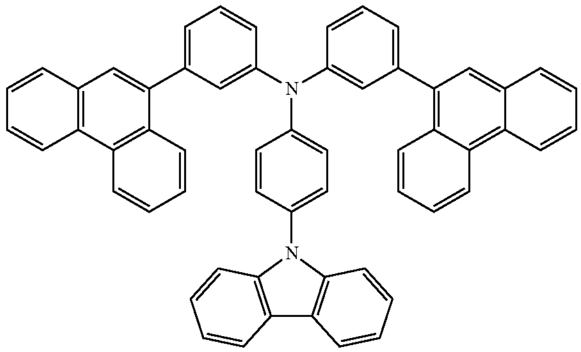
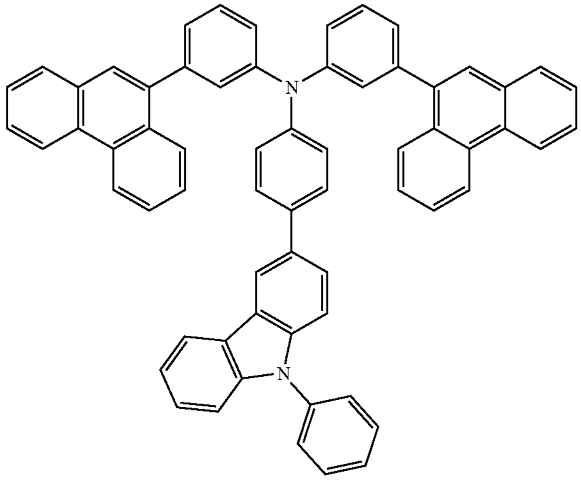
-continued
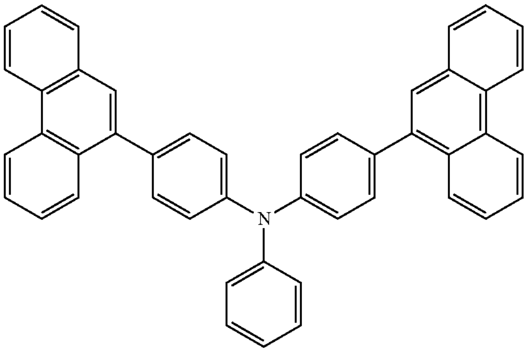
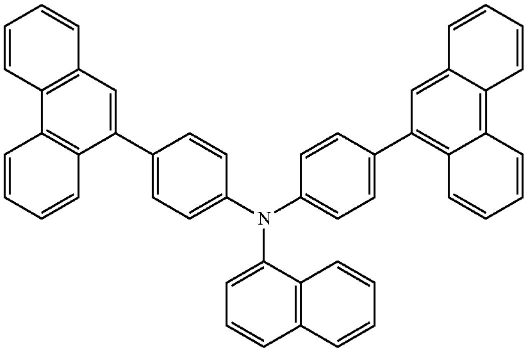
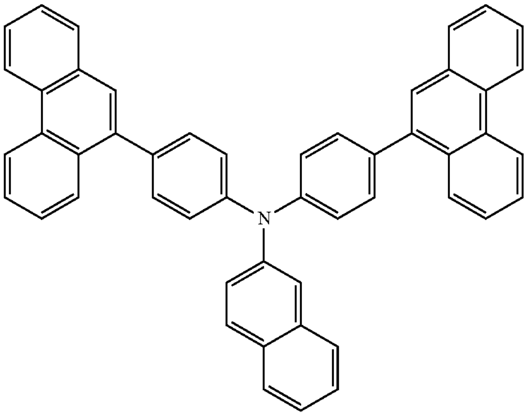
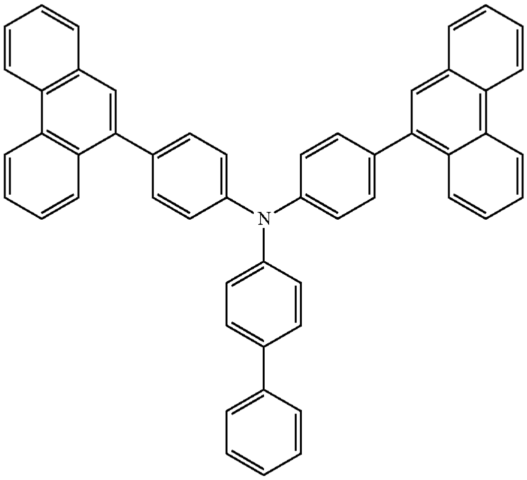

-continued
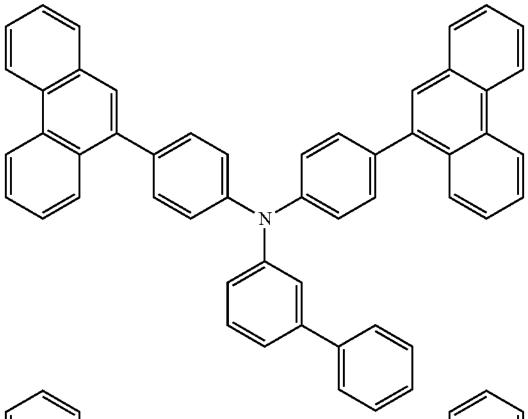
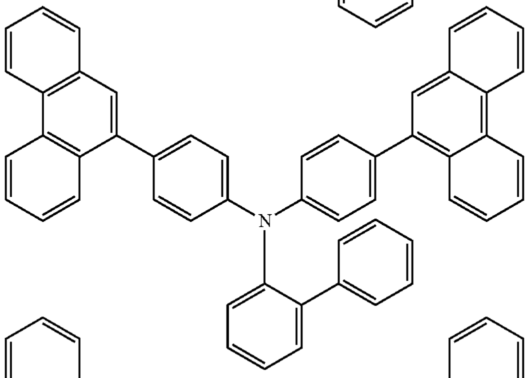
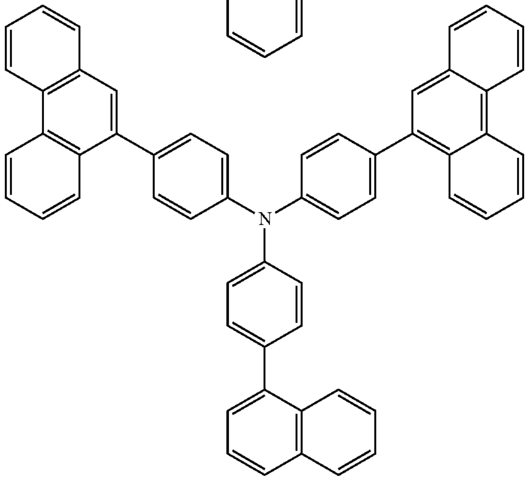
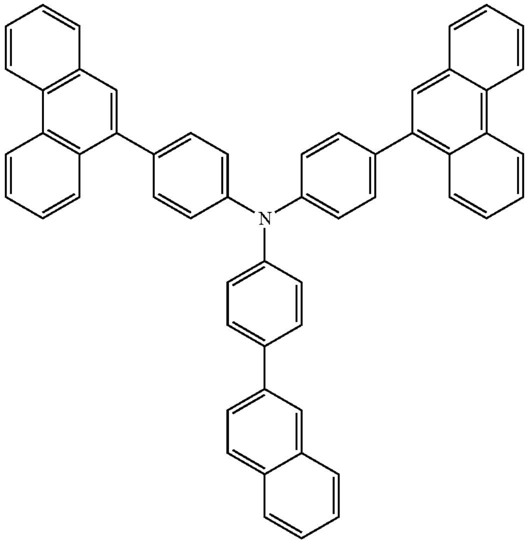
-continued
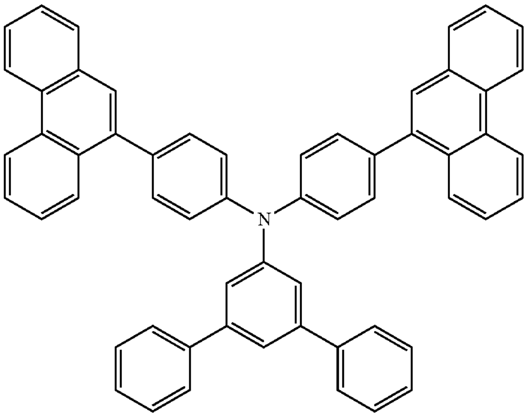
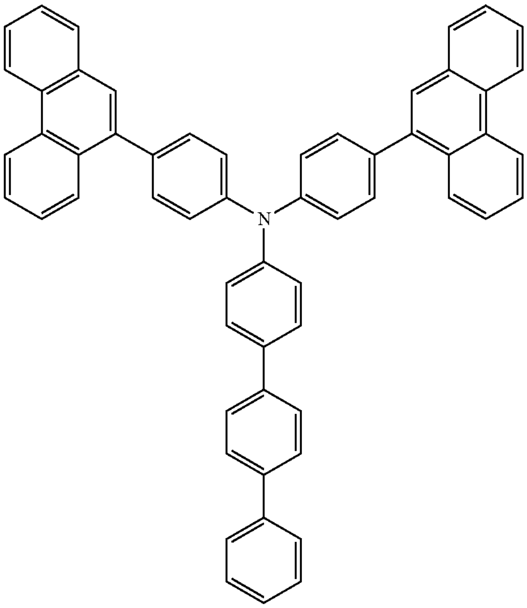
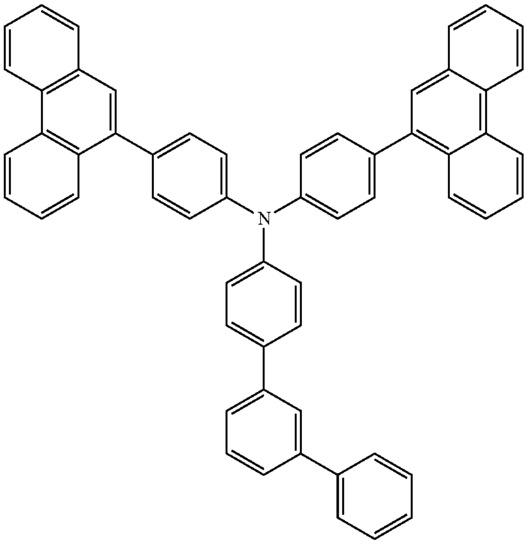

-continued
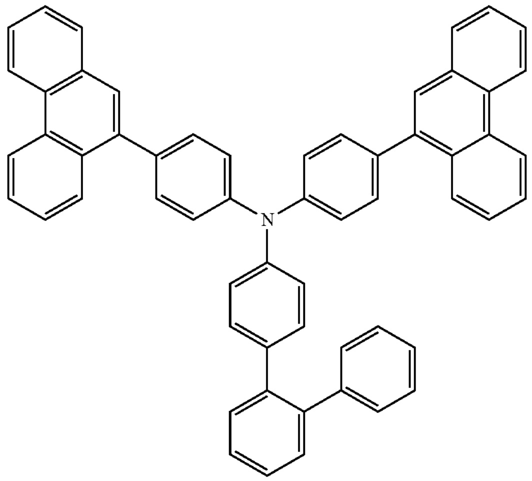
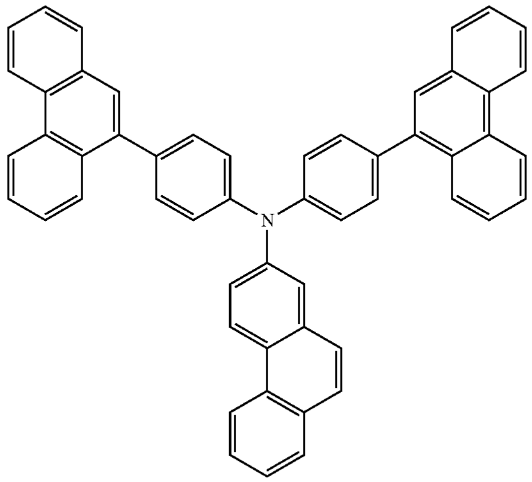
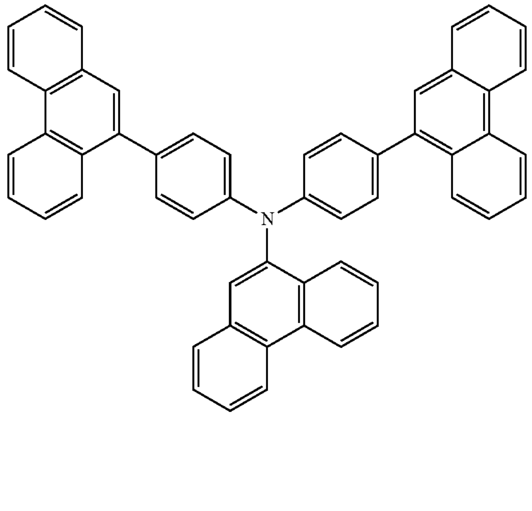
-continued
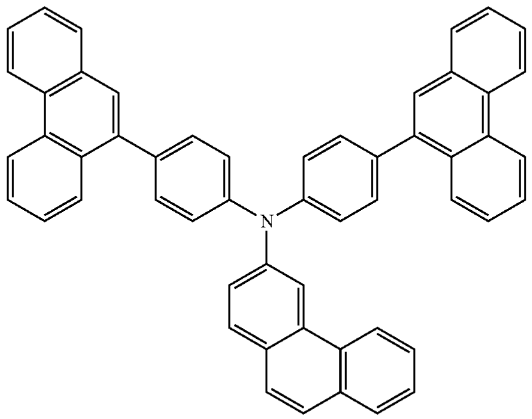
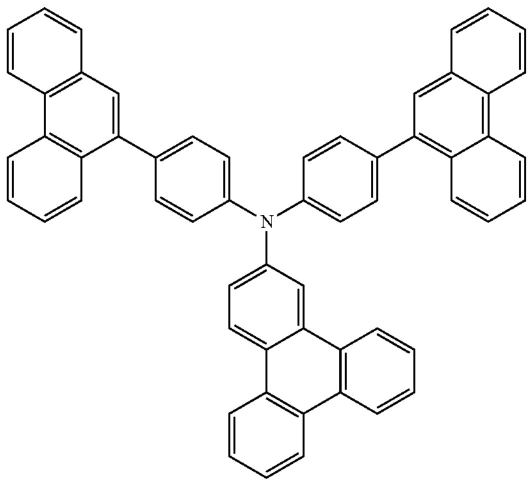
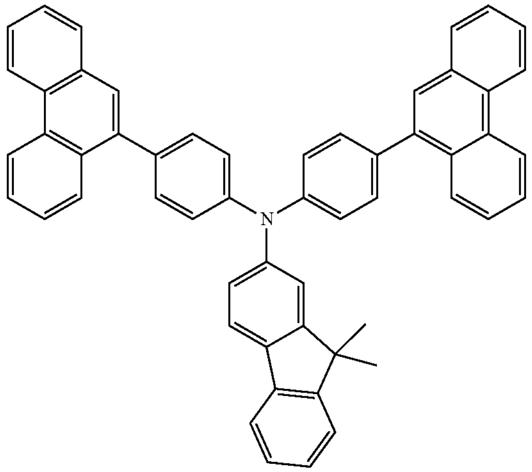

-continued
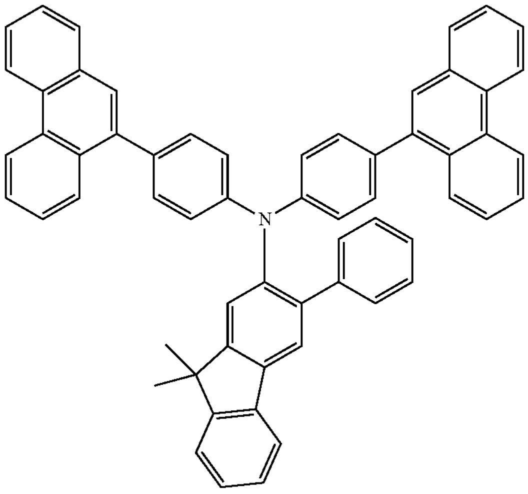
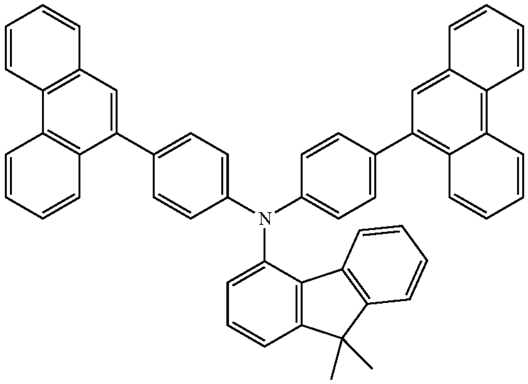
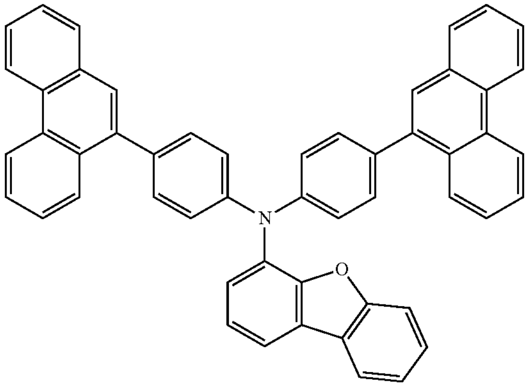
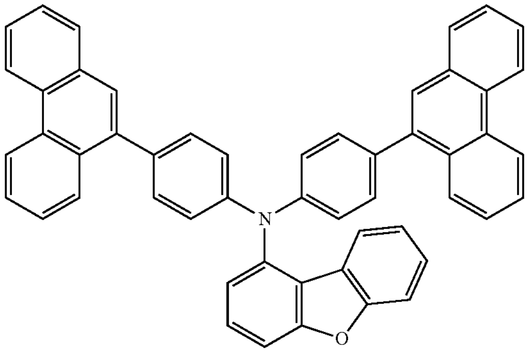
-continued
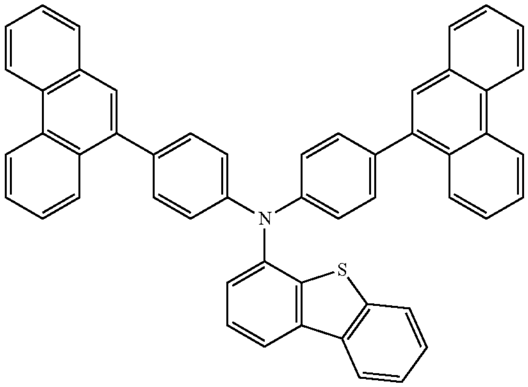
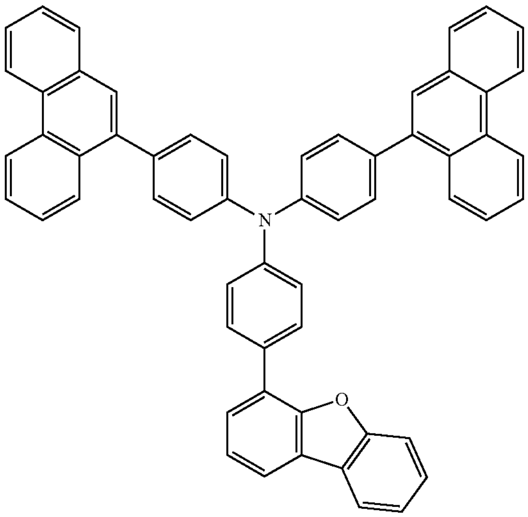
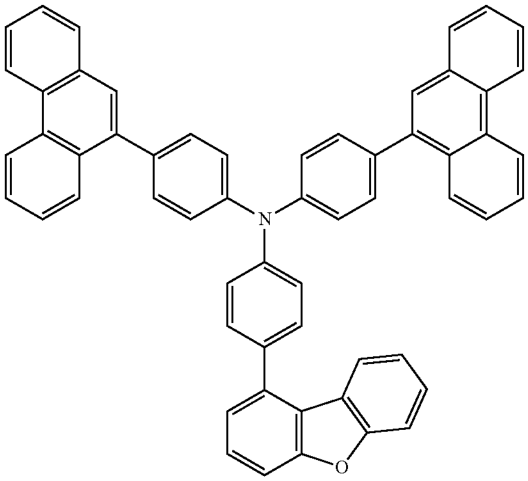

-continued
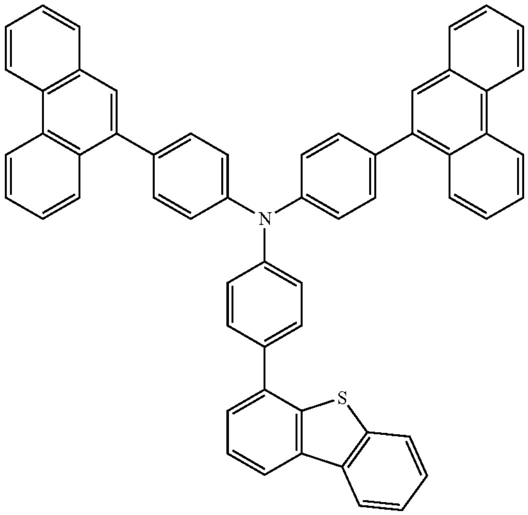
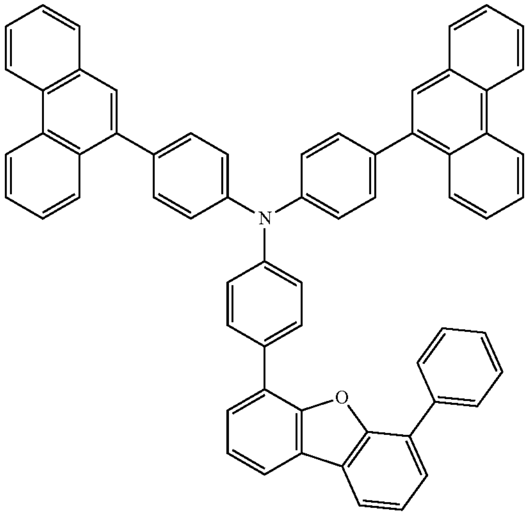
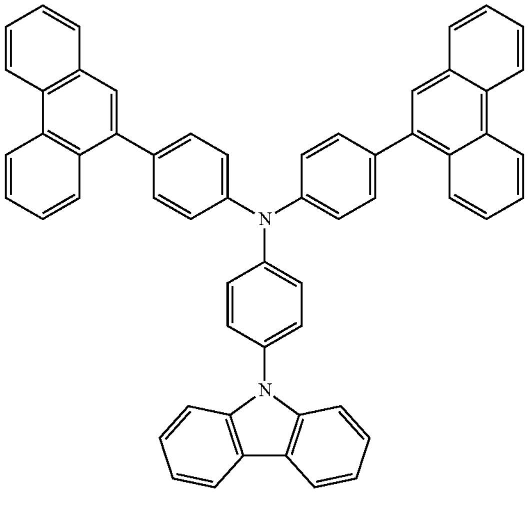
-continued
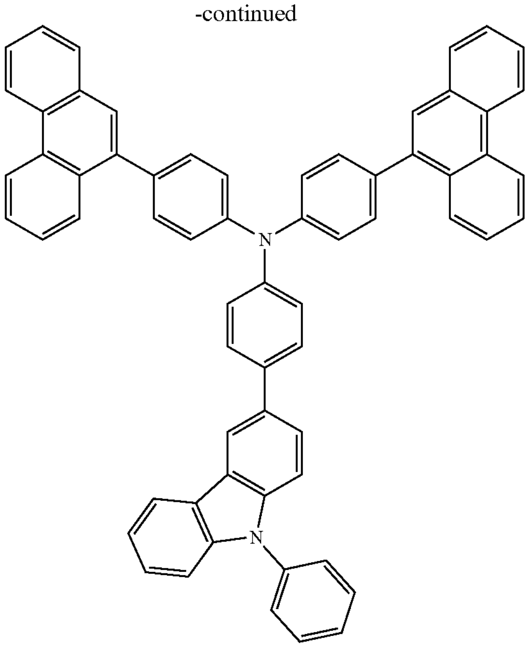
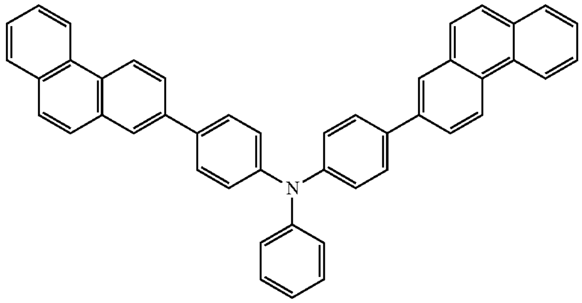
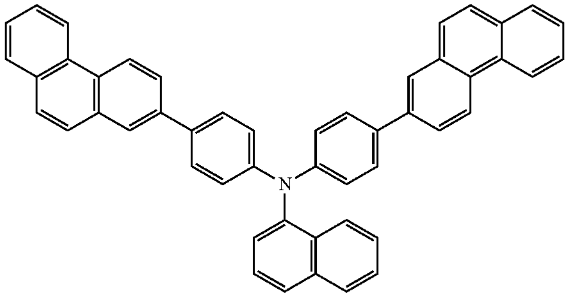
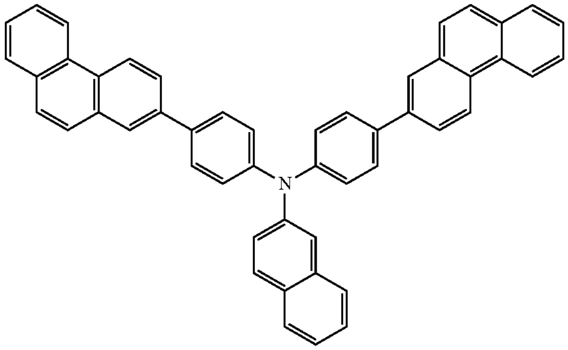

-continued
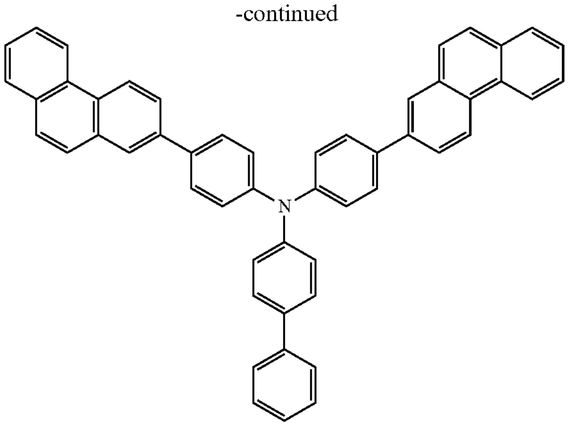
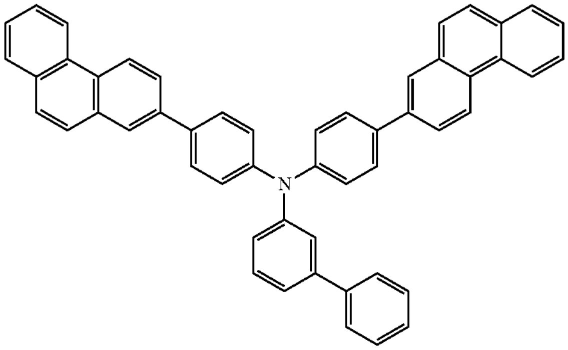
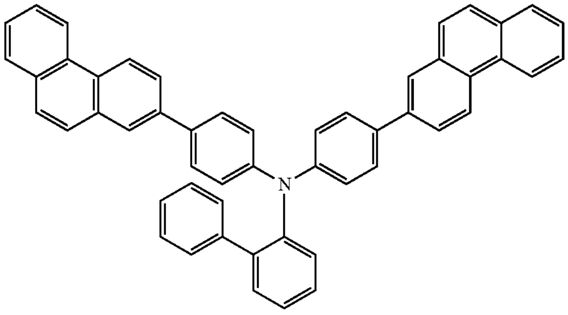
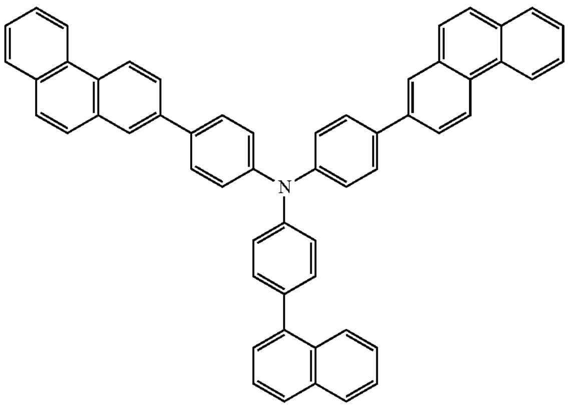
-continued
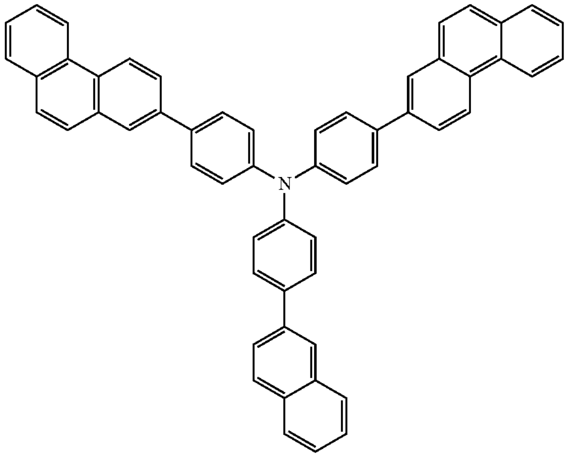
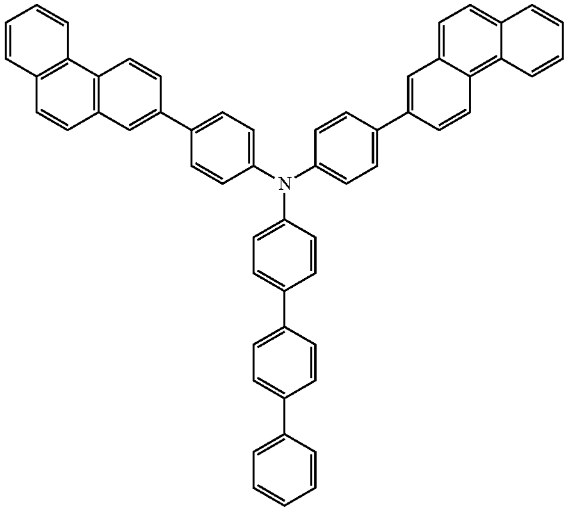
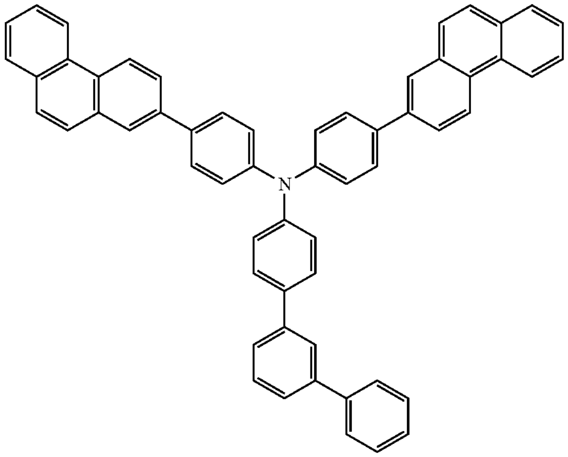

-continued
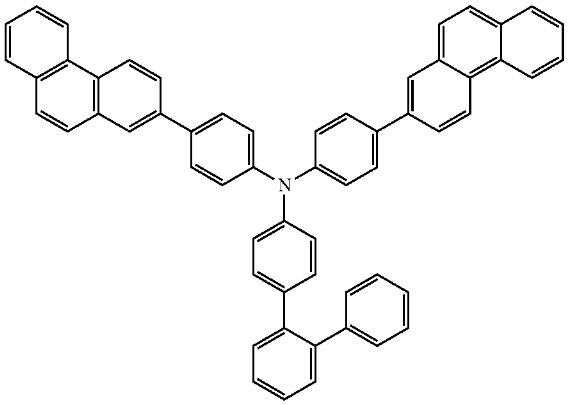
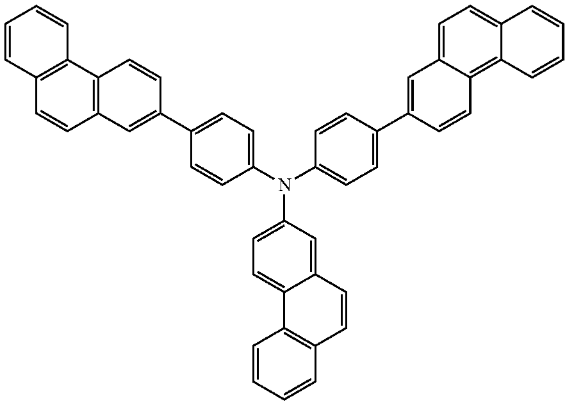
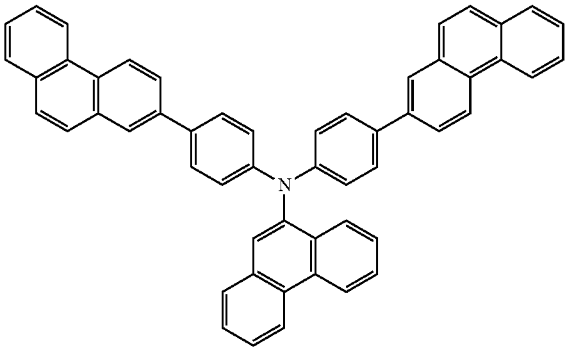
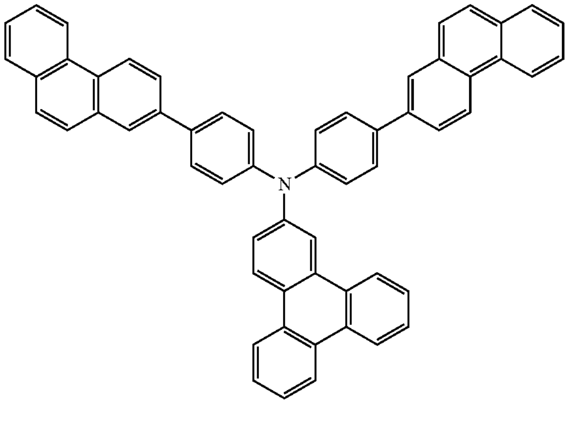
-continued
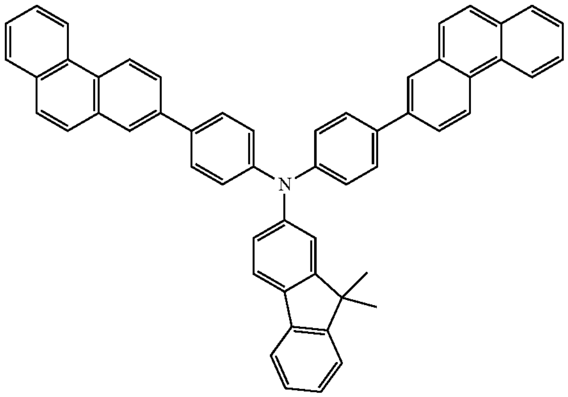
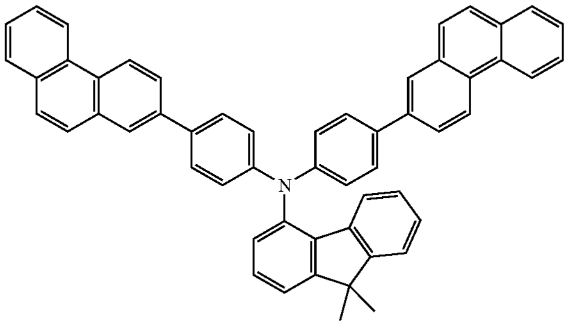
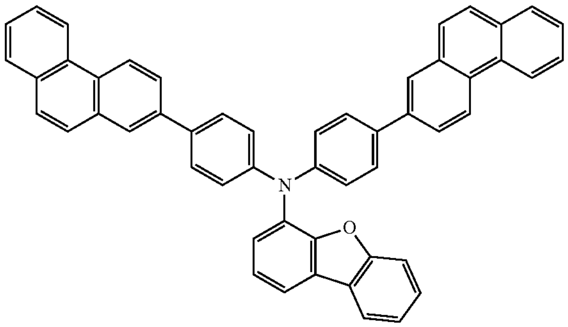
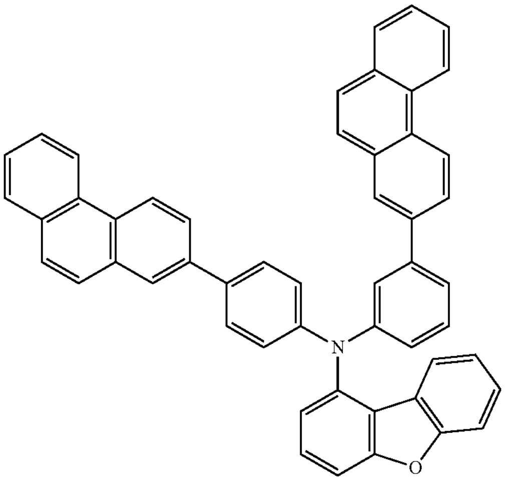

-continued
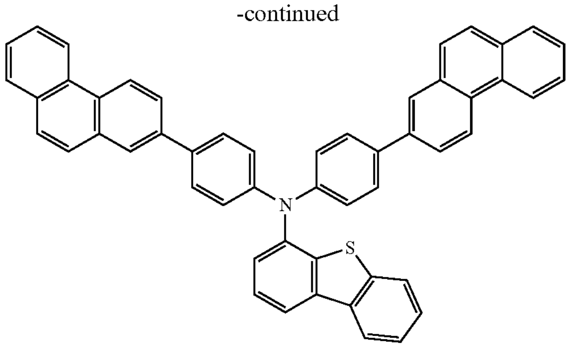
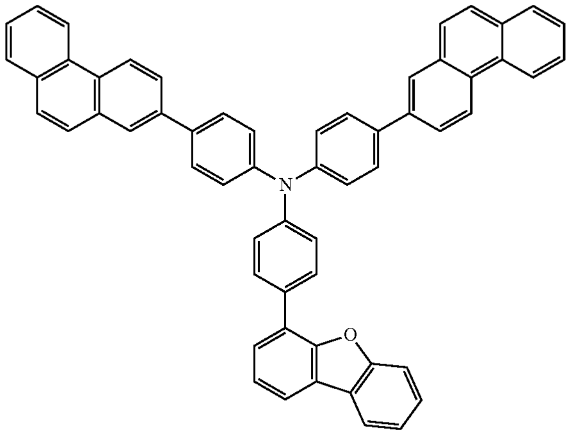
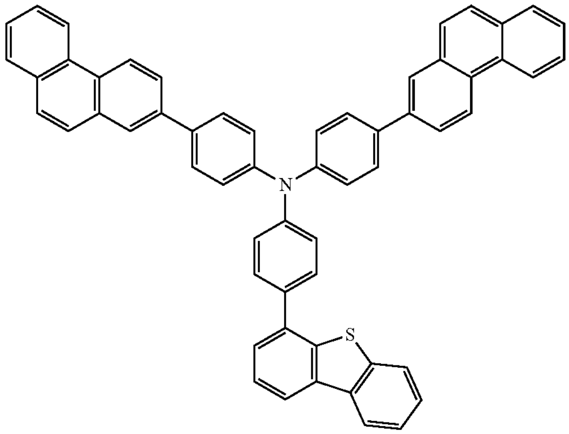
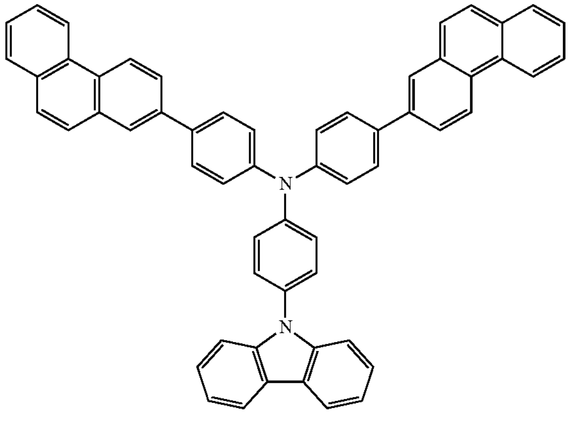
-continued
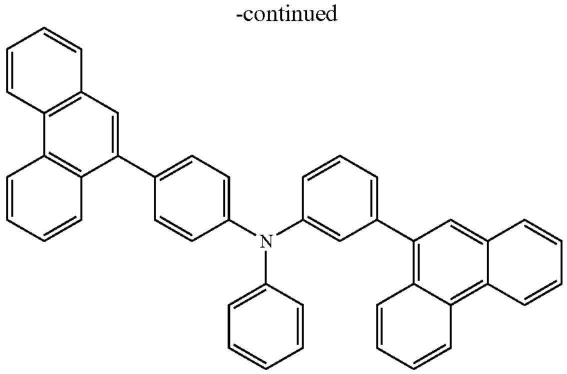
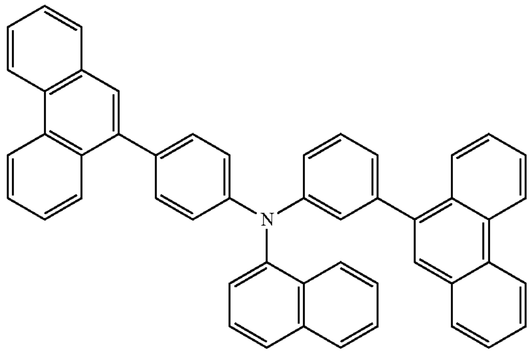
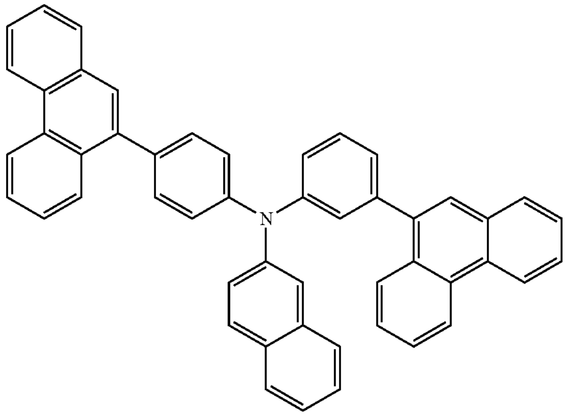
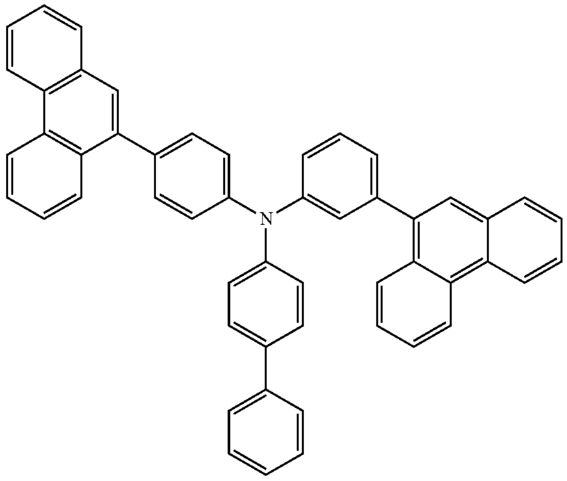

-continued
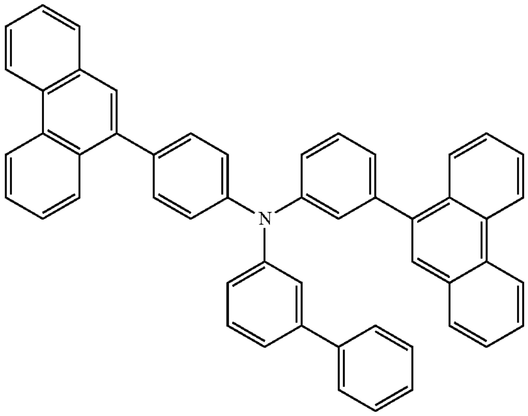
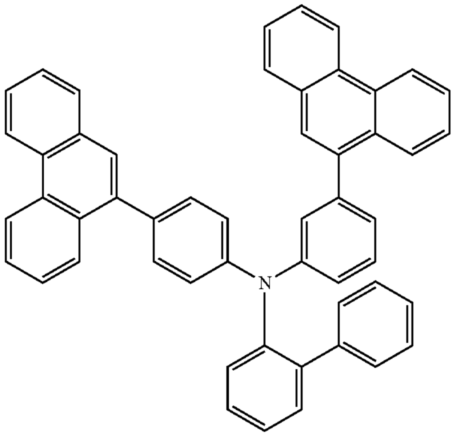
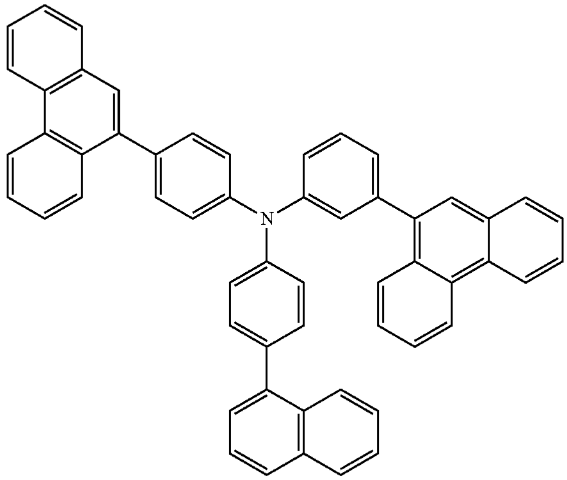
-continued
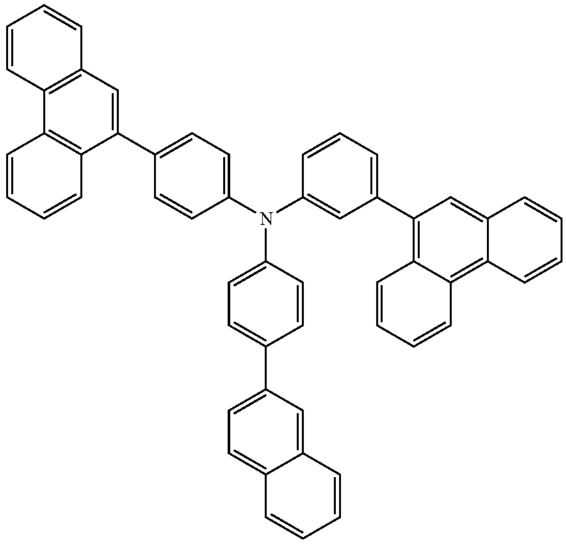
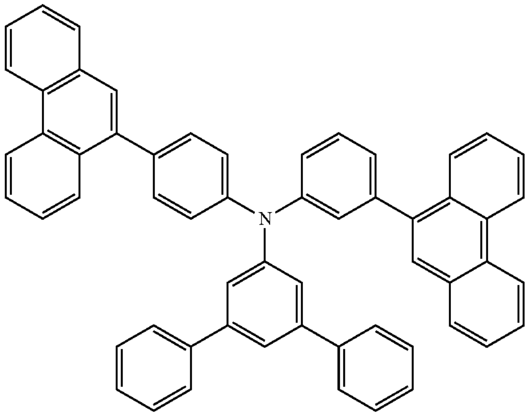
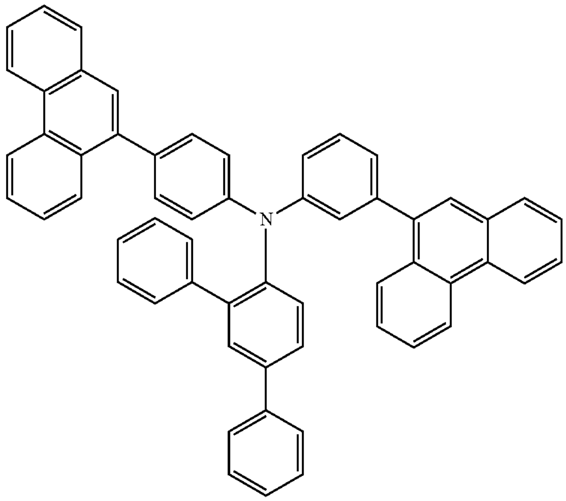

-continued
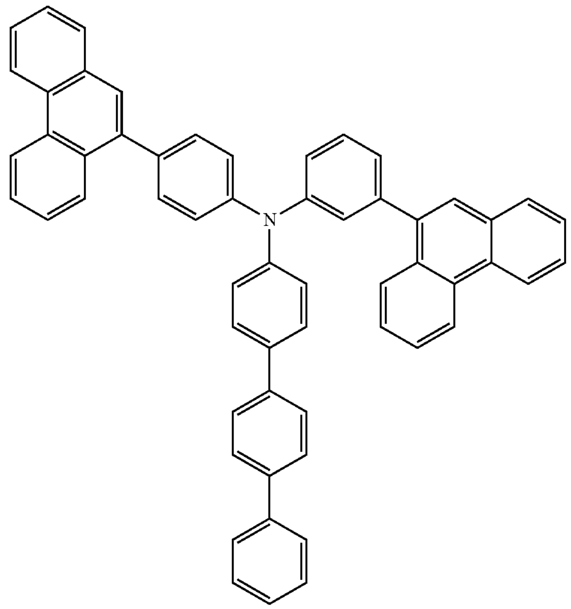
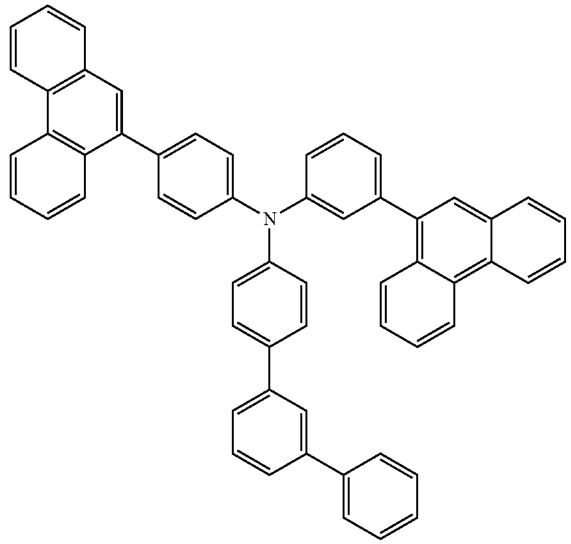
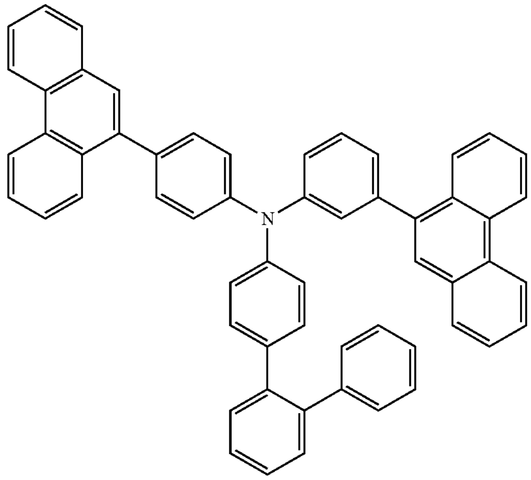
-continued
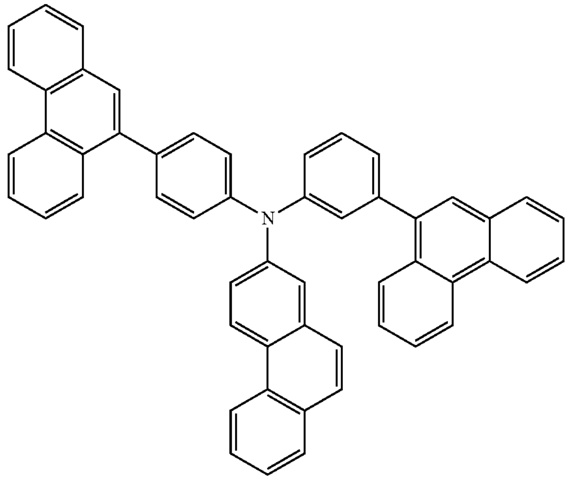
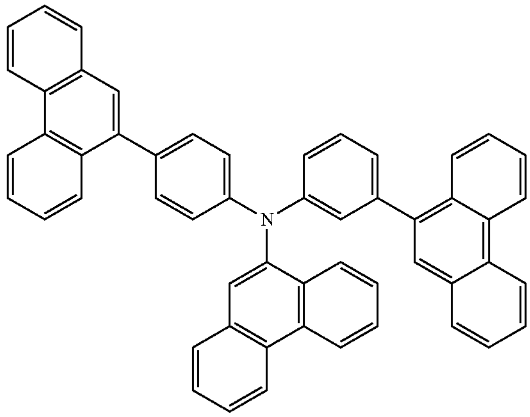
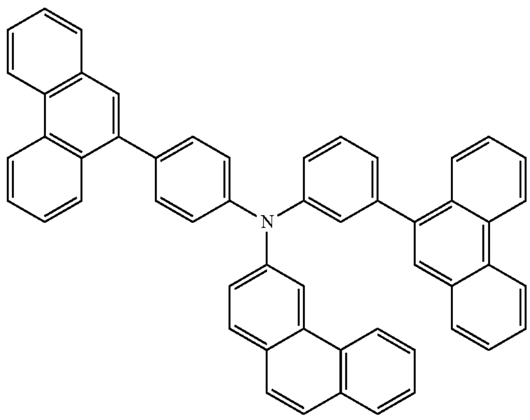

-continued
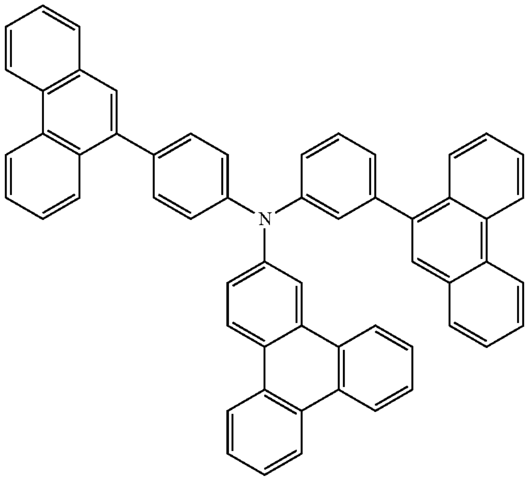
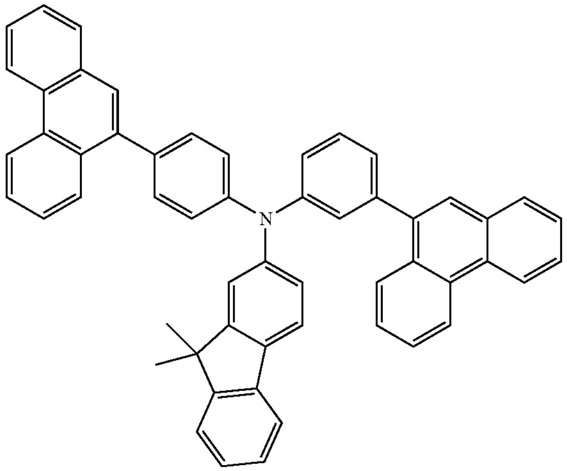
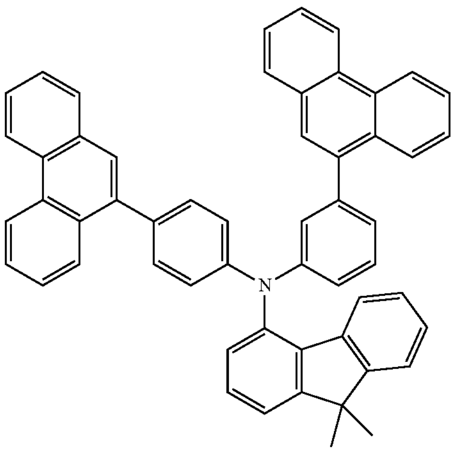
-continued
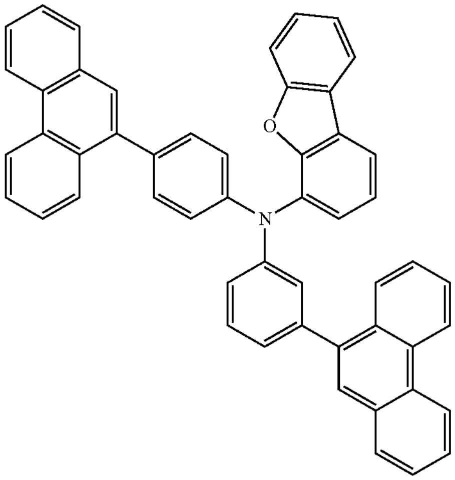
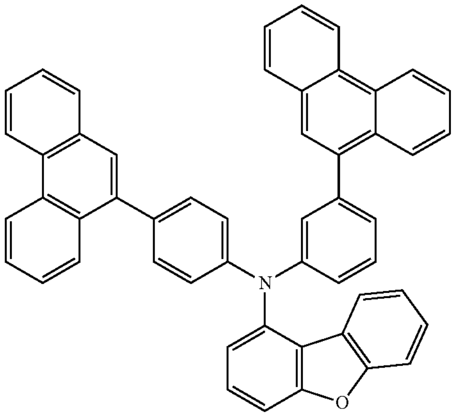
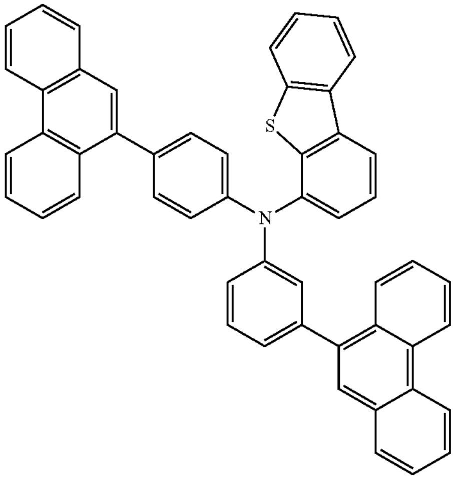

-continued
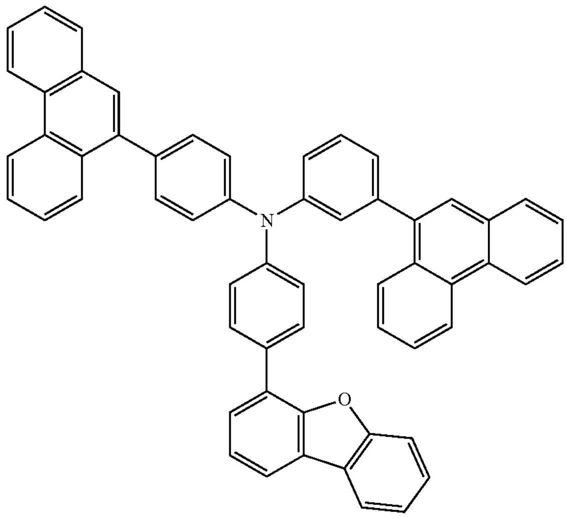
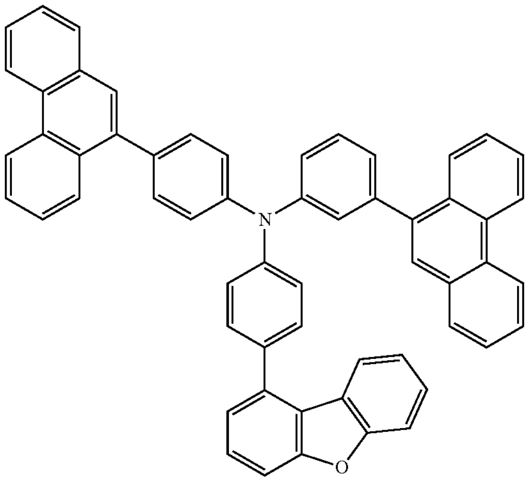
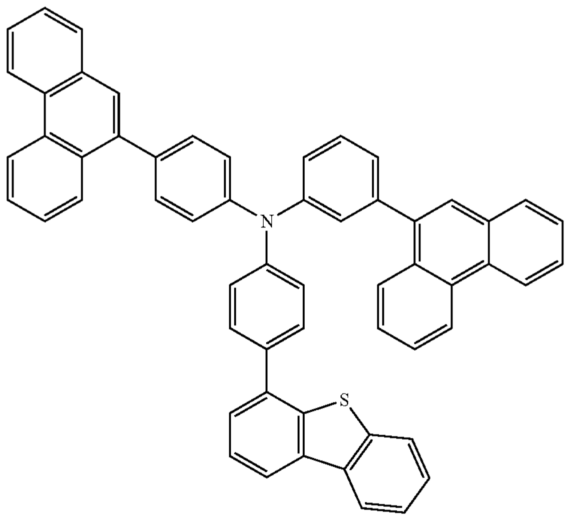
-continued
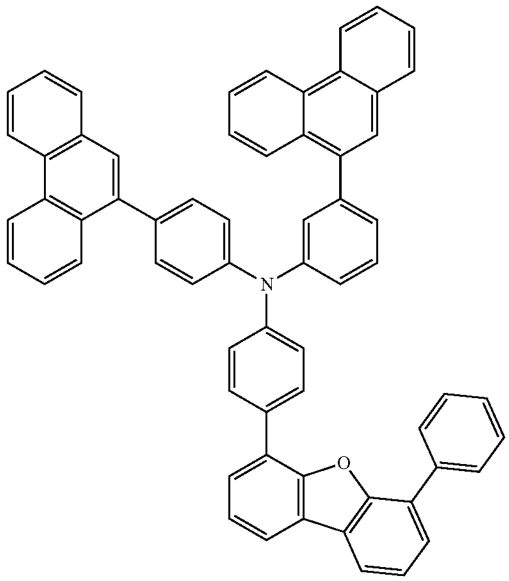
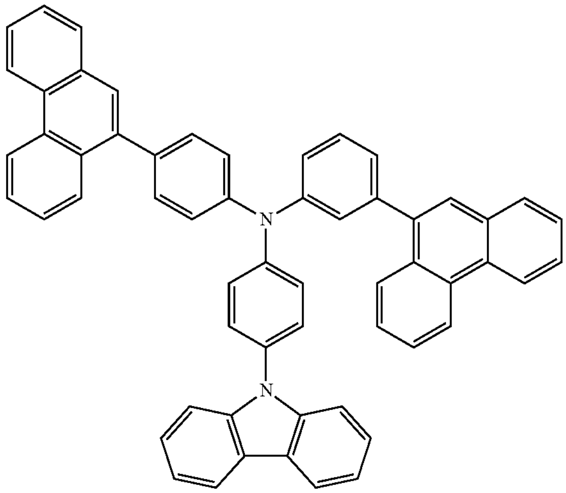
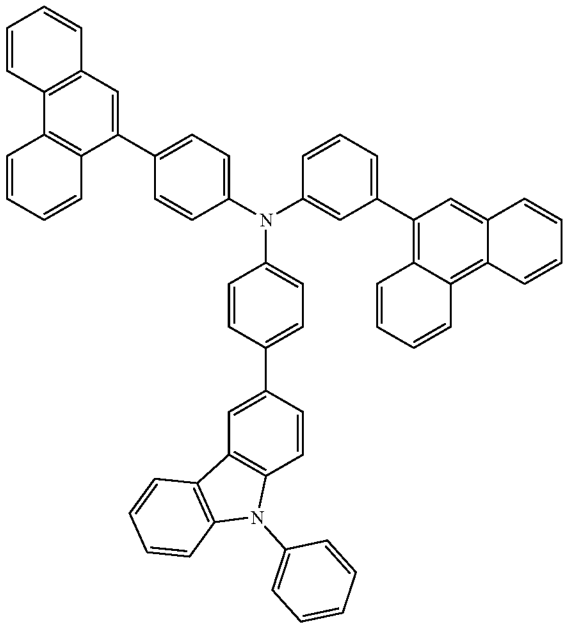

-continued
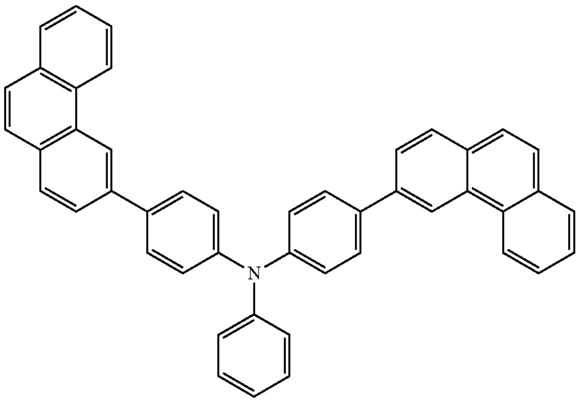
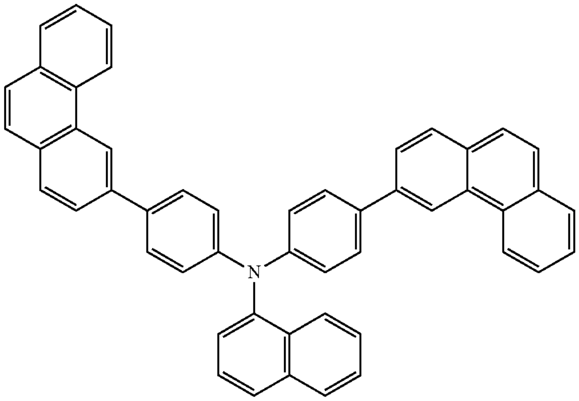
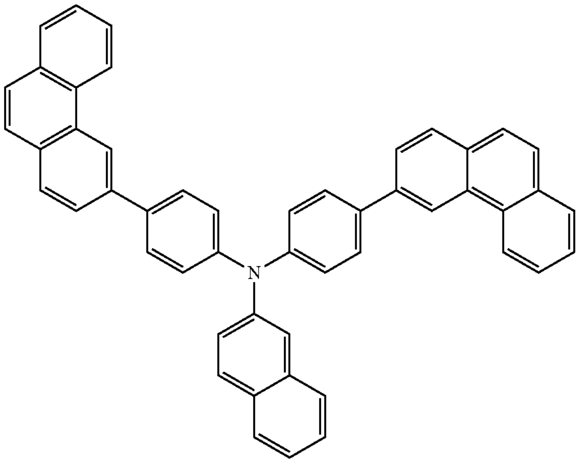
-continued
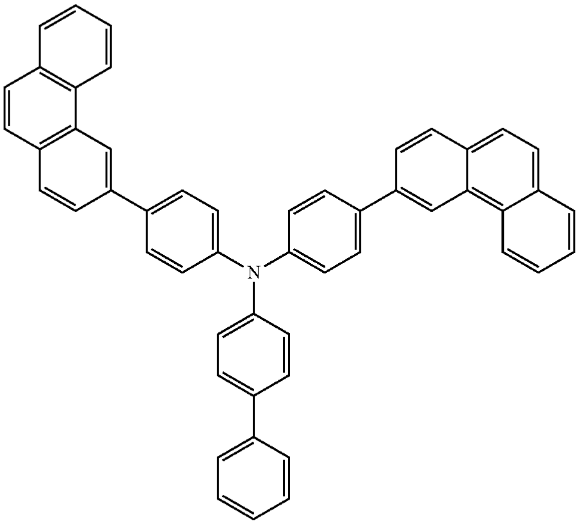
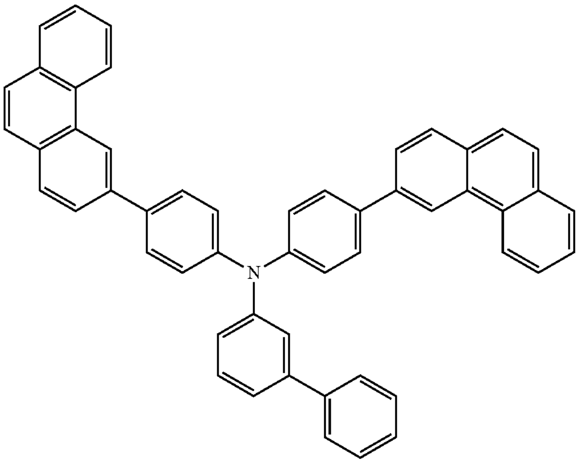
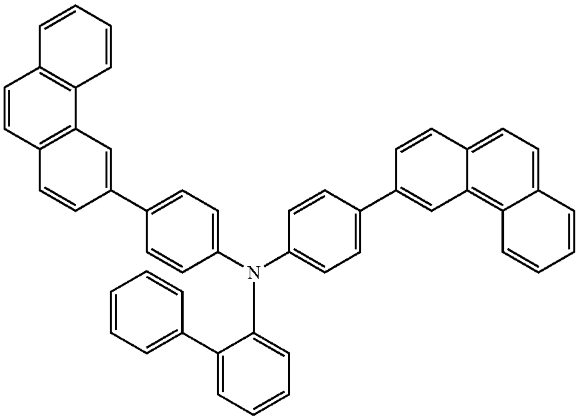

-continued
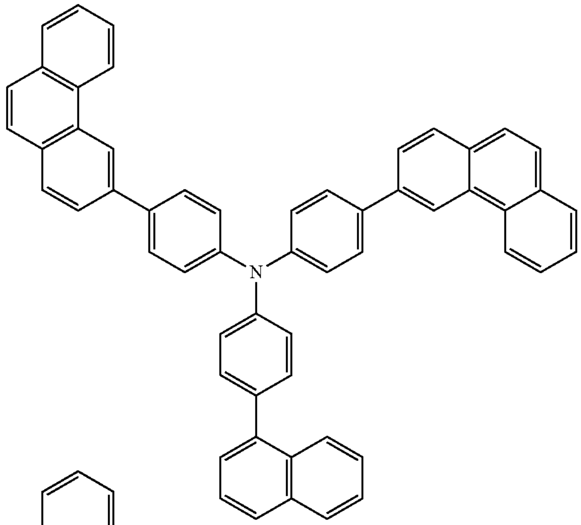
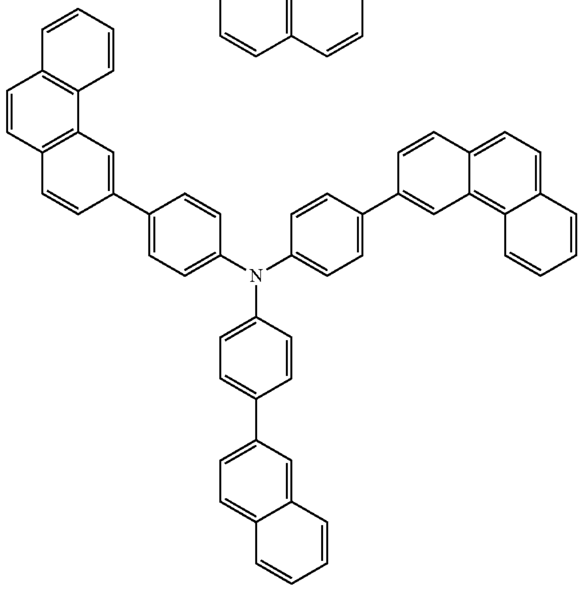
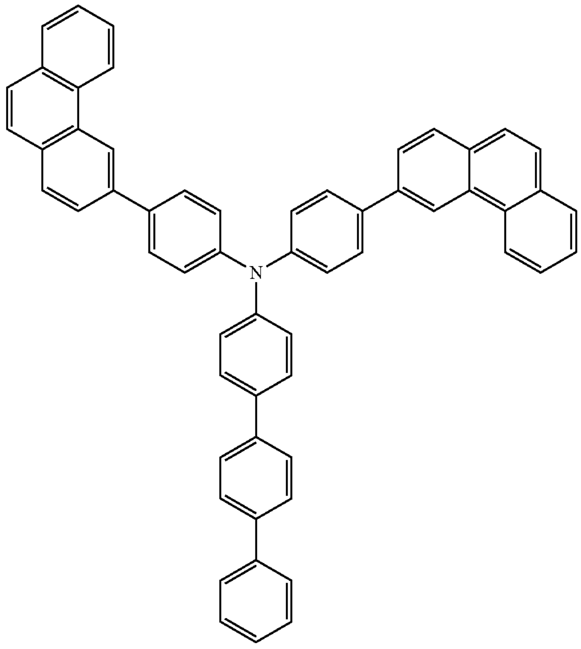
-continued
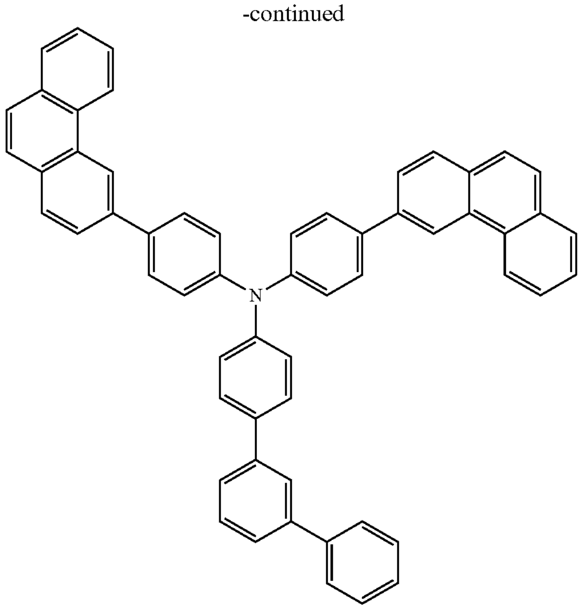
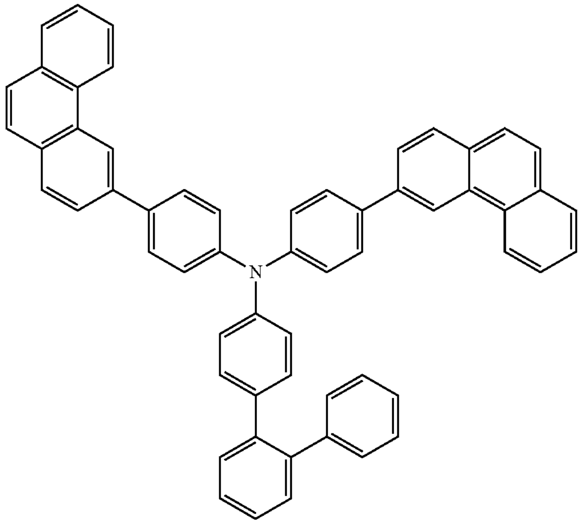
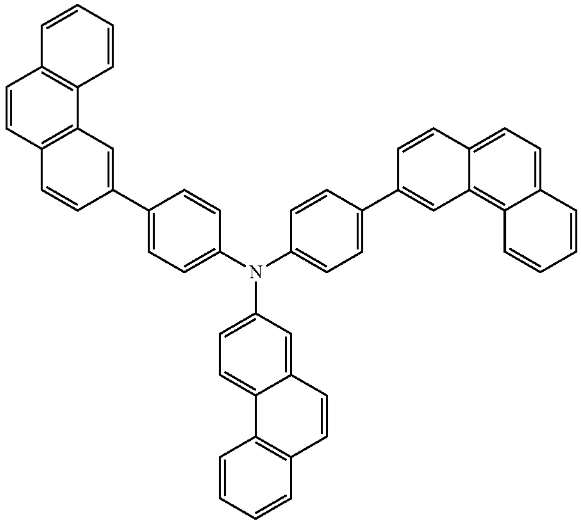

-continued
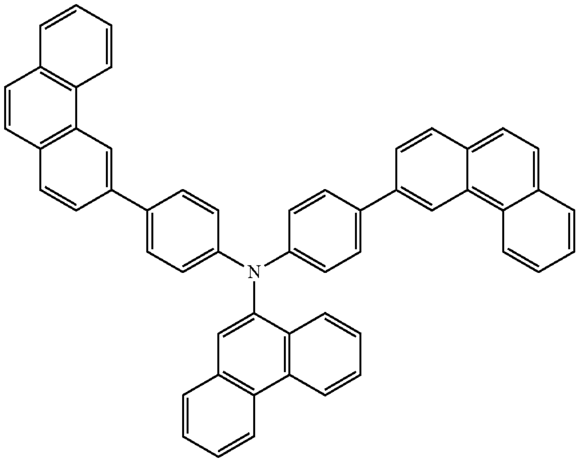
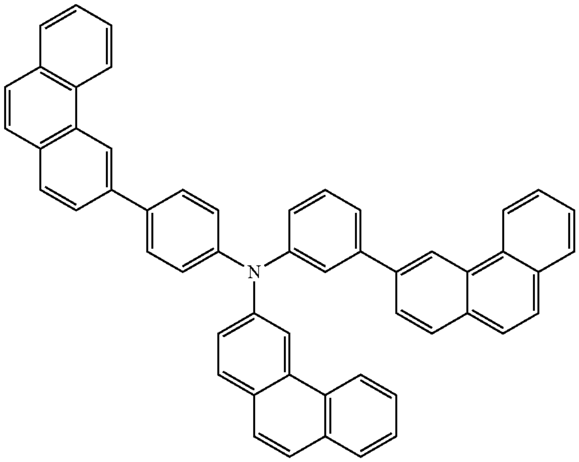
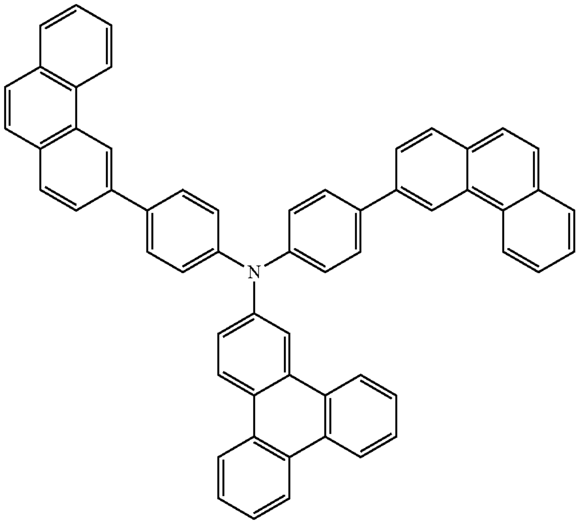
-continued
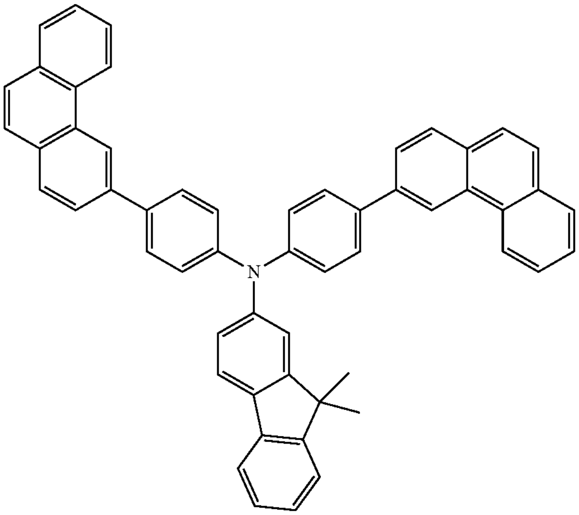
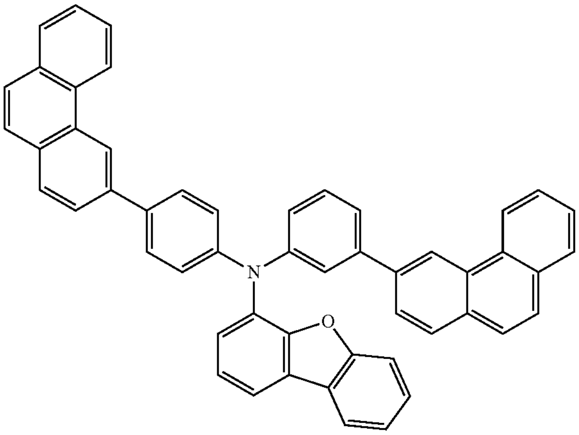
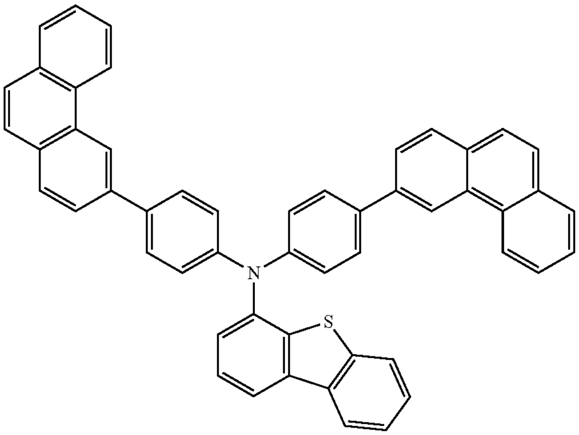

-continued

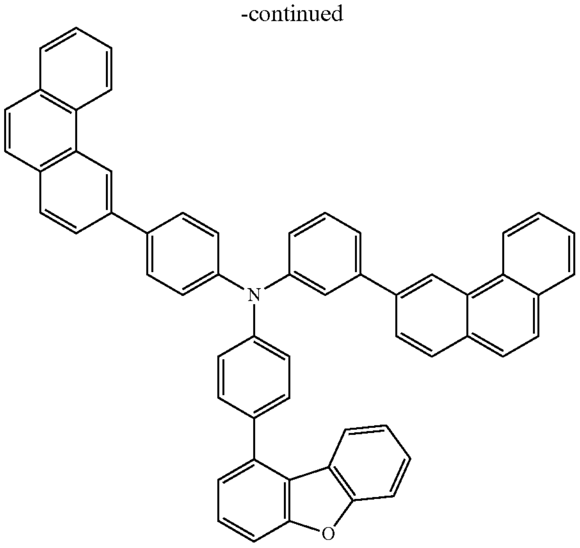

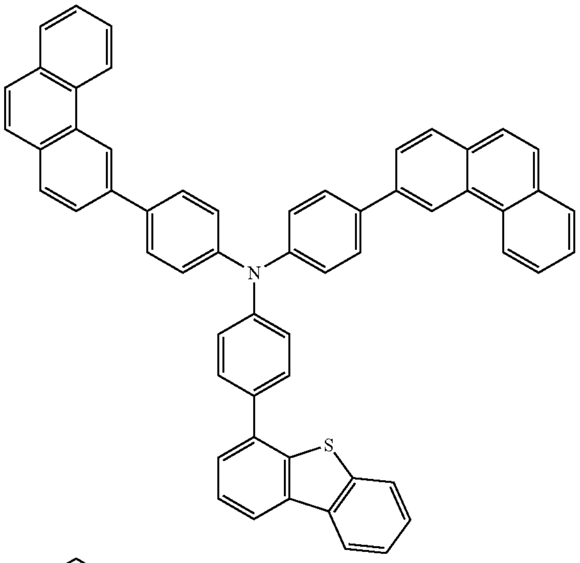

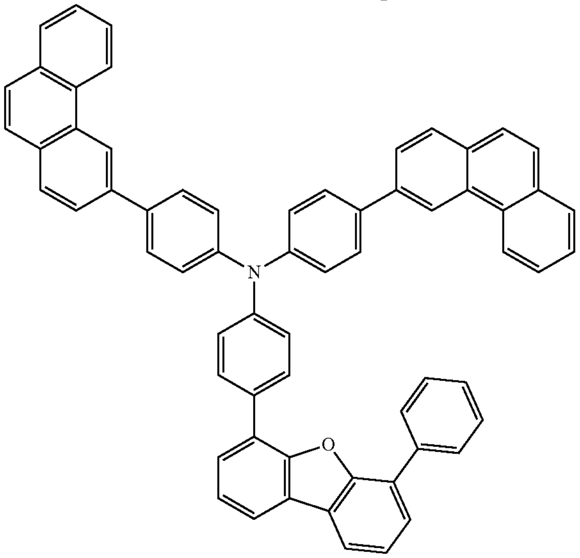

-continued

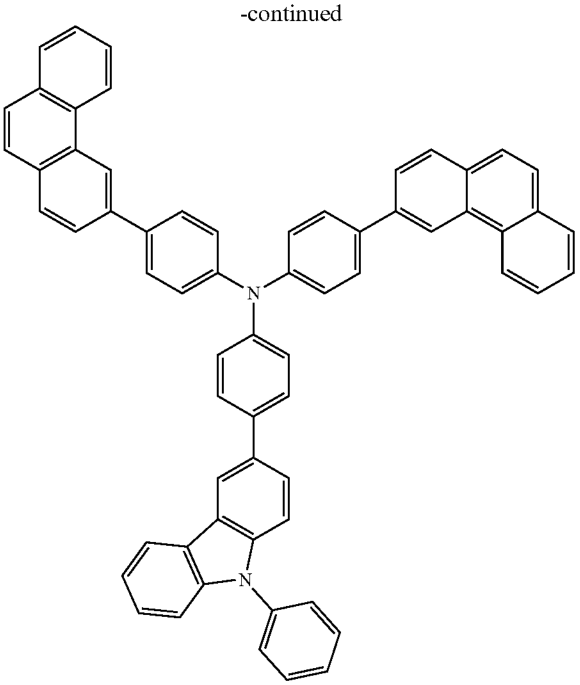

The structure of the organic light emitting device of the present invention can have a structure illustrated in FIGS. 1 and 2, but is not limited thereto.

FIG. 1 exemplifies a structure of an organic light emitting device in which a first electrode 2, an organic material layer 3, and a second electrode 4 are sequentially stacked on a substrate 1.

FIG. 1 exemplifies an organic light emitting device, and the organic light emitting device is not limited thereto.

FIG. 2 exemplifies a structure of an organic light emitting device in which a first electrode 2, a hole injection layer 5, a hole transport layer 6, a hole transport auxiliary layer 7, an electron blocking layer 8, a light emitting layer 9, a hole blocking layer 10, an electron injection and transport layer 11, and a second electrode 4 are sequentially stacked on a substrate 1. The compound of Formula 1 of the present invention can be preferably included in the light emitting layer 9, and the compound of Formula 2 can be preferably included in an electron blocking layer 8.

In addition to the stacking structure used in FIGS. 1 and 2, the organic light emitting device can further comprise an additional layer, and can be used by excluding some layers.

In an exemplary embodiment of the present invention, the organic material layer comprises a light emitting layer, and the light emitting layer comprises the compound of Formula 1.

In an exemplary embodiment of the present invention, the organic material layer comprises a light emitting layer, and the light emitting layer comprises the compound of Formula 1 as a host of the light emitting layer.

In an exemplary embodiment of the present invention, the organic material layer can comprise a hole injection layer, a hole transport layer, or a hole injection and transport layer, and the hole injection layer, the hole transport layer, or the hole injection and transport layer can comprise the compound of Formula 1.

In an exemplary embodiment of the present invention, the organic material layer can comprise an electron injection layer, an electron transport layer, or an electron injection and transport layer, and the electron injection layer, the electron transport layer, or the electron injection and transport layer can comprise the compound of Formula 1.

In an exemplary embodiment of the present invention, the organic material layer can comprise an electron blocking layer or a hole blocking layer, and the electron blocking layer or the hole blocking layer can comprise the compound of Formula 1.

In an exemplary embodiment of the present invention, the organic material layer can comprise a hole injection layer, a hole transport layer, or a hole injection and transport layer, and the hole injection layer, the hole transport layer, or the hole injection and transport layer can comprise the compound of Formula 2.

In an exemplary embodiment of the present invention, the organic material layer can comprise an electron injection layer, an electron transport layer, or an electron injection and transport layer, and the electron injection layer, the electron transport layer, or the electron injection and transport layer can comprise the compound of Formula 2.

In an exemplary embodiment of the present invention, the organic material layer can comprise an electron blocking layer or a hole blocking layer, and the electron blocking layer or the hole blocking layer can comprise the compound of Formula 2.

In an exemplary embodiment of the present invention, the organic material layer comprises an electron blocking layer, and the electron blocking layer comprises the compound of Formula 2.

When the organic light emitting device comprises a plurality of organic material layers, the organic material layers can be formed of the same material or different materials.

The organic light emitting device of the present specification can be manufactured by the materials and methods known in the art, except that one or more layers of the organic material layer are formed by using the compound of Formula 1 or 2.

The present specification also provides a method for manufacturing an organic light emitting device formed by using the compound.

For example, the organic light emitting device according to the present invention can be manufactured by depositing a metal or a metal oxide having conductivity, or an alloy thereof on a substrate to form a positive electrode, forming an organic material layer comprising the compound of Formula 1 and an organic material layer comprising the compound of Formula 2 thereon, and then depositing a material, which can be used as a negative electrode, thereon, by using a physical vapor deposition (PVD) method such as sputtering or e-beam evaporation. In addition to the method described above, an organic light emitting device can also be made by sequentially depositing a negative electrode material, an organic material layer, and a positive electrode material on a substrate.

As the positive electrode material, materials having a high work function are usually preferred so as to facilitate the injection of holes into an organic material layer. Specific examples of the positive electrode material that can be used in the present invention comprise: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SNO_2$:Sb; a conductive polymer such as poly(3-methylthiophene), poly [3,4-(ethylene-1,2-dioxy)thiophene] (PEDT), polypyrrole, and polyaniline; and the like, but are not limited thereto.

As the negative electrode material, materials having a low work function are usually preferred so as to facilitate the injection of electrons into an organic material layer. Specific examples of the negative electrode material comprise: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection material is a material that can proficiently receive holes from a positive electrode at low voltage, and the highest occupied molecular orbital (HOMO) of the hole injection material is preferably a value between the work function of the positive electrode material and the HOMO of the neighboring organic material layer. Specific examples of the hole injection material comprise metal porphyrin, oligothiophene, arylamine-based organic materials, hexanitrile hexaazatriphenylene-based organic materials, quinacridone-based organic materials, perylene-based organic materials, anthraquinone, polyaniline and polycompound-based conductive polymer, and the like, but are not limited thereto.

The hole transport material is suitably a material having high hole mobility that can receive holes from a positive electrode or a hole injection layer and transfer the holes to a light emitting layer. Specific examples thereof comprise arylamine-based organic materials, conductive polymers, block copolymers having both conjugated portions and non-conjugated portions, and the like, but are not limited thereto.

The light emitting material is a material that can receive holes and electrons from a hole transport layer and an electron transport layer, and combine the holes and the electrons to emit light in a visible ray region, and is preferably a material having high quantum efficiency for fluorescence or phosphorescence. Specific examples thereof comprise: 8-hydroxy-quinoline aluminum complexes ($Alq_3$), carbazole-based compounds, dimerized styryl compounds, BAlq, 10-hydroxybenzoquinoline-metal compounds, benzoxazole-based compounds, benzothiazole-based compounds, benzimidazole-based compounds, poly (p-phenylenevinylene) (PPV)-based polymers, spiro compounds, polyfluorene, rubrene, and the like, but are not limited thereto.

Examples of the dopant material comprise aromatic compounds, styrylamine compounds, boron complexes, fluoranthene compounds, metal complexes, and the like. Specifically, the aromatic compound is a fused aromatic ring derivative having a substituted or unsubstituted arylamino group, and examples thereof comprise a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof comprise styrylamine, styryldiamine, styryltriamine, styryltetramine, and the like, but are not limited thereto. Further, examples of the metal complex comprise iridium complexes, platinum complexes, and the like, but are not limited thereto.

In an exemplary embodiment of the present invention, the light emitting layer can comprise a host and a dopant. In an exemplary embodiment of the present invention, the organic material layer comprises a light emitting layer, and the light emitting layer comprises a host and a dopant at a mass ratio of 99:1 to 70:30. The host can comprise the compound of Formula 1 of the present invention, and the dopant can comprise a compound of the following structural formula Dp-1 to Dp-35. In an exemplary embodiment of the present invention, the light emitting layer comprises the compound of Formula 1 as a red host.
Dp-1
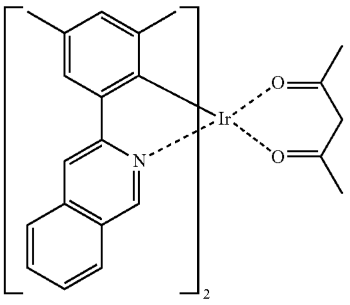
Dp-2
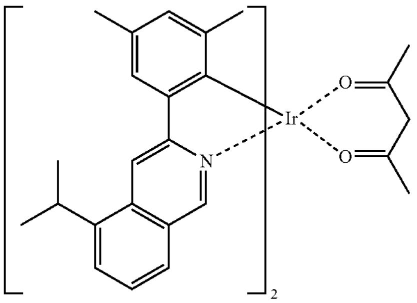
Dp-3
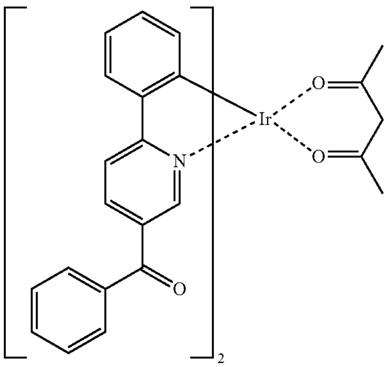
Dp-4
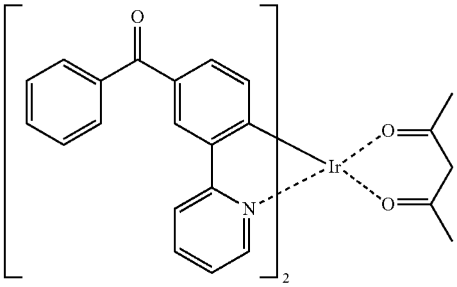
-continued
Dp-5
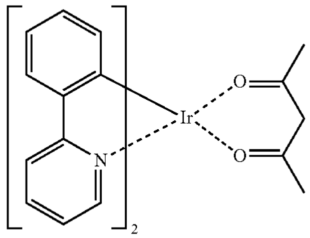
Dp-6
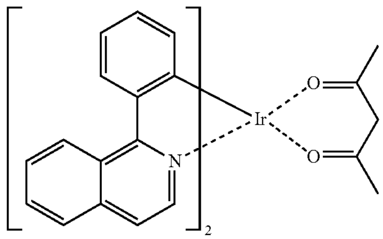
Dp-7
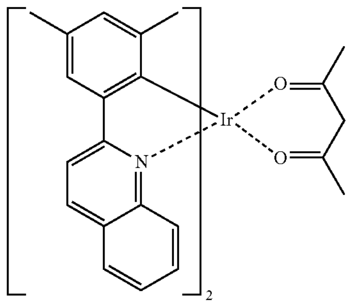
Dp-8
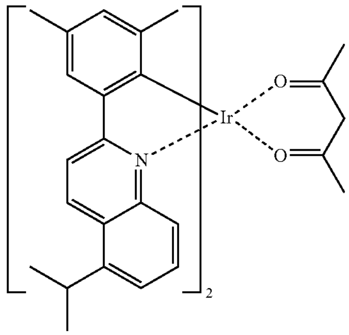
Dp-9
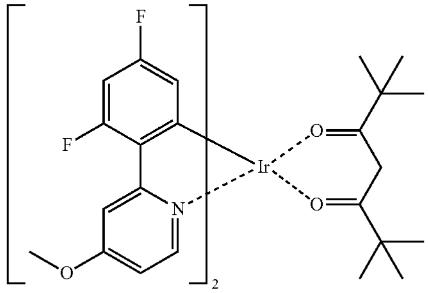

-continued
Dp-10
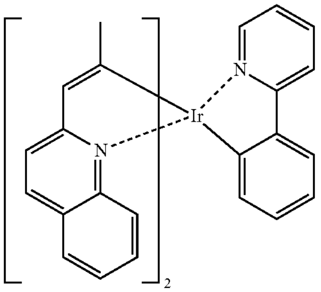
Dp-11
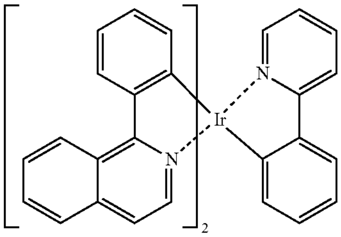
Dp-12
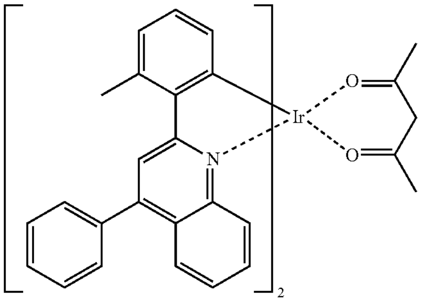
Dp-13
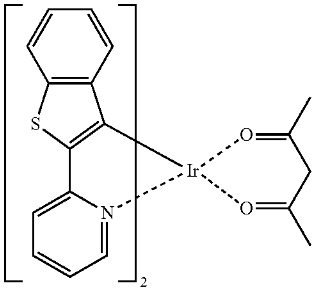
Dp-14
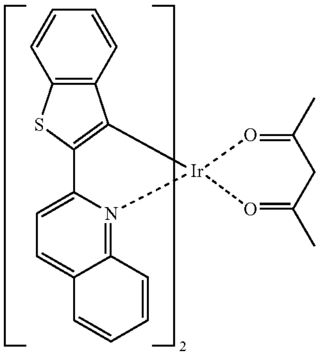
-continued
Dp-15
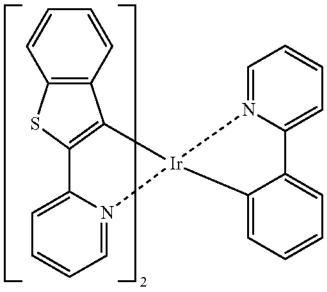
Dp-13
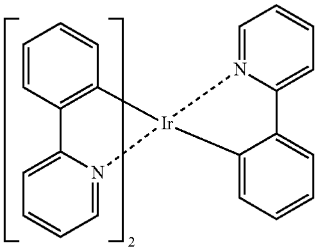
Dp-14
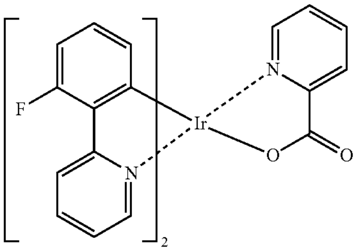
Dp-15
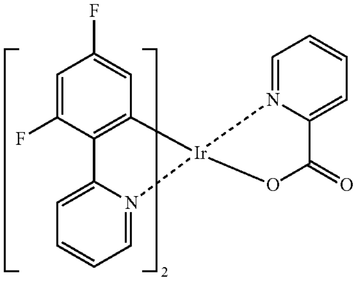
Dp-16
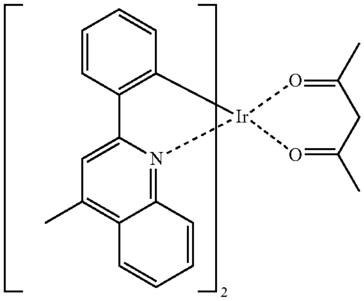

-continued
Dp-17
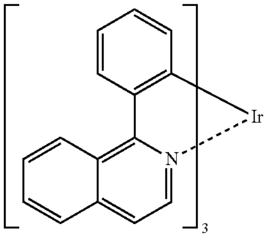
Dp-8
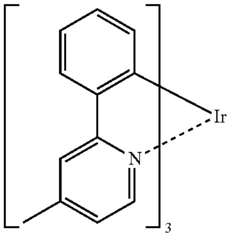
Dp-19
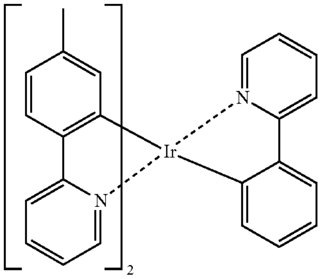
Dp-20
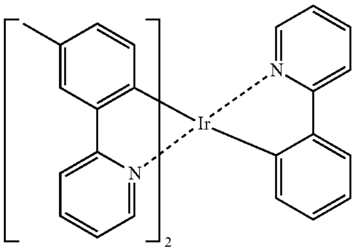
Dp-21
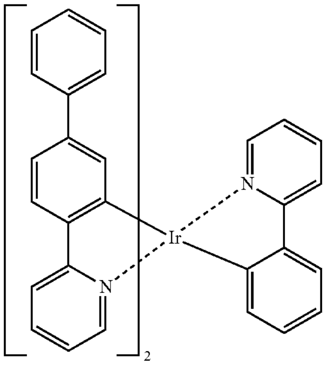
-continued
Dp-22
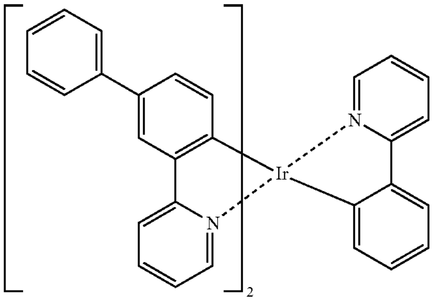
Dp-23
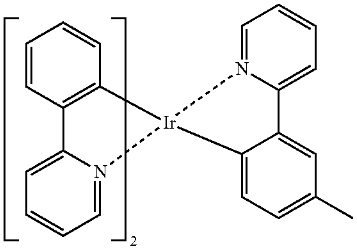
Dp-24
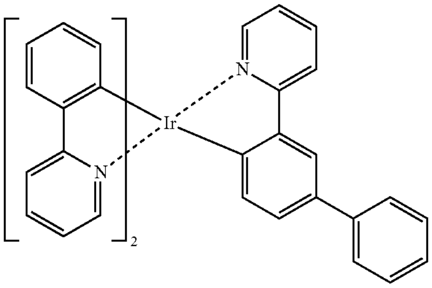
Dp-25
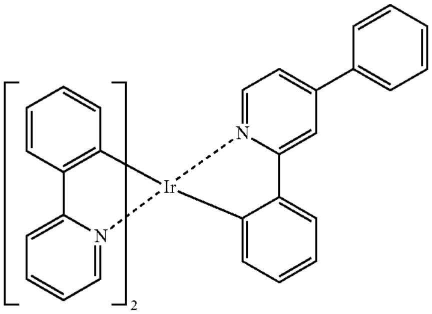
Dp-26
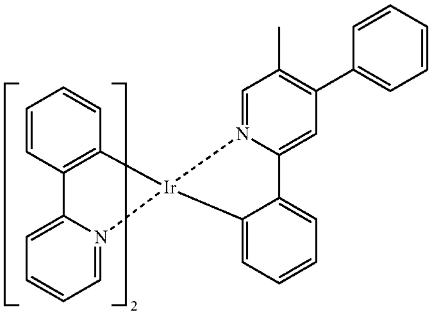

-continued

Dp-27

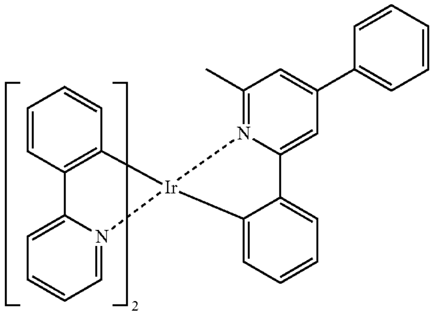

Dp-28

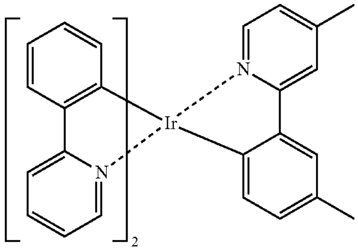

Dp-29

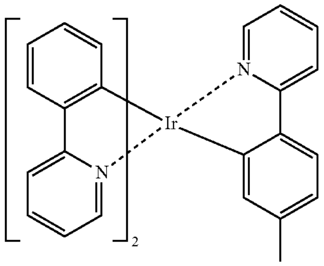

Dp-30

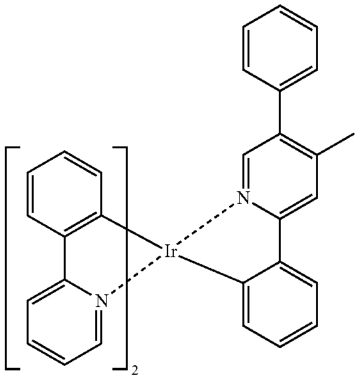

Dp-31

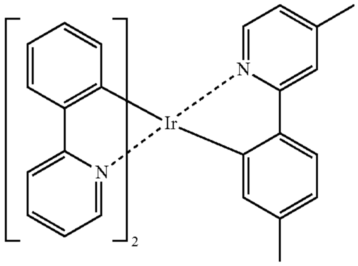

-continued

Dp-32

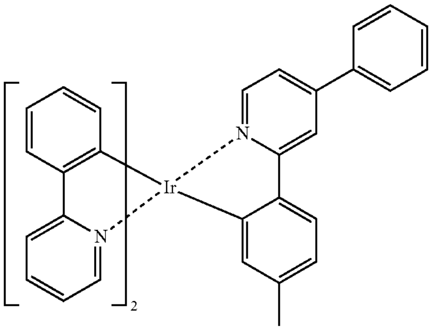

Dp-33

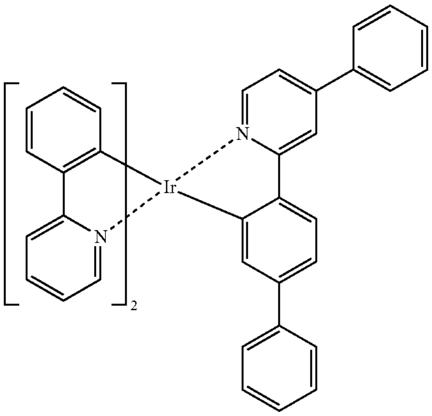

Dp-34

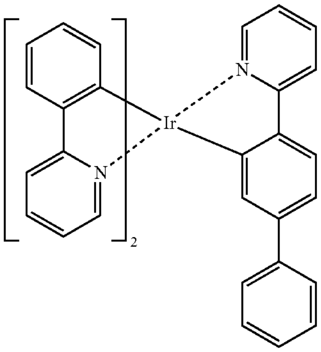

Dp-35

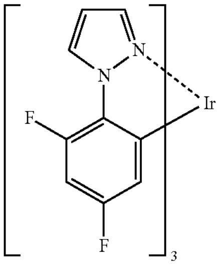

The electron transport layer is a layer that accepts electrons from an electron injection layer and transports the electrons to a light emitting layer, and an electron transport material is suitably a material having high electron mobility that can proficiently accept electrons from a cathode and transfer the electrons to a light emitting layer. Specific examples thereof comprise: Al complexes of 8-hydroxyquinoline, complexes comprising $Alq_3$, organic radical compounds, hydroxyflavone-metal complexes, and the like, but are not limited thereto. The electron transport layer can be used with any desired cathode material, as used according to the related art. In particular, examples of an appropriate cathode material comprise a typical material that has a low work function, followed by an aluminum layer or a silver layer. Specific examples thereof comprise cesium, barium, calcium, ytterbium, and samarium, in each case followed by an aluminum layer or a silver layer.

The electron injection layer is a layer that injects electrons from an electrode, and is preferably a compound that has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof comprise fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds comprise 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer that blocks holes from reaching a cathode, and can be generally formed under the same conditions as those of the hole injection layer. Specific examples thereof comprise oxadiazole derivatives or triazole derivatives, phenanthroline derivatives, BCP, aluminum complexes, and the like, but are not limited thereto.

The organic light emitting device according to the present specification can be a top emission type, a bottom emission type, or a dual emission type according to the materials to be used.

The organic light emitting device of the present invention can be manufactured using typical manufacturing methods and materials of an organic light emitting device, except that the above-described compound is used to form an organic material layer having one or more layers.

EXAMPLES

Hereinafter, the present specification will be described in more detail through Examples. However, the following Examples are provided only for exemplifying the present specification, but are not intended to limit the present specification.

EXAMPLES

The compounds of the present invention were prepared using Buchwald-Hartwig coupling reaction, Heck coupling reaction, Suzuki coupling reaction, and the like as representative reactions.

Preparation Example 1

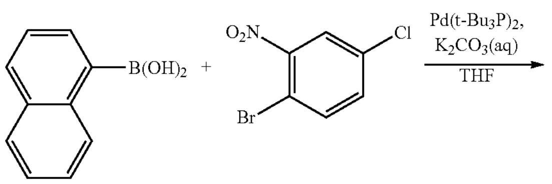

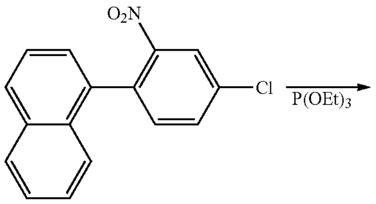

a-1

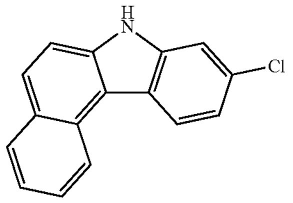

a

1) Preparation of Formula a-1

Under a nitrogen atmosphere, naphthalen-1-ylboronic acid (100 g, 581.2 mmol) and 1-bromo-4-chloro-2-nitrobenzene (150.2 g, 639.3 mmol) were put into 2,000 ml of THF, and the resulting solution was stirred and refluxed. Thereafter, potassium carbonate (321.3 g, 2324.6 mmol) was dissolved in 964 ml of water, the resulting solution was introduced thereinto, the resulting mixture was sufficiently stirred, and then bis(tri-tert-butylphosphine)palladium(0) (3 g, 5.8 mmol) was introduced thereinto. After reacting for 2 hours, the temperature of the mixture was cooled to room temperature, the organic layer and the aqueous layer were separated, and then the organic layer was distilled. The distilled organic layer was again dissolved in chloroform, the solution was washed twice with water, and then the organic layer was separated, anhydrous magnesium sulfate was put thereinto, and the resulting mixture was stirred, and then filtered, and the filtrate was distilled under reduced pressure. The concentrated compound was purified with silica gel column chromatography to prepare 111.9 g of Compound a-1 (yield 68%, MS: [M+H]+=284).

2) Preparation of Formula a 111.9 g (1.0 eq) of Formula a-1 was put into 500 mL of $P(OEt)_3$, and the resulting mixture was refluxed and stirred. After 3 hours, crystals were precipitated by pouring the reactant into water, and filtered. After the filtered solid was completely dissolved in chloroform, the resulting solution was washed with water, crystals were precipitated by concentrating the solution in which the product was dissolved, under reduced pressure, cooled, and then filtered. The residue was purified with column chromatography to obtain 50.6 g (yield 51%) of Formula a. [M+H]=252

Preparation Example 2

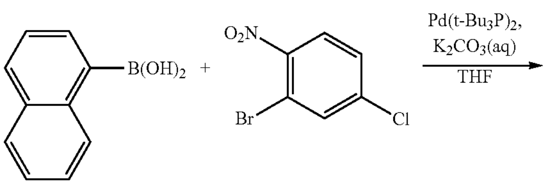

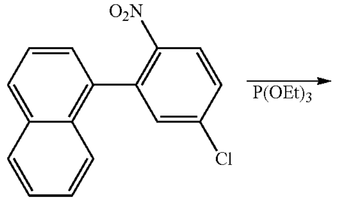

b-1

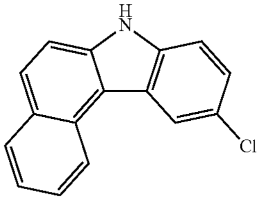

b

Formula b-1 was synthesized using 2-bromo-4-chloro-1-nitrobenzene instead of 1-bromo-4-chloro-2-nitrobenzene used in Preparation Example 1, and Formula b was subsequently synthesized.

<Synthesis Example 1> Synthesis of Compound 1

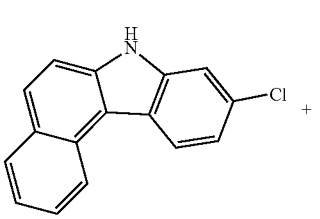

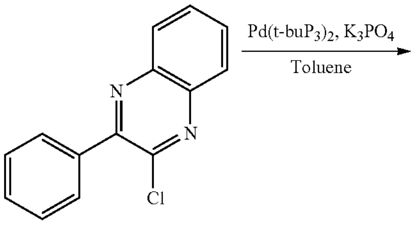

-continued

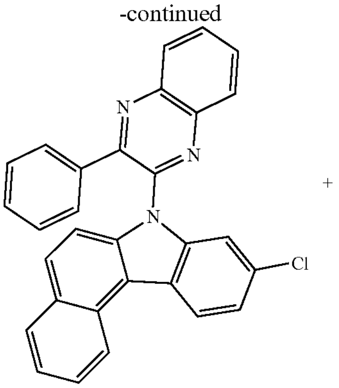

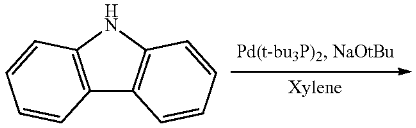

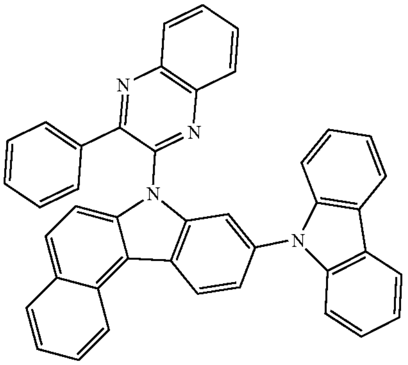

1) Synthesis of Intermediate 1

Under a nitrogen atmosphere, Formula a (20 g, 79.7 mmol), 2-chloro-3-phenylquinoxaline (19.1 g, 79.7 mmol), and tripotassium phosphate (15.3 g, 159.3 mmol) were put into 400 ml of toluene, and the resulting solution was stirred and refluxed. Thereafter, bis(tri-tert-butylphosphine)palladium(0) (0.8 g, 1.6 mmol) was introduced thereinto. After 2 hours, the reaction was terminated, so that the resulting product was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 21.8 g of Intermediate 1 (yield 60%, MS: [M+H]+=456).

2) Synthesis of Compound 1

Under a nitrogen atmosphere, Intermediate 1 (20 g, 43.9 mmol), 9H-carbazole (7.3 g, 43.9 mmol), and sodium tert-butoxide (8.4 g, 87.9 mmol) were put into 400 ml of xylene, and the resulting solution was stirred and refluxed. Thereafter, bis(tri-tert-butylphosphine)palladium(0) (0.4 g, 0.9 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 15.2 g of Compound 1 (yield 59%, MS: [M+H]+=587).

<Synthesis Example 2> Synthesis of Compound 2

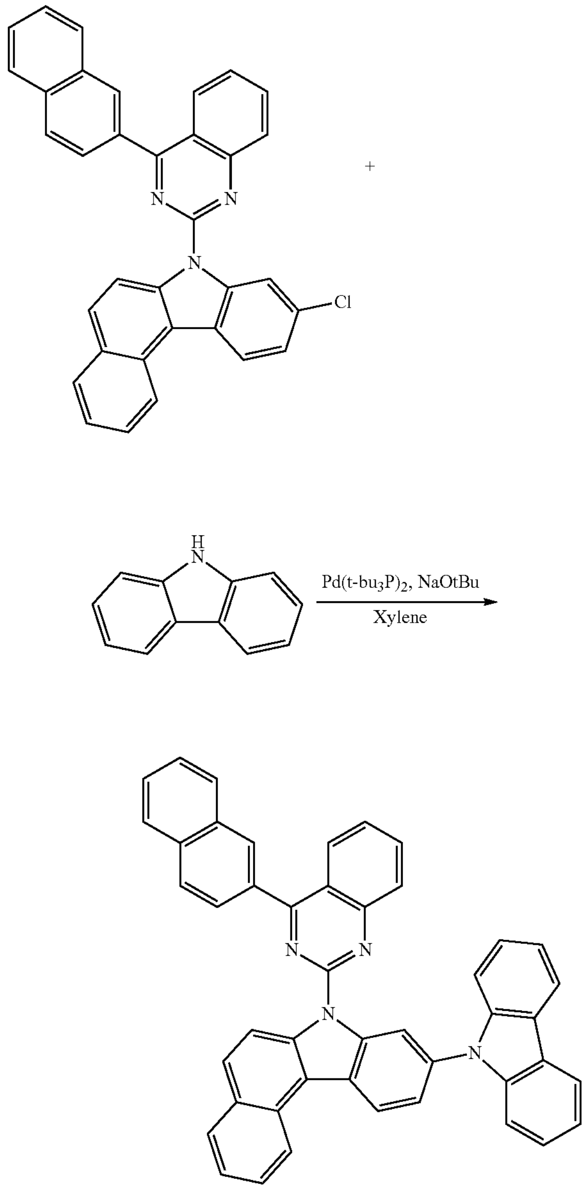

Under a nitrogen atmosphere, Intermediate 2 (10 g, 19.8 mmol), 9H-carbazole (3.5 g, 20.8 mmol), and sodium tert-butoxide (3.8 g, 39.6 mmol) were put into 200 ml of xylene, and the resulting solution was stirred and refluxed. Thereafter, bis(tri-tert-butylphosphine)palladium(0) (0.2 g, 0.4 mmol) was introduced thereinto. After 2 hours, the reaction was terminated, so that the resulting product was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.2 g of Compound 2 (yield 65%, MS: [M+H]+=637).

<Synthesis Example 3> Synthesis of Compound 3

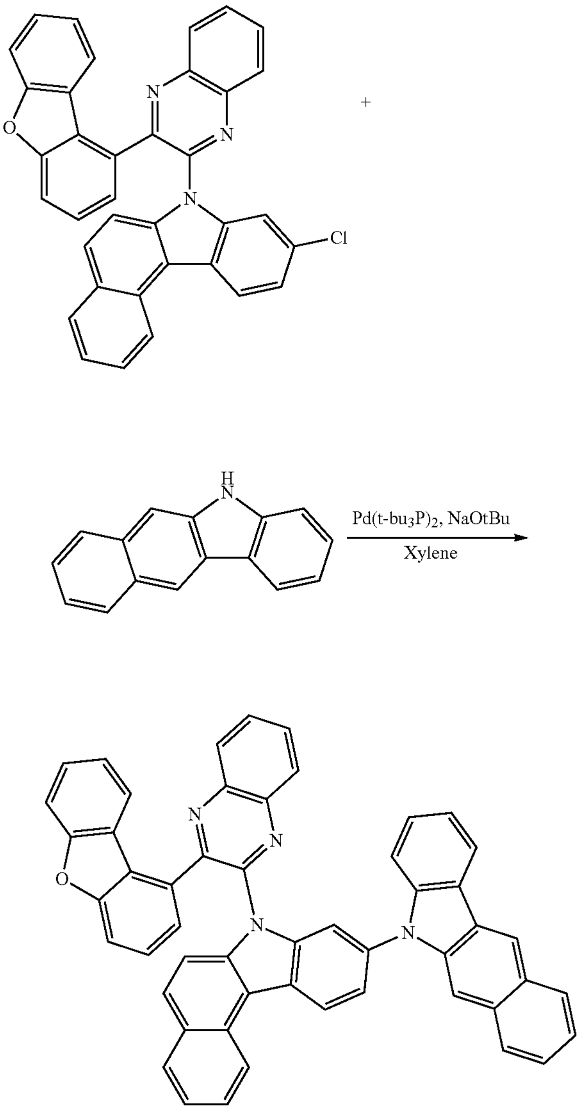

Under a nitrogen atmosphere, Intermediate 3 (10 g, 18.3 mmol), 5H-benzo[b]carbazole (4.2 g, 19.3 mmol), and sodium tert-butoxide (3.5 g, 36.7 mmol) were put into 200 ml of xylene, and the resulting solution was stirred and refluxed. Thereafter, bis(tri-tert-butylphosphine)palladium (0) (0.2 g, 0.4 mmol) was introduced thereinto. After 2 hours, the reaction was terminated, so that the resulting product was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7.3 g of Compound 3 (yield 55%, MS: [M+H]+=727).

<Synthesis Example 4> Synthesis of Compound 4

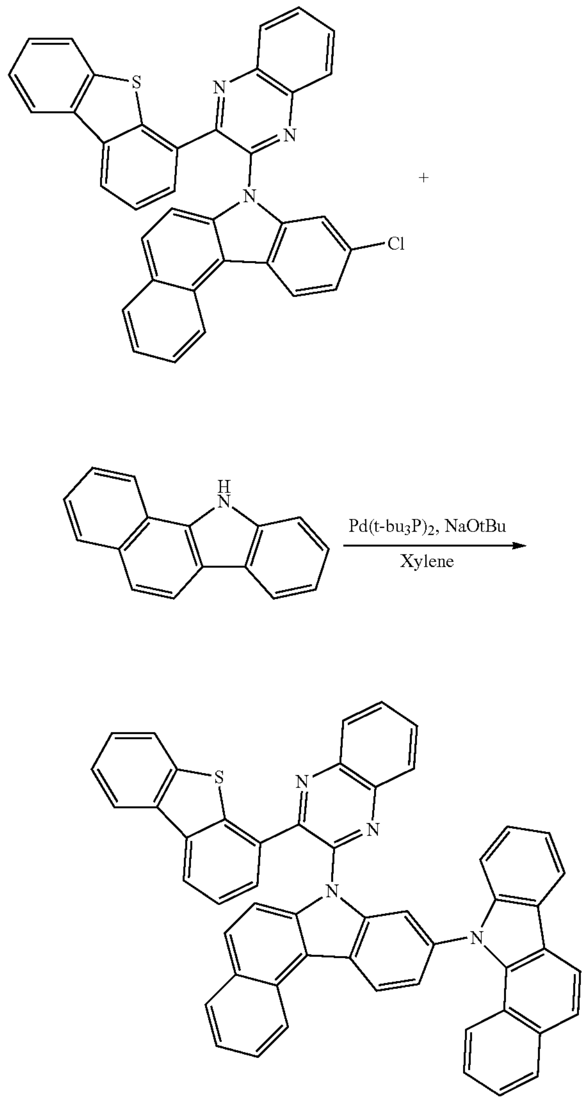

Under a nitrogen atmosphere, Intermediate 4 (10 g, 17.8 mmol), 11H-benzo[a]carbazole (4.1 g, 18.7 mmol), and sodium tert-butoxide (3.4 g, 35.6 mmol) were put into 200 ml of xylene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the resulting product was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.9 g of Compound 4 (yield 67%, MS: [M+H]+=743).

<Synthesis Example 5> Synthesis of Compound 5

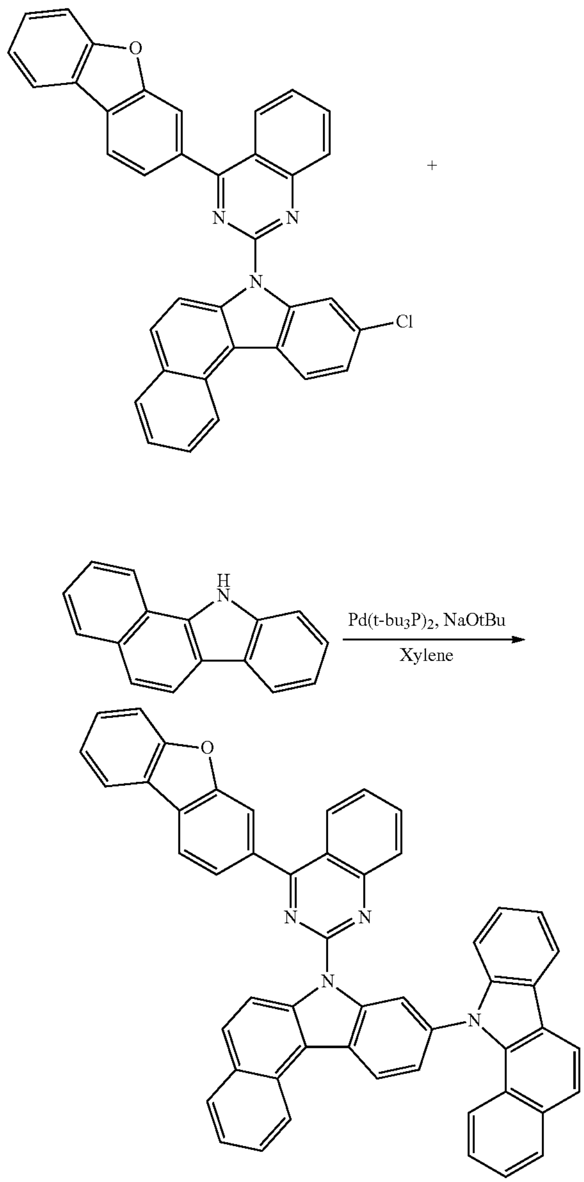

Under a nitrogen atmosphere, Intermediate 5 (10 g, 18.3 mmol), 11H-benzo[a]carbazole (4.2 g, 19.3 mmol), and sodium tert-butoxide (3.5 g, 36.7 mmol) were put into 200 ml of xylene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the resulting product was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 9.3 g of Compound 5 (yield 70%, MS: [M+H]+=727).

<Synthesis Example 6> Synthesis of Compound 6

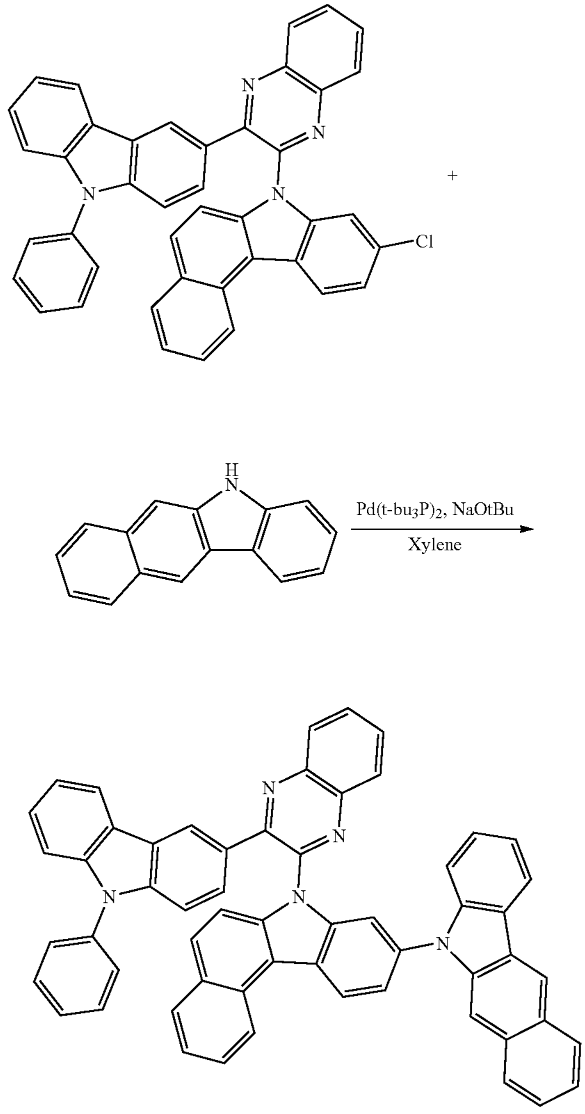 [SMILES: Clc1ccc2c3c4ccccc4ccc3n(-c3nc4ccccc4nc3-c3ccc4c(c3)c3ccccc3n4-c3ccccc3)c2c1 ; "+" ; c1ccc2cc3c(cc2c1)[nH]c1ccccc13 ; c1ccc(-n2c3ccccc3c3cc(-c4nc5ccccc5nc4-n4c5cc(-n6c7ccccc7c7cc8ccccc8cc76)ccc5c5c6ccccc6ccc54)ccc32)cc1]

Under a nitrogen atmosphere, Intermediate 6 (10 g, 16.1 mmol), 5H-benzo[b]carbazole (3.7 g, 16.9 mmol), and sodium tert-butoxide (3.1 g, 32.2 mmol) were put into 200 ml of xylene, and the resulting solution was stirred and refluxed. Thereafter, bis(tri-tert-butylphosphine)palladium (0) (0.2 g, 0.3 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.1 g of Compound 6 (yield 63%, MS: [M+H]+=802).

<Synthesis Example 7> Synthesis of Compound 7

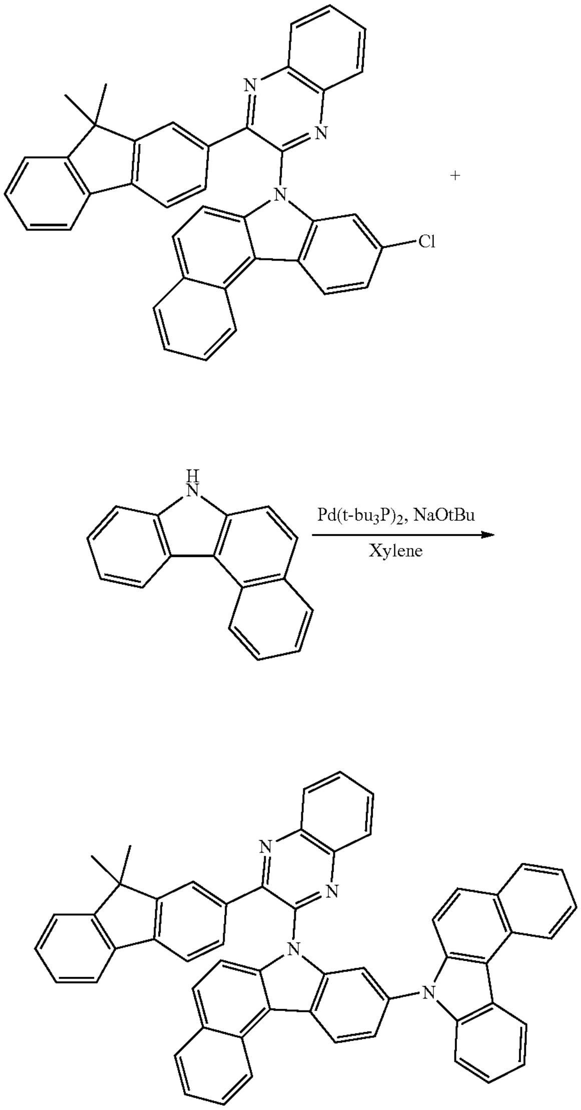

Under a nitrogen atmosphere, Intermediate 7 (10 g, 17.5 mmol), 7H-benzo[c]carbazole (4 g, 18.4 mmol), and sodium tert-butoxide (3.4 g, 35 mmol) were put into 200 ml of xylene, and the resulting solution was stirred and refluxed. Thereafter, bis(tri-tert-butylphosphine)palladium(0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7.6 g of Compound 7 (yield 58%, MS: [M+H]+=753).

<Synthesis Example 8> Synthesis of Compound 8

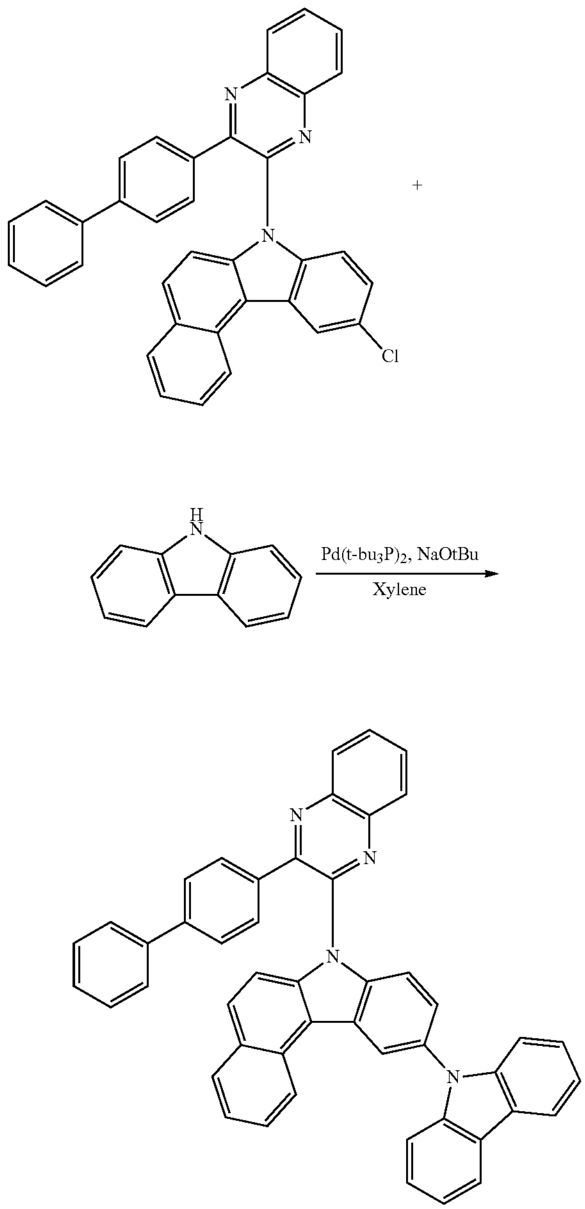

Under a nitrogen atmosphere, Intermediate 8 (10 g, 18.8 mmol), 9H-carbazole (3.3 g, 19.8 mmol), and sodium tert-butoxide (3.6 g, 37.7 mmol) were put into 200 ml of xylene, and the resulting solution was stirred and refluxed. Thereafter, bis(tri-tert-butylphosphine)palladium(0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure.

The concentrated compound was purified with silica gel column chromatography to obtain 6.5 g of Compound 8 (yield 52%, MS: [M+H]+=663).

<Synthesis Example 9> Synthesis of Compound 9

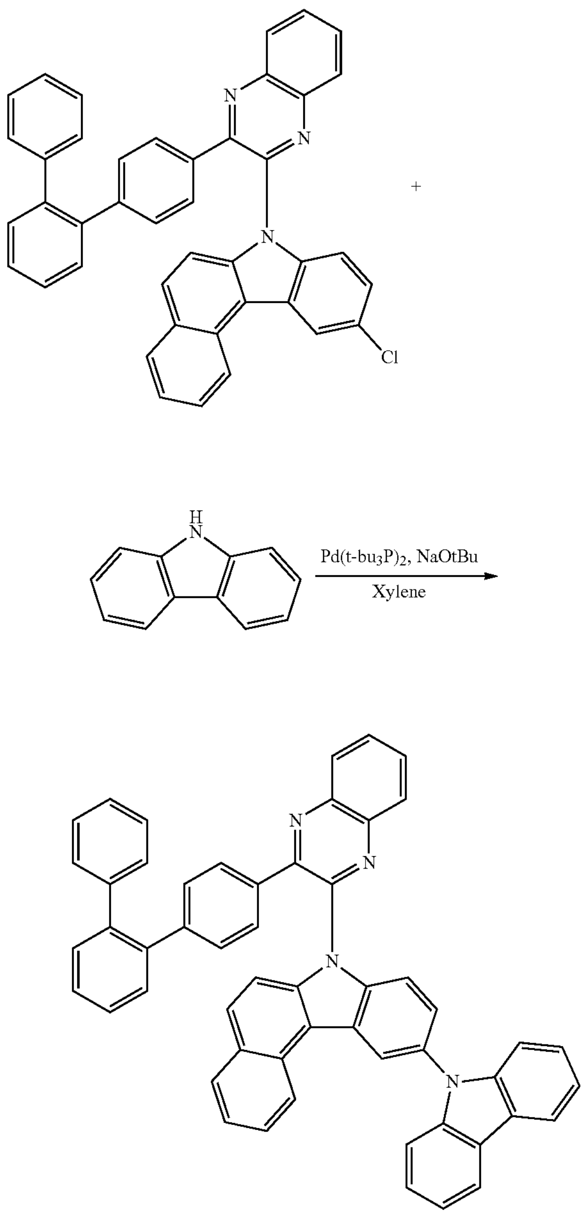

Under a nitrogen atmosphere, Intermediate 9 (10 g, 16.5 mmol), 9H-carbazole (2.9 g, 17.3 mmol), and sodium tert-butoxide (3.2 g, 32.9 mmol) were put into 200 ml of xylene, and the resulting solution was stirred and refluxed. Thereafter, bis(tri-tert-butylphosphine)palladium(0) (0.2 g, 0.3 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 6.9 g of Compound 9 (yield 57%, MS: [M+H]+=739).

<Synthesis Example 10> Synthesis of Compound 10

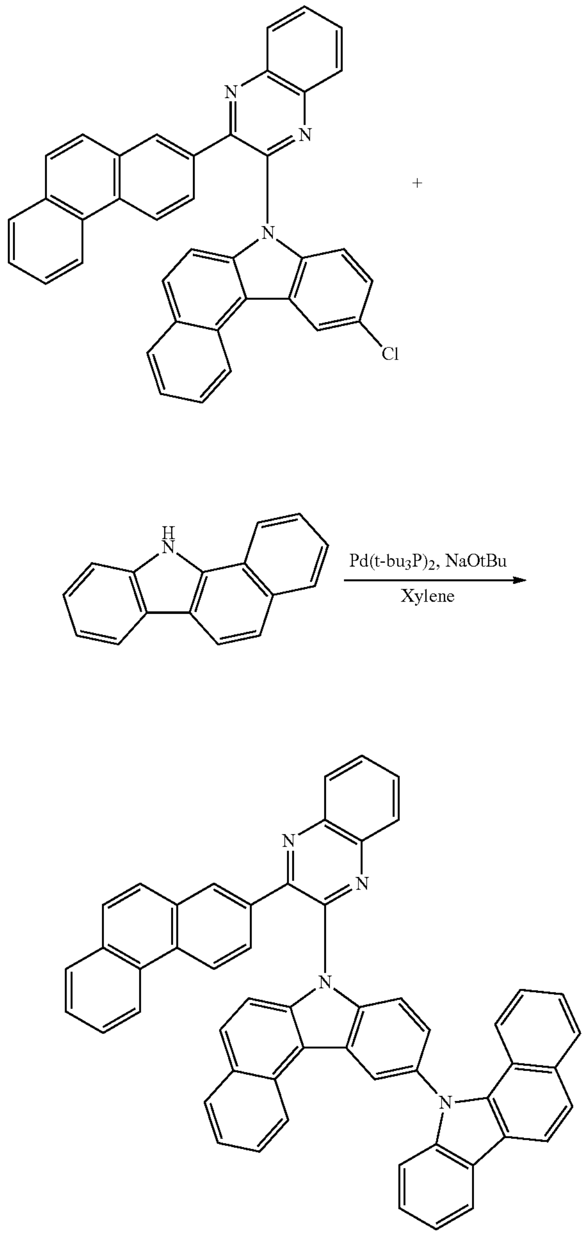

Under a nitrogen atmosphere, Intermediate 10 (10 g, 18 mmol), 11H-benzo[a]carbazole (4.1 g, 18.9 mmol), and sodium tert-butoxide (3.5 g, 36 mmol) were put into 200 ml of xylene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.2 g of Compound 10 (yield 62%, MS: [M+H]+=737).

<Synthesis Example 11> Synthesis of Compound 11

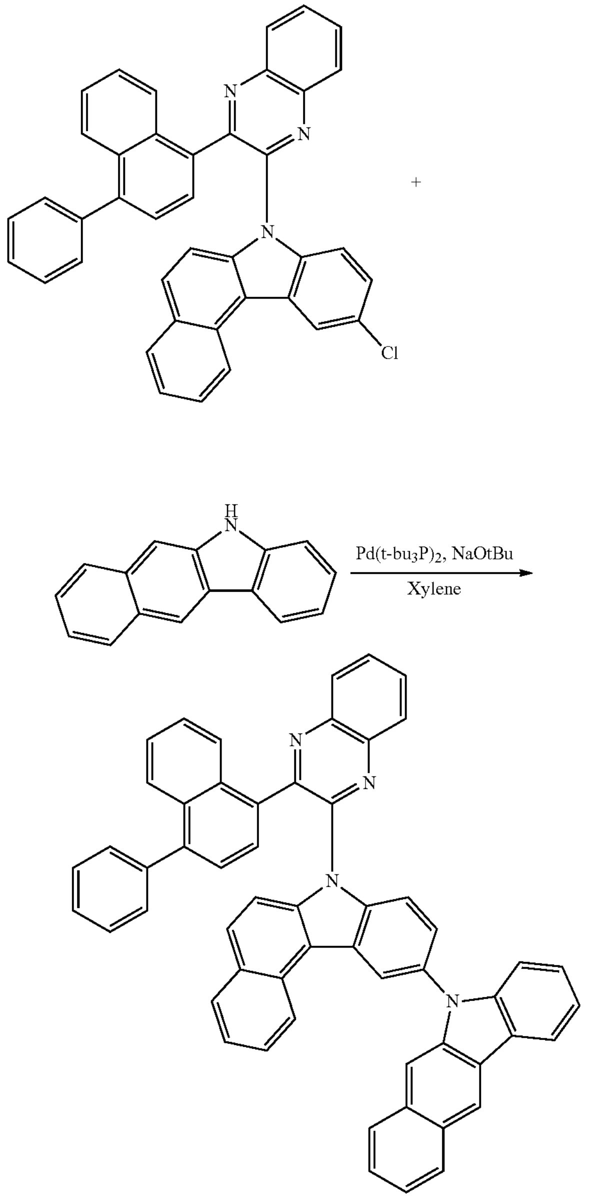

Under a nitrogen atmosphere, Intermediate 11 (10 g, 17.2 mmol), 5H-benzo[b]carbazole (3.9 g, 18.1 mmol), and sodium tert-butoxide (3.3 g, 34.4 mmol) were put into 200 ml of xylene, and the resulting solution was stirred and refluxed. Thereafter, bis(tri-tert-butylphosphine)palladium (0) (0.2 g, 0.3 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.3 g of Compound 11 (yield 63%, MS: [M+H]+=763).

<Synthesis Example 12> Synthesis of Compound 12

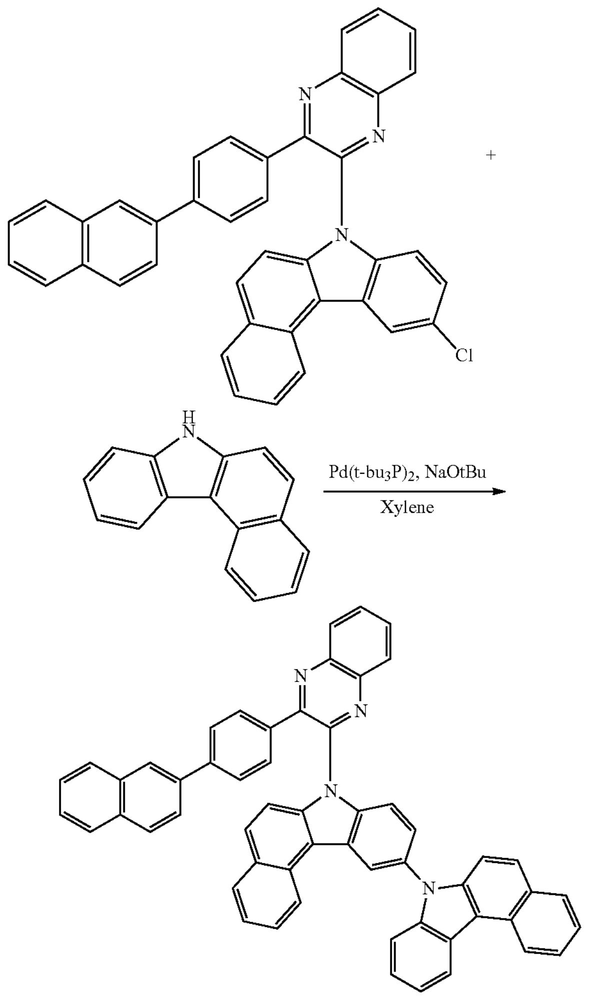

Under a nitrogen atmosphere, Intermediate 12 (10 g, 17.2 mmol), 7H-benzo[c]carbazole (3.9 g, 18.1 mmol), and sodium tert-butoxide (3.3 g, 34.4 mmol) were put into 200 ml of xylene, and the resulting solution was stirred and refluxed. Thereafter, bis(tri-tert-butylphosphine)palladium (0) (0.2 g, 0.3 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8 g of Compound 12 (yield 61%, MS: [M+H]+=763).

<Synthesis Example 13> Synthesis of Compound 13

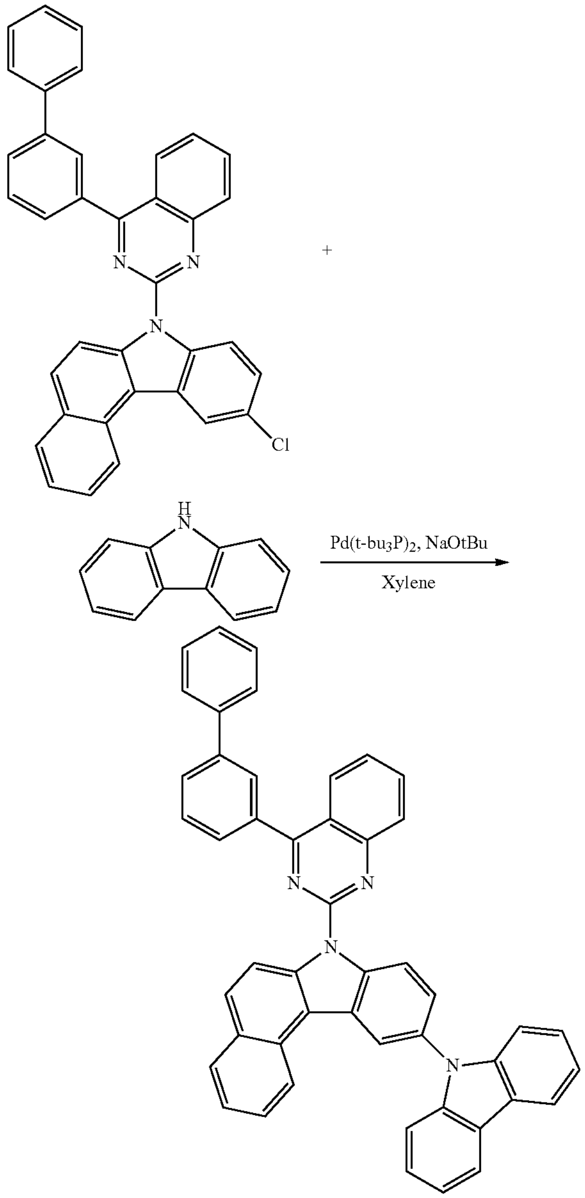

Under a nitrogen atmosphere, Intermediate 13 (10 g, 18.8 mmol), 9H-carbazole (3.3 g, 19.8 mmol), and sodium tert-butoxide (3.6 g, 37.7 mmol) were put into 200 ml of xylene, and the resulting solution was stirred and refluxed. Thereafter, bis(tri-tert-butylphosphine)palladium(0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7.9 g of Compound 13 (yield 63%, MS: [M+H]+=663).

<Synthesis Example 14> Synthesis of Compound 14

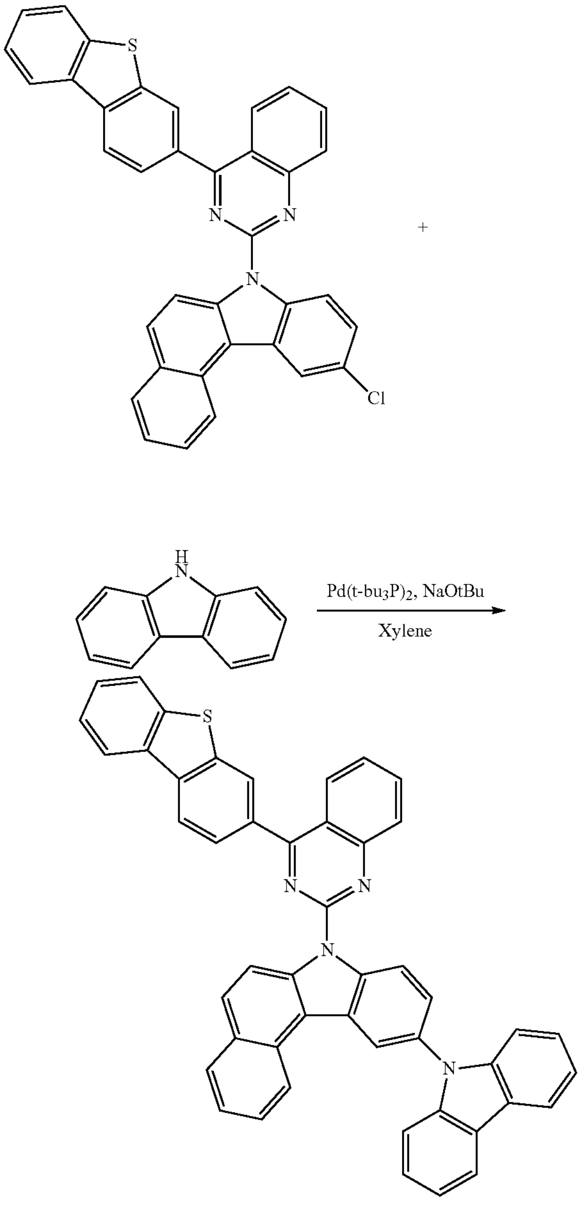

Under a nitrogen atmosphere, Intermediate 14 (10 g, 17.8 mmol), 9H-carbazole (3.1 g, 18.7 mmol), and sodium tert-butoxide (3.4 g, 35.6 mmol) were put into 200 ml of xylene, and the resulting solution was stirred and refluxed. Thereafter, bis(tri-tert-butylphosphine)palladium(0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7.3 g of Compound 14 (yield 59%, MS: [M+H]+=693).

<Synthesis Example 15> Synthesis of Compound 15

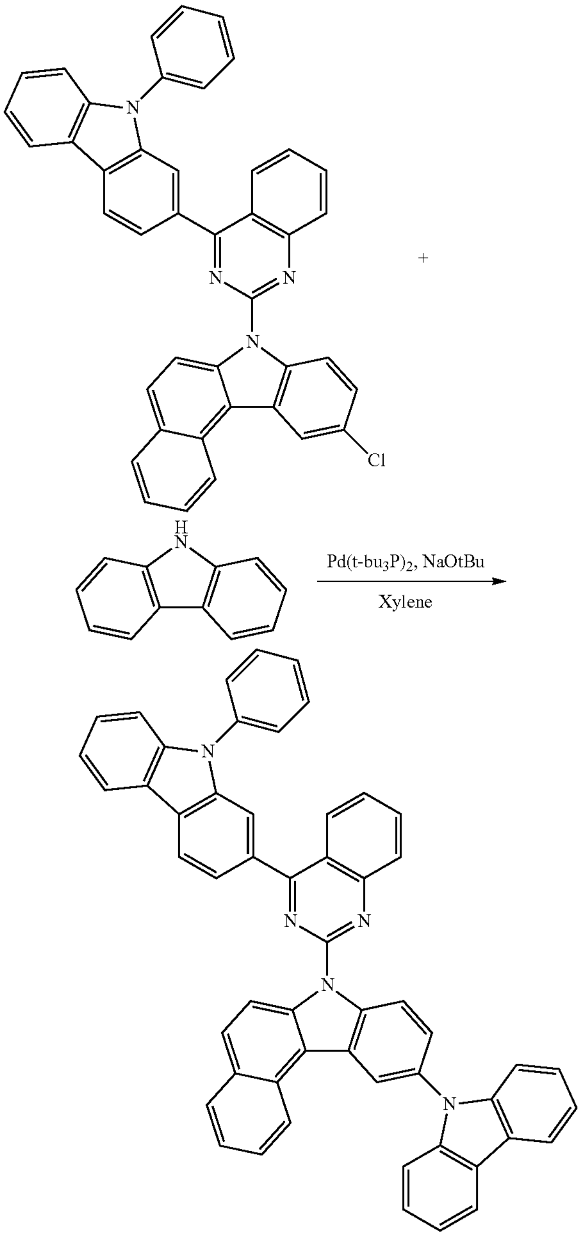

Under a nitrogen atmosphere, Intermediate 15 (10 g, 16.1 mmol), 9H-carbazole (2.8 g, 16.9 mmol), and sodium tert-butoxide (3.1 g, 32.2 mmol) were put into 200 ml of xylene, and the resulting solution was stirred and refluxed. Thereafter, bis(tri-tert-butylphosphine)palladium(0) (0.2 g, 0.3 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7.1 g of Compound 15 (yield 59%, MS: [M+H]+=752).

<Synthesis Example 16> Synthesis of Compound 16

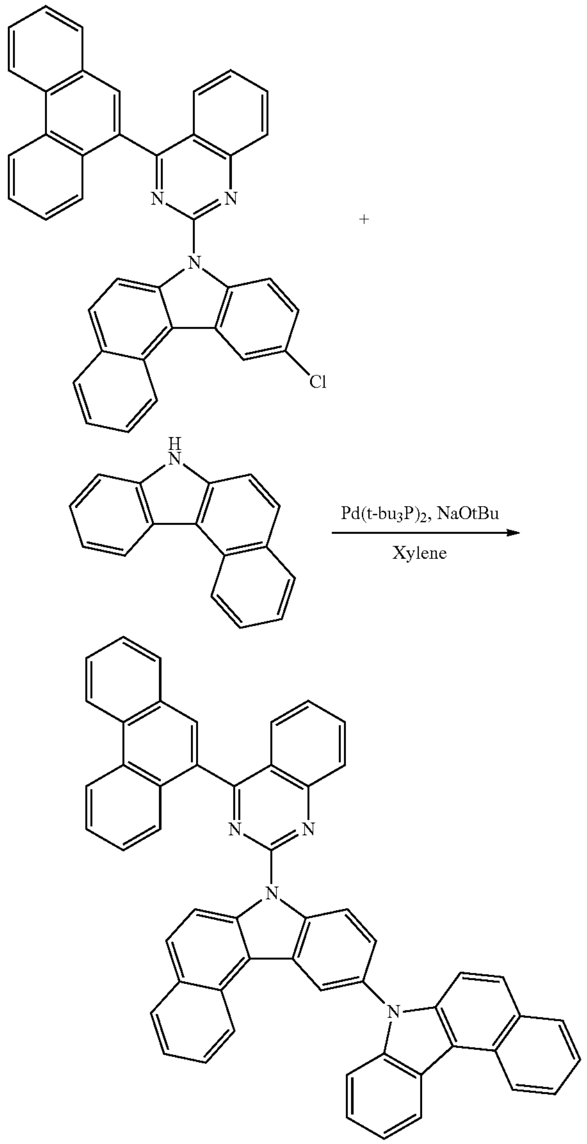

Under a nitrogen atmosphere, Intermediate 16 (10 g, 18 mmol), 7H-benzo[c]carbazole (4.1 g, 18.9 mmol), and sodium tert-butoxide (3.5 g, 36 mmol) were put into 200 ml of xylene, and the resulting solution was stirred and refluxed. Thereafter, bis(tri-tert-butylphosphine)palladium (0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.9 g of Compound 16 (yield 67%, MS: [M+H]+=737).

<Synthesis Example 17> Synthesis of Compound 17

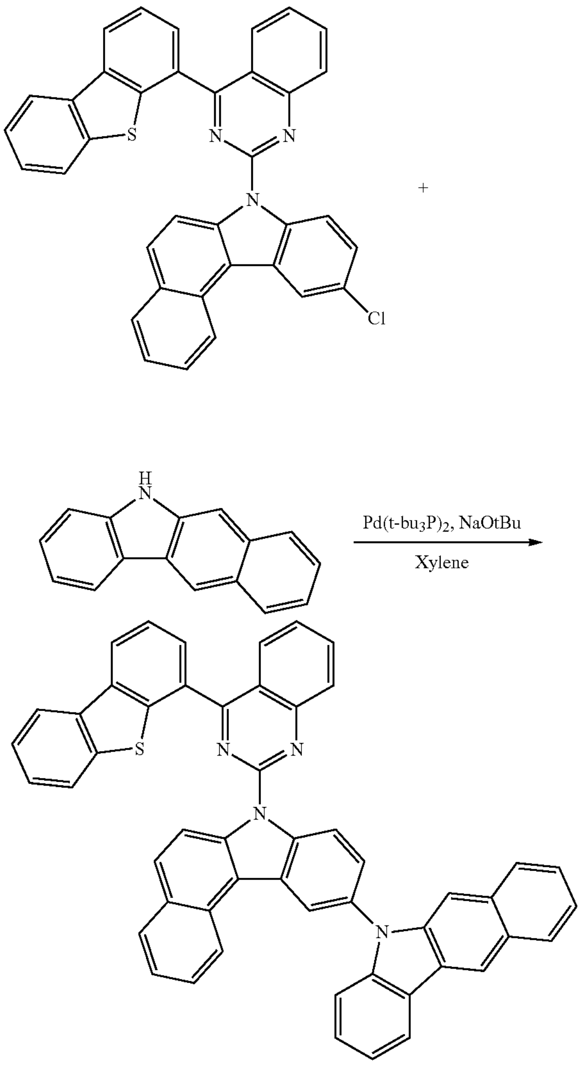

Under a nitrogen atmosphere, Intermediate 17 (10 g, 17.8 mmol), 5H-benzo[b]carbazole (4.1 g, 18.7 mmol), and sodium tert-butoxide (3.4 g, 35.6 mmol) were put into 200 ml of xylene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7 g of Compound 17 (yield 53%, MS: [M+H]+=743).

<Synthesis Example 18> Synthesis of Compound 18

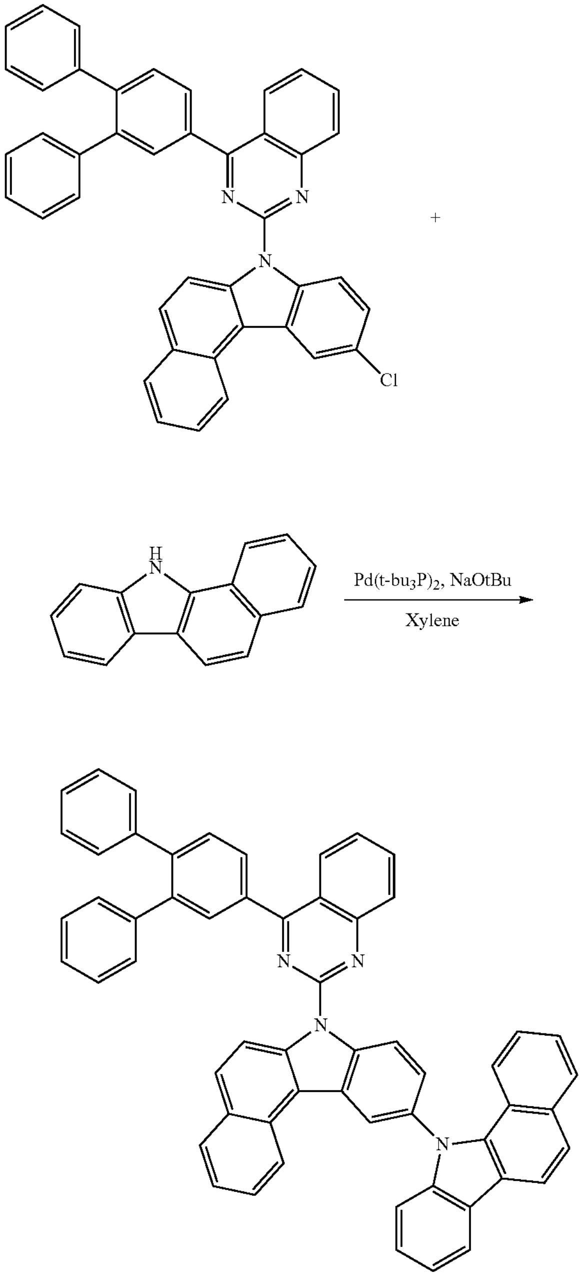

Under a nitrogen atmosphere, Intermediate 18 (10 g, 16.5 mmol), 11H-benzo[a]carbazole (3.8 g, 17.3 mmol), and sodium tert-butoxide (3.2 g, 32.9 mmol) were put into 200 ml of xylene, and the resulting solution was stirred and refluxed. Thereafter, bis(tri-tert-butylphosphine)palladium (0) (0.2 g, 0.3 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7.5 g of Compound 18 (yield 58%, MS: [M+H]+=789).

<Synthesis Example 19> Synthesis of Compound 19

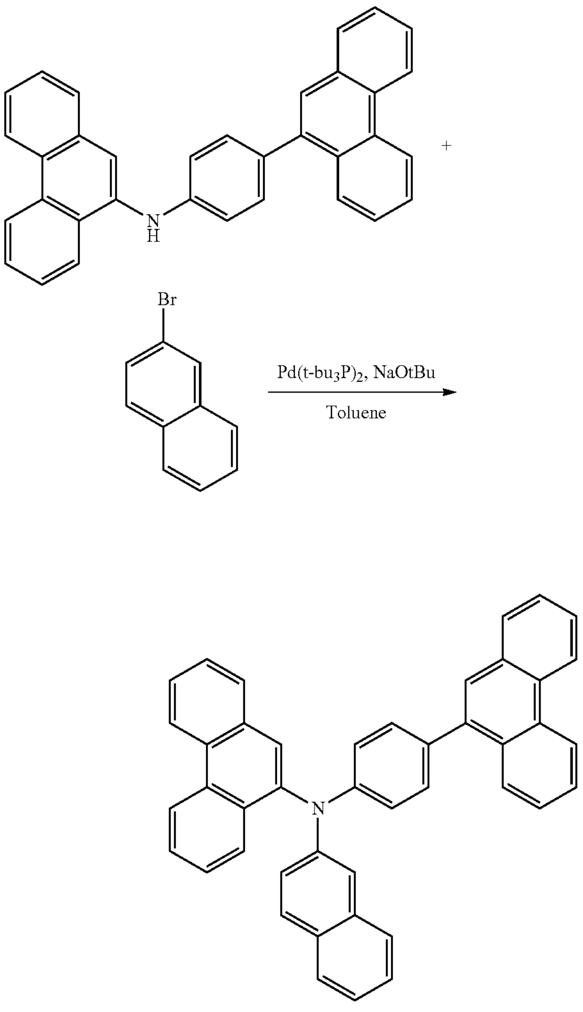

Under a nitrogen atmosphere, Intermediate 19 (10 g, 22.5 mmol), 2-bromonaphthalene (4.6 g, 22.5 mmol), and sodium tert-butoxide (4.3 g, 44.9 mmol) were put into 200 ml of toluene, and the resulting solution was stirred and refluxed. Thereafter, bis(tri-tert-butylphosphine)palladium(0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.5 g of Compound 19 (yield 66%, MS: [M+H]+=572).

<Synthesis Example 20> Synthesis of Compound 20

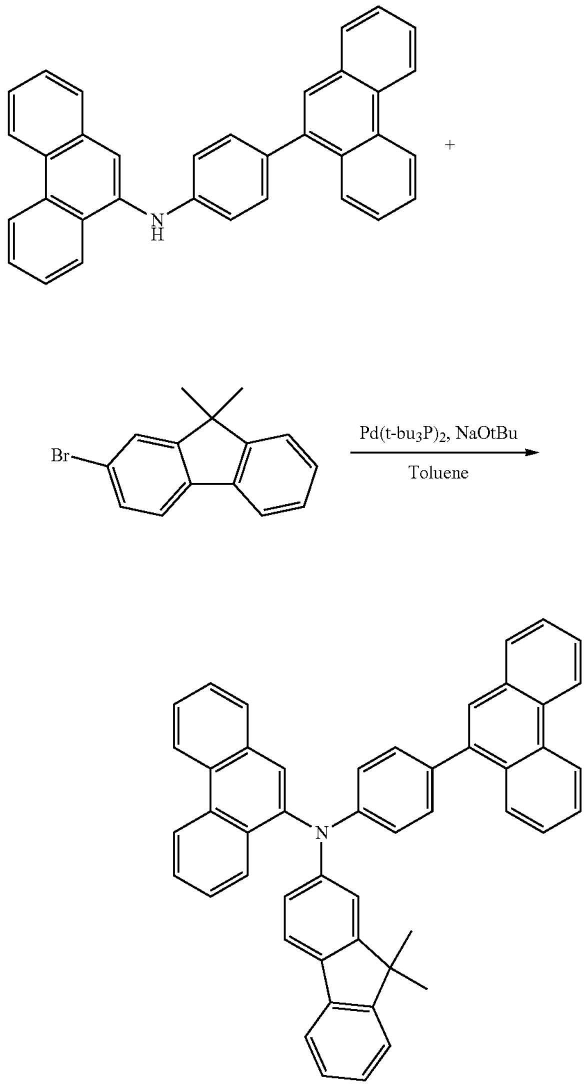

Under a nitrogen atmosphere, Intermediate 20 (10 g, 22.5 mmol), 2-bromo-9,9-dimethyl-9H-fluorene (6.1 g, 22.5 mmol), and sodium tert-butoxide (4.3 g, 44.9 mmol) were put into 200 ml of toluene, and the resulting solution was stirred and refluxed. Thereafter, bis(tri-tert-butylphosphine) palladium(0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 9 g of Compound 20 (yield 63%, MS: [M+H]+=638).

<Synthesis Example 21> Synthesis of Compound 21

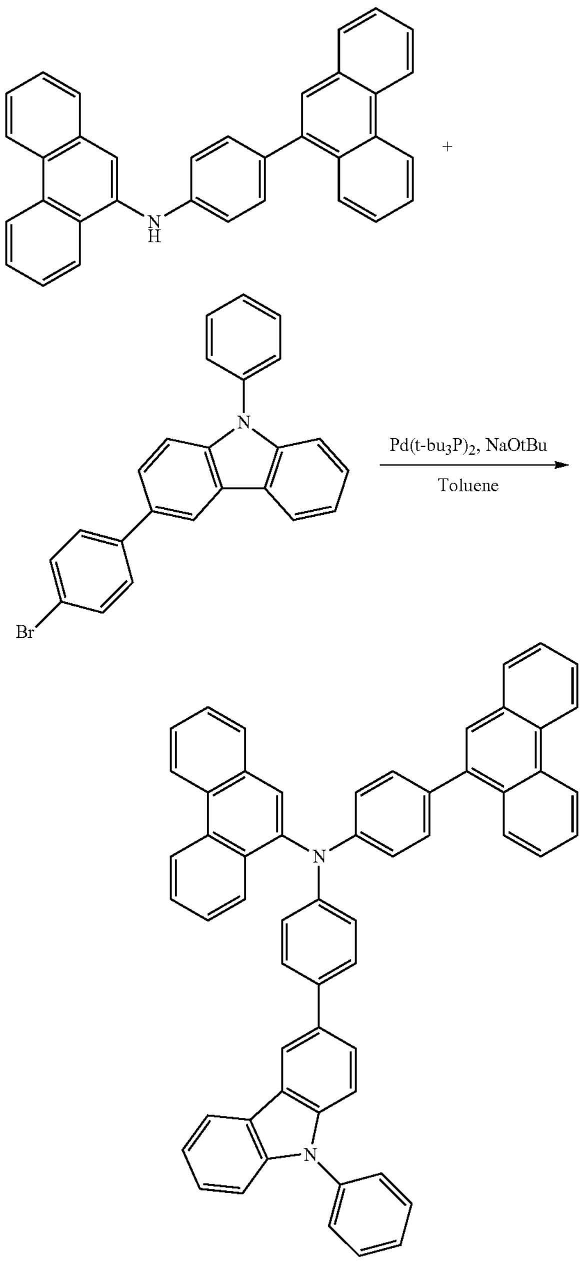

Under a nitrogen atmosphere, Intermediate 21 (10 g, 22.5 mmol), 3-(4-bromophenyl)-9-phenyl-9H-carbazole (8.9 g, 22.5 mmol), and sodium tert-butoxide (4.3 g, 44.9 mmol) were put into 200 ml of toluene, and the resulting solution was stirred and refluxed. Thereafter, bis(tri-tert-butylphosphine)palladium(0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 11.3 g of Compound 21 (yield 66%, MS: [M+H]+=763).

<Synthesis Example 22> Synthesis of Compound 22

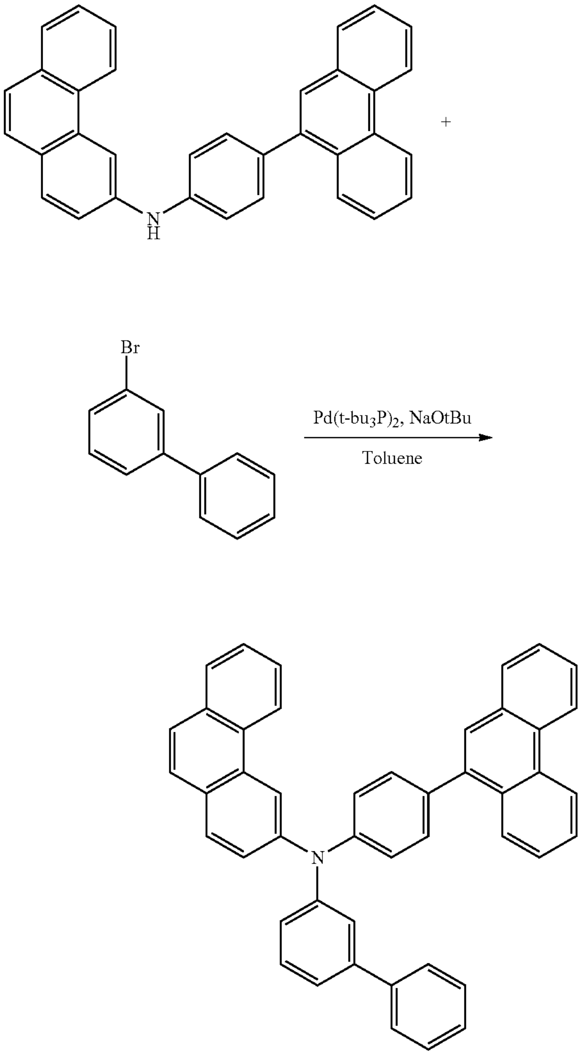

Under a nitrogen atmosphere, Intermediate 22 (10 g, 22.5 mmol), 3-bromo-1,1'-biphenyl (5.2 g, 22.5 mmol), and sodium tert-butoxide (4.3 g, 44.9 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.3 g of Compound 22 (yield 62%, MS: [M+H]+=598).

<Synthesis Example 23> Synthesis of Compound 23

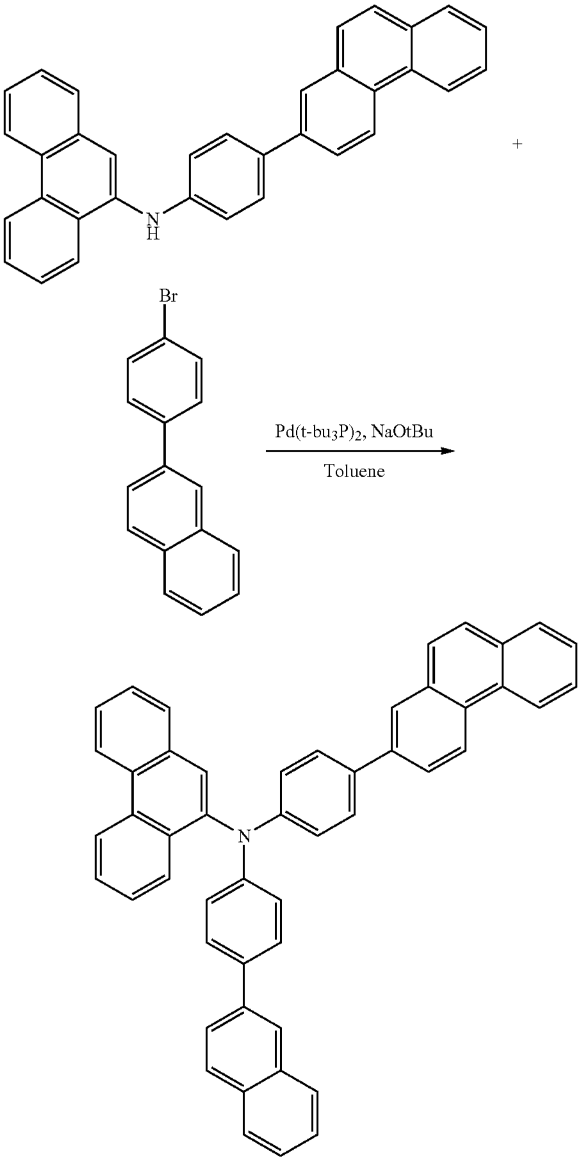

Under a nitrogen atmosphere, Intermediate 23 (10 g, 22.5 mmol), 2-(4-bromophenyl)naphthalene (6.3 g, 22.5 mmol), and sodium tert-butoxide (4.3 g, 44.9 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 10 g of Compound 23 (yield 69%, MS: [M+H]+=648).

<Synthesis Example 24> Synthesis of Compound 24

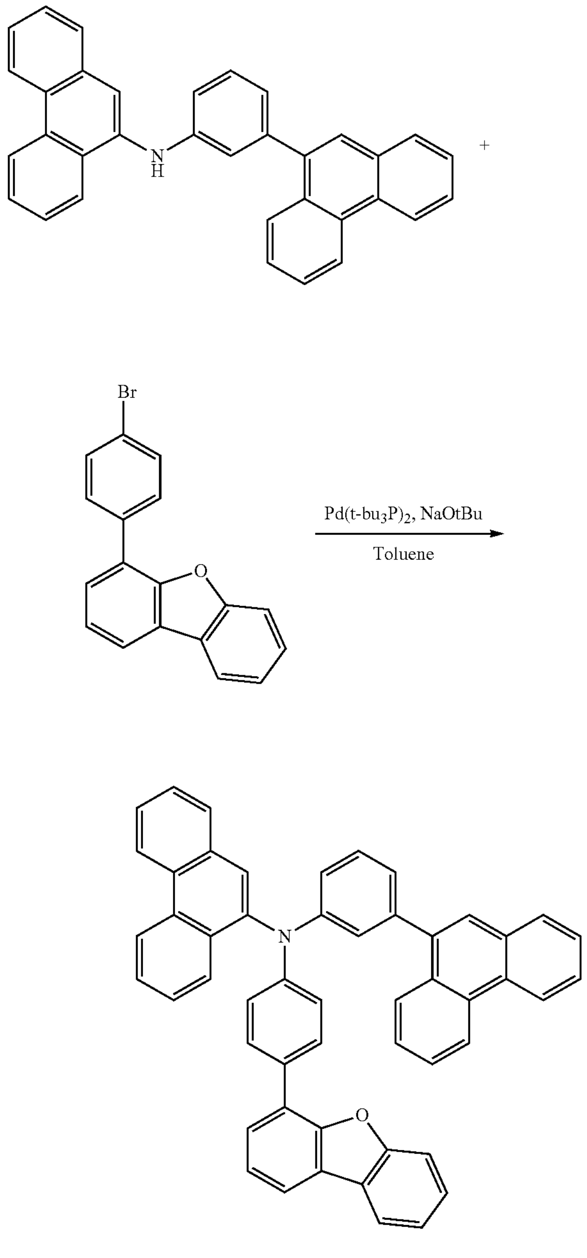

Under a nitrogen atmosphere, Intermediate 24 (10 g, 22.5 mmol), 4-(4-bromophenyl)dibenzo[b,d]furan (7.2 g, 22.5 mmol), and sodium tert-butoxide (4.3 g, 44.9 mmol) were put into 200 ml of toluene, and the resulting solution was stirred and refluxed. Thereafter, bis(tri-tert-butylphosphine) palladium(0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 10 g of Compound 24 (yield 65%, MS: [M+H]+=688).

<Synthesis Example 25> Synthesis of Compound 25

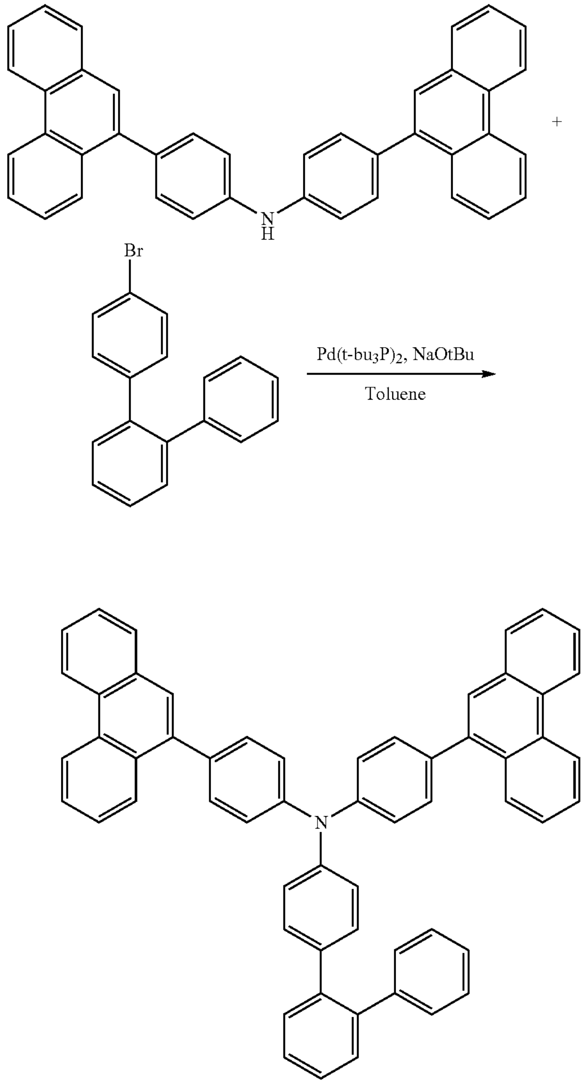

Under a nitrogen atmosphere, Intermediate 25 (10 g, 19.2 mmol), 4-bromo-1,1':2',1"-terphenyl (5.9 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.8 g of Compound 25 (yield 61%, MS: [M+H]+=750).

<Synthesis Example 26> Synthesis of Compound 26

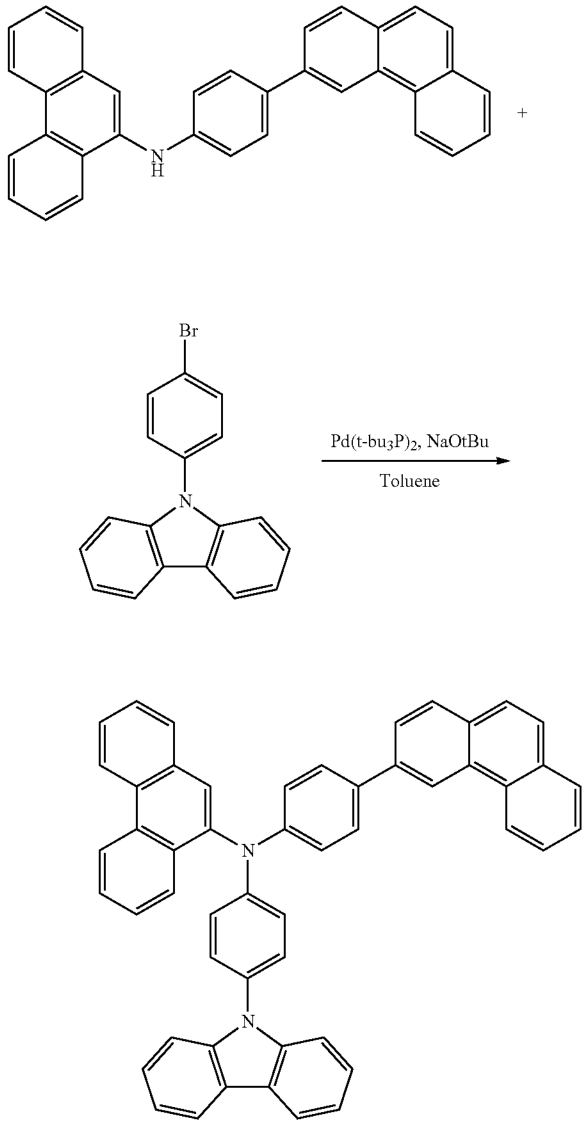

Under a nitrogen atmosphere, Intermediate 26 (10 g, 22.5 mmol), 9-(4-bromophenyl)-9H-carbazole (7.2 g, 22.5 mmol), and sodium tert-butoxide (4.3 g, 44.9 mmol) were put into 200 ml of toluene, and the resulting solution was stirred and refluxed. Thereafter, bis(tri-tert-butylphosphine) palladium(0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 9.6 g of Compound 26 (yield 62%, MS: [M+H]+=687).

<Synthesis Example 27> Synthesis of Compound 27

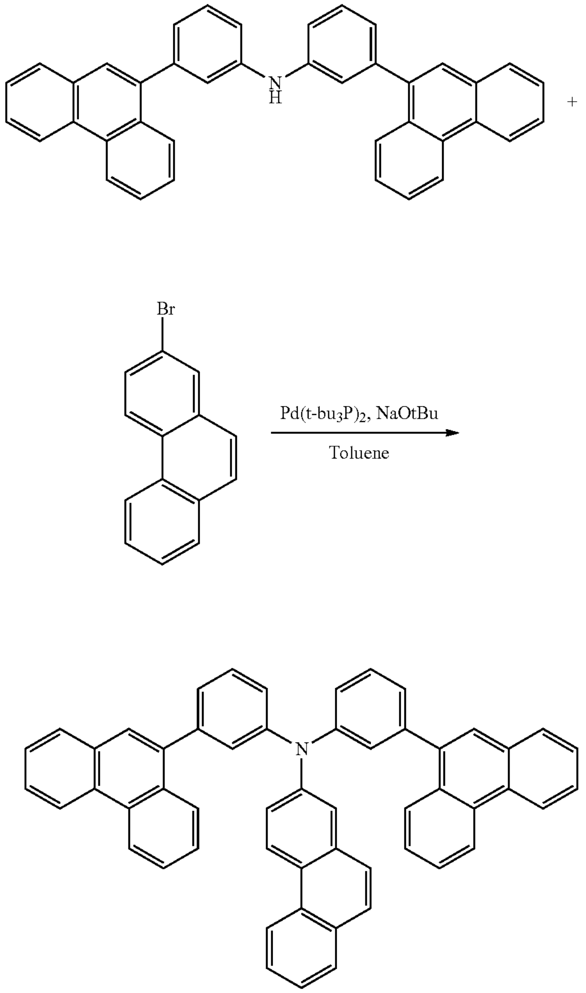 [SMILES: c1cc(Nc2cccc(-c3cc4ccccc4c4ccccc34)c2)cc(-c2cc3ccccc3c3ccccc23)c1 ; Brc1ccc2c(ccc3ccccc32)c1 ; c1cc(-c2cc3ccccc3c3ccccc23)cc(N(c2cccc(-c3cc4ccccc4c4ccccc34)c2)c2ccc3c(ccc4ccccc43)c2)c1]

Under a nitrogen atmosphere, Intermediate 27 (10 g, 19.2 mmol), 2-bromophenanthrene (4.9 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.4 g of Compound 27 (yield 63%, MS: [M+H]+=698).

<Synthesis Example 28> Synthesis of Compound 28

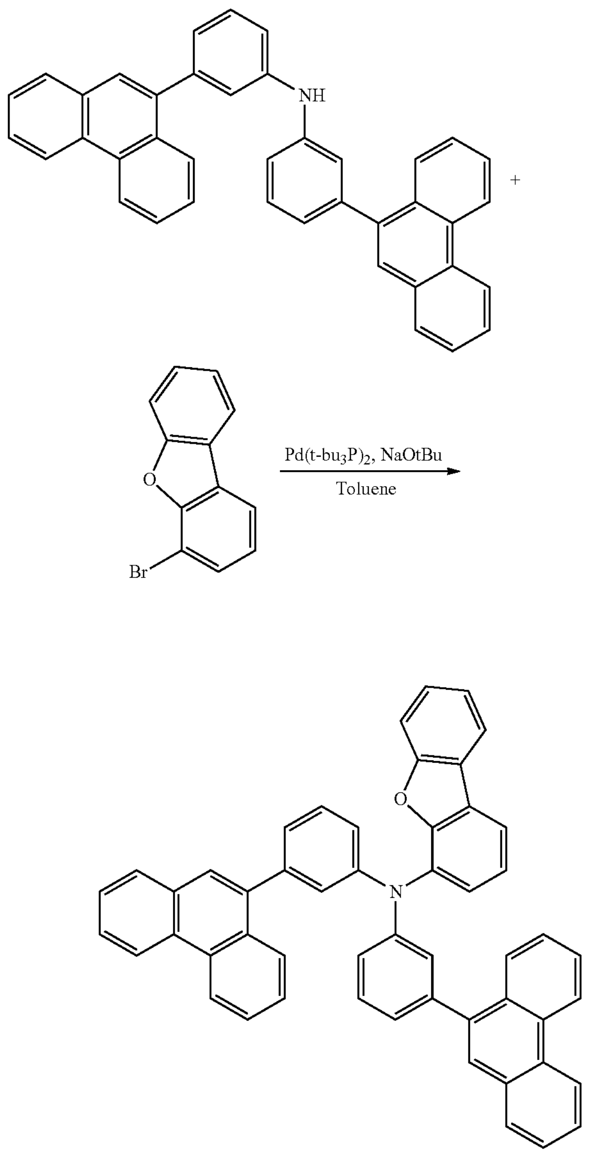

Under a nitrogen atmosphere, Intermediate 28 (10 g, 19.2 mmol), 4-bromodibenzo[b,d]furan (4.7 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 9 g of Compound 28 (yield 68%, MS: [M+H]+=688).

<Synthesis Example 29> Synthesis of Compound 29

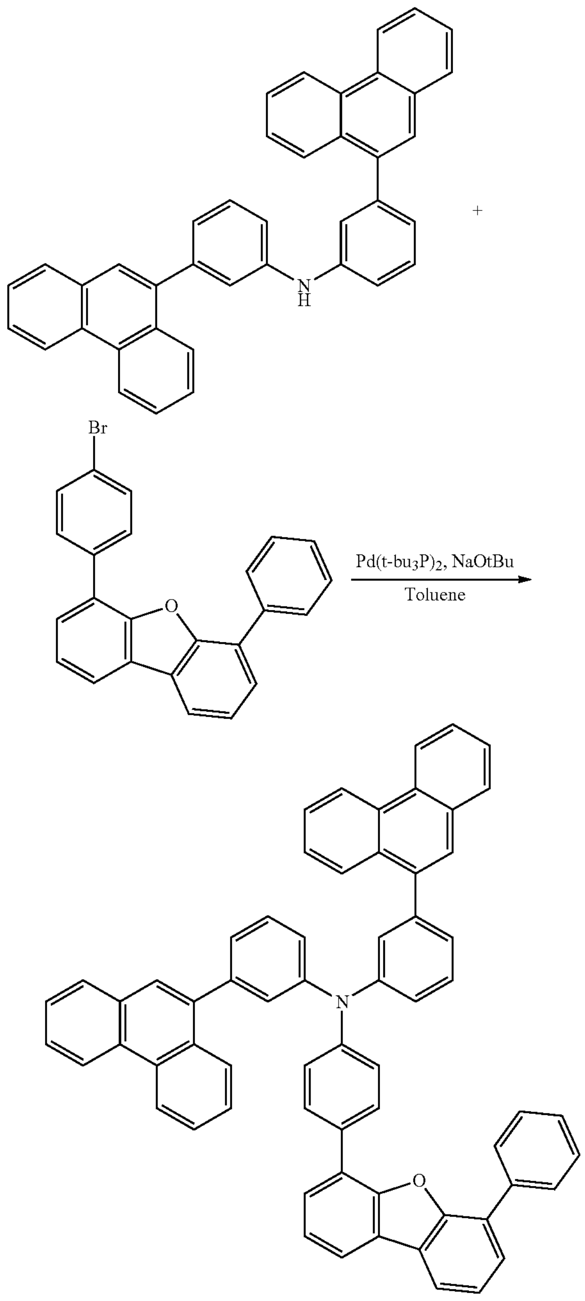

Under a nitrogen atmosphere, Intermediate 29 (10 g, 19.2 mmol), (4-bromophenyl)-6-phenyldibenzo[b,d]furan (7.6 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium(0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 11.1 g of Compound 29 (yield 69%, MS: [M+H]+=840).

<Synthesis Example 30> Synthesis of Compound 30

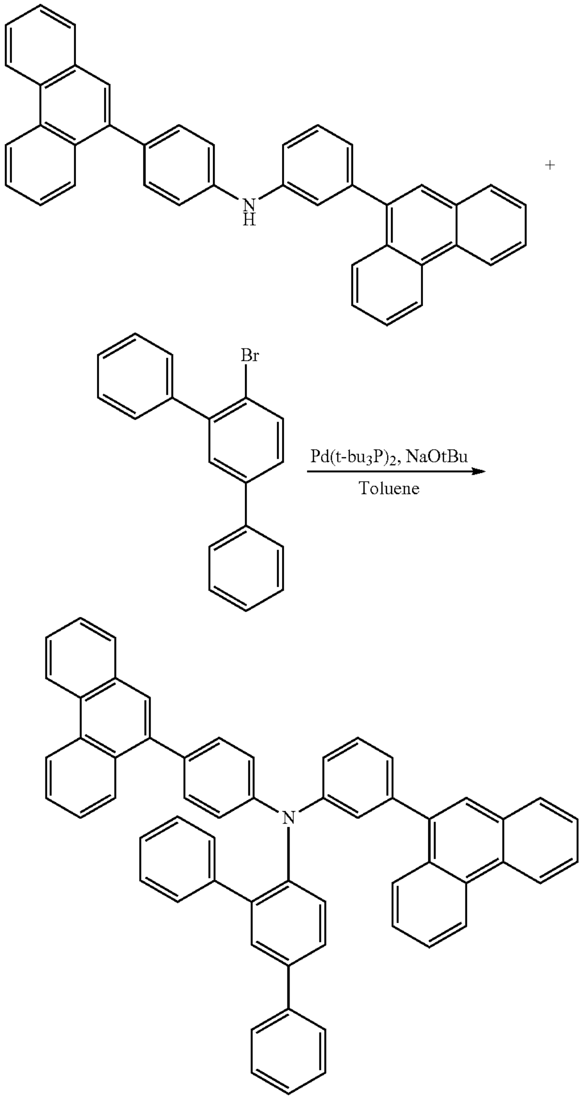

Under a nitrogen atmosphere, Intermediate 30 (10 g, 19.2 mmol), 4-bromo-1,1':3',1"-terphenyl (5.9 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 10.1 g of Compound 30 (yield 70%, MS: [M+H]+=750).

<Synthesis Example 31> Synthesis of Compound 31

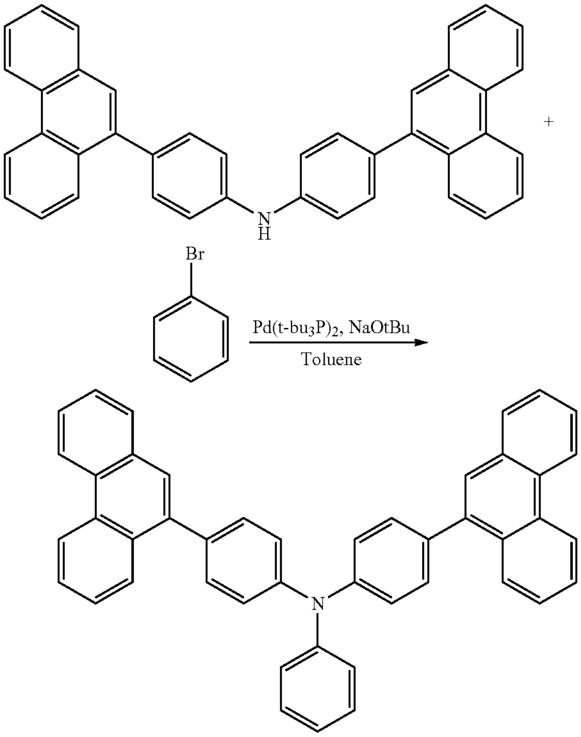

Under a nitrogen atmosphere, Intermediate 31 (10 g, 19.2 mmol), bromobenzene (3 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium(0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 7.8 g of Compound 31 (yield 68%, MS: [M+H]+=598).

<Synthesis Example 32> Synthesis of Compound 32

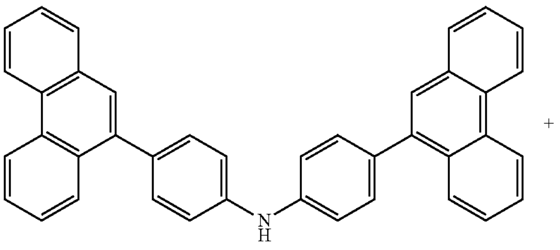

-continued

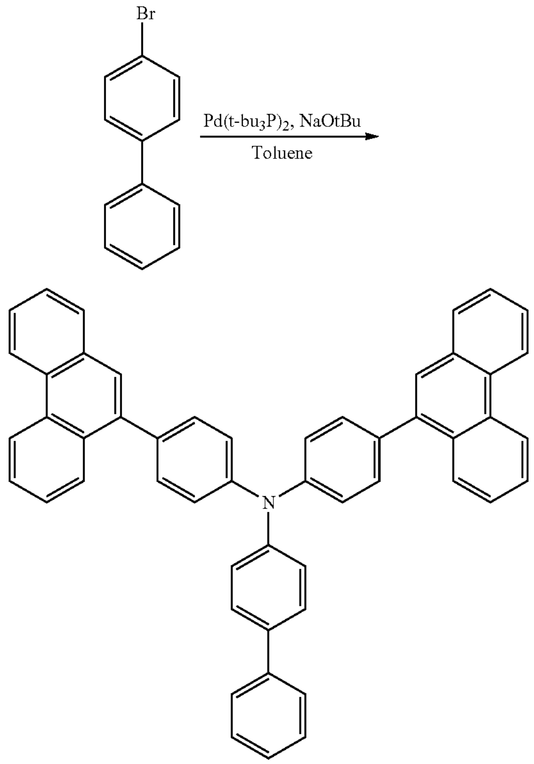

Under a nitrogen atmosphere, Intermediate 32 (10 g, 19.2 mmol), 4-bromo-1,1'-biphenyl (4.5 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.9 g of Compound 32 (yield 69%, MS: [M+H]+=674).

<Synthesis Example 33> Synthesis of Compound 33

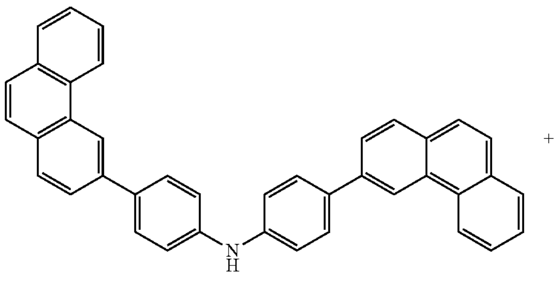

-continued

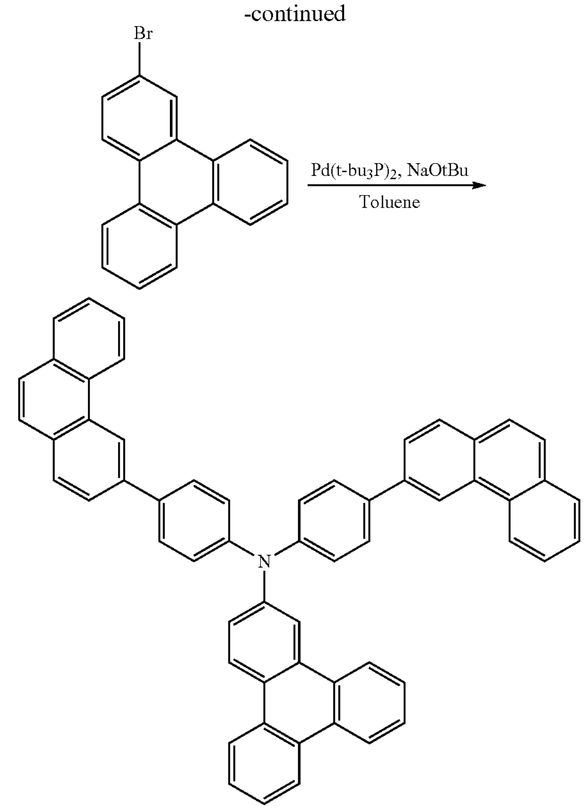

Under a nitrogen atmosphere, Intermediate 33 (10 g, 19.2 mmol), 2-bromotriphenylene (5.9 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 3 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 9 g of Compound 33 (yield 63%, MS: [M+H]+=748).

<Synthesis Example 34> Synthesis of Compound 34

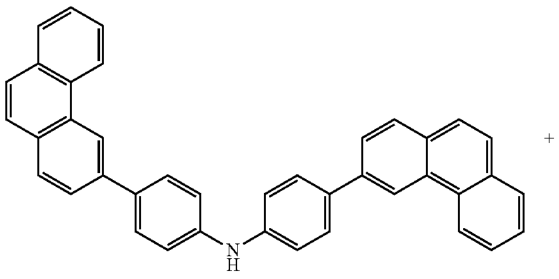

-continued

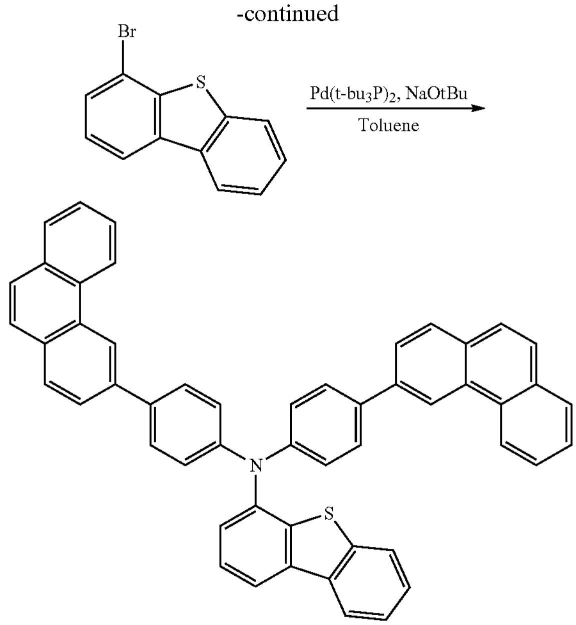

Under a nitrogen atmosphere, Intermediate 34 (10 g, 19.2 mmol), 4-bromodibenzo[b,d]thiophene (5 g, 19.2 mmol), and sodium tert-butoxide (3.7 g, 38.4 mmol) were put into 200 ml of toluene, and the resulting solution was stirred and refluxed. Thereafter, bis(tri-tert-butylphosphine)palladium (0) (0.2 g, 0.4 mmol) was introduced thereinto. After 2 hours, the reaction was terminated, so that the temperature was cooled to room temperature and pressure was reduced to remove the solvent. Thereafter, the compound was again completely dissolved in chloroform, the solution was washed twice with water, and then the organic layer was separated, treated with anhydrous magnesium sulfate, and then filtered to distill the filtrate under reduced pressure. The concentrated compound was purified with silica gel column chromatography to obtain 8.4 g of Compound 34 (yield 62%, MS: [M+H]+=704).

Comparative Example 1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. The substrate was cleaned by using oxygen plasma for 5 minutes, and then was transported to a vacuum deposition machine.

The following HI-1 compound was formed to have a thickness of 1,150 Å as a hole injection layer on the thus prepared ITO transparent electrode, and the hole injection layer was p-doped with the following A-1 compound at a concentration of 1.5%. The following HT-1 compound was vacuum deposited on the hole injection layer, thereby forming a hole transport layer having a film thickness of 1,000 Å. Next, the following HT-2 compound was vacuum deposited to have a film thickness of 500 Å on the hole transport layer, thereby forming a hole transport auxiliary layer. The following EB-1 compound was vacuum deposited to have a film thickness of 150 Å on the hole transport auxiliary layer, thereby forming an electron blocking layer. Subsequently, the following RH-1 compound and the following Dp-8 compound were vacuum deposited at a weight ratio of 98:2 on the EB-1 deposition film, thereby forming a red light emitting layer having a thickness of 400 Å. The following HB-1 compound was vacuum deposited to have a film thickness of 30 Å on the light emitting layer, thereby forming a hole blocking layer. Next, the following ET-1 compound and the following LiQ compound were vacuum deposited at a weight ratio of 2:1 on the hole blocking layer, thereby forming an electron injection and transport layer having a thickness of 300 Å. Lithium fluoride (LiF) and aluminum were sequentially deposited on the electron injection and transport layer to have a thickness of 12 Å and 1,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec, and at 2 Å/sec, respectively, and the degree of vacuum during the deposition was maintained at $2\times10^{-7}$ to $5\times10^{-6}$ torr, thereby manufacturing an organic light emitting device.

A-1

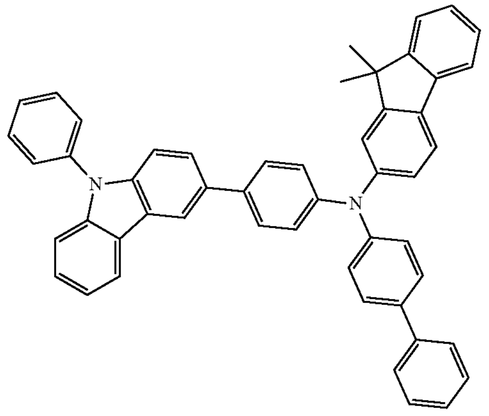

HI-1

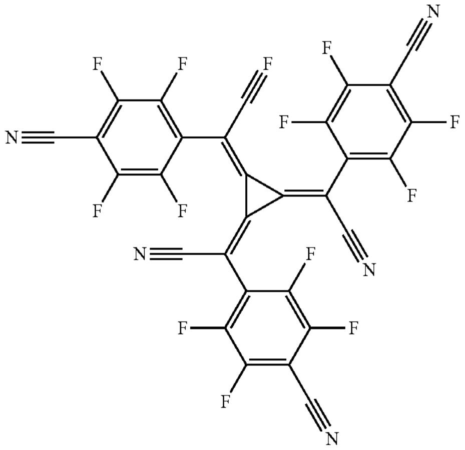

-continued
HT-1
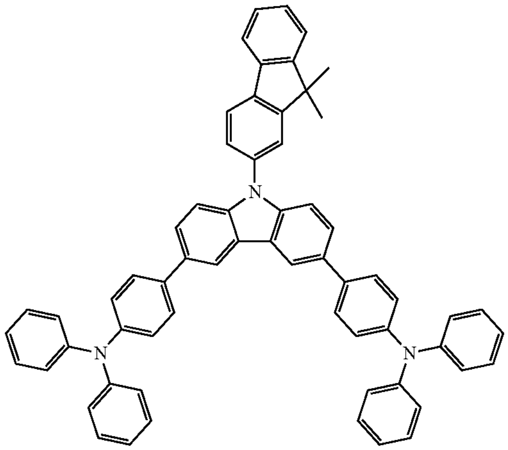
HT-2
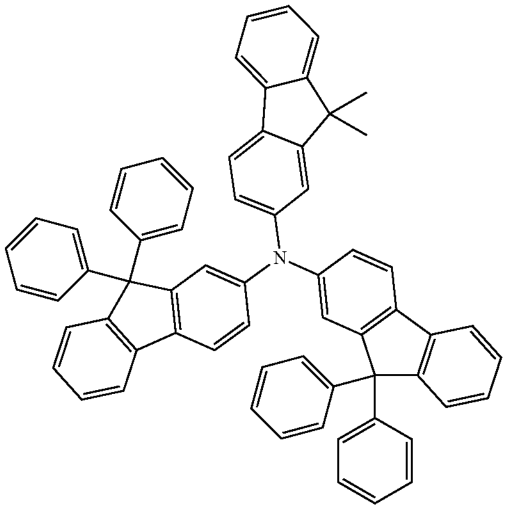
EB-1
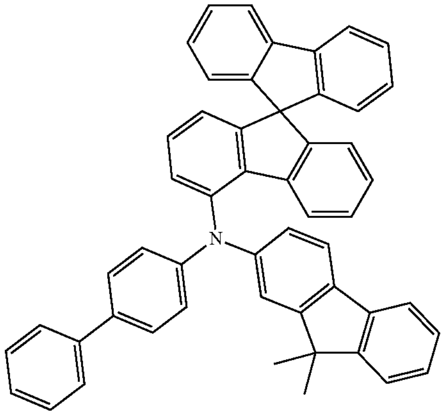
RH-1
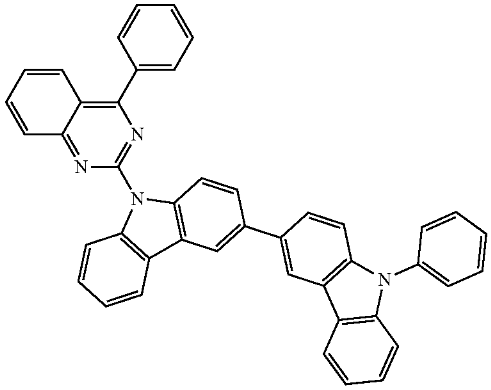
Dp-8
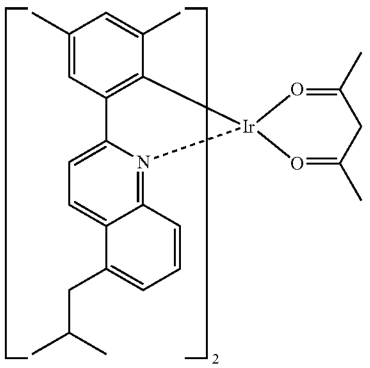
HB-1
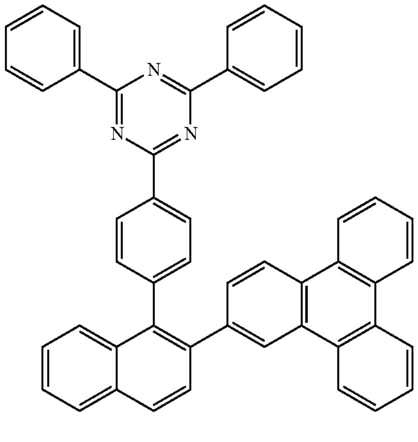

-continued
ET-1
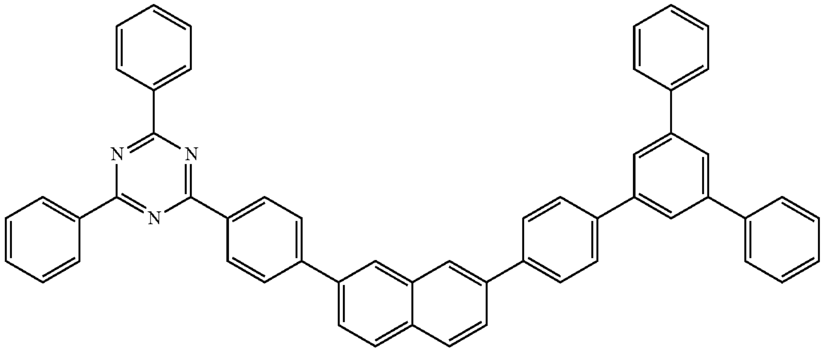
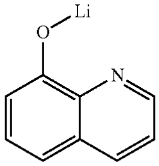
LiQ
RH-2
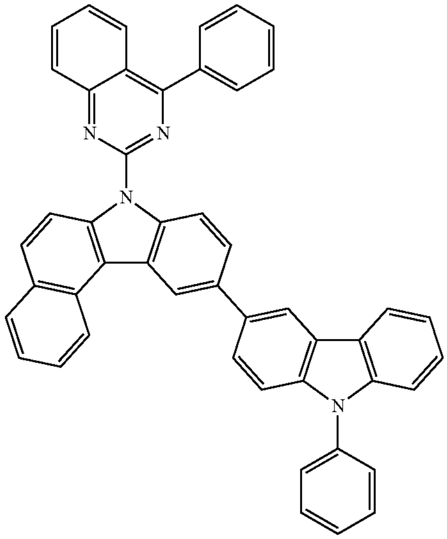
RH-3
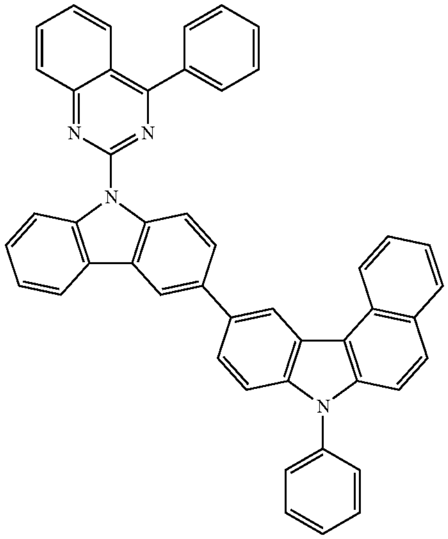
EB-2
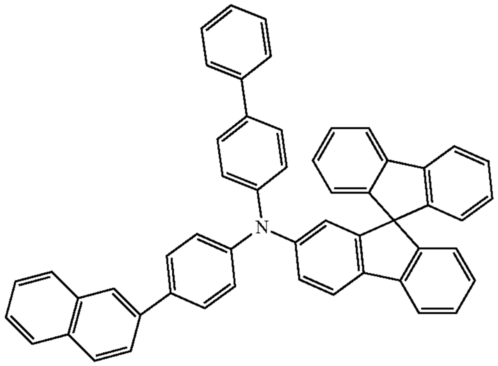

-continued

EB-3

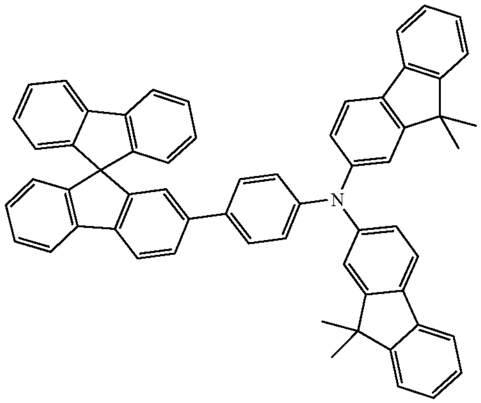

Examples 1 to 36

Organic light emitting devices were manufactured in the same manner as in Comparative Example 1, except that the compounds described in the following Table 1 were used instead of RH-1 and/or EB-1 in the organic light emitting device in Comparative Example 1.

Comparative Examples 2 to 21

Organic light emitting devices were manufactured in the same manner as in Comparative Example 1, except that in the organic light emitting device in Comparative Example 1, the compounds described in the following Table 1 were used instead of RH-1 and/or EB-1.

When a current of 10 $mA/cm^2$ was applied to each of the organic light emitting devices manufactured in the Examples and the Comparative Examples, the voltage, efficiency, and service life were measured, and the results thereof are shown in the following Table 1. T95 means the time taken for the luminance to be reduced to 95% of the initial luminance (5,000 nit).

TABLE 1

| | Electron blocking layer | Light emitting layer | Driving voltage (V) | Efficiency (cd/A) | Service life (T95) |
|---|---|---|---|---|---|
| Example 1 | Compound 19 | Compound 1 | 4.0 | 43 | 311 |
| Example 2 | | Compound 2 | 4.3 | 42 | 369 |
| Example 3 | | Compound 5 | 4.3 | 41 | 315 |
| Example 4 | | Compound 6 | 4.1 | 45 | 303 |
| Example 5 | | Compound 12 | 4.0 | 43 | 274 |
| Example 6 | | Compound 16 | 4.3 | 37 | 328 |
| Example 7 | Compound 23 | Compound 1 | 4.1 | 44 | 321 |
| Example 8 | | Compound 2 | 4.3 | 41 | 351 |
| Example 9 | | Compound 5 | 4.3 | 40 | 333 |
| Example 10 | | Compound 6 | 4.0 | 46 | 305 |
| Example 11 | | Compound 12 | 4.1 | 43 | 306 |
| Example 12 | | Compound 16 | 4.2 | 38 | 332 |
| Example 13 | Compound 24 | Compound 1 | 4.1 | 45 | 321 |
| Example 14 | | Compound 2 | 4.3 | 43 | 362 |
| Example 15 | | Compound 5 | 4.3 | 40 | 341 |
| Example 16 | | Compound 6 | 4.0 | 44 | 307 |
| Example 17 | | Compound 12 | 4.0 | 45 | 272 |
| Example 18 | | Compound 16 | 4.2 | 40 | 338 |
| Example 19 | Compound 27 | Compound 1 | 4.1 | 45 | 328 |
| Example 20 | | Compound 2 | 4.3 | 41 | 361 |
| Example 21 | | Compound 5 | 4.3 | 42 | 335 |
| Example 22 | | Compound 6 | 4.0 | 45 | 314 |

TABLE 1-continued

| | Electron blocking layer | Light emitting layer | Driving voltage (V) | Efficiency (cd/A) | Service life (T95) |
|---|---|---|---|---|---|
| Example 23 | | Compound 12 | 4.1 | 43 | 281 |
| Example 24 | | Compound 16 | 4.2 | 39 | 340 |
| Example 25 | Compound 32 | Compound 1 | 4.0 | 46 | 331 |
| Example 26 | | Compound 2 | 4.2 | 45 | 395 |
| Example 27 | | Compound 5 | 4.3 | 41 | 363 |
| Example 28 | | Compound 6 | 4.0 | 45 | 351 |
| Example 29 | | Compound 12 | 4.1 | 44 | 304 |
| Example 30 | | Compound 16 | 4.2 | 38 | 372 |
| Example 31 | Compound 34 | Compound 1 | 4.1 | 45 | 324 |
| Example 32 | | Compound 2 | 4.3 | 43 | 377 |
| Example 33 | | Compound 5 | 4.2 | 42 | 331 |
| Example 34 | | Compound 6 | 4.1 | 46 | 305 |
| Example 35 | | Compound 12 | 4.0 | 44 | 299 |
| Example 36 | | Compound 16 | 4.2 | 38 | 342 |
| Comparative Example 1 | EB-1 | RH-1 | 4.8 | 33 | 221 |
| Comparative Example 2 | EB-2 | Compound 1 | 4.1 | 44 | 295 |
| Comparative Example 3 | | Compound 2 | 4.2 | 41 | 350 |
| Comparative Example 4 | | Compound 5 | 4.1 | 40 | 312 |
| Comparative Example 5 | | Compound 6 | 4.3 | 45 | 294 |
| Comparative Example 6 | | Compound 12 | 4.1 | 43 | 250 |
| Comparative Example 7 | EB-2 | Compound 16 | 4.3 | 37 | 317 |
| Comparative Example 8 | EB-3 | Compound 1 | 4.2 | 44 | 296 |
| Comparative Example 9 | | Compound 2 | 4.3 | 41 | 348 |
| Comparative Example 10 | | Compound 5 | 4.2 | 40 | 308 |
| Comparative Example 11 | | Compound 6 | 4.2 | 45 | 290 |
| Comparative Example 12 | | Compound 12 | 4.1 | 43 | 251 |
| Comparative Example 13 | | Compound 16 | 4.3 | 37 | 314 |
| Comparative Example 14 | Compound 19 | RH-2 | 4.7 | 36 | 274 |
| Comparative Example 15 | Compound 23 | | 4.7 | 37 | 281 |
| Comparative Example 16 | Compound 32 | | 4.6 | 38 | 278 |
| Comparative Example 17 | Compound 34 | | 4.6 | 37 | 269 |
| Comparative Example 18 | Compound 19 | RH-3 | 4.6 | 38 | 265 |

TABLE 1-continued

| | Electron blocking layer | Light emitting layer | Driving voltage (V) | Effi-ciency (cd/A) | Ser-vice life (T95) |
|---|---|---|---|---|---|
| Comparative Example 19 | Compound 23 | | 4.7 | 37 | 270 |
| Comparative Example 20 | Compound 32 | | 4.6 | 39 | 268 |
| Comparative Example 21 | Compound 34 | | 4.5 | 37 | 272 |

By examining Table 1 showing the results of the experiments, it can be confirmed that the light emitting efficiency, driving voltage, and service life characteristics can be improved in driving the red organic light emitting device with the combination of the compounds of the present invention. The experimental results of the combination of the light emitting layer and the electronic blocking layer according to the present invention exhibited better results than the experimental results of the combination of the compounds of the Comparative Examples. The driving voltage and the efficiency were increased, and a very excellent result particularly for the service life could be confirmed. Through this, it can be determined that holes between the light emitting layer and the electron blocking layer according to the present invention smoothly move and the electron blocking capability of the electron blocking layer makes excitons generated in the light emitting layer allow energy to be proficiently transferred to a red dopant, thereby improving all of the driving voltage, efficiency, and service life characteristics.

The invention claimed is:

1. An organic light emitting device, comprising:

a first electrode;

a second electrode provided to face the first electrode; and an organic material layer provided between the first electrode and the second electrode, wherein the organic material layer comprises a light emitting layer, and the light emitting layer comprises a compound of Formula 1:

Formula 1

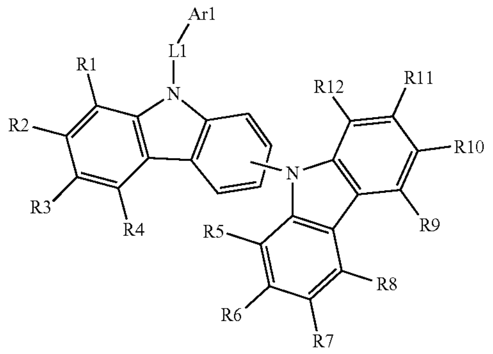

wherein in Formula 1:

L1 is a quinazolinylene group or a quinoxalinylene group;

Ar1 is a phenyl group; a naphthyl group; a phenanthrene group; a phenyl group substituted with a naphthyl group; a dibenzofuran group; a dibenzothiophene group; a carbazole group; or a carbazole group substituted with a phenyl group;

R1, R2, and R5 to R12 are the same as or different from each other, and are each independently hydrogen, or a substituted or unsubstituted C1 to C6 alkyl group, or any two adjacent groups are bonded to each other to form a ring; and R3 and R4 are bonded to each other to form an unsubstituted aromatic ring; and wherein the organic material layer comprises an electron blocking layer, and the electron blocking layer comprises a compound that is any one of the following compounds:

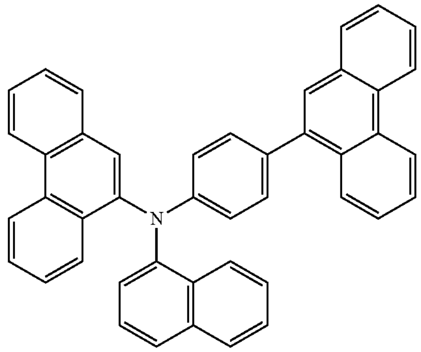

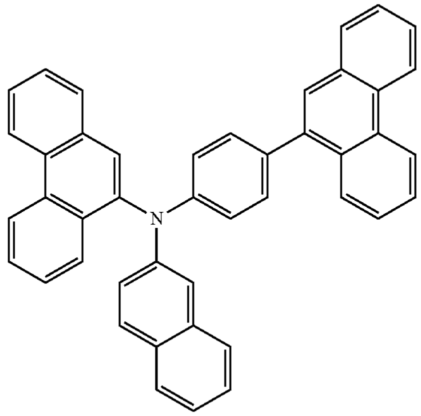

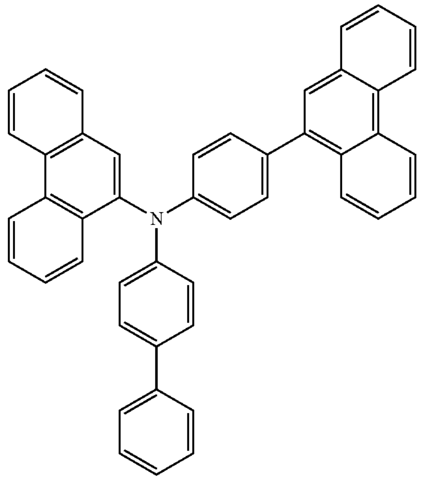

-continued
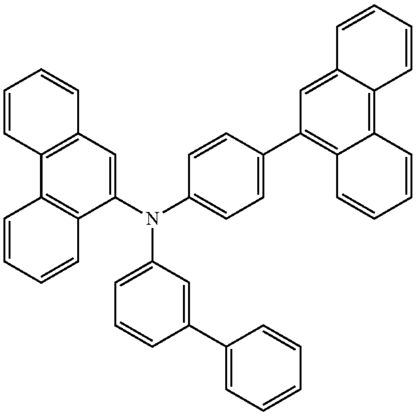
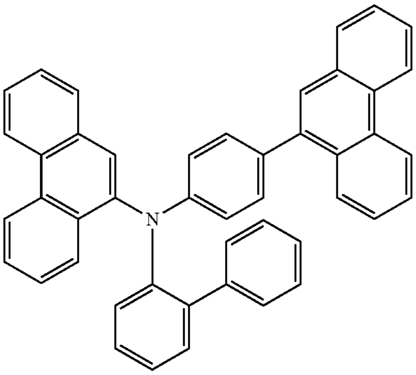
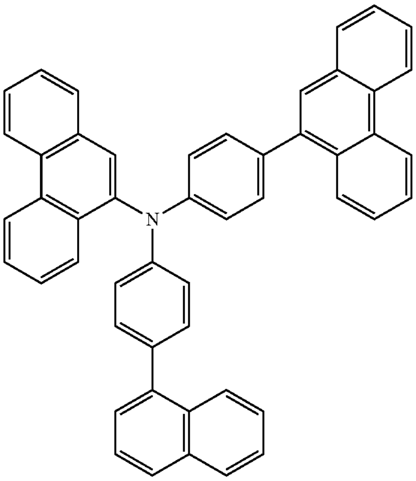
-continued
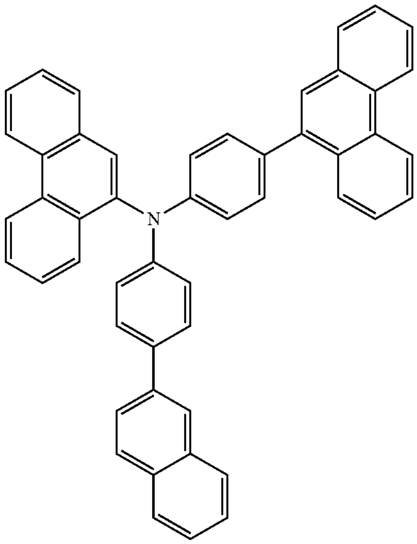 [SMILES: c1ccc2cc(-c3ccc(N(c4ccc(-c5cc6ccccc6c6ccccc56)cc4)c4cc5ccccc5c5ccccc45)cc3)ccc2c1]
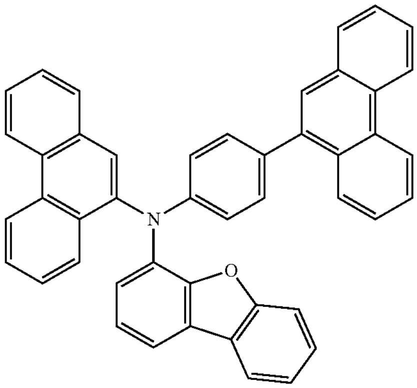
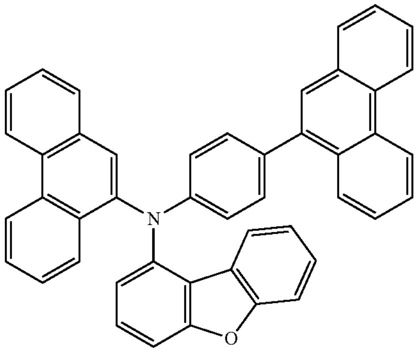
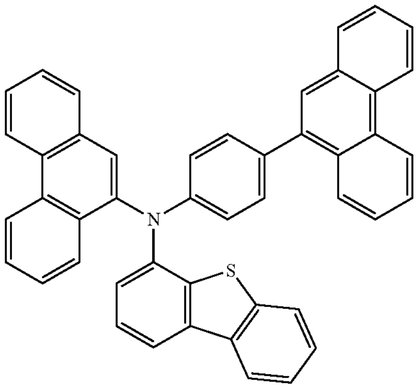

-continued
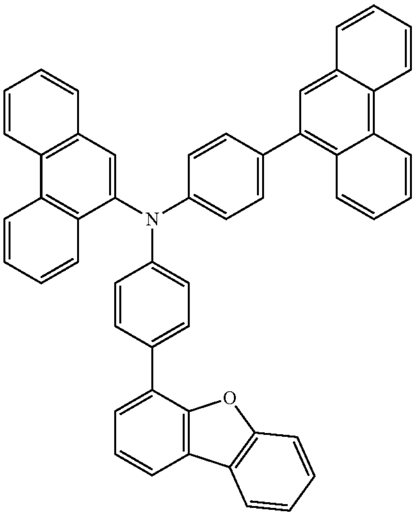
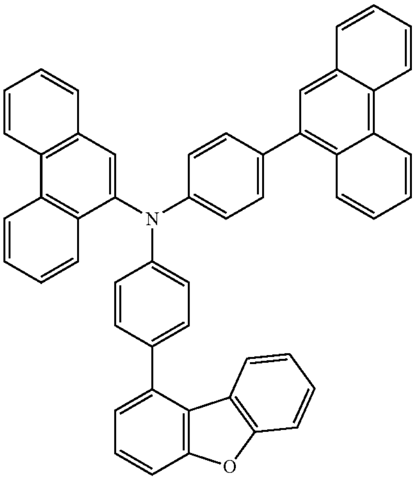
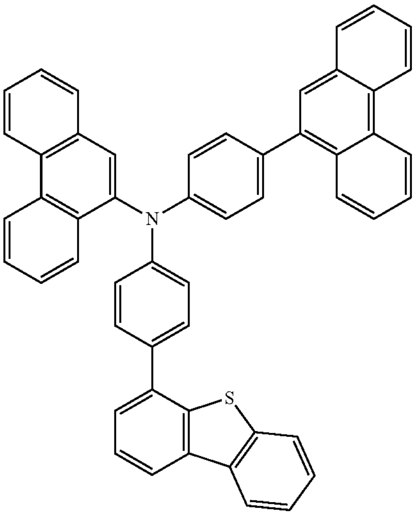
-continued
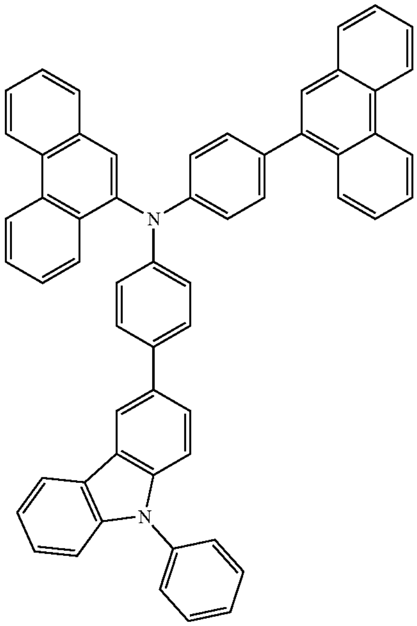 [SMILES: c1ccc(-n2c3ccccc3c3cc(-c4ccc(N(c5ccc(-c6cc7ccccc7c7ccccc67)cc5)c5cc6ccccc6c6ccccc56)cc4)ccc32)cc1]
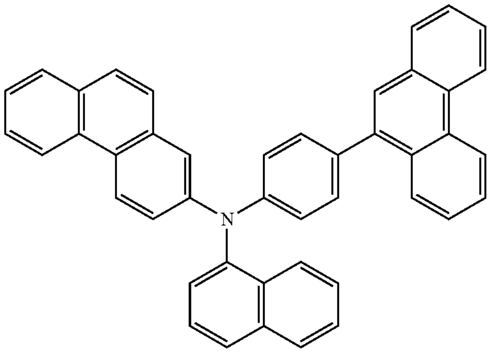
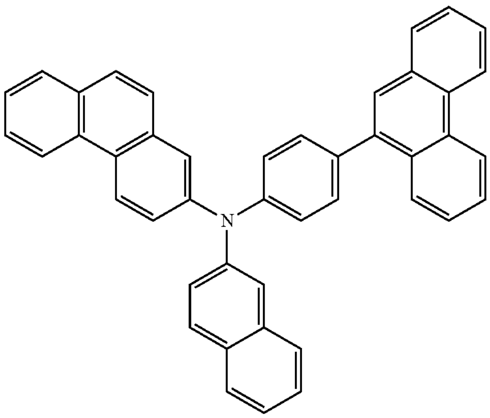

-continued
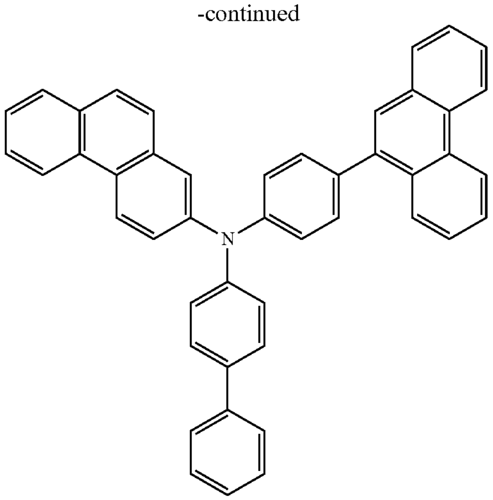
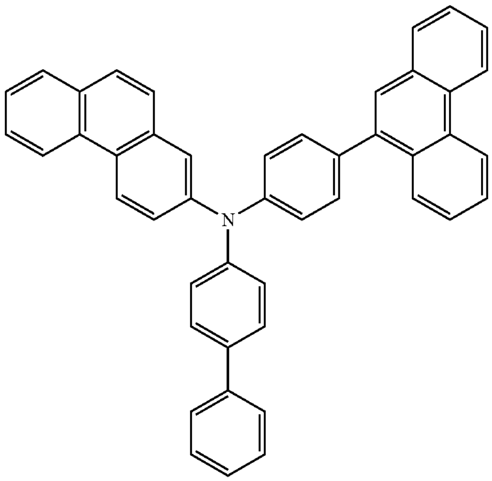
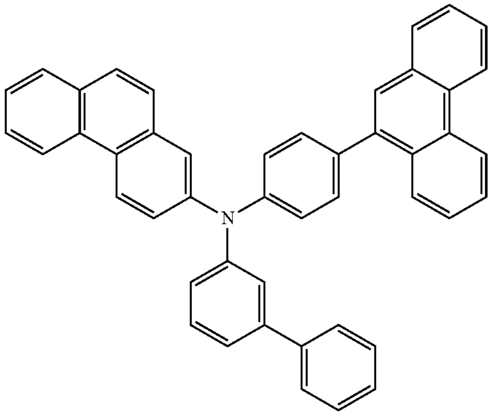
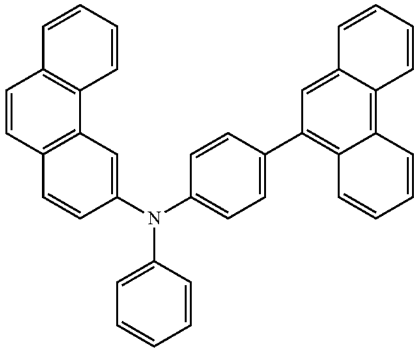
-continued
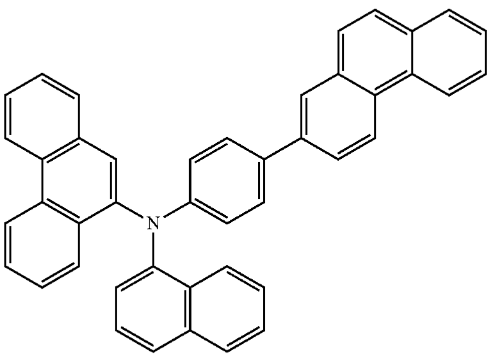 [SMILES: c1ccc2c(N(c3ccc(-c4ccc5c(ccc6ccccc65)c4)cc3)c3cc4ccccc4c4ccccc34)cccc2c1]
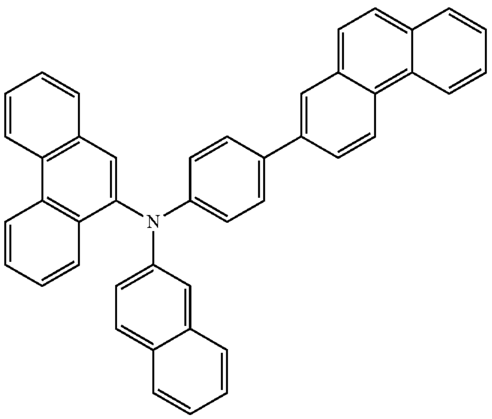
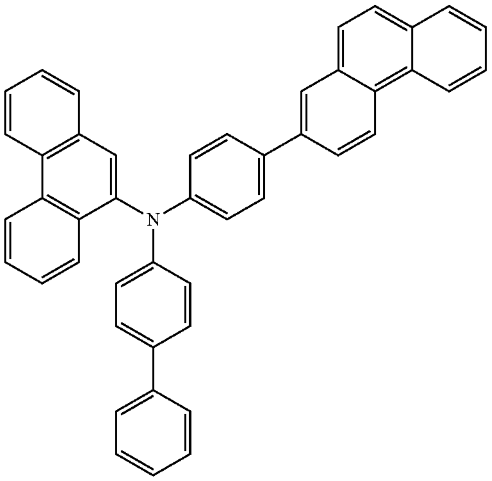
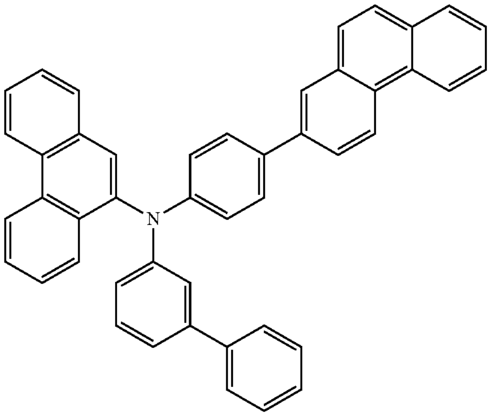

-continued
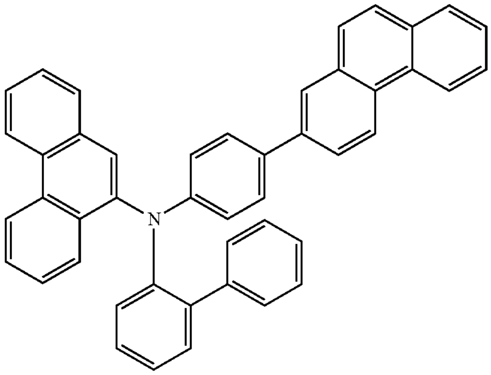
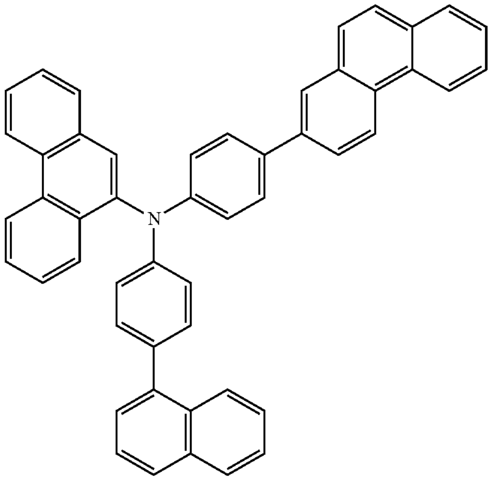
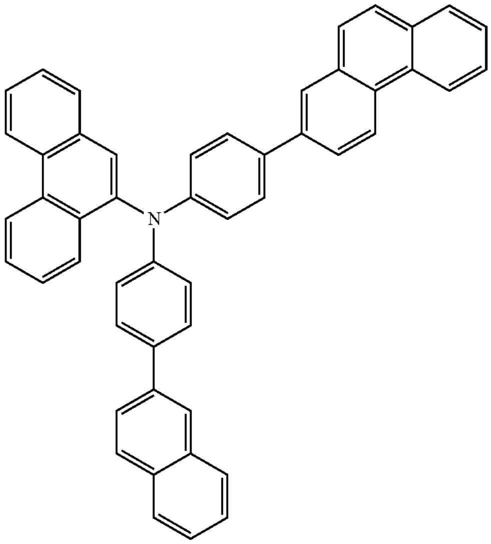
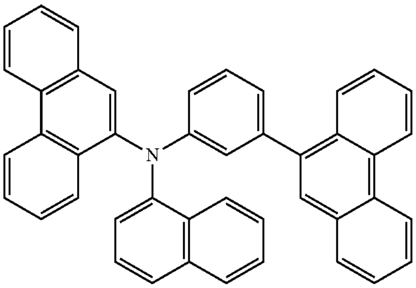
-continued
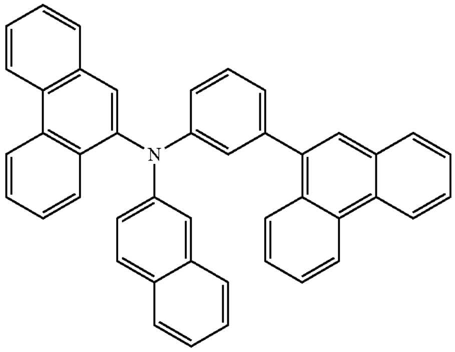
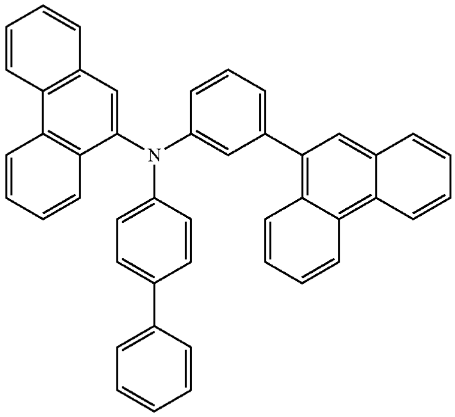
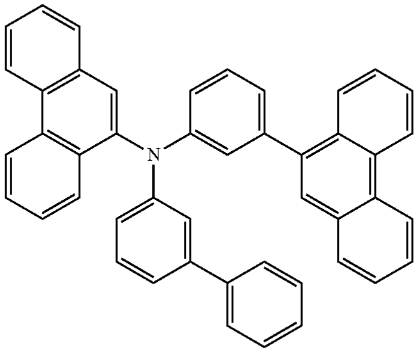
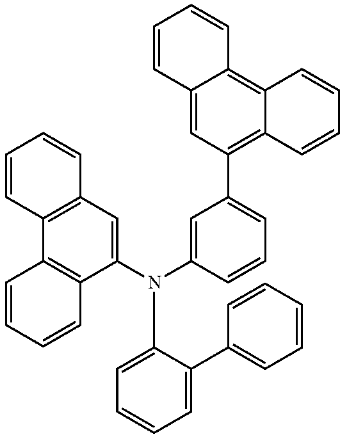

-continued
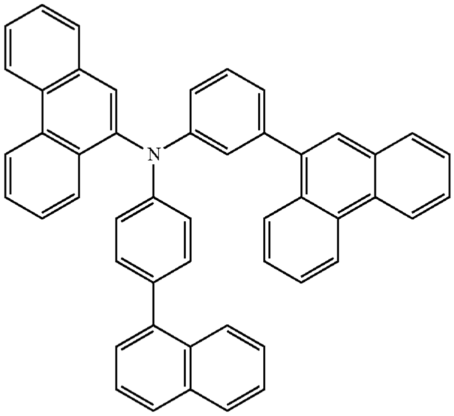
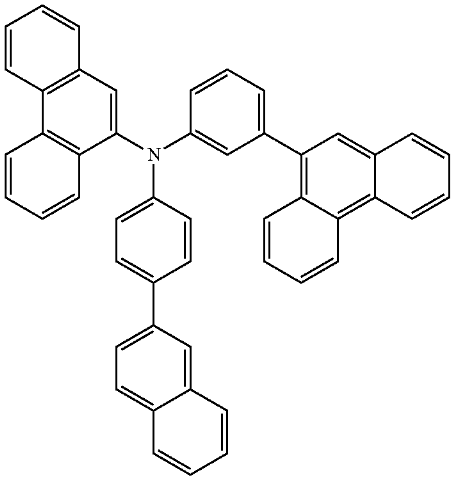 [SMILES: c1cc(-c2cc3ccccc3c3ccccc23)cc(N(c2ccc(-c3ccc4ccccc4c3)cc2)c2cc3ccccc3c3ccccc23)c1]
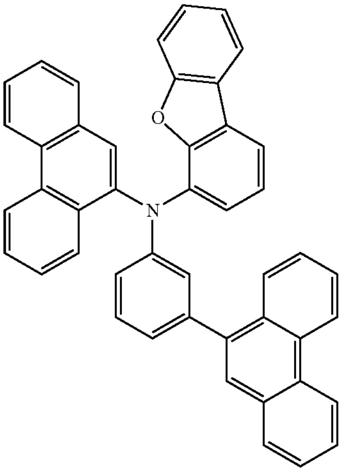
-continued
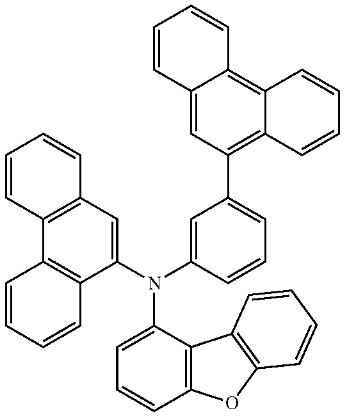
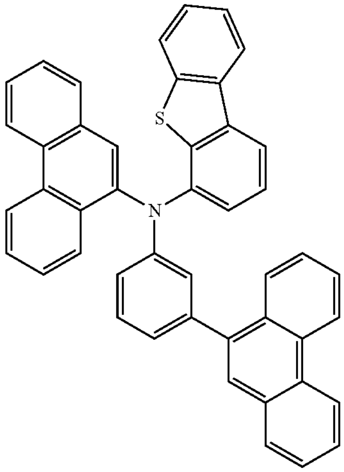
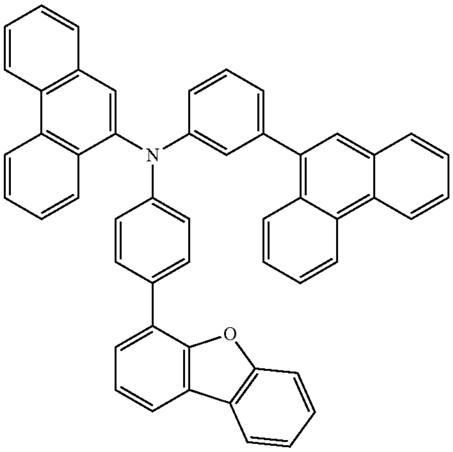

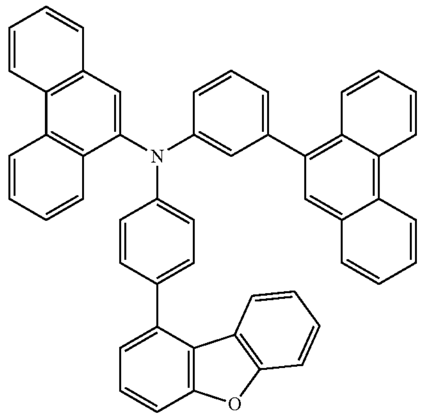
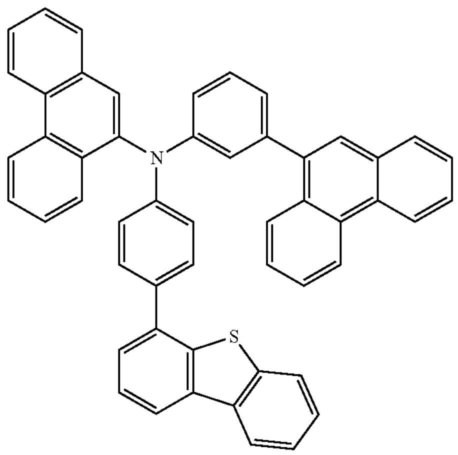
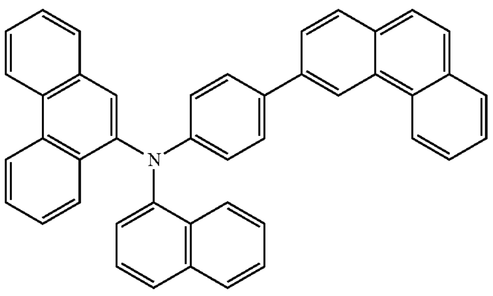
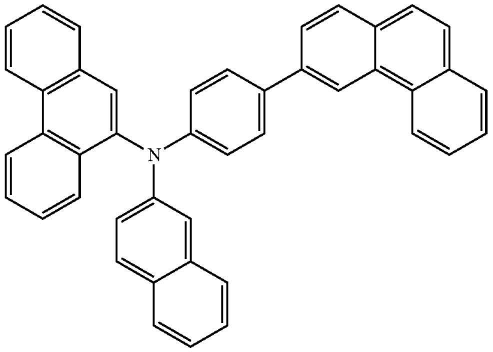
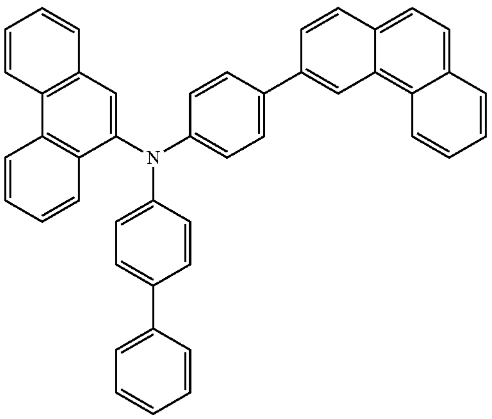
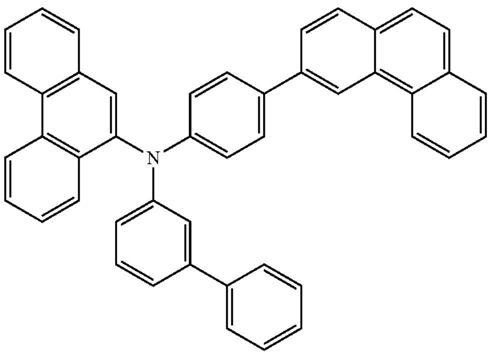
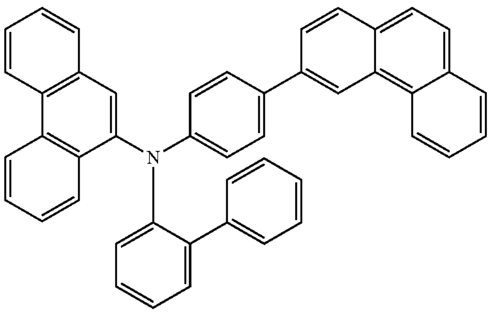
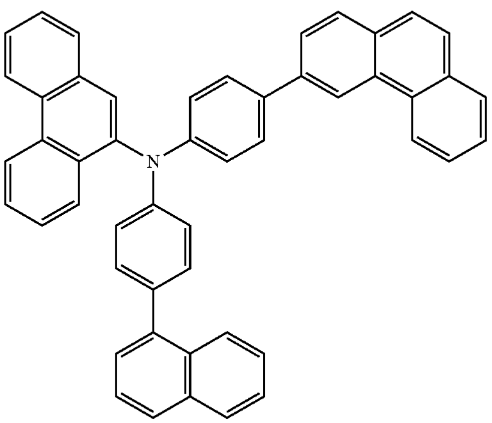

-continued
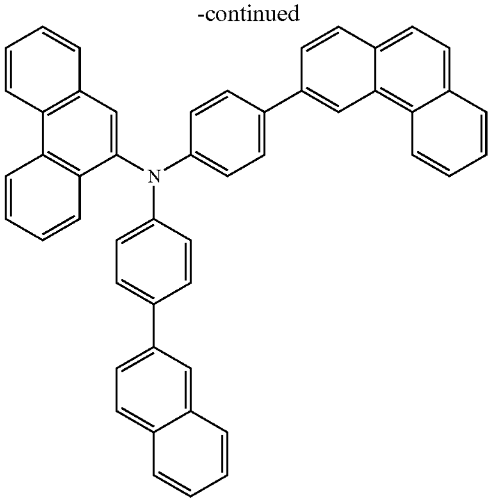
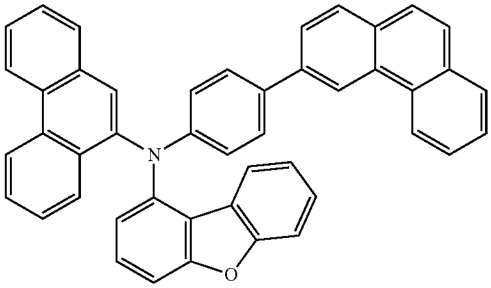
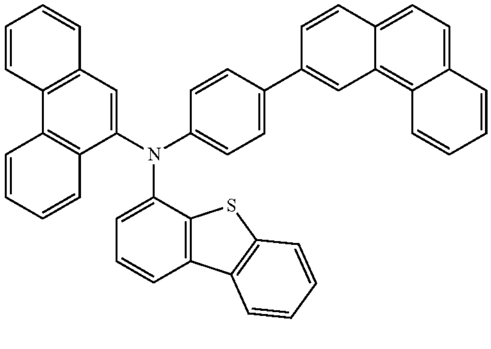
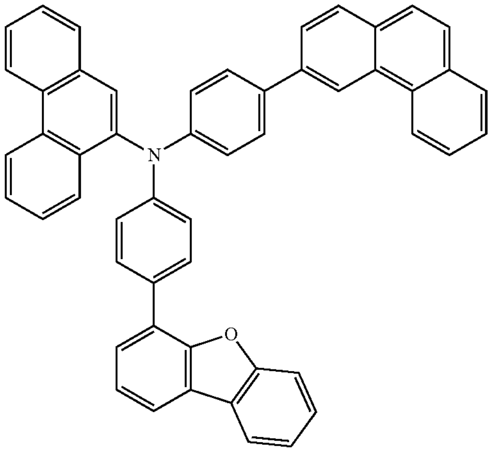
-continued
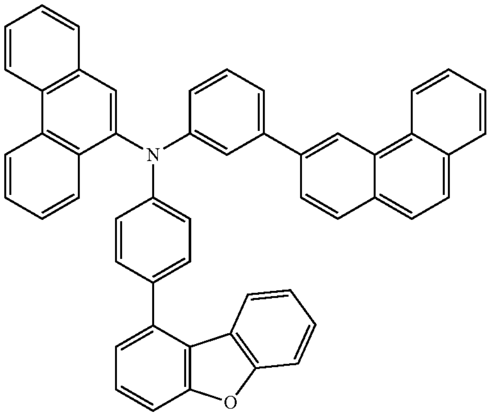
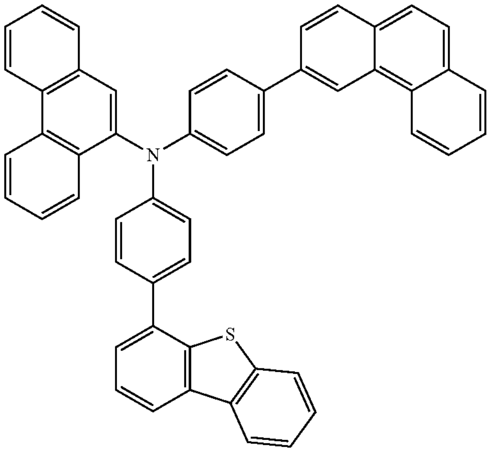
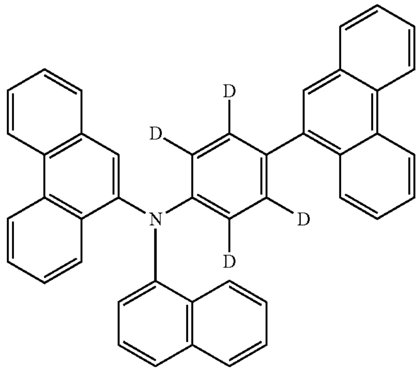
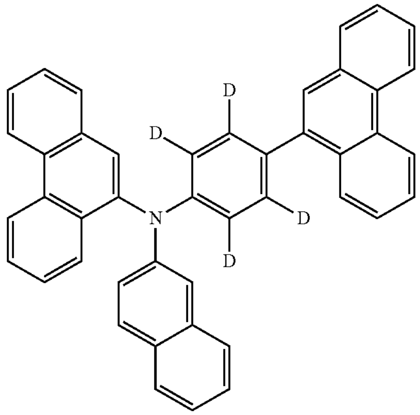

-continued
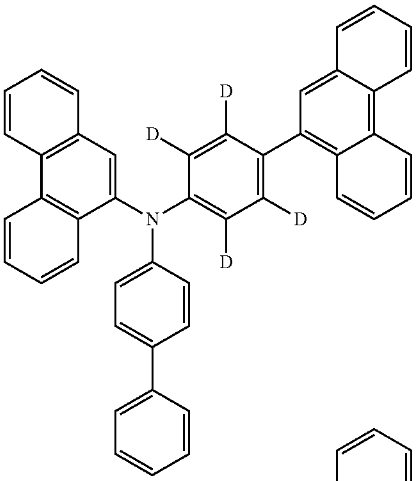
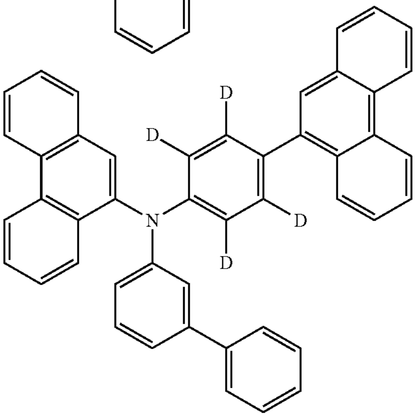
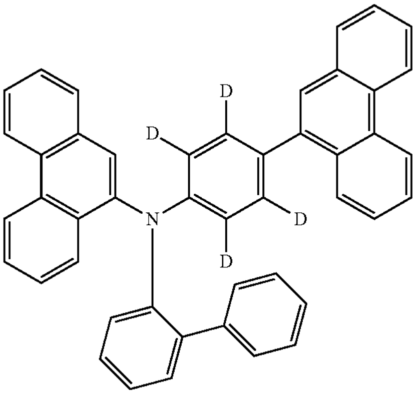
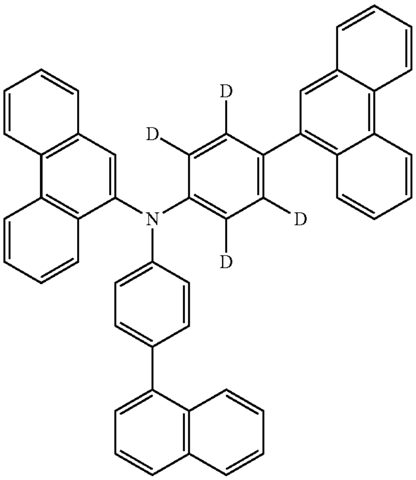
-continued
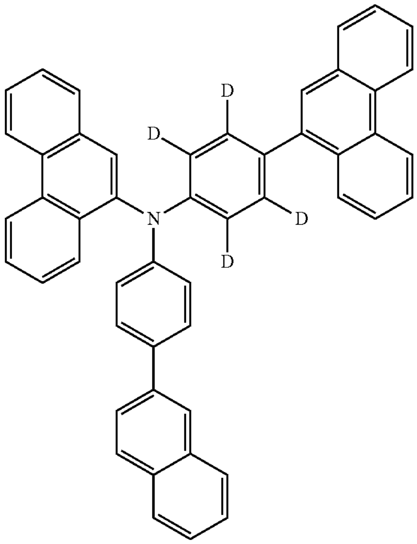 [SMILES: [2H]c1c([2H])c(N(c2ccc(-c3ccc4ccccc4c3)cc2)c2cc3ccccc3c3ccccc23)c([2H])c([2H])c1-c1cc2ccccc2c2ccccc12]
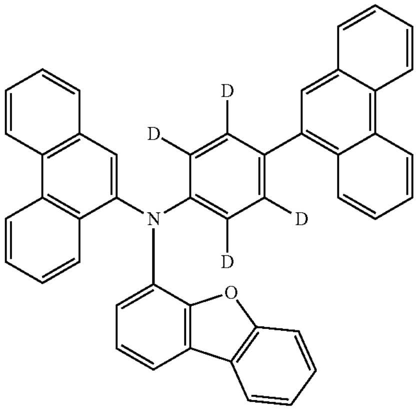
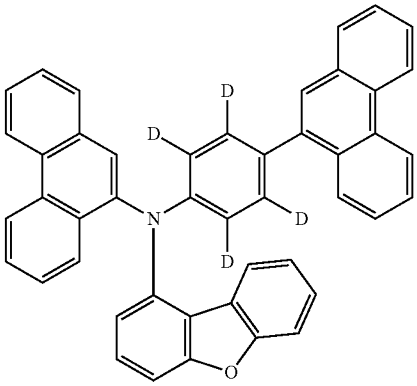

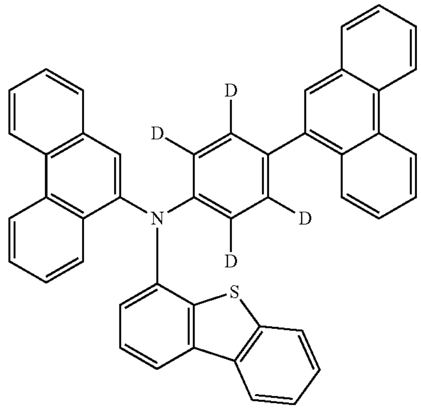
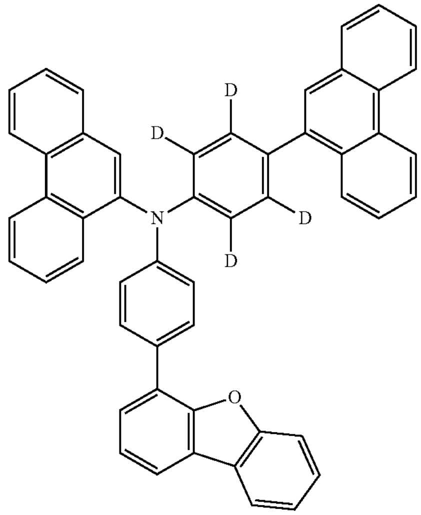
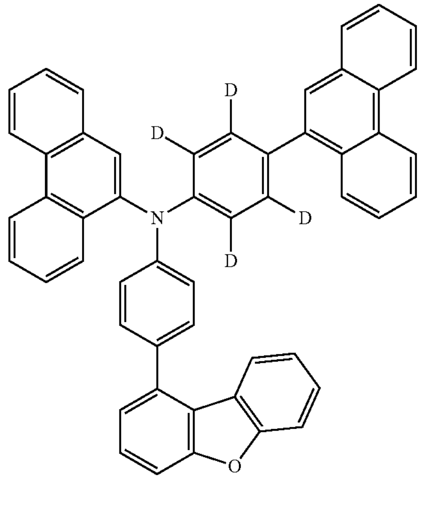
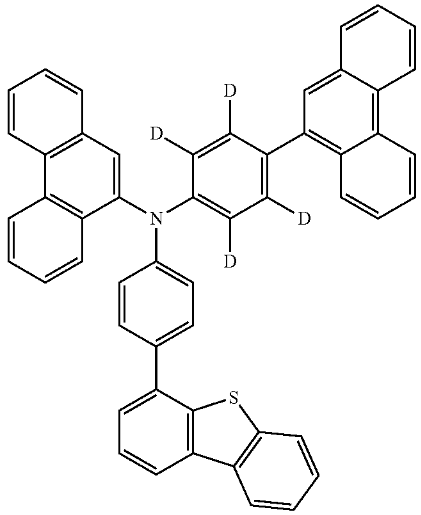
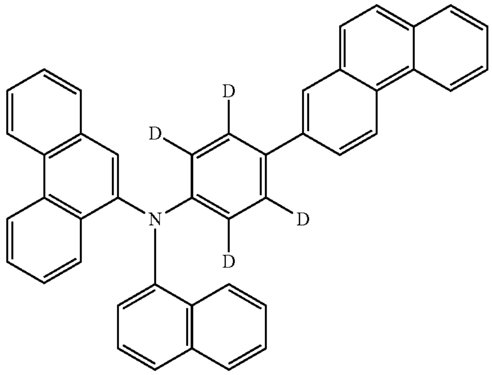
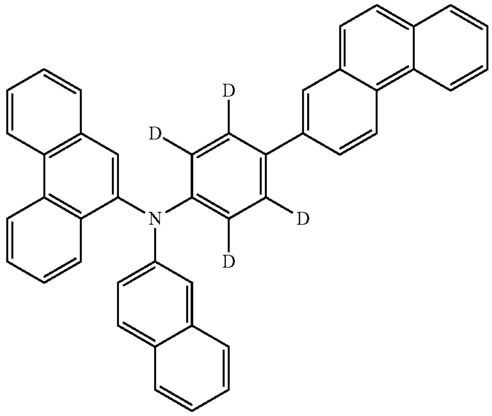

-continued
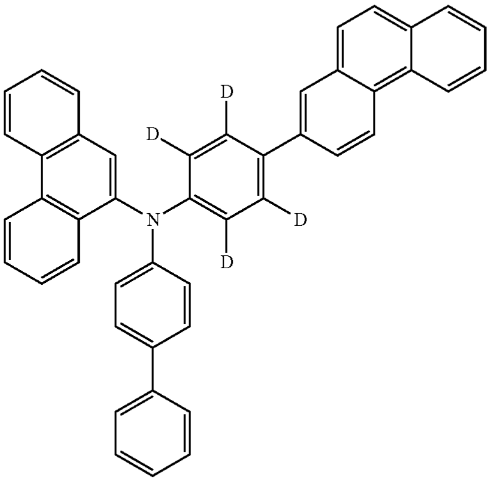
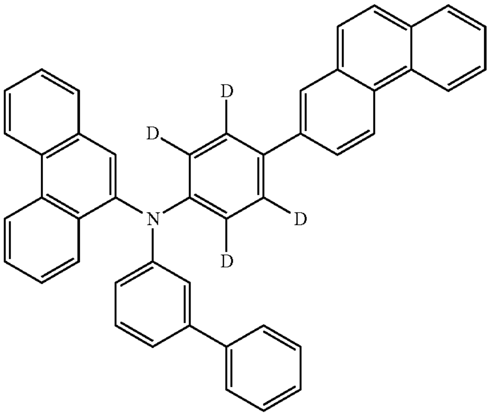
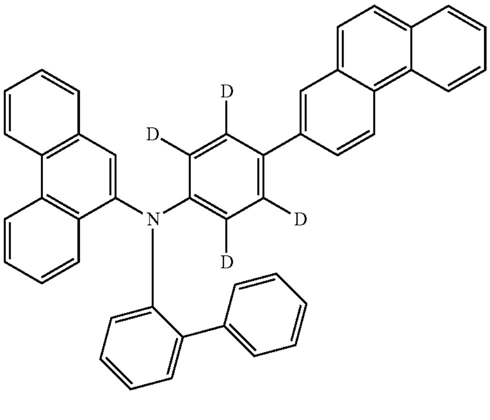
-continued
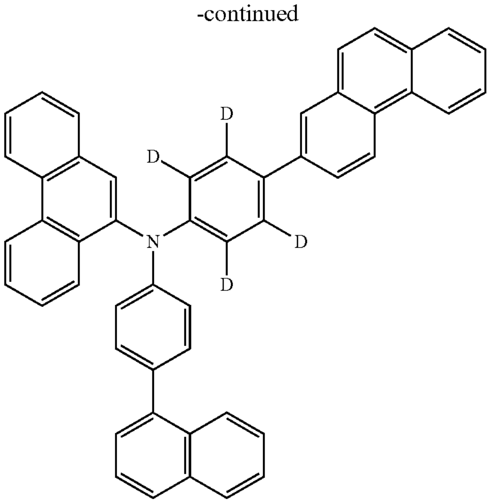
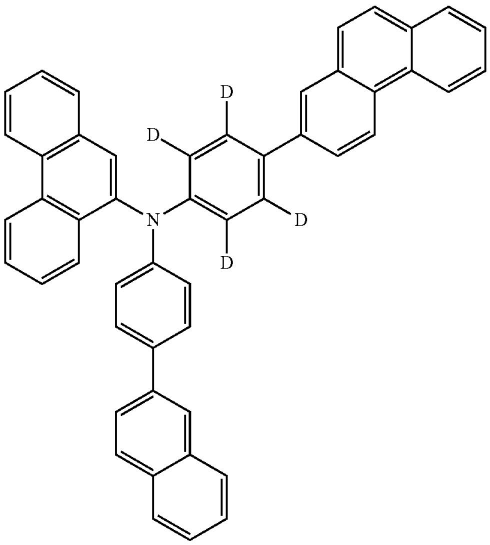 [SMILES: [2H]c1c([2H])c(N(c2ccc(-c3ccc4ccccc4c3)cc2)c2cc3ccccc3c3ccccc23)c([2H])c([2H])c1-c1ccc2c(ccc3ccccc32)c1]
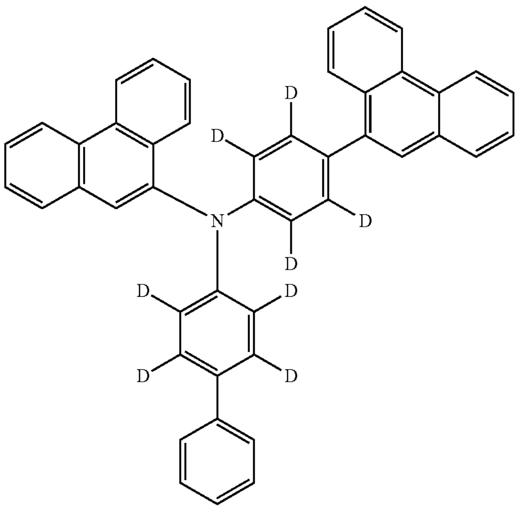 [SMILES: [2H]c1c([2H])c(N(c2c([2H])c([2H])c(-c3cc4ccccc4c4ccccc34)c([2H])c2[2H])c2cc3ccccc3c3ccccc23)c([2H])c([2H])c1-c1ccccc1]

-continued
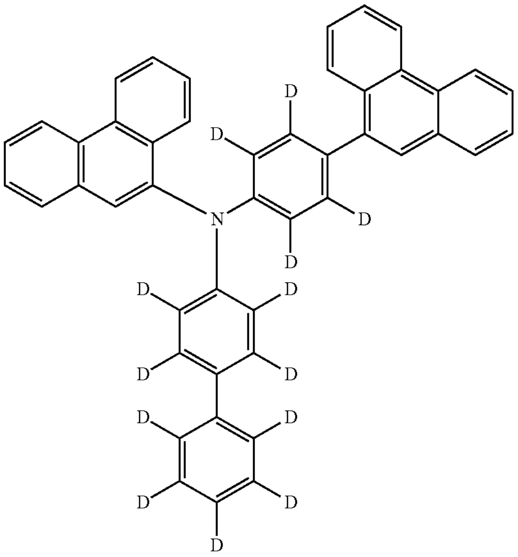 [SMILES: [2H]c1c([2H])c([2H])c(-c2c([2H])c([2H])c(N(c3c([2H])c([2H])c(-c4cc5ccccc5c5ccccc45)c([2H])c3[2H])c3cc4ccccc4c4ccccc34)c([2H])c2[2H])c([2H])c1[2H]]
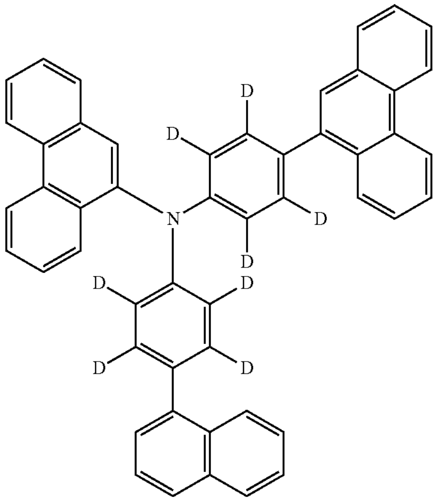
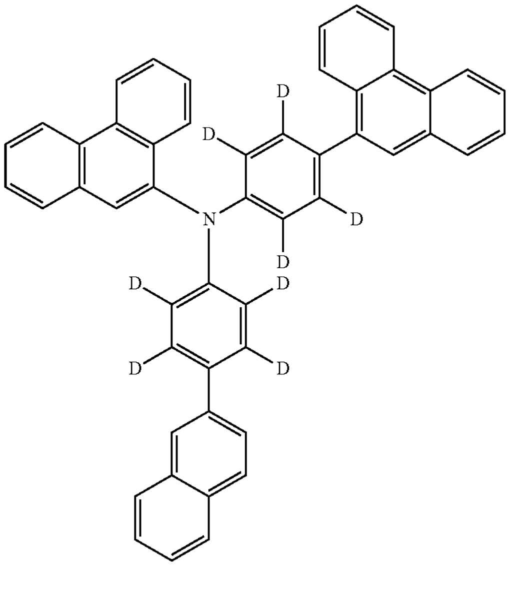
-continued
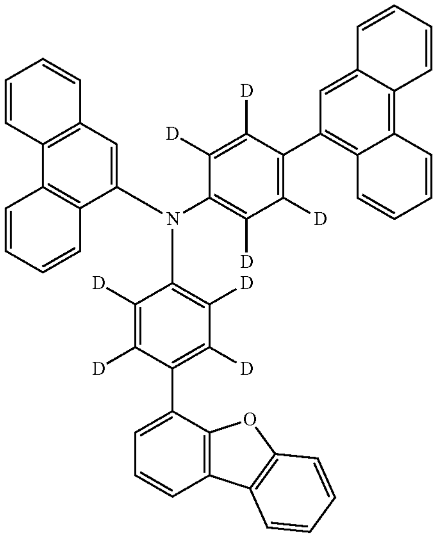
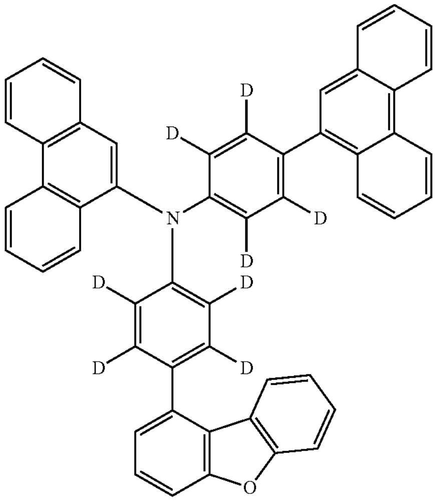
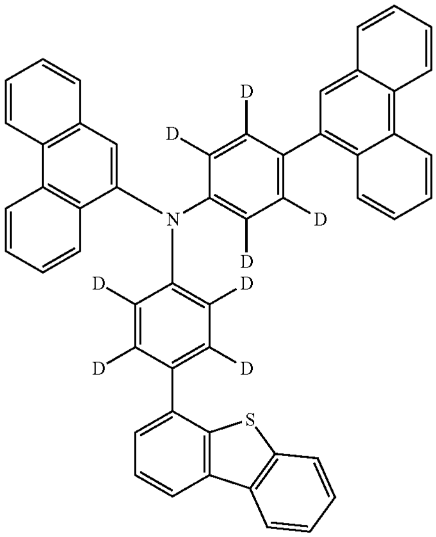

-continued
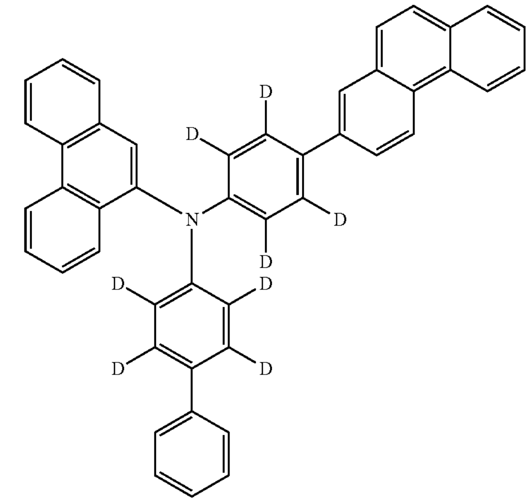
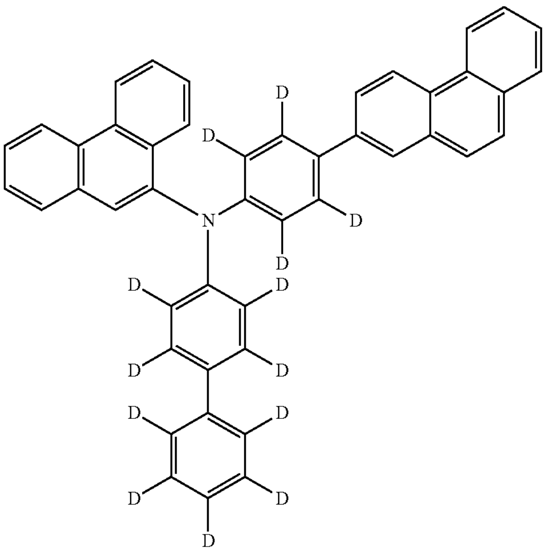
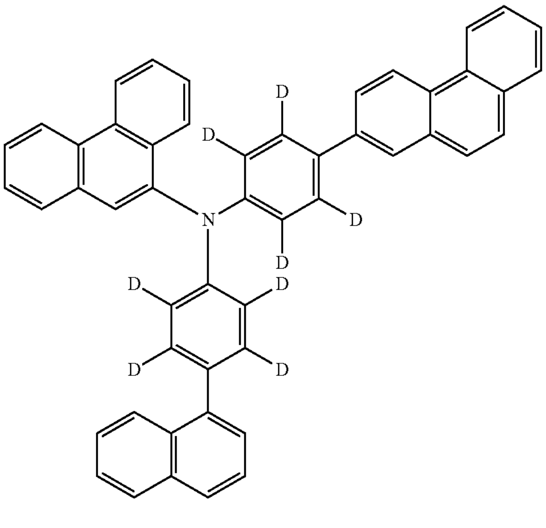
-continued
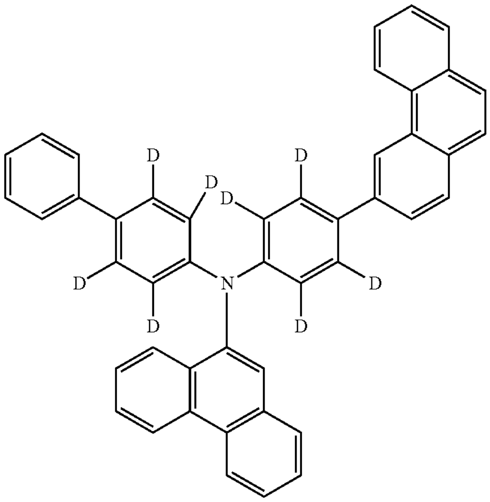
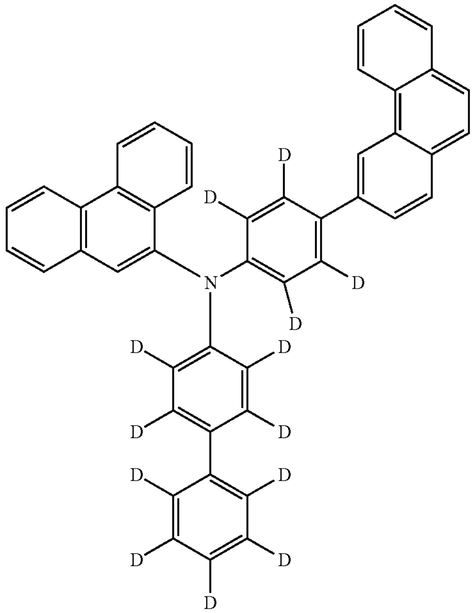
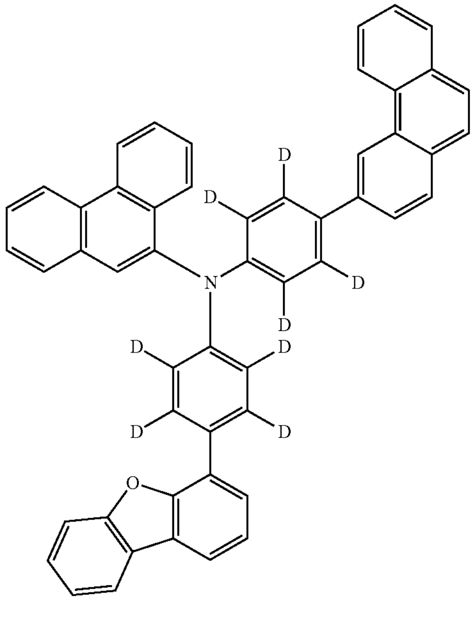

-continued
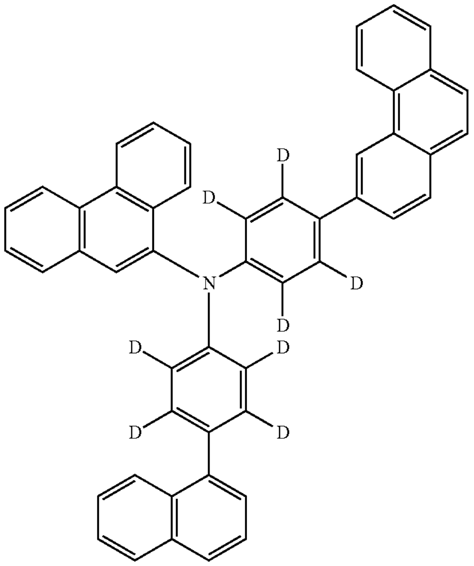
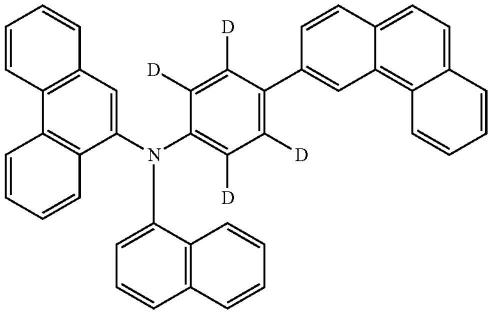
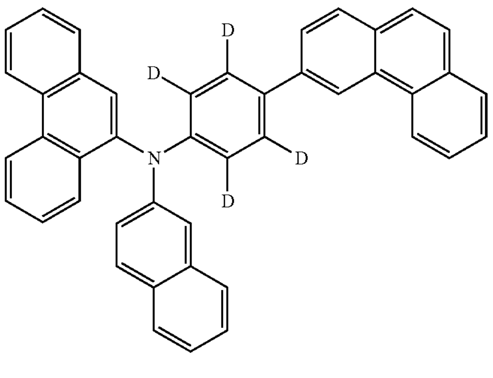
-continued
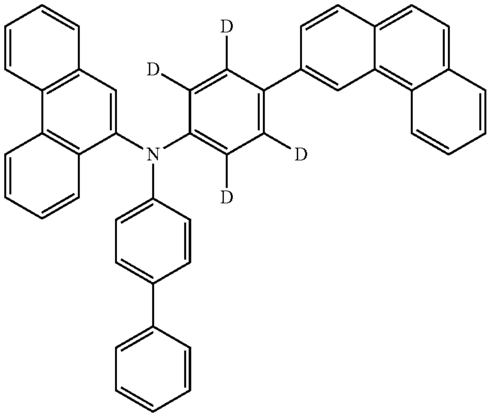
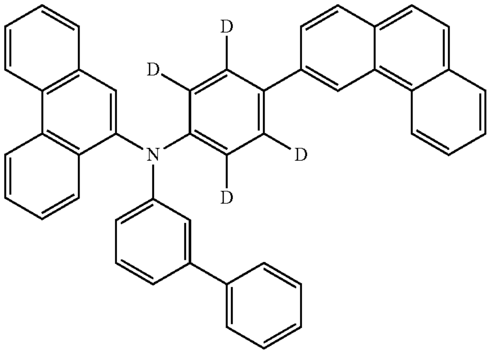
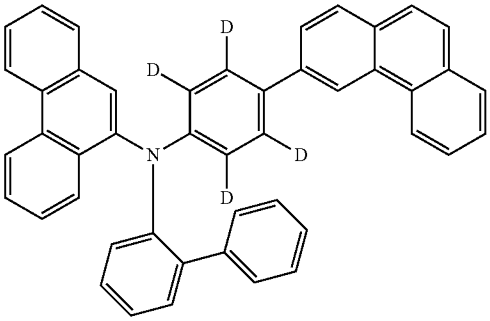
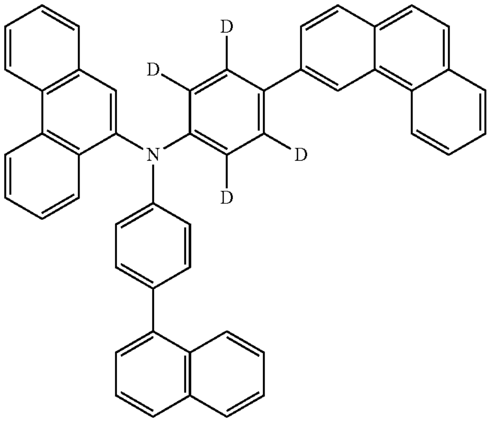

-continued
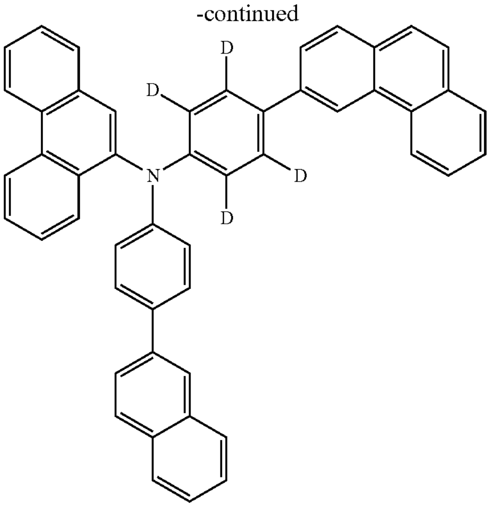
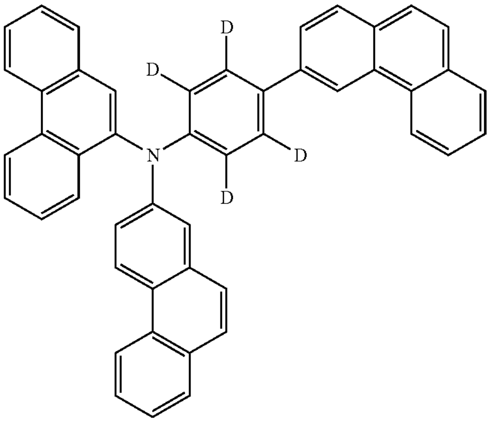
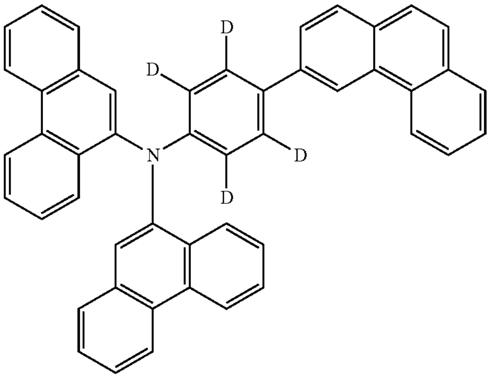
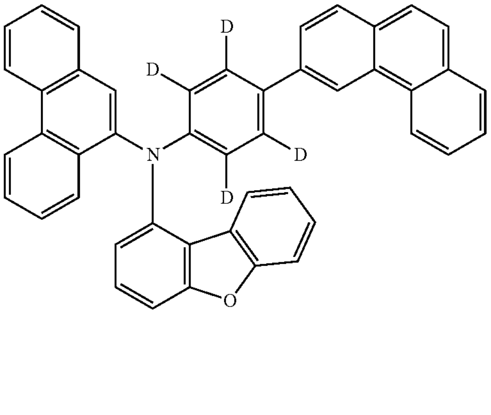
-continued
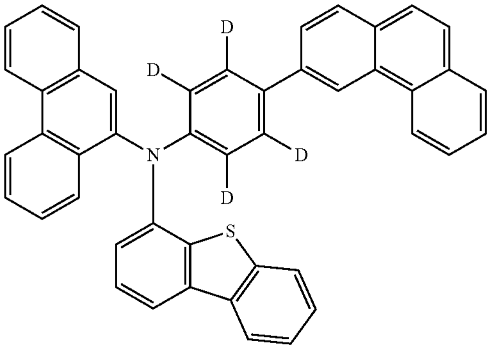
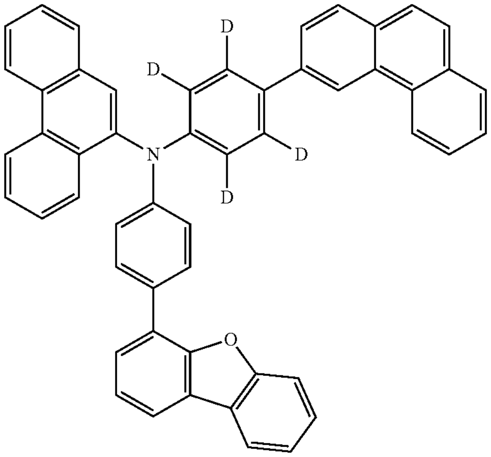
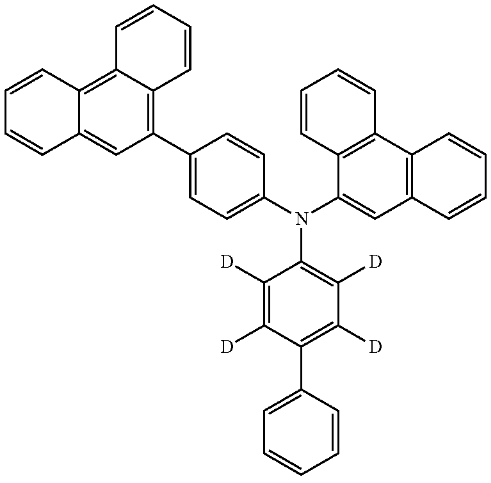
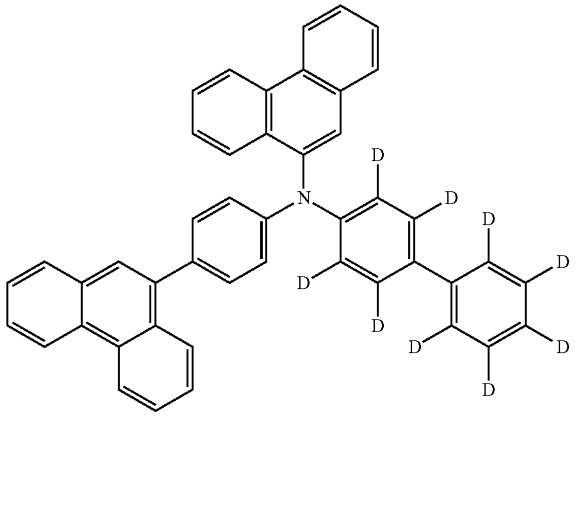

-continued
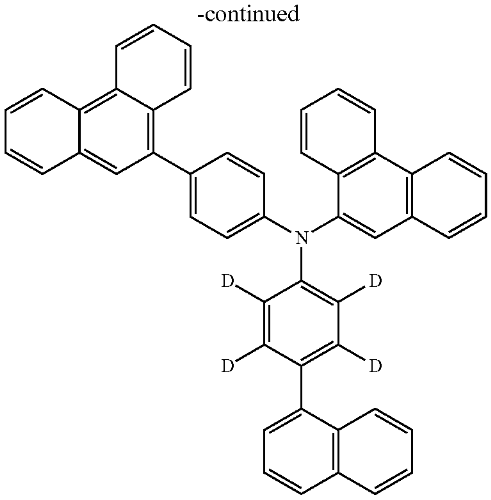
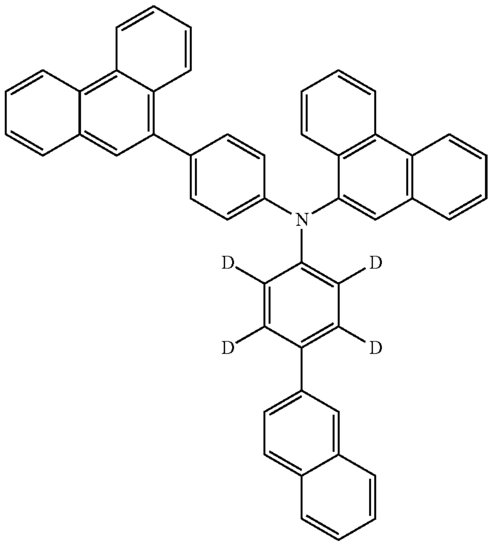 [SMILES: [2H]c1c([2H])c(N(c2ccc(-c3cc4ccccc4c4ccccc34)cc2)c2cc3ccccc3c3ccccc23)c([2H])c([2H])c1-c1ccc2ccccc2c1]
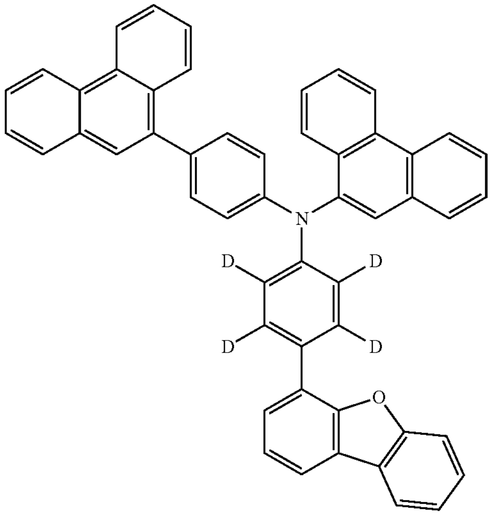
-continued
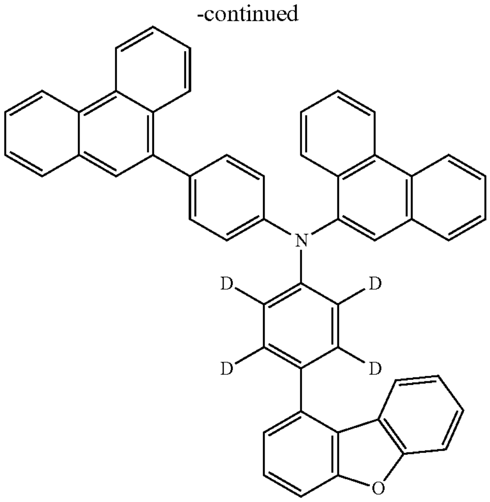
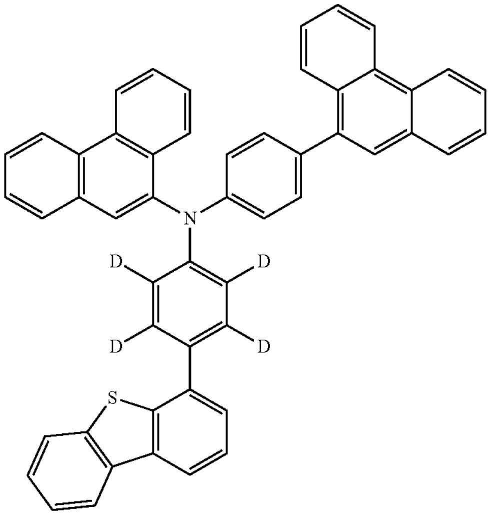 [SMILES: [2H]c1c([2H])c(N(c2ccc(-c3cc4ccccc4c4ccccc34)cc2)c2cc3ccccc3c3ccccc23)c([2H])c([2H])c1-c1cccc2c1sc1ccccc12]
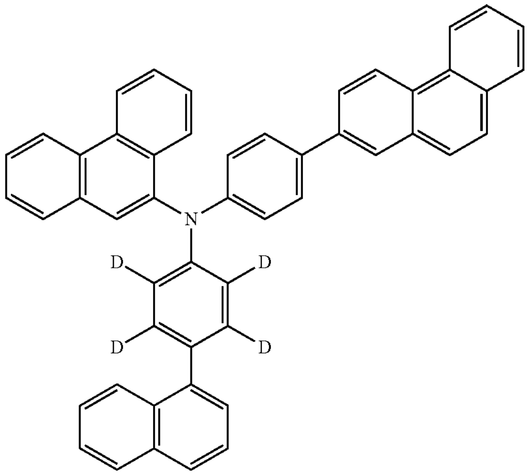

-continued
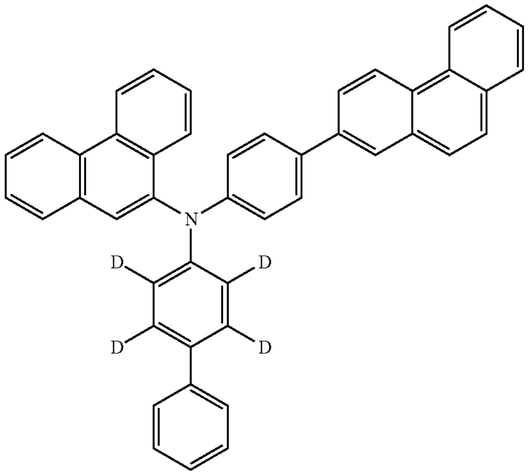
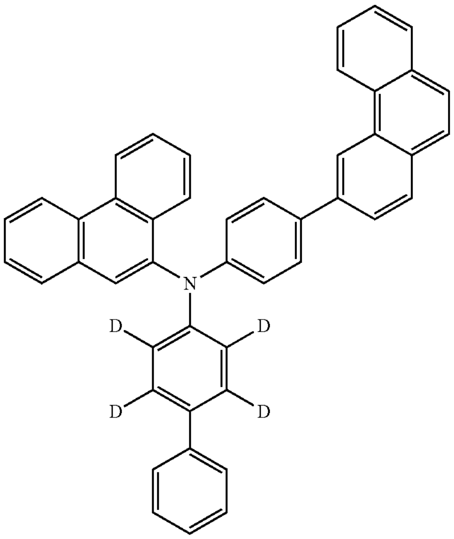
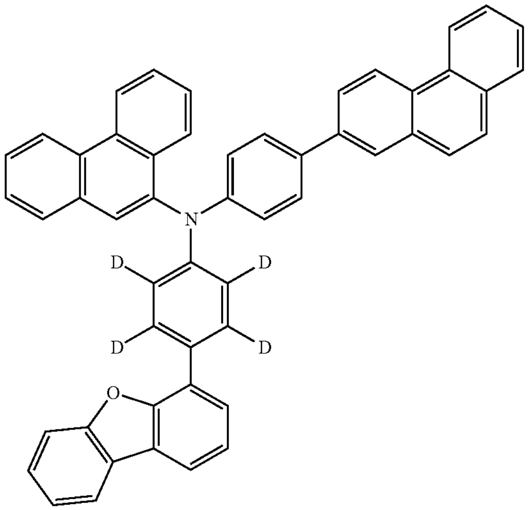 [SMILES: [2H]c1c([2H])c(N(c2ccc(-c3ccc4c(ccc5ccccc54)c3)cc2)c2cc3ccccc3c3ccccc23)c([2H])c([2H])c1-c1cccc2c1oc1ccccc12]
-continued
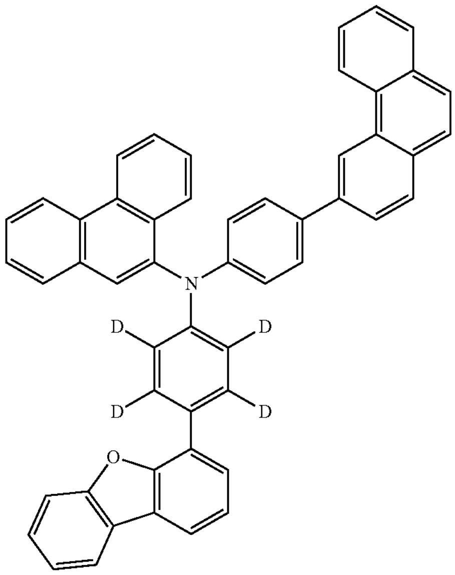
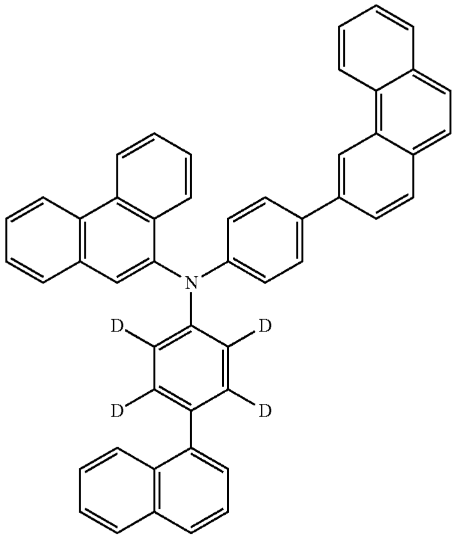
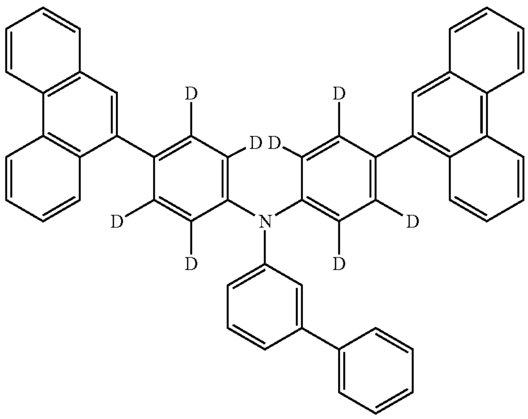

-continued
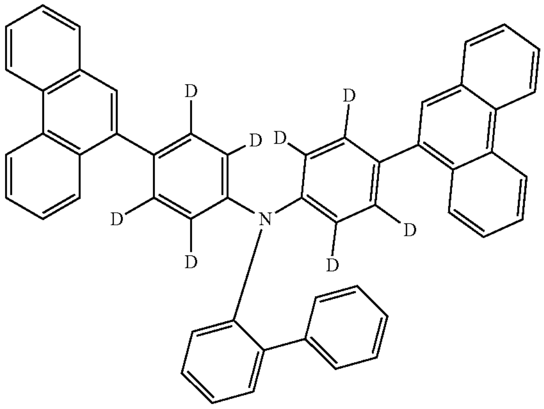
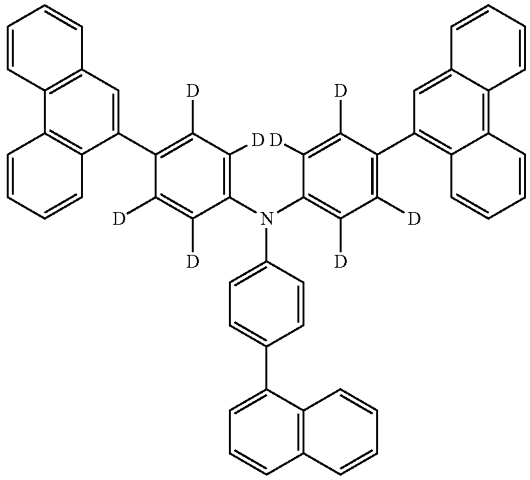
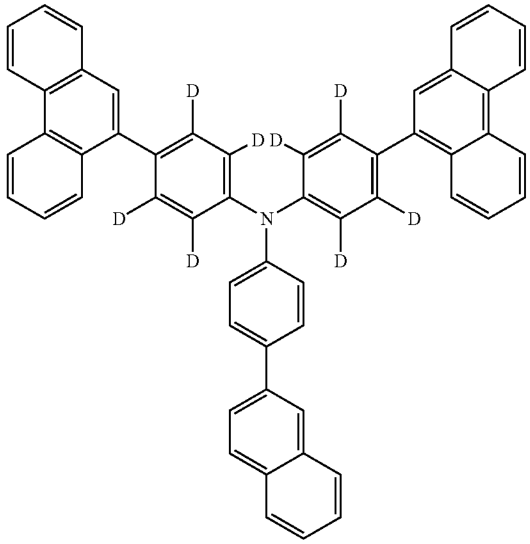 [SMILES: [2H]c1c([2H])c(N(c2ccc(-c3ccc4ccccc4c3)cc2)c2c([2H])c([2H])c(-c3cc4ccccc4c4ccccc34)c([2H])c2[2H])c([2H])c([2H])c1-c1cc2ccccc2c2ccccc12]
-continued
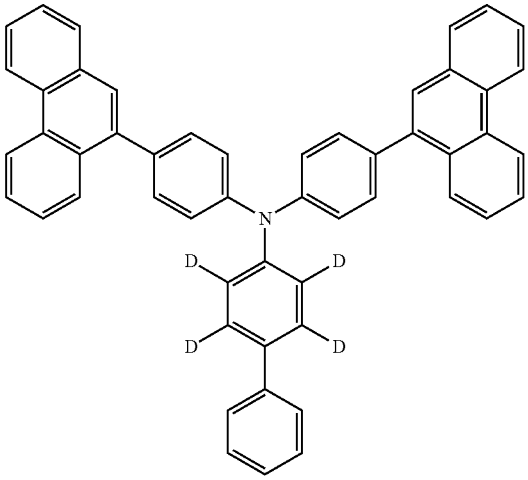 [SMILES: [2H]c1c([2H])c(N(c2ccc(-c3cc4ccccc4c4ccccc34)cc2)c2ccc(-c3cc4ccccc4c4ccccc34)cc2)c([2H])c([2H])c1-c1ccccc1]
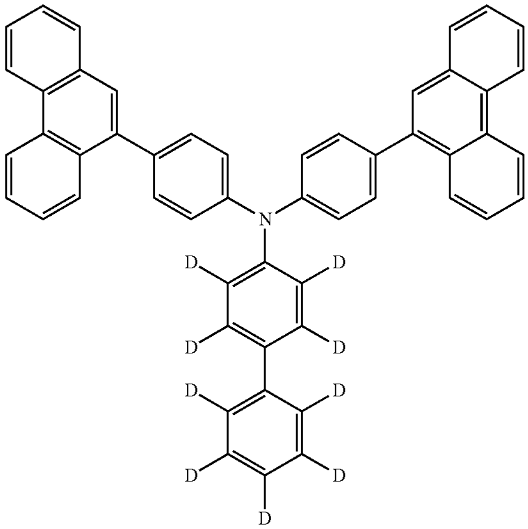
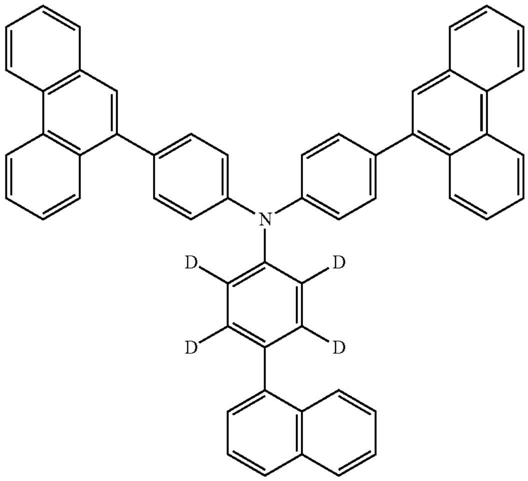

-continued
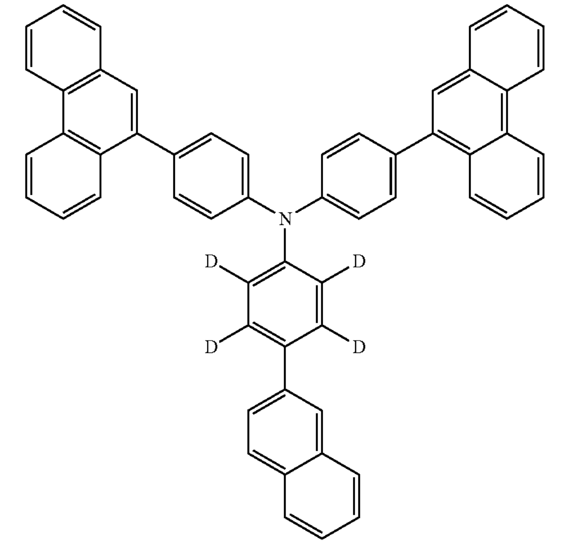
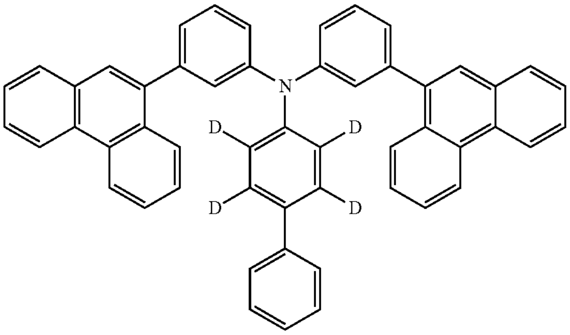 [SMILES: [2H]c1c([2H])c(N(c2cccc(-c3cc4ccccc4c4ccccc34)c2)c2cccc(-c3cc4ccccc4c4ccccc34)c2)c([2H])c([2H])c1-c1ccccc1]
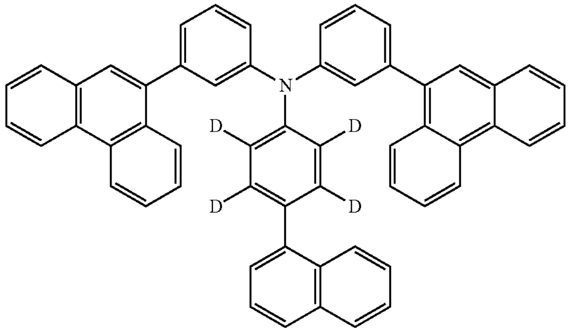
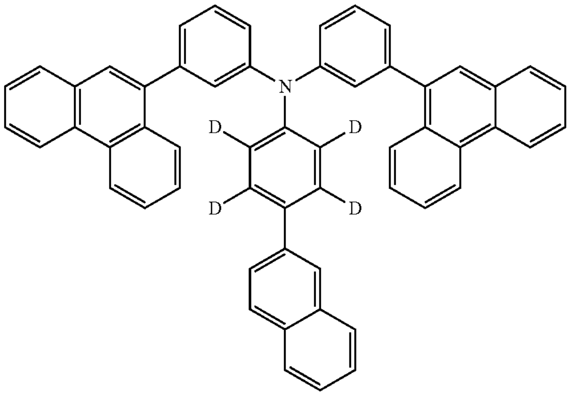
-continued
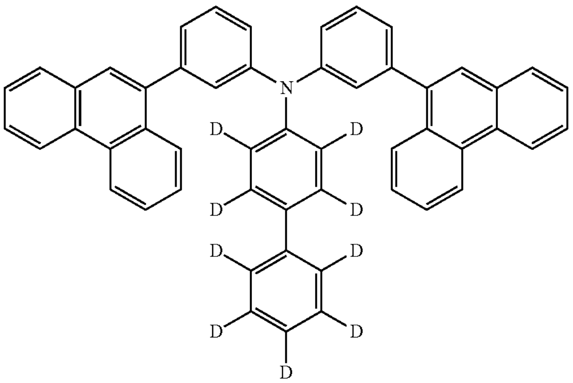
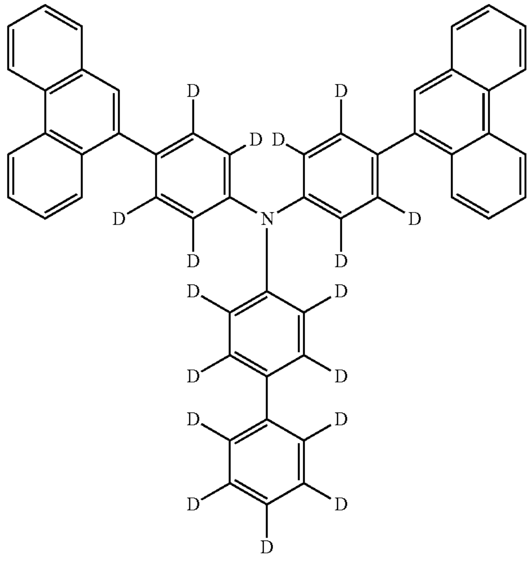
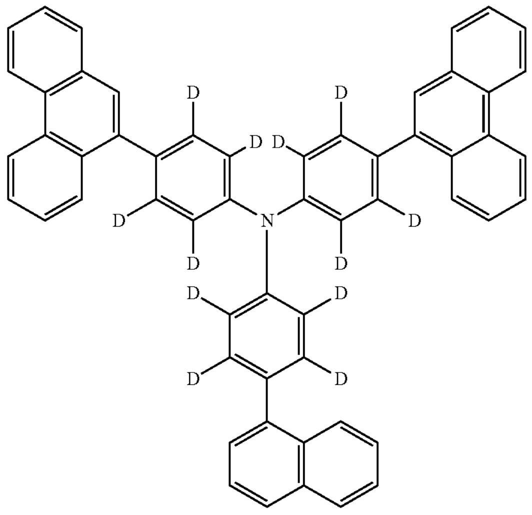

-continued
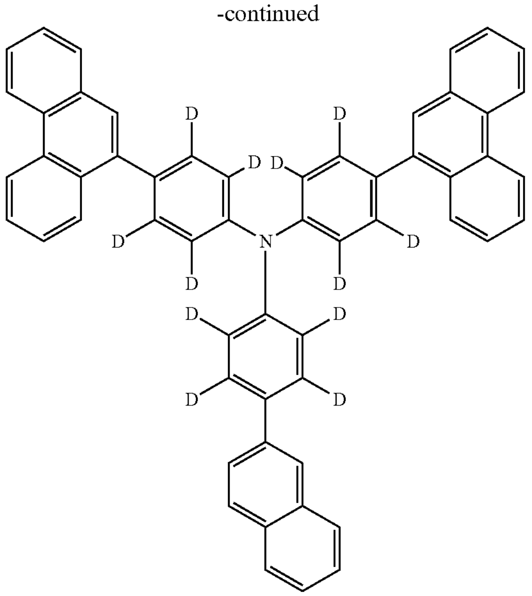
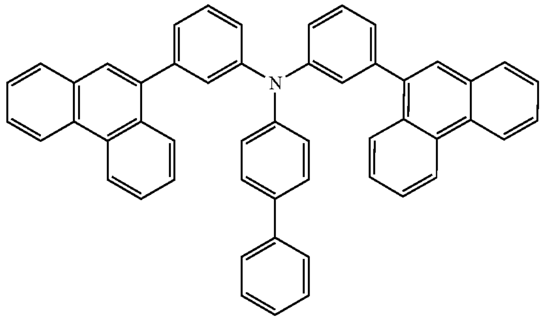
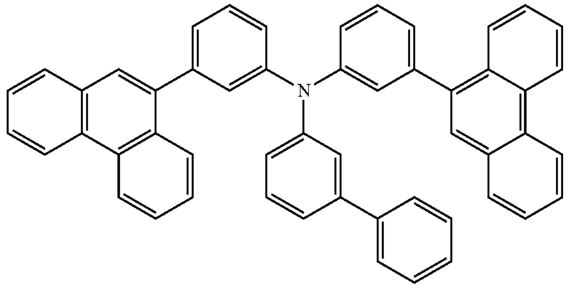
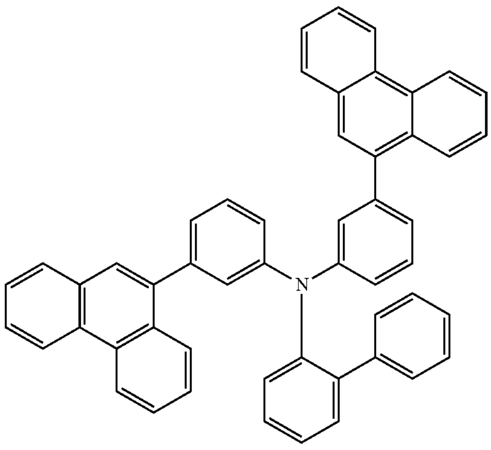
-continued
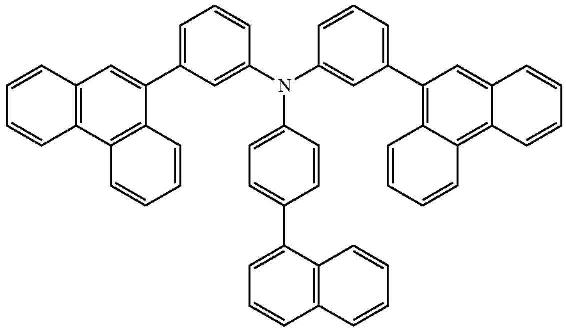
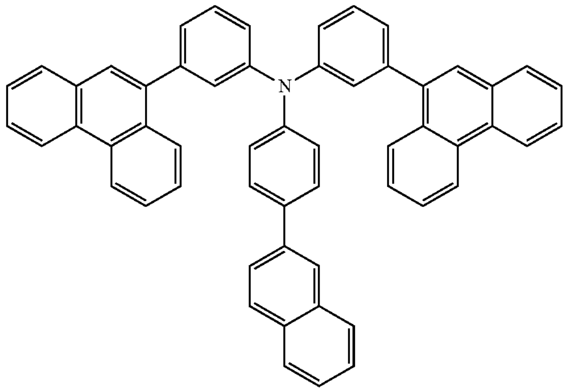
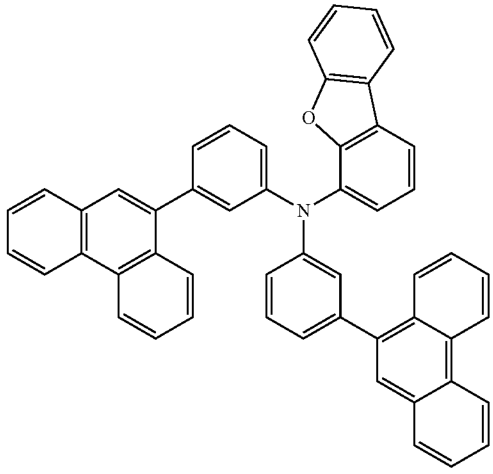
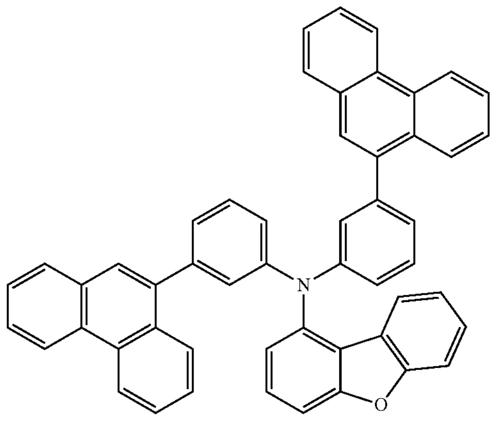

-continued
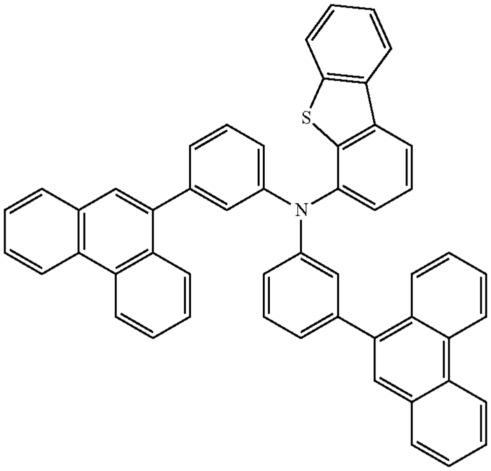
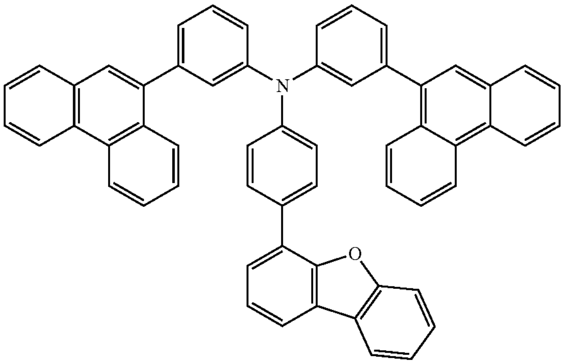
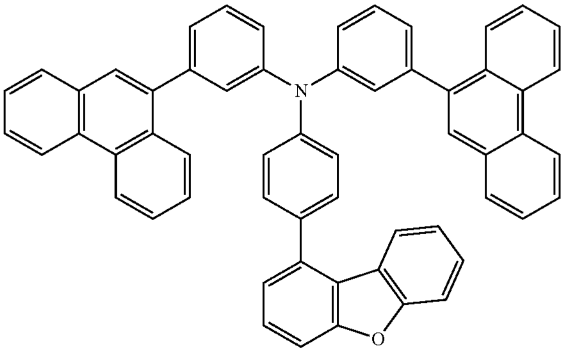
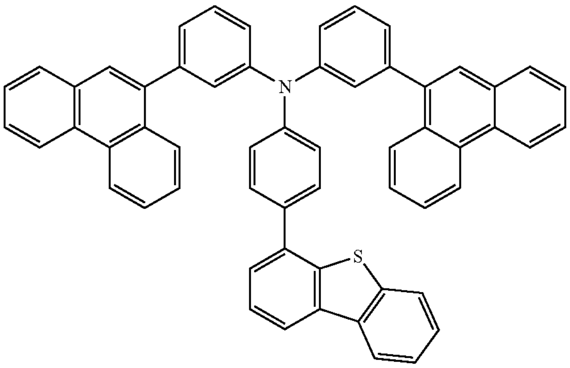 [SMILES: c1cc(-c2cc3ccccc3c3ccccc23)cc(N(c2ccc(-c3cccc4c3sc3ccccc34)cc2)c2cccc(-c3cc4ccccc4c4ccccc34)c2)c1]
-continued
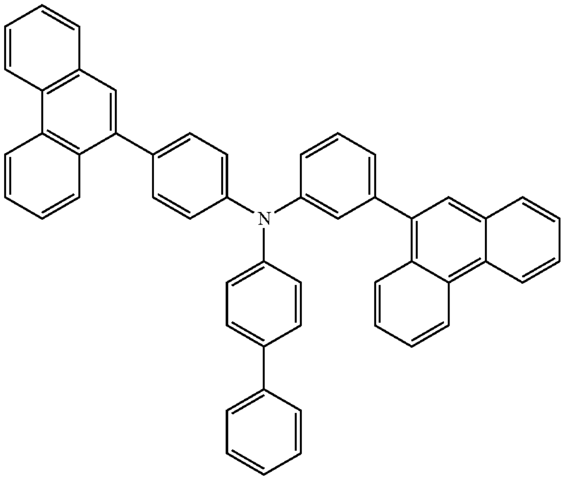 [SMILES: c1ccc(-c2ccc(N(c3ccc(-c4cc5ccccc5c5ccccc45)cc3)c3cccc(-c4cc5ccccc5c5ccccc45)c3)cc2)cc1]
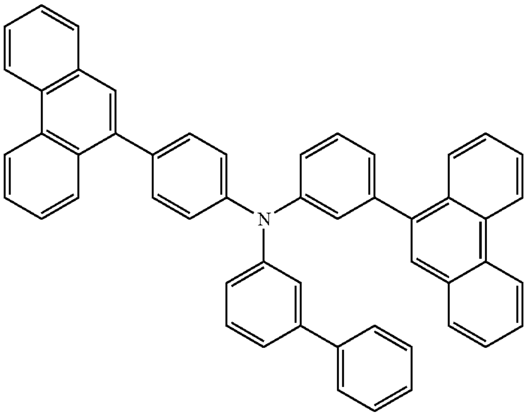
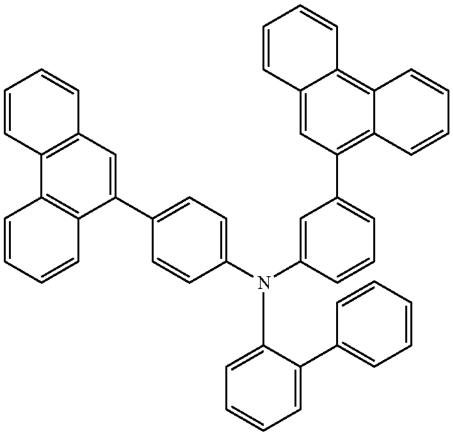

-continued
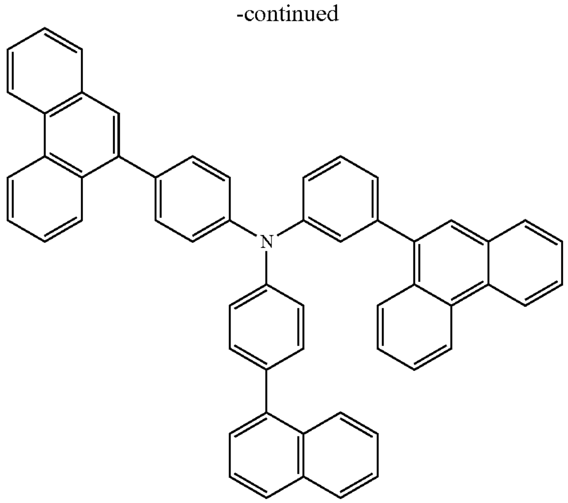
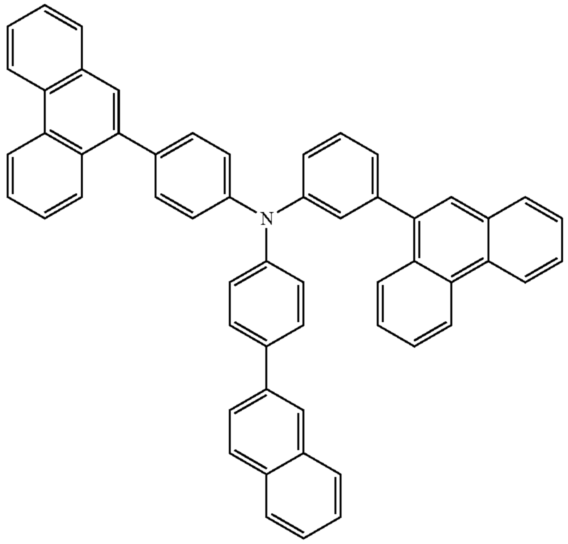
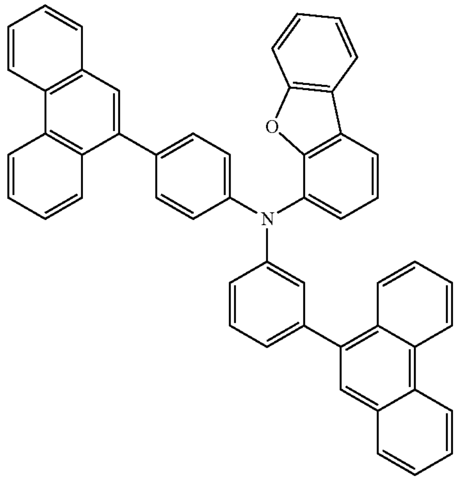
-continued
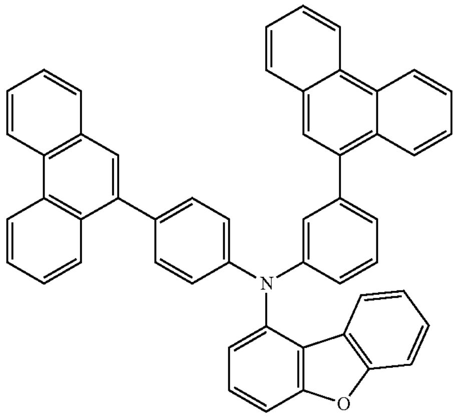
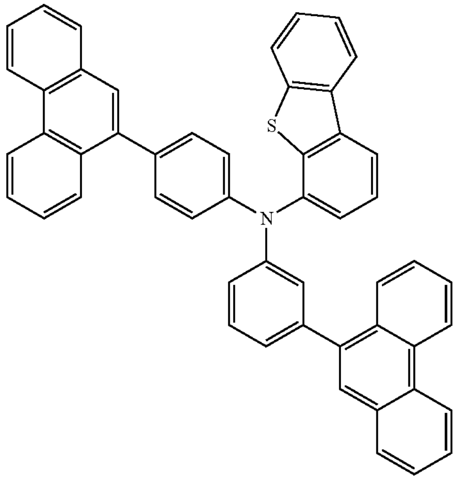
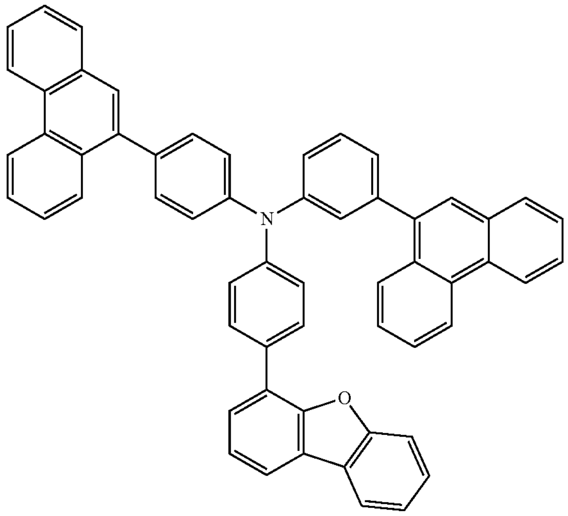

-continued
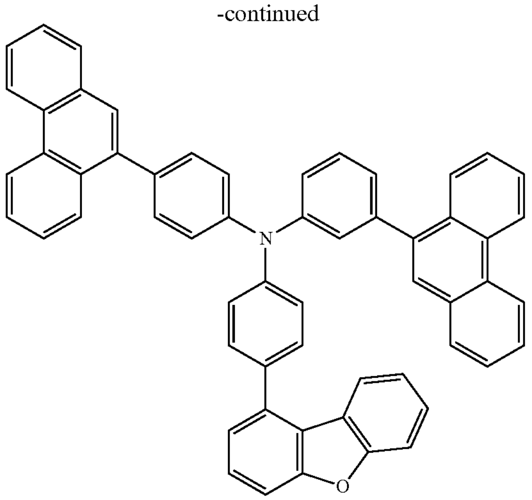
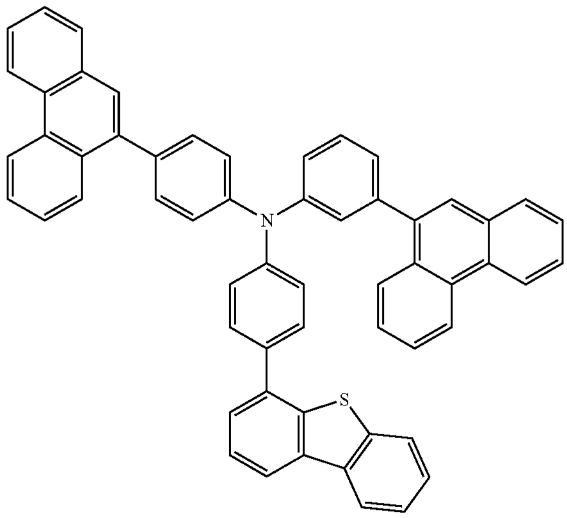 [SMILES: c1cc(-c2cc3ccccc3c3ccccc23)cc(N(c2ccc(-c3cc4ccccc4c4ccccc34)cc2)c2ccc(-c3cccc4c3sc3ccccc34)cc2)c1]
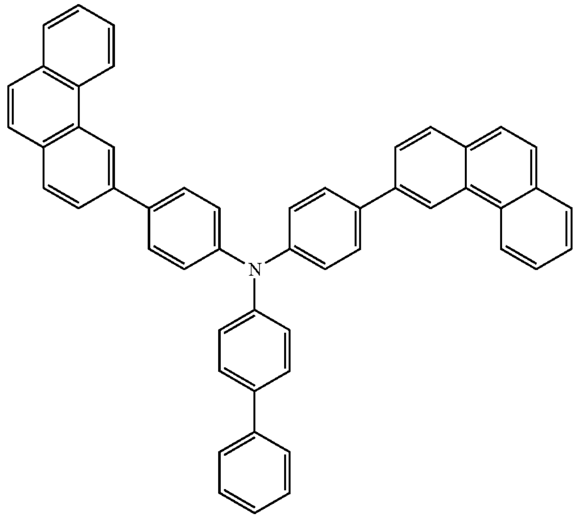
-continued
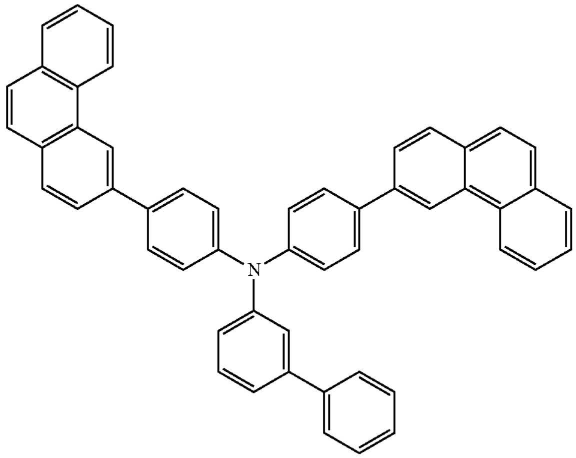
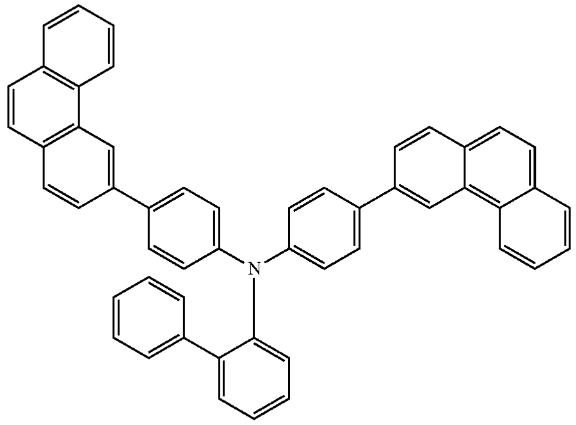
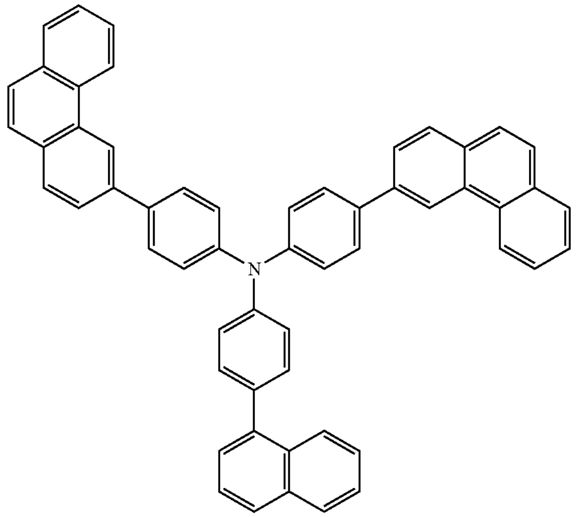

-continued
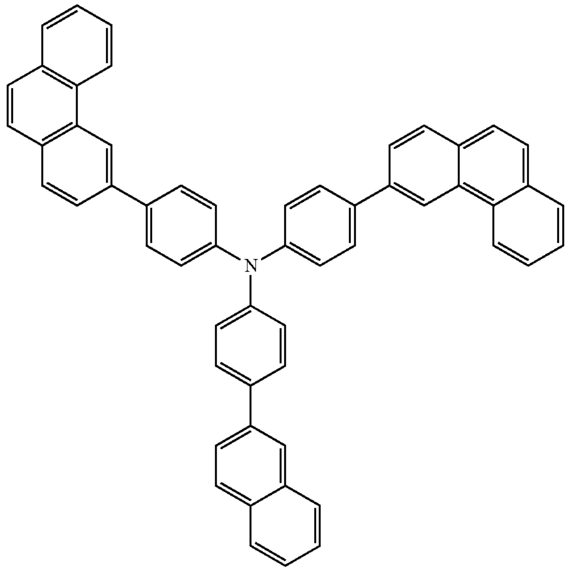
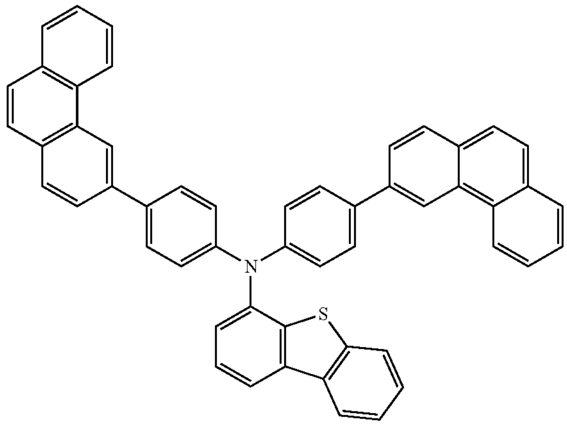 [SMILES: c1ccc2c(c1)ccc1ccc(-c3ccc(N(c4ccc(-c5ccc6ccc7ccccc7c6c5)cc4)c4cccc5c4sc4ccccc45)cc3)cc12]
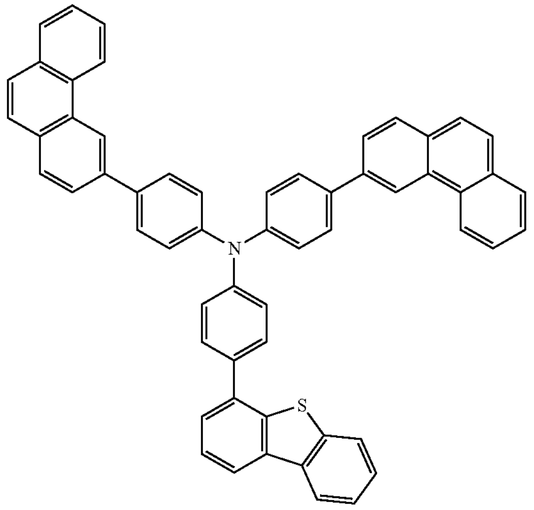
.
2. The organic light emitting device of claim 1, wherein Formula 1 is the following Formula 1-1 or 1-2:
Formula 1-1
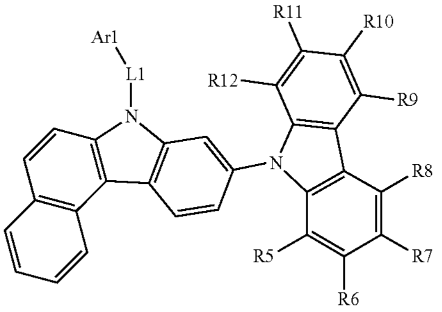
Formula 1-2
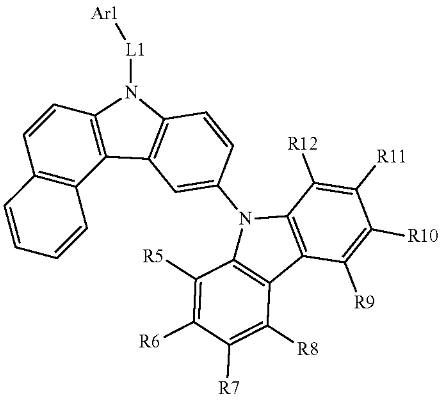
wherein in Formulae 1-1 and 1-2:
L1, Ar1, and R5 to R12 are the same as defined in Formula 1.
3. The organic light emitting device of claim 1, wherein Formula 1 is any one of the following Formulae 1-3 to 1-6:
Formula 1-3
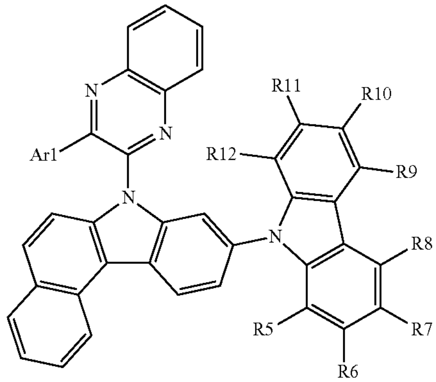

-continued
Formula 1-4
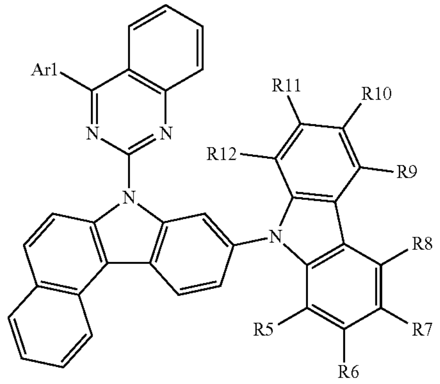
Formula 1-5
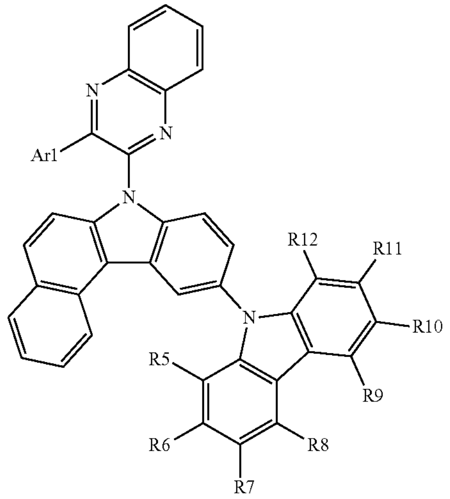
Formula 1-6
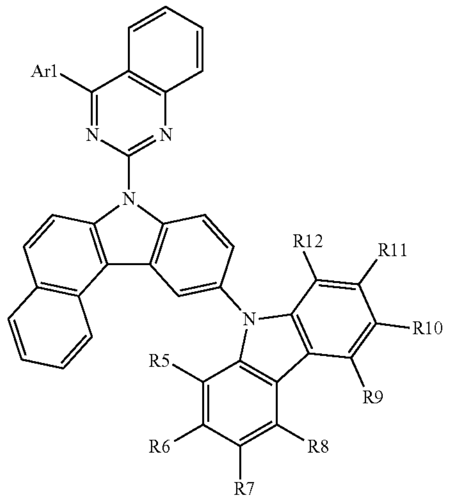
wherein in Formulae 1-3 to 1-6:
Ar1, and R5 to R12 are the same as defined in Formula 1.
4. The organic light emitting device of claim 1, wherein the compound of Formula 1 is any one of the following compounds:
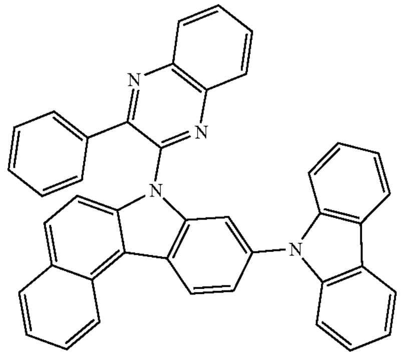
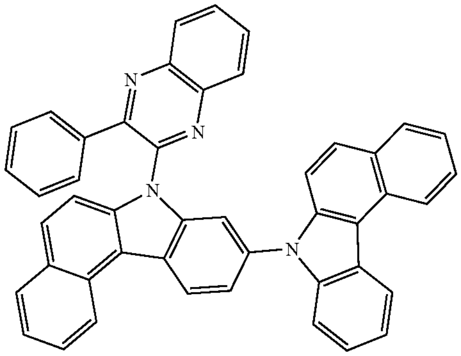
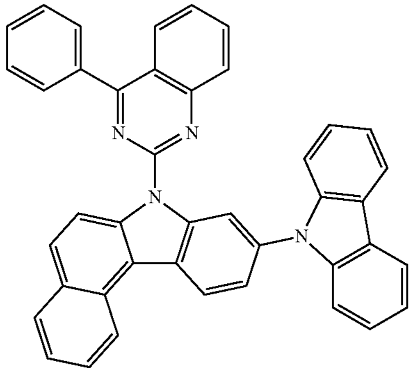
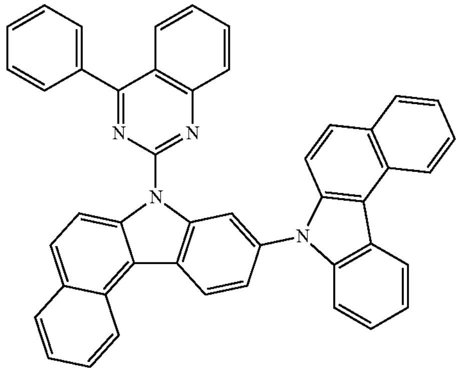

-continued
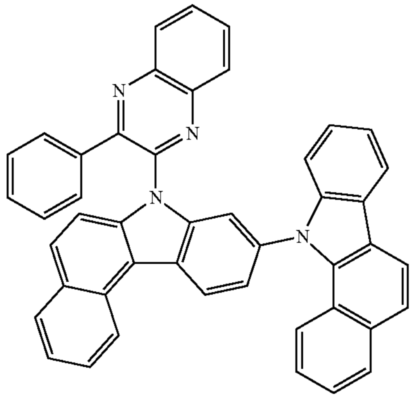
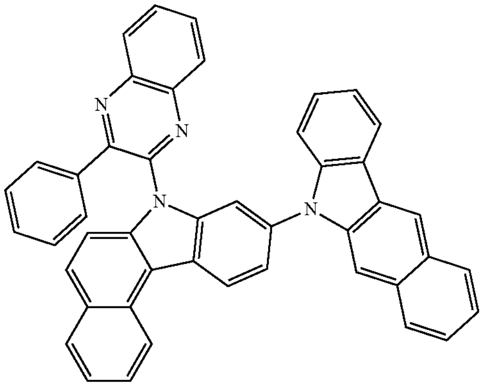
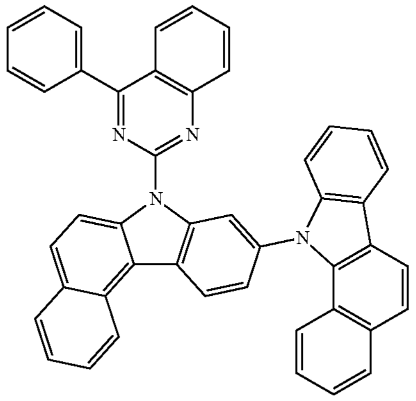
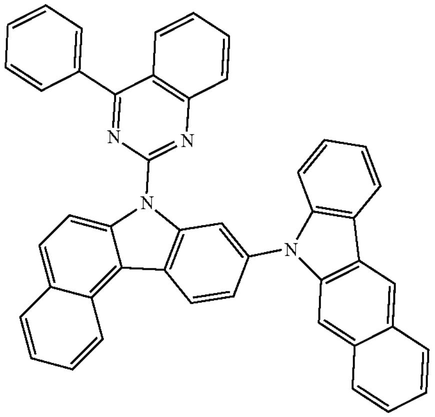
-continued
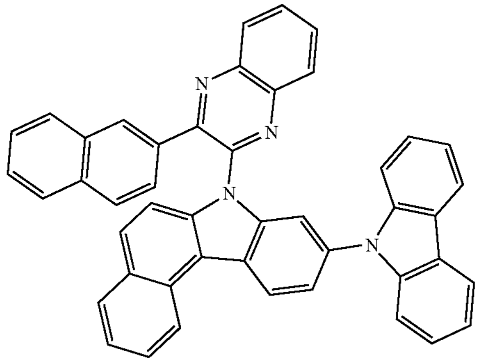
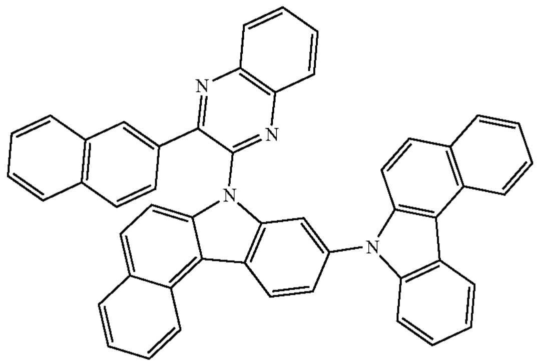
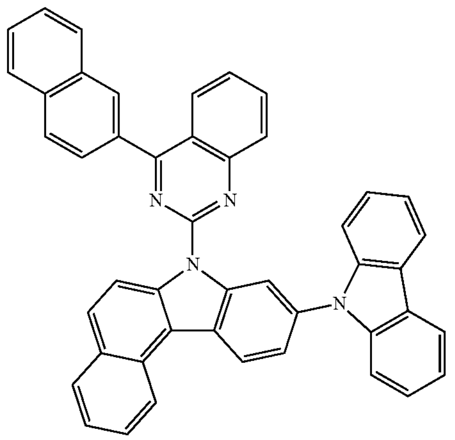
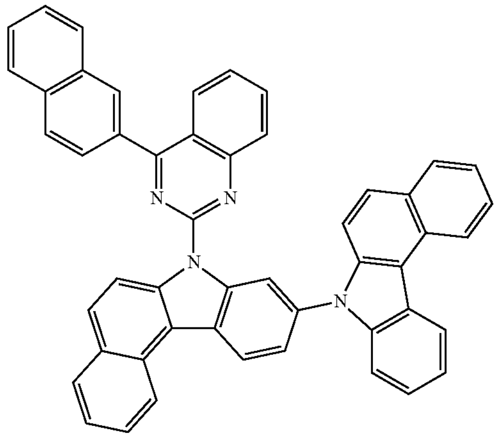

-continued
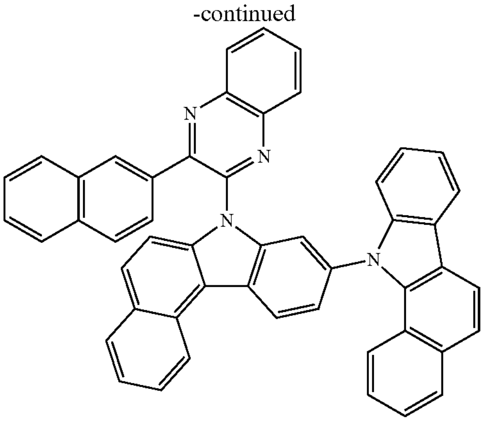
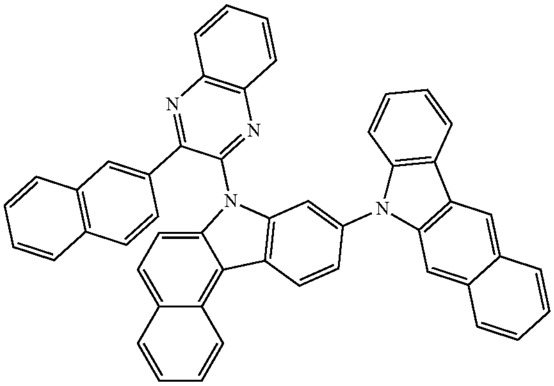
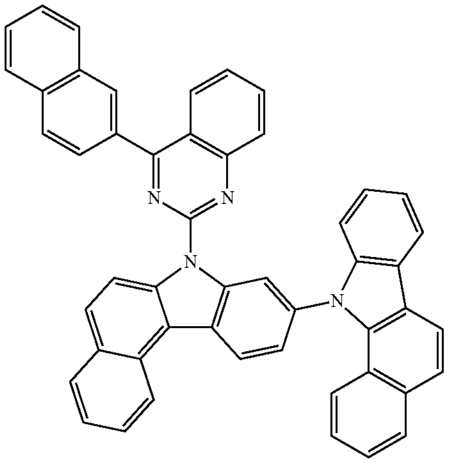
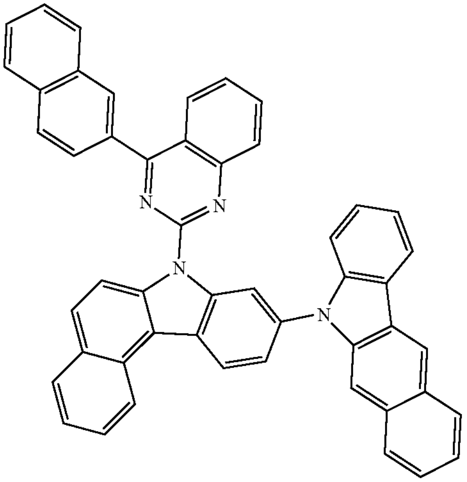
-continued
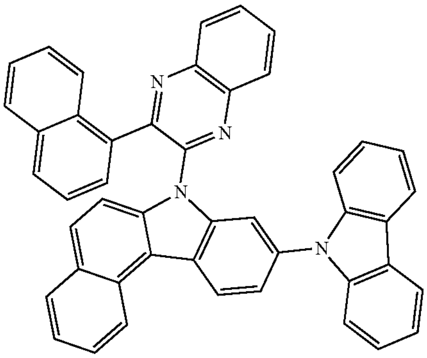
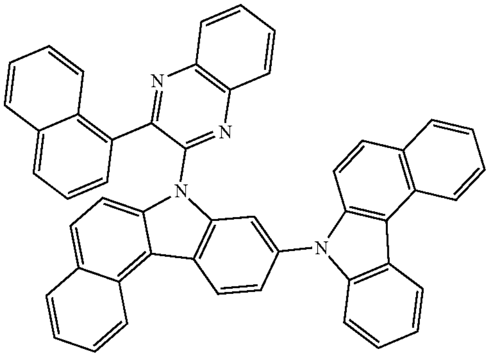
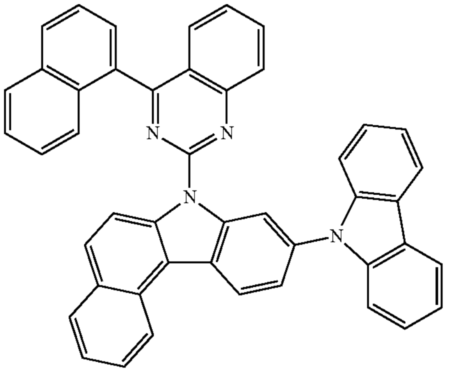
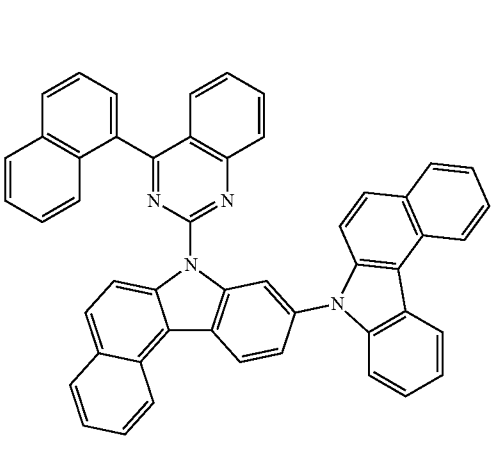

-continued
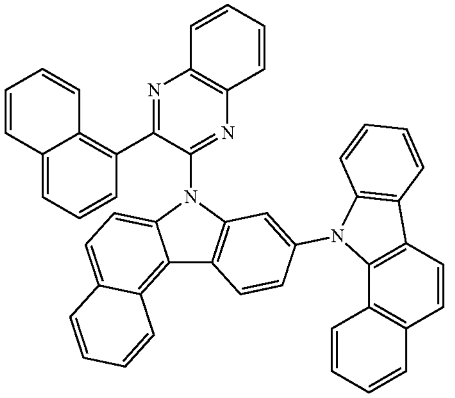
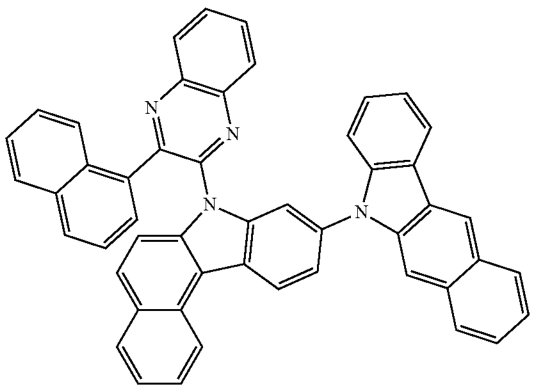
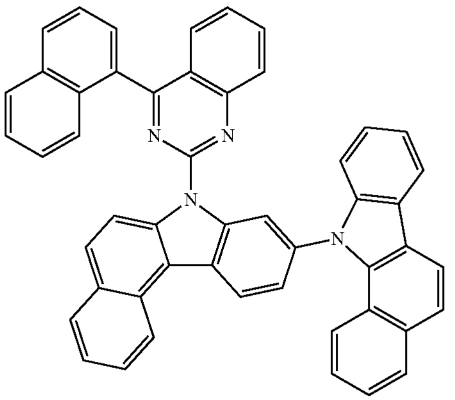
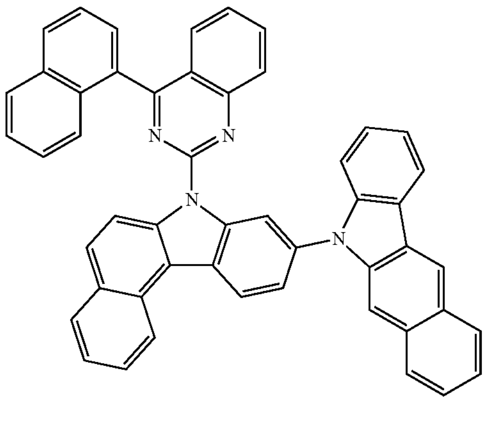
-continued
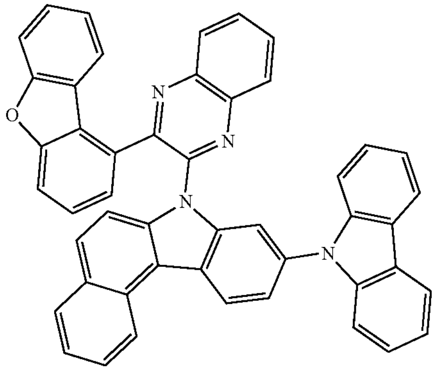
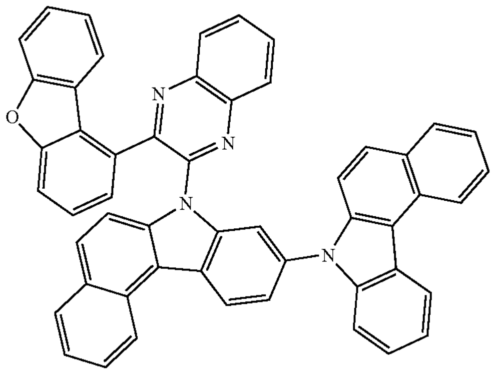
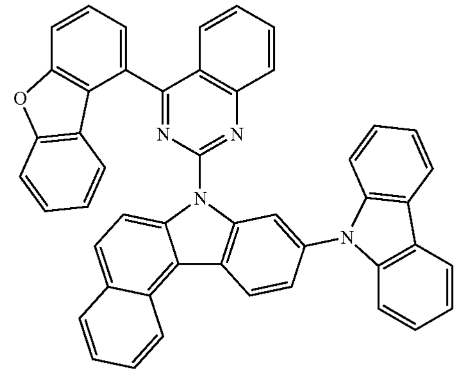
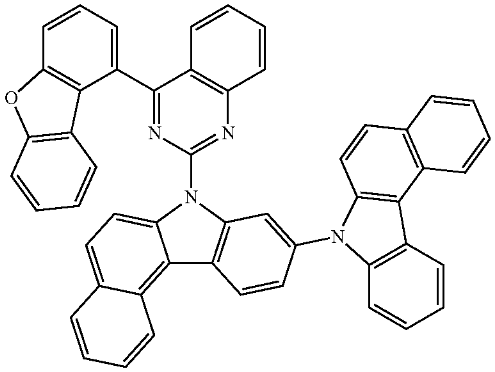

-continued
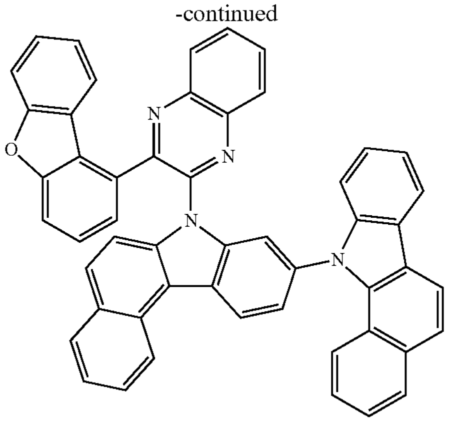
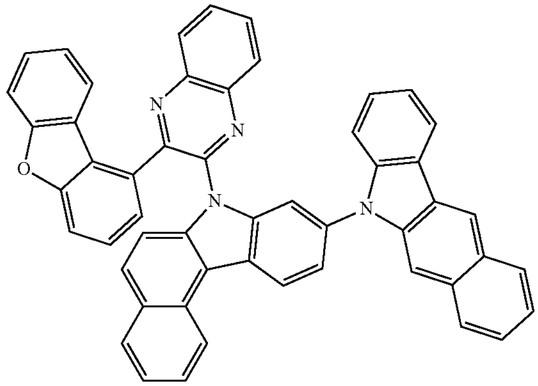
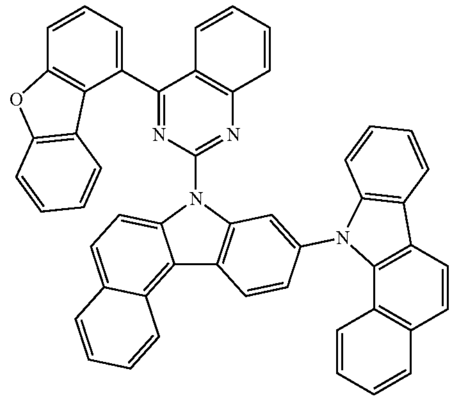
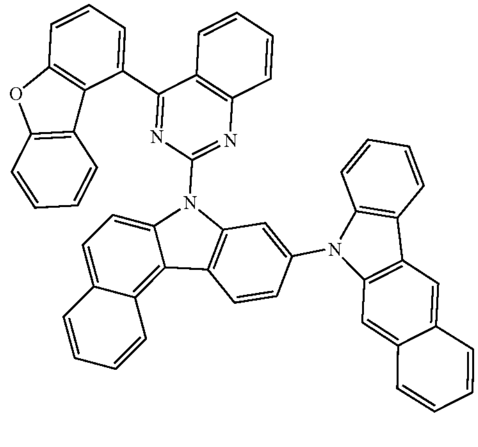
-continued
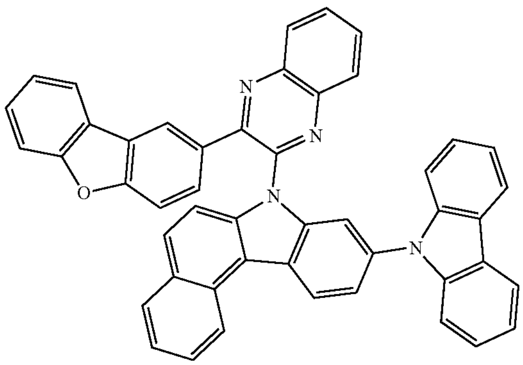
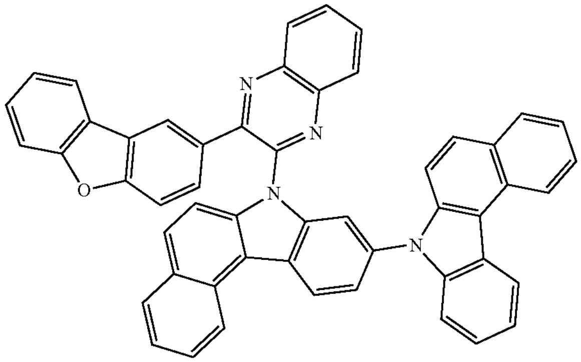
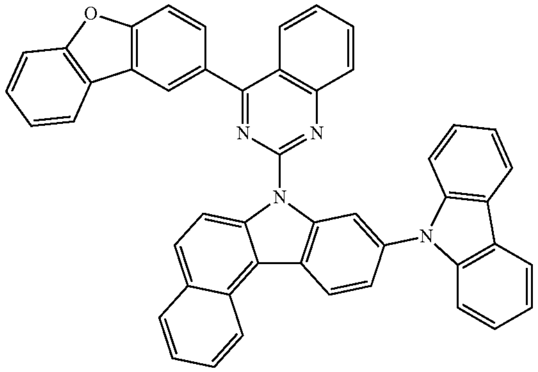
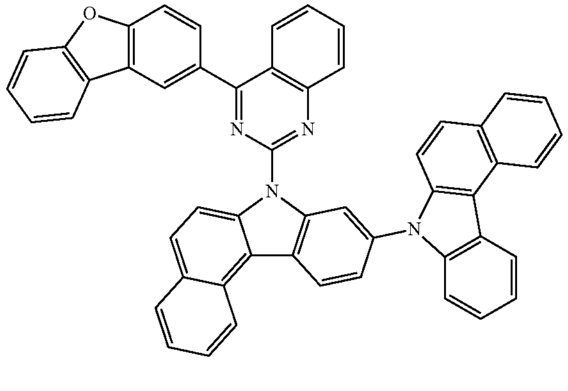

-continued
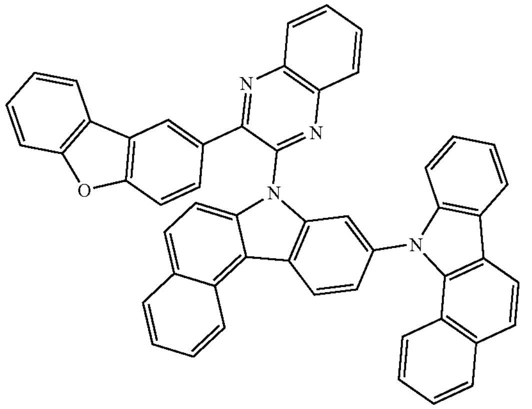
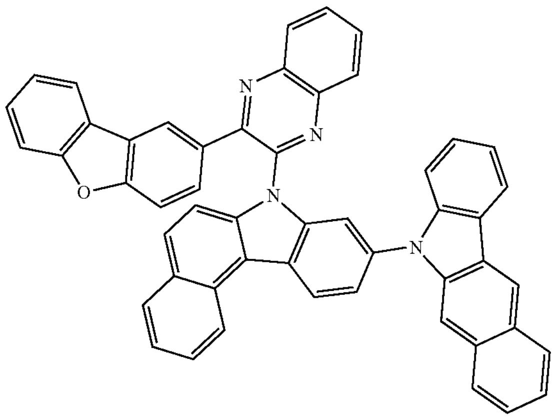
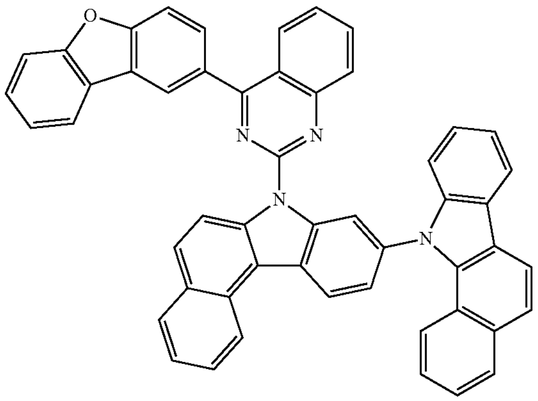
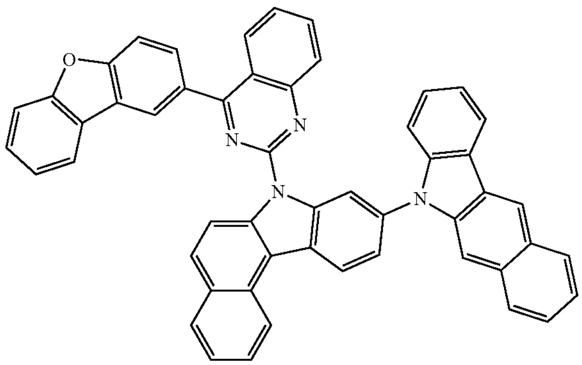
-continued
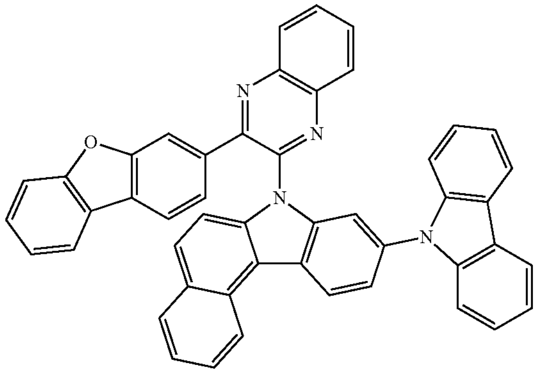
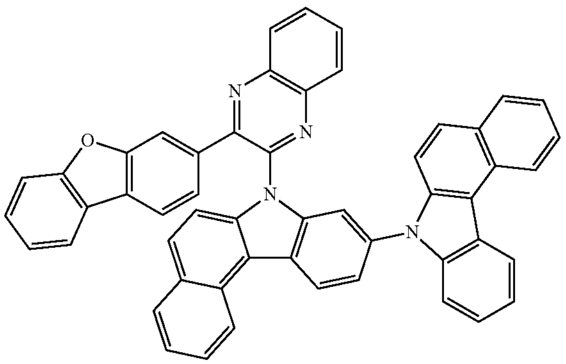
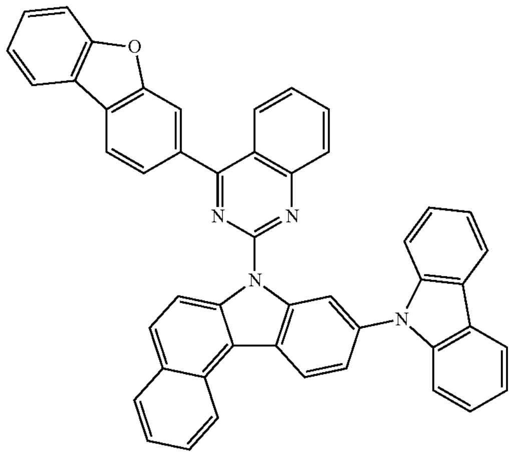
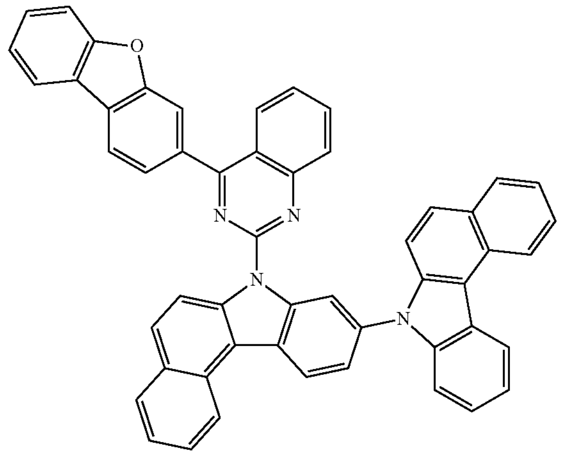

-continued
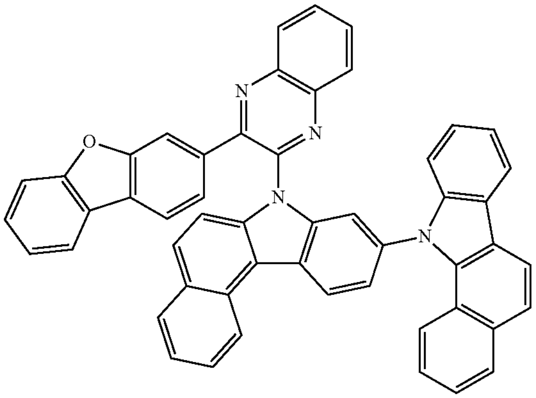
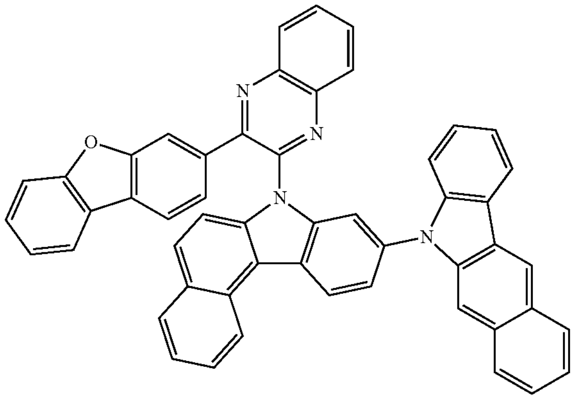
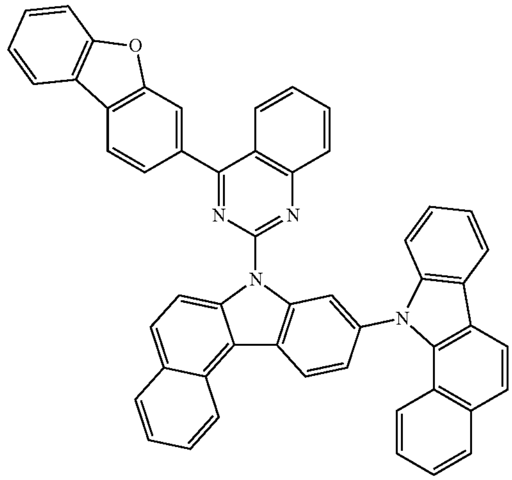
-continued
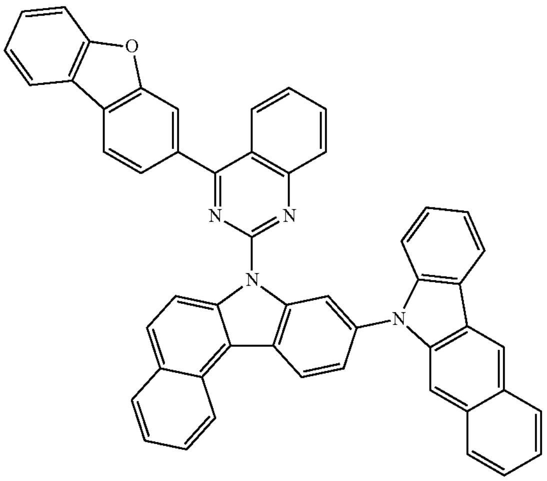
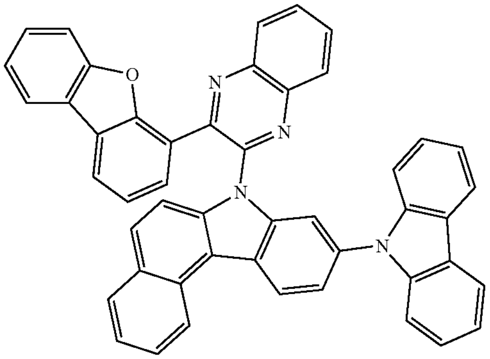
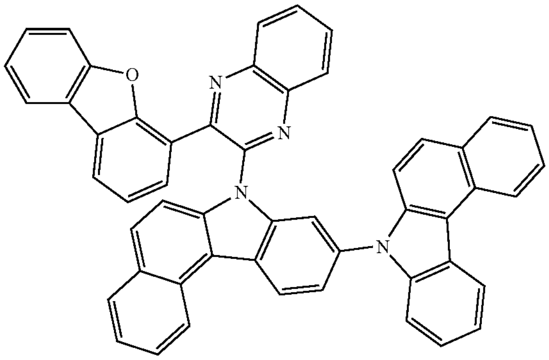
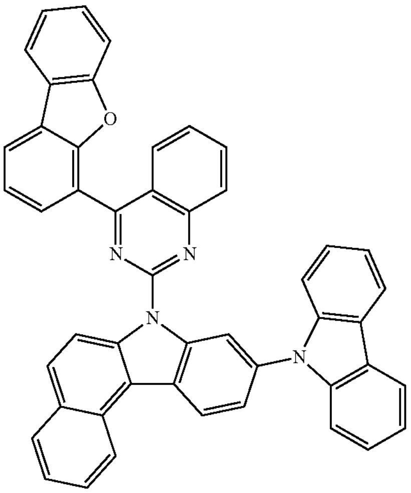

-continued
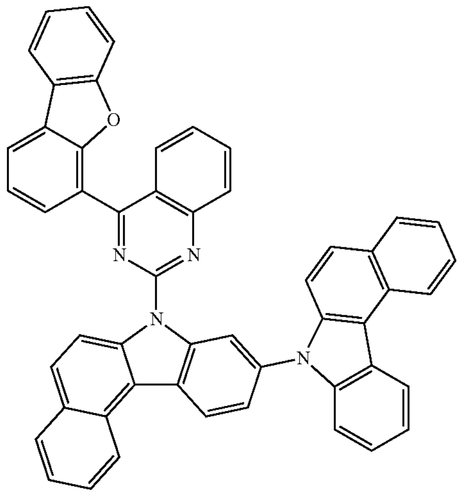
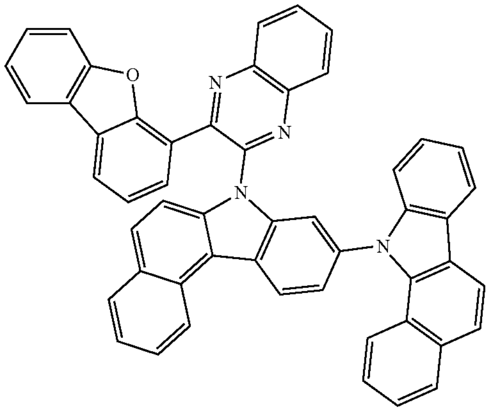
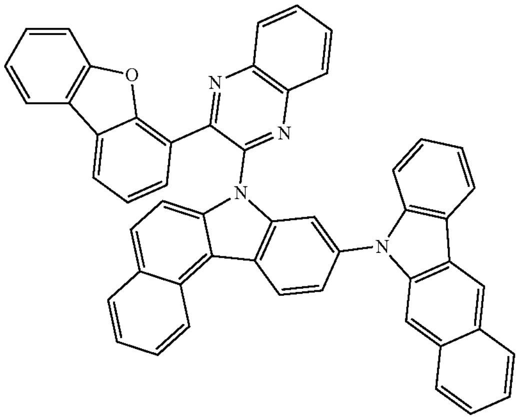
-continued
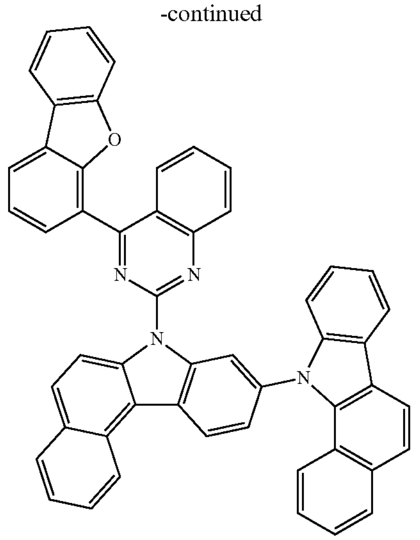
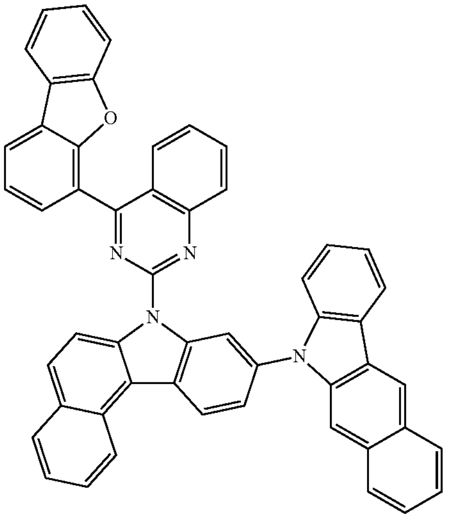
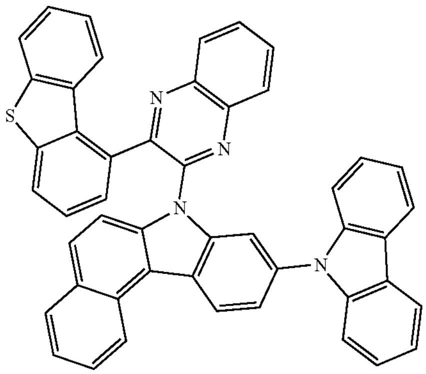

-continued
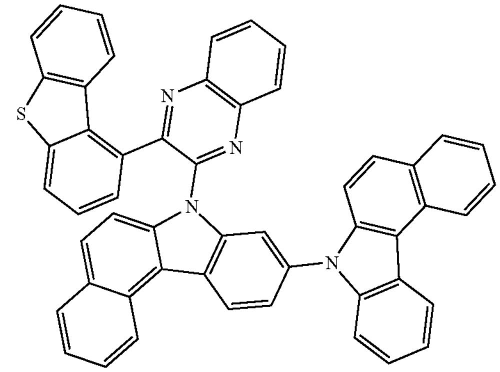
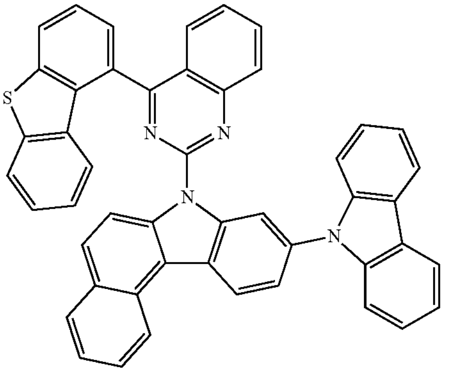
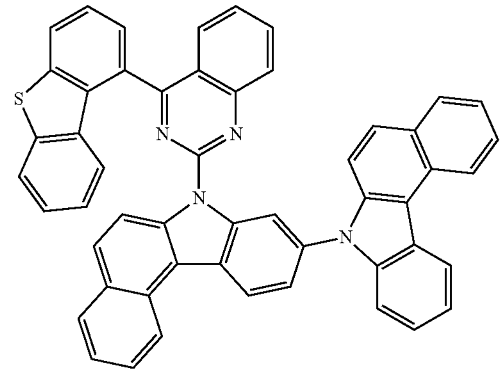
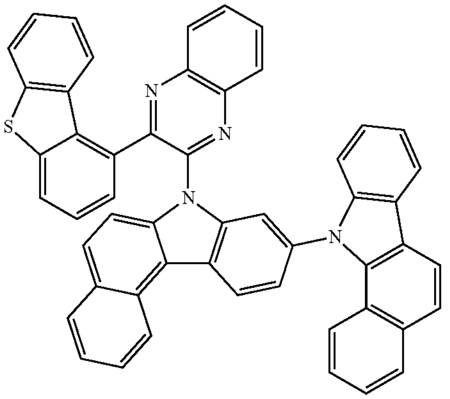
-continued
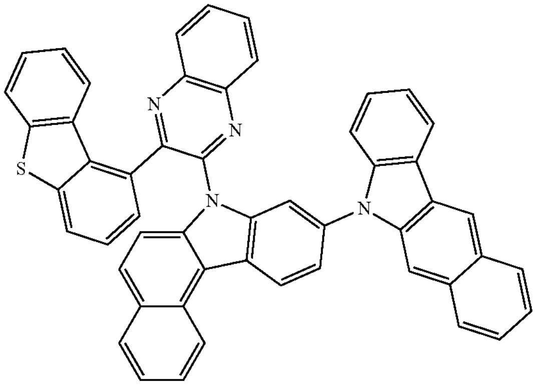
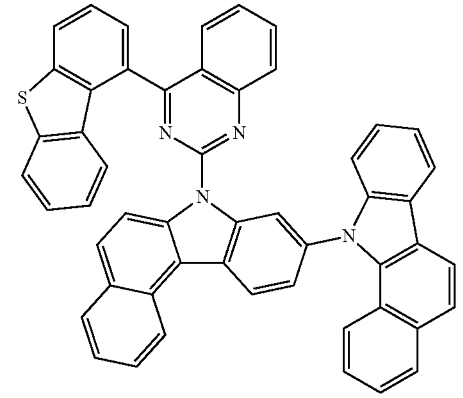
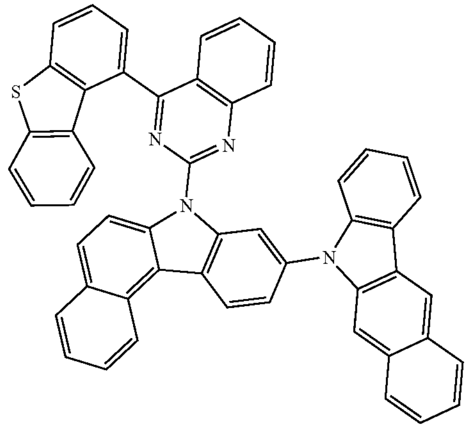
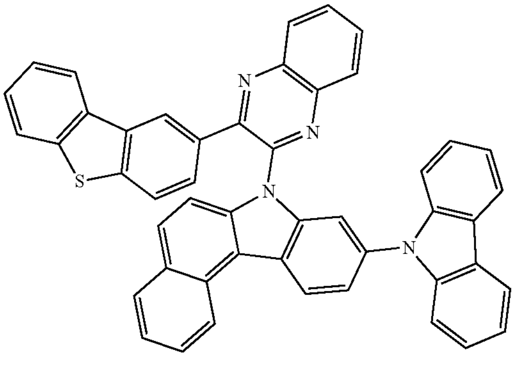

-continued
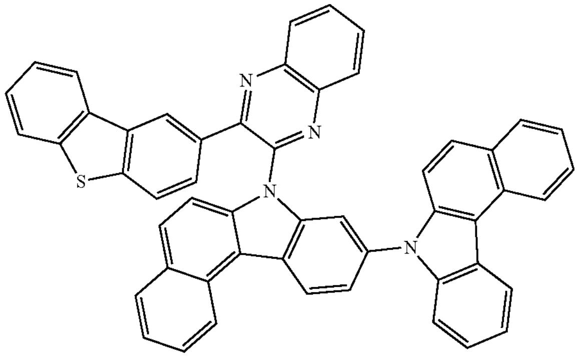
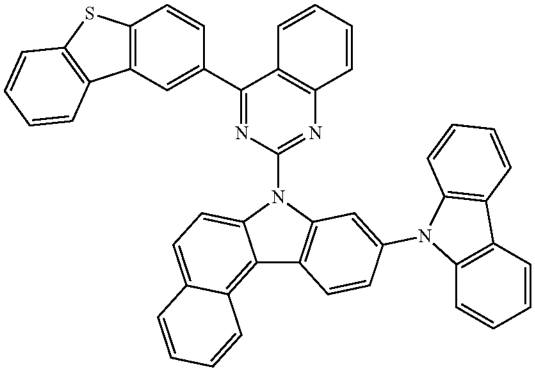
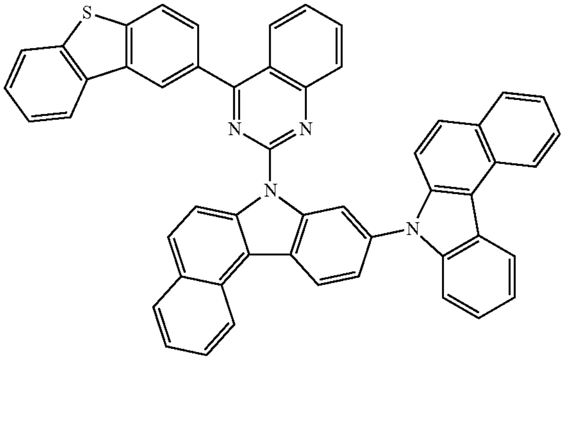
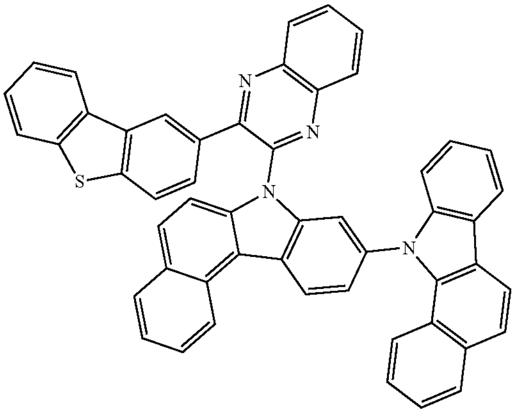
-continued
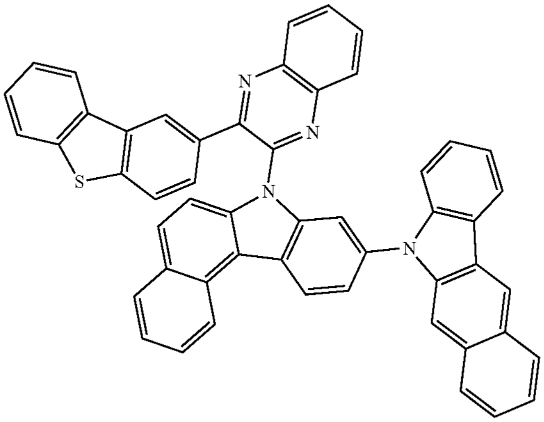
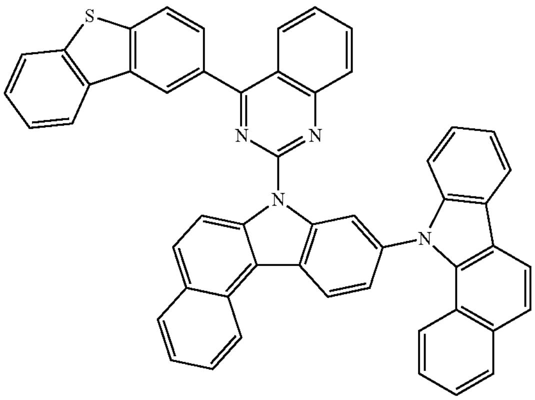
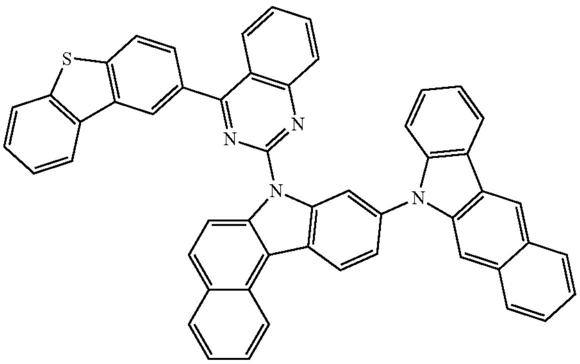
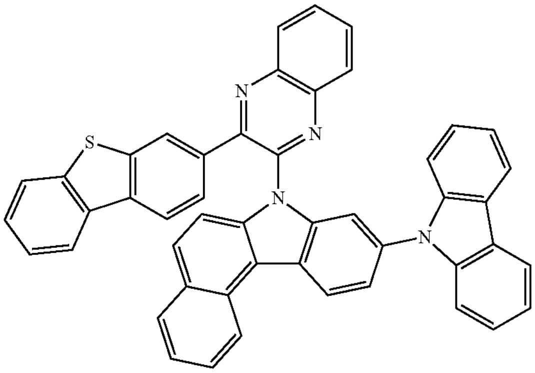

-continued
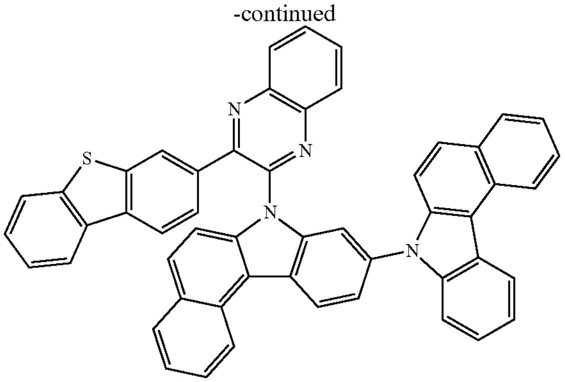
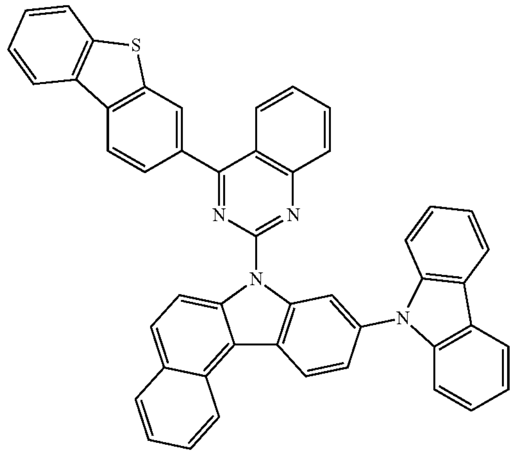
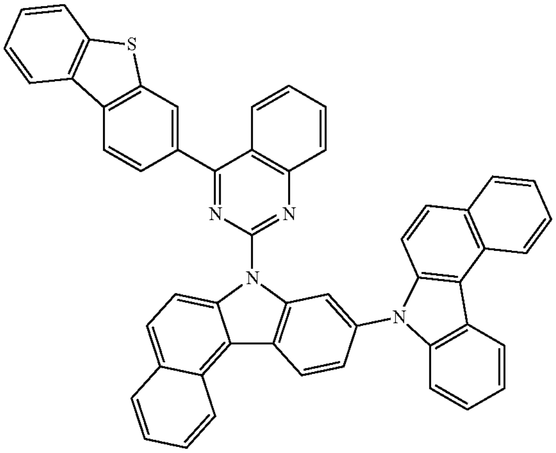
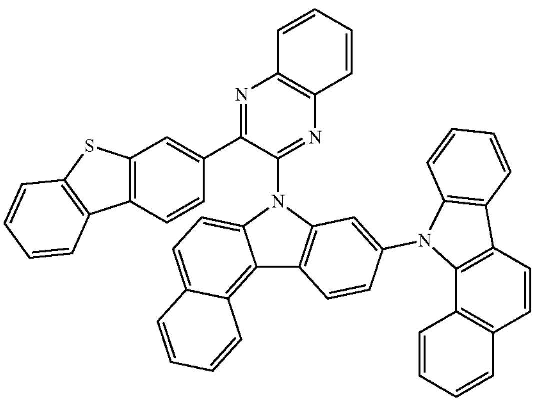
-continued
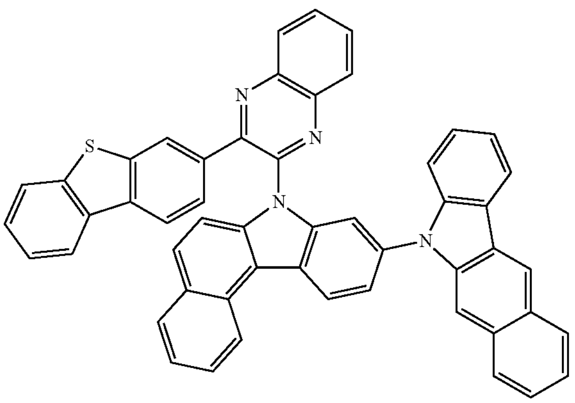
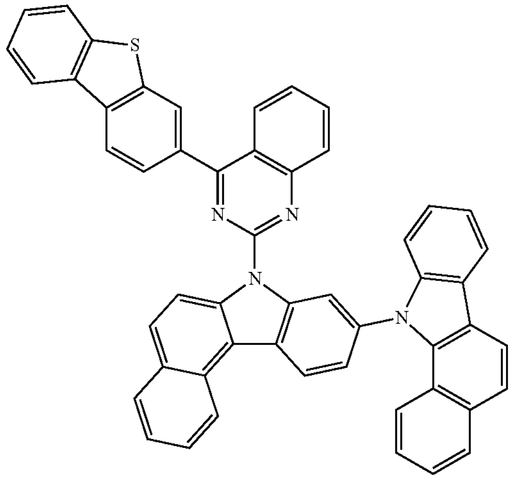
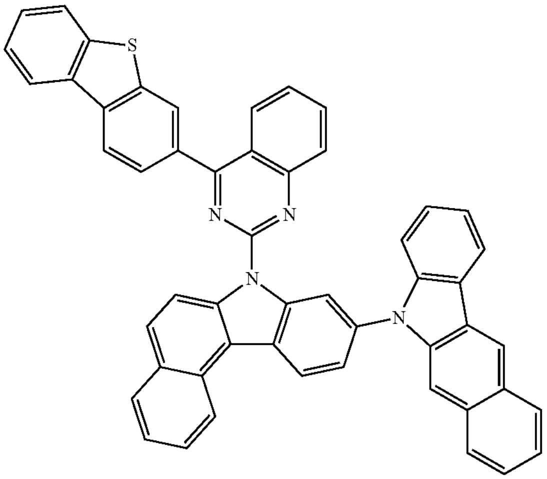
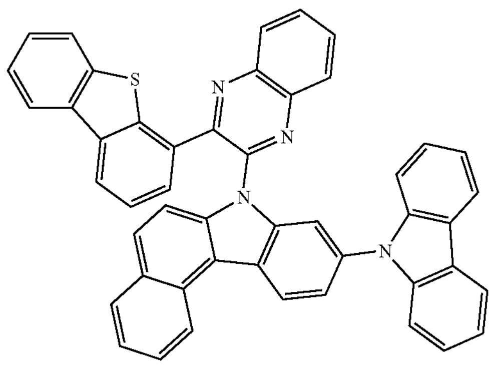

-continued
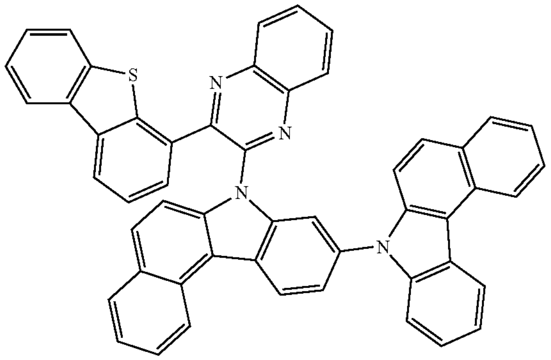
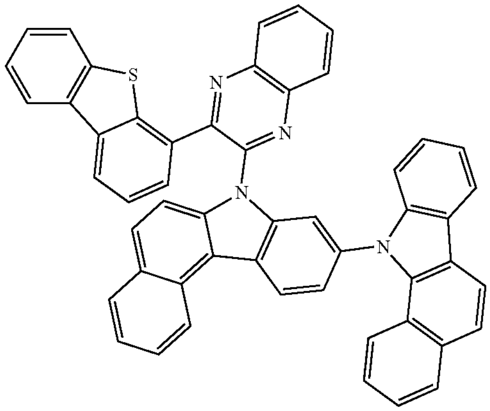
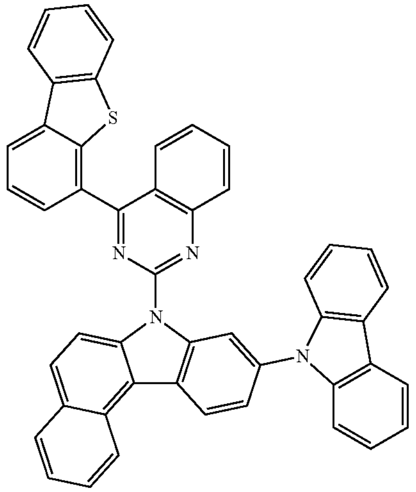
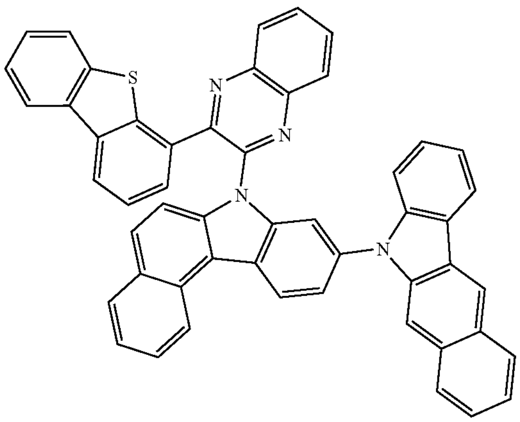
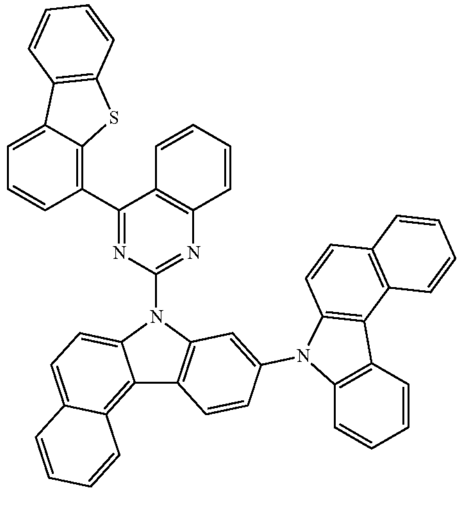
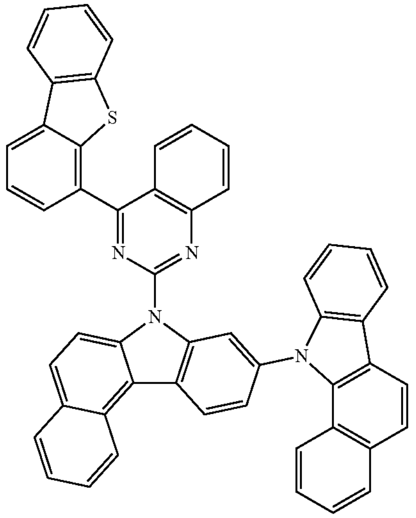
-continued -continued
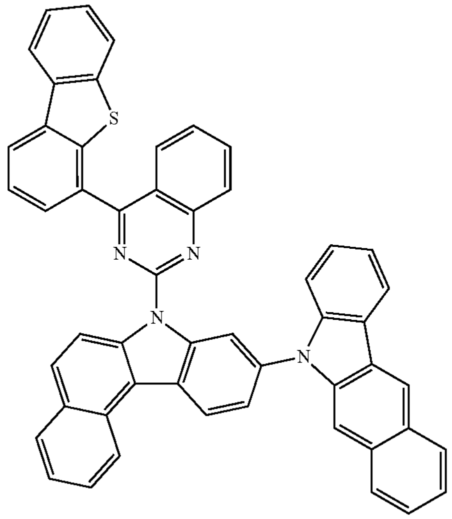 [SMILES: c1ccc2cc3c(cc2c1)c1ccccc1n3-c1ccc2c3c4ccccc4ccc3n(-c3nc(-c4cccc5c4sc4ccccc45)c4ccccc4n3)c2c1]
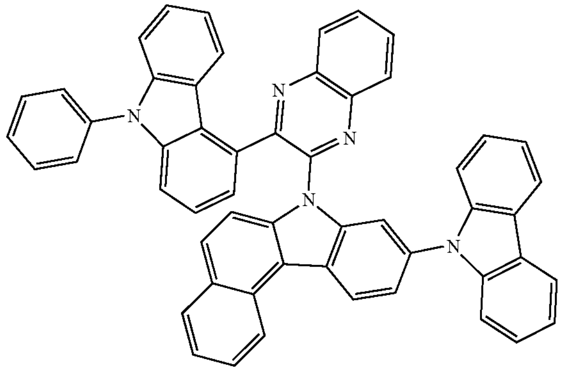
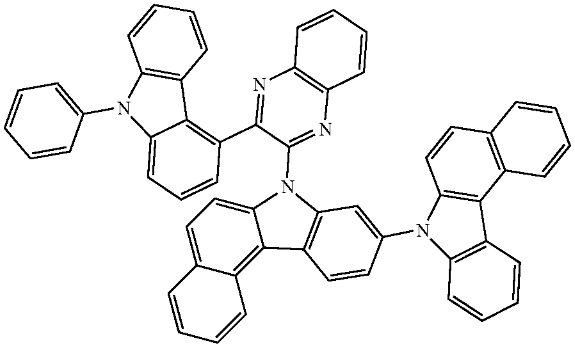
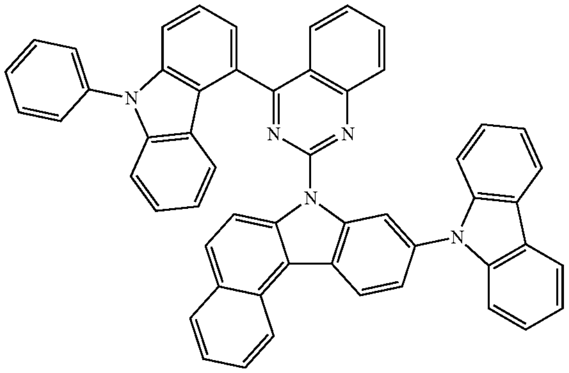
-continued
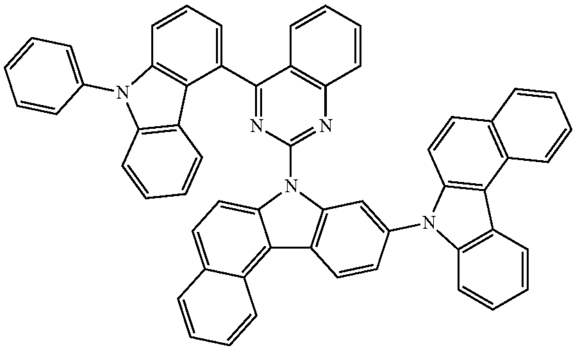
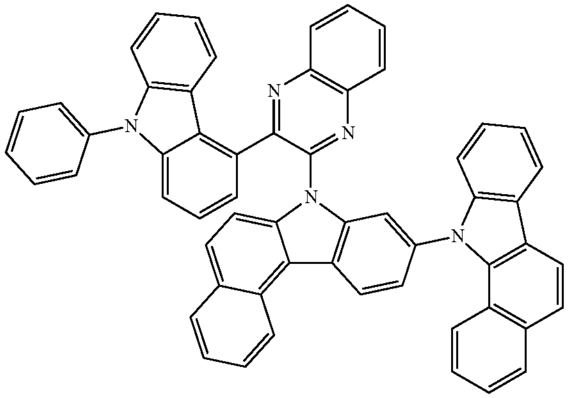
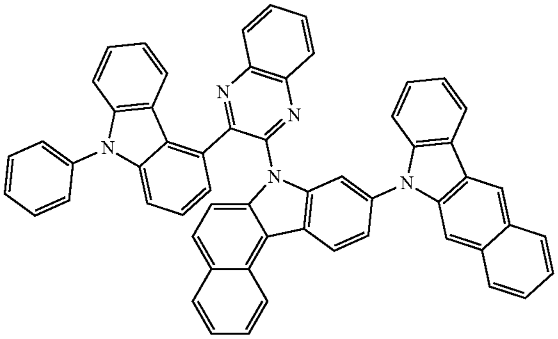
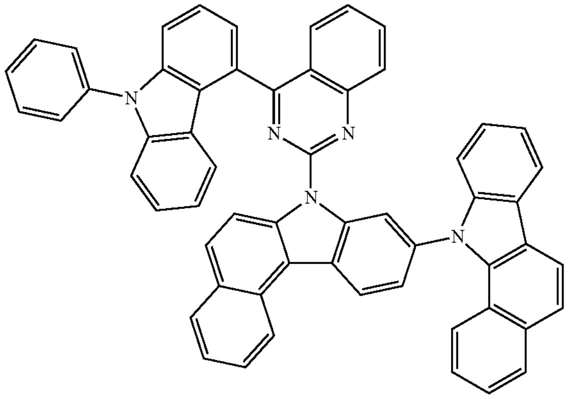

-continued
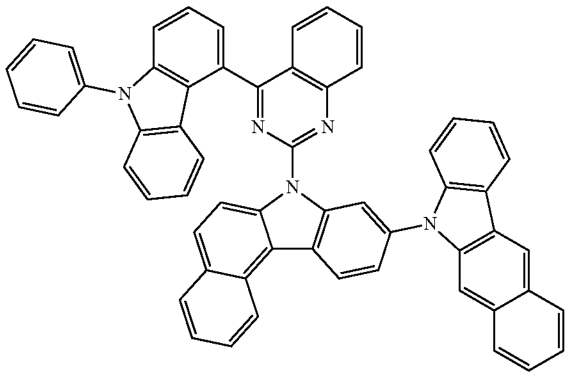
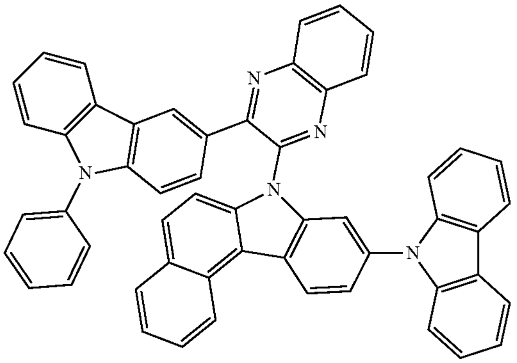
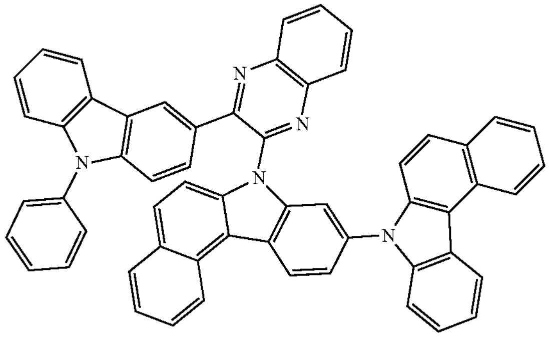
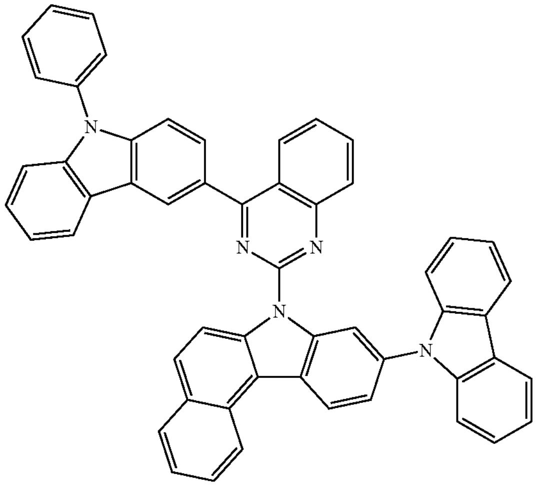
-continued
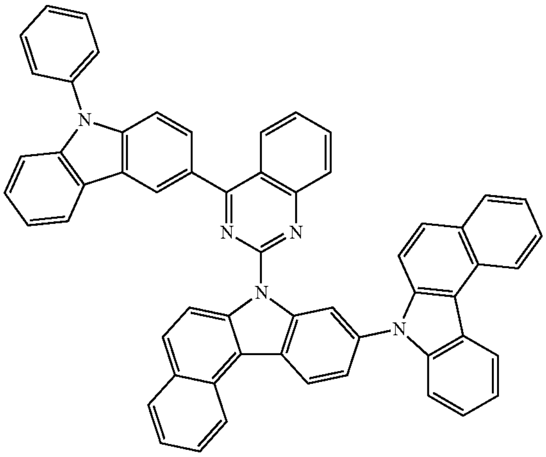
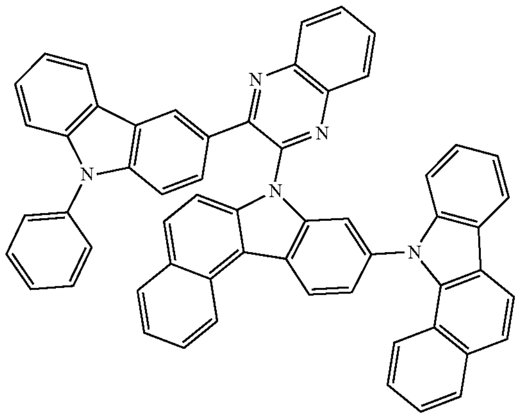
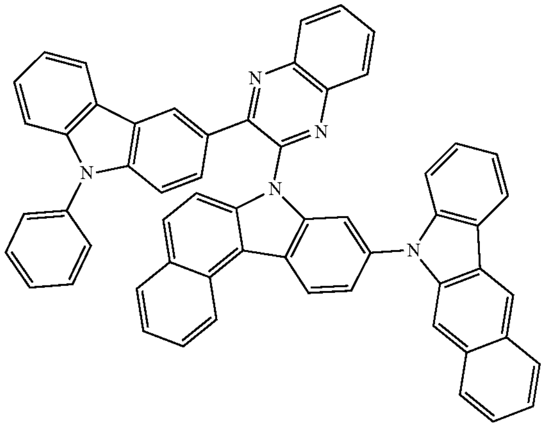

-continued
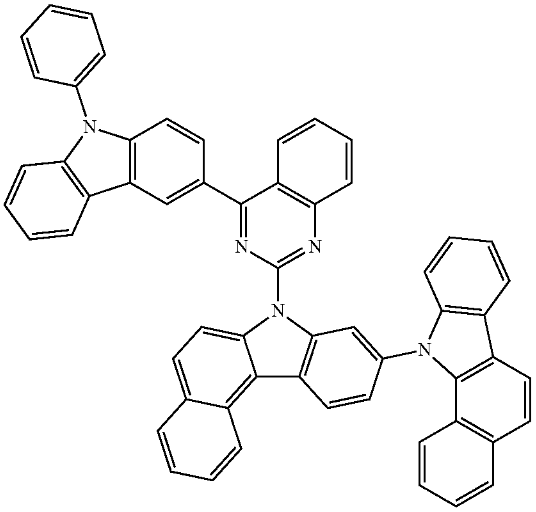
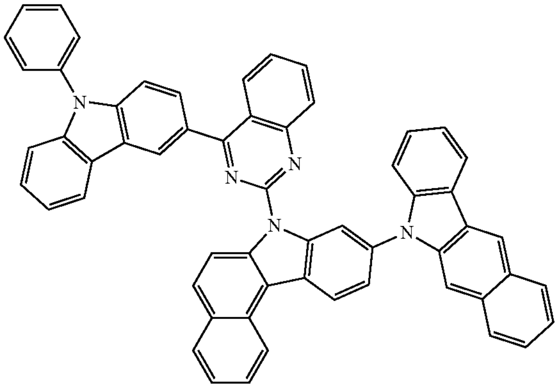 [SMILES: c1ccc(-n2c3ccccc3c3cc(-c4nc(-n5c6cc(-n7c8ccccc8c8cc9ccccc9cc87)ccc6c6c7ccccc7ccc65)nc5ccccc45)ccc32)cc1]
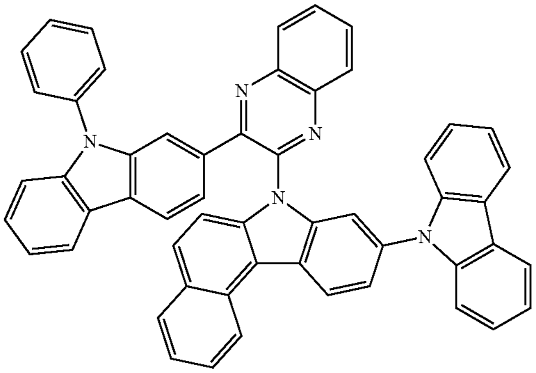
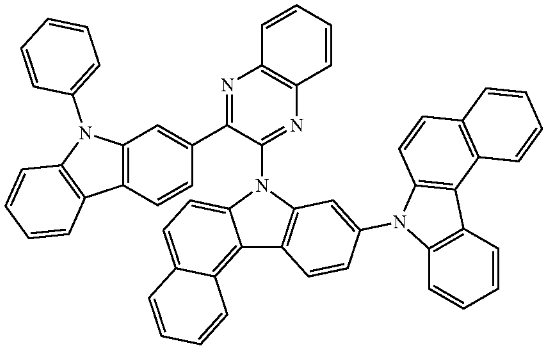
-continued
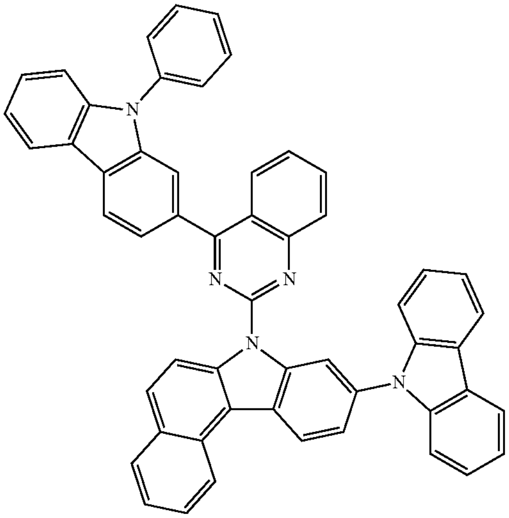
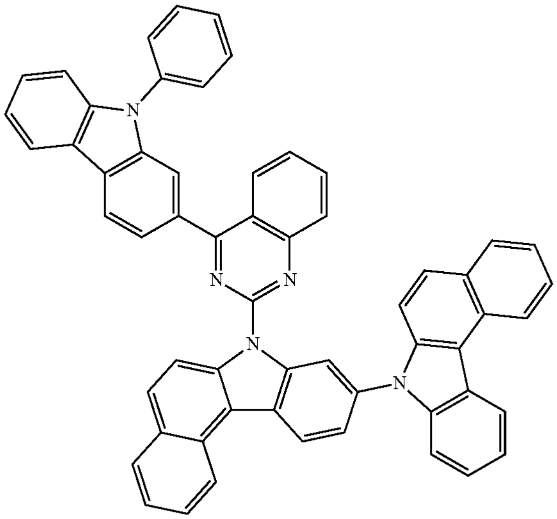
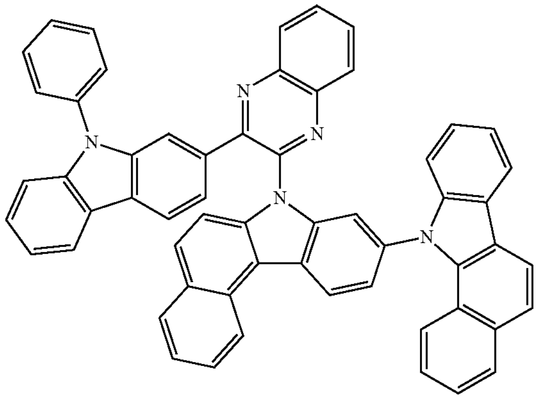

-continued
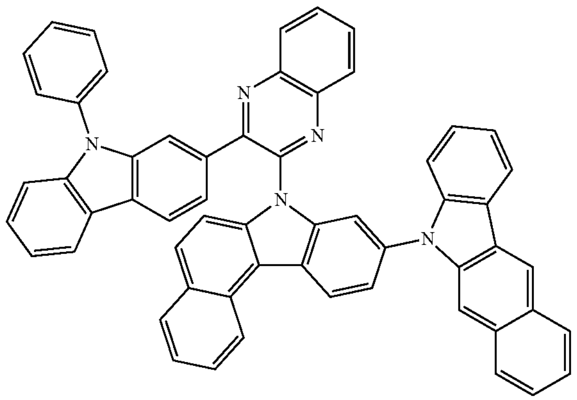
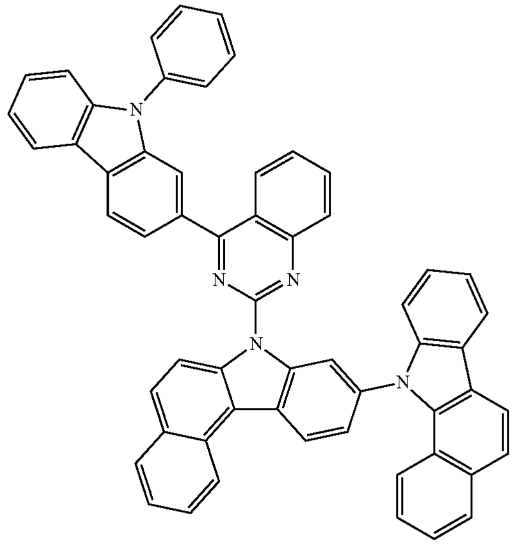
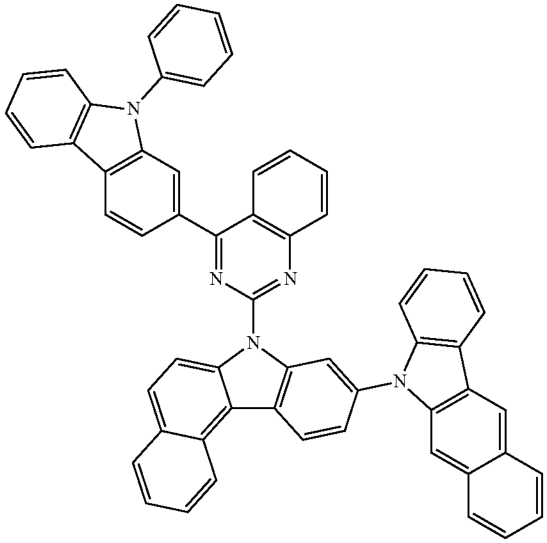
-continued
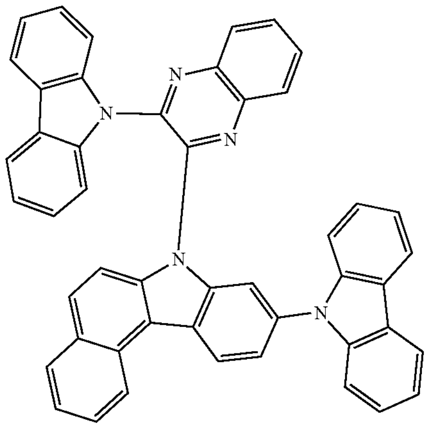
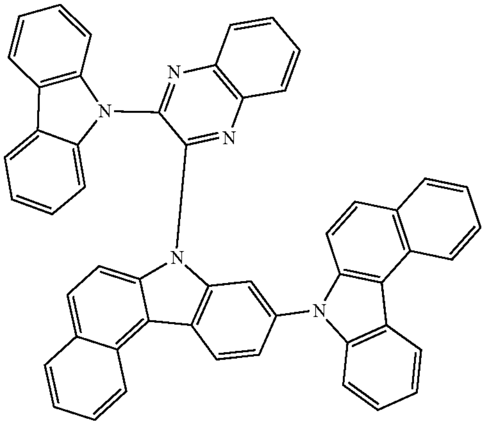
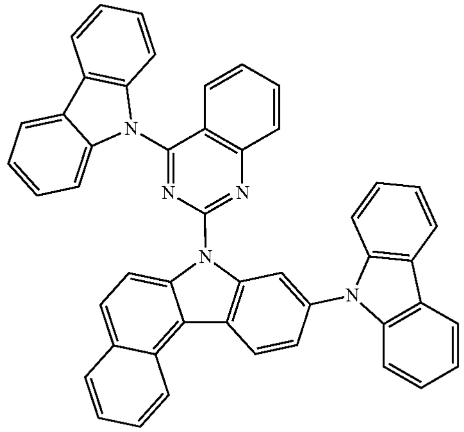
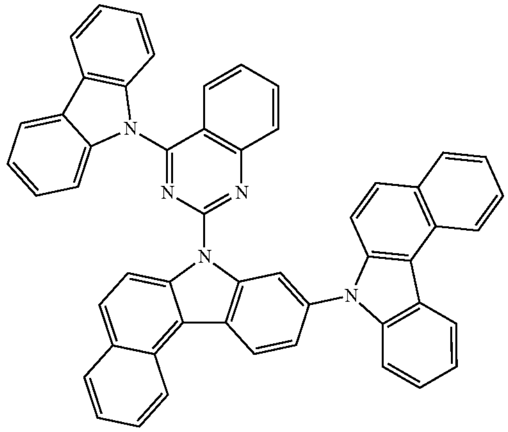

-continued
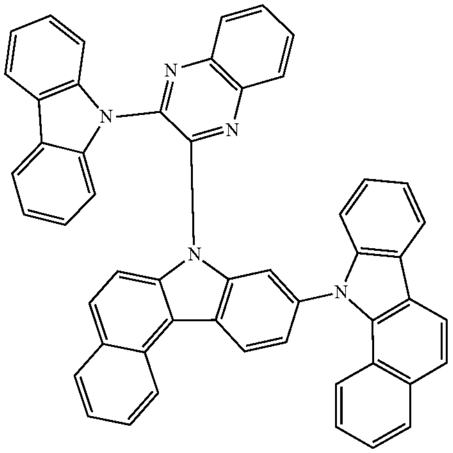
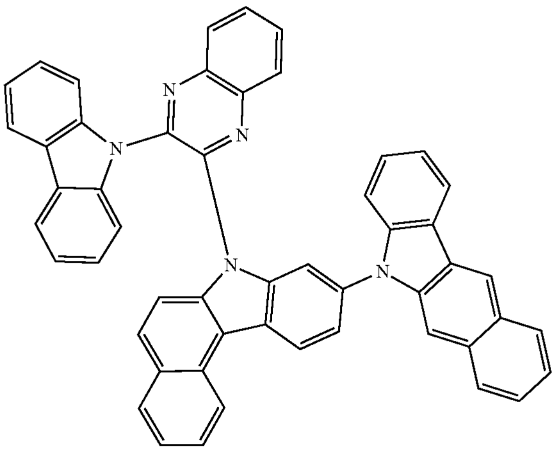
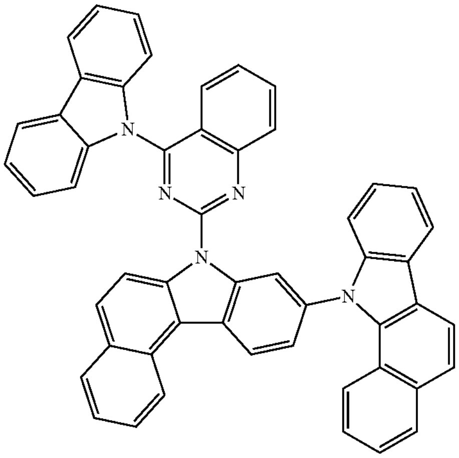
-continued
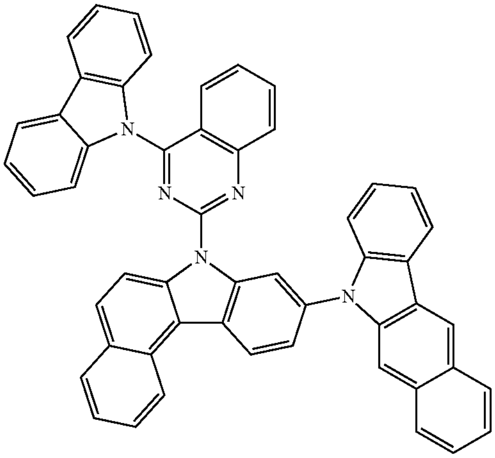
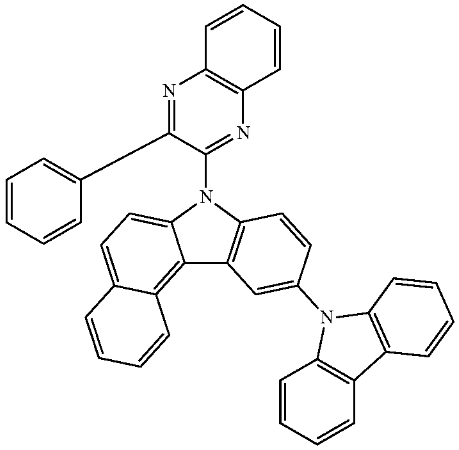
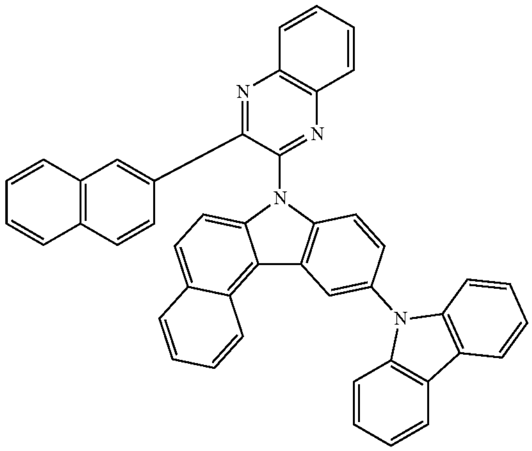

-continued
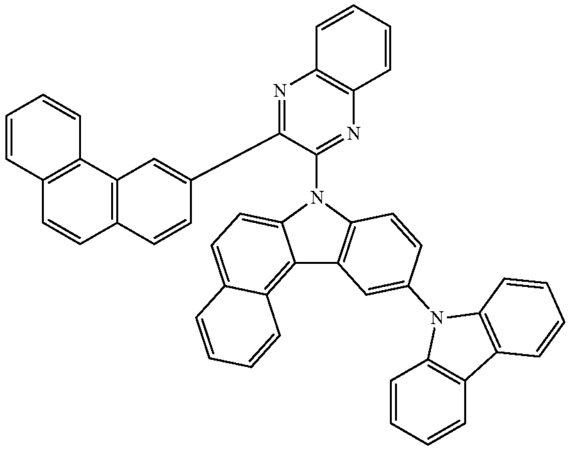
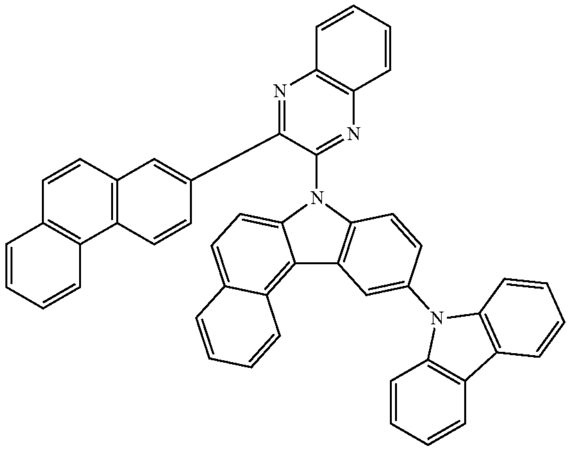
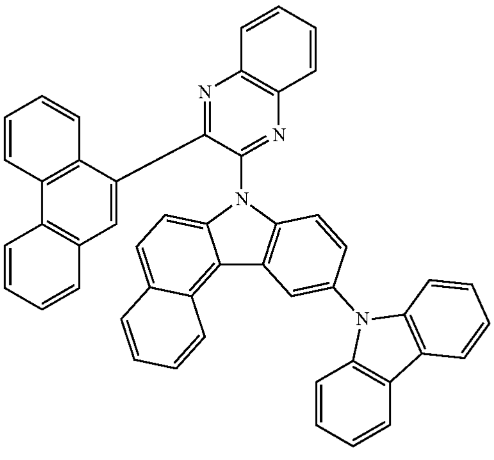
-continued
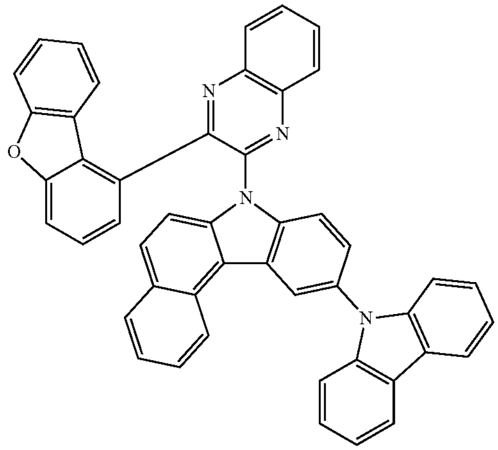
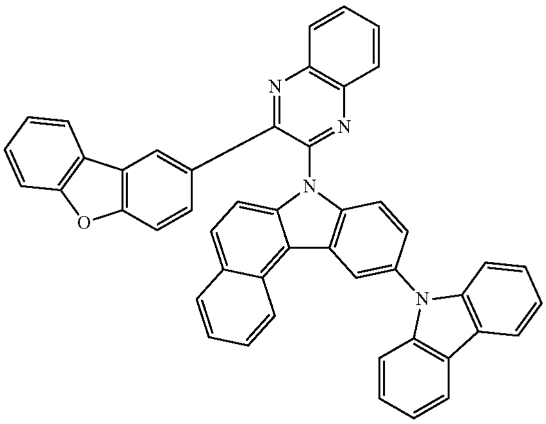
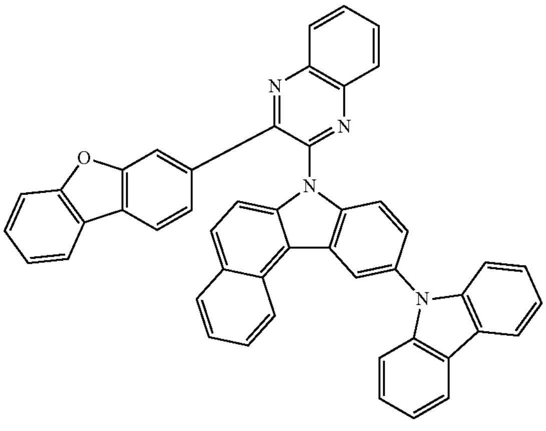

-continued
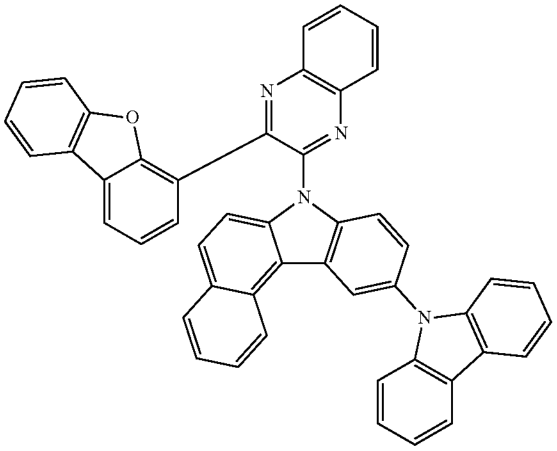
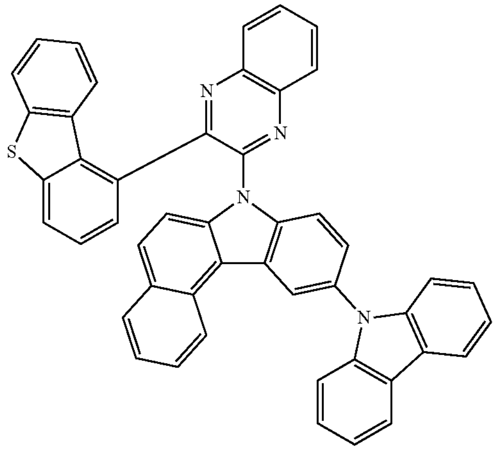
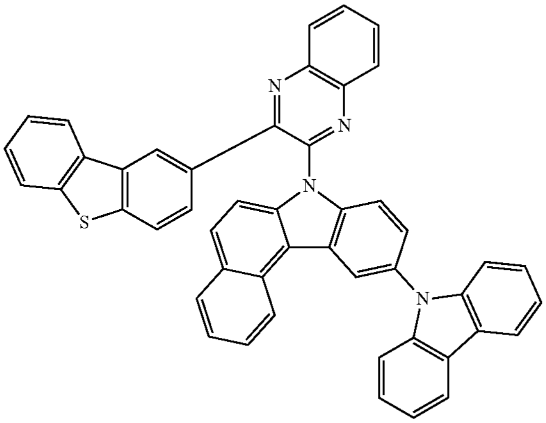
-continued
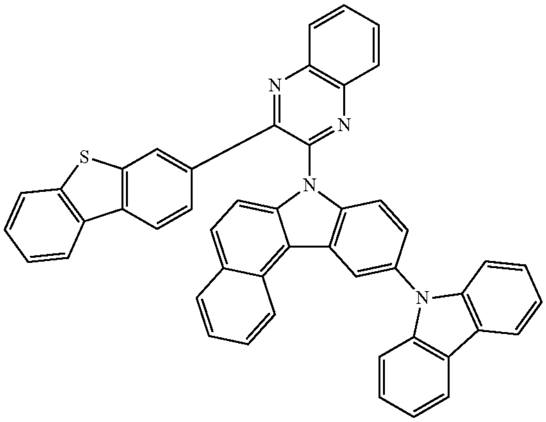
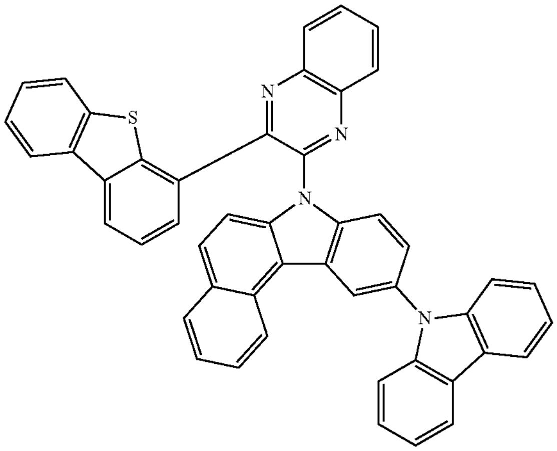
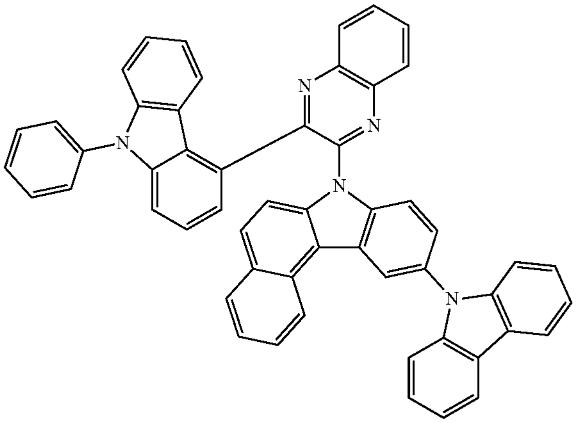
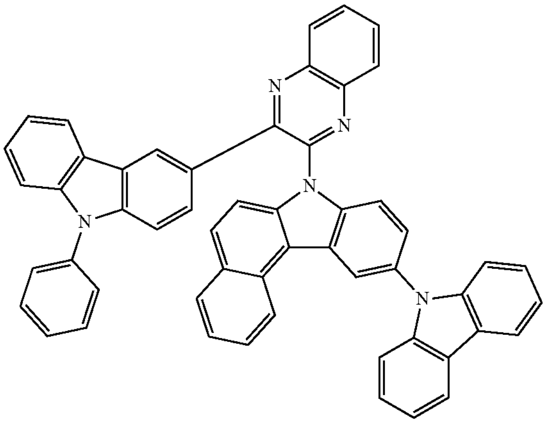

-continued
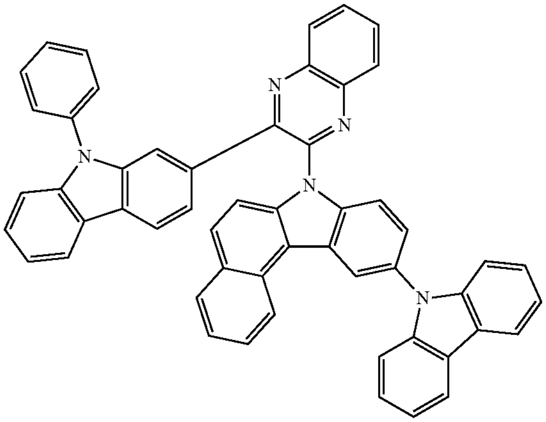
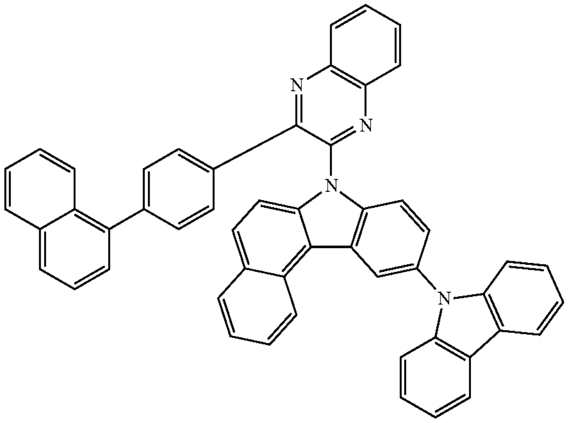
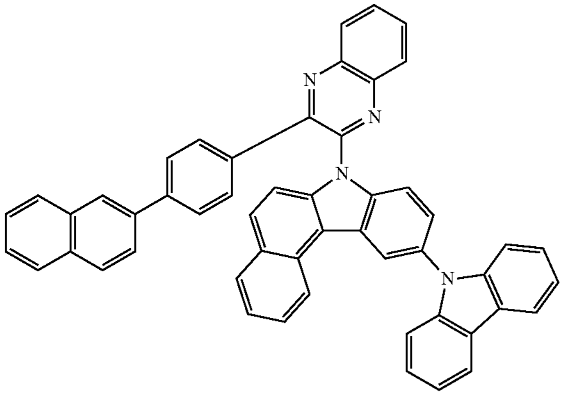
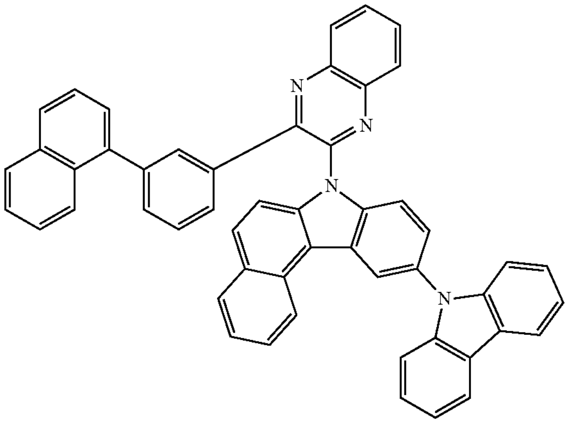
-continued
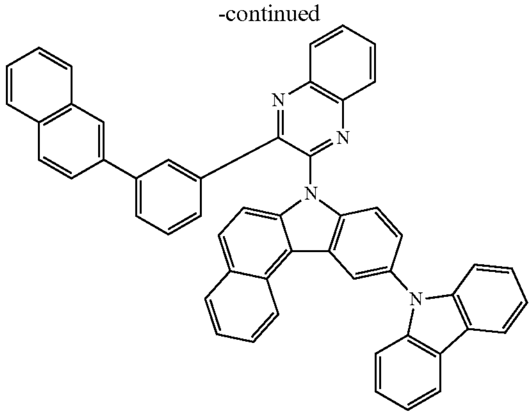
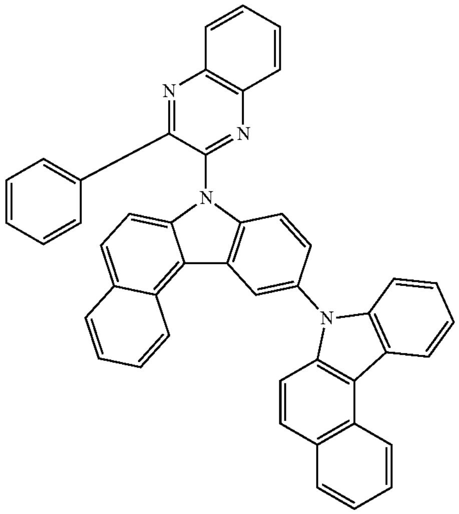
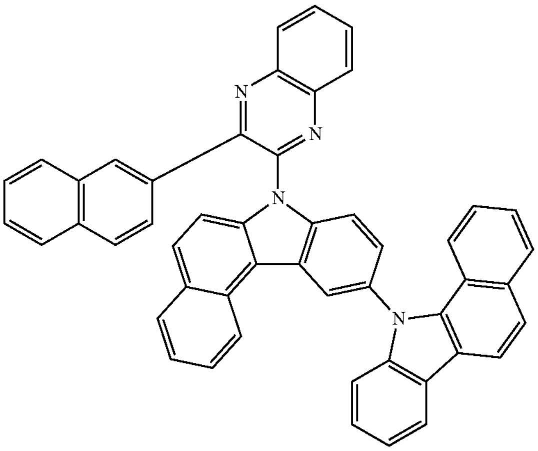

-continued
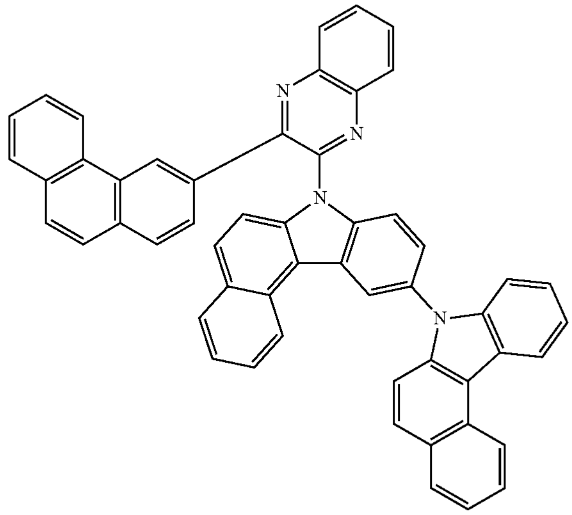
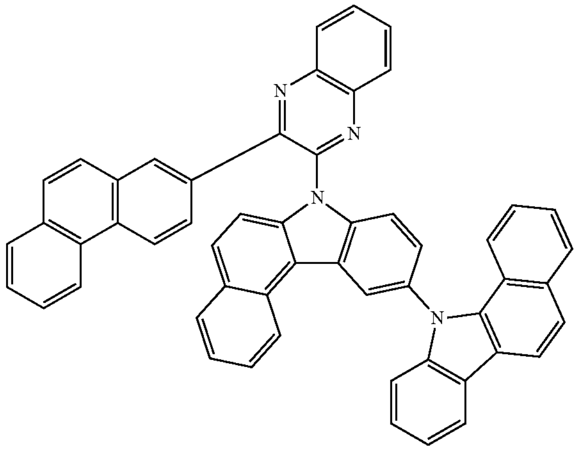
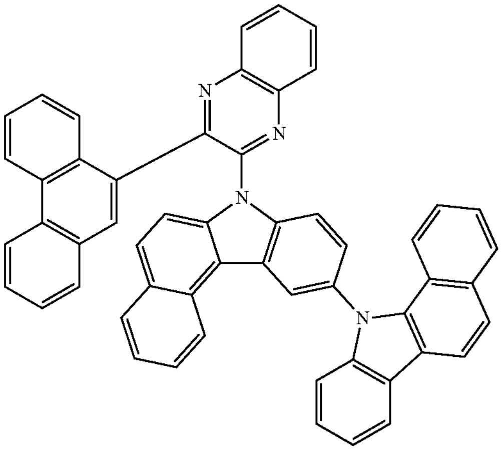
-continued
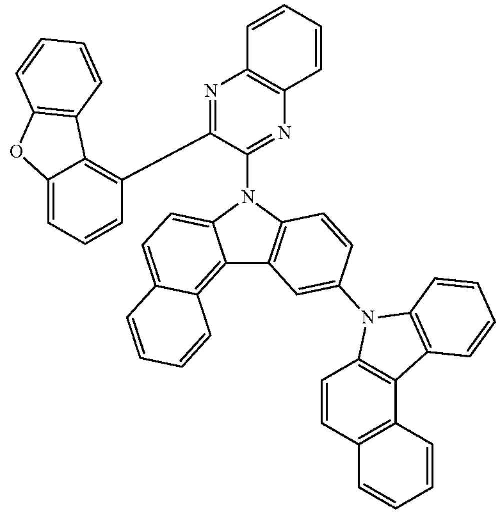
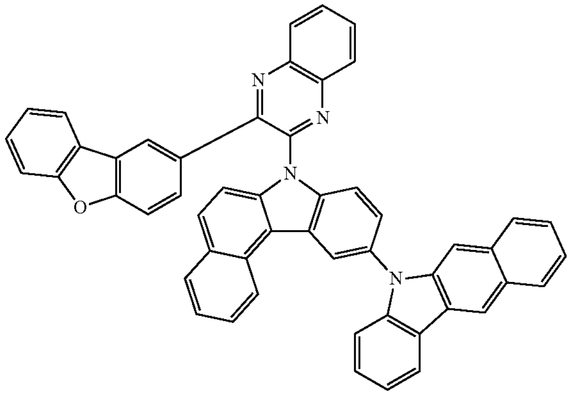
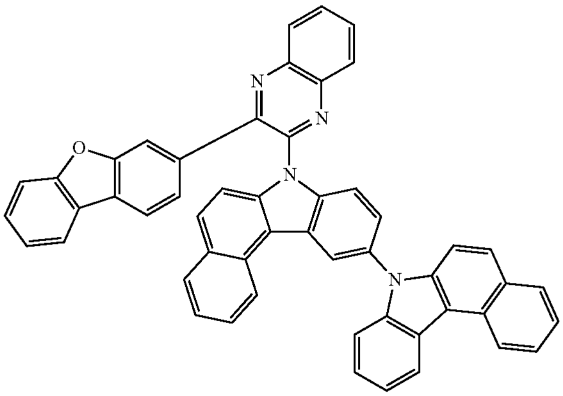

-continued
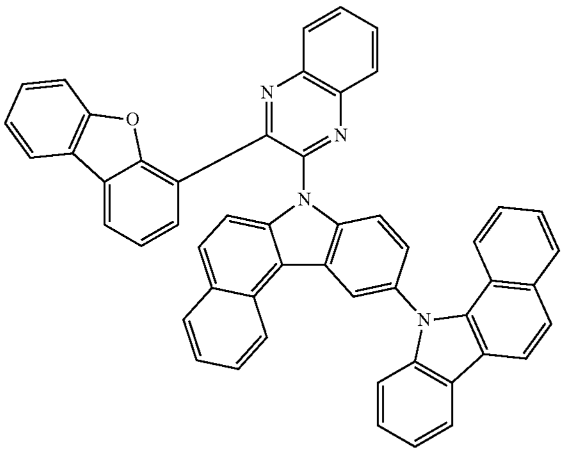
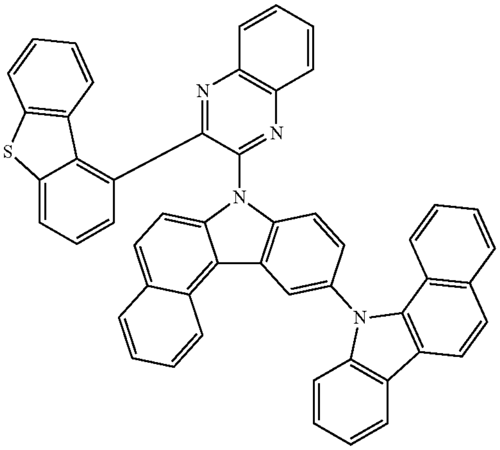
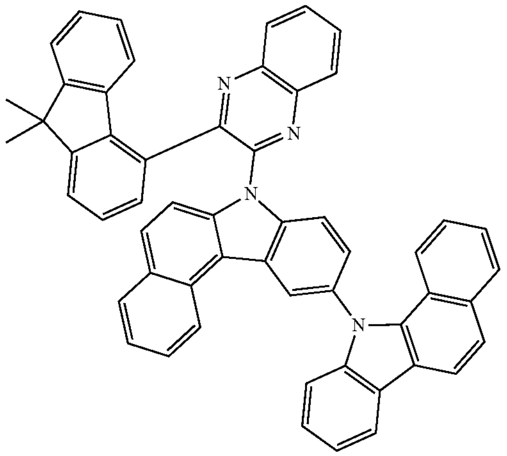
-continued
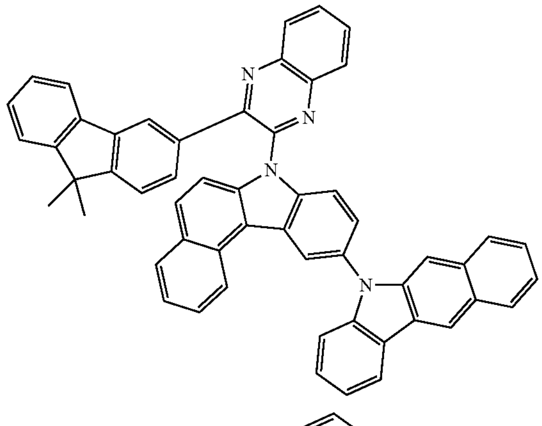
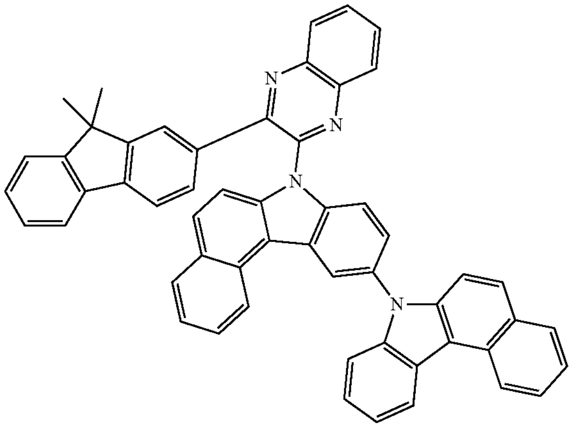
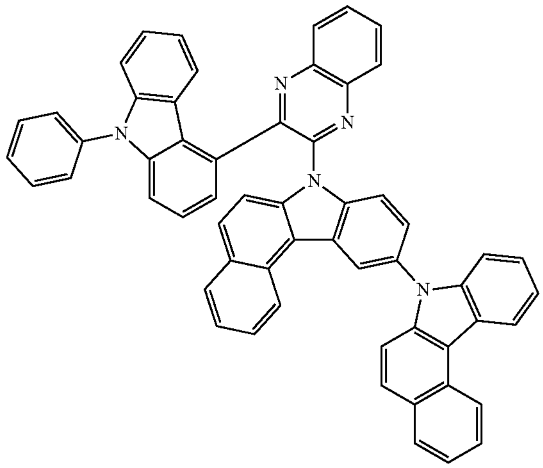
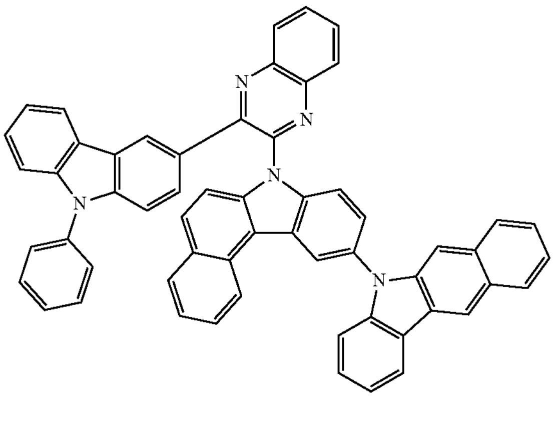

-continued
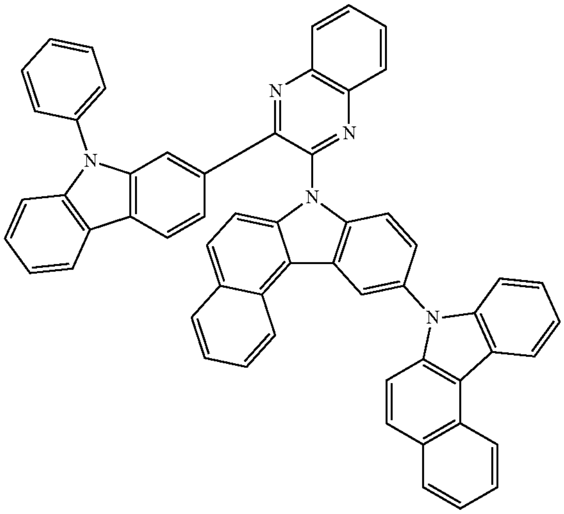
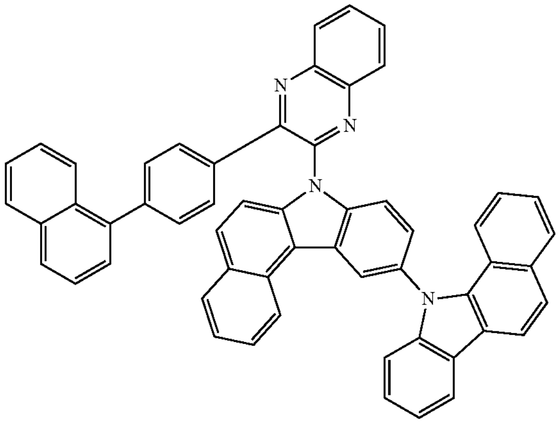
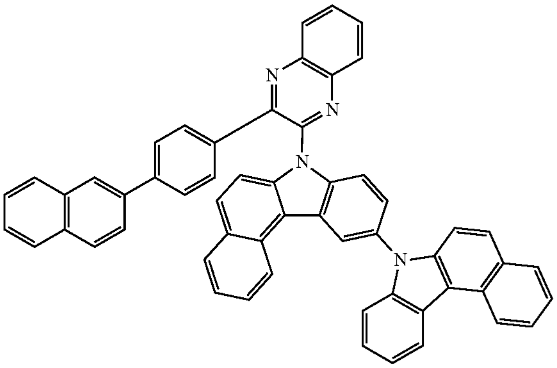
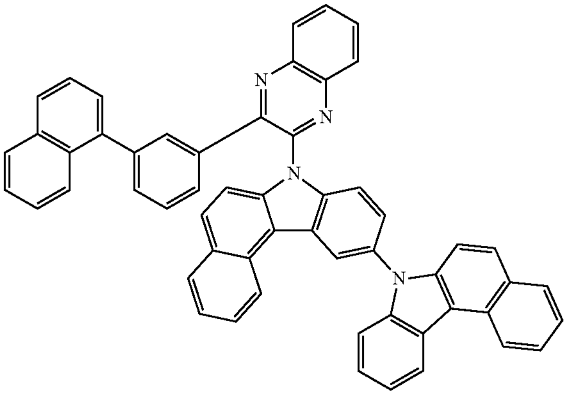
-continued
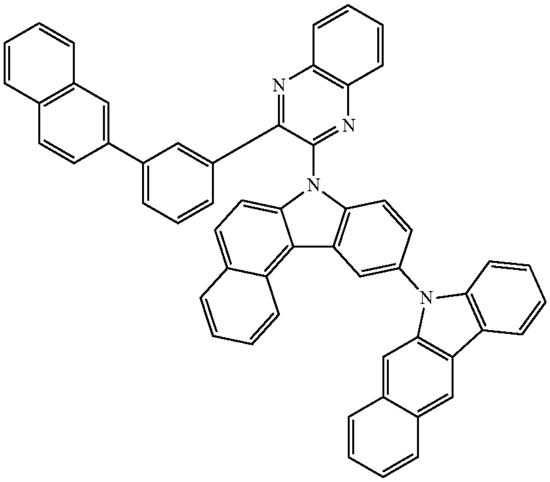
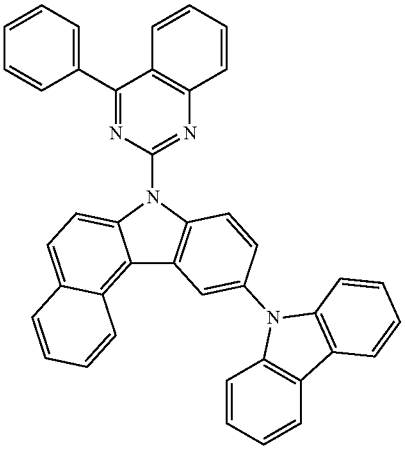
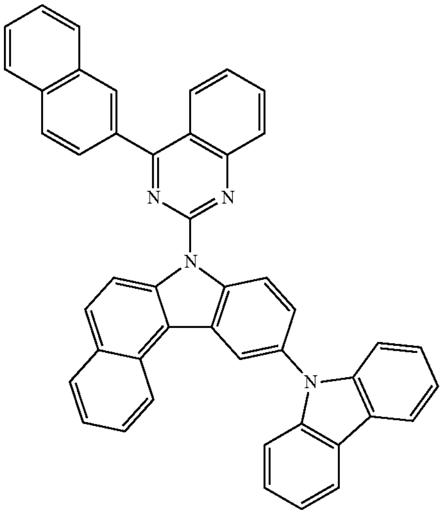

-continued
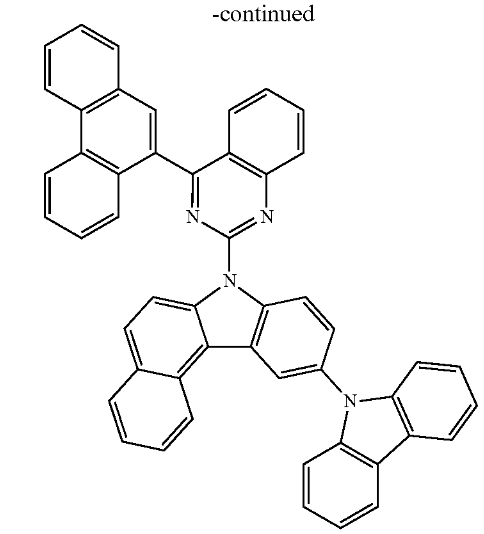
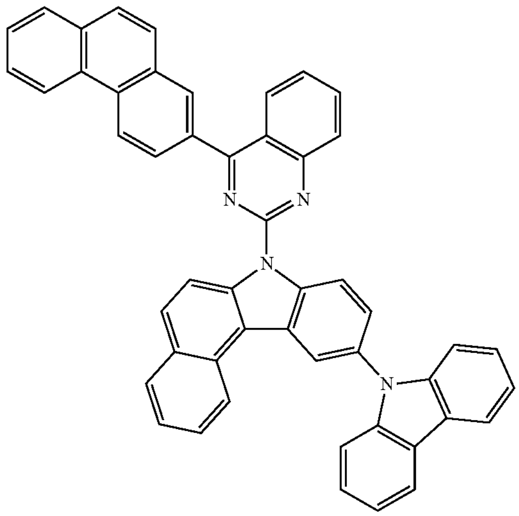
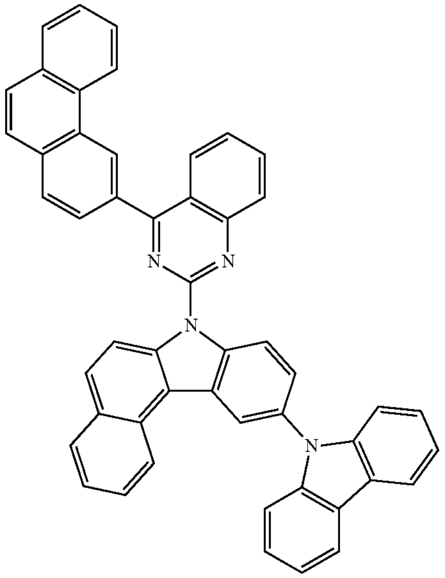
-continued
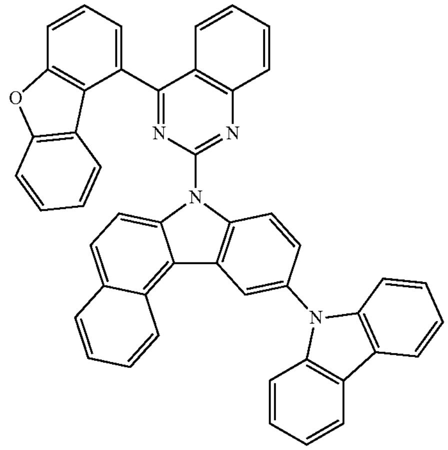
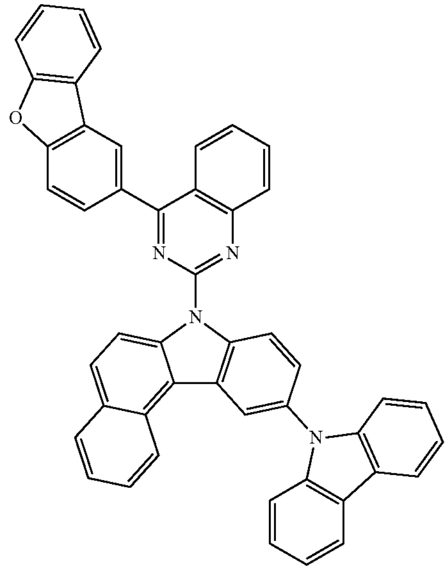
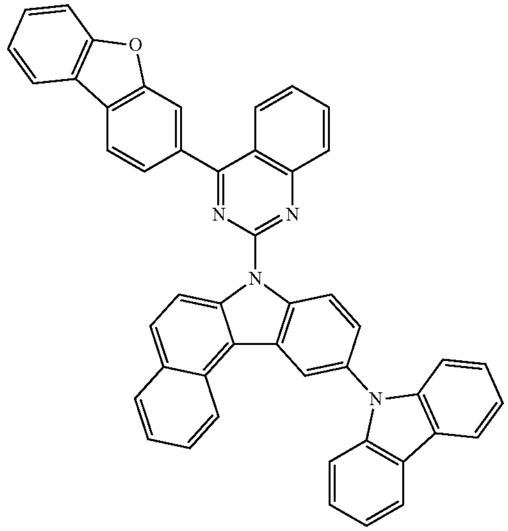

-continued
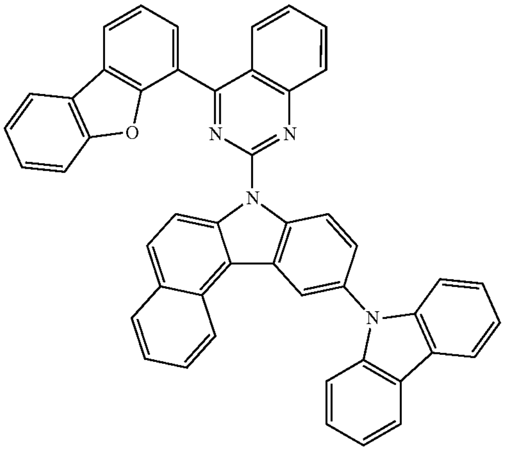
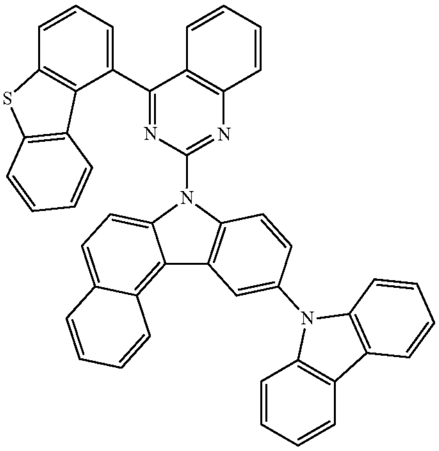
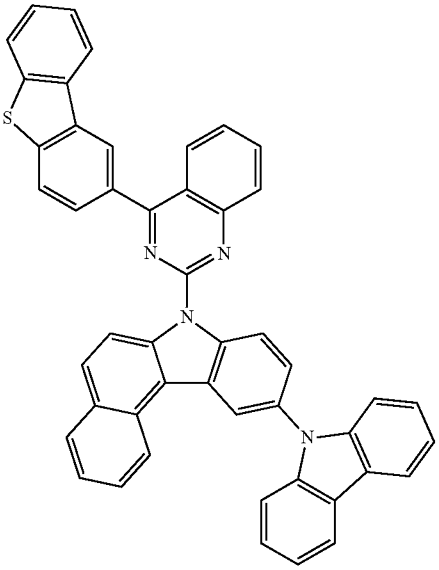
-continued
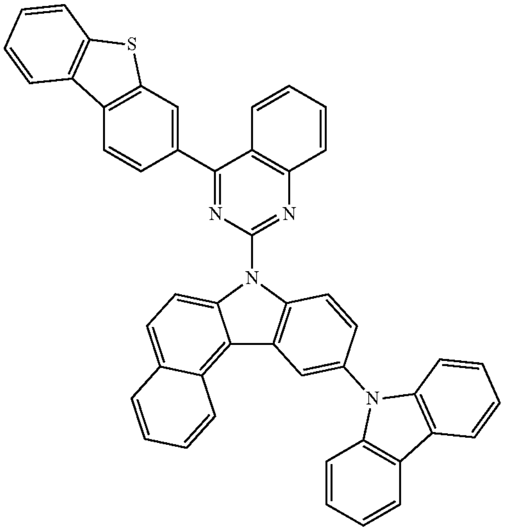
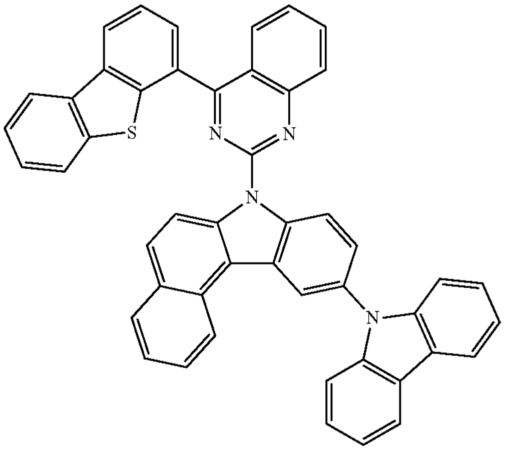
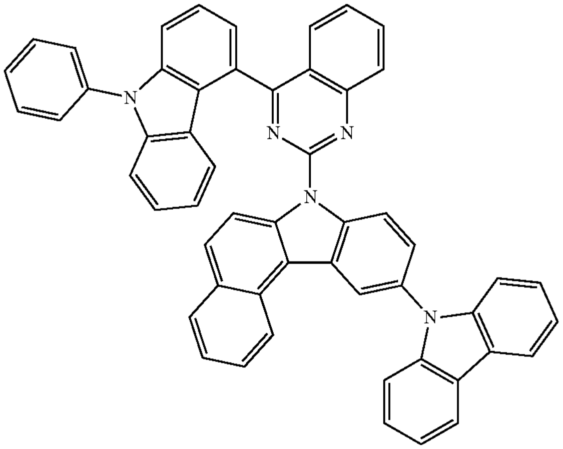

-continued
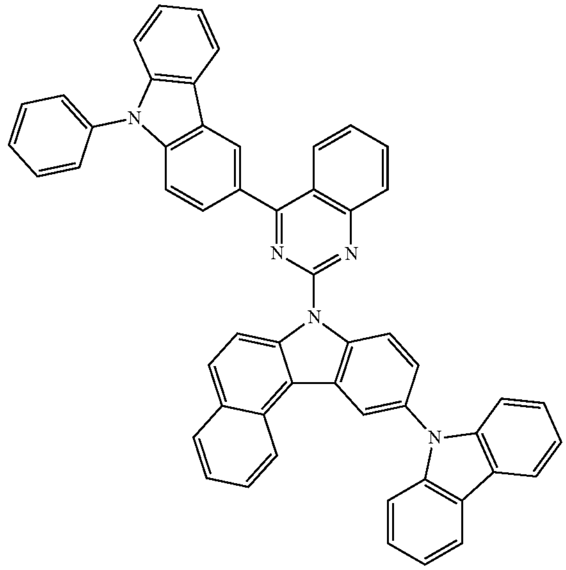
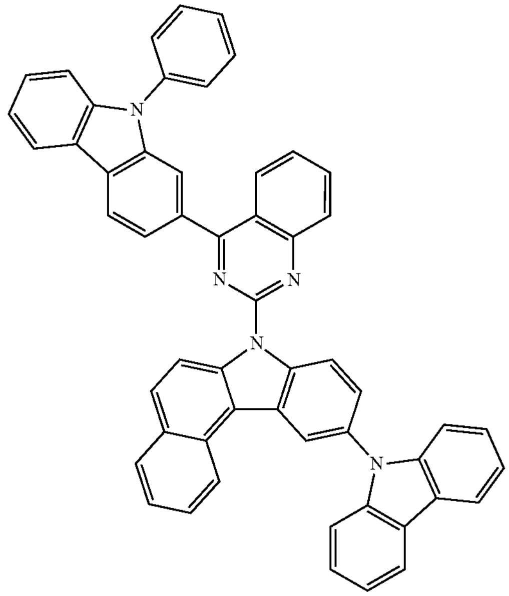
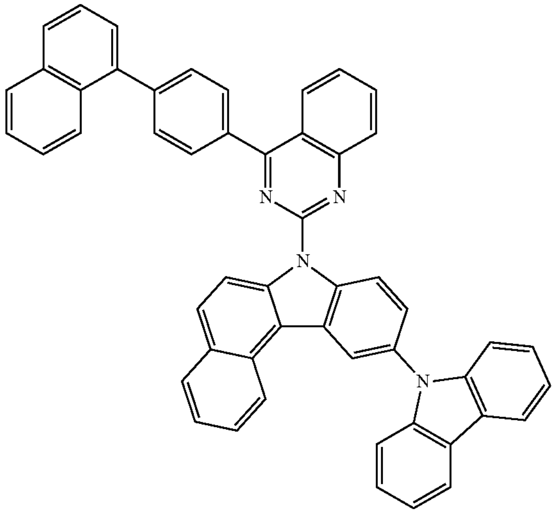
-continued
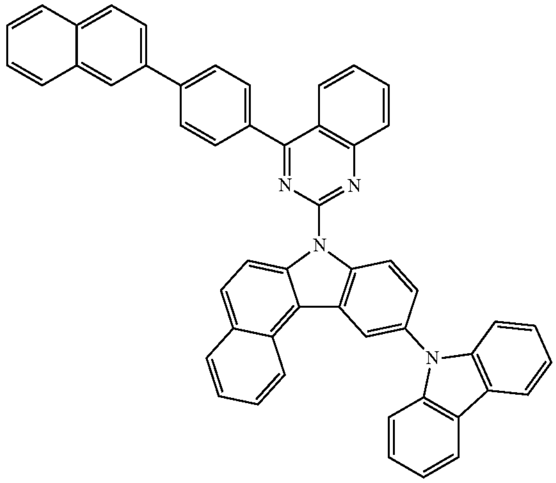
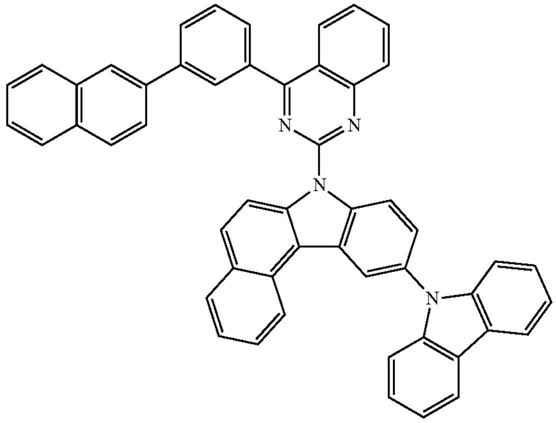
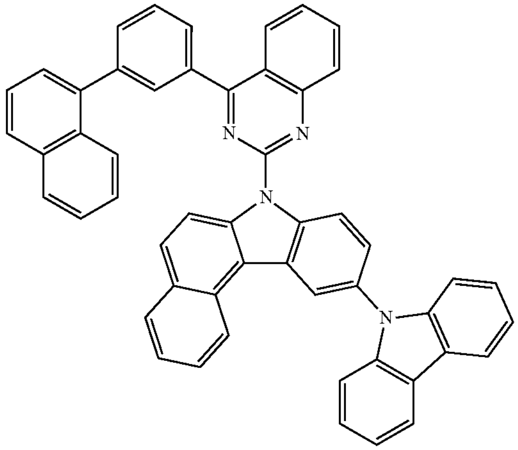

-continued
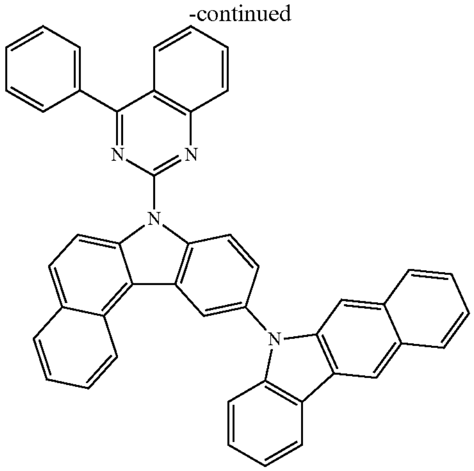
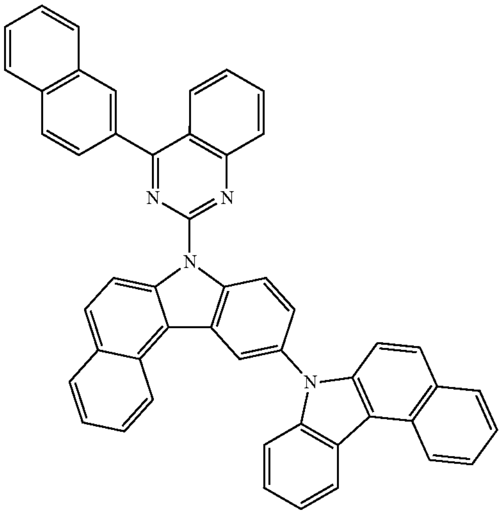
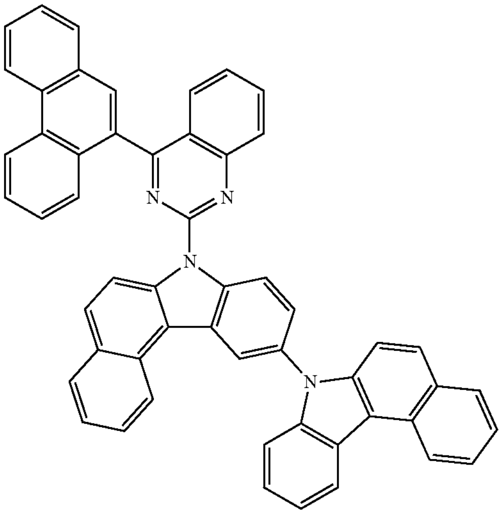
-continued
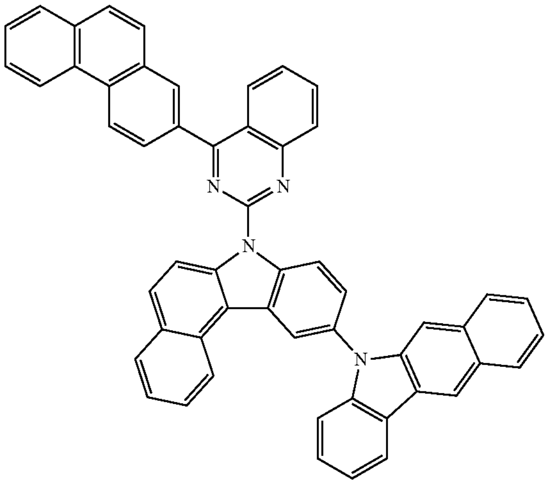
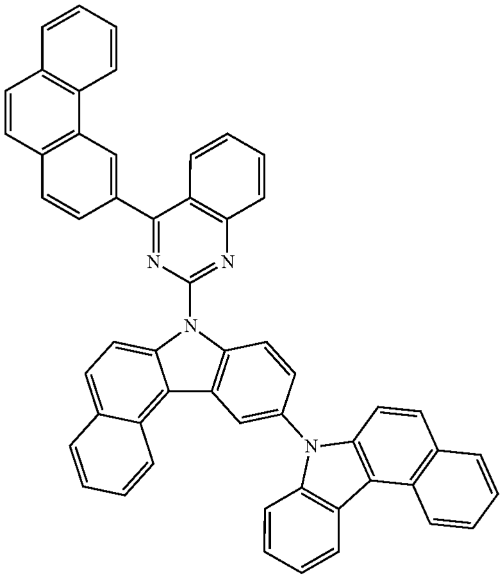
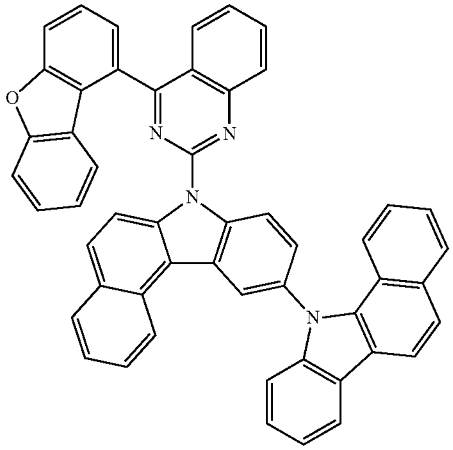

-continued
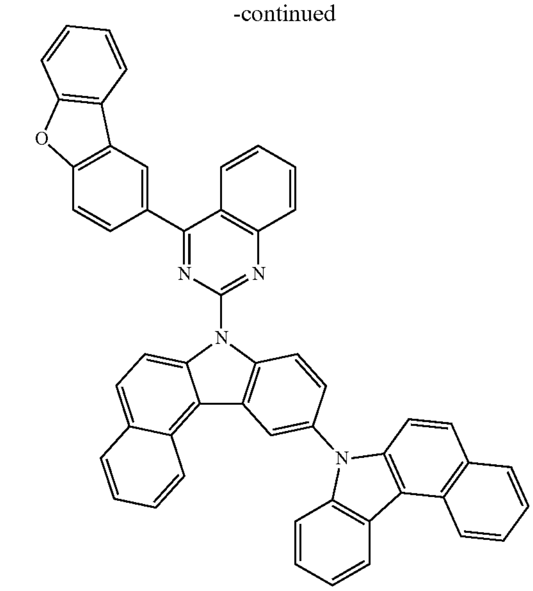
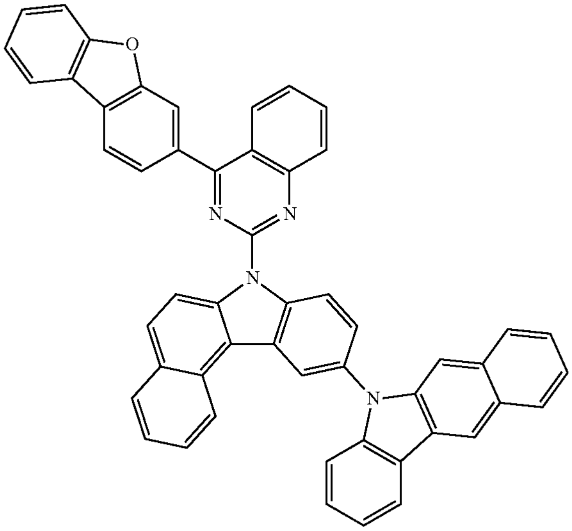
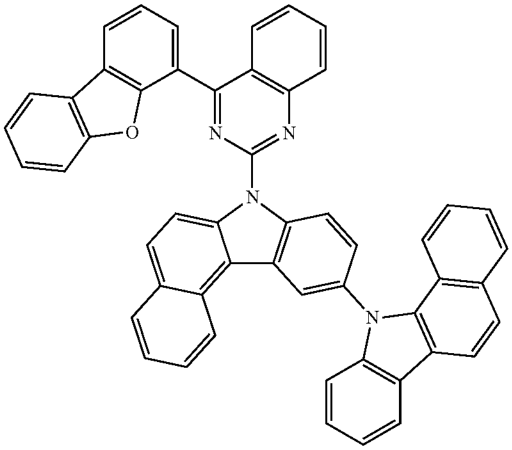
-continued
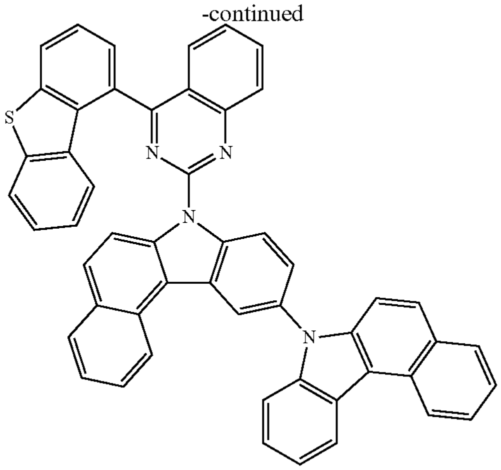
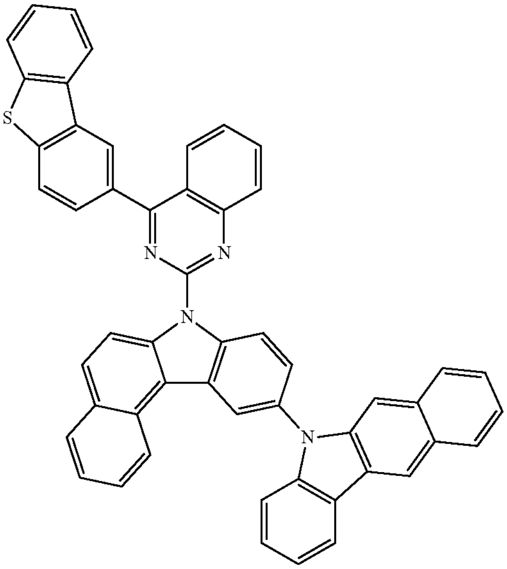
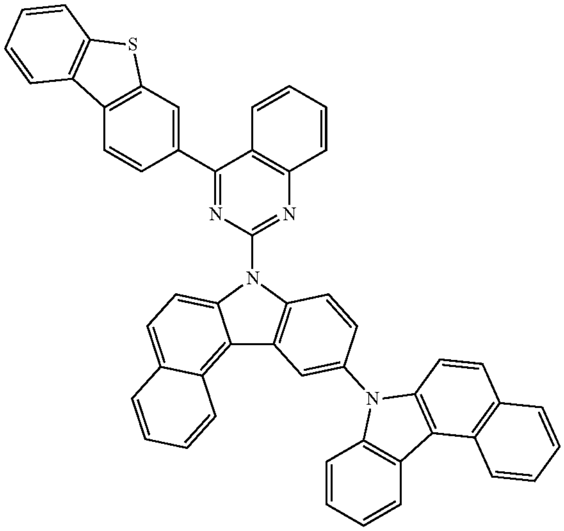

-continued
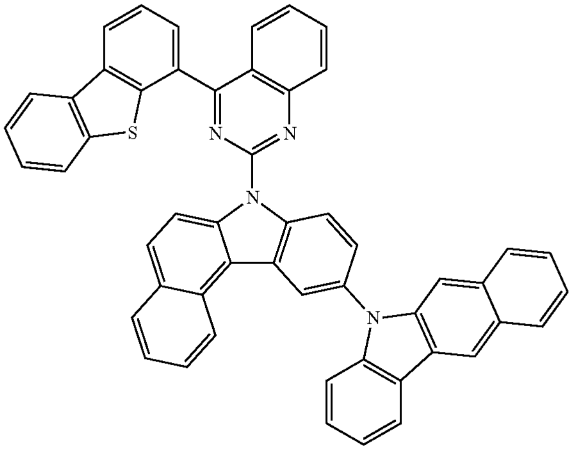
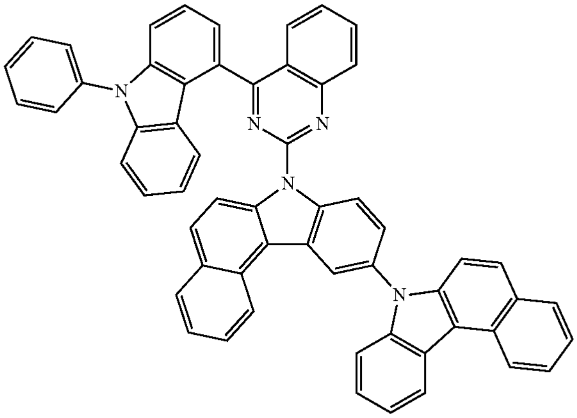
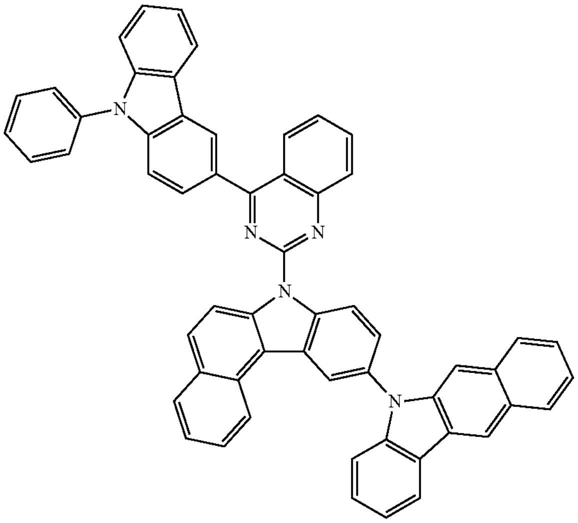
-continued
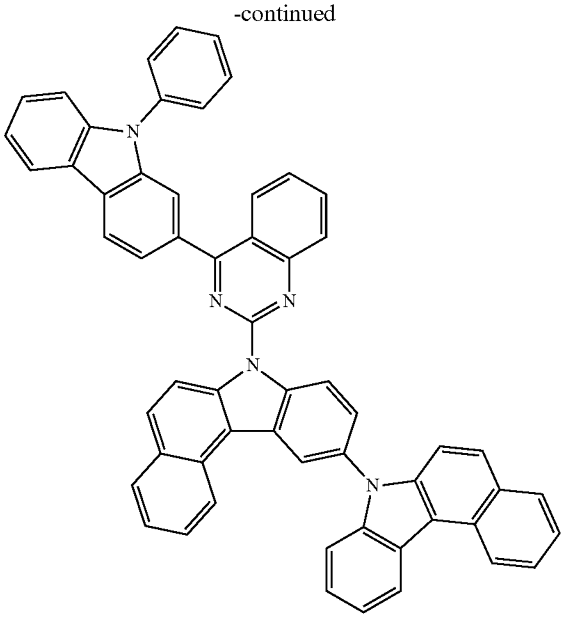
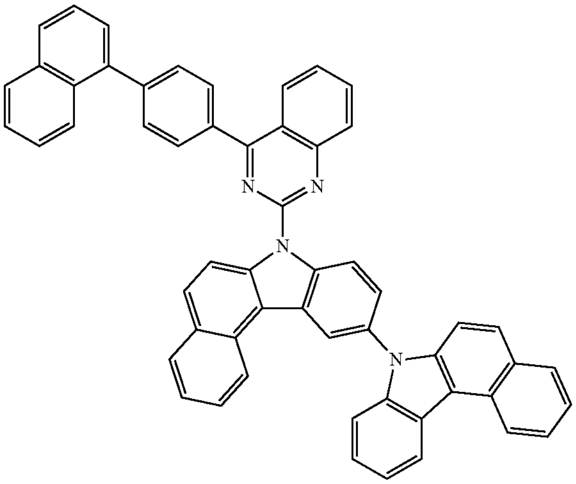
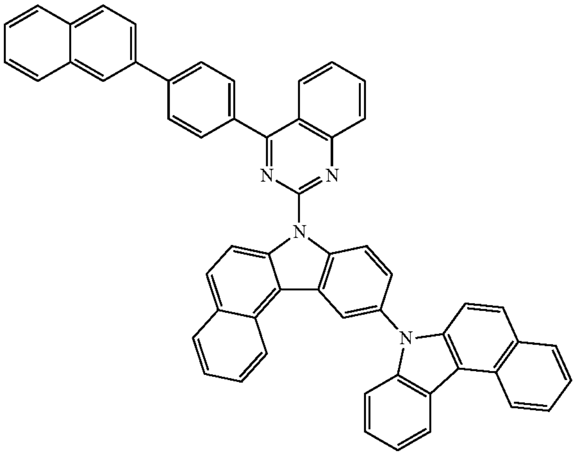

-continued
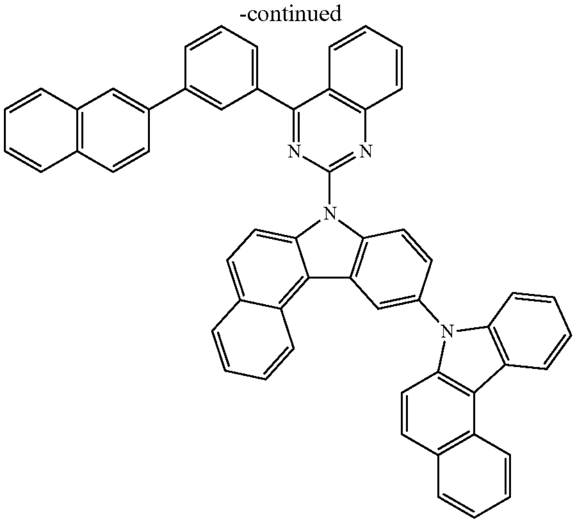
-continued
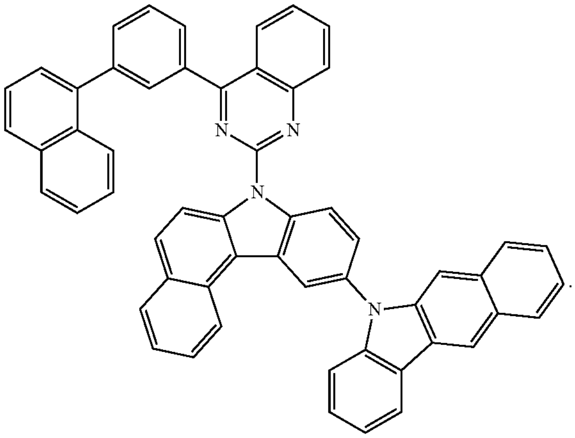 [SMILES: c1cc(-c2cccc3ccccc23)cc(-c2nc(-n3c4ccc(-n5c6ccccc6c6cc7ccccc7cc65)cc4c4c5ccccc5ccc43)nc3ccccc23)c1]
.
* * * * *